United States Patent
Cohen et al.

(10) Patent No.: US 6,265,546 B1
(45) Date of Patent: Jul. 24, 2001

(54) PROSTATE CANCER GENE

(75) Inventors: Daniel Cohen, Neuilly sur Seine; Marta Blumenfeld, Paris; Ilya Chumakov, Vaux-le-Penil; Lydie Bougueleret, Vanves, all of (FR)

(73) Assignee: Genset (FR)

( * ) Notice: Subject to any disclaimer, the term of this patent is extended or adjusted under 35 U.S.C. 154(b) by 0 days.

(21) Appl. No.: 09/338,907

(22) Filed: Jun. 23, 1999

Related U.S. Application Data

(63) Continuation-in-part of application No. 09/218,207, filed on Dec. 22, 1998, which is a continuation-in-part of application No. 08/996,306, filed on Dec. 22, 1997, now Pat. No. 5,945,522.
(60) Provisional application No. 60/099,658, filed on Sep. 9, 1998.

(51) Int. Cl.$^7$ .......................... C07K 1/00; A61K 39/395; A01N 37/18; G01N 35/53
(52) U.S. Cl. ........................ 530/350; 424/174.1; 435/7.1; 514/2
(58) Field of Search ..................................... 530/350, 300, 530/324, 325; 514/2, 10, 12; 424/174.1; 435/7.1

(56) References Cited

U.S. PATENT DOCUMENTS 5,807,680   9/1998   Sutcliffe et al. .......................... 435/6

FOREIGN PATENT DOCUMENTS

WO 96/20288   7/1996   (WO) .
WO 97/36535   10/1997   (WO) .
WO 97/46702   12/1997   (WO) .

OTHER PUBLICATIONS

Bova, S., et al. (1993) Homozygous deletion and frequent allelic loss of chromosome 8p22 Loci in human prostate cancer. Cancer Research 53(1):3869–3873.
Hillier, L., et al. (1995) y177g12.r1 homosapiens cDNA clone 442645. XP 002109141—EMBL Database Entry HS 164152, Accession No. H06164.
Kruglyak, L. (1997) The use of a genetic map of biallelic markers in linkage studies. Nature Genetics 17(1): 21–24.
Schork, N.J. et al. (1997) Linkage disequiibrum mapping for quantitative traits within case/control settings. American Journal of Human Genetics 61(4) p. A293.
Wang, D., et al. (1996) Toward a third generation genetic map of the human genome based on bi–allelic polymorphisms. American Journal of Human Genetics 59(4) p. A03.
Wu, C., et al. (1997) Deletion mapping defines three discrete areas of allelic imbalance on chromosome arm 8p in oral and oropharyngeal squamous cell carcinomas. Genes, Chromosomes & Cancer 20:347–353.

Auffray, et al., "[IMAGE: molecular integration of the analysis of the human genome and its expression]", C R ACAD SCI III, 318(2) P263–2721 (Feb. 1995).
Ashagbley, et al., "Synthesis of Ether–Linked Analogues of Lysophosphatidate and their Effect on the Proliferation of Human Epithelial Cancer Cells", Anticancer Research, 16(4A) : 1813–1818 (1996).
Coleman, J., "Characterization of the *Escherichia coli* gene for 1–acyl–sn–glycerol–3–phosphate acyltransferase (plsC)", Mol. Gen. Genet, 232(2) :295–303 (1992).
Chumakov, et al., "A YAC contig map of the human genome", Nature, 377 Supp : 175–297 (1995).
Durieux, et al., "Signalling properties of lysophosphatidic acid", Trends in Pharmacol. Sci., 14(6) : 249–254 (1993).
Eberhardt, et al., "Human Lysophosphatidic Acid Acyltransferase", J. Biol. Chem. 272(32) : 20299–20305 (1997).
Emi, et al., "Frequent Loss of Heterozygosity for Loci on Chromosome 8p n Hepatocellular Carcinoma, Colorectal Cancer, and Lung Cancer", Cancer Research, 52(19) : 5368–5372 (1992).
Faas, et al., "Increased phospholipid fatty acid remodeling in human and rat prostatic adenocarcinoma tissues", J. Urol (Baltimore), 156(1): 243–248 (1996).
Gronwald, et al., "Comparison of DNA Gains and Losses in Primary Renal Clear Cell Carcinomas and Metastatic Sites: Importance of 1q and 3p Copy Number Changes In Metastatic Events", Cancer Research, 57(3) : 481–487 (1997).
Gu, et al., "Identification. cloning, and expression of a cytosolic megakaryocyte protein–tyrosine–phosphatase with sequence homology to cytoskeletal protein 4.1", Proc. Natl. Acad. Sci. USA. 88(13)): P5867–71 (1991).
Hsuan, et al., "Growth Factor–dependent Phosphoinositide Signalling", Int. J. Biochem. Cell. Biol., 29(3) : 415–435 (1997).
Ichikawa, et al., "*"Prostate Suppl., 6 : 31–35 (1996).

(List continued on next page.)

*Primary Examiner*—Karen Cochrane Carlson
*Assistant Examiner*—Patricia Robinson
(74) *Attorney, Agent, or Firm*—Knobbe, Martens, Olson & Bear, LLP

(57) ABSTRACT

The present invention relates to PG1, a gene associated with prostate cancer. The invention provides polynucleotides including biallelic markers derived from PG1 and from flanking genomic regions. Primers hybridizing to these biallelic markers and regions flanking are also provided. This invention provides polynucleotides and methods suitable for genotyping a nucleic acid containing sample for one or more biallelic markers of the invention. Further, the invention provides methods to detect a statistical correlation between a biallelic marker allele and prostate cancer and between a haplotype and prostate cancer. The invention also relates to diagnostic methods of determining whether an individual is at risk for developing prostate cancer, and whether an individual suffers from prostate cancer as a result of a mutation in the PG1 gene.

21 Claims, 30 Drawing Sheets

OTHER PUBLICATIONS

Kume, et al., "cDNA Cloning and Expression of Murine 1–Acyl–sn–glycerol–3–phosphate Acyltransferase", Biochemical and Biophysical Research Communications, 237(3) : 663–666 (1997).

Levine, et al., "Lysophosphatidic acid: a novel growth and survival factor for renal proximal tubular cells", American Physiological Society, 273(4PT2) : F575–F585 (1997).

Martin, T.F.J., "Phosphoinositides as spatial regulators of membrane traffic", Curr. Opin. Neurobiol., 7(3) : 331–338 (1997.

Matsuyama, et al., "Deletion mappping of chromosome 8p in prostate cancer by fluorescense in situ hybridization", Oncogene, 9(10 :3071–3076 (1994).

Nagai, et al., "Comprehensive allelotyping of human hepatocellular carcinoma", Oncogene, 14(24) :2927–2933 (1997).

Nagiec, et al., "A Suppressor Gene That Enables *Saccharomyces cerevisiae* to Grow without Making Sphingolipids Encodes a Protein That Resembles an *Escherichia coli* Fatty Acyltransferase", Journal of Biological Chemistry, 268(29) : 22156–22163 (1993).

Qi C, et al., "Lysophosphatidic acid stimulates phospholipase D activity and cell proliferation in PC–3 human prostate cancer cells", J. Cell. Physiol., 174(2) : 261–272 (1998).

Scholnick, et al., "Chromosome 8 Allelic Loss and the Outcome of Patients With Squamous Cell Carcinoma of the Supraglottic Larynx", Journal of the National Cancer Institute, 88(22) : 1676–1682 (1996).

Sunkara, et al., A novel class of low molecular weight (MW) phospholipid (PL) signaling inhibitors is selectively cytotoxi for tumor cells (Meeting abstract): & Proc Annu Meet AM Assoc Cancer Res, 35: A2441 (1994).

Sunwoo, et al., "Evidence of Multiple Tumor Suppressor Genes on Chromosome Arm 8p in Supraglottic Laryngeal Cancer", Genes, Chromosomes & Cancer, 16 :167–169 (1996).

Toker, et al., "Signalling through the lipid products of phosphoinositid–3–OH kinase", Nature, 387 : 673–676 (1997).

Washburn, et al., "Deletion of loci mapping to 8p23–pter in human prostate cancers", Proceedings of the American Association for Cancer Research, 38(#3456) : 515 (Mar. 1997).

Wilson, et al., "2.2 Mb of contiguous nucleotide sequence from chromosome III of *C. elegans*", Nature 368(6466): P32–38 (1994).

Yaremko, et al., :Deletion Mapping Reveals Two Regions of Chromosome 8 Allele Loss in Colorectal Carcinomas, Genes, Chromosomes & Cancer, 10 : 1–6 (1994).

SwissProt: P26647, date Nov. 1, 1998.

SwissProt: P33333, date Nov. 1, 1998.

SwissProt: P38226, date Nov. 1, 1997.

Genbank Accession No. Z29518, date Nov. 12, 1994.

Genbank Accession No. AB005623, date Oct. 6, 1997.

Genbank Accession No. U56417, date Jun. 4, 1997.

Genbank Accession No. U89336, date Feb. 15, 1997.

Genbank Accession No. Z49860, date Jan. 6, 1996.

Genbank Accession No. Z49770, date Aug. 11 1997.

Genbank Accession No. Z72511, date Sep. 21, 1998.

Genbank Accession No. AF003136, date Dec. 31, 1997.

Search Report listing sequence EMEST7, Accession No. AA280082.

Public Database Chart.

Patented Sequences Database Chart.

Bender et al., Genbank Locus MUSPHKGZ, Accession No. L08057, Jun. 1997.

Hillier et al., Genbank Locus AA056643, Accession No. AA056643, Sep. 1995.

Auffray et al., Genbank Locus HSC2CG051, Accession No. Z45294, Sep. 1995.

Hillier et al., Genbank Locus W01144, Accession No. W01144, Apr. 1996.

Auffray et al., Genbank Locus HSC2E0111, Accession No. Z44999, Sep. 1995.

Stratagene Catalog, pp. 62–63, 1995.

West et al., "Cloning and expression of two human lysophosphatidic acid acyltransferase cDNAs that enhance cytokine–induced signaling responses in cells", DNA Cell Biol., 16(6) : 691–701 (Jun. 1997).

Chart listing homologous sequences in the Genbank database, 1 page.

Chart listing homologous sequences in the EMBL Update, EMBL, TREMBL, PRI, and SwissProt database, 10 pages.

HAPLOTYPE FREQUENCY ANALYSIS

POPULATIONS

| | AFFECTED<br>CASES 2 (281) | UNAFFECTED<br>CONTROLS 3 (130) |
|---|---|---|
| CHARACTERISTICS<br>OF POPULATIONS | 143 SPORADIC CASES<br>+138 FAMILIAL CASES | >65 YEARS<br>PSA<4 |

| MARKERS | 99-123 | 4-26 | 4-14 | 4-77 | 99-217 | 4-67 | 99-213 | 99-22 | 99-135 | HAPLOTYPE FREQUENCIES | | RELATIVE RISK | PVALUE |
|---|---|---|---|---|---|---|---|---|---|---|---|---|---|
| BACS | H0287B09 | B0189E08 | | 11453 | | B0463F01 | | | B0725B12 | CASES (2) | CONTROLS (3) | | |
| CONTIGS | | | | ←——— PG1 ———→ | | | | | | | | | |
| GENES | | | | | | | | | | | | | |
| P VALUE | 2,00E-01<br>* | 1,00E-01<br>* | 1,00E-01<br>* | 2,00E-02<br>** | 2,00E-02<br>** | 2,00E-04<br>*** | 9,00E-02<br>* | 7,00E-02<br>* | 2,00E-01<br>* | | | | |
| DISTANCE BETWEEN MARKERS(KB) | <18KB> | <15KB> | <15KB> | <88KB> | <22KB> | <17KB> | <15KB> | <29KB> | >100KB< | | | | |
| HAPLOTYPE 8>304KB< | C | A | C | G | T | T | G | A | A | 0,075 | 0,018 | 4,42 | 9,00E-04 *** |
| HAPLOTYPE 7>286KB< | | A | C | G | T | T | G | A | A | 0,095 | 0,016 | 6,46 | 6,00E-05 **** |
| HAPLOTYPE 6<186KB> | | A | C | G | T | T | G | A | | 0,116 | 0,019 | 6,78 | 1,00E-05 ***** |
| HAPLOTYPE 5<171KB> | | | C | G | T | T | G | A | | 0,117 | 0,013 | 10,06 | **9,00E-07 *******|
| HAPLOTYPE 4<83KB> | | | | G | T | T | G | A | | 0,117 | 0,025 | 5,17 | 2,00E-05 ***** |
| HAPLOTYPE 3.1<54KB> | | | | | T | T | G | A | | 0,117 | 0,027 | 4,78 | 2,00E-05 ***** |
| HAPLOTYPE 3.2<54KB> | | | | G | T | T | G | | | 0,222 | 0,109 | 2,33 | 4,00E-05 ***** |
| HAPLOTYPE 2.2<39KB> | | | | | T | T | G | | | 0,251 | 0,134 | 2,17 | 2,00E-04 **** |
| HAPLOTYPE 2<32KB> | | | | | T | T | G | | | 0,226 | 0,112 | 2,32 | 1,00E-04 ** |
| HAPLOTYPE 1.1<17KB> | | | | | T | T | | | | | | | |
| HAPLOTYPE 1.2<15KB> | | | | | | T | | | | | | | |

| BAC | MARKER | SEQ ID N° | SEQ ID N°(MUT) | PU SEQUENCE | SEQ ID N° | RP SEQUENCE | POLYMORPHISM POSITION* | BASE | MICROSEQ. OLIGOS POSITIONS* |
|---|---|---|---|---|---|---|---|---|---|
| 228 | 99-123 | 21 | 30 | AAAGCCAGGACTAGAAGG | 39 | TATTCAGAAAGGAGTGGG | 24 | C/T | 1-23 25-47 (COMPLEMENTARY) |
| 189 | 4-26 | 22 | 31 | TACAGCCCTGTAAGACAC | 40 | TGAGGACTGCTAGGAAAG | 24 | A/G | 1-23 25-47 (COMPLEMENTARY) |
| 228/189 | 4-14 | 23 | 32 | TCTAACCTCTCATCCAAC | 41 | GACTGTATCCTTTGATGCAC | 24 | C/T | 1-23 25-47 (COMPLEMENTARY) |
| 189/463 | 4-77 | 24 | 33 | TGTTGATTTACAGGCGGC | 42 | GGAAAGTACTCATTCATAG | 24 | G/C | 1-23 25-47 (COMPLEMENTARY) |
| 463 | 99-217 | 25 | 34 | GGTGGGAATTACTATATG | 43 | GTTTATTTTGTGTGAGCTTTG | 24 | C/T | 1-23 25-47 (COMPLEMENTARY) |
| 189/463 | 4-67 | 26 | 35 | AAGTTCACCTTCTCAAGC | 44 | TGAAAGAGTTTATTCTCTGG | 24 | C/T | 1-23 25-47 (COMPLEMENTARY) |
| 463 | 99-213 | 27 | 36 | ATACTGGCAGCGTGTGCTTC | 45 | TTATTGCCCCACATGCTTGAG | 24 | C/T | 1-23 25-47 (COMPLEMENTARY) |
| 463 | 99-221 | 28 | 37 | CCCTTTTCTTCACTGTTC | 46 | TCATTCGTCTGGCTAGGTC | 24 | A/C | 1-23 25-47 (COMPLEMENTARY) |
| 725 | 99-135 | 29 | 38 | TGGAAGTTGTTATTGCCC | 47 | AAACACCTCCCATTGTGC | 24 | A/G | 1-23 25-47 (COMPLEMENTARY) |

*: POSITIONS ARE GIVEN RELATIVE TO THE SEQUENCE OF THE CORRESPONDING MARKER (i.e. SEQ ID N° 21-38 AND 57-62)

FIG. 6B

| BAC | MARKER | SEQ ID N° | SEQ ID N°(MUT) | PU SEQUENCE | SEQ ID N° | RP SEQUENCE | POLYMORPHISM POSITION* | BASE | MICROSEQ. OLIGOS POSITIONS* |
|---|---|---|---|---|---|---|---|---|---|
| 189/463 | 99-1482 | 57 | 60 | ATCAAATCAGTGAAGTCTGAG | 63 | ACAAATCTATATAAGGCTGG | 24 | A/C | 1-23 25-47 (COMPLEMENTARY) |
| 463 | 4-73 | 58 | 61 | ATCGCTGGAACATTCTGG | 64 | CTCTTGGTTAAACAGCAGTG | 24 | G/C | 1-23 25-47 (COMPLEMENTARY) |
| 463 | 4-65 | 59 | 62 | GATTTAAGCTACGCTATTAG | 65 | TGGCTCTGCATTTCTTCC | 24 | C/T | 1-23 25-47 (COMPLEMENTARY) |

*: POSITIONS ARE GIVEN RELATIVE TO THE SEQUENCE OF THE CORRESPONDING MARKER (i.e. SEQ ID N° 21-38 AND 57-62)

| EXON Phase | START | END | 5' SPsite | PHASE | 3' SPsite |
|---|---|---|---|---|---|
| Ex1 +0 | 2001 | 2216 | | | GTGAGC |
| Ex2 +1 | 18196 | 18265 | TAG | +0 | GTTTGTA |
| Ex3 +0 | 23717 | 23832 | CAG | +2 | GTAACT |
| Ex4 +0 | 25571 | 25660 | CAG | +0 | GTAAGA |
| Ex5 +2 | 34669 | 34759 | CAG | +0 | GTAAGT |
| Ex6 +1 | 40688 | 40846 | TAG | +1 | GTAAGT |
| Ex7 +2 | 48070 | 48193 | TAG | +2 | GTGAGT |
| Ex8 | 50182 | 54523 | TAG | +1 | |
| ATG codon | 2031 | 2033 | | | |
| STOP codon | 50405 | 50407 | | | |
| POLY Ad site | 54445 | 54450 | | | |

FIG. 7

|  |  | box 1 | box 2 | box 3 |
|---|---|---|---|---|
| PG1 | Hs | NHQ *81-83* | FPEGTR *160-165* | LDAIYDVTV *211-219* |
| AF003136 (Genbank) | Ce | NHQ *630-632* | FPEGTR *712-717* | LDAIYDVTV *762-770* |
| Z72511 (Genbank) | Ce | 48 NHR 50 | FPEGTD *129-134* | VEYIYDITI *204-212* |
| P38226 (Swissport) | Sc | 111 NHQ 113 | FPEGTN *223-228* | IESLYDITI *271-279* |
| P33333 (Swissport) | Sc | 81 NHQ 83 | FPEGTR *154-159* | - |
| Z49770 (Genbank) | Sc | 116 NHQ 118 | FPEGTN *215-220* | LDAIYDVTI *265-273* |
| P26647 (Swissport) | Ec | 72 NHQ 74 | FPEGTR *145-150* | - |
| Z49860 (Genbank) | Bn | - | FVEGTR *90-95* | VPAIYDMTV *138-146* |
| U89336 (Genbank) | Hs | 95 NHQ 97 | FPEGTR *168-173* | - |
| U56417 (Genbank) | Hs | 103 NHQ 105 | FPEGTR *176-181* | - |
| AB005623 (Genbank) | Mm | 100 NHQ 102 | FPEGTR *173-178* |  |
| Z29518 (Genbank) | Zm | 91 NHR 93 | FVEGTR *170-175* | VPAIYDTTV *218-226* |

Hs = Homo sapiens, Ce = Caenorabibitis elegans, Ec = Escherichia coli; Sc = Saccharomyces cerevisiae, Bn = Brassica napus, Zm = Zea maize, Mm = Mus Musculus

- = pattern absent from protein sequence

Note: Functional acyl glycerol transferases all contain boxes 1 and 2 and not box 3. Proteins most related to PG1 contain the 3 boxes with a high degree of conservation.

FIG. 9

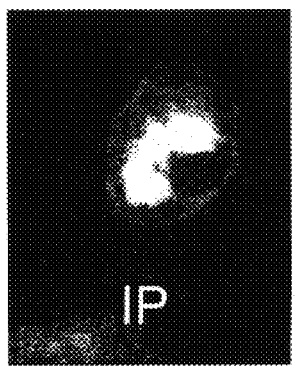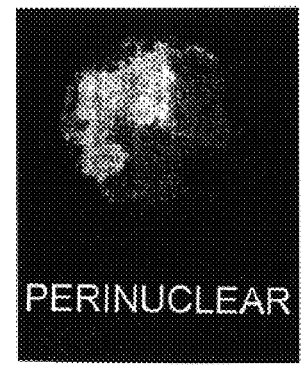
PC3
PG1
1-4
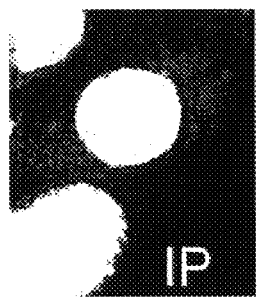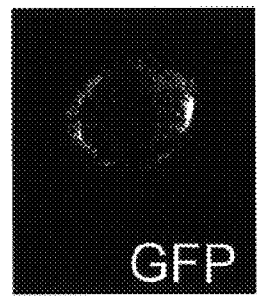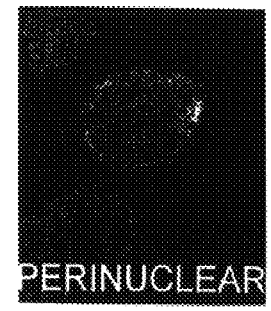
PNT2
PG1
1-4
*FIG. 11*

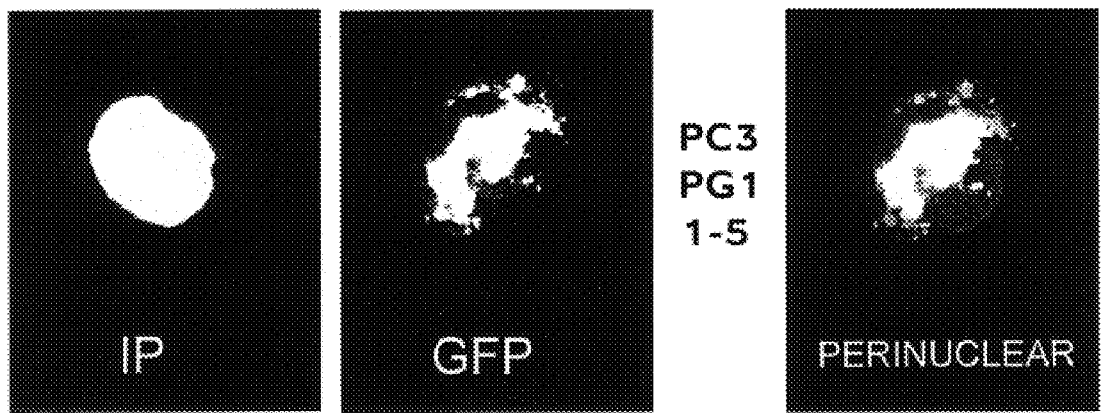
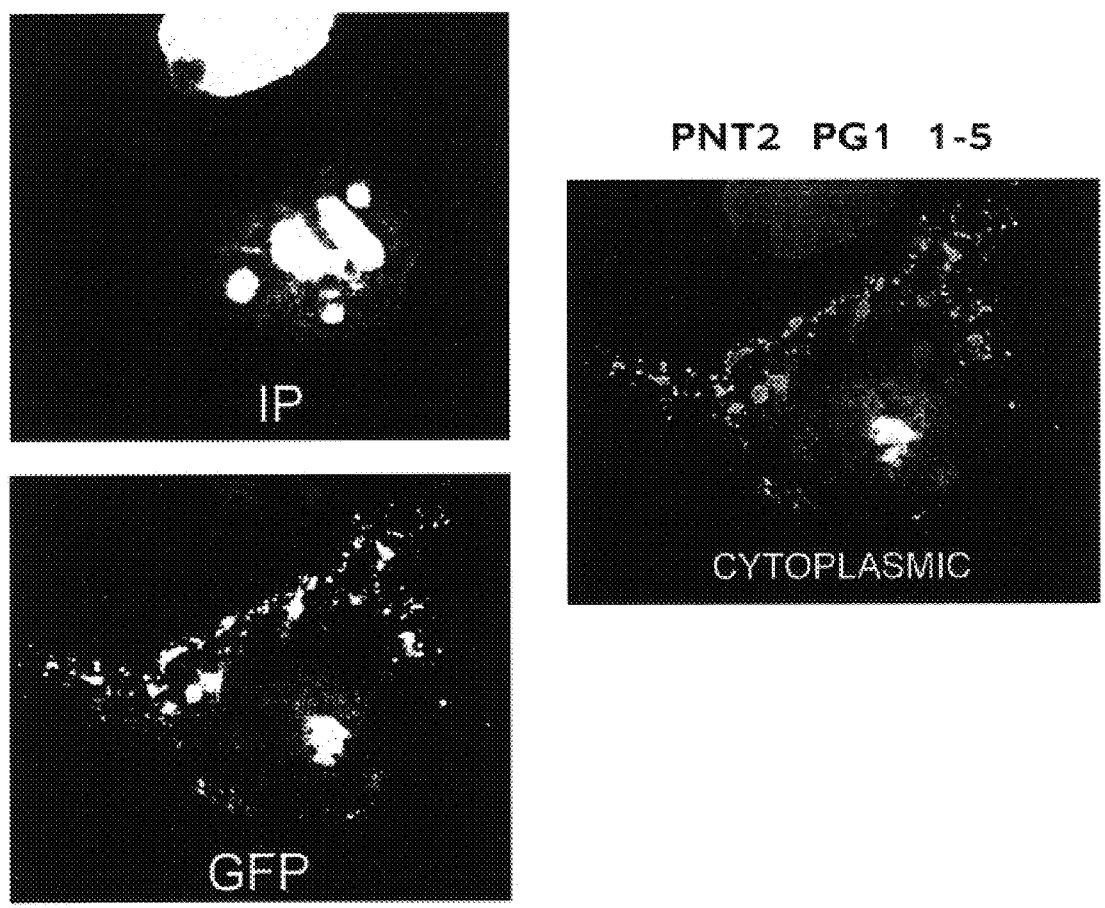
FIG. 12

PNT2  PG1  mut229

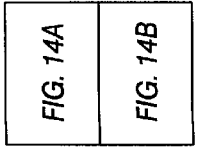
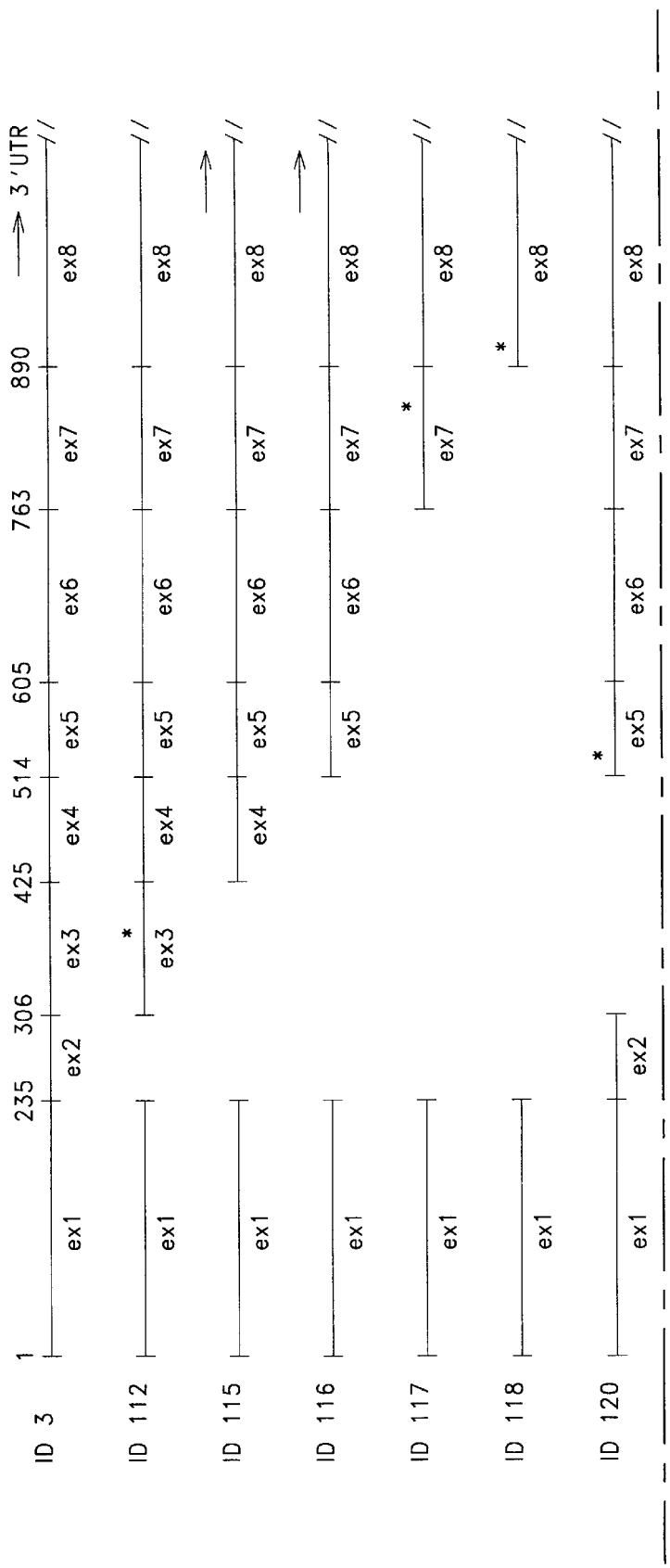
FIG. 14A

Combination of exons of PG1 gene discovered by PCR with primers specific for exon borders

| Printer | Clones | prostate | PNT1A | PNT1B | PNT2 | LnCaPFCG | LNCaPJMB | CoHPV | Du145 | PC3 | ECP5 | ECP6 | ECP7 | ECP8 | ECP9 | ECP10 | ECP11 | ECP12 | ECP13 | ECP14 | ECP15 | ECP16 | ECP17 | ECP18 | ECP19 | ECP20 | ECP21 | ECP22 | ECP23 | ECP24 |
|---|---|---|---|---|---|---|---|---|---|---|---|---|---|---|---|---|---|---|---|---|---|---|---|---|---|---|---|---|---|---|
| PG1exon13 | + | + | + | + | + | [+] | + | + | + | + | + | + | + | + | + | + | + | + | + | + | + | + | + | + | + | + | + | + | + | + |
| PG1exon14 | + | + | + | + | + | + | + | + | + | + | + | + | + | + | + | + | + | + | + | + | + | + | + | + | + | + | + | + | + | + |
| PG1exon15 | + | − | − | − | − | − | − | NT | − | − | + | − | − | − | − | − | − | − | − | − | − | − | − | − | − | − | − | − | − | − |
| PG1exon16 | − | + | − | + | + | − | − | NT | − | − | − | − | + | − | − | − | − | − | − | − | − | − | − | − | − | − | + | − | − | − |
| PG1exon17 | + | + | + | + | + | + | + | NT | + | + | − | − | + | − | − | − | + | + | + | + | + | + | + | − | − | + | + | − | + | + |
| PG1exon18 | + | + | + | + | + | − | − | NT | + | + | − | − | − | − | − | − | − | − | + | − | − | − | − | − | − | − | − | − | − | − |
| PG1exon24 | − | + | + | + | + | + | + | + | + | + | + | + | + | + | + | + | + | + | + | + | + | + | + | + | + | + | + | + | + | + |
| PG1exon25 | + | + | − | + | + | − | − | NT | + | − | − | − | − | − | − | + | − | − | − | + | − | − | − | − | − | − | − | − | + | + |
| PG1exon26 | − | + | − | + | + | + | + | NT | + | + | + | + | + | − | + | + | + | + | + | + | + | + | + | + | + | + | + | + | + | + |
| PG1exon27 | − | − | − | + | + | − | − | NT | + | − | − | − | − | − | − | − | + | − | − | + | − | − | − | − | − | − | − | − | + | + |
| PG1exon28 | − | − | + | − | − | − | − | NT | − | − | − | − | − | − | − | − | − | − | − | − | − | − | − | − | − | − | − | − | − | − |
| PG1exon35 | − | + | + | + | + | + | + | NT | + | + | − | − | − | − | − | + | + | − | + | + | − | + | + | + | + | − | − | | | |
| PG1exon36 | − | + | + | + | + | + | + | NT | + | + | + | + | + | + | + | + | + | + | + | + | + | + | + | + | + | + | + | + | + | + |
| PG1exon37 | − | − | − | − | − | − | − | NT | − | − | − | − | − | − | − | − | − | − | − | − | − | − | − | − | − | − | − | − | − | − |
| PG1exon38 | − | − | − | − | − | − | − | NT | − | + | − | − | − | − | − | − | − | − | − | + | − | − | − | − | − | + | − | − | − | − |
| PG1exon46 | − | + | + | + | + | + | + | + | + | + | + | + | + | + | + | + | + | + | + | + | + | + | + | + | + | + | + | + | + | + |
| PG1exon47 | + | + | + | + | + | + | + | NT | + | + | + | + | + | + | − | + | + | − | + | + | + | + | + | + | + | + | + | + | + | + |
| PG1exon48 | − | − | − | − | + | − | − | NT | − | − | − | − | + | − | − | − | − | − | − | − | − | − | − | − | − | − | − | − | − | − |
| PG1exon57 | + | + | + | + | + | + | + | NT | + | + | + | + | + | − | + | − | + | + | + | + | + | + | + | + | + | + | + | + | + | + |
| PG1exon58 | − | − | − | − | − | + | + | NT | − | − | − | − | − | − | − | − | − | − | − | − | − | − | − | − | − | − | − | + | − | − |
| PG1exon68 | − | + | + | − | + | + | + | NT | + | + | − | − | − | − | + | + | − | − | + | + | − | − | + | − | − | − | + | − | + | + |
| PG1exon11b | + | + | + | + | + | + | + | NT | + | + | − | + | − | + | + | + | + | + | + | − | − | + | − | − | + | + | + | − | + | + |
| PG1exon1b2 | + | + | + | + | + | + | + | NT | + | + | − | + | − | + | + | + | + | + | + | − | − | + | − | − | + | + | + | − | + | + |
| PG1exon1b3 | | + | − | + | + | + | + | NT | + | + | + | + | − | + | + | + | + | + | + | + | + | + | + | + | + | + | + | + | + | + |
| PG1exon1b4 | | + | − | + | + | + | + | + | + | + | − | − | + | − | + | + | − | − | + | + | − | + | + | − | − | + | − | | | |
| PG1exon1b5 | | + | − | + | + | + | + | NT | + | + | − | − | + | − | − | − | + | + | − | + | − | + | − | + | − | + | + | + | − | |
| PG1exon1b6 | | + | − | + | + | + | + | NT | + | + | + | + | + | − | + | − | + | − | + | + | + | + | + | + | + | + | + | + | + | + |
| PG1exon1b7 | | + | − | + | + | − | + | NT | + | + | + | + | − | − | + | − | − | − | − | − | − | − | − | − | − | − | − | − | − | − |
| PG1exon1b8 | | − | − | + | − | + | − | NT | − | − | − | + | − | − | − | − | − | − | − | − | − | − | − | − | − | − | − | − | − | − |
| PG1exon3b4 | + | + | + | − | + | + | + | NT | + | + | + | + | + | + | + | + | + | + | + | + | + | + | + | + | + | + | + | + | + | + |
| PG1exon3b5 | − | − | + | + | − | − | − | NT | − | − | − | − | − | − | − | − | − | − | − | − | − | − | − | − | − | − | − | − | − | − |
| PG1exon3b6 | | + | + | + | + | + | + | NT | + | + | + | − | + | + | + | + | + | + | + | + | + | + | + | + | + | + | + | + | + | + |
| PG1exon3b7 | | + | − | + | + | − | + | NT | − | + | − | + | − | − | − | − | − | + | − | − | + | − | − | − | − | − | − | − | − | − |
| PG1exon3b8 | | − | − | − | − | − | + | NT | − | − | − | − | − | − | − | − | − | − | − | − | − | − | − | − | − | − | − | − | − | − |
| PG1exon5b6 | + | + | − | − | − | − | + | NT | − | + | − | + | − | − | − | − | + | + | − | − | − | − | − | − | − | − | − | − | − | − |
| PG1exon5b7 | + | + | − | + | + | + | + | NT | + | − | − | − | − | − | − | − | − | + | − | − | + | − | − | − | − | − | − | − | − | − |
| PG1exon5b8 | − | − | − | − | + | − | − | NT | − | − | − | − | − | − | − | − | − | − | − | − | − | − | − | − | − | − | − | − | − | − |
| PG1exon56b | + | + | − | + | + | + | + | NT | + | + | + | − | + | + | + | + | + | + | + | + | + | + | + | + | + | + | + | + | + | + |
| PG1exon46b | | + | − | + | + | + | + | NT | + | + | + | + | + | + | + | + | + | + | + | + | + | + | + | + | + | + | + | + | + | + |
| PG1exon36b | | + | + | + | + | + | + | NT | + | + | + | + | + | + | + | + | + | + | + | + | + | + | + | + | + | + | + | + | + | + |
| PG1exon26b | | + | + | + | + | + | + | NT | + | + | + | + | + | + | + | + | + | + | + | + | + | + | + | + | + | + | + | + | + | + |
| PG1exon16b | | + | + | + | + | + | + | NT | + | + | + | + | + | + | − | + | + | + | + | + | + | + | + | + | + | + | + | + | + | + |

[+] alternative splicing form with combination of exons 13478 instead of 1345678

*FIG. 15*

| name of markers | PG1 | Polym. | Freq(cas) | Freq(controls) | abs diff % (fq(cases)-(fq(controls))) | Odd Ratio | Pvalue | Freq(randoms) | Attributable Risk |
|---|---|---|---|---|---|---|---|---|---|
| 99-1485/251 | prom | G*/T | 0.32 | 0.24 | 7.4 | 1.44 | 2.53E-02 | 0.29 | 17.58 |
| 99-622/95 | in1 | G/T | 0.52 | 0.42 | 10.1 | 1.51 | 9.64E-03 | ND$ | ND |
| 99-619/141 | in1 | C/T | 0.28 | 0.22 | 5.8 | 1.37 | 6.93E-02 | ND | ND |
| 4-76/222 | in1 | G/A | 0.43 | 0.38 | 5 | 1.23 | 1.57E-01 | 0.41 | 13.15 |
| 4-77/151 | in1 | G/C | 0.34 | 0.26 | 7.4 | 1.43 | 1.35E-02 | 0.31 | 18.16 |
| 4-71/233 | in1 | A/G | 0.34 | 0.26 | 8.3 | 1.49 | 1.43E-02 | 0.28 | 18.64 |
| 4-72/127 | in1 | A/G | 0.36 | 0.30 | 5.7 | 1.29 | 9.43E-02 | 0.31 | 13.25 |
| 4-73/134 | in1 | G/C | 0.52 | 0.42 | 9.7 | 1.48 | 7.29E-03 | 0.52 | 26.76 |
| 99-610/250 | in1 | G/A | 0.43 | 0.37 | 6.2 | 1.30 | 8.33E-02 | ND | ND |
| 99-609/225 | in1 | A/T | 0.37 | 0.30 | 7 | 1.36 | 4.83E-02 | ND | ND |
| 4-90/283 | in1 | A/C | 0.29 | 0.25 | 4.4 | 1.25 | 1.68E-01 | 0.28 | 9.32 |
| 99-602/258 | in2 | A/G | 0.33 | 0.25 | 7.4 | 1.44 | 2.69E-02 | ND | ND |
| 99-600/492 | in3 | T/A | 0.34 | 0.34 | 0.3 | 1.01 | 7.52E-01 | ND | ND |
| 99-598/130 | in4 | G/A | 0.35 | 0.25 | 9.2 | 1.55 | 7.29E-03 | ND | ND |
| 99-217/277 | in4 | T/C | 0.31 | 0.28 | 3.8 | 1.20 | 1.07E-01 | 0.28 | 8.46 |
| 99-576/421 | in6 | G/C | 0.27 | 0.17 | 9.2 | 1.72 | 3.18E-03 | 0.24 | 18.40 |
| 4-61/269 | 3'UTR | G/A | 0.01 | 0.00 | 0.3 | 1.76 | 0.527§ | ND | ND |
| 4-66/145 | 3'UTR | C/T | 0.25 | 0.19 | 6.2 | 1.43 | 4.68E-03 | 0.24 | 13.16 |
| 4-67/40 | 3'UTR | T/C | 0.25 | 0.20 | 4.9 | 1.33 | 2.39E-02 | 0.24 | 10.97 |

§ Test Fisher–$ ND: Not done –* disease associated allele / not associated allele

FIG. 18B

FIG. 19A  HAPLOTYPE FREQUENCY ANALYSIS

| POPULATIONS | AFFECTED | UNAFFECTED |
|---|---|---|
| sample sizes | CASES (n=491) | CONTROLS (n=317) |
| characteristics of populations | 294 sporadic cases + 197 familial cases | 28 unaffected (65 years or older) + 289 controls (65 years or older with PSA<4) |

| PG1 (8p23) | | | 4-14/240 | 99-217/277 in4 | 4-66/145 3'UTR | 99-221/377 |
|---|---|---|---|---|---|---|
| distance between mks | | | <100kb> | <17kb> | <43kb> | |
| size (cases vs controls) | | | 481 vs 305 | 481 vs 302 | 481 vs 300 | 481 vs 303 |
| frequency % (cases/controls) | | | 65,7/62,1(C) | 31,3/27,5(C) | 25,1/19(C) | 42,7/42,91(A) |
| abs diff freq. all.(cases-controls) | | | 3.6 | 3.8 | 6.2 | 0 |
| pvalue | | | 1.47E-01 | 1.07E-01 | 4.68E-03 | 7.52E-01 |
| Hardy Weindeberg Disequilibrium | cases | | 5.84E-01 | 6.55E-01 | 2.54E-01 | 5.84E-01 |
|  | controls | | 4.80E-01 | 2.21E-01 | 3.71E-01 | 2.54E-01 |
| HAP 1 <43kb> | | 451 vs 297 | | | C | A |
| HAP 2 <17kb> | | 451 vs 296 | | T | C | |
| HAP 3 <117kb> | | 452 vs 299 | C | | C | |
| HAP 4 <100kb> | | 479 vs 302 | C | T | | |
| HAP 5 <60kb> | | 476 vs 300 | | T | | A |
| HAP 6 <160kb> | PT2 | 476 vs 303 | C | | | C |
| HAP 7 <160kb> | | 447 vs 297 | C | | C | A |
| HAP 8 <60kb> | | 446 vs 294 | | T | C | A |
| HAP 9 <117kb> | | 450 vs 296 | C | T | C | |
| HAP 10 <160kb> | PT3 | 474 vs 300 | C | T | | A |
| HAP 11 <160kb> | PT4 | 445 vs 294 | C | T | C | A |

| haplotype frequencies | | Odd ratio | Chi-S | Pvalue | |
|---|---|---|---|---|---|
| cases | controls | | | | |
| 0.116 | 0.067 | 1.83 | 9.85 | (1.7e-03) | *** |
| 0.243 | 0.183 | 1.43 | 7.49 | (6.2e-03) | ** |
| 0.182 | 0.130 | 1.49 | 7.18 | (7.3e-03) | ** |
| 0.217 | 0.188 | 1.20 | 1.88 | (1.7e-01) | * |
| 0.155 | 0.132 | 1.20 | 1.54 | (2.1e-01) | * |
| 0.373 | 0.346 | 1.12 | 1.16 | (2.7e-01) | * |
| 0.095 | 0.042 | 2.39 | 14.62 | (1.3e-04) | **** |
| 0.117 | 0.065 | 1.93 | 11.33 | (7.3e-04) | *** |
| 0.178 | 0.125 | 1.53 | 7.80 | (5.2e-03) | ** |
| 0.114 | 0.089 | 1.32 | 2.44 | (1.1e-01) | * |
| 0.095 | 0.032 | 3.18 | 21.59 | (3.4e-06) | ***** |

FIG. 19B

HAPLOTYPE FREQUENCY ANALYSIS
PG1 (8p23)

| markers of haplotype Max | 4-14/240 | 99-217/277 in4 | 4-66/145 3'UTR | 99-221/377 |
|---|---|---|---|---|
| | C | T | C | A |
| distance between mks | <100kb> | <17kb> | <43kb> | |

| PG1 | sample sizes | haplotype frequencies | | odd ratio | chi-S | P value | |
|---|---|---|---|---|---|---|---|
| | cases vs control | cases | controls | | | | |
| cases vs control | 455 vs 294 | 0.095 | 0.032 | 3.18 | 21.59 | 3.40E-06 | ****** |
| cases (<=65 years) vs controls | 171 vs 294 | 0.105 | 0.032 | 3.56 | 20.91 | 4.60E-06 | ****** |
| cases (>65 years) vs control | 271 vs 294 | 0.079 | 0.032 | 2.60 | 12.13 | 4.80E-04 | **** |
| sporadic cases vs controls | 266 vs 294 | 0.096 | 0.032 | 3.23 | 19.73 | 8.60E-06 | ****** |
| sporadic cases (<=65 years) vs controls | 85 vs 294 | 0.095 | 0.032 | 3.20 | 12.04 | 5.00E-04 | **** |
| sporadic cases (>65 years) vs controls | 178 vs 294 | 0.085 | 0.032 | 2.82 | 12.75 | 3.50E-04 | **** |
| *informative sporadic cases vs controls* | 67 vs 294 | 0.062 | 0.032 | 2.00 | 2.70 | 9.40E-02 | ** |
| familial cases vs controls | 179 vs 294 | 0.098 | 0.032 | 3.32 | 18.33 | 1.80E-05 | ***** |
| familial cases (<=65 years) vs controls | 86 vs 294 | 0.112 | 0.032 | 3.83 | 17.98 | 2.20E-05 | ***** |
| familial cases (>65 years) vs controls | 93 vs 294 | 0.075 | 0.032 | 2.48 | 6.59 | 1.00E-02 | ** |
| *familial cases (>=3 caP) vs controls* | 79 vs 294 | 0.123 | 0.032 | 4.26 | 21.33 | 3.70E-06 | ****** |

FIG. 20  HAPLOTYPE FREQUENCY ANALYSIS (PG1)

| Markers in PG1 | | 99-622/95 | 4-77/151 | 4-71/233 | 4-73/134 | 99-598/130 | 99-576/421 | 4-66/145 |
|---|---|---|---|---|---|---|---|---|
| | | G/T | C/G | A/G | C/G | A/G | C/G | C/T |
| | | | in1 | in1 | in1 | in4 | in6 | 3'UTR |
| size (cases vs controls) | | 336 vs 108 | 363 vs 173 | 336 vs 130 | 352 vs 129 | 347 vs 126 | 355 vs 129 | 456 vs 306 |
| allelic frequency % (cases / controls) | | 52/42 (G) | 34/26 (G) | 34/26 (A) | 52/42 (G) | 35/25 (G) | 27/17 (G) | 25/19 (C) |
| allelic frequency % (randoms) | | ND | 31 (G) | 28 (A) | 52 (G) | ND | 24 (G) | 24 (C) |
| diff freq. all. % (cases-controls) | | 10.1 | 7.4 | 8.3 | 9.7 | 9.2 | 9.2 | 6.2 |
| pvalue (cases vs controls) | | 9.64E-03 | 1.35E-02 | 1.43E-02 | 7.29E-03 | 7.29E-03 | 3.18E-03 | 4.68E-03 |
| | | ** | ** | ** | ** | ** | ** | ** |
| Odd Ratio | | 1.51 | 1.43 | 1.49 | 1.48 | 1.55 | 1.72 | 1.43 |
| Attributable Risk % | | ND | 18.16 | 18.64 | 26.76 | ND | 8.46 | 13.16 |
| Hardy Weindeberg Disequilibrium | cases | 7.52E-01 | 7.52E-01 | 5.84E-01 | 7.52E-01 | 7.52E-01 | 7.52E-01 | 3.43E-01 |
| | controls | 4.39E-01 | 4.03E-01 | 1.21E-01 | 1.21E-01 | 6.52E-02 | 7.52E-01 | 1.29E-01 |

| | cases | controls | | | | | | | haplotype frequencies cases | controls | Odd Ratio | Attributable Risk % | Pvalue (cases vs controls) |
|---|---|---|---|---|---|---|---|---|---|---|---|---|---|
| haplotype 1 | 2 MKS | 339 vs 167 | G | | | | | | 0.263 | 0.152 | 1.99 | 18.55 | (6.7e-05) **** |
| haplotype 2 | 3 MKS | 330 vs 122 | G | G | | | | | 0.259 | 0.147 | 2.02 | ND | (3.9e-04) *** |
| haplotype 3 | 4 MKS | 312 vs 122 | G | G | A | | | | 0.259 | 0.147 | 2.02 | ND | (4.1e-04) *** |
| haplotype 4 | 5 MKS | 311 vs 121 | G | G | A | G | | | 0.26 | 0.148 | 2.01 | ND | (4.8e-04) *** |
| haplotype 5 | 6 MKS | 309 vs 121 | G | G | A | G | G | | 0.258 | 0.149 | 2 | ND | (5.3e-04) *** |
| haplotype 6 | 7 MKS | 290 vs 99 | G | G | A | G | G | G | 0.255 | 0.146 | 2 | ND | (1.6e-03) ** |

ND: Not Done

PROSTATE CANCER GENE

This application is a continuation-in-part of U.S. patent application Ser. No. 09/218,207, filed Dec. 22, 1998, which is a continuation-in-part of U.S. patent application Ser. No. 08/996,306, filed Dec. 22, 1997 U.S. Pat. No. 5,945,522, and claims priority from U.S. Provisional Patent Application Serial No. 60/099,658, filed Sep. 9, 1998, the disclosures of which are all incorporated herein by reference in their entireties.

BACKGROUND OF THE INVENTION

A cancer is a clonal proliferation of cells produced as a consequence of cumulative genetic damage that finally results in unrestrained cell growth, tissue invasion and metastasis (cell transformation). Regardless of the type of cancer, transformed cells carry damaged DNA in many forms: as gross chromosomal translocations or, more subtly, as DNA amplification, rearrangement or even point mutations.

Some oncogenic mutations is inherited in the germline, thus predisposing the mutation carrier to an increased risk of cancer. However, in a majority of cases, cancer does not occur as a simple monogenic disease with clear Mendelian inheritance. There is only a two- or threefold increased risk of cancer among first-degree relatives for many cancers (Mulvihill J J, Miller R W & Fraumeni J F, 1977, Genetics of human cancer Vol 3, New York Raven Press). Alternatively, DNA damage is acquired somatically, probably induced by exposure to environmental carcinogens. Somatic mutations are generally responsible for the vast majority of cancer cases.

Studies of the age dependence of cancer have suggested that several successive mutations are needed to convert a normal cell into an invasive carcinoma. Since human mutation rates are typically $10^{-6}$/gene/cell, the chance of a single cell undergoing many independent mutations is very low (Loeb LA, Cancer Res 1991, 51: 3075–3079). Cancer nevertheless happens because of a combination of two mechanisms. Some mutations enhance cell proliferation, increasing the target population of cells for the next mutation. Other mutations affect the stability of the entire genome, increasing the overall mutation rate, as in the case of mismatch repair proteins (reviewed in Arnheim N & Shibata D, Curr. Op. Genetics & Development, 1997, 7:364–370).

An intricate process known as the cell cycle drives normal proliferation of cells in an organism. Regulation of the extent of cell cycle activity and the orderly execution of sequential steps within the cycle ensure the normal development and homeostasis of the organism. Conversely, many of the properties of cancer cells—uncontrolled proliferation, increased mutation rate, abnormal translocations and gene amplifications—can be attributed directly to perturbations of the normal regulation or progression of the cycle. In fact, many of the genes that have been identified over the past several decades as being involved in cancer, can now be appreciated in terms of their direct or indirect role in either regulating entry into the cell cycle or coordinating events within the cell cycle.

Recent studies have identified three groups of genes which are frequently mutated in cancer. The first group of genes, called oncogenes, are genes whose products activate cell proliferation. The normal non-mutant versions are called protooncogenes. The mutated forms are excessively or inappropriately active in promoting cell proliferation, and act in the cell in a dominant way in that a single mutant allele is enough to affect the cell phenotype. Activated oncogenes are rarely transmitted as germline mutations since they may probably be lethal when expressed in all the cells. Therefore oncogenes can only be investigated in tumor tissues.

Oncogenes and protooncogenes can be classified into several different categories according to their function. This classification includes genes that code for proteins involved in signal transduction such as: growth factors (i.e., sis, int-2); receptor and non-receptor protein-tyrosine kinases (i.e., erbB, src, bcr-abl, met, trk); membrane-associated G proteins (i.e., ras); cytoplasmic protein kinases (i.e., mitogen-activated protein kinase -MAPK- family, raf, mos, pak), or nuclear transcription factors (i.e., myc, myb, fos, jun, rel) (for review see Hunter T, 1991 Cell 64:249; Fanger G R et al., 1997 Curr.Op.Genet.Dev.7:67–74; Weiss F U et al., ibid. 80–86).

The second group of genes which are frequently mutated in cancer, called tumor suppressor genes, are genes whose products inhibit cell growth. Mutant versions in cancer cells have lost their normal function, and act in the cell in a recessive way in that both copies of the gene must be inactivated in order to change the cell phenotype. Most importantly, the tumor phenotype can be rescued by the wild type allele, as shown by cell fusion experiments first described by Harris and colleagues (Harris H et al.,1969, Nature 223:363–368). Germline mutations of tumor suppressor genes is transmitted and thus studied in both constitutional and tumor DNA from familial or sporadic cases. The current family of tumor suppressors includes DNA-binding transcription factors (i.e., p53, WT1), transcription regulators (i.e., RB, APC, probably BRCA1), protein kinase inhibitors (i.e., p16), among others (for review, see Haber D & Harlow E, 1997, Nature Genet. 16:320–322).

The third group of genes which are frequently mutated in cancer, called mutator genes, are responsible for maintaining genome integrity and/or low mutation rates. Loss of function of both alleles increase cell mutation rates, and as consequence, proto-oncogenes and tumor suppressor genes is mutated. Mutator genes can also be classified as tumor suppressor genes, except for the fact that tumorigenesis caused by this class of genes cannot be suppressed simply by restoration of a wild-type allele, as described above. Genes whose inactivation may lead to a mutator phenotype include mismatch repair genes (i.e., MLH1, MSH2), DNA helicases (i.e., BLM, WRN) or other genes involved in DNA repair and genomic stability (i.e., p53, possibly BRCA1 and BRCA2) (For review see Haber D & Harlow E, 1997, Nature Genet. 16:320–322; Fishel R & Wilson T. 1997, Curr.Op.Genet.Dev.7: 105–113; Ellis N A,1997 ibid.354–363).

The recent development of sophisticated techniques for genetic mapping has resulted in an ever expanding list of genes associated with particular types of human cancers. The human haploid genome contains an estimated 80,000 to 100,000 genes scattered on a $3 \times 10^9$ base-long double-stranded DNA. Each human being is diploid, i.e., possesses two haploid genomes, one from paternal origin, the other from maternal origin. The sequence of a given genetic locus may vary between individuals in a population or between the two copies of the locus on the chromosomes of a single individual. Genetic mapping techniques often exploit these differences, which are called polymorphisms, to map the location of genes associated with human phenotypes.

One mapping technique, called the loss of heterozygosity (LOH) technique, is often employed to detect genes in which a loss of function results in a cancer, such as the tumor suppressor genes described above. Tumor suppressor genes often produce cancer via a two hit mechanism in which a first mutation, such as a point mutation (or a small deletion or insertion) inactivates one allele of the tumor suppressor gene. Often, this first mutation is inherited from generation to generation.

A second mutation, often a spontaneous somatic mutation such as a deletion which deletes all or part of the chromosome carrying the other copy of the tumor suppressor gene, results in a cell in which both copies of the tumor suppressor gene are inactive.

As a consequence of the deletion in the tumor suppressor gene, one allele is lost for any genetic marker located close to the tumor suppressor gene. Thus, if the patient is heterozygous for a marker, the tumor tissue loses heterozygosity, becoming homozygous or hemizygous. This loss of heterozygosity generally provides strong evidence for the existence of a tumor suppressor gene in the lost region.

By genotyping pairs of blood and tumor samples from affected individuals with a set of highly polymorphic genetic markers, such as microsatellites, covering the whole genome, one can discover candidate locations for tumor suppressor genes. Due to the presence of contaminant non-tumor tissue in most pathological tumor samples, a decreased relative intensity rather than total loss of heterozygosity of informative microsatellites is observed in the tumor samples. Therefore, classic LOH analysis generally requires quantitative PCR analysis, often limiting the power of detection of this technique. Another limitation of LOH studies resides on the fact that they only allow the definition of rather large candidate regions, typically spanning over several megabases. Refinement of such candidate regions requires the definition of the minimally overlapping portion of LOH regions identified in tumor tissues from several hundreds of affected patients.

Another approach to genetic mapping, called linkage analysis, is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offspring of all families. Those that co-segregate with the trait are tracked. After pooling data from all families, statistical methods are used to determine the likelihood that the marker and the trait are segregating independently in all families. As a result of the statistical analysis, one or several regions are selected as candidates, based on their high probability to carry a trait causing allele. The result of linkage analysis is considered as significant when the chance of independent segregation is lower than 1 in 1000 (expressed as a LOD score >3). Identification of recombinant individuals using additional markers allows further delineation of the candidate linked region, which most usually ranges from 2 to 20 Mb.

Linkage analysis studies have generally relied on the use of microsatellite markers (also called simple tandem repeat polymorphisms, or simple sequence length polymorphisms). These include small arrays of tandem repeats of simple sequences (di- tri- tetra-nucleotide repeats), which exhibit a high degree of length polymorphism, and thus a high level of informativeness. To date, only just more than 5,000 microsatellites have been ordered along the human genome (Dib et al., Nature 1996, 380: 152), thus limiting the maximum attainable resolution of linkage analysis to ca. 600 kb on average.

Linkage analysis has been successfully applied to map simple genetic traits that show clear Mendelian inheritance patterns. About 100 pathological trait-causing genes were discovered by linkage analysis over the last 10 years.

However, linkage analysis approaches have proven difficult for complex genetic traits, those probably due to the combined action of multiple genes and/or environmental factors. In such cases, too large an effort and cost are needed to recruit the adequate number of affected families required for applying linkage analysis to these situations, as recently discussed by Risch, N. and Merikangas, K. (Science 1996, 273: 1516–1517). Finally, linkage analysis cannot be applied to the study of traits for which no available large informative families are available. Typically, this will be the case in any attempt to identify trait-causing alleles involved in sporadic cases.

The incidence of prostate cancer has dramatically increased over the last decades. It averages 30–50/100,000 males both in Western European countries as well as within the US White male population. In these countries, it has recently become the most commonly diagnosed malignancy, being one of every four cancers diagnosed in American males. Prostateg cancer's incidence is very much population specific, since it varies from 2/100,000 in China, to over 80/100,000 among African-American males.

In France, the incidence of prostate cancer is 35/100,000 males and it is increasing by 10/100,000 per decade. Mortality due to prostate cancer is also growing accordingly. It is the second cause of cancer death among French males, and the first one among French males aged over 70. This makes prostate cancer a serious burden in terms of public health, especially in view of the aging of populations.

An average 40% reduction in life expectancy affects males with prostate cancer. If completely localized, prostate cancer can be cured by surgery, with however an average success rate of only ca. 50%. If diagnosed after metastasis from the prostate, prostate cancer is a fatal disease for which there is no curative treatment.

Early-stage diagnosis relies on Prostate Specific Antigen (PSA) dosage, and would allow the detection of prostate cancer seven years before clinical symptoms become apparent. The effectiveness of PSA dosage diagnosis is however limited, due to its inability to discriminate between malignant and non-malignant affections of the organ.

Therefore, there is a strong need for both a reliable diagnostic procedure which would enable early-stage prostate cancer prognosis, and for preventive and curative treatments of the disease. The present invention relates to the PG1 gene, a gene associated with prostate cancer, as well as diagnostic methods and reagents for detecting alleles of the gene which may cause prostate cancer, and therapies for treating prostate cancer.

SUMMARY OF THE INVENTION

The present invention relates to the identification of a gene associated with prostate cancer, identified as the PG1 gene, and reagents, diagnostics, and therapies related thereto. The present invention is also based on the discovery of a novel set of PG1-related biallelic markers. See the definition of PG1-related biallelic markers in the Detailed Description Section. These markers are located in the coding regions as well as non-coding regions adjacent to the PG1 gene. The position of these markers and knowledge of the surrounding sequence has been used to design polynucleotide compositions which are useful in determining the identity of nucleotides at the marker position, as well as more complex association and haplotyping studies which are useful in determining the genetic basis for diseases including cancer and prostate cancer. In addition, the compositions and methods of the invention find use in the identification of the targets for the development of pharmaceutical agents and diagnostic methods, as well as the characterization of the differential efficacious responses to and side effects from pharmaceutical agents acting on diseases including cancer and prostate cancer.

A first embodiment of the invention is a recombinant, purified or isolated polynucleotide comprising, or consisting of a mammalian genomic sequence, gene, or fragments thereof. In one aspect the sequence is derived from a human, mouse or other mammal. In a preferred aspect, the genomic sequence is the human genomic sequence of SEQ ID NO: 179 or the complement thereto. In a second preferred aspect, the genomic sequence is selected from one of the two mouse genomic fragments of SEQ ID NO: 182 and 183. In yet another aspect of this embodiment, the nucleic acid comprises nucleotides 1629 through 1870 of the sequence of SEQ ID NO: 179. Optionally, said polynucleotide consists of, consists essentially of, or comprises a contiguous span of nucleotides of a mammalian genomic sequence, preferably a sequence selected the following SEQ ID NOs: 179, 182, and 183, wherein said contiguous span is at least 6, 8, 10, 12, 15, 20, 25, 30, 50, 100, 200, or 500 nucleotides in length.

A second embodiment of the present invention is a recombinant, purified or isolated polynucleotide comprising, or consisting of a mammalian cDNA sequence, or fragments thereof. In one aspect the sequence is derived from a human, mouse or other mammal. In a preferred aspect, the cDNA sequence is selected from the human cDNA sequences of SEQ ID NO: 3, 69, 112–124 or the complement thereto. In a second preferred aspect, the cDNA sequence is the mouse cDNA sequence of SEQ ID NO: 184. Optionally, said polynucleotide consists of, consists essentially of, or comprises a contiguous span of nucleotides of a mammalian genomic sequence, preferably a sequence selected the following SEQ ID NOs: 3, 69, 112–124 and 184, wherein said contiguous span is at least 6, 8, 10, 12, 15, 20, 25, 30, 50, 100, 200, or 500 nucleotides in length.

A third embodiment of the present invention is a recombinant, purified or isolated polynucleotide, or the complement thereof, encoding a mammalian PG1 protein, or a fragment thereof. In one aspect the PG1 protein sequence is from a human, mouse or other mammal. In a preferred aspect, the PG1 protein sequence is selected from the human PG1 protein sequences of SEQ ID NO: 4, 5, 70, and 125–136. In a second preferred aspect, the PG1 protein sequence is the mouse PG1 protein sequences of SEQ ID NO: 74. Optionally, said fragment of PG1 polypeptide consists of, consists essentially of, or comprises a contiguous stretch of at least 8, 10, 12, 15, 20, 25, 30, 50, 100 or 200 amino acids from SEQ ID NOs: 4, 5, 70, 74, and 125–136, as well as any other human, mouse or mammalian PG1 polypeptide.

A fourth embodiment of the invention are the polynucleotide primers and probes disclosed herein.

A fifth embodiment of the present invention is a recombinant, purified or isolated polypeptide comprising or consisting of a mammalian PG1 protein, or a fragment thereof. In one aspect the PG1 protein sequence is from a human, mouse or other mammal. In a preferred aspect, the PG1 protein sequence is selected from the human PG1 protein sequences of SEQ ID NO: 4, 5, 70, and 125–136. In a second preferred aspect the PG1 protein sequence is the mouse PG1 protein sequences of SEQ ID NO: 74. Optionally, said fragment of PG1 polypeptide consists of, consists essentially of, or comprises a contiguous stretch of at least 8, 10, 12, 15, 20, 25, 30, 50, 100 or 200 amino acids from SEQ ID NOs: 4, 5, 70, 74, and 125–136, as well as any other human, mouse or mammalian PG1 polypeptide.

A sixth embodiment of the present invention is an antibody composition capable of specifically binding to a polypeptide of the invention. Optionally, said antibody is polyclonal or monoclonal. Optionally, said polypeptide is an epitope-containing fragment of at least 8, 10, 12, 15, 20, 25, or 30 amino acids of a human, mouse, or mammalian PG1 protein, preferably a sequence selected from SEQ ID NOs: 4, 5, 70, 74, or 125–136.

A seventh embodiment of the present invention is a vector comprising any polynucleotide of the invention. Optionally, said vector is an expression vector, gene therapy vector, amplification vector, gene targeting vector, or knock-out vector.

An eighth embodiment of the present invention is a host cell comprising any vector of the invention.

A ninth embodiment of the present invention is a mammalian host cell comprising a PG1 gene disrupted by homologous recombination with a knock out vector.

A tenth embodiment of the present invention is a nonhuman host mammal or animal comprising a vector of the invention.

A further embodiment of the present invention is a nonhuman host mammal comprising a PG1 gene disrupted by homologous recombination with a knock out vector.

Another embodiment of the present invention is a method of determining whether an individual is at risk of developing cancer or prostate cancer at a later date or whether the individual suffers from cancer or prostate cancer as a result of a mutation in the PG1 gene comprising obtaining a nucleic acid sample from the individual; and determining whether the nucleotides present at one or more of the PG1-related biallelic markers of the invention are indicative of a risk of developing prostate cancer at a later date or indicative of prostate cancer resulting from a mutation in the PG1 gene. Optionally, said PG1-related biallelic is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71, 4-99-598, 99-576, and 4-66.

Another embodiment of the present invention is a method of determining whether an individual is at risk of developing prostate cancer at a later date or whether the individual suffers from prostate cancer as a result of a mutation in the PG1 gene comprising obtaining a nucleic acid sample from the individual and determining whether the nucleotides present at one or more of the polymorphic bases in a PG1-related biallelic marker. Optionally, said PG1-related biallelic is a PG1-related biallelic marker positioned in SEQ ID NO: 179; a PG1-related biallelic marker selected from the group consisting of 99-1485/251, 99-622/95, 99-619/

141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71, 4-73, 99-598, 99-576, and 4-66.

Another embodiment of the present invention is a method of obtaining an allele of the PG1 gene which is associated with a detectable phenotype comprising obtaining a nucleic acid sample from an individual expressing the detectable phenotype, contacting the nucleic acid sample with an agent capable of specifically detecting a nucleic acid encoding the PG1 protein, and isolating the nucleic acid encoding the PG1 protein. In one aspect of this method, the contacting step comprises contacting the nucleic acid sample with at least one nucleic acid probe capable of specifically hybridizing to said nucleic acid encoding the PG1 protein. In another aspect of this embodiment, the contacting step comprises contacting the nucleic acid sample with an antibody capable of specifically binding to the PG1 protein. In another aspect of this embodiment, the step of obtaining a nucleic acid sample from an individual expressing a detectable phenotype comprises obtaining a nucleic acid sample from an individual suffering from prostate cancer.

Another embodiment of the present invention is a method of obtaining an allele of the PG1 gene which is associated with a detectable phenotype comprising obtaining a nucleic acid sample from an individual expressing the detectable phenotype, contacting the nucleic acid sample with an agent capable of specifically detecting a sequence within the 8p23 region of the human genome, identifying a nucleic acid encoding the PG1 protein in the nucleic acid sample, and isolating the nucleic acid encoding the PG1 protein. In one aspect of this embodiment, the nucleic acid sample is obtained from an individual suffering from cancer or prostate cancer.

Another embodiment of the present invention is a method of categorizing the risk of prostate cancer in an individual comprising the step of assaying a sample taken from the individual to determine whether the individual carries an allelic variant of PG1 associated with an increased risk of prostate cancer. In one aspect of this embodiment, the sample is a nucleic acid sample. In another aspect a nucleic acid sample is assayed by determining the frequency of the PG1 transcripts present. In another aspect of this embodiment, the sample is a protein sample. In another aspect of this embodiment, the method further comprises determining whether the PG1 protein in the sample binds an antibody specific for a PG1 isoform associated with prostate cancer.

Another embodiment of the present invention is a method of categorizing the risk of prostate cancer in an individual comprising the step of determining whether the identities of the polymorphic bases of one or more biallelic markers which are in linkage disequilibrium with the PG1 gene are indicative of an increased risk of prostate cancer.

Another embodiment of the present invention comprises a method of identifying molecules which specifically bind to a PG1 protein, preferably the protein of SEQ ID NO:4 or a portion thereof: comprising the steps of introducing a nucleic a nucleic acid encoding the protein of SEQ ID NO:4 or a portion thereof into a cell such that the protein of SEQ ID NO:4 or a portion thereof contacts proteins expressed in the cell and identifying those proteins expressed in the cell which specifically interact with the protein of SEQ ID NO:4 or a portion thereof.

Another embodiment of the present invention is a method of identifying molecules which specifically bind to the protein of SEQ ID NO: 4 or a portion thereof. One step of the method comprises linking a first nucleic acid encoding the protein of SEQ ID NO:4 or a portion thereof to a first indicator nucleic acid encoding a first indicator polypeptide to generate a first chimeric nucleic acid encoding a first fusion protein. The first fusion protein comprises the protein of SEQ ID NO:4 or a portion thereof and the first indicator polypeptide. Another step of the method comprises linking a second nucleic acid nucleic acid encoding a test polypeptide to a second indicator nucleic acid encoding a second indicator polypeptide to generate a second chimeric nucleic acid encoding a second fusion protein. The second fusion protein comprises the test polypeptide and the second indicator polypeptide. Association between the first indicator protein and the second indicator protein produces a detectable result. Another step of the method comprises introducing the first chimeric nucleic acid and the second chimeric nucleic acid into a cell. Another step comprises detecting the detectable result.

A further embodiment of the invention is a purified or isolated mammalian PG1 gene or cDNA sequence.

Further embodiments of the present invention include the nucleic acid and amino acid sequences of mutant or low frequency PG1 alleles derived from prostate cancer patients, tissues or cell lines. The present invention also encompasses methods which utilize detection of these mutant PG1 sequences in an individual or tissue sample to diagnosis prostate cancer, assess the risk of developing prostate cancer or assess the likely severity of a particular prostate tumor.

Another embodiment of the invention encompasses any polynucleotide of the invention attached to a solid support. In addition, the polynucleotides of the invention which are attached to a solid support encompass polynucleotides with any further limitation described in this disclosure, or those following: Optionally, said polynucleotides is specified as attached individually or in groups of at least 2, 5, 8, 10, 12, 15, 20, or 25 distinct polynucleotides of the inventions to a single solid support. Optionally, polynucleotides other than those of the invention may attached to the same solid support as polynucleotides of the invention. Optionally, when multiple polynucleotides are attached to a solid support they are attached at random locations, or in an ordered array. Optionally, said ordered array is addressable.

An additional embodiment of the invention encompasses the use of any polynucleotide for, or any polynucleotide for use in, determining the identity of an allele at a PG1-related biallelic marker. In addition, the polynucleotides of the invention for use in determining the identity of an allele at a PG1-related biallelic marker encompass polynucleotides with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622 , 4-77, 4-71 , 4-73, 99-598, 99-576, and 4-66. Optionally, said polynucleotide may comprise a sequence disclosed in the present specification. Optionally, said polynucleotide may consist of, or consist essentially of any polynucleotide described in the present specification. Optionally, said determining is performed in a hybridization assay, sequencing assay, microsequencing assay, or allele-specific amplification assay. Optionally, said polynucleotide is attached to a solid support, array, or addressable array. Optionally, said polynucleotide is labeled.

Another embodiment of the invention encompasses the use of any polynucleotide for, or any polynucleotide for use in, amplifying a segment of nucleotides comprising an PG1-related biallelic marker. In addition, the polynucleotides of the invention for use in amplifying a segment of nucleotides comprising a PG1-related biallelic marker encompass polynucleotides with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71 , 4-, 99-598, 99-576, and 4-66. Optionally, said polynucleotide may comprise a sequence disclosed in the present specification. Optionally, said polynucleotide may consist of, or consist essentially of any polynucleotide described in the present specification. Optionally, said amplifying is performed by a PCR or LCR. Optionally, said polynucleotide is attached to a solid support, array, or addressable array. Optionally, said polynucleotide is labeled.

A further embodiment of the invention encompasses methods of genotyping a biological sample comprising determining the identity of an allele at an PG1-related biallelic marker. In addition, the genotyping methods of the invention encompass methods with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4 or a PG1-related biallelic marker selected from the group consisting of 99-622, 4-77, 4-71, 4-73, 99-598, 99-576, and 4-66. Optionally, said method further comprises determining the identity of a second allele at said biallelic marker, wherein said first allele and second allele are not base paired (by Watson & Crick base pairing) to one another. Optionally, said biological sample is derived from a single individual or subject. Optionally, said method is performed in vitro. Optionally, said biallelic marker is determined for both copies of said biallelic marker present in said individual's genome. Optionally, said biological sample is derived from multiple subjects or individuals. Optionally, said method further comprises amplifying a portion of said sequence comprising the biallelic marker prior to said determining step. Optionally, wherein said amplifying is performed by PCR, LCR, or replication of a recombinant vector comprising an origin of replication and said portion in a host cell. Optionally, wherein said determining is performed by a hybridization assay, sequencing assay, microsequencing assay, or allele-specific amplification assay.

An additional embodiment of the invention comprises methods of estimating the frequency of an allele in a population comprising determining the proportional representation of an allele at a PG1-related biallelic marker in said population. In addition, the methods of estimating the frequency of an allele in a population of the invention encompass methods with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71, 4-, 99-598, 99-576, and 4-66. Optionally, determining the proportional representation of an allele at a PG1-related biallelic marker is accomplished by determining the identity of the alleles for both copies of said biallelic marker present in the genome of each individual in said population and calculating the proportional representation of said allele at said PG1-related biallelic marker for the population. Optionally, determining the proportional representation is accomplished by performing a genotyping method of the invention on a pooled biological sample derived from a representative number of individuals, or each individual, in said population, and calculating the proportional amount of said nucleotide compared with the total.

A further embodiment of the invention comprises methods of detecting an association between a genotype and a phenotype, comprising the steps of a) genotyping at least one PG1-related biallelic marker in a trait positive population according to a genotyping method of the invention; b) genotyping said PG1-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71 4-, 99-598, 99-576, and 4-66. Optionally, said contro population is a trait negative population, or a random population. Optionally, each of said genotyping steps a) and b) is performed on a single pooled biological sample derived from each of said populations. Optionally, each of said genotyping of steps a) and b) is performed separately on biological samples derived from each individual in said population or a subsample thereof. Optionally, said phenotype is a disease, cancer or prostate cancer; a response to an anti-cancer agent or an anti-prostate cancer agent; or a side effect to an anti-cancer or anti-prostate cancer agent. Optionally, said method comprises the additional steps of determining the phenotype in said trait positive and said control populations prior to step c).

An additional embodiment of the present invention encompasses methods of estimating the frequency of a haplotype for a set of biallelic markers in a population, comprising the steps of: a) genotyping at least one PG1-related biallelic marker for both copies of said set of biallelic marker present in the genome of each individual in said population or a subsample thereof, according to a genotyping method of the invention; b) genotyping a second biallelic marker by determining the identity of the allele at said second biallelic marker for both copies of said second biallelic marker present in the genome of each individual in said population or said subsample, according to a genotyping method of the invention; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following: Optionally, said PG1-related biallelic marker is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71 , 4-, 99-598, 99-576, and 4-66. Optionally, said second biallelic marker is a PG1-related biallelic marker; a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/145, and 4-67/40; or a PG1-related biallelic marker selected from the group consisting of 99-622, 4-77, 4-71 , 4-, 99-598, 99-576, and 4-66. Optionally, said PG1-related biallelic marker and said second biallelic marker are 4-77/151 and 4-66/145. Optionally, said haplotype determination method is an expectation-maximization algorithm.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: Optionally, said PG1-related biallelic is a PG1-related biallelic marker positioned in SEQ ID NO: 179; a PG1-related biallelic marker selected from the group consisting of 99-1485/251, 99-622/95, 99-619/141, 4-76/222, 4-77/151, 4-71/233, 4-72/127, 4-73/134, 99-610/250, 99-609/225, 4-90/283, 99-602/258, 99-600/492, 99-598/130, 99-217/277, 99-576/421, 4-61/269, 4-66/1 and 4-67/40; or a PG1-related biallelic marker selected from the group consisting of 99-622, 4-77, 4-71, 4-73, 99-598, 99-576, and 4-66. Optionally, said PG1-related biallelic marker and said second biallelic marker are 4-77/151 and 4-66/145. Optionally, said haplotype exhibits a p-value of <1 ×10$^{-3}$ in an association with a trait positive population with cancer, preferably prostate cancer. Optionally, said control population is a trait negative population, or a random population. Optionally, said phenotype is a disease, cancer or prostate cancer; a response to an anti-cancer agent or an anti-prostate cancer agent, or a side effects to an anti-cancer or anti-prostate cancer agent. Optionally, said method comprises the additional steps of determining the phenotype in said trait positive and said control populations prior to step c).

Additional embodiments and aspects of the present invention are set forth in the Detailed Description of the Invention and the Examples.

BRIEF DESCRIPTION OF THE DRAWINGS

FIG. 4 is a table demonstrating the results of an haplotype analysis. Among all the theoretical potential different haplotypes based on 2 to 9 markers, 11 haplotypes showing a strong association with prostate cancer were selected, and their haplotype analysis results are shown here.

FIG. 6A is a table listing the biallelic markers used in the haplotype analysis of FIG. 4. FIG. 6B is a table listing additional biallelic markers in linkage disequilibrium with the PG1 gene.

FIG. 7 is a table listing the positions of exons, splice sites, a stop codon, and a poly A site in the PG1 gene.

FIG. 9 is a table listing some of the homologies between the PG1 protein and known proteins.

FIG. 11 is a half-tome reproduction of a fluorescence micrograph of the perinuclear/nuclear expression of PG1/1-4 in tumoral (PC3) and normal prostatic cell lines (PNT2). Vector "PG1/1-4" corresponds to an alternative messenger which is due to an alternative splicing, joining exon 1 to exon 4, and resulting in the absence of exons 2 and 3. For PC3 (upper panel) and PNT2 (lower panel), the nucleus was labelled with Propidium iodide (IP, left panel). Note that EGFP fluorescence was detected in and around the nucleus (GFP, middle panel), as shown when the two pictures were overlapped (right panel).

FIG. 12 is a half-tome reproduction of a fluorescence micrograph of the perinuclear/nuclear expression of PG1/1-5 in tumoral prostatic cell line (PC3) and cytoplasmic expression of PG1/1-5 in normal prostatic cell line (PNT2). Vector "PG1/1-5" corresponds to an alternative messenger which is due to an alternative splicing, joining exon 1 to exon 5, and resulting in the absence of exons 2, 3 and 4. For PC3 (upper panel) and PNT2 (lower panels), the nucleus was labelled with Propidium iodide (IP). Note that in PC3 cells, EGFP fluorescence was detected in and around the nucleus (GFP, upper middle panel), as shown when the two picture were overlapped (upper right panel). In PNT2A cells, EGFP fluorescence was detected in the cytoplasm (GFP, lower left panel), as shown when the two pictures were overlapped (lower right panel).

Figure 13:

FIG. 13 is a half-tome reproduction of a fluorescence micrograph of the perinuclear/nuclear expression of a mutated form PG1 (PG1 mut229) in normal prostatic cell line (PNT2). Vector "PG1/1-7" includes exons 1 to 6, and corresponds to the mutated form identified in genomic DNA of the prostatic tumoural cell line LNCaP. The nucleus was labelled with Propidium iodide (IP, left panel). EGFP fluorescence was detected in the cytoplasm (GFP, middle panel), as shown when the two pictures were overlapped (lower right panel).

Figure 14B:
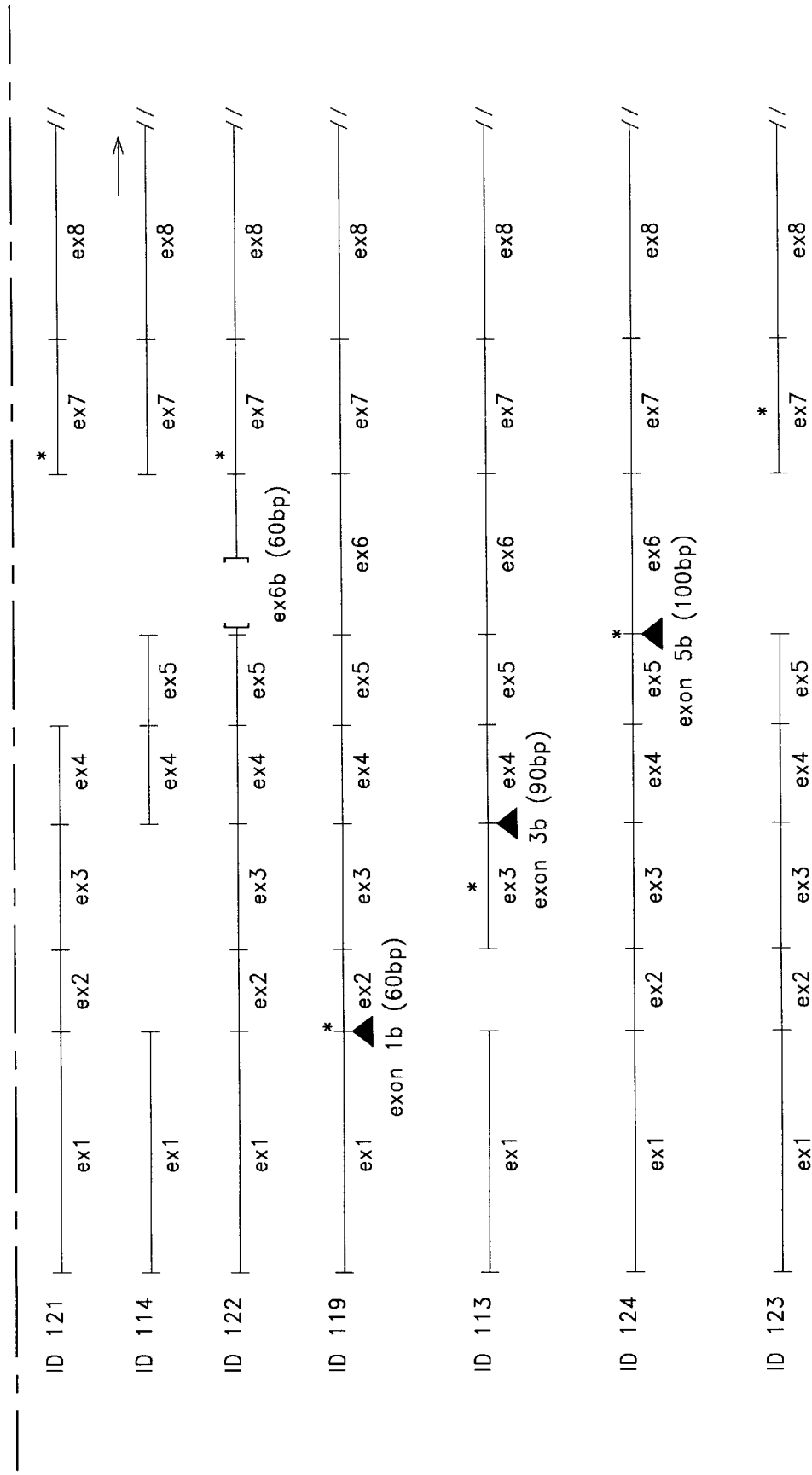

FIG. 14 is a diagram of the structure of the 14 alternative splice species found for human PG1 by the exons present. An * indicates that there is a stop codon in frame at that location. An arrow to the right at the right-hand side of a splice species indicates that the open-reading frame continues off the chart. a space between exons indicates that the exon(s) is missing from that particular alternative splice species. An up arrow indicates that either exon 1bis, 3bis, or 5bis has been inserted depending upon which is indicated. A bracket notation in exon 6, over an exon 6bis notation indicates that the first 60 bases is missing from exon 6, and exon 6bis is therefor present as a truncated form of exon 6.

FIG. 15 is a table listing the results of a series of RT-PCR experiments that were performed on RNA of normal prostate, normal prostatic cell lines (PNT1A, PNT1B and PNT2), and tumoral prostatic cell lines (LnCaPFCG, LnCaPJMB, CaHPV, Du45, PC3, and prostate tumors (ECP5 to ECP24) using all the possible combinations of primers (SEQ ID NOs: 137–178) specific to all of the possible splice junctions or exon borders in human PG1. An NT indicates that the experiment was not performed. An [+] indicates the use of an alternative splice species with exons 1, 3, 4, 7, and 8.

Figure 16:
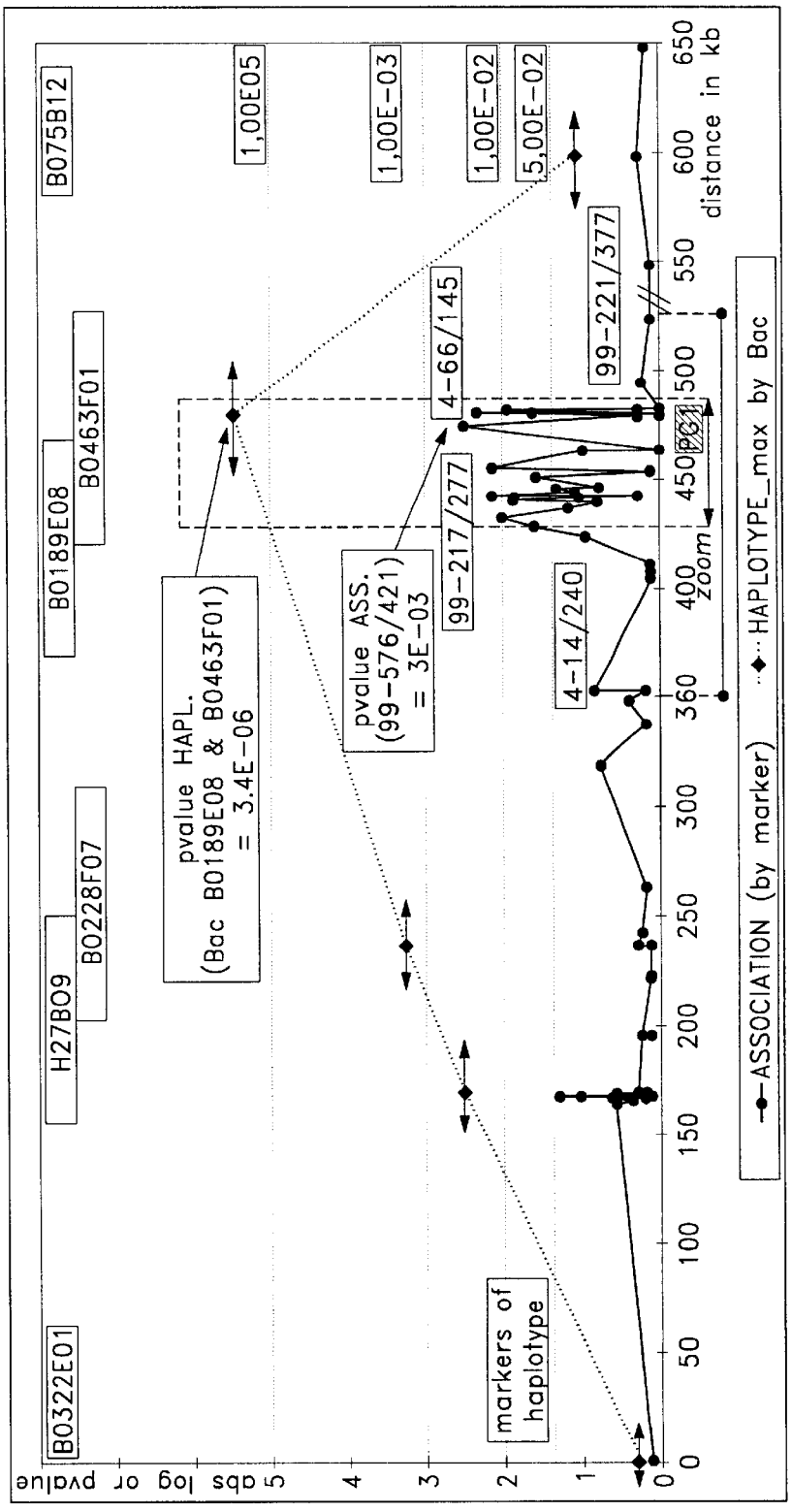

FIG. 16 is a graph showing the results of association studies using markers spanning the 650 kb region of the 8p23 locus around PG1, using both single point analysis and haplotyping studies.

Figure 17:
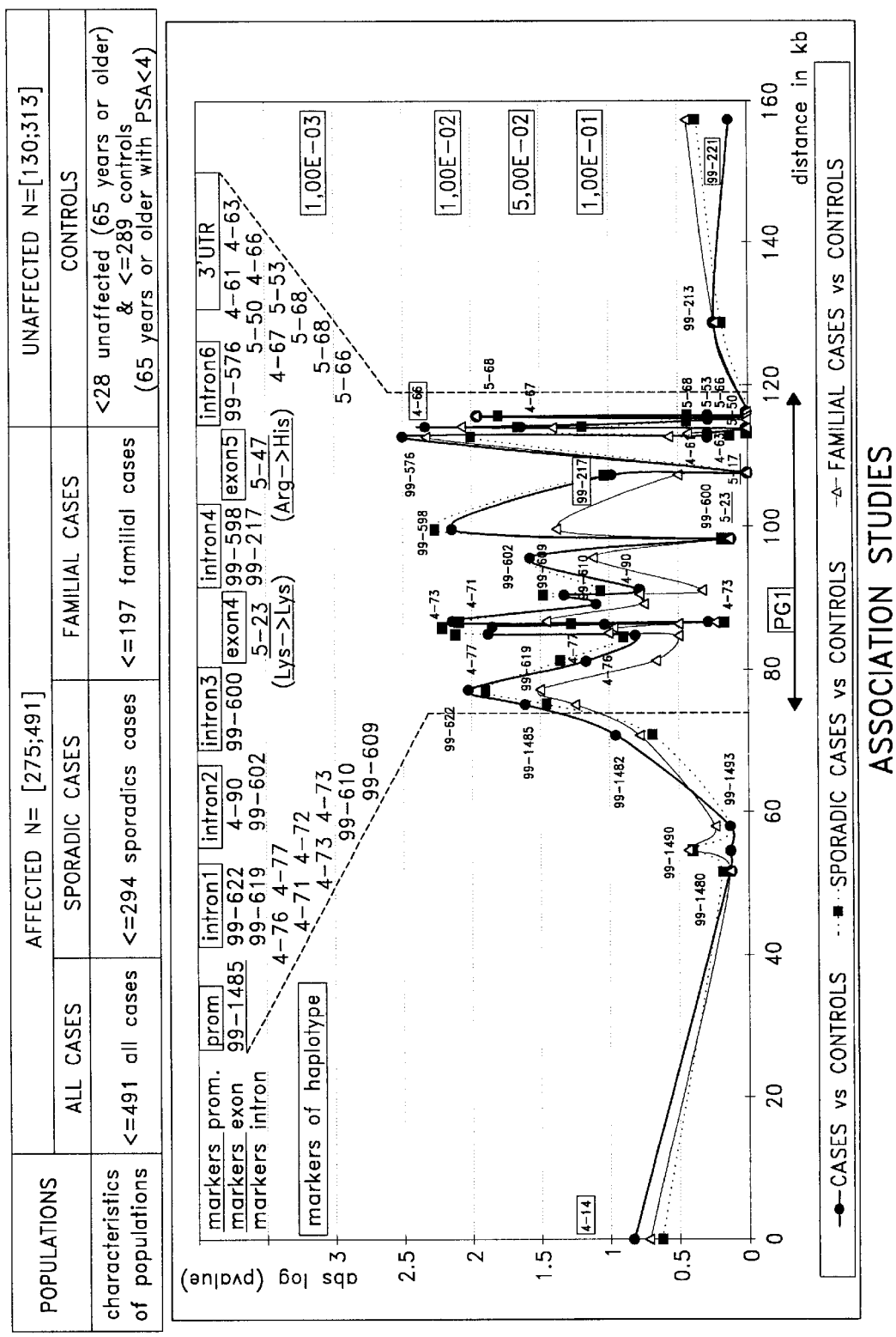

FIG. 17 is a graph showing an enlarged view of the single point association results within a 160 kb region comprising the PG1 gene.

Figure 18A:
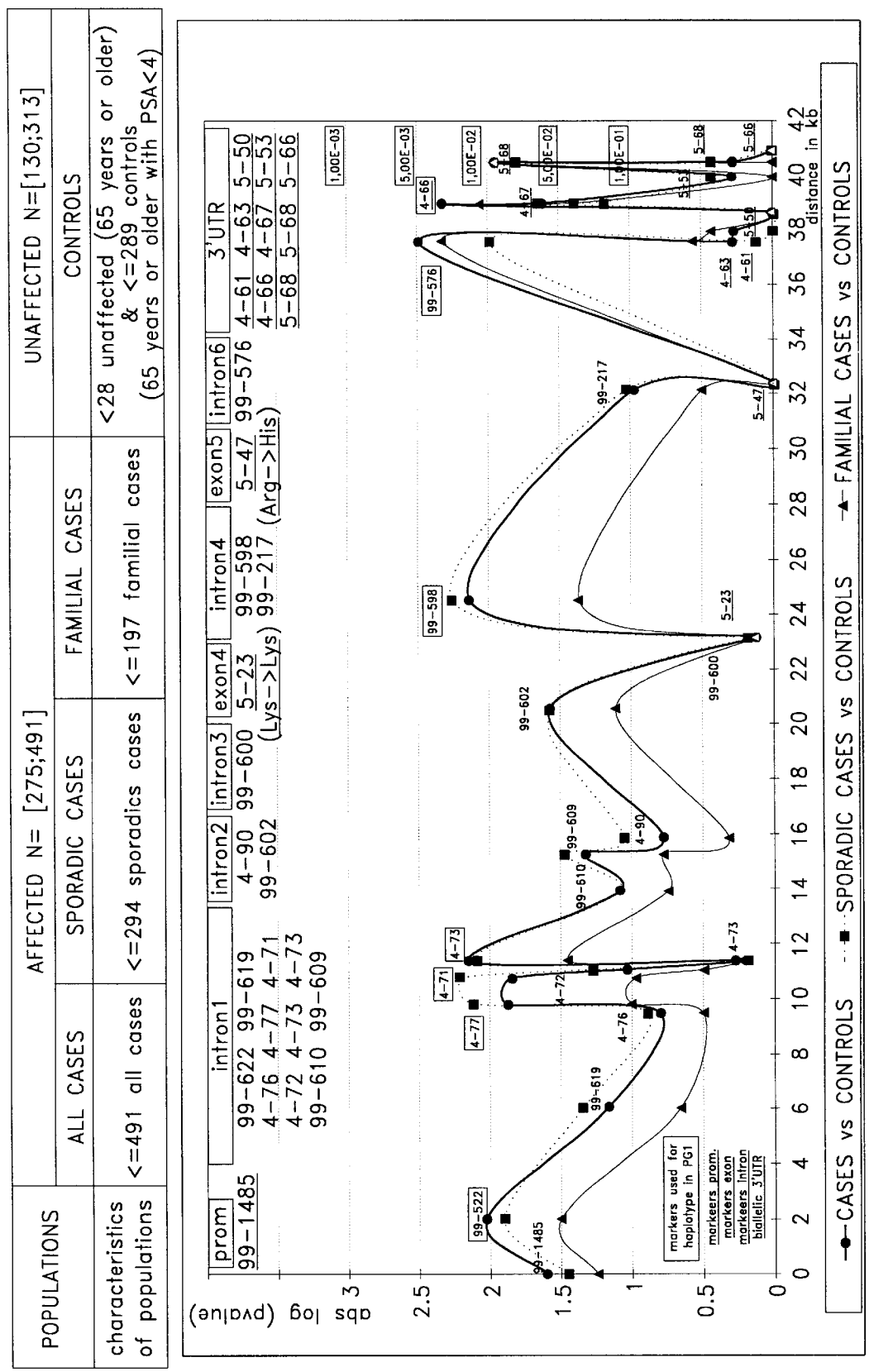

FIG. 18A is a graph showing an enlarged view of the single point association results of 40 kb within the PG1 gene. FIG. 18B is a table listing the location of markers within PG1 gene, the two possible alleles at each site. For each marker, the disease-associated allele is indicated first; its frequencies in cases and controls as well as the difference between both are shown; the odd-ratio and the p-value of each individual marker association are also shown.

FIG. 19A is a table showing the results of a haplotype analysis study using 4 markers (marker Nos. 4-14, 99-217, 4-66 and 99-221)) within the 160 kb region shown in FIG. 17. FIG. 19B is a table showing the segmented haplotyping results according to the subject's age, and whether the prostate cancer cases were sporadic or familial, using the same markers 4 markers and the same individuals as were used to generate the results in FIG. 19A.

FIG. 20 is a table listing the haplotyping results and odd ratios for combinations of the 7 markers (99-622 ; 4-77 ; 4-71; 4-; 99-598 ; 99-576 ; 4-66) within PG1 gene were shown in FIG. 18 to have p-values more significant than $1.10^{-2}$. All of the 2-, 3-, 4-, 5-, 6- and 7-marker haplotypes were tested.

Figure 21:
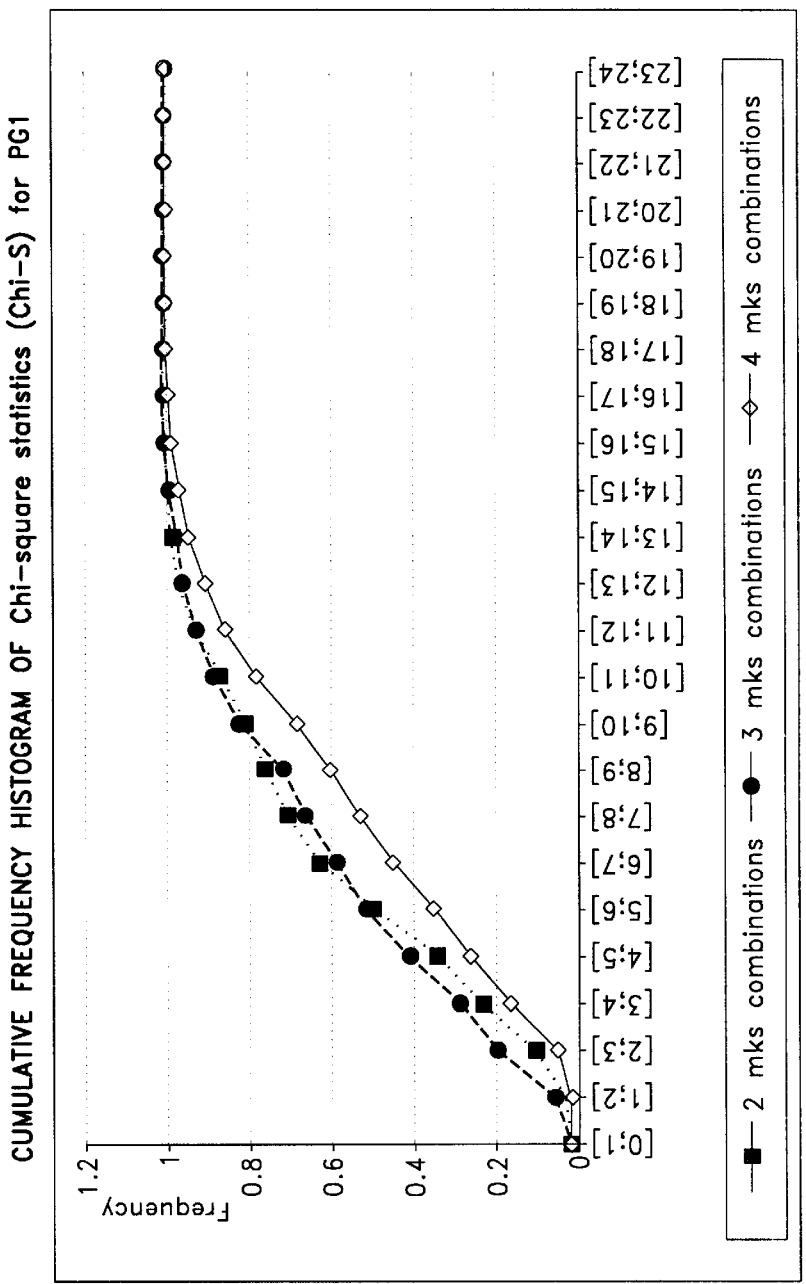

FIG. 21 is a graph showing the distribution of statistical significance, as measured by Chi-square values, for each series of possible x-marker haplotypes, (=2, 3 or 4) using all of the 19 markers listed in FIG. 18B.

Figure 22:
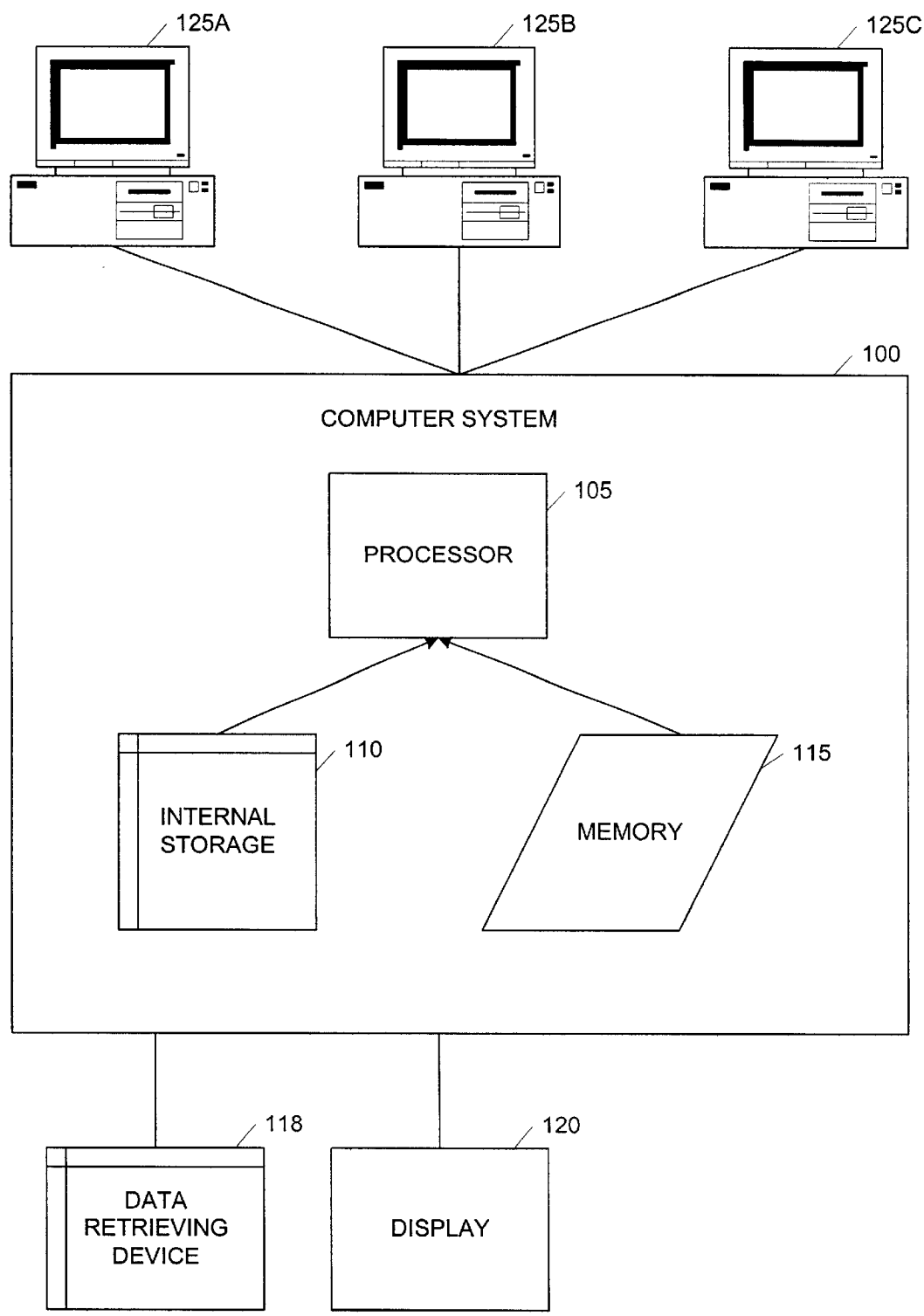

FIG. 22 is a block diagram of an exemplary computer system.

Figure 23:
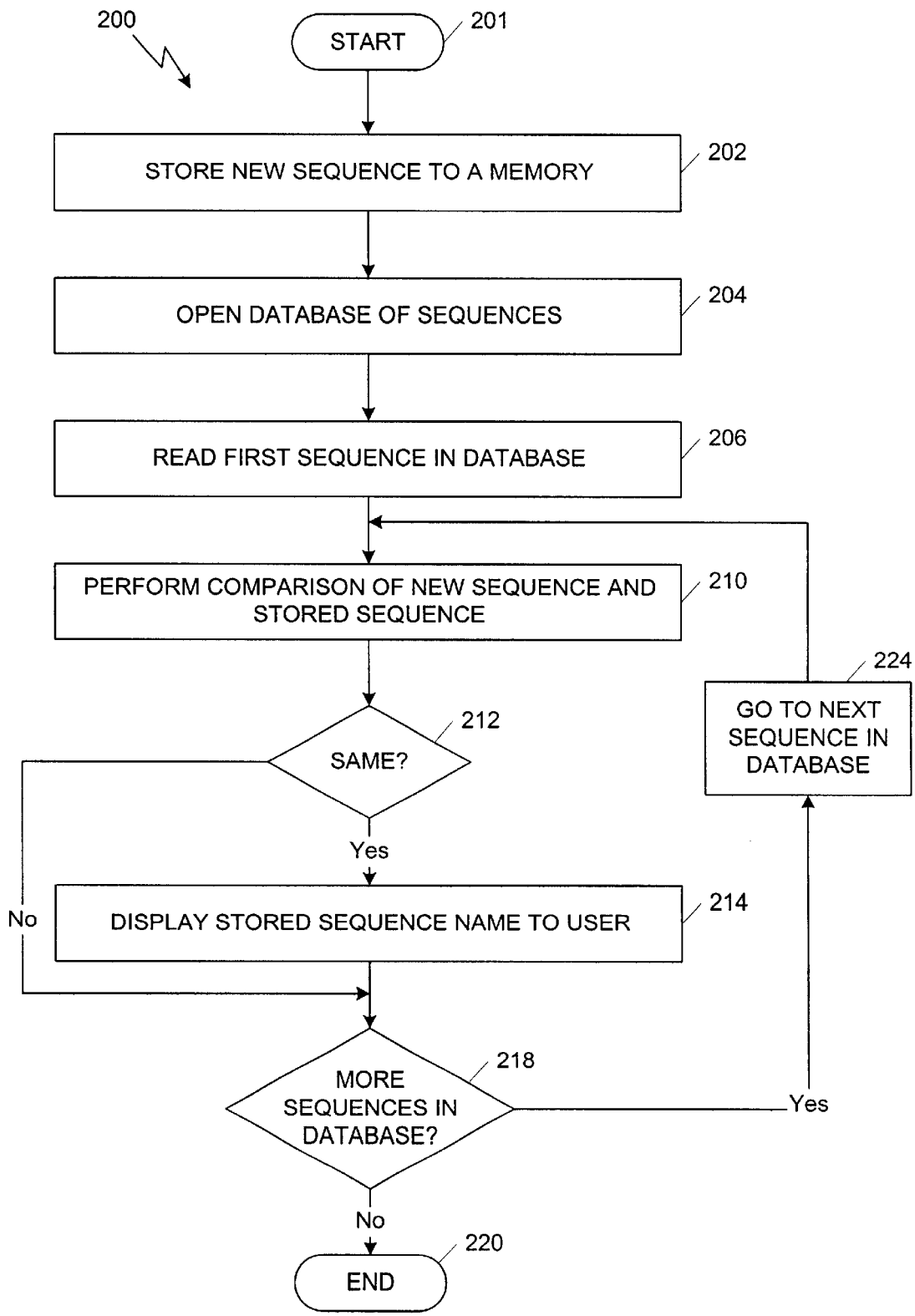

FIG. 23 is a flow diagram illustrating one embodiment of a process 200 for comparing a new nucleotide or protein sequence with a database of sequences in order to determine the homology levels between the new sequence and the sequences in the database.

Figure 24:
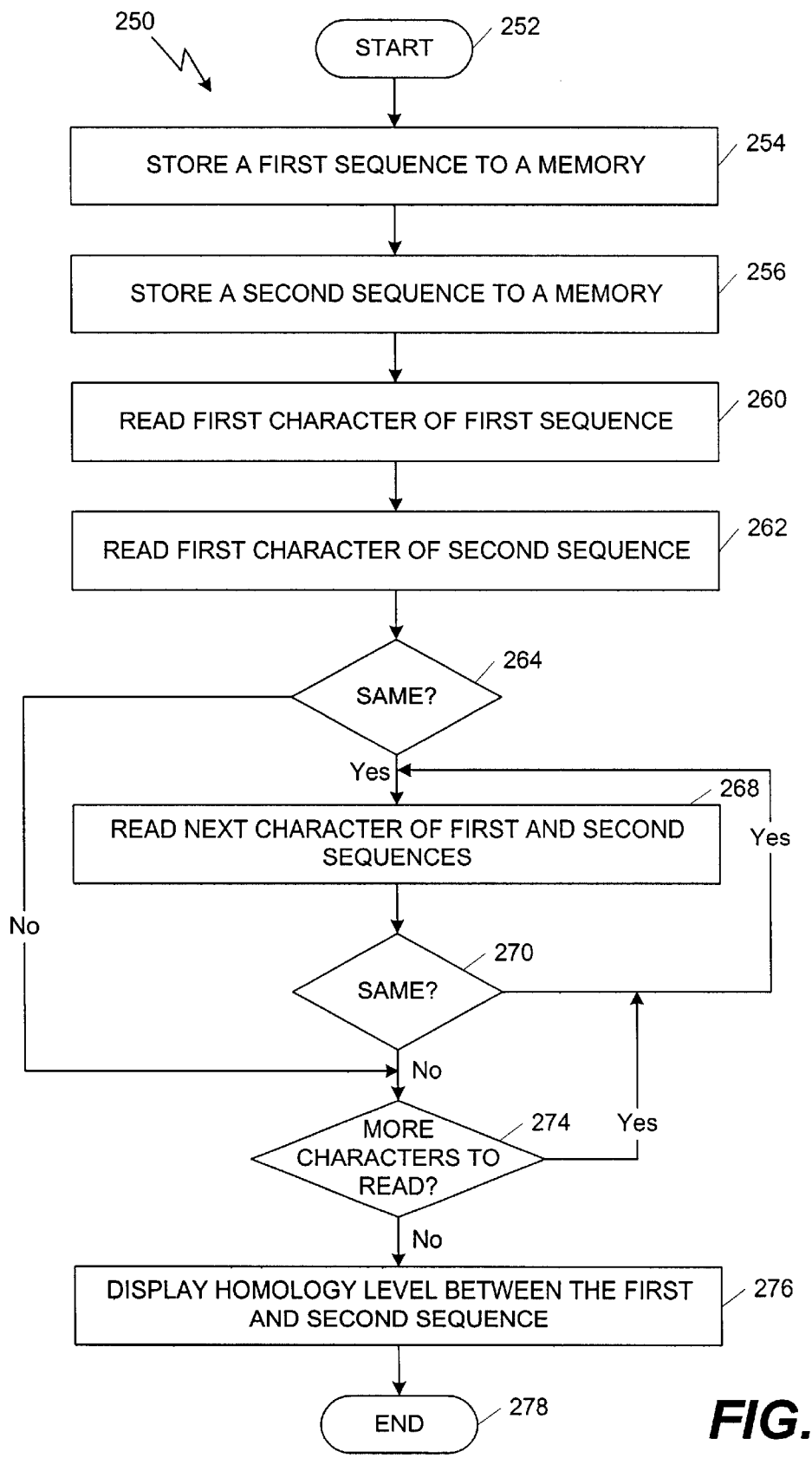

FIG. 24 is a flow diagram illustrating one embodiment of a process 250 in a computer for determining whether two sequences are homologous.

Figure 25:
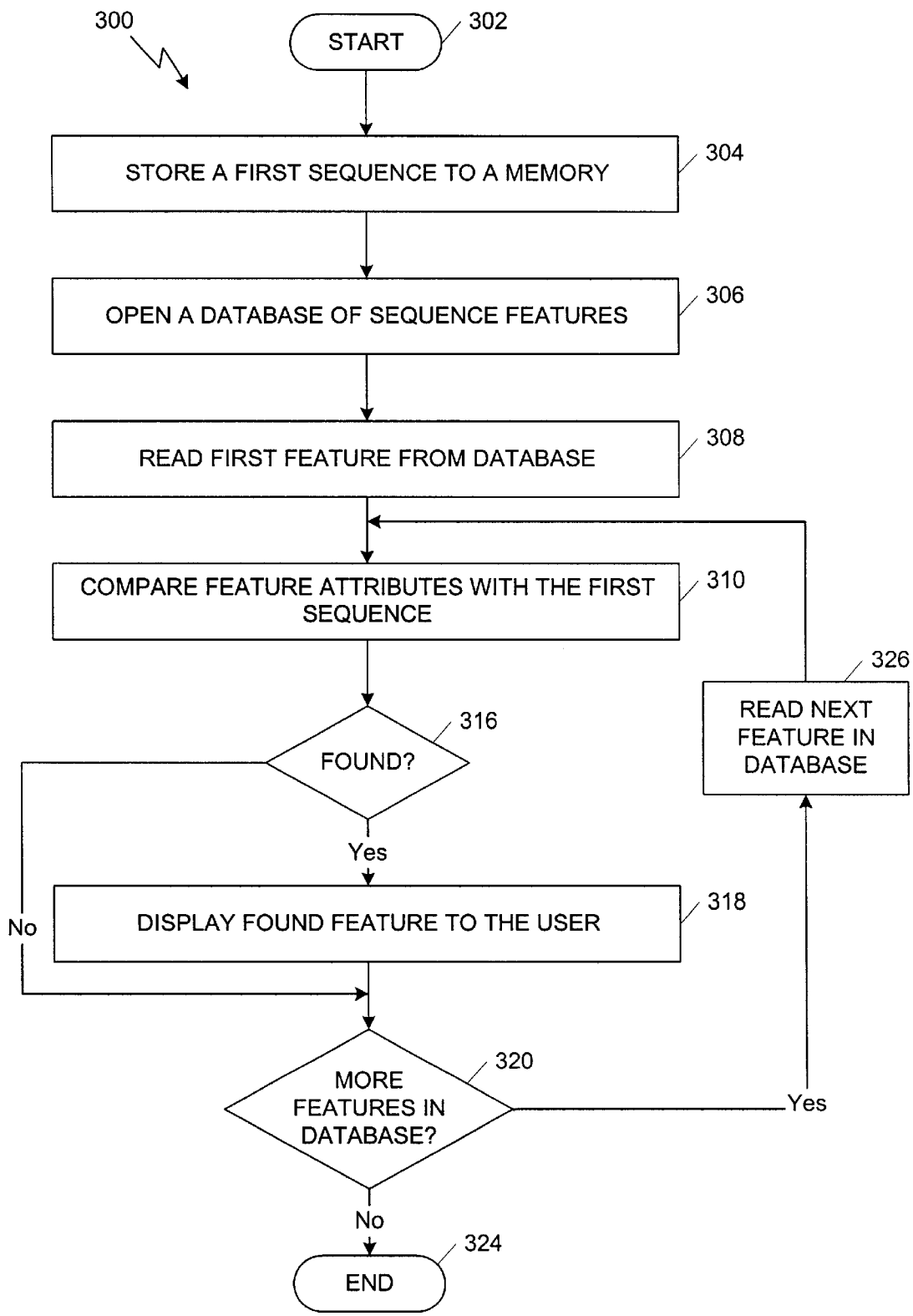

FIG. 25 is a flow diagram illustrating one embodiment of an identifier process 300 for detecting the presence of a feature in a sequence.

DETAILED DESCRIPTION OF THE PREFERRED EMBODIMENT

The practice of the present invention encompasses conventional techniques of chemistry, immunology, molecular biology, biochemistry, protein chemistry, and recombinant DNA technology, which are within the skill of the art. Such techniques are explained fully in the literature. See, e.g., *Oligonucleotide Synthesis* (M. Gait ed. 1984); *Nucleic Acid Hybridization* (B. Hames & S. Higgins, eds., 1984); Sambrook, Fritsch & Maniatis, *Molecular Cloning: A Laboratory Manual*, Second Edition (1989); PCR Technology (H. A. Erlich ed., Stockton Press); R. Scope, *Protein Purification Principles and Practice* (Springer-Verlag); and the series *Methods in Enzymology* (S. Colowick and N. Kaplan eds., Academic Press, Inc.).

Definitions:

As used interchangeably herein, the terms "nucleic acid" "oligonucleotide", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention is prepared by any known method, including synthetic, recombinant, ex vivo generation, or a combination thereof, as well as utilizing any purification methods known in the art.

As used herein, the term "purified" does not require absolute purity; rather, it is intended as a relative definition Purification of starting material or natural material to at least one order of magnitude, preferably two or three orders, and more preferably four or five orders of magnitude is expressly contemplated.

The term "purified" is used herein to describe a polynucleotide or polynucleotide vector of the invention which has been separated from other compounds including, but not limited to other nucleic acids, charbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polynucleotide typically comprises about 50%, preferably 60 to 90% weight/weight of a nucleic acid sample, more usually about 95%, and preferably is over about 99% pure. Polynucleotide purity or homogeneity is indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "polypeptide" refers to a polymer of amino without regard to the length of the polymer; thus, peptides, oligopeptides, and proteins are included within the definition of polypeptide. This term also does not specify or exclude prost-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

As used herein, the term "isolated" requires that the material be removed from its original environment (e.g., the natural environment if it is naturally occurring).

The term "purified" is used herein to describe a polypeptide of the invention which has been separated from other compounds including, but not limited to nucleic acids, lipids, charbohydates and other proteins. A polypeptide is substantially pure when at least about 50 %, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as agarose or polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen., which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case an PG1 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8–10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. Proc. Natl. Acad. Sci. U.S.A. 81:3998–4002; PCT Publication No. WO 84/03564; and PCT Publication No. WO 84/03506.

The term "DNA construct" and "vector" are used herein to mean a purified or isolated polynucleotide that has been artificially designed and which comprises at least two nucleotide sequences that are not found as contiguous nucleotide sequences in their natural environment.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to cancer or prostate cancer; or to refer to an individual's response to an anti-cancer agent or an anti-prostate cancer agent; or to refer to symptoms of, or susceptibility to side effects to an anticancer agent or an anti-prostate cancer agent.

The term "allele" is used herein to refer to variants of a nucleotide sequence. A biallelic polymorphism has two forms. Typically the first identified allele is designated as the original allele whereas other alleles are designated as alternative alleles. Diploid organisms is homozygous or heterozygous for an allelic form.

The term "heterozygosity rate" is used herein to refer to the incidence of individuals in a population, which are heterozygous at a particular allele. In a biallelic system the heterozygosity rate is on average equal to $2P_a(1-P_a)$, where $P_a$ is the frequency of the least common allele. In order to be useful in genetic studies a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention a haplotype preferably refers to a combination of biallelic marker alleles found in a given individual and which is associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. Typically, between different genomes or between different individuals, the polymorphic site is occupied by two different nucleotides.

The terms "biallelic polymorphism" and "biallelic marker" are used interchangeably herein to refer to a nucleotide polymorphism having two alleles at a fairly high frequency in the population. A "biallelic marker allele" refers to the nucleotide variants present at a biallelic marker site. Usually a biallelic marker is a single nucleotide polymorphism. However, less commonly there are also insertions and deletions of up to 5 nucleotides which constitute biallelic markers for the purposes of the present invention. Typically the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker."

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, 4th edition, 1995).

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

As used herein the term "PG1-related biallelic marker" relates to a set of biallelic markers in linkage disequilibrium with PG1. The term PG1-related biallelic marker includes all of the biallelic markers used in the initial association studies shown below in Section I.D., including those biallelic markers contained in SEQ ID NOs: 21–38 and 57–62. The term PG1-related biallelic marker encompasses all of the following polymorphisms positioned in SEQ ID 179, and listed by internal reference number, including: 5-63-169 G or C in position 2159; 5-63-453 C or T in position 2443; 99-622-95 T or C in position 4452; 99-621-215 T or C in position 5733; 99-619-141 G or A in position 8438; 4-76-222 deletion of GT in position 11843; 4-76-361 C or T in position 11983; 4-77-151 G or C in position 12080; 4-77-294 A or G in position 12221; 4-71-33 G or T in position 12947;4-71-233 A or G in position 13147; 4-71-280 G or A in position 13194; 4-71-396 G or C in position 13310; 4-72-127 A or G in position 13342; 4-152 A or G in position 13367; 4-71-380 deletion of A in position 13594; 4-73-134 G or C in position 13680; 4-73-356 G or C in position 13902; 99-610-250 T or C in position 16231; 99-610-93 A or T in position 16388; 99-609-225 A or T in position 17608; 4-90-27 A or C in position 18034; 4-90-283 A or C in position 18290; 99-607-397 T or C in position 18786; 99-602-295 deletion of A in position 22835; 99-602-258 T or C in position 22872; 99-600-492 deletion of TATTG in position 25183; 99-600-483 T or G in position 25192; 5-23-288 A or G in position 25614; 99-598-130 T or C in position 26911; 99-592-139 A or T in position 32703; 99-217-277 C or T in position 34491; 5-47-284 A or G in position 34756; 99-589-267 T or G in position 34934; 99-589-41 G or C in position 35160; 99-12899-307 C or T in position 39897; 4-12-68 A or G in position 40598; 99-582-263 T or C in position 40816; 99-582-132 T or C in position 40947; 99-576-421 G or C in position 45783; 4-13-51 C or T in position 47929; 4-13-328 A or T in position 48206; 4-13-329 G or C in position 48207; 99-12903-381 C or T in position 49282; 5-56-208 A or G in position 50037; 5-56-225 A or G in position 50054; 5-56-272 A or G in position 50101; 5-56-391 G or T in position 50220; 4-61-269 A or G in position 50440; 4-61-391 A or G in position 50562; 4-63-99 A or G in position 50653; 4-62-120 A or G in position 50660; 4-62-205 A or G in position 50745; 4-64-113 A or T in position 50885; 4-65-104 A or G in position 51249; 5-28-300 A or G in position 51333; 5-50-269 C or T in position 51435; 4-65-324 C or T in position 51468; 5-71-129 G or C in position 51515; 5-50-391 G or C in position 51557; 5-71-180 A or G in position 51566; 4-67-40 C or T in position 51632; 5-71-280 A or C in position 51666; 5-58-167 A or G in position 52016; 5-30-125 C or T in position 52096; 5-58-302 A or T in position 52151; 5-31-178 A orG in position 52282; 5-31-244 A or G in position 52348; 5-31-306 deletion of A in position 52410; 5-32-190 C or T in position 52524; 5-32-246 C or T in position 52580; 5-32-378 deletion of A in position 52712; 5-53-266 G or C in position 52772; 5-60-158 C or T in position 52860; 5-60-190 A or G in position 53092; 5-68-272 G or C in position 53272; 5-68-385 A or T in position 53389; 5-66-53 deletion of GA in position 53511; 5-66-142 G or C in position 53600; 5-66-207 A or G in position 53665; 5-37-294 A or G in position 53815; 5-62-163 insertion of A in position 54365; 5-62-340 A or T in position 54541; and the compliments thereof. The term PG1-related biallelic marker also includes all of the following biallelic markers listed by internal reference number, and two SEQ ID NOs each of which contains a 47-mers with one of the two alternative bases at position 24: 4-14-107 of SEQ ID NOs 185 and 262; 4-14-317 of SEQ ID NOs 186 and 263; 4-14-35 of SEQ ID NOs 187 and 264; 4-20-149 of SEQ ID NOs 188 and 265; 4-20-77 of SEQ ID NOs 189and 266; 4-22-174 of SEQ ID NOs 190 and 267; 4-22-176 of SEQ ID NOs 191 and 268; 4-26-60 of SEQ ID NOs 192 and 269; 4-26-72 of SEQ ID NOs 193 and 270; 4-3-130 of SEQ ID NOs 194 and 271; 4-38-63 of SEQ ID NOs 195 and 272; 4-38-83 of SEQ ID NOs 196 and 273; 4-4-152 of SEQ ID NOs 197 and 274; 4-4-187 of SEQ ID NOs 198 and 275; 4-4-288 of SEQ ID NOs 199 and 276; 4-42-304 of SEQ ID NOs 200 and 277; 4-42-401 of SEQ ID NOs 201 and 278; 4-43-328 of SEQ ID NOs 202 and 279; 4-43-70 of SEQ ID NOs 203 and 280; 4-50-209 of SEQ ID NOs 204 and 281; 4-50-293 of SEQ ID NOs 205 and 282; 4-50-123 of SEQ ID NOs 206 and 283; 4-50-129 of SEQ ID NOs 207 and 284; 4-50-130 of SEQ ID NOs 208 and 285; 4-52-163 of SEQ ID NOs 209 and 286; 4-52-88 of SEQ ID NOs 210 and 287; 4-53-258 of SEQ ID NOs 211 and 288; 4-54-283 of SEQ ID NOs 212 and 289; 4-54-388 of SEQ ID NOs 213 and 290; 4-55-70 of SEQ ID NOs 214 and 291; 4-55-95 of SEQ ID NOs 215 and 292; 4-56-159 of SEQ ID NOs 216 and 293; 4-56-213 of SEQ ID NOs 217 and 294; 4-58-289 of SEQ ID NOs 218 and 295; 4-58-318 of SEQ ID NOs 219 and 296; 4-60-266 of SEQ ID NOs 220 and 297; 4-60-293 of SEQ ID NOs 221 and 298; 4-84-241 of SEQ ID NOs 222 and 299; 4-84-262 of SEQ ID NOs 223 and 300; 4-86-206 of SEQ ID NOs 224 and 301; 4-86-309 of SEQ ID NOs 225 and 302; 4-88-349 of SEQ ID NOs 226 and 303; 4-89-87 of SEQ ID NOs 227 and 304; 99-123-184 of SEQ ID NOs 228 and 305; 99-128-202 of SEQ ID NOs 229 and 306; 99-128-275 of SEQ ID NOs 230 and 307; 99-128-313 of SEQ ID NOs 231 and 308; 99-128-60 of SEQ ID NOs 232 and 309; 99-12907-295 of SEQ ID NOs 233 and 310; 99-130of SEQ ID NOs 234 and 311; 99-134-362 of SEQ ID NOs 235 and 312; 99-140-130 of SEQ ID NOs 236 and 313; 99-1462-238 of SEQ ID NOs 237 and 314; 99-147-181of SEQ ID NOs 238and315;99-1474-156of SEQ ID NOs 239and316; 99-1474-359 of SEQ ID NOs 240 and 317; 99-1479-158 of SEQ ID NOs 241 and 318; 99-1479-379 of SEQ ID NOs 242 and 319; 99-148-129 of SEQ ID NOs 243 and 320; 99-148-132 of SEQ ID NOs 244 and 321; 99-148-139 of SEQ ID NOs 245 and 322; 99-148-140 of SEQ ID NOs 246 and 323; 99-148-182 of SEQ ID NOs 247 and 324; 99-148-366 of SEQ ID NOs 248 and 325; 99-148-76 of SEQ ID NOs 249 and 326; 99-1480-290 of SEQ ID NOs 250 and 327; 99-1481-285 of SEQ ID NOs 251 and 328; 99-1484-101 of SEQ ID NOs 252 and 329; 99-1484-328 of SEQ ID NOs 253 and 330; 99-1485-251 of SEQ ID NOs 254 and 331; 99-1490-181 of SEQ ID NOs 255 and 332; 99-1493-280 of SEQ ID NOs 256 and 333; 99-151-94 of SEQ ID NOs 257 and 334; 99-211-291 of SEQ ID NOs 258 and 335; 99-213-37 of SEQ ID NOs 259 and 336; 99-221-442 of SEQ ID NOs 260 and 337; 99-222-109 of SEQ ID NOs 261 and 338; and the compliments thereof.

The term "non-genic" is used herein to describe PG1-related biallelic markers, as well as polynucleotides and primers which do not occur in the human PG1 genomic sequence of SEQ ID NO: 179. The term "genic" is used herein to describe PG1-related biallelic markers as well as polynucleotides and primers which do occur in the human PG1 genomic sequence of SEQ ID NO: 179.

The terms "an anti-cancer agent" refers to a drug or a compound that is capable of reducing the growth rate, rate of metastasis, or viability of tumor cells in a mammal, is capable of reducing the size or eliminating tumors in a mammal, or is capable of increasing the average life span of a mammal or human with cancer. Anti-cancer agents also include compounds which are able to reduce the risk of cancer developing in a population, particularly a high risk population. The terms "an anti-prostate cancer agent" is an anti-cancer agent that has these effects on cells or tumors that are derived from prostate cancer cells.

The terms "response to an anti-cancer agent" and "response to an anti-prostate cancer agent" refer to drug efficacy, including but not limited to ability to metabolize a compound, to the ability to convert a pro-drug to an active drug, and to the pharmacokinetics (absorption, distribution, elimination) and the pharrnacodynamics (receptor-related) of a drug in an individual.

The terms "side effects to an anti-cancer agent" and "side effects to an anti-prostate cancer agent" refer to adverse effects of therapy resulting from extensions of the principal pharmacological action of the drug or to idiosyncratic adverse reactions resulting from an interaction of the drug with unique host factors. These side effects include, but are not limited to, adverse reactions such as dermatological, hematological or hepatological toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, sexual dysfunction, and shock.

As used herein the term "homology" refers to comparisons between protein and/or nucleic acid sequences and is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444–2448; Altschul et al., 1990, J. Mol. Biol. 215(3):403–410; Thompson et al., 1994, Nucleic Acids Res. 22(2):4673–4680; Higgins et al., 1996, Methods Enzymol. 266:383–402; Altschul et al., 1990, J. Mol. Biol. 215(3):403–410; Altschul et al., 1993, Nature Genetics 3:266–272). In a particularly preferred embodiment, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267–2268; Altschul et al., 1990, J. Mol. Biol. 215:403–410; Altschul et al., 1993, Nature Genetics 3:266–272; Altschul et al., 1997, Nuc. Acids Res. 25:3389–3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, Science 256:1443–1445; Henikoff and Henikoff, 1993, Proteins 17:49–61). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, Proc. Natl. Acad. Sci. USA 87:2267–2268).

I. ISOLATION AND CHARACTERIZATION OF THE PG1 GENE AND PROTEINS

I.A. The 8p23 Region- LOH Studies: Implications of 8p23 Region in Distinct Cancer Types Substantial amounts of LOH data support the hypothesis that genes associated with distinct cancer types are located within 8p23 region of the human genome. Emi, et al., demonstrated the implication of 8p23.1–8p21.3 region in cases of hepatocellular carcinoma, colorectal cancer, and non-small cell lung cancer. (Emi M, Fujiwara Y, Nakajima T, Tsuchiya E, Tsuda H, Hirohashi S, Maeda Y, Tsuruta K, Miyaki M, Nakamura Y, Cancer Res. 1992 Oct 1; 52(19): 5368–5372) Yaremko, et al., showed the existence of two major regions of LOH for chromosome 8 markers in a sample of 87 colorectal carcinomas. The most prominent loss was found for 8p23.1-pter, where 45% of informative cases demonstrated loss of alleles. (Yaremko M. L., Wasylyshyn M. L. Paulus K. L., Michelassi F, Westbrook C. A., Genes Chromosomes Cancer 1994 May;10(1): 1–6). Scholnick et al. demonstrated the existence of three distinct regions of LOH for the markers of chromosome 8 in cases of squamous cell carcinoma of the supraglottic larynx. They showed that the allelic loss of 8p23 marker D8S264 serves as a statistically significant, independent predictor of poor prognosis for patients with supraglottic squamous cell carcinoma. (Scholnick S. B., Haughey BH, Sunwoo J. B., el-Mofty S. K., Baty J. D., Piccirillo J. F., Zequeira M. R., J. Natl. Cancer Inst. 1996 Nov 20; 88(22): 1676–1682 and Sunwoo J. B., Holt M. S., Radford D. M., Deeker C, Scholnick S, Genes Chromosomes Cancer 1996 Jul; 16(3) :164-169).

In other studies, Nagai et al. demonstrated the highest loss of heterozygosity in the specific region of 8p23 by genome wide scanning of LOH in 120 cases of hepatocellular carcinoma (HCC). (Nagai H, Pineau P, Tiollais P, Buendia M. A., Dejean A, Oncogene 1997 Jun 19; 14(24): 2927–2933). Gronwald et al. demonstrated 8p23-pter loss in renal clear cell carcinomas. (Gronwald J, Storkel S, Holtgreve-Grez H, Hadaczek P, Brinkschmidt C, Jauch A, Lubinski J, Cremer, Cancer Res. 1997 Feb 1; 57(3): 481–487).

The same region is involved in specific cases of prostate cancer. Matsuyama et al. showed the specific deletion of the 8p23 band in prostate cancer cases, as monitored by FISH with D8S7 probe. (Matsuyama H, Pan Y, Skoog L, Tribukait B, Naito K, Ekman P, Lichter P, BergerheimU.S. Oncogene 1994 Oct; 9(10): 3071–3076). They were able to document a substantial number of cases with deletions of 8p23 but retention of the 8p22 marker LPL. Moreover, Ichikawa et al. deduced the existence of a prostate cancer metastasis suppressor gene and localized it to 8p23-q12 by studies of metastasis suppression in highly metastatic rat prostate cells after transfer of human chromosomes. (Ichikawa T, Nihei N, Kuramochi H, Kawana Y, Killary A. M., Rinker-Schaeffer C. W., Barrett J. C., Isaacs J. T., Kugoh H, Oshimura M, Shimazaki J, Prostate Suppl. 1996; 6: 31–35).

Recently Washbum et al. were able to find substantial numbers of tumors with the allelic loss specific to 8p23 by LOH studies of 31 cases of human prostate cancer. (Washbum J, Woino K, and Macoska J, Proceedings of American Association for Cancer Research, March 1997; 38). In these samples they were able to define the minimal overlapping region with deletions covering genetic interval D8S262-D8S277.

Linkage Analysis Studies: Search for Prostate Cancer Linked Regions on Chromosome 8

Microsatellite markers mapping to chromosome 8 were used by the inventors to perform linkage analysis studies on 194 individuals issued from 47 families affected with prostate cancer. While multiple point analysis led to weak linkage results, two point lod score analysis led to non significant results, as shown below.

| Two point lod (parametric analysis) | | |
| --- | --- | --- |
| MARKER | Distance (cM) | Z(lod) scores |
| D8S1742 |  | −0.13 |
| D8S561 | 0.8 | −0.07 |
| # of families analyzed | | 47 |
| Total # of individuals genotyped | | 194 |
| Total # of affected individuals genotyped | | 122 |

In view of the non-significant results obtained with linkage analysis, a new mapping approach based on linkage disequilibrium of biallelic markers was utilised to identify genes responsible for sporadic cases of prostate cancer.

I.B. Linkage Disequilibrium Using Biallelic Markers To Identify Candidate Loci Responsible For Disease Linkage Disequilibrium Once a chromosomal region has been identified as potentially harboring a candidate gene associated with a sporadic trait, an excellent approach to refine the candidate gene's location within the identified region is to look for statistical associations between the trait and some marker genotype when comparing an affected (trait[+]) and a control (trait[−]) population.

Association studies have most usually relied on the use of biallelic markers. Biallelic markers are genome-derived polynucleotides that exhibit biallelic polymorphism at one single base position. By definition, the lowest allele frequency of a biallelic polymorphism is 1%; sequence variants that show allele frequencies below 1% are called rare mutations. There are potentially more than $10^7$ biallelic markers lying along the human genome.

Association studies seek to establish correlations between traits and genetic markers and are based on the phenomenon of linkage disequilibrium (LD). LD is defined as the trend for alleles at nearby loci on haploid genomes to correlate in the population. If two genetic loci lie on the same chromosome, then sets of alleles on the same chromosomal segment (i.e., haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium.

Since results generated by association studies are essentially based on the quantitative calculation of allele frequencies, they best apply to the analysis of germline mutations. This is mainly due to the fact that allelic frequencies are difficult to quantify within tumor tissue samples because of the usual presence of normal cells within the studied tumor samples. Association studies applied to cancer genetics will therefore be best suited to the identification of tumor suppressor genes.

Trait Localization by Linkage Disequilibrium Mapping

Any gene responsible or partly responsible for a given trait will be in LD with some flanking markers. To map such a gene, specific alleles of these flanking markers which are associated with the gene or genes responsible for the trait are identified. Although the following discussion of techniques for finding the gene or genes associated with a particular trait using linkage disequilibrium mapping, refers to locating a single gene which is responsible for the trait, it will be appreciated that the same techniques may also be used to identify genes which are partially responsible for the trait.

Association studies is conducted within the general population (as opposed to the linkage analysis techniques discussed above which are limited to studies performed on related individuals in one or several affected families).

Association between a biallelic marker A and a trait T may primarily occur as a result of three possible relationships between the biallelic marker and the trait. First, allele a of biallelic marker A is directly responsible for trait T (e.g., Apo E e4 allele and Alzheimer's disease). However, since the majority of the biallelic markers used in genetic mapping studies are selected randomly, they mainly map outside of genes. Thus, the likelihood of allele a being a functional mutation directly related to trait T is therefore very low.

An association between a biallelic marker A and a trait T may also occur when the biallelic marker is very closely linked to the trait locus. In other words, an association occurs when allele a is in linkage disequilibrium with the trait-causing allele. When the biallelic marker is in close proximity to a gene responsible for the trait, more extensive genetic mapping will ultimately allow a gene to be discovered near the marker locus which carries mutations in people with trait T (i.e. the gene responsible for the trait or one of the genes responsible for the trait). As will be further exemplified below using a group of biallelic markers which are in close proximity to the gene responsible for the trait, the location of the causal gene can be deduced from the profile of the association curve between the biallelic markers and the trait. The causal gene will be found in the vicinity of the marker showing the highest association with the trait.

Finally, an association between a biallelic marker and a trait may occur when people with the trait and people without the trait correspond to genetically different subsets of the population who, coincidentally, also differ in the frequency of allele a (population stratification). This phenomenon is avoided by using large heterogeneous samples.

Association studies are particularly suited to the efficient identification of susceptibility genes that present common polymorphisms, and are involved in multifactorial traits whose frequency is relatively higher than that of diseases with monofactorial inheritance.

Application of Linkage Disequilibrium Mapping to Candidate Gene Identification

The general strategy of association studies using a set of biallelic markers, is to scan two pools of individuals (affected individuals and unaffected controls) characterized by a well defined phenotype in order to measure the allele frequencies for a number of the chosen markers in each of these pools. If a positive association with a trait is identified using an array of biallelic markers having a high enough density, the causal gene will be physically located in the vicinity of the associated markers, since the markers showing positive association to the trait are in linkage disequilibrium with the trait locus. Regions harboring a gene responsible for a particular trait which are identified through association studies using high density sets of biallelic markers will, on average, be 20–40 times shorter in length than those identified by linkage analysis.

Once a positive association is confirmed as described above, BACs (bacterial artificial chromosomes) obtained from human genomic libraries, constructed as described below, harboring the markers identified in the association analysis are completely sequenced.

Once a candidate region has been sequenced and analyzed, the functional sequences within the candidate region (exons and promoters, and other potential regulatory regions) are scanned for mutations which are responsible for the trait by comparing the sequences of a selected number of controls and affected individuals using appropriate software. Candidate mutations are further confirmed by screening a larger number of affected individuals and controls using the microsequencing techniques described below.

Candidate mutations are identified as follows. A pair of oligonucleotide primers is designed in order to amplify the sequences of every predicted functional region. PCR amplification of each predicted functional sequence is carried out on genomic DNA samples from affected patients and unaffected controls. Amplification products from genomic PCR are subjected to automated dideoxy terminator sequencing reactions and electrophoresed on ABI 377 sequencers. Following gel image analysis and DNA sequence extraction, the sequence data are automatically analyzed to detect the presence of sequence variations among affected cases and unaffected controls. Sequences are systematically verified by comparing the sequences of both DNA strands of each individual.

Polymorphisms are then verified by screening a larger population of affected individuals and controls using the microsequencing technique described below in an individual test format. Polymorphisms are considered as candidate mutations when present in affected individuals and controls at frequencies compatible with the expected association results.

Association Studies: Statistical Analysis and Haplotyping

As mentioned above, linkage analysis typically localizes a disease gene to a chromosomal region of several megabases. Further refinement in location requires the analysis of additional families in order to increase the number of recombinants. However, this approach becomes unfeasible because recombination is rarely observed even within large pedigrees (Boehnke, M, 1994, Am. J. Hum. Genet. 55: 379–390).

Linkage disequilibrium, the nonrandom association of alleles at linked loci, may offer an alternative method of obtaining additional recombinants. When a chromosome carrying a mutant allele of a gene responsible for a given trait is first introduced into a population as a result of either mutation or migration, the mutant allele necessarily resides on a chromosome having a unique set of linked markers (haplotype). Consequently, there is complete disequilibrium between these markers and the disease mutation: the disease mutation is present only linked to a specific set of marker alleles. Through subsequent generations, recombinations occur between the disease mutation and these marker polymorphisms, resulting in a gradual disappearance of disequilibrium. The degree of disequilibrium dissipation depends on the recombination frequency, so the markers closest to the disease gene will tend to show higher levels of disequilibrium than those that are farther away (Jorde LB, 1995, Am. J. Hum. Genet. 56: 11–14). Because linkage disequilibrium patterns in a present-day population reflect the action of recombination through many past generations, disequilibrium analysis effectively increases the sample of recombinants. Thus the mapping resolution achieved through the analysis of linkage disequilibrium patterns is much higher than that of linkage analysis.

In practice, in order to define the regions bearing a candidate gene, the affected and control populations are genotyped using an appropriate number of biallelic markers (at a density of 1 marker every 50–150 kilobases). Then, a marker/trait association study is performed that compares the genotype frequency of each biallelic marker in the affected and control populations by means of a chi square statistical test (one degree of freedom).

After the first screening, additional markers within the region showing positive association are genotyped in the affected and control populations. Two types of complementary analysis are then performed. First, a marker/trait association study (as described above) is performed to refine the location of the gene responsible for the trait. In addition, a haplotype association analysis is performed to define the frequency and the type of the ancestral/preferential carrier haplotype. Haplotype analysis, by combining the informativeness of a set of biallelic markers increases the power of the association analysis, allowing false positive and/or negative data that may result from the single marker studies to be eliminated.

The haplotype analysis is performed by estimating the frequencies of all possible haplotypes for a given set of biallelic markers in the case and control populations, and comparing these frequencies by means of a chi square statistical test (one degree of freedom). Haplotype estimations are performed by applying the Expectation-Maximization (EM) algorithm (Excoffier L & Slatkin M, 1995, Mol. Biol. Evol. 12: 921–927), using the EM-HAPLO program (Hawley M E., Pakstis A J. & Kidd K K., 1994, Am. J. Phys. Anthropol. 18:104). The EM algorithm is used to estimate haplotype frequencies in the case when only genotype data from unrelated individuals are available. The EM algorithm is a generalized iterative maximum likelihood approach to estimation that is useful when data are ambiguous and/or incomplete.

The application of biallelic marker based linkage disequilibrium analysis to the 8p23 region to identify a gene associated with prostate cancer is described below.

I.C. Application of Linkage Disequilibrium Mapping to the 8p23 Region

YAC Contig Construction in 8p23 Region

First, a YAC contig which contains the 8p23 region was constructed as follows. The CEPH-Genethon YAC map for the entire human genome (Chumakov I. M. et al. A YAC contig map of the human genome, Nature, 377 Supp.: 175–297, 1995) was used for detailed contig building in the region around D8S262 and D8S277 genetic markers. Screening data available for regional genetic markers D8S1706, D8S277, D8S1742, D8S518, D8S262, D8S1798, D8S1140, D8S561 and D8S1819 were used to select the following set of CEPH YACs, localized within this region: 832_g_12, 787_c_11, 920_h_7, 807_a_1, 842_b_1, 745_a_3, 910_d_3, 879_f_11,918_c_6, 764_c_7, 910_f_12, 967_c_11, 856_d_8, 792_a_6, 812_$_h$_4, 873_c_8, 930_a_2, 807_a_1, 852_$_d$_10. This set of YACs was tested by PCR with the above mentioned genetic markers as well as with other publicly available markers supposedly located within the 8p23 region. As a result of these studies, a YAC STS contig map was generated around genetic markers D8S262 and D8S277. The two CEPH YACs, 920_h_7 (1170 kb insert size) and 910_f_12 (1480 kb insert size) constitute a minimal tiling path in this region, with an estimated size of ca. 2 Megabases.

During this mapping effort, the following publicly known STS markers were precisely located within the contig: WI-14718, WI-3831, D8S1413E, WI-8327, WI-3823, ND4. BAC Contig Construction Covering D8S262–D8S277 Fragment Within 8p23 Region of the Human Genome Following construction of the YAC contig, a BAC contig was constructed as follows. BAC libraries were obtained as described in Woo et al. Nucleic Acids Res., 1994, 22, 4922–4931. Briefly, two different whole human genome libraries were produced by cloning BamHI or HindIII partially digested DNA from a lymphoblastoid cell line (derived from individual N°8445, CEPH families) into the pBelo-BACll vector (Kim et al. Genomics, 1996, 34, 213–218). The library produced with the BamHI partial digestion contained 110,000 clones with an average insert size of 150 kb, which corresponds to 5 human haploid genome equivalents. The library prepared with the HindIII partial digestion corresponds to 3 human genome equivalents with an average insert size of 150 kb.

BAC Screening

The human genomic BAC libraries obtained as described above were screened with all of the above mentioned STSs. DNA from the clones in both libraries was isolated and pooled in a three dimensional format ready for PCR screening with the above mentioned STSs using high throughput PCR methods (Chumakov et al., Nature 1995, 377: 175–298). Briefly, three dimensional pooling consists in rearranging the samples to be tested in a manner which allows the number of PCR reactions required to screen the clones with STSs to be reduced by at least 100 fold, as compared to screening each clone individually. PCR amplification products were detected by conventional agarose gel electrophoresis combined with automated image capturing and processing.

In a final step, STS-positive clones were checked individually. Subchromosomal localization of BACs was systematically verified by fluorescence in situ hybridization (FISH), performed on metaphasic chromosomes as described by Cherif et al. Proc. Natl. Acad. Sci. USA 1990, 87: 6639–6643.

BAC insert size was determined by Pulsed Field Gel Electrophoresis after digestion with restriction enzyme NotI.

BAC Contig Analysis

The ordered BACs selected by STS screening and verified by FISH, were assembled into contigs and new markers were generated by partial sequencing of insert ends from some of them. These markers were used to fill the gaps in the contig of BAC clones covering the chromosomal region around D8S277, having an estimated size of 2 megabases. Selected BAC clones from the contig were subcloned and sequenced.

BAC Subcloning

Each BAC human DNA was first extracted using the alkaline lysis procedure and then sheared by sonication. The obtained DNA fragments were end-repaired and electrophoresed on preparative agarose gels. The fragments in the desired size range were isolated from the gel, purified and ligated to a linearized, dephosphorylated, blunt-ended plasmid cloning vector (pBluescript II Sk (+)). Example 1 describes the BAC subcloning procedure.

EXAMPLE 1

The cells obtained from three liters overnight culture of each BAC clone were treated by alkaline lysis using conventional techniques to obtain the BAC DNA containing the genomic DNA inserts. After centrifugation of the BAC DNA in a cesium chloride gradient, ca. 50 µg of BAC DNA was purified. 5–10 µg of BAC DNA was sonicated using three distinct conditions, to obtain fragments of the desired size. The fragments were treated in a 50 µl volume with two units of Vent polymerase for 20 min at 70° C., in the presence of the four deoxytriphosphates (100 µM). The resulting blunt-ended fragments were separated by electrophoresis on low-melting point 1% agarose gels (60 Volts for 3 hours). The fragments were excised from the gel and treated with agarase. After chloroform extraction and dialysis on Microcon 100 columns, DNA in solution was adjusted to a 100 ng/µl concentration. A ligation was performed overnight by adding 100 ng of BAC fragmented DNA to 20 ng of pBluescript II Sk (+) vector DNA linearized by enzymatic digestion, and treated by alkaline phosphatase. The ligation reaction was performed in a 10 µl final volume in the presence of 40 units/µl T4 DNA ligase (Epicentre). The ligated products were electroporated into the appropriate cells (ElectroMAX $E. coli$ DH10B cells). IPTG and X-gal were added to the cell mixture, which was then spread on the surface of an ampicillin-containing agar plate. After overnight incubation at 37° C., recombinant (white) colonies were randomly picked and arrayed in 96 well microplates for storage and sequencing.

Partial Sequencing of BACs

At least 30 of the obtained BAC clones were sequenced by the end pair-wise method (500 bp sequence from each end) using a dye-primer cycle sequencing procedure. Pair-wise sequencing was performed until a map allowing the relative positioning of selected markers along the corresponding DNA region was established. Example 2 describes the sequencing and ordering of the BAC inserts.

EXAMPLE 2

The subclone inserts were amplified by PCR on overnight bacterial cultures, using vector primers flanking the insertions. The insert extremity sequences (on average 500 bases at each end) were determined by fluorescent automated sequencing on ABI 377 sequencers, with a ABI Prism DNA Sequencing Analysis software (2.1.2 version).

The sequence fragments from BAC subclones were assembled using Gap4 software from R. Staden (Bonfield et al. 1995). This software allows the reconstruction of a single sequence from sequence fragments. The sequence deduced from the alignment of different fragments is called the consensus sequence. We used directed sequencing techniques (primer walking) to complete sequences and link contigs.

Figure 1:
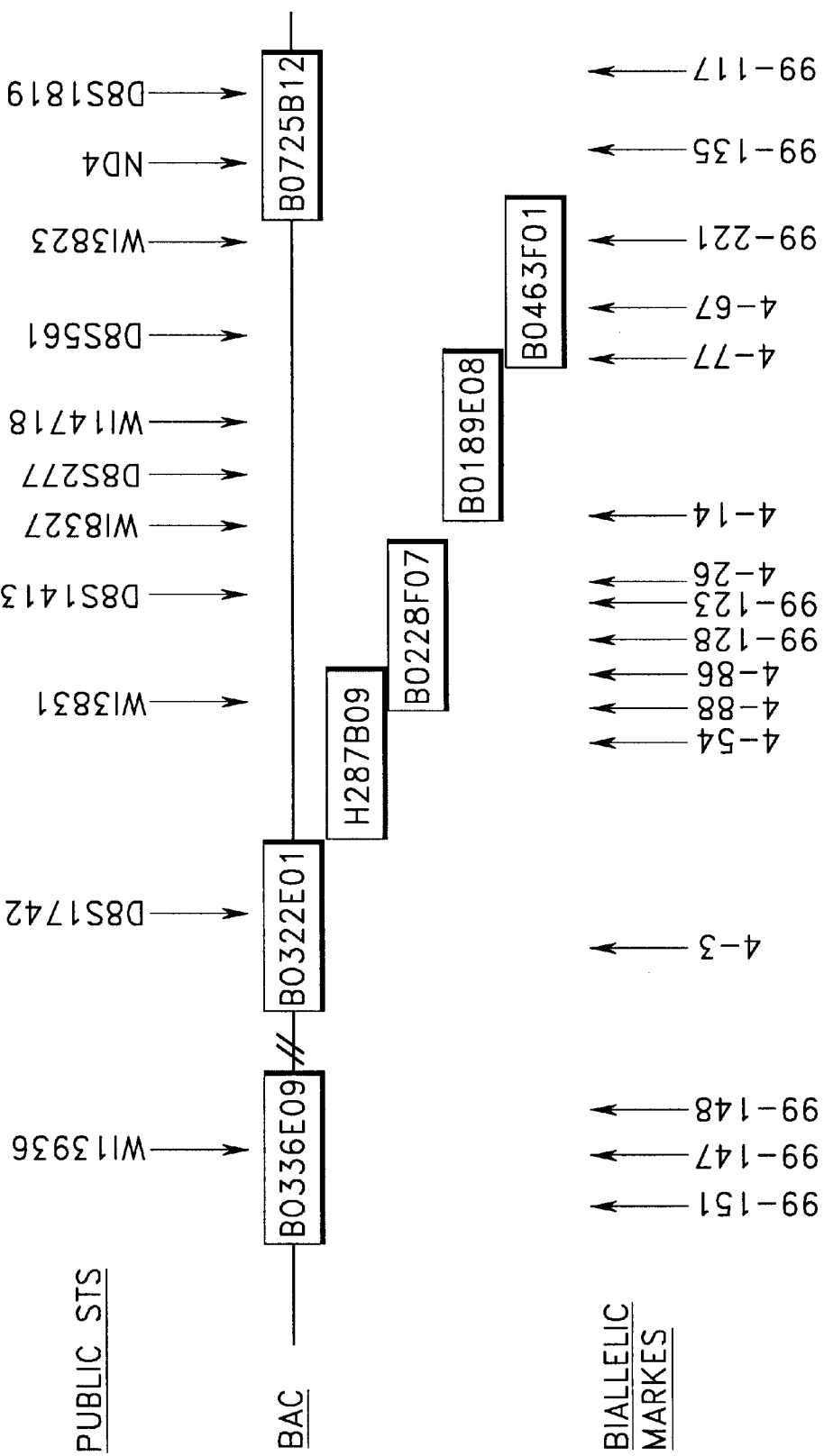
FIG. 1 is a diagram showing the BAC contig containing the PG1 gene and the positions of biallelic markers along the contig.

FIG. 1 shows the overlapping BAC subclones (labeled BAC) which make up the assembled contig and the positions of the publicly known STS markers along the contig.

Identification of Biallelic Markers Lying Along the BAC Contig

Following assembly of the BAC contig, biallelic markers lying along the contig were then identified. Given that the assessed distribution of informative biallelic markers in the human genome (biallelic polymorphisms with a heterozygosity rate higher than 42%) is one in 2.5 to 3 kb, six 500 bp genomic fragments have to be screened in order to identify 1 biallelic marker. Six pairs of primers per potential marker, each one defining a ca. 500 bp amplification fragment, were derived from the above mentioned BAC partial sequences. All primers contained a common upstream oligonucleotide tail enabling the easy systematic sequencing of the resulting amplification fragments. Amplification of each BAC-derived sequence was carried out on pools of DNA from ca. 100 individuals. The conditions used for the polymerase chain reaction were optimized so as to obtain more than 95% of PCR products giving 500bp-sequence reads.

The amplification products from genomic PCR using the oligonucleotides derived from the BAC subclones were subjected to automated dideoxy terminator sequencing reactions using a dye-primer cycle sequencing protocol. Following gel image analysis and DNA sequence extraction, sequence data were automatically processed with appropriate software to assess sequence quality and to detect the presence of biallelic sites among the pooled amplified fragments. Biallelic sites were systematically verified by comparing the sequences of both strands of each pool.

The detection limit for the frequency of biallelic polymorphisms detected by sequencing pools of 100 individuals is 0.3+/−0.05 for the minor allele, as verified by sequencing pools of known allelic frequencies. Thus, the biallelic markers selected by this method will be "informative biallelic markers" since they have a frequency of 0.3 to 0.5 for the minor allele and 0.5 to 0.7 for the major allele, therefore an average heterozygosity rate higher than 42%.

Example 3 describes the preparation of genomic DNA samples from the individuals screened to identify biallelic markers.

EXAMPLE 3

The population used in order to generate biallelic markers in the region of interest consisted of ca. 100 unrelated individuals corresponding to a French heterogeneous population.

DNA was extracted from peripheral venous blood of each donor as follows.

30 ml of blood were taken in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent steps described below.

GDNA Amplification

Once each BAC was isolated, pairs of primers, each one defining a 500 bp-amplification fragment, were designed. Each of the primers contained a common oligonucleotide tail upstream of the specific bases targeted for amplification, allowing the amplification products from each set of primers to be sequenced using the common sequence as a sequencing primer. The primers used for the genomic amplification of sequences derived from BACs were defined with the OSP software (Hillier L. and Green P. Methods Appl., 1991, 1: 124-8). The synthesis of primers was performed following the phosphoramidite method, on a GENSET UFPS 24.1 synthesizer.

Example 4 provides the procedures used in the amplification reactions.

EXAMPLE 4

The amplification of each sequence was performed by PCR (Polymerase Chain Reaction) as follows:

| | |
|---|---|
| final volume | 50 µl |
| genomic DNA | 100 ng |
| MgCl$_2$ | 2 mM |
| dNTP (each) | 200 µM |
| primer (each) | 7.5 pmoles |
| Ampli Taq Gold DNA polymerase (Perkin) | 1 unit |
| PCR buffer (10X = 0.1 M Tris HCl pH 8.3, 0.5 M KCl) | 1X. |

The amplification was performed on a Perkin Elmer 9600 Thermocycler or MJ Research PTC200 with heating lid. After heating at 94° C. for 10 minutes, 35 cycles were performed. Each cycle comprised: 30 sec at 94° C., 1 minute at 55° C., and 30 sec at 72° C. For final elongation, 7 minutes at 72° C. ended the amplification.

The obtained quantity of amplification products was determined on 96-well microtiter plates, using a fluorimeter and Picogreen as intercalating agent (Molecular Probes).

The sequences of the amplification products were determined for each of the approximately 100 individuals from whom genomic DNA was obtained. Those amplification products which contained biallelic markers were identified.

FIG. 1 shows the locations of the biallelic markers along the 8p23 BAC contig. This first set of markers corresponds to a medium density map of the candidate locus, with an intermarker distance averaging 50 kb–150 kb.

A second set of biallelic markers was then generated as described above in order to provide a very high-density map of the region identified using the first set of markers which can be used to conduct association studies, as explained below. The high density map has markers spaced on average every 2–50 kb.

The biallelic markers were then used in association studies as described below.

Collection of DNA Samples from Affected and Non-affected Individuals

Prostate cancer patients were recruited according to clinical inclusion criteria based on pathological or radical prostatectomy records. Control cases included in this study were both ethnically- and age-matched to the affected cases; they were checked for both the absence of all clinical and biological criteria defining the presence or the risk of prostate cancer, and for the absence of related familial prostate cancer cases. Both affected and control individuals corresponded to unrelated cases.

The two following pools of independent individuals were used in the association studies. The first pool, comprising individuals suffering from prostate cancer, contained 185 individuals. Of these 185 cases of prostate cancer, 45 cases were sporadic and 140 cases were familial. The second pool, the control pool, contained 104 non-diseased individuals.

Haplotype analysis was conducted using additional diseased (total samples: 281) and control samples (total samples: 130), from individuals recruited according to similar criteria.

Genotyping Affected and Control Individuals

The general strategy to perform the association studies was to individually scan the DNA samples from all individuals in each of the two populations described above in order to establish the allele frequencies of the above described biallelic markers in each of these populations.

Allelic frequencies of the above-described biallelic markers in each population were determined by performing microsequencing reactions on amplified fragments obtained by genomic PCR performed on the DNA samples from each individual.

DNA samples and amplification products from genomic PCR were obtained in similar conditions as those described above for the generation of biallelic markers, and subjected to automated microsequencing reactions using fluorescent ddNTPs (specific fluorescence for each ddNTP) and the appropriate oligonucleotide microsequencing primers which hybridized just upstream of the polymorphic base. Once specifically extended at the 3' end by a DNA polymerase using the complementary fluorescent dideoxynucleotide analog (thermal cycling), the primer was precipitated to remove the unincorporated fluorescent ddNTPs. The reaction products were analyzed by electrophoresis on ABI 377 sequencing machines.

Example 5 describes one microsequencing procedure.

EXAMPLE 5

5 µl of PCR products in a microtiter plate were added to 5 µl purification mix {2U SAP (Amersham); 2U Exonuclease I (Amersham); 1 µl SAP10× buffer: 400 mM Tris-HCl pH8, 100 mM MgCl2; H2O final volume 5 µl}. The reaction mixture was incubated 30 minutes at 37° C., and denatured 10 minutes at 94° C. After 10 sec centrifugation, the microsequencing reaction was performed on line with the whole purified reaction mixture (10 µl) in the microplate using 10 pmol microsequencing oligonucleotide (23 mers, GENSET, crude synthesis, 5 OD), 0.5 U Thermosequenase (Amersham), 1.25 µl Thermosequenase 16× buffer (Amersham), both of the fluorescent ddNTPs (Perkin Elmer) corresponding to the polymorphism {0.025 µl ddTTP and ddCTP, 0.05 µl ddATP and ddGTP}, H2O to a final volume of 20 µl. A PCR program on a GeneAmp 9600 thermocycler was carried out as follows: 4 minutes at 94° C.; 5 sec at 55° C./10 sec at 94° C. for 20 cycles. The reaction product was incubated at 4° C. until precipitation. The microtiter plate was centrifuged 10 sec at 1500 rpm. 19 µl MgCl2 2 mM and 55 µl 100% ethanol were added in each well. After 15 minute incubation at room temperature, the microtiter plate was centrifuged at 3300 rpm 15 minutes at 4° C. Supernatants were discarded by inverting the microtitre plate on a box folded to proper size and by centrifugation at 300 rpm 2 minutes at 4° C. afterwards. The microplate was then dried 5 minutes in a vacuum drier. The pellets were resuspended in 2.5 µl formamide EDTA loading buffer (0.7 µl of 9 µg/µl dextran blue in 25 mM EDTA and 1.8 µl formamide). A 10% polyacrylamide gel/12 cm/64 wells was pre-run for 5 minutes on a 377 ABI 377 sequencer. After 5 minutes denaturation at 100° C., 0.8 µl of each microsequencing reaction product was loaded in each well of the gel. After migration (2 h 30 for 2 microtiter plates of PCR products per gel), the fluorescent signals emitted by the incorporated ddNTPs were analyzed on the ABI 377 sequencer using the GENES-CAN software (Perkin Elmer). Following gel analysis, data were automatically processed with a software that allowed the determination of the alleles of biallelic markers present in each amplified fragment.

I.D. INITIAL ASSOCIATION STUDIES

Figure 2:
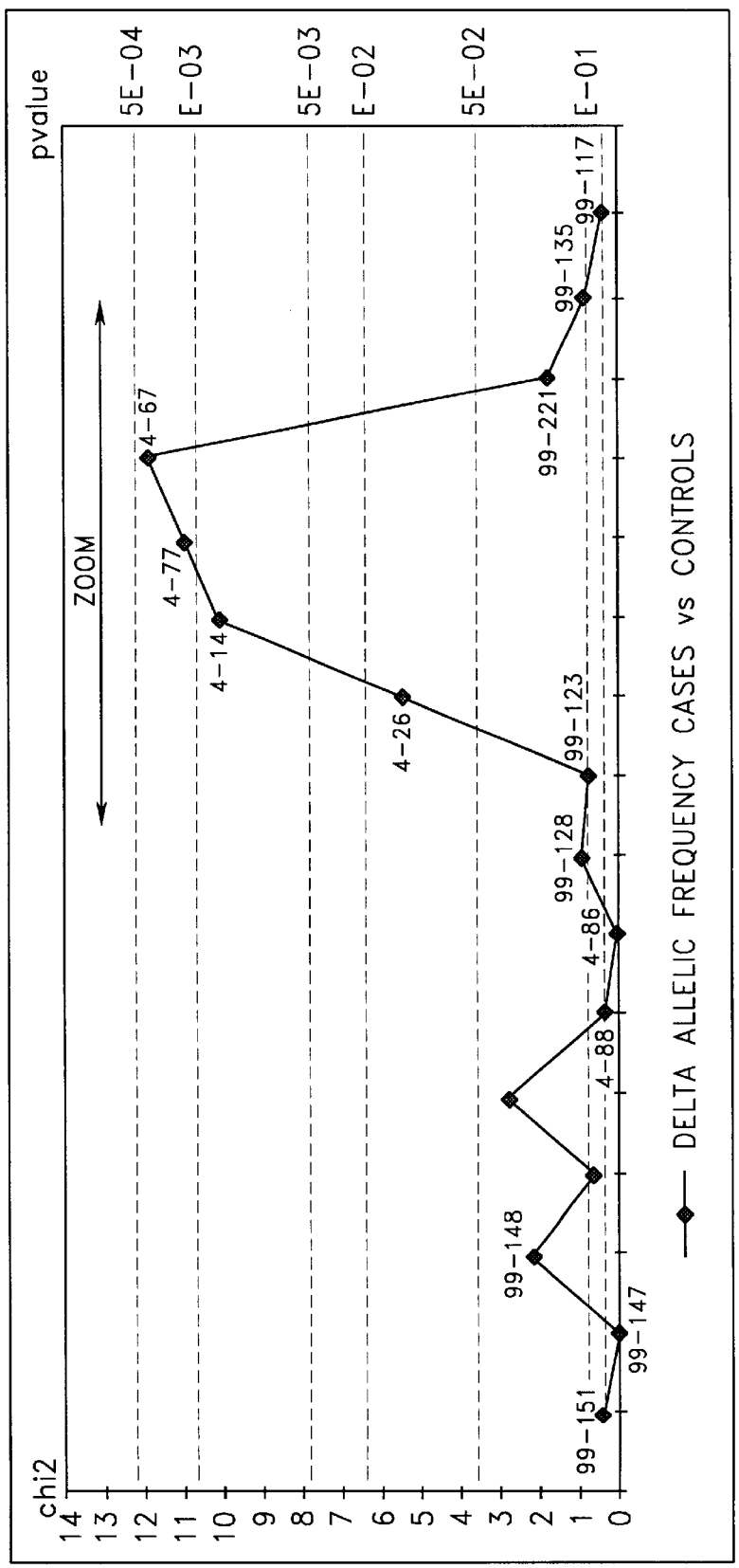
FIG. 2 is a graph showing the results of the first screening of a prostate cancer association study and the significance of various biallelic markers as measured by their chi squared and p-values for a low density set of markers.

Association studies were run in two successive steps. In a first step, a rough localization of the candidate gene was achieved by determining the frequencies of the biallelic markers of FIG. 1 in the affected and unaffected populations. The results of this rough localization are shown in FIG. 2. This analysis indicated that a gene responsible for prostate cancer was located near the biallelic marker designated 4–67.

In a second phase of the analysis, the position of the gene responsible for prostate cancer was further refined using the very high density set of markers described above. The results of this localization are shown in FIG. 3.

Figure 3:
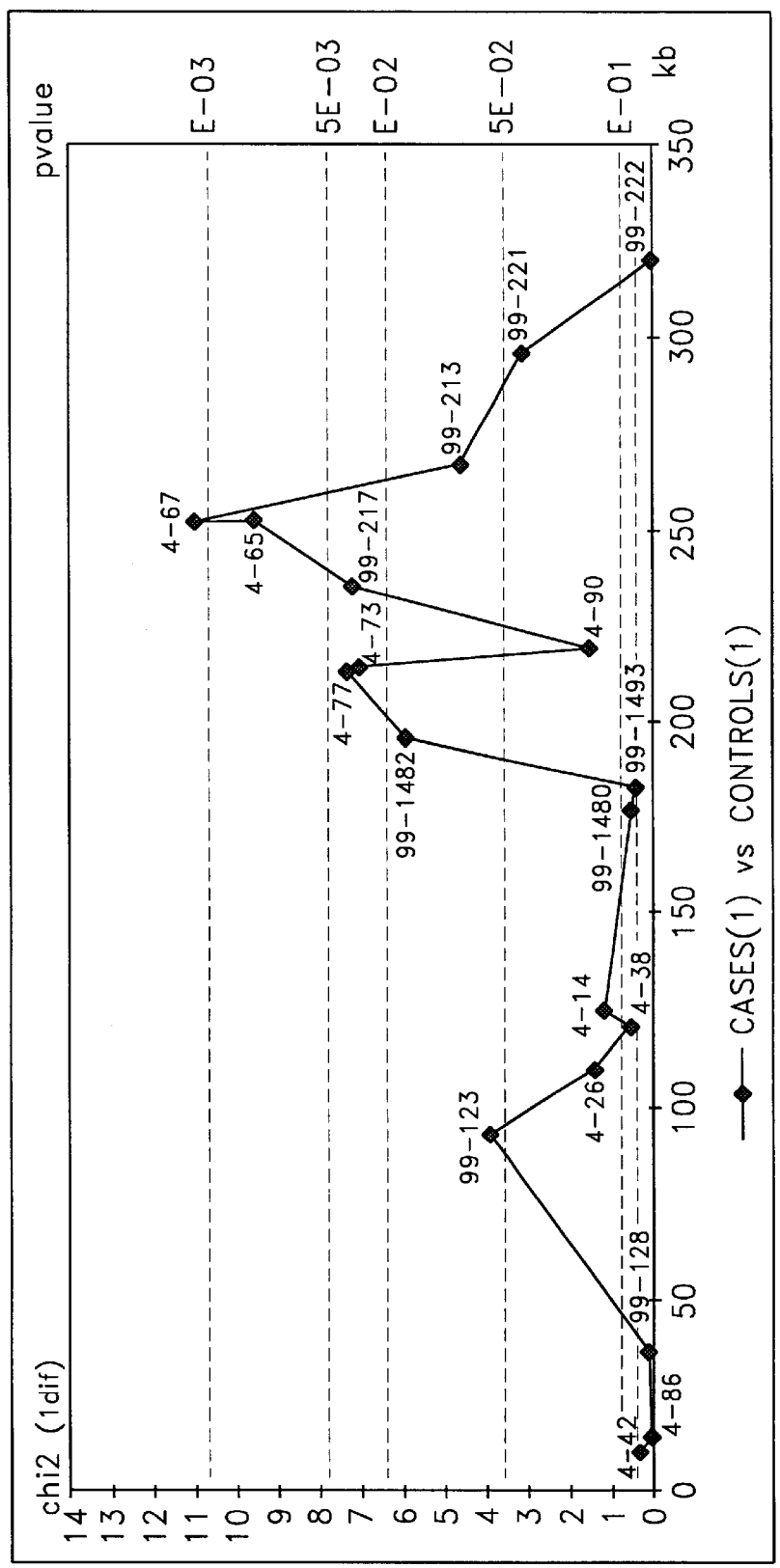
FIG. 3 is a graph showing the results of the first screening of a prostate cancer association study and the significance of various biallelic markers as measured by their chi squared and p-values for a higher density set of markers.

As shown in FIG. 3, the second phase of the analysis confirmed that the gene responsible for prostate cancer was near the biallelic marker designated 4–67, most probably within a ca. 150 kb region comprising the marker.

Haplotype Analysis

The allelic frequencies of each of the alleles of biallelic markers 99-123, 4-26, 4-14, 4-77, 99-217, 4-67, 99-213, 99-221, and 99-135 (SEQ ID NOs: 21–38) were determined in the affected and unaffected populations. Table 1 lists the internal identification numbers of the markers used in the haplotype analysis (SEQ ID NOs: 21–38), the alleles of each marker, the most frequent allele in both unaffected individuals and individuals suffering from prostate cancer, the least frequent allele in both unaffected individuals and individuals suffering from prostate cancer, and the frequencies of these alleles in each population.

Among all the theoretical potential different haplotypes based on 2 to 9 markers, 11 haplotypes showing a strong association with prostate cancer were selected. The results of these haplotype analyses are shown in FIG. 4.

FIGS. 2, 3, and 4 aggregate linkage analysis results with sequencing results which permitted the physical order and/or the distance between markers to be estimated.

Figure 5A:
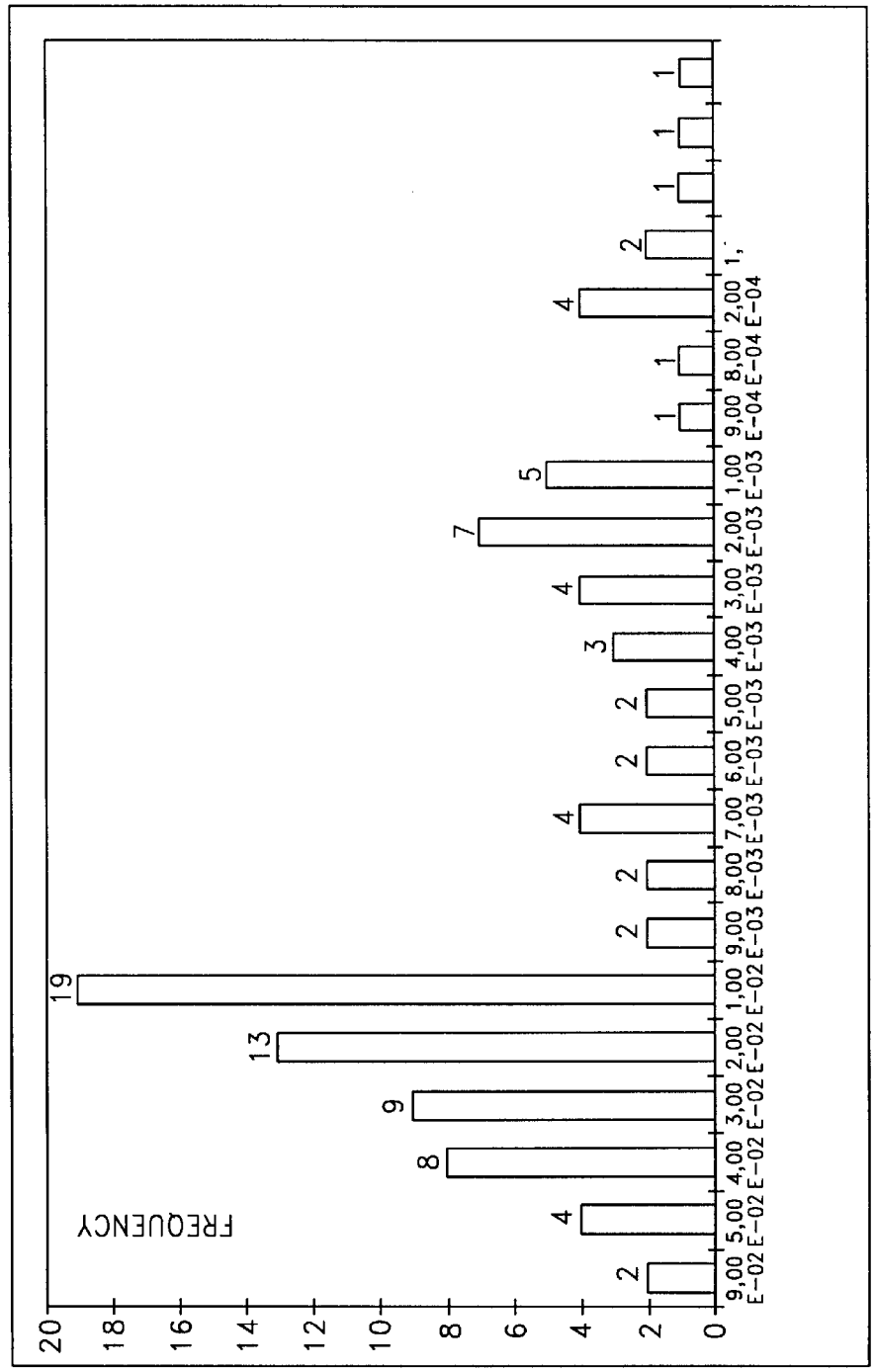
FIG. 5 is a bar graph demonstrating the results of an experiment evaluating the significance (p-values) of the haplotype analysis shown in FIG. 4.
Figure 5B:
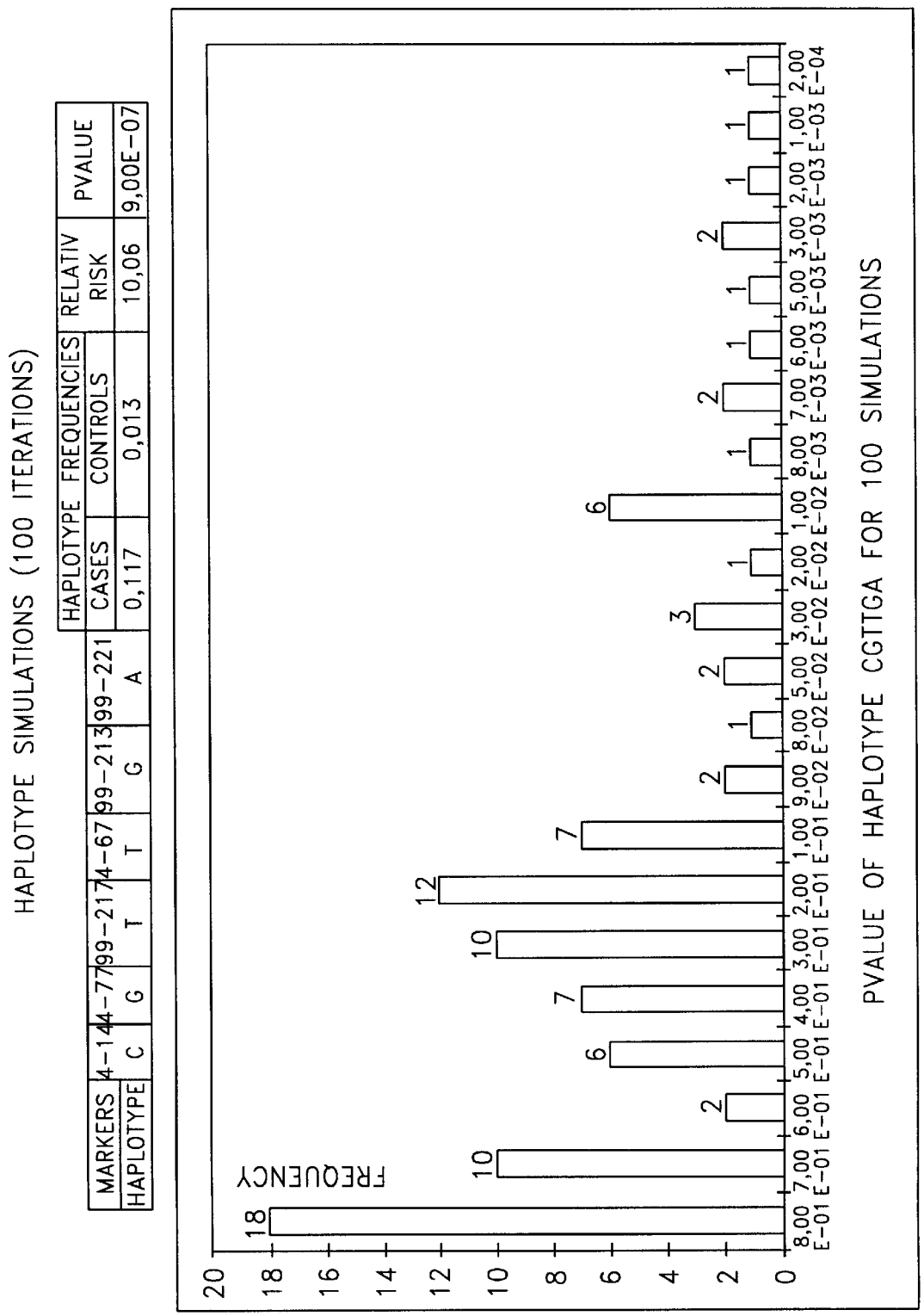

The significance of the values obtained in FIG. 4 are underscored by the following results of computer simulations. For the computer simulations, the data from the affected individuals and the unaffected controls were pooled and randomly allocated to two groups which contained the same number of individuals as the affected and unaffected groups used to compile the data summarized in FIG. 4. A haplotype analysis was run on these artificial groups for the six markers included in haplotype 5 of FIG. 4. This experiment was reiterated 100 times and the results are shown in FIG. 5. Among 100 iterations, only 5% of the obtained haplotypes are present with a p-value below $1 \times 10^{-4}$ as compared to the p-value of $9 \times 10^{-7}$ for haplotype 5 of FIG. 4. Furthermore, for haplotype 5 of FIG. 4, only 6% of the obtained haplotypes have a significance level below $5 \times 10^{-3}$, while none of them show a significance level below $5 \times 10^{-5}$.

Thus, using the data of FIG. 4 and evaluating the associations for single maker alleles or for haplotypes will permit estimation of the risk a corresponding carrier has to develop prostate cancer. Significance thresholds of relative risks will be adapted to the reference sample population used.

The diagnostic techniques may employ a variety of methodologies to determine whether a test subject has a biallelic marker pattern associated with an increased risk of developing prostate cancer or suffers from prostate cancer resulting from a mutant PG1 allele. These include any method enabling the analysis of individual chromosomes for haplotyping, such as family studies, single sperm DNA analysis or somatic hybrids.

In each of these methods, a nucleic acid sample is obtained from the test subject and the biallelic marker pattern for one or more of the biallelic markers listed in FIGS. 4, 6A and 6B is determined. The biallelic markers listed in FIG. 6A are those which were used in the haplotype analysis of FIG. 4. The first column of FIG. 6A lists the BAC clones in which the biallelic markers lie. The second column of FIG. 6A lists the internal identification number of the marker. The third column of FIG. 6A lists the sequence identification number for a first allele of the biallelic markers. The fourth column of FIG. 6A lists the sequence identification number for a second allele of the biallelic markers. For example, the first allele of the biallelic marker 99-123 has the sequence of SEQ ID NO:21 and the second allele of the biallelic marker has the sequence of SEQ ID NO: 30.

The fifth column of FIG. 6A lists the sequences of upstream primers which is used to generate amplification products containing the polymorphic bases of the biallelic markers. The sixth column of FIG. 6A lists the sequence identification numbers for the upstream primers.

The seventh column of FIG. 6A lists the sequences of downstream primers which is used to generate amplification products containing the polymorphic bases of the biallelic markers. The eighth column of FIG. 6A lists the sequence identification numbers for the downstream primers.

The ninth column of FIG. 6A lists the position of the polymorphic base in the amplification products generated using the upstream and downstream primers. The tenth column lists the identities of the polymorphic bases found at the polymorphic positions in the biallelic markers. The eleventh and twelfth columns list the locations of microsequencing primers in the biallelic markers which can be used to determine the identities of the polymorphic bases.

In addition to the biallelic markers of SEQ ID NOs: 21–38, other biallelic markers (designated 99-1482, 4-73, 4-65) have been identified which are closely linked to one or more of the biallelic markers of SEQ ID NOs: 21–38, SEQ ID NOs: 57–62, and the PG1 gene. These biallelic markers include the markers of SEQ ID NOs: 57–62, which are listed in FIG. 6B. The columns in FIG. 6B are identical to the corresponding columns in FIG. 6A. SEQ ID NOs: 58, 59, 61, and 62 lie within the PG1 gene of SEQ ID NO:1 at the positions indicated in the accompanying Sequence Listing.

Genetic analysis of these additional biallelic markers is performed as follows. Nucleic acid samples are obtained from individuals suffering from prostate cancer and unaffected individuals. The frequencies at which each of the two alleles occur in the affected and unaffected populations is determined using the methodologies described above. Association values are calculated to determine the correlation between the presence of a particular allele or spectrum of alleles and prostate cancer. The markers of SEQ ID NOs: 21–38 may also be included in the analysis used to calculate the risk factors. The markers of SEQ ID NOs: 21–38 and SEQ ID NOs: 57–62 is used in diagnostic techniques, such as those described below, to determine whether an individual is at risk for developing prostate cancer or suffers from prostate cancer as a result of a mutation in the PG1 gene.

Example 6 describes methods for determining the biallelic marker pattern.

EXAMPLE 6

A nucleic acid sample is obtained from an individual to be tested for susceptibility to prostate cancer or PG1 mediated prostate cancer. The nucleic acid sample is an RNA sample or a DNA sample.

A PCR amplification is conducted using primer pairs which generate amplification products containing the polymorphic nucleotides of one or more biallelic markers associated with prostate cancer-related forms of PG1, such as the biallelic markers of SEQ ID NOs: 21–38, SEQ ID NOs: 57–62, biallelic markers which are in linkage disequilibrium with the biallelic markers of SEQ ID NOs: 21–38, SEQ ID NOs: 57–62, biallelic markers in linkage disequilibrium with the PG1 gene, or combinations thereof. In some embodiments, the PCR amplification is conducted using primer pairs which generate amplification products containing the polymorphic nucleotides of several biallelic markers. For example, in one embodiment, amplification products containing the polymorphic bases of several biallelic markers selected from the group consisting of SEQ ID NOs: 21–38, SEQ ID NOs: 57–62, and biallelic markers which are in linkage disequilibrium with the biallelic markers of SEQ ID NOs: 21–38, SEQ ID NOs: 57–62 or with the PG1 gene is generated. In another embodiment, amplification products containing the polymorphic bases of two or more biallelic markers selected from the group consisting of SEQ ID NOs: 21–38, SEQ ID NOs: 57–62, and biallelic markers which are in linkage disequilibrium with the biallelic markers of SEQ ID NOs: 21–38, SEQ ID NOs: 57–62 or with the PG1 gene is generated. In another embodiment, amplification products containing the polymorphic bases of five or more biallelic markers selected from the group consisting of SEQ ID NOs: 21–38, SEQ ID NOs: 57–62, and biallelic markers which are in linkage disequilibrium with the biallelic markers of SEQ ID NOs: 21–38, SEQ ID NOs: 57–62 or with the PG1 gene is generated. In another embodiment, amplification products containing the polymorphic bases of more than five of the biallelic markers selected from the group consisting of SEQ ID NOs: 21–38, SEQ ID NOs: 57–62, and biallelic markers which are in linkage disequilibrium with the biallelic markers of SEQ ID NOs: 21–38, SEQ ID NOs: 57–62 or with the PG1 gene is generated.

For example, the primers used to generate the amplification products may comprise the primers listed in FIG. 6A or 6B (SEQ ID NOs: 39–56 and SEQ ID NOs: 63–68). FIG. 6A and FIG. 6B provide exemplary primers which is used in the amplification reactions and the identities and locations of the polymorphic bases in the amplification products which are produced with the exemplary primers. The sequences of each of the alleles of the biallelic markers resulting from amplification using the primers in FIGS. 6A and 6B are listed in the accompanying Sequence Listing as SEQ ID NOs:21–38 and 57–62.

The PCR primers is oligonucleotides of 10, 15, 20 or more bases in length which enable the amplification of the polymorphic site in the markers. In some embodiments, the amplification product produced using these primers is at least 100 bases in length (i.e. 50 nucleotides on each side of the polymorphic base). In other embodiments, the amplification product produced using these primers is at least 500 bases in length (i.e. 250 nucleotides on each side of the polymorphic base). In still further embodiments, the amplification product produced using these primers is at least 1000 bases in length (i.e. 500 nucleotides on each side of the polymorphic base).

It will be appreciated that the primers listed in FIGS. 6A and 6B are merely exemplary and that any other set of primers which produce amplification products containing the polymorphic nucleotides of one or more of the biallelic markers of SEQ ID NOs. 21–38 and SEQ ID NOs: 57–62 or biallelic markers in linkage disequilibrium with the sequences of SEQ ID NOs. 21–38 and SEQ ID NOs: 57–62 or with the PG1 gene, or a combination thereof is used in the diagnostic methods.

Following the PCR amplification, the identities of the polymorphic bases of one or more of the biallelic markers of SEQ ID NOs: 21–38 and SEQ ID NOs: 57–62, or biallelic markers in linkage disequilibrium with the sequences of SEQ ID NOs. 21–38 and SEQ ID NOs: 57–62 or with the PG1 gene, or a combination thereof, are determined. The identities of the polymorphic bases is determined using the microsequencing procedures described in Example 5 above and the microsequencing primers listed as features in the sequences of SEQ ID NOs: 21–38 and SEQ ID NOs: 57–62. It will be appreciated that the microsequencing primers listed as features in the sequences of SEQ ID NOs: 21–38 and SEQ ID NOs: 57–62 are merely exemplary and that any primer having a 3' end near the polymorphic nucleotide, and preferably immediately adjacent to the polymorphic nucleotide, is used. Alternatively, the microsequencing analysis is performed as described in Pastinen et al., Genome Research 7:606–614 (1997), which is described in more detail below.

Alternatively, the PCR product is completely sequenced to determine the identities of the polymorphic bases in the biallelic markers. In another method, the identities of the polymorphic bases in the biallelic markers is determined by hybridizing the amplification products to microarrays containing allele specific oligonucleotides specific for the polymorphic bases in the biallelic markers. The use of microarrays comprising allele specific oligonucleotides is described in more detail below.

It will be appreciated that the identities of the polymorphic bases in the biallelic markers is determined using techniques other than those listed above, such as conventional dot blot analyses.

Nucleic acids used in the above diagnostic procedures may comprise at least 10 consecutive nucleotides in the biallelic markers of SEQ ID NOs: 21–38 and SEQ ID NOs: 57–62 or the sequences complementary thereto. Alternatively, the nucleic acids used in the above diagnostic procedures may comprise at least 15 consecutive nucleotides in the biallelic markers of SEQ ID NOs: 21–38 and SEQ ID NOs: 57–62 or the sequences complementary thereto In some embodiments, the nucleic acids used in the above diagnostic procedures may comprise at least 20 consecutive nucleotides in the biallelic markers of SEQ ID NOs: 21–38 and SEQ ID NOs: 57–62 or the sequences complementary thereto. In still other embodiments, the nucleic acids used in the above diagnostic procedures may comprise at least 30 consecutive nucleotides in the biallelic markers of SEQ ID NOs: 21–38 and SEQ ID NOs: 57–62 or the sequences complementary thereto. In further embodiments, the nucleic acids used in the above diagnostic procedures may comprise more than 30 consecutive nucleotides in the biallelic markers of SEQ ID NOs: 21–38 and SEQ ID NOs: 57–62 or the sequences complementary thereto. In still further embodiments, the nucleic acids used in the above diagnostic procedures may comprise the entire sequence of the biallelic markers of SEQ ID NOs: 21–38 and SEQ ID NOs: 57–62 or the sequences complementary thereto.

I.E. IDENTIFICATION AND SEQUENCING, OF THE PG1 GENE, AND LOCALIZATION OF THE PG1 PROTEIN

The above haplotype analysis indicated that 171 kb of genomic DNA between biallelic markers 4–14 and 99-221 totally or partially contains a gene responsible for prostate cancer. Therefore, the protein coding sequences lying within this region were characterized to locate the gene associated with prostate cancer. This analysis, described in further detail below, revealed a single protein coding sequence in the 171 kb, which was designated as the PG1 gene.

Template DNA for sequencing the PG1 gene was obtained as follows. BACs 189EO8 and 463FO1 were subcloned as previously described Plasmid inserts were first amplified by PCR on PE 9600 thermocyclers (Perkin-Elmer), using appropriate primers, AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers were labeled with the JOE, FAM, ROX and TAM. R. A dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data obtained as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector oligonucleotides were automatically removed from the sequence. However, the resulting sequence may contain 1 to 5 bases belonging to the vector sequences at their 5' end. If needed, these can easily be removed on a case by case basis.

The genomic sequence of the PG1 gene is provided in the accompanying Sequence Listing and is designated as SEQ ID NO: 1.

Potential exons in BAC-derived human genomic sequences were located by homology searches on protein, nucleic acid and EST (Expressed Sequence Tags) public databases. Main public databases were locally reconstructed. The protein database, NRPU (Non-redundant Protein Unique) is formed by a non-redundant fusion of the Genpept (Benson D. A. et al., Nucleic Acids Res. 24: 1–5 (1996), Swissprot (Bairoch, A. and Apweiler, R, Nucleic Acids Res. 24: 21–25 (1996) and PIR/NBRF (George, D. G. et al., Nucleic Acids Res. 24:17–20(1996) databases. Redundant data were eliminated by using the NRDB software (Benson et al., supra) and internal repeats were masked with the XNU software (Benson et al., supra). Homologies found using the NRPU database allowed the identification of sequences corresponding to potential coding exons related to known proteins.

The EST local database is composed by the gbest section (1–9) of GenBank (Benson et al., supra), and thus contains all publicly available transcript fragments. Homologies found with this database allowed the localization of potentially transcribed regions.

The local nucleic acid database contained all sections of GenBank and EMBL (Rodriguez-Tome, P. et al., Nucleic Acids Res. 24: 6–12(1996) except the EST sections. Redundant data were eliminated as previously described.

Similarity searches in protein or nucleic acid databases were performed using the BLAS software (Altschul, S. F. et al., J. Mol. Biol. 215: 403–410 (1990). Alignments were refmed using the Fasta software, and multiple alignments used Clustal W. Homology thresholds were adjusted for each analysis based on the length and the complexity of the tested region, as well as on the size of the reference database.

Potential exon sequences identified as above were used as probes to screen cDNA libraries. Extremities of positive clones were sequenced and the sequence stretches were positioned on the genomic sequence of SEQ ID NO:1. Primers were then designed using the results from these alignments in order to enable the PG1 cloning procedure described below.

Cloning PG1 cDNA

PG1 cDNA was obtained as follows. 4 µl of ethanol suspension containing 1 mg of human prostate total RNA (Clontech laboratories, Inc., Palo Alto, USA; catalogue N. 64038-1, lot 7040869) was centrifuged, and the resulting pellet was air dried for 30 minutes at room temperature.

First strand cDNA synthesis was performed using the AdvantageTM RT-for-PCR kit (Clontech laboratories, Inc., Palo Alto, USA; catalogue N. K1402-1). 1 µl of 20 mM solution of primer PGRT32: TTTTTTTTTTTTTTTTTTGAAAT(SEQ ID NO:10) wasaddedto 12.5 µl of RNA solution in water, heated at 74° C. for two and a half minutes and rapidly quenched in an ice bath. 10 µl of 5×RT buffer (50 mM Tris-HCl, pH 8.3, 75 mM KCl, 3 mM MgCl2), 2.5 µl of DNTP mix (10 mM each), 1.25 µl of human recombinant placental RNA inhibitor were mixed with 1 ml of MMLV reverse transcriptase (200 units). 6.5 µl of this solution were added to RNA-primer mix and incubated at 42° C. for one hour. 80 µl of water were added and the solution was incubated at 94° C. for 5 minutes.

5 µl of the resulting solution were used in a Long Range PCR reaction with hot start, in 50 µl final volume, using 2 units of rtTHXL, 20 pmol/µl of each of GC1.5p.1: CTGTC-CCTGGTGCTCCACACGTACTC (SEQ ID NO:6) or GC1.5p2 TGGTGCTCCACACGTACTCCATGCGC (SEQ ID NO: 7) and GC1.3p: CTTGCCTGCTGGAGACACA-GAATTTCGATAGCAC (SEQ ID NO:9) primers with 35 cycles of elongation for 6 minutes at 67° C. in thermocycler.

The sequence of the PG1 cDNA obtained as described above (SEQ ID NO 3) is provided in the accompanying Sequence Listing. Results of Northern blot analysis of prostate mRNAs support the existence of a major PG1 cDNA having a 5–6 kb length.

Characterization of the PG1 Gene

The intron/exon structure of the gene was deduced by aligning the mRNA sequence from the cDNA of SEQ ID NO:3 and the genomic DNA sequence of SEQ ID NO: 1.

Figure 8A:
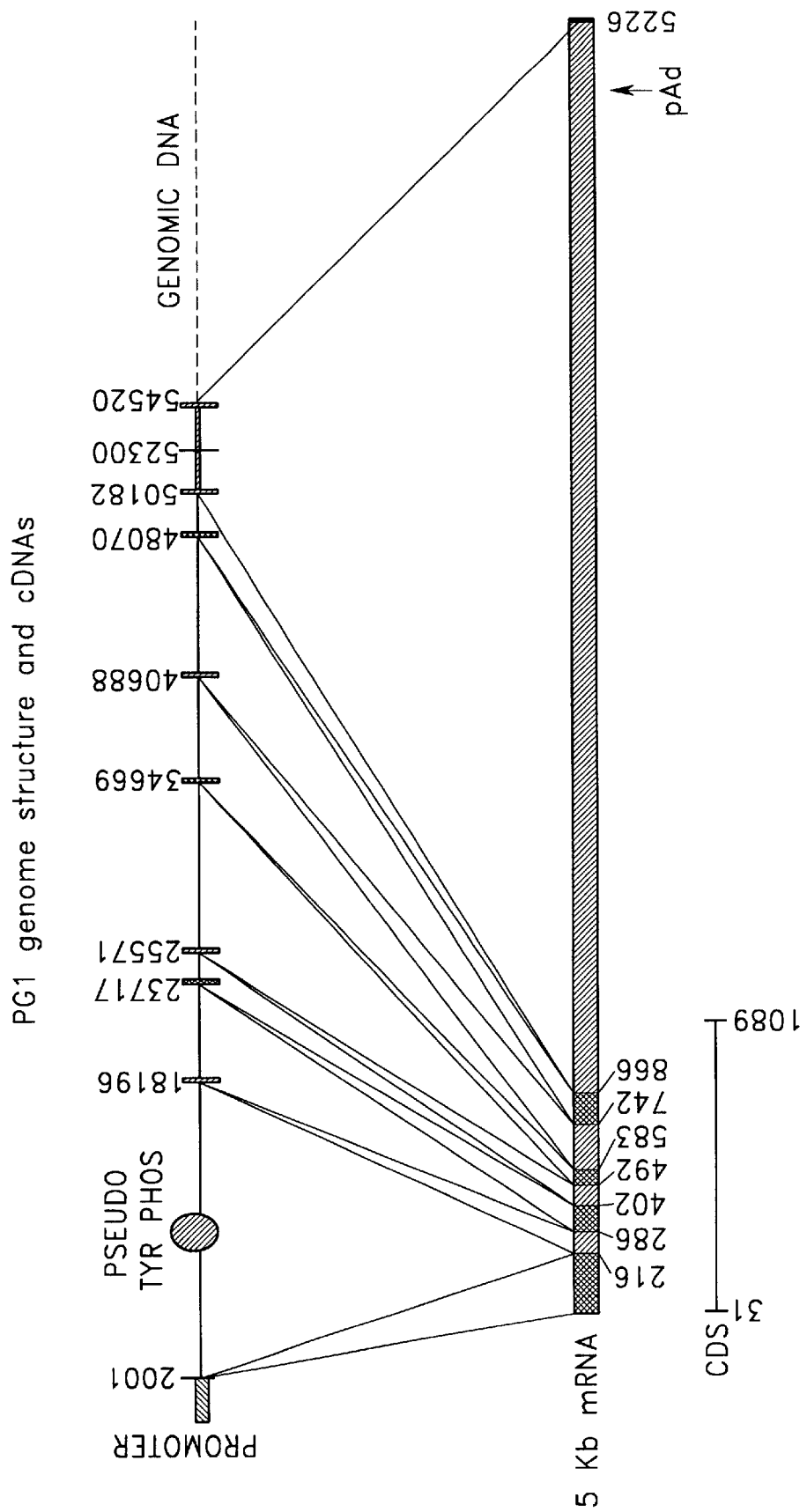
FIG. 8A is a diagram showing the genomic structure of PG1 in comparison with its most abundant mRNA transcript.
Figure 8B:
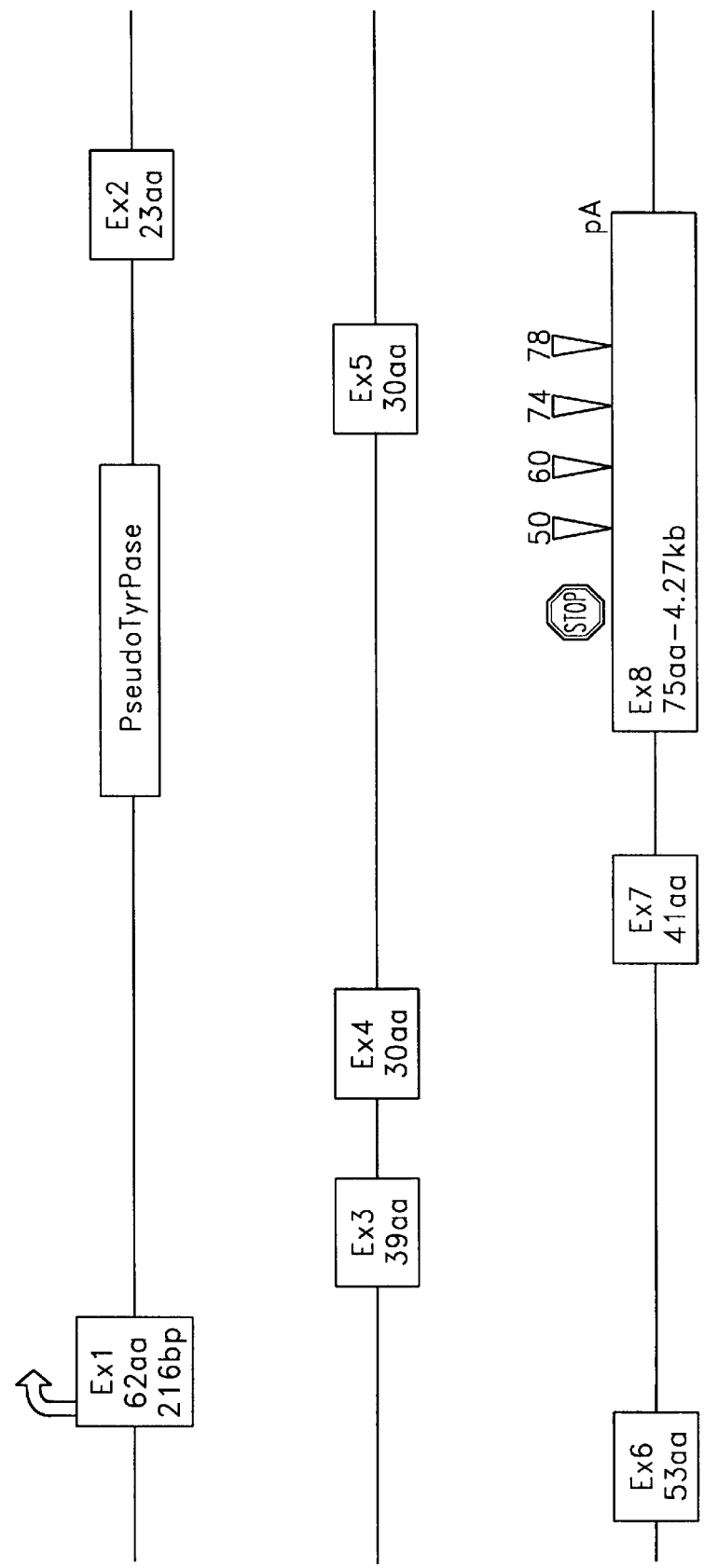
FIG. 8B is a more detailed diagram showing the genomic structure of PG1, including exons and introns.

The positions of the introns and exons in the PG1 genomic DNA are provided in FIGS. 7 and 8. FIG. 7 lists positions of the start and end nucleotides defining each of the at least 8 exons (labeled Exons A–H) in the sequence of SEQ ID NO: 1, the locations and phases of the 5' and 3' splice sites in the sequence of SEQ ID NO: 1, the position of the stop codon in the sequence of SEQ ID NO: 1, and the position of the polyadenylation site in the sequence of SEQ ID NO: 1. FIG. 8 shows the positions of the exons within the PG1 genomic DNA and the PG1 mRNA, the location of a tyrosine phosphatase retro-pseudogene in the PG1 genomic DNA, the positions of the coding region in the mRNA, and the locations of the polyadenylation signal and polyA stretch in the mRNA.

As indicated in FIGS. 7 and 8, the PG1 gene comprises at least 8 exons, and spans more than 52 kb. The first intron contains a tyrosine phosphatase retropseudogene. A G/C rich putative promoter region lies between nucleotide 1629 and 1870 of SEQ ID NO: 1. A CCAAT box is present at nucleotide 1661 of SEQ ID NO: 1. The promoter region was identified as described in Prestridge, D. S., Predicting Pol II Promoter Sequences Using Transcription Factor Binding Sites, J. Mol. Biol. 249:923–932 (1995).

It is possible that the methionine listed as being the initiating methionine in the PG1 protein sequence of SEQ ID NO: 4 (based on the cDNA sequence of SEQ ID NO: 3) may actually be downstream but in phase with another methionine which acts as the initiating methionine. The genomic DNA sequence of SEQ ID NO: 1 contains a methionine upstream from the methionine at position number 1 of the protein sequence of SEQ ID NO: 4. If the upstream methionine is in fact the authentic initiation site, the sequence of the PG1 protein would be that of SEQ ID NO: 5. This possibility is investigated by determining the exact position of the 5' end of the PG1 mRNA as follows.

One way to determine the exact position of the 5' end of the PG1 mRNA is to perform a 5' RACE reaction using the Marathon-Ready human prostate cDNA kit from Clontech (Catalog. No. PT1156-1). For example, the RACE reaction may employ the PG1 primers PG15RACE196 CAATATCTGGACCCCGGTGTAATTCTC (SEQ ID NO: 8) as the first primer. The second primer in the RACE reaction is PG1-5RACE130 n having the sequence GGTCGTCCAGCGCTTGGTAGAAG (SEQ ID NO: 2). The sequence analysis of the resulting PCR product, or the product obtained with other PG1 specific primers, will give the exact sequence of the initiation point of the PG1 transcript.

Alternatively, the 5' sequence of the PG1 transcript can be determined by conducting a PCR amplification with a series of primers extending from the 5' end of the presently identified coding region. In any event, the present invention contemplates use of PG1 nucleic acids and/or polypeptides coding for or corresponding to either SEQ ID NO:4 or SEQ ID NO:5 or fragments thereof.

It is also possible that alternative splicing of the PG1 gene may result in additional translation products not described above. It is also possible that there are sequences upstream or downstream of the genomic sequence of SEQ ID NO: 1 which contribute to the translation products of the gene. Finally, alternative promoters may result in PG1 derived transcripts other than those described herein.

The promoter activity of the region between nucleotides 1629 and 1870 can be verified as described below. Alternatively, should this region lack promoter activity, the promoter responsible for driving expression of the PG1 gene is identified as described below.

Genomic sequences lying upstream of the PG1 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the PG1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Promoter sequences within the upstream genomic DNA is further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters is defined. If desired, potential individual regulatory sites within the promoter is identified using site directed mutagenesis or linker scanning to obliterate potential transcription factor binding sites within the promoter individually or in combination. The effects of these mutations on transcription levels is determined by inserting the mutations into the cloning sites in the promoter reporter vectors.

Sequences within the PG1 promoter region which are likely to bind transcription factors is identified by homology to known transcription factor binding sites or through conventional mutagenesis or deletion analyses of reporter plasmids containing the promoter sequence. For example, deletions is made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels is further localized using site directed mutagenesis, linker scanning analysis, or other techniques familiar to those skilled in the art.

The promoters and other regulatory sequences located upstream of the PG1 gene is used to design expression vectors capable of directing the expression of an inserted gene in a desired spatial, temporal, developmental, or quantitative manner. For example, since the PG1 promoter is presumably active in the prostate, it can be used to construct expression vectors for directing gene expression in the prostate.

Preferably, in such expression vectors, the PG1 promoter is placed near multiple restriction sites to facilitate the cloning of an insert encoding a protein for which expression is desired downstream of the promoter, such that the promoter is able to drive expression of the inserted gene. The promoter is inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Nucleic acids encoding proteins which interact with sequences in the PG1 promoter is identified using one-hybrid systems such as those described in the manual accompanying the Matchmaker One-Hybrid System kit available from Clontech (Catalog No. K1603-1). Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts is inserted into expression vectors or in vitro transcription vectors. Binding of the polypeptides encoded by the inserts to the promoter DNA is confirmed by techniques familiar to those skilled in the art, such as gel shift analysis or DNAse protection analysis.

Analysis of PG1 Protein Sequence

The PG1 cDNA of SEQ ID NO: 3 encodes a 353 amino-acid protein (SEQ ID NO:4). As indicated in the accompanying Sequence Listing, a Prosite analysis indicated that the PG1 protein has a leucine zipper motif, a potential glycosylation site, 3 potential casein kinase II phosphorylation sites, a potential cAMP dependent protein kinase phosphorylation site, 2 potential tyrosine kinase phosphorylation sites, 4 potential protein kinase C phosphorylation sites, 5 potential N-myristoylation sites, 1 potential tyrosine sulfation site, and one potential amidation site.

A search for membrane associated domains was conducted according to the methods described in Argos, P. et al., Structural Prediction of Membrane-bound Proteins, Elur. J. Biochem. 128:565–575 (1982); Klein et al., Biochimica & Biophysica Acta 815:468–476 (1985); and Eisenberg et al., J. Mol. Biol. 179:125–142 (1984). The search revealed 5 potential transmembrane domains predicted to be integral membrane domains. These results suggest that the PG1 protein is likely to be membrane-associated and is an integral membrane protein.

A homology search was conducted to identify proteins homologous to the PG1 protein. Several proteins were identified which share homology with the PG1 protein. FIG. 9 lists the accession numbers of several proteins which share homology with the PG1 protein in three regions designated box1, box2 and box3.

It will be appreciated that each of the motifs described above is also present in the protein of SEQ ID NO: 5, which would be produced if by translation initiation translated from the potential upstream methionine in the nucleic acid of SEQ ID NO: 1.

As indicated in FIG. 9, a distinctive pattern of homology to box 1, box 2 (SEQ ID NOs: 11–14) and box 3 (SEQ ID NOs: 15–20) is found amongst acyl glyerol transferases. For example, the plsC protein from E. coli (Accession Number P26647) shares homology with the box1 and box2 sequences, but not the box 3 sequence, of the PG1 protein. The product of this gene transfers acyl from acyl-coenzymeA to the sn2 position of 1-Acyl-sn-glycerol-3-phosphate (lysophosphatidic acid, LPA)(Coleman J., Mol Gen Genet. 1992 Mar 1; 232(2): 295–303).

Box1 and box2 homologies, but not box 3 homologies, are also found in the SLCI gene product from baker's yeast (Accession Number P33333) and the mouse gene AB005623. Each of these genes are able to complement in vivo mutations in the bacterial plsC gene. (Nagiec M M, Wells G B, Lester R L, Dickson R C, J. Biol. Chem., 1993 Oct 15; 268(29): 22156–22163, A suppressor gene that enables Saccharomyces cerevisiae to grow without making sphingolipids encodes a protein that resembles an Escherichia coli fatty acyltransferase; and Kume K, Shimizu T, Biochem. Biophys. Res. Commun. 1997, Aug. 28; 237(3): 663–666, cDNA cloning and expression of murine 1-acyl-sn-glycerol-3-phosphate acyltransferase).

Recently two different human homologues of the mouse AB005623 gene, Accession Numbers U89336 and U56417 were cloned and found to be localized to human chromosomes 6 and 9 (Eberhardt. C., Gray, P. W. and Tjoelker, L. W., J. Biol. Chem. 1997; 272, 20299–20305, Human lysophosphatidic acid acyltransferase cDNA cloning, expression, and localization to chromosome 9q34.3; and West, J., Tompkins, C. K., Balantac, N., Nudelman, E., Meengs, B., White, T., Bursten, S., Coleman, J., Kumar, A., Singer, J. W. and Leung, D. W, DNA Cell Biol. 6, 691–701 (1997), Cloning and expression of two human lysophosphatidic acid acyltransferase cDNAs that enhance cytokine induced signaling responses in cells).

The enzymatic acylation of LPA results in 1,2-diacyl-sn-glycerol 3-phosphate, an intermediate to the biosynthesis of both glycerophospholipids and triacylglycerol. Several important signaling messengers participating in the transduction of mitogenic signals, induction of apoptosis, transmission of nerve impulses and other cellular responses mediated by membrane bound receptors belong to this metabolic pathway.

LPA itself is a potent regulator of mammalian cell proliferation. In fact, LPA is one of the major mitogens found in blood serum. (For a review: Durieux M E, Lynch K R, Trends Pharmacol. Sci. 1993 June; 14(6):249–254, Signaling properties of lysophosphatidic acid. LPA can act as a survival factor to inhibit apoptosis of primary cells; and Levine J S, Koh J S, Triaca V, Lieberthal W, Am. J. Physiol. 1997 October; 273(4Pt2): F575–F585, Lysophosphatidic acid: a novel growth and survival factor for renal proximal tubular cells). This function of LPA is mediated by the lipid kinase phosphatidylinositol 3-kinase.

Phosphatidylinositol and its derivatives present another class of messengers emerging from the 1-acyl-sn-glycerol-3-phosphate acyltransferase pathway. (Toker A, Cantley L C, Nature 1997 Jun 12; 387(6634): 673–676, Signaling through the lipid products of phosphoinositide-3-OH kinase; Martin TF, Curr. Opin. Neurobiol. 1997 June; 7(3):331–338, Phosphoinositides as spatial regulators of membrane traffic; and Hsuan J J, et al., Int. J. Biochem. Cell Biol. 1997 Mar $1^{st}$; 29(3): 415–435, Growth factor-dependent phosphoinositide signaling).

Cell growth, differentiation and apoptosis can be affected and modified by enzymes involved in this metabolic pathway. Consequently, alteration of this pathway could facilitate cancer cell progression. Modulation of the activity of enzymes in this pathway using agents such as enzymatic inhibitors could be a way to restore a normal phenotype to cancerous cells.

Ashagbley A, Samadder P, Bittman R, Erukulla R K, Byun H S, Arthur G have recently shown that ether-linked analogue of lysophosphatidic acid: 4-O-hexadecyl-3(S)-O-methoxybutanephosphonate can effectively inhibit the proliferation of several human cancerous cell lines, including DU145 line of prostate cancer origin. (Anticancer Res 1996 July; 16(4A): 1813–1818, Synthesis of ether-linked analogues of lysophosphatidate and their effect on the proliferation of human epithelial cancer cells in vitro).

Structural differences between the PG1 family of cellular proteins and the functionally confirmed 1-acyl-sn-glycerol-3-phosphate acyltransferase family, evidenced by the existence of a different pattern of homology to box3, could point to unique substrate specificity in the phospholipid metabolic pathway, to specific interaction with other cellular components or to both.

Further analysis of the function of the PG1 gene can be conducted, for example, by constructing knockout mutations in the yeast homologues of the PG1 gene in order to elucidate the potential function of this protein family, and to test potential substrate analogs in order to revert the malignant phenotype of human prostate cancer cells as described in Section VIII, below.

EXAMPLE 7

Analysis of the Intracellular Localisation of the PG1 Isoforms

To study the intracellular localisation of PG1 protein, different isoforms of PG1 were cloned in the expression vector pEGFP-N1(Clontech), transfected and expressed in normal (PNT2A) or adenocarcinoma (PC3) prostatic cell line.

First, to generate cDNA inserts, 5' and 3' primers were synthesised allowing to amplify different regions of the PG1 open reading frame. Respectively, these primers were designed with an internal EcoRI or BamHI site which allowed the insertion of the amplified product into the EcoRI and BamHI sites of the expression vector. The restriction sites were introduced into the primer so that after cloning into pEGFP-N1, the PG1 open reading frame would be fused in frame, to the EGFP open reading frame. The translated protein would be a fusion between PG1 and EGFP. EGFP being a variant form of the GFP protein (Green Fluorescent Protein), it is possible to detect the intracellular localisation of the different PG1 isoforms by examining the fluorescence emitted by the EGFP fused protein.

The different forms that were analysed correspond either to different messengers identified by RT-PCR performed on total normal human prostatic RNA or to a truncated form resulting from a non sense mutation identified in a tumoural prostatic cell line LnCaP. The different PG1 constructions were transfected using the lipofectine technique and EGFP expression was examined 20 hours post transfection.

Name and Description of the Different forms Transfected are Listed Below:

A) PG1 includes all the coding exons from exon 1 to 8.
B) PG1/1-4 corresponds to an alternative messenger which is due to an alternative splicing, joining exon 1 to exon 4, and resulting in the absence of exons 2 and 3.
C) PG1/1-5 corresponds to an alternative messenger which is due to an alternative splicing, joining exon 1 to exon 5, and resulting in the absence of exons 2, 3 and 4.
D) PG1/1-7 includes exons 1 to 6, and corresponds to the mutated form identified in genomic DNA of the prostatic tumoural cell line LNCAP.

Cloning of the PG1 cDNA Inserts in the EGFP-N 1 Expression Vector cDNAs from human prostate were obtained by RT-PCR using the Advantage RT-for-PCR Kit (CLONTECH ref K1402-2). First, 1 µl of oligodT-containing PG1 specific primer PGRT32 TTTTTTTTTTTTTTTTTTTGAAAT (20 pmoles) and 11.5 µl of DEPC treated $H_2O$ were added to 1 µl of total mRNA (1 µg) extracted from human prostate (CLONTECH ref 64038-1). The mRNA was heat denaturated for 2.5 min at 74° C. and then quickly chilled on ice. A mix containing 4 µl of 5× buffer, 1 µl of dNTPs (10 mM each), 0.5 µl of recombinant RNase inhibitor (20U) and 1 µl of MoMuLV Reverse Transcriptase (200U) was added to the denaturated mRNA. Reverse transcription was performed for 60 min. at 42° C. Enzymes were heat denaturated for 5 min. at 94° C. Then, 80 µl of DEPC treated $H_2O$ were added to the reaction mix and the cDNA mix was stored at −20° C. Primers PG15Eco3 (5' CCTGAATTCCGCCGAGCT-GAGAAGATGC 3'), and PG13Bam2 (5' CCTGGATC-CGCTTTAATAGTAACCCACAGGCAG 3') were used for PCR amplification of the different PG1 cDNAs. A 50 µl PCR reaction mix containing 5 µl of the previously prepared prostate cDNA mix, 15 µl of 3.3×PCR buffer, 4 µl of dNTPs (2.5 mM each), 20 pmoles of primer PG15Eco3, 20 pmoles of primer PG13Bam2 µl of RtthXL enzyme, 2.2 µl Mg(OAc)$_2$ (Hot Start) was set up and amplification was performed for 35 cycles of 30 sec at 94° C., 10 min. at 72° C., 4 min. at 67° C. after an initial denaturation step of 10 min. at 94° C. Size and integrity of the PCR product was assessed by migration on a 1% agarose gel. 2 µdig of the amplification product were digested with 2.4 units of EcoRI (PROMEGA ref R601A) and 2.0 units of BamHI (PROMEGA ref R602A) in 50 µl of 1 X Multicore buffer for 2 hours at 37° C. Enzymes were then heat inactivated for 20 min, at 68° C., DNA was phenol/chloroform extracted and ethanol-precipitated and its concentration was estimated by migration on a 1% agarose gel.

To prepare the vector, 2 µl of pEGFP-N1 vector (CLONTECH ref 6085-1) were digested with 2.4 units of EcoRI (PROMEGA ref R601A) and 2.0 units of BamH (PROMEGA ref R602A) in 50 µl of 1× multicore buffer for 2 hours at 37° C. Enzymes were then heat inactivated for 20 min, at 68° C., DNA was phenol/chloroform extracted and ethanol-precipitated and its concentration and integrity were estimated by migration on a 1% agarose gel. 20 ng of the BamHI and EcoRI digested pEGFP-N1 vector were added to 50 ng of BamHI-EcoRI digested PG1 cDNAs. Ligation was performed over night at 13° C. using 0.5 units of T4 DNA ligase (BOEHRINGER ref 84333623) in a final volume of 20 µl containing 1× ligase buffer. The ligation reaction mix was desalted by dialysis against water (MILLIPORE ref VSWP01300) for 30 min. at room temperature. One fifth of the desalted ligation reaction was electroporated in 25 µl of competent cells ElectroMAX DH10B (GIBCO BRL ref 18290–015) using a resistance of 126 Ohms, capacitance of 50 µF, and voltage of 2.5 KV. Bacteria were then incubated in 500 µl of SOB medium for 30 min at 37° C. One fifth was plated on LB AGAR containing 40 µg/µl KANAMYCINE (SIGMA ref K4000) and incubated over night at 37° C. Plasmid DNA was prepared from an overnight liquid culture of individual colonies and sequenced. Among the different forms identified 3 were used:

A) PG1 which includes all the coding exons from exon 1 to 8.
B) PG1/1-4 which corresponds to an alternative messenger which is due to an alternative splicing, joining exon 1 to exon 4, and resulting in the absence of exons 2 and 3.
C) PG1/1-5 which corresponds to an alternative messenger which is due to an alternative splicing, joining exon 1 to exon 5, and resulting in the absence of exons 2, 3 and 4.
D) Vector PG1/1-7: A cDNA insert encoding for a truncated protein was synthesized by PCR amplification, using primers PG15Eco3 and PG1 mut29Bam (5' CCTGGATCCCCTCCATCGTCTTTCCCTT 3') and vector PG1 as a template. The resulting PCR product was cloned following the same protocol as described above.

Transfection of the PG1 Expression Vectors in Human Prostate Cell Lines.

The DNA/lipofectin solution was prepared as followed: 1.5 µl of lipofectin (GIBCO BRL ref 18292-011) was diluted in 100 µl of OPTI-MEM medium (GIBCO BRL ref 31985-018), and incubated for 30 min. at room temperature before being mixed to 0.511 g of vector diluted in 100 µl of OPTI-MEM medium and incubated for 15 min. at room temperature. Cells were inoculated in RPMI1640 medium (Gibco BRL ref 61870-010) containing 5% fetal calf serum (Dutscher ref P30-1302) on slides (NUNC Lab-Tek ref 177402A) and grown at 37° C. in 5%$CO_2$. Cells reaching 40–60% confluency were rinsed with 300 µl OPTI-MEM medium and incubated with the DNA/lipofectin solution for 6 hours at 37° C. The medium containing DNA was replaced by medium supplemented in fetal calf serum and cells were incubated for at least 36 hours at 37° C. Slides were rinsed in PBS and cells were fixed in ethanol, treated with Propidium iodide, and examined with a fluorescence microscope using a double-pass filter set for FITC/PI.

Figure 10:
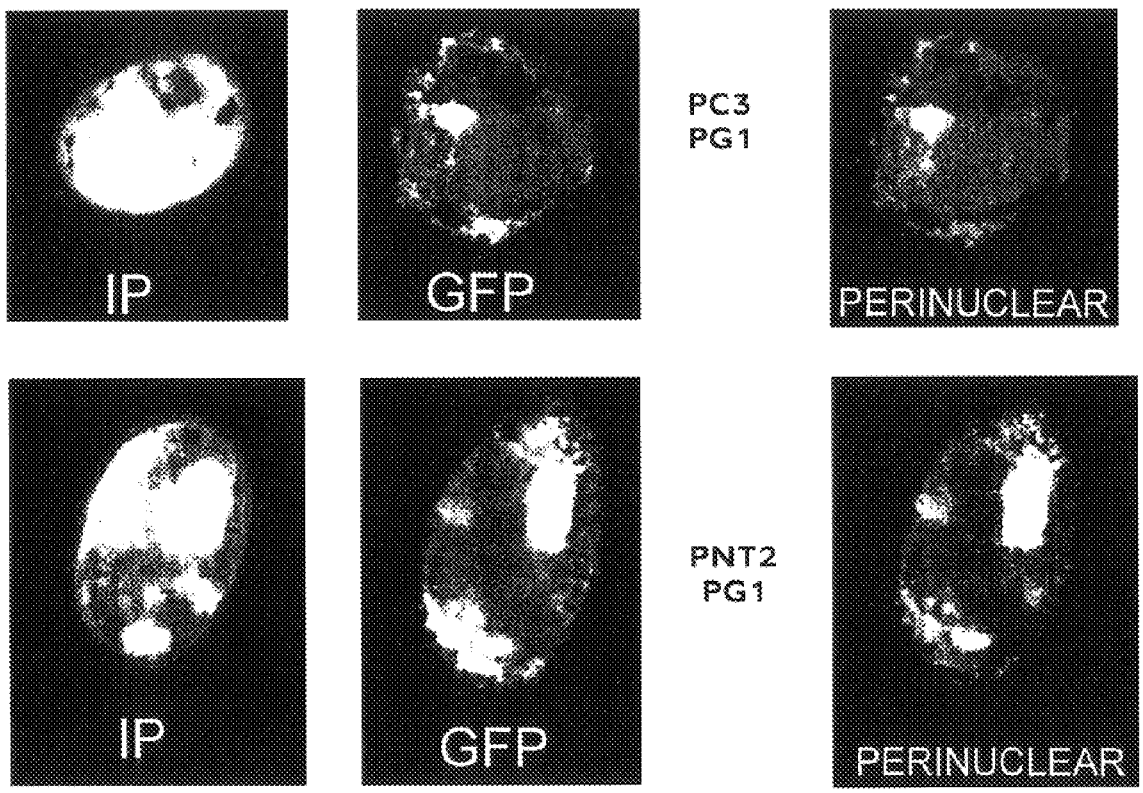
FIG. 10 is a half-tome reproduction of a fluorescence micrograph of the perinuclear/nuclear expression of PG1 in tumoral (PC3) and normal prostatic cell lines (PNT2). Vector "PG1": includes all the coding exons from exon 1 to 8. For PC3 (upper panel) and PNT2 (lower panel), the nucleus was labelled with Propidium iodide (IP, left panel). Note that EGFP fluorescence was detected in and around the nucleus (GFP, middle panel), as shown when the two pictures were overlapped (right panel).

After transfection of PG1 and PG1/1-4 in both the normal and tumoural prostatic cell line, green fluorescence was detected into and around the nucleus (FIGS. 10 and 11). This result shows that the PG1 protein is localised in the nucleus and/or the nuclear membrane. Furthermore, it suggests that exons 2 and 3 are dispensable for translocation of PG1 to the nucleus. In addition, no difference in the intracellular localisation of these two forms was detected between the tumoral and the normal prostatic cell line.

On the contrary, transfection experiments using PG1/1-5 show that this form is cytoplasmic in the normal prostatic cell line PNT2A. It suggests that exon 4 might be important for the regulation of the translocation to the nucleus. Interestingly, similar transfection experiments in the tumoral cell line PC3 show that PG1/1-5 remains nuclear and or perinuclear (FIG. 12). This result shows that there is an abnormality in the regulation of the intracellular localization of the PG1 isoforms in this tumoral cell line. Furthermore, it indicates that the normal function of PG1 can be altered indirectly in prostatic tumors by an abnormality in the regulation of its intracellular location.

Finally, a non-sense mutation has been identified in the prostatic tumoural cell line LNCaP, in exon 6 of PG1 (SEQ ID NO: 69). This mutation is responsible for the production of a truncated protein (SEQ ID NO: 70). To determine the intracellular location of this truncated protein, PG1/1-7 and PG1 were transfected in the normal prostatic cell line PNT2A. Comparison of the fluorescence detected in both sets of experiments clearly showed that the truncated form was localised in the cytoplasm as the non-truncated protein was located in and/or around the nucleus (FIG. 13). This result indicates that this mutated PG1 is translated in a truncated protein which is unable to reach the nucleus. It also suggests that exons 7 and 8 may play an important role in the regulation of the intracellular localisation of PG1. Furthermore, it supports the previous hypothesis that an altered regulation of PG1 intracellular localisation might be involved in prostate tumorigenesis.

|  | pEGFP N1 | PG1 | PG11-4 | PG11-5 | PG11-7 |
| --- | --- | --- | --- | --- | --- |
| Transfection PNT2 06/17/98 | NA | nuclear | nuclear | ND | ND |
| Transfection PNT2 06/30/98 | cytoplasmic | nuclear | nuclear | ND | ND |

-continued

|  | pEGFP N1 | PG1 | PG11-4 | PG11-5 | PG11-7 |
|---|---|---|---|---|---|
| Transfection PNT2 07/16/98 | cytoplasmic | NA | NA | cytoplasmic | ND |
| Transfection PC3 07/16/98 | NA | nuclear | nuclear | nuclear | ND |
| Transfection PC3 07/16/98 bis | cytoplasmic | nuclear | NA | NA | ND |
| Transfection PC3 08/27/98 | cytoplasmic | nuclear | nuclear | nuclear | NA |
| Transfection PNT2 08/28/98 | cytoplasmic | nuclear | NA | cytoplasmic | cytoplasmic |
|  |  | All exons | X2-3 Spliced out | X2-3-4 Spliced out | mut aa229 |

NA: Not assessable
ND: Not done
Nuclear: localized in and around the nucleus (nuclear and perinuclear localization).

Alternative Splice Species

Alternative splicing is a common natural tool for the inhibition of function of full length gene products. Alternative splicing is known to result in enzyme isoforms, possesing different kinitec characteristics (pyruvate kinase: M1 and M2 Yamada K, Noguchi T, Biochem J. 1999 Janl;337(Pt 1):1–11. Estrogen receptor (ER) gene is known to possess variant splicing yelding the deletions of exon 3, 5, or 7. The truncated ER protein induced from variant mRNA could mainly be exhibited as a repressor through dominant negative effects on normal ER protein (Iwase H, Omoto Y, Iwata H, Hara Y, Ando Y, Kobayashi S, Oncology 1998 Dec;55 Suppl S1:11–16)' Yu et al (Yu J J, Mu C, Dabholkar M, Guo Y, Bostick-Bruton F, Reed E, Int J Mol Med 1998 Mar;1 (3):617–620) demonstrated that there is an association between alternative splicing of ERCC1, and reduction in cellular capability to repair cisplatin-DNA adduct. Munoz-Sanjuan et al (Munoz-Sanjuan I, Simandl BK, Fallon J. F., Nathans J, Development 1998 Dec 14;126(Pt 2):409–421) demonstrated existence of two differentially spliced isoforms of fibroblast growth factor(FGF) type two genes that are present in non-overlapping spatial distributions in the neural tube and adjacent structures in developing chiken embryo. One of these forms is secreted and activates the expression of Hox D13, HoxD11, Fgf-4 and BMP-2 ectopically, consistent with cFHF-2 playing a role in anterior-posterior patterning of the limb.

The CD44 is a cell adhesion molecule that is present as numerous isoforms created by mRNA alternative splicing. Expression of variant isoforms of CD44 is associated with tumor growth and metastasis.(Shibuya Y, Okabayashi T, Oda K, Tanaka N, Jpn J Clin Oncol 1998 Oct; 28(10):609–14) they showed that ratio of two particular isoforms is a useful indicator of prognosis in gastric and colorectal carcinoma. Zhang Y F et al (Zhang Y F, Jeffery S, Burchill S A, Berry P A, Kaski J C, Carter N D, Br J Cancer 1998 Nov;78(9): 1141–6° showed that human endothelin receptor A is the subject to alternative spicing giving at least two isoforms. The truncated receptor was expressed in all tissues and cells examined, but the level of expression varied. In melanoma cell lines and melanoma tissues, the truncated receptor gene was the major species, whereas the wild-type ETA was predominant in other tissues. Zhang et al. conclude that the function and biological significance of this truncated ETA receptor is not clear, but it may have regulatory roles for cell responses to ETs.

EXAMPLE 8

Identification of PG1 Alternative Splice Species

The PG1 cDNA was first cloned by screening of a human prostate cDNA library. Sequence analysis of about 400 cDNA clones showed that at least 14 isoforms were present in this cDNA library. Comparison of their sequences to the genomic sequence showed that these isoforms resulted from a complex set of different alternative splicing events between numerous exons (FIG. 14).

To rule out the possibility of a cloning artefact generated during the cDNA library construction and to systematically identify all existing alternative splice junctions, RT-PCR experiments were performed on RNA of normal prostate as well as normal prostatic cell lines PNT1A, PNT1B and PNT2 using all the possible combinations of primers specific to the different exon borders SEQ ID NOs: 137–178. The presence of multiple PCR bands in each reaction was assessed by migration in an agarose gel. Each band was analysed by sequencing, and the presence or absence of specific splicing events, as seen in the sequence by a specific splice junction, was scored as plus or minus in FIG. 15.

Furthermore, to identify aberrant splicing event in prostate tumors, similar experiments were performed on RNA extracted from tumoral prostatic cell lines LnCaP (obtained from two different sources and named FCG and JMB), CaHPV, Du145 and PC3 as well as on RNA obtained from prostate tumors (ECP5 to ECP24).

As shown in the first five columns, all isoforms identified in the cDNA library were detected in RNA of normal prostate, normal prostatic cell lines or prostate tumors. In addition to the different splice junctions detected in the cDNA library, 19 other splice junctions were detected in normal prostate or in normal prostatic cell lines. Two types of exon junctions (exons 3–7, exons 3b–8) were never detected in either normal prostate, normal prostatic cell lines, prostate tumors or prostatic tumoral cell lines. Comparison between normal and tumoral samples showed the presence of 2 additional exon junctions (exons 3–8, exons 5–8) in the tumoral samples that were not detected previously in the normal samples. This result demonstrate that during tumorigenesis, the complex regulation of the PG1 splicing has been altered, resulting in an abnormal ratio of the different isoforms. It is of a specific interest since it has been shown in patients with a genetic predisposition to Wilms tumor, that an imbalance between different RNA isoforms might be involved in tumorigenesis (Bickmore et al., Science 1992, 257:325–7; Little et al, Hum Mol Genet 1995, 4:351–8).

Interestingly, comparison between normal and tumoral samples, also showed that some exon junctions are present in all normal samples, but are absent in numerous tumoral samples. It further indicates that the normal function of PG1 can be altered by an abnormality in the regulation of PG1 splicing and further support the previous hypothesis.

Furthermore, comparison between the different types of normal samples (Col. 2 versus Col. 3, 4 and 5) also showed differences in the presence or absence of some exon junctions. It indicates that the transformation process necessary to the generation of these normal prostatic cell lines might result in similar alteration which further support the previous hypothesis.

EXAMPLE 9

Determining the Tumor Suppressor Activity of the PG1 Gene Product, Mutants and Other PG1 Polypeptides PG1 variants which results from either alternate splicing of the PG1 mRNA or from mutation of PG1 that introduce a stop codon (nucleotide of SEQ ID NO: 69 and protein of SEQ ID NO: 70) can no longer perform its role of tumor suppressor. It is possible and even likely that PG1 tumor suppressor role extends beyond prostate cancer to other form of malignancies. PG1 therefore represent a prime candidate for gene therapy of cancer by creating a targeting vector which knocks out the mutant and/or introduces a wild-type PG1 gene (e.g. SEQ ID NO 3 or 179) or a fragment thereof.

To validate this model, PG1 and its alternatively spliced or mutated variants are stably transfected in tumor cell line using methods described in Section VIII. The efficiency of transfection is determined by northern and western blotting; the latter is performed using antibodies prepared against PG1 synthetic peptides designed to distinguish the product of the most abundant PG1 mRNA from the alternatively spliced variants, the truncated variant, or other functional mutants. The production of synthetic peptides and of polyclonal antibodies is performed using the methods described herein in Sections III and VII. After demonstrating that PG1 and its variant are efficiently expressed in various tumor cell line preferably derived from human prostate cancer, hepatocarcinoma, lung and colon carcinoma; we the effect of this gene on the rate of cell division, DNA synthesis, ability to grow in soft agar and ability to induce tumor progression and metastasis when injected in immunologically deficient nude mide are determined.

Alternatively the PG1 gene and its variant are inserted in adenoviruses that are used to obtain a high level of expression of these genes. This method is preferred to test the effect of PG1 expression in animal that are spontaneously developing tumor. The production of specific adenoviruses is obtained using methods familiar to those with normal skills in cell and molecular biology.

POLYNUCLEOTIDES

The present invention encompasses polynucleotides in the form of PG1 genomic or cDNA as well as polynucleotides for use as primers and probes in the methods of the invention. These polynucleotides may consist of, consist essentially of, or comprise a contiguous span of nucleotides of a sequence from any sequence in the Sequence Listing as well as sequences which are complementary thereto ("complements thereof"). Preferably said sequence is selected from SEQ ID NOs: 3, 112–125, 179, 182–184. The "contiguous span" is at least 6, 8, 10, 12, 15, 20, 25, 30, 50, 100, 200, or 500 nucleotides in length. It should be noted that the polynucleotides of the present invention are not limited to having the exact flanking sequences surrounding the polymorphic bases which are enumerated in Sequence Listing. Rather, it will be appreciated that the flanking sequences surrounding the biallelic markers, or any of the primers of probes of the invention which are more distant from a biallelic markers, is lengthened or shortened to any extent compatible with their intended use and the present invention specifically contemplates such sequences. It will be appreciated that the polynucleotides referred to in the Sequence Listing is of any length compatible with their intended use. Also the flanking regions outside of the contiguous span need not be homologous to native flanking sequences which actually occur in humans. The addition of any nucleotide sequence, which is compatible with the nucleotides intended use is specifically contemplated. The contiguous span may optionally include the PG1-related biallelic marker in said sequence. Optionally either allele of the biallelic markers described above in the definition of PG1-related biallelic marker is specified as being present at the PG1-related biallelic marker.

The invention also relates to polynucleotides that hybridize, under conditions of high or intermediate stringency, to a polynucleotide of a sequence from any sequence in the Sequence Listing as well as sequences, which are complementary thereto. Preferably said sequence is selected from SEQ ID NOs: 3, 112–125, 179, 182–184. Preferably such polynucleotides is at least 6, 8, 10, 12, 15, 20, 25, 30, 35, 40, 50, 60, 70, 80, 90, 100, 200, or 500 nucleotides in length. Preferred polynucleotides comprise an PG1-related biallelic marker. Optionally either allele of the biallelic markers described above in the definition of PG1-related biallelic marker is specified as being present at the biallelic marker site. Conditions of high and intermediate stringency are further described in Section X.C.4, below.

The invention embodies polynucleotides which encode an entire human, mouse or mammalian PG1 protein, or fragments thereof. Generally the polynucleotides of the invention comprise the naturally occurring nucleotide sequence of the PG1. However, any naturally occurring silent codon variation or other silent codon variation can be employed to encode the PG1 amino acids sequence. As for those amino acids which are changed or added to the PG1 gene for any embodiment of the invention which requires the expression of a nucleotide sequence, the nucleic acid sequences generally will be chosen to optimize expression in the specific human or non-human animal system in which the polynucleotide is intended to be used, making use of known codon preferences. The PG1 polynucleotides of the invention can be the native nucleotide sequence which encodes a human, mouse, or mammalian PG1 protein, preferably the PG1 polynucleotide sequence of SEQ ID NOs: 3, 112–125, 179, 182–184, and the compliments thereof. The polynucleotides of the invention include those which encode PG1 polypeptides with a contiguous stretch of at least 8, 10, 12, 15, 20, 25, 30, 50, 100 or 200 amino acids from SEQ ID NOs: 4, 5, 70, 74, and 125–136, as well as any other human, mouse or mammalian PG1 polypeptide. In addition the present invention encompasses polynucleotides which comprise a contiguous stretch of at least 8, 10, 12, 15, 20, 25, 30, 50, 100, 200, 500 nucleotides of a human, mouse or mammalian PG1 genomic sequence as well as complete human, mouse, or mammalian PG1 genes, preferably of SEQ ID NOs: 179, 182, 183, and the compliments thereof.

The present invention encompasses polynucleotides which consist of, consist essentially of, or comprise a contiguous stretch of at least 8, 10, 12, 15, 20, 25, 30, 50, 100, 200, or 500 nucleotides of a human, mouse or mammalian PG1 cDNA sequences as well as an entire human, mouse, or mammalian PG1 cDNA. The cDNA species and polynucleotide fragments comprised by the polynucleotides of the invention include the predominant species derived from any human, mouse or mammal source, preferably SEQ ID NOs: 3, 184, and the compliments thereof. In addition, the polynucleotides of the invention comprise cDNA species, and fragments thereof, that result from the alternative splicing of PG1 transcripts in any human, mouse or other mammal, preferably the cDNA species of SEQ ID NOs: 112–124, and compliments thereof Moreover, the invention encompasses cDNA species and other polynucleotides which consist of or comprise the polynucleotides which span a splice junction, preferably including any one of SEQ ID NOs: 137 to 178, and the compliments thereof; more preferably any one of SEQ ID NOs: 137 to 149, 151 to 169, 171 to 178, and the compliments thereof. The polynucleotides of the invention also include cDNA and other polynucleotides which comprise two covalently linked PG1 exons, derived from a single human, mouse or mammalian species, immediately adjacent to one another in the order shown, and selected from the followingpairs of PG1 exons: 1:2, 1:3, 1:4, 1:5, 1:6, 1:7, 1:8, 2:3, 2:4, 2:5, 2:6, 2:7, 2:8, 3:4, 3:5, 3:6, 3:7, 3:8, 4:5, 4:6, 4:7, 4:8, 5:6, 5:7, 5:8, 6:7, 6:8, 7:8, 1:1bis, 1bis:2, 1bis:3, 1bis:4, 1bis:5, 1bis:6, 1bis:7, 1bis:8, 3:3bis, 3bis:4, 3bis:5, 3bis:6, 3bis:7, 3bis:8, 5:5bis, 5bis:6, 5bis:7, 5bis:8, 1:6bis, 2:6bis, 3:6bis, 4:6bis, 5:6bis, 6bis:7, 6bis:8, and the compliments thereof. In preferred embodiment the sequences of the PG1 exons in each of the pairs of exons is selected as follows: exon 1—SEQ ID NO: 100; exon 2—SEQ ID NO: 101; exon 3—SEQ ID NO: 102; exon 4—SEQ ID NO: 103; exon 5—SEQ ID NO: 104; exon 6—SEQ ID NO: 105; exon 7—SEQ ID NO: 106; exon 8—SEQ ID NO: 107; exon 1bis—SEQ ID NO: 108; exon 3bis —SEQ ID NO: 109; exon 5bis—SEQ ID NO: 110; and exon 6bis—SEQ ID NO: 111. Because of the 8 different polyadenylation sites in exon 8, any cDNA or polynucleotide of the invention comprising a human cDNA fragment encompassing exon 8 is truncated such that only the first 330 nucleotides, 699 nucleotides, 833 nucleotides, 1826 nucleotides, 2485 nucleotides, 2805 nucleotides, 4269 nucleotides or 4315 nucleotides of exon 8 shown in SEQ ID NO: 107 are present.

The primers of the present invention is designed from the disclosed sequences for any method known in the art. A preferred set of primers is fashioned such that the 3' end of the contiguous span of identity with the sequences of the Sequence Listing is present at the 3' end of the primer. Such a configuration allows the 3' end of the primer to hybridize to a selected nucleic acid sequence and dramatically increases the efficiency of the primer for amplification or sequencing reactions. Allele specific primers is designed such that a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of primer of the invention is located within or at least 2, 4, 6, 8, 10, 12, 15, 18, 20, 25, 50, 100, 250, 500, or 1000 nucleotides upstream of an PG1-related biallelic marker in said sequence or at any other location which is appropriate for their intended use in sequencing, amplification or the location of novel sequences or markers.

Preferred amplification primers include the polynucleotides disclosed in SEQ ID NOs: 39–56, and 63–68. Additional preferred amplification primers for particular non-genic PG1-related biallelic markers are listed as follows by the internal reference number for the marker and the SEQ ID NOs for the PU and RP amplification primers respectively: 4-14-107 use SEQ ID NOs 339 and 382; 4-14-317 use SEQ ID NOs 339 and 382; 4-14-35 use SEQ ID NOs 339 and 382; 4-20-149 use SEQ ID NOs 340 and 383; 4-22-174 use SEQ ID NOs 341 and 384; 4-22-176 use SEQ ID NOs 341 and 384; 4-26-60 use SEQ ID NOs 342 and 385; 4-26-72 use SEQ ID NOs 342 and 385; 4-3-130 use SEQ ID NOs 343 and 386; 4-38-63 use SEQ ID NOs 344 and 387; 4-38-83 use SEQ ID NOs 344 and 387; 4-4-152 use SEQ ID NOs 345 and 388; 4-4-187 use SEQ ID NOs 345 and 388; 4-4-288 use SEQ ID NOs 345 and 388; 4-42-304 use SEQ ID NOs 346 and 389; 4-42-401 use SEQ ID NOs 346 and 389; 4-43-328 use SEQ ID NOs 347 and 390; 4-43-70 use SEQ ID NOs 347 and 390; 4-50-209 use SEQ ID NOs 348 and 391; 4-50-293 use SEQ ID NOs 348 and 391; 4-50-123 use SEQ ID NOs 348 and 391; 4-50-129 use SEQ ID NOs 348 and 391; 4-50-130 use SEQ ID NOs 348 and 391; 4-52-163 use SEQ ID NOs 349 and 392; 4-52-88 use SEQ ID NOs 349 and 392; 4-53-258 use SEQ ID NOs 350 and 393; 4-54-283 use SEQ ID NOs 351 and 394; 4-54-388 use SEQ ID NOs 351 and 394; 4-55-70 use SEQ ID NOs 352 and 395; 4-55-95 use SEQ ID NOs 352 and 395; 4-56-159 use SEQ ID NOs 353 and 396; 4-56-213 use SEQ ID NOs 353 and 396; 4-58-289 use SEQ ID NOs 354 and 397; 4-58-318 use SEQ ID NOs 354 and 397; 4-60-266 use SEQ ID NOs 355 and 398; 4-60-293 use SEQ ID NOs 355 and 398; 4-84-241 use SEQ ID NOs 356 and 399; 4-84-262 use SEQ ID NOs 356 and 399; 4-86-206 use SEQ ID NOs 357 and 400; 4-86-309 use SEQ ID NOs 357 and 400; 4-88-349 use SEQ ID NOs 358 and 401; 4-89-87 use SEQ ID NOs 359 and 402; 99-123-184 use SEQ ID NOs 360 and 403; 99-128-202 use SEQ ID NOs 361 and 404; 99-128-275 use SEQ ID NOs 361 and 404; 99-128-313 use SEQ ID NOs 361 and 404; 99-128-60 use SEQ ID NOs 361 and 404; 99-12907-295 use SEQ ID NOs 362 and 405; 99-130-58 use SEQ ID NOs 363 and 406; 99-134-362 use SEQ ID NOs 364 and 407; 99-140-130 use SEQ ID NOs 365 and 408; 99-1462-238 use SEQ ID NOs 366 and 409; 99-147-181 use SEQ ID NOs 367 and 410; 99-1474-156 use SEQ ID NOs 368 and 411; 99-1474-359 use SEQ ID NOs 368 and 411; 99-1479-158 use SEQ ID NOs 369 and 412; 99-1479-379 use SEQ ID NOs 369 and 412; 99-148-129 use SEQ ID NOs 370 and 413; 99-148-132 use SEQ ID NOs 370 and 413; 99-148-139 use SEQ ID NOs 370 and 413; 99-148-140 use SEQ ID NOs 370 and 413; 99-148-182 use SEQ ID NOs 370 and 413; 99-148-366 use SEQ ID NOs 370 and 413; 99-148-76 use SEQ ID NOs 370 and 413; 99-1480-290 use SEQ ID NOs 371 and 414; 99-1481-285 use SEQ ID NOs 372 and 415; 99-1484-101 use SEQ ID NOs 373 and 416; 99-1484-328 use SEQ ID NOs 373 and 416; 99-1485–251 use SEQ ID NOs 374 and 417; 99-1490–181 use SEQ ID NOs 375 and 418; 99-1493-280 use SEQ ID NOs 376 and 419; 99-151-94 use SEQ ID NOs 377 and 420; 99-211-291 use SEQ ID NOs 378 and 421; 99-213-37 use SEQ ID NOs 379 and 422; 99-221-442 use SEQ ID NOs 380 and 423; 99-222-109 use SEQ ID NOs 381 and 424; and the compliments thereof.

Primers with their 3' ends located 1 nucleotide upstream or downstream of a PG1-related biallelic marker have a special utility in microsequencing assays. Preferred microsequencing primers include the polynucleotides from position 1 to position 23 and from position 25 to position 47 of SEQ ID NOs: 21–38, and as well as the compliments thereof. Additional preferred microsequencing primers for particular non-genic PG1-related biallelic markers are listed as follows by the internal reference number for the marker and the SEQ ID NOs of the two preferred microsequencing primers: 4-14-107 of SEQ ID NOs 425 and 502*; 4-14-317 of SEQ ID NOs 426 and 503*; 4-14-35 of SEQ ID NOs 427 and 504*; 4-20-149 of SEQ ID NOs 428* and 505; 4-20-77 of SEQ ID NOs 429 and 506; 4-22-174 of SEQ ID NOs 430* and 507; 4-22-176 of SEQ ID NOs 431 and 508; 4-26-60 of SEQ ID NOs 432 and 509*; 4-26-72 of SEQ ID NOs 433 and 510; 4-3-130 of SEQ ID NOs 434 and 511*; 4-38-63 of SEQ ID NOs 435 and 512; 4-38-83 of SEQ ID NOs 436 and 513*; 4-4-152 of SEQ ID NOs 437 and 514; 4-4-187 of SEQ ID NOs 438* and 515; 4-4-288 of SEQ ID NOs 439 and 516; 4-42-304 of SEQ ID NOs 440 and 517; 4-42-401 of SEQ ID NOs 441* and 518; 4-43-328 of SEQ ID NOs 442 and 519; 4-43-70 of SEQ ID NOs 443* and 520; 4-50-209 of SEQ ID NOs 444* and 521; 4-50-293 of SEQ ID NOs 445* and 522; 4-50-123 of SEQ ID NOs 446* and 523; 4-50-129 of SEQ ID NOs 447* and 524; 4-50-130 of SEQ ID NOs 448 and 525; 4-52-163 of SEQ ID NOs 449* and 526; 4-52-88 of SEQ ID NOs 450* and 527; 4-53-258 of SEQ ID NOs 451 and 528*;4-54-283 of SEQ ID NOs 452* and 529; 4-54-388 of SEQ ID NOs 453 and 530; 4-55-70 of SEQ ID NOs 454 and 531*; 4-55-95 of SEQ ID NOs 455* and 532; 4-56-159 of SEQ ID NOs 456* and 533; 4-56-213 of SEQ ID NOs 457 and 534; 4-58-289 of SEQ ID NOs 458* and 535; 4-58-318 of SEQ ID NOs 459* and 536; 4-60-266 of SEQ ID NOs 460* and 537; 4-60-293 of SEQ ID NOs 461 * and 538; 4-84-241 of SEQ ID NOs 462 and 539*; 4-84-262 of SEQ ID NOs 463 and 540; 4-86-206 of SEQ ID NOs 464 and 541*; 4-86-309 of SEQ ID NOs 465 and 542; 4-88-349 of SEQ ID NOs 466 and 543.; 4-89-87 of SEQ ID NOs 467* and 544.; 99-123-184 of SEQ ID NOs 468 and 545; 99-128-202 of SEQ ID NOs 469 and 546; 99-128-275 of SEQ ID NOs 470 and 547; 99-128-313 of SEQ ID NOs 471 and 548; 99-128-60 of SEQ ID NOs 472* and 549; 99-12907-295 of SEQ ID NOs 473 and 550*; 99-130-58 of SEQ ID NOs 474* and 551*; 99-134-362 of SEQ ID NOs 475 and 552*; 99-140-130 of SEQID NOs 476* and 553*; 99-1462-238 of SEQ ID NOs 477* and 554; 99-147-181 of SEQ ID NOs 478 and 555*; 99-1474-156 of SEQ ID NOs 479 and 556*; 99-1474-359 of SEQ ID NOs 480 and 557; 99-1479-158 of SEQ ID NOs 481 * and 558; 99-1479-379 of SEQ ID NOs 482 and 559; 99-148-129 of SEQ ID NOs 483 and 560; 99-148-132 of SEQ ID NOs 484 and 561; 99-148-139 of SEQ ID NOs 485 and 562; 99-148-140 of SEQ ID NOs 486 and 563; 99-148-182 of SEQ ID NOs 487 and 564*; 99-148-366 of SEQ ID NOs 488 and 565; 99-148-76 of SEQ ID NOs 489 and 566; 99-1480-290 of SEQ ID NOs 490 and 567*; 99-1481-285 of SEQ ID NOs 491 and 568*; 99-1484-101 of SEQ ID NOs 492 and 569; 99-1484-328 of SEQ ID NOs 493* and 570; 99-1485–251 of SEQ ID NOs 494 and 571*; 99-1490–181 of SEQ ID NOs 495* and 572; 99-1493-280 of SEQ ID NOs 496 and 573*; 99-151-94 of SEQ ID NOs 497 and 574*; 99-211-291 of SEQ ID NOs 498* and 575; 99-213-37 of SEQ ID NOs 499 and 576; 99-221-442 of SEQ ID 500 and 577; 99-222-109 of SEQ ID NOs 501* and 578; and compliments thereof.

Additional preferred microsequencing primers for particular genic PG1-related biallelic markers include a polynucleotide selected from the group consisting of the nucleotide sequences from position N–X to position N–1 of SEQ ID NO: 179, nucleotide sequences from position N+1 to position N+X of SEQ ID NO:179, and the compliments thereof, wherein X is equal to 15, 18, 20, 25, 30, or a range of 15 to 30, and N is equal to one of the following values: 2159; 2443; 4452; 5733; 8438; 11843; 1983; 12080; 12221; 12947; 13147; 13194; 13310; 13342; 13367; 13594; 13680; 13902; 16231; 16388; 17608; 18034; 18290; 18786; 22835; 22872; 25183; 25192; 25614; 26911; 32703; 34491; 34756; 34934; 5160; 39897; 40598; 40816; 40947; 45783; 47929; 48206; 48207; 49282; 50037; 50054; 50101; 50220; 50440; 50562; 50653; 50660; 50745; 50885; 51249; 51333; 51435; 51468; 51515; 51557; 51566; 51632; 51666; 52016; 52096; 52151; 52282; 52348; 52410; 52580; 52712; 52772; 52860; 53092; 53272; 53389; 53511; 53600; 53665; 53815; 54365; and 54541.

The probes of the present invention is designed from the disclosed sequences for any method known in the art, particularly methods which allow for testing if a particular sequence or marker disclosed herein is present. A preferred set of probes is designed for use in the hybridization assays of the invention in any manner known in the art such that they selectively bind to one allele of a biallelic marker, but not the other under any particular set of assay conditions. Preferred hybridization probes may consists of, consist essentially of, or comprise a contiguous span which ranges in length from 8, 10, 12, 15, 18 or 20 to 25, 35, 40, 50, 60, 70, or 80 nucleotides, or be specified as being 12, 15, 18, 20, 25, 35, 40, or 50 nucleotides in length and including a PG1-related biallelic marker of said sequence. Optionally either of the two alleles specified in the definition of PG1-realted biallelic marker is specified as being present at the biallelic marker site. Optionally, said biallelic marker is within 6, 5, 4, 3, 2, or 1 nucleotides of the center of the hybridization probe or at the center of said probe. A preferred set of hybridization probes is disclosed in SEQ ID NOs: 21–38, 57–62, 185–338, and the compliments thereof. Another particularly preferred set of hybridization probes includes the polynucleotides from position X to position Y of any one of SEQ ID NOs: 21–38, 57–62, 185–338, or the compliments thereof, wherein X is equal to 5, 8, 10, 12, 14, 16, 18 or a range of 5 to 18, and Y is equal to 30, 32, 34, 36, 38, 40, 43 or a range of 30 to 43; preferably X equals 12 and Y equals 36. Additional preferred hybridization probes for particular genic PG1-related biallelic markers include a polynucleotide selected from the group consisting of the nucleotide sequences from position N–X to position N+Y of SEQ ID NO: 179, and the compliments thereof, wherein X is equal to 8, 10, 12, 15, 20, 25, or a range of 8 to 30, Y is equal to 8, 10, 12, 15, 20, 25, or a range of 8 to 30, and N is equal to one of the following values: 2159; 2443; 4452; 5733; 8438; 11843; 1983; 12080; 12221; 12947; 13147; 13194; 13310; 13342; 13367; 13594; 13680; 13902; 16231; 16388; 17608; 18034; 18290; 18786; 22835; 22872; 25183; 25192; 25614; 26911; 32703; 34491; 34756; 34934; 5160; 39897; 40598; 40816; 40947; 45783; 47929; 48206; 48207; 49282; 50037; 50054; 50101; 50220; 50440; 50562; 50653; 50660; 50745; 50885; 51249; 51333; 51435; 51468; 51515; 51557; 51566; 51632; 51666; 52016; 52096; 52151; 52282; 52348; 52410; 52580; 52712; 52772; 52860; 53092; 53272; 53389; 53511; 53600; 53665; 53815; 54365; and 54541; wherein the nucleotide at position N is selected from one of the two alleles specified in the definition of PG1-realted biallelic marker at the biallelic marker site at position N.

Any of the polynucleotides of the present invention can be labeled, if desired, by incorporating a label detectable by spectroscopic, photochemical, biochemical, immunochemical, or chemical means. For example, useful labels include radioactive substances, fluorescent dyes or biotin. Preferably, polynucleotides are labeled at their 3' and 5' ends. A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it is employed to capture or to detect the target DNA. Further, it will be understood that the polynucleotides, primers or probes provided herein, may, themselves, serve as the capture label. For example, in the case where a solid phase reagent's binding member is a nucleic acid sequence, it is selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes® and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the inventions to a single solid support. In addition, polynucleotides other than those of the invention may attached to the same solid support as one or more polynucleotides of the invention.

Any polynucleotide provided herein is attached in overlapping areas or at random locations on the solid support. Alternatively the polynucleotides of the invention is attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods, which incorporate a combination of photolithographic methods and solid phase oligonucleotide synthesis (Fodor et al., Science, 251:767–777, 1991). The immobilization of arrays of oligonucleotides on solid supports has been rendered possible by the development of a technology generally identified as "Very Large Scale Immobilized Polymer Synthesis" (VLSIPS ™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

Oligonucleotide arrays may comprise at least one of the sequences selected from the group consisting of SEQ ID NOs: 3, 21–38, 57–62, 100–124, 179, 185–338, the preferred hybridization probes for genic PG1-related biallelic markers described above; and the sequences complementary thereto; or a fragment thereof of at least 15 consecutive nucleotides for determining whether a sample contains one or more alleles of the biallelic markers of the present invention. Oligonucleotide arrays may also comprise at least one of the sequences selected from the group consisting of SEQ ID NOs: 179, 339–424; and the sequences complementary thereto or a fragment thereof of at least 15 consecutive nucleotides for amplifying one or more alleles of the PG1-realted biallelic markers. In other embodiments, arrays may also comprise at least one of the sequences selected from the group consisting of SEQ ID 425–578, the preferred microsequencing primers for genic PG1-related biallelic markers described above; and the sequences complementary thereto or a fragment thereof of at least 15 consecutive nucleotides for conducting microsequencing analyses to determine whether a sample contains one or more alleles of PG1-related biallelic marker.

The present invention further encompasses polynucleotide sequences that hybridize to any one of SEQ ID NOs: 3, 69, 100–112, or 179–184 under conditions of high or intermediate stringency as described below:

(i) By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in prehybridization mixture containing 100 μg/ml denatured salmon sperm DNA and 5–20× $10^6$ cpm of $^{32}$p-labeled probe. Alternatively, the hybridization step can be performed at 65° C. in the presence of SSC buffer, 1×SSC corresponding to 0.15 M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which is used are well known in the art and as cited in Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y. Preferably, such sequences encode a homolog of a polypeptide encoded by one of 0RF2 to 0RF1297. In one embodiment, such sequences encode a mammalian PG1 polypeptide.

(ii) By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which is used are well known in the art and as cited in Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y. Preferably, such sequences encode a homolog of a polypeptide encoded by one of SEQ ID NOs: 3, 69, 100–112, or 179–184. In one embodiment, such sequences encode a mammalian PG1 polypeptide.

The present invention also encompasses diagnostic kits comprising one or more polynucleotides of the invention with a portion or all of the necessary reagents and instructions for genotyping a test subject by determining the identity of a nucleotide at a PG1-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an allele specific amplification method. Optionally such a kit may include instructions for scoring the results of the determination with respect to the test subjects' risk of contracting a cancer or prostate cancer, or likely response to an anti-cancer agent or anti-prostate cancer agent, or chances of suffering from side effects to an anti-cancer agent or anti-prostate cancer agent.

Preferred Genomic Sequences Of The PG-1 Gene

The present invention concerns the genomic sequence of PG-1. The present invention encompasses the PG-1 gene, or PG-1 genomic sequences consisting of, consisting essentially of, or comprising the sequence of SEQ ID No 179, a sequence complementary thereto, as well as fragments and variants thereof. These polynucleotides may be purified, isolated, or recombinant.

The invention also encompasses a purified, isolated, or recombinant polynucleotide comprising a nucleotide sequence having at least 70, 75, 80, 85, 90, or 95% nucleotide identity with a nucleotide sequence of SEQ ID No 179 or a complementary sequence thereto or a fragment thereof. The nucleotide differences as regards to the nucleotide sequence of SEQ ID No 179 may be generally randomly distributed throughout the entire nucleic acid. Nevertheless, preferred nucleic acids are those wherein the nucleotide differences as regards to the nucleotide sequence of SEQ ID No 179 are predominantly located outside the coding sequences contained in the exons. These nucleic acids, as well as their fragments and variants, may be used as oligonucleotide primers or probes in order to detect the presence of a copy of the PG-1 gene in a test sample, or alternatively in order to amplify a target nucleotide sequence within the PG-1 sequences.

Another object of the invention consists of a purified, isolated, or recombinant nucleic acid that hybridizes with the nucleotide sequence of SEQ ID No 179 or a complementary sequence thereto or a variant thereof, under the stringent hybridization conditions as defmed above.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 179 or the complements thereof, wherein said contiguous span comprises at least 1, 2, 3, 5, 10, or 25 of the following nucleotide positions of SEQ ID No 179: 1–2324, 2852–2936, 3204–3249, 3456–3572, 3899–4996, 5028–6086, 6310–8710, 9136–11170, 11534–12104, 12733–13163, 13206–14150, 14191–14302, 14338–14359, 14788–15589, 16050–16409, 16440–21718, 21959–22007, 22086–23057, 23488–23712, 23832–24099, 24165–24376, 24429–24568, 24607–25096, 25127–25269, 25300–27576, 27612–29217, 29415–30776, 30807–30986, 31628–32658, 32699–36324, 36772–39149, 39184–40269, 40580–40683, 40844–41048, 41271–43539, 43570–47024, 47510–48065, 48192–49692, 49723–50174, 52626–53599, 54516–55209, and 55666–56146.

Preferred PG-1 cDNA Sequences

The expression of the PG-1 gene has been shown to lead to the production of at least one mRNA species, the nucleic acid sequence of which is set forth in SEQ ID No 3.

Another object of the invention is a purified, isolated, or recombinant nucleic acid comprising the nucleotide sequence of SEQ ID No 3, complementary sequences thereto, as well as allelic variants, and fragments thereof. Moreover, preferred polynucleotides of the invention include purified, isolated, or recombinant PG-1 cDNAs consisting of, consisting essentially of, or comprising the sequence of SEQ ID No 3. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, 10, or 25 of the following nucleotide positions of SEQ ID No 3: 1–280, 651–690, 3315–4288, and 5176–5227. The invention also pertains to a purified or isolated nucleic acid comprising a polynucleotide having at least 95% nucleotide identity with a polynucleotide of SEQ ID No 3, advantageously 99% nucleotide identity, preferably 99.5% nucleotide identity and most preferably 99.8% nucleotide identity with a polynucleotide of SEQ ID No 3, or a sequence complementary thereto or a biologically active fragment thereof.

Preferred Oligonucleotide Probes And Primers

Polynucleotides derived from the PG-1 gene are useful in order to detect the presence of at least a copy of a nucleotide sequence of SEQ ID No 179, or a fragment, complement, or variant thereof in a test sample.

S Particularly preferred probes and primers of the invention include isolated, purified, or recombinant polynucleotides comprising a contiguous span of at least 12, 15, 18, 20, 25, 30, 35, 40, 50, 60,70, 80, 90, 100, 150,200, 500, or 1000 nucleotides of SEQ ID No 179 or the complements thereof, wherein said contiguous span comprises at least 1, 2, 3, 5, 10, or 25 of the following nucleotide positions of SEQ ID No 179:1–2324, 2852–2936, 3204–3249, 3456–3572, 3899–4996, 5028–6086, 6310–8710, 9136–11170, 11534–12104, 12733–13163, 13206–14150, 14191–14302, 14338–14359, 14788–15589, 16050–16409, 16440–21718, 21959–22007, 22086-23057, 23488-23712, 23832–24099, 24165–24376, 24429–24568, 24607–25096, 25127–25269, 25300–27576, 27612–29217, 29415–30776, 30807–30986, 31628–32658, 32699–36324, 36772–39149, 39184–40269, 40580–40683, 40844–41048, 41271–43539, 43570–47024, 47510–48065, 48192–49692, 49723–50174, 52626–53599, 54516–55209, and 55666–56146.

Another object of the invention is a purified, isolated, or recombinant nucleic acid comprising the nucleotide sequence of SEQ ID No 3, complementary sequences thereto, as well as allelic variants, and fragments thereof. Moreover, preferred probes and primers of the invention include purified, isolated, or recombinant PG-1 cDNAs consisting of, consisting essentially of, or comprising the sequence of SEQ ID No 3. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, 10, or 25 of the following nucleotide positions of SEQ ID No 3: 1–280, 651–690,3315–4288, and 5176–5227.

Use of PG1 Nucleic Acids as Reazents

The PG1 genomic DNA of SEQ ID NO: 179, the PG1 cDNA of SEQ ID NO: 3, 112–124 and PG1 alleles responsible for a detectable phenotype (such as those obtainable by the methods of Example 12, and SEQ ID NO:69) can be used to prepare PCR primers for use in diagnostic techniques or genetic engineering methods such as those described above. Example 10 describes the use of the PG1 genomic DNA of SEQ ID NO: 179, the PG1 cDNA of SEQ ID NO: 3, 112–124 and PG1 alleles responsible for a detectable phenotype (such as those obtainable by the methods of Example 12) in PCR amplification procedures.

EXANOKE 10

The PG1 genomic DNA of SEQ ID NO: 179, the PG1 cDNA of SEQ ID NO: 3, and PG1 alleles responsible for a detectable phenotype (such as those obtainable by the methods of Example 12) is used to prepare PCR primers for a variety of applications, including isolation procedures for cloning nucleic acids capable of hybridizing to such sequences, diagnostic techniques and forensic techniques. The PCR primers comprise at least 10 consecutive bases of the PG1 genomic DNA of SEQ ID NO: 179, the PG1 cDNA of SEQ ID NO: 3, 112–124 and PG1 alleles responsible for a detectable phenotype (such as those obtainable by the methods of Example 12) or the sequences complementary thereto. Preferably, the PCR primers comprise at least 12, 15, or 17 consecutive bases of these sequences. More preferably, the PCR primers comprise at least 20-10 consecutive bases of the PG1 genomic DNA of SEQ ID NO: 179, the PG1 cDNA of SEQ ID NO: 3, 112–124 and PG1 alleles responsible for a detectable phenotype (such as those obtainable by the methods of Example 12) or the sequences complementary thereto. In some embodiments, the PCR primers may comprise more than 30 consecutive bases of the PG1 genomic DNA of SEQ ID NO: 179, the PG1 cDNA of SEQ ID NO: 3, 112–124 and PG1 alleles responsible for a detectable phenotype (such as those obtainable by the methods of Example 12) or the sequences complementary thereto. It is preferred that the primer pairs to be used together in a PCR amplification have approximately the same G/C ratio, so that melting temperatures are approximately the same.

A variety of PCR techniques are familiar to those skilled in the art. For a review of PCR technology, see Molecular Cloning to Genetic Engineering White, B. A. Ed. in Methods in Molecular Biology 67: Humana Press, Totowa 1997. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

The polynucleotides of the Invention also encompass vectors and DNA constructs as well as other forms of primers and probes. For a thorough description of these embodiments please see Sections VIII, X, and XI below.

III. POLYPEPTIDES

PG1 Proteins and Polypeptide Fragments:

The term "PG1 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies PG1 proteins from human (SEQ ID NOs: 4, and 5), and mouse (SEQ ID NO: 74). However, PG1 species from other varieties of mammals are expressly contemplated and is isolated using the antibodies of the present invention in conjunction with standard affinity chromatography methods as well as being expressed from the PG1 genes isolated from other mammalian sources using human and mouse PG1 nucleic acid sequences as primers and probes as well as the methods described herein.

The invention also embodies PG1 proteins translated from less common alternative splice species, including SEQ ID NOs: 125–136, and PG1 proteins which result from naturally occurring mutant, particularly functional mutants of PG1, including SEQ ID NO: 70, which is identified and obtained by the described herein. The present invention also embodies polypeptides comprising a contiguous stretch of at least 6 amino acids, preferably at least 8 to 10 amino acids, more preferably at least 12, 15, 20, 25, 50, or 100 amino acids of a PG1 protein. In a preferred embodiment the contiguous stretch of amino acids comprises the site of a mutation or functional mutation, including a deletion, addition, swap or truncation of the amino acids in the PG1 protein sequence. For instance, polypeptides that contain either the Arg and His residues at amino acid position 184, and polypeptides that contain either the Arg or Ile residue at amino acid position 293 of the SEQ ID NO: 4 in said contiguous stretch are particularly preferred embodiments of the invention and useful in the manufacture of antibodies to detect the presence and absence of these mutations. Similarly, polypeptides with a carboxy terminus at position 228 is a particularly preferred embodiment of the invention and useful in the manufacture of antibodies to detect the presence and absence of the mutation shown in SEQ ID NOs: 69 and 70.

Similarly, polypeptides that that contain an peptide sequences of 8, 10, 12, 15, or 25 amino acids encoded over a naturally-occurring splice junction (the point at which two human PG1 exon (SEQ ID NOs: 100–111) are covalently linked) in said contiguous stretch are particularly preferred embodiments and useful in the manufacture of antibodies to detect the presence, localization, and quantity of the various protein products of the PG1 alternative splice species.

PG1 proteins are preferably isolated from human, mouse or mammalian tissue samples or expressed from human, mouse or mammalian genes.

The PG1 polypeptides of the invention can be made using routine expression methods known in the art, see, for instance, Example 11, below. The polynucleotide encoding the desired polypeptide, is ligated into an expression vector suitable for any convenient host. Both eukaryotic and prokaryotic host systems is used in forming recombinant polypeptides, and a summary of some of the more common systems are included in Sections II and VIII. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments is produced by chemical synthesis. Alternatively the proteins of the invention is extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Preferred PG-1 Proteins and Polypeptide Fragments

The invention embodies PG-1 proteins from humans, including isolated or purified PG-1 proteins consisting, consisting essentially, or comprising the sequence of SEQ ID No 4.

The present invention also embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 4, wherein said contiguous span includes at least 1, 2, 3, or 5 of the amino acid positions 1–26, 295–302, and 333–353. In other preferred embodiments the contiguous stretch of amino acids comprises the site of a mutation or functional mutation, including a deletion, addition, swap or truncation of the amino acids in the PG-1 protein sequence.

Expression of the PG1 Protein

Any PG1 cDNA, including SEQ ID NO: 3, 69, 112–124, or 184 or synthetic DNAs is use as described in Example 11 below to express PG1 proteins and polypeptides.

EXAMPLE 11

The nucleic acid encoding the PG1 protein or polypeptide to be expressed is operably linked to a promoter in an expression vector using conventional cloning technology. The PG1 insert in the expression vector may comprise the full coding sequence for the PG1 protein or a portion thereof. For example, the PG1 derived insert may encode a polypeptide comprising at least 10 consecutive amino acids of the PG1 proteins of SEQ ID NO: 4.

The expression vector is any of the mammalian, yeast, insect or bacterial expression systems known in the art, see for example Section VIII. Commercially available vectors and expression systems are available from a variety of suppliers including Genetics Institute (Cambridge, Mass.), Stratagene (La Jolla, Calif.), Promega (Madison, Wisconsin), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767.

The following is provided as one exemplary method to express the PG1 protein or a portion thereof. In one embodiment, the entire coding sequence of the PG1 cDNA through the poly A signal of the cDNA are operably linked to a promoter in the expression vector. Alternatively, if the nucleic acid encoding a portion of the PG1 protein lacks a methionine to serve as the initiation site, an initiating methionine can be introduced next to the first codon of the nucleic acid using conventional techniques. Similarly, if the insert from the PG1 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the PG1 protein or a portion thereof is obtained by PCR from a bacterial vector containing the PG1 cDNA of SEQ ID NO: 3 using oligonucleotide primers complementary to the PG1 CDNA or portion thereof and containing restriction endonuclease sequences for Pst 1 incorporated into the 5' primer and BglII at the 5' end of the corresponding cDNA 3' primer, taking care to ensure that the sequence encoding the PG1 protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600ug/ml G418 (Sigma, St. Louis, Miss.).

Alternatively, the nucleic acids encoding the PG1 protein or a portion thereof is cloned into pED6dpc2 (Genetics Institute, Cambridge, Mass.). The resulting pED6dpc2 constructs is transfected into a suitable host cell, such as COS 1 cells. Methotrexate resistant cells are selected and expanded.

The above procedures may also be used to express a mutant PG1 protein responsible for a detectable phenotype or a portion thereof.

The expressed proteins is purified using conventional purification techniques such as ammonium sulfate precipitation or chromatographic separation based on size or charge. The protein encoded by the nucleic acid insert may also be purified using standard immunochromatography techniques. In such procedures, a solution containing the expressed PG1 protein or portion thereof, such as a cell extract, is applied to a column having antibodies against the PG1 protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the PG1 protein or a portion thereof, the proteins expressed from host cells containing an expression vector containing an insert encoding the PG1 protein or a portion thereof can be compared to the proteins expressed in host cells containing the expression vector without an insert. The presence of a band in samples from cells containing the expression vector with an insert which is absent in samples from cells containing the expression vector without an insert indicates that the PG1 protein or a portion thereof is being expressed. Generally, the band will have the mobility expected for the PG1 protein or portion thereof. However, the band may have a mobility different than that expected as a result of modifications such as glycosylation, ubiquitination, or enzymatic cleavage.

Antibodies capable of specifically recognizing the expressed PG1 protein or a portion thereof is generated as described below in Section VII.

If antibody production is not possible, the nucleic acids encoding the PG1 protein or a portion thereof is incorporated into expression vectors designed for use in purification schemes employing chimeric polypeptides. In such strategies the nucleic acid encoding the PG1 protein or a portion thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites is engineered between the β-globin gene or the nickel binding polypeptide and the PG1 protein or portion thereof. Thus, the two polypeptides of the chimera is separated from one another by protease digestion. One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

IV. IDENTIFICATION OF MUTATIONS IN THE PG1 GENE WHICH ARE ASSOCIATED WITH A DETECTABLE PHENOTYPE

Mutations in the PG1 gene which are responsible for a detectable phenotype is identified by comparing the sequences of the PG1 genes from affected and unaffected individuals as described in Example 12, below. The detectable phenotype may comprise a variety of manifestations of altered PG1 function, including prostate cancer, hepatocellular carcinoma, colorectal cancer, non-small cell lung cancer, squamous cell carcinoma, or other conditions. The mutations may comprise point mutations, deletions, or insertions of the PG1 gene. The mutations may lie within the coding sequence for the PG1 protein or within regulatory regions in the PG1 gene.

EXAMPLE 12

Oligonucleotide primers are designed to amplify the sequences of each of the exons or the promoter region of the PG1 gene. The oligonucleotide primers may comprise at least 10 consecutive nucleotides of the PG1 genomic DNA of SEQ ID NO: 179 or the PG1 cDNA of SEQ ID NO: 3 or the sequences complementary thereto. Preferably, the oligonucleotides comprise at least 15 consecutive nucleotides of the PG1 genomic DNA of SEQ ID NO: 179 or the PG1 cDNA of SEQ ID NO: 3 or the sequences complementary thereto. In some embodiments, the oligonucleotides may comprise at least 20 consecutive nucleotides of the PG1 genomic DNA of SEQ ID NO: 179 or the PG1 cDNA of SEQ ID NO:3 or the sequences complementary thereto. In other embodiments, the oligonucleotides may comprise 25 or more consecutive nucleotides of the PG1 genomic DNA of SEQ ID NO: 179 or the PG1 cDNA of SEQ ID NO: 3 or the sequences complementary thereto.

Each primer pair is used to amplify the exon or promoter region from which it is derived. Amplification is carried out on genomic DNA samples from affected patients and unaffected controls using the PCR conditions described above. Amplification products from the genomic PCRs are subjected to automated dideoxy terminator sequencing reactions and electrophoresed on ABI 377 sequencers. Following gel image analysis and DNA sequence extraction, ABI sequence data are automatically analyzed to detect the presence of sequence variations among affected and unaffected individuals. Sequences are verified by determining the sequences of both DNA strands for each individual. Preferably, these candidate mutations are detected by comparing individuals homozygous for haplotype 5 of FIG. 4 and controls not carrying haplotype 5 or related haplotypes.

Candidate polymorphisms suspected of being responsible for the detectable phenotype, such as prostate cancer or other conditions, are then verified by screening a larger population of affected and unaffected individuals using the microsequencing technique described above. Polymorphisms which exhibit a statistically significant correlation with the detectable phenotype are deemed responsible for the detectable phenotype.

Other techniques may also be used to detect polymorphisms associated with a detectable phenotype such as prostate cancer or other conditions. For example, polymorphisms is detected using single stranded conformation analyses such as those described in Orita et al., Proc. Natl. Acad. Sci. U.S.A. 86: 2776–2770 (1989). In this approach, polymorphisms are detected through altered migration on SSCA gels.

Alternatively, polymorphisms is identified using clamped denaturing gel electrophoresis, heteroduplex analysis, chemical mismatch cleavage, and other conventional techniques as described in Sheffield, V. C. et al, Proc. Natl. Acad. Sci. U.S.A 49:699–706 (1991); White, M. B. et al., Genomics 12:301–306 (1992); Grompe, M. et al., Proc. Natl. Acad. Sci. U.S.A 86:5855–5892 (1989); and Grompe, M. Nature Genetics 5:111–117 (1993).

The PG1 genes from individuals carrying PG1 mutations responsible for the detectable phenotype, or cDNAs derived therefrom, is cloned as follows. Nucleic acid samples are obtained from individuals having a PG1 mutation associated with the detectable phenotype. The nucleic acid samples are contacted with a probe derived from the PG1 genomic DNA of SEQ ID NO: 179 or the PG1 cDNA of SEQ ID NO:3. Nucleic acids containing the mutant PG1 allele are identified using conventional techniques. For example, the mutant PG1 gene, or a cDNA derived therefrom, is obtained by conducting an amplification reaction using primers derived from the PG1 genomic DNA of SEQ ID NO: 179 or the PG1 cDNA of SEQ ID NO:3. Alternatively, the mutant PG1 gene, or a cDNA derived therefrom, is identified by hybridizing a genomic library or a cDNA library obtained from an individual having a mutant PG1 gene with a detectable probe derived from the PG1 genomic DNA of SEQ ID NO: 179 or the PG1 cDNA of SEQ ID NO: 3. Alternatively, the mutant PG1 allele is obtained by contacting an expression library from an individual carrying a PG1 mutation with a detectable antibody against the PG1 proteins of SEQ ID NO: 4 or SEQ ID NO: 5 which has been prepared as described below. Those skilled in the art will appreciate that the PG1 genomic DNA of SEQ ID NO: 179, the PG1 cDNA of SEQ ID NO: 3 and the PG1 proteins of SEQ ID NOs: 4 and 5 is used in a variety of other conventional techniques to obtain the mutant PG1 gene.

In another embodiment the mutant PG1 allele which causes a detectable phenotype can be isolated by obtaining a nucleic acid sample such as a genomic library or a cDNA library from an individual expressing the detectable phenotype. The nucleic acid sample can be contacted with one or more probes lying in the 8p23 region of the human genome. Nucleic acids in the sample which contain the PG1 gene can be identified by conducting sequencing reactions on the nucleic acids which hybridize to the markers from the 8p23 region of the human genome.

The region of the PG1 gene containing the mutation responsible for the detectable phenotype may also be used in diagnostic techniques such as those described below. For example, oligonucleotides containing the mutation responsible for the detectable phenotype is used in amplification or hybridization based diagnostics, such as those described herein, for detecting individuals suffering from the detectable phenotype or individuals at risk of developing the detectable phenotype at a subsequent time. In addition, the PG1 allele responsible for the detectable phenotype is used in gene therapy as described herein. The PG1 allele responsible for the detectable phenotype may also be cloned into an expression vector to express the mutant PG1 protein a described herein.

During the search for biallelic markers associated with prostate cancer, a number of polymorphic bases were discovered which lie within the PG1 gene. The identities and positions of these polymorphic bases are listed as features in the accompanying Sequence Listing for the PG1 genomic DNA of SEQ ID NO: 179. The polymorphic bases is used in the above-described diagnostic techniques for determining whether an individual is at risk for developing prostate cancer at a subsequent date or suffers from prostate cancer as a result of a PG1 mutation. The identities of the nucleotides present at the polymorphic positions in a nucleic acid sample is determined using the techniques, such as microsequencing analysis, which are described above.

It is possible that one or more of these polymorphisms (or other polymorphic bases) is mutations which are associated with prostate cancer. To determine whether a polymorphism is responsible for prostate cancer, the frequency of each of the alleles in individuals suffering from prostate cancer and unaffected individuals is measured as described in the haplotype analysis above. Those mutations which occur at a statistically significant frequency in the affected population are deemed to be responsible for prostate cancer.

cDNAs containing the identified mutant PG1 gene is prepared as described above and cloned into expression vectors as described below. The proteins expressed from the expression vectors is used to generate antibodies specific for the mutant PG1 proteins as described below. In addition, allele specific probes containing the PG1 mutation responsible for prostate cancer is used in the diagnostic techniques described below.

Genes sharing homology to the PG1 gene is identified as follows.

EXAMPLE 13

Alternatively, a cDNA library or genomic DNA library to be screened for genes sharing homology to the PG1 gene is obtained from a commercial source or made using techniques familiar to those skilled in the art. The cDNA library or genomic DNA library is hybridized to a detectable probe comprising at least 10 consecutive nucleotides from the PG1 cDNA of SEQ ID NO:3, the PG1 genomic DNA of SEQ ID NO: 179, or the sequences complementary thereto, using conventional techniques. Preferably, the probe comprises at least 12, 15, or 17 consecutive nucleotides from the PG1 cDNA of SEQ ID NO:3, the PG1 genomic DNA of SEQ ID NO: 179, or the sequences complementary thereto. More preferably, the probe comprises at least 20–10 consecutive nucleotides from the PG1 cDNA of SEQ ID NO:3, the PG1 genomic DNA of SEQ ID NO: 179, or the sequences complementary thereto. In some embodiments, the probe comprises more than 30 nucleotides from the PG1 cDNA of SEQ ID NO:3, the PG1 genomic DNA of SEQ ID NO: 179, or the sequences complementary thereto.

Techniques for identifying cDNA clones in a cDNA library which hybridize to a given probe sequence are disclosed in Sambrook et al., Molecular Cloning: A Laboratory Manual 2d Ed., Cold Spring Harbor Laboratory Press, 1989. The same techniques is used to isolate genomic DNAs sharing homology with the PG1 gene.

Briefly, cDNA or genomic DNA clones which hybridize to the detectable probe are identified and isolated for further manipulation as follows. A probe comprising at least 10 consecutive nucleotides from the PG1 cDNA of SEQ ID NO:3, the PG1 genomic DNA of SEQ ID NO: 179, or the sequences complementary thereto, is labeled with a detectable label such as a radioisotope or a fluorescent molecule. Preferably, the probe comprises at least 12, 15, or 17 consecutive nucleotides from the PG1 cDNA of SEQ ID NO:3, the PG1 genomic DNA of SEQ ID NO: 179, or the sequences complementary thereto. More preferably, the probe comprises 20-30 consecutive nucleotides from the PG1 cDNA of SEQ ID NO:3, the PG1 genomic DNA of SEQ ID NO: 179, or the sequences complementary thereto. In some embodiments, the probe comprises more than 30 nucleotides from the PG1 cDNA of SEQ ID NO:3, the PG1 genomic DNA of SEQ ID NO: 179, or the sequences complementary thereto.

Techniques for labeling the probe are well known and include phosphorylation with polynucleotide kinase, nick translation, in vitro transcription, and non-radioactive techniques. The cDNAs or genomic DNAs in the library are transferred to a nitrocellulose or nylon filter and denatured. After incubation of the filter with a blocking solution, the filter is contacted with the labeled probe and incubated for a sufficient amount of time for the probe to hybridize to cDNAs or genomic DNAs containing a sequence capable of hybridizing to the probe.

By varying the stringency of the hybridization conditions used to identify cDNAs or genomic DNAs which hybridize to the detectable probe, cDNAs or genomic DNAs having different levels of homology to the probe can be identified and isolated. To identify cDNAs or genomic DNAs having a high degree of homology to the probe sequence, the melting temperature of the probe is calculated using the following formulas:

For probes between 14 and 70 nucleotides in length the melting temperature ™ is calculated using the formula: Tm=81.5+16.6(log (Na+))+0.41(fraction G+C)−(600/N) where N is the length of the probe.

If the hybridization is carried out in a solution containing formamide, the melting temperature is calculated using the equation Tm=81.5+16.6(log (Na+))+0.41(fraction G+C)−(0.63% formamide)−(600/N) where N is the length of the probe.

Prehybridization is carried out in 6×SSC, 5×Denhardt's reagent, 0.5% SDS, 100 μg denatured fragmented salmon sperm DNA or 6×SSC, 5×Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization is carried out at 15–25° C. below the Tm. For shorter probes, such as oligonucleotide probes, the hybridization is conducted at 15–25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

cDNAs or genomic DNAs homologous to the PG1 gene which have hybridized to the probe are identified by autoradiography or other conventional techniques.

The above procedure is modified to identify cDNAs or genomic DNAs having decreasing levels of homology to the probe sequence. For example, to obtain cDNAs or genomic DNAs of decreasing homology to the detectable probe, less stringent conditions is used. For example, the hybridization temperature is decreased in increments of 5° C. from 68° C. to 42° C. in a hybridization buffer having a Na+ concentration of approximately 1 M. Following hybridization, the filter is washed with 2×SSC, 0.5% SDS at the temperature of hybridization. These conditions are considered to be "moderate" conditions above 50° C. and "low" conditions below 50° C.

Alternatively, the hybridization is carried out in buffers, such as 6×SSC, containing formamide at a temperature of 42° C. In this case, the concentration of formamide in the hybridization buffer is reduced in 5% increments from 50% to 0% to identify clones having decreasing levels of homology to the probe. Following hybridization, the filter is washed with 6×SSC, 0.5% SDS at 50C. These conditions are considered to be "moderate" conditions above 25% formamide and "low" conditions below 25% formamide.

cDNAs or genomic DNAs which have hybridized to the probe are identified by autoradiography.

If it is desired to obtain nucleic acids homologous to the PG1 gene, such as allelic variants thereof or nucleic acids encoding proteins related to the PG1 protein, the level of homology between the hybridized nucleic acid and the PG1 gene may readily be determined. To determine the level of homology between the hybridized nucleic acid and the PG1 gene, the nucleotide sequences of the hybridized nucleic acid and the PG1 gene are compared. For example, using the above methods, nucleic acids having at least 95% nucleic acid homology to the PG1 gene is obtained and identified. Similarly, by using progressively less stringent hybridization conditions one can obtain and identify nucleic acids having at least 90%, at least 85%, at least 80% or at least 75% homology to the PG1 gene.

To determine whether a clone encodes a protein having a given amount of homology to the PG1 protein, the amino acid sequence of the PG1 protein is compared to the amino acid sequence encoded by the hybridizing nucleic acid. Homology is determined to exist when an amino acid sequence in the PG1 protein is closely related to an amino acid sequence in the hybridizing nucleic acid. A sequence is closely related when it is identical to that of the PG1 sequence or when it contains one or more amino acid substitutions therein in which amino acids having similar characteristics have been substituted for one another. Using the above methods, one can obtain nucleic acids encoding proteins having at least 95%, at least 90%, at least 85%, at least 80% or at least 75% homology to the proteins encoded by the PG1 probe.

Isolation and Use of Mutant or Low Frequency PG1 Alleles from Mammalian Prostate Tumor Tissues and Cell Lines A single mutant PG1 gene was isolated from a human prostate cancer cell line. The nucleic acid sequence and amino acid sequence of this mutant PG1 are disclosed in SEQ IN NOs: 69 and 70, respectively. This mutant was found to contain a stop codon at codon position number 229, and therefore results in a truncated gene product of only 228 amino acids. The present invention encompasses purified or isolated nucleic acids comprising at least 8, 10, 12, 15, 20, or 25 consecutive nucleotides of SEQ ID NO: 69, preferably containing the mutation in codon number 229. A preferred embodiment of the present invention encompasses purified or isolated nucleic acids comprising at least 8, 10, 12, 15, 20, or 25 consecutive nucleotides of SEQ ID NO: 71.

The present invention is also directed to methods of determining whether an individual is at risk of developing prostate cancer at a later date or whether said individual suffers from prostate cancer as a result of a mutation in the PG1 gene comprising: obtaining a nucleic acid sample from said individual; and determining whether the nucleotides present at one or more of the polymorphic bases in the sequences selected from the group consisting of SEQ ID NOs: 69 and 71 are indicative of a risk of developing prostate cancer at a later date or indicative of prostate cancer resulting from a mutation in the PG1 gene. The present invention also includes purified or isolated nucleic acids encoding at least 4, 8, 10, 12, 15, or 20 consecutive amino acids of the polypeptide of SEQ ID NO: 70, preferably including the carboxy terminus of said polypeptide. The isolated or purified polypeptides of the invention include polypeptides comprising at least 4, 8, 10, 12, 15, or 20 consecutive amino acids of the polypeptide of SEQ ID NO: 70, preferably including the carboxy terminus of said polypeptide.

V. DIAGNOSIS OF INDIVIDUALS AT RISK FOR DEVELOPING PROSTATE CANCER OR INDIVIDUALS SUFFERING FROM PROSTATE CANCER AS A RESULT OF A MUTATION IN THE PG1 GENE

Individuals may then be screened for the presence of polymorphisms in the PG1 gene or protein which are associated with a detectable phenotype such as cancer, prostate cancer or other conditions as described in Example 14, below. The individuals is screened while they are asymptomatic to determine their risk of developing cancer, prostate cancer or other conditions at a subsequent time. Alternatively, individuals suffering from cancer, prostate cancer or other conditions is screened for the presence of polymorphisms in the PG1 gene or protein in order to determine whether therapies which target the PG1 gene or protein should be applied.

EXAMPLE 14

Nucleic acid samples are obtained from a symptomatic or asymptomatic individual. The nucleic acid samples is obtained from blood cells as described above or is obtained from other tissues or organs. For individuals suffering from prostate cancer, the nucleic acid sample is obtained from the tumor. The nucleic acid sample may comprise DNA, RNA, or both. The nucleotides at positions in the PG1 gene where mutations lead to prostate cancer or other detectable phenotypes are determined for the nucleic acid sample.

In one embodiment, a PCR amplification is conducted on the nucleic acid sample as described above to amplify regions in which polymorphisms associated with prostate cancer or other detectable phenotypes have been identified. The amplification products are sequenced to determine whether the individual possesses one or more PG1 polymorphisms associated with prostate cancer or other detectable phenotypes.

Alternatively, the nucleic acid sample is subjected to microsequencing reactions as described above to determine whether the individual possesses one or more PG1 polymorphisms associated with prostate cancer or another detectable phenotype resulting from a mutation in the PG1 gene.

In another embodiment, the nucleic acid sample is contacted with one or more allele specific oligonucleotides which specifically hybridize to one or more PG1 alleles associated with prostate cancer or another detectable phenotype. The nucleic acid sample is also contacted with a second PG1 oligonucleotide capable of producing an amplification product when used with the allele specific oligonucleotide in an amplification reaction. The presence of an amplification product in the amplification reaction indicates that the individual possesses one or more PG1 alleles associated with prostate cancer or another detectable phenotype.

Determination of PG1 Expression Levels

As discussed above, PG1 polymorphisms associated with cancer, prostate cancer or other detectable phenotypes may exert their effects by increasing, decreasing, or eliminating PG1 expression, or in altering the frequency of various transcription species. Accordingly, PG1 expression levels in individuals suffering from cancer, prostate cancer or other detectable phenotypes is compared to those of unaffected individuals to determine whether over-expression, under-expression, loss of expression, or changes in the relative frequency of transcription species of PG1 causes cancer, prostate cancer or another detectable phenotype. Individuals is tested to determine whether they are at risk of developing cancer, or prostate cancer at a subsequent time or whether they suffer from prostate cancer resulting from a mutation in the PG1 gene by determining whether they exhibit a level of PG1 expression associated with prostate cancer. Similarly, individuals is tested to determine whether they suffer from another PG1 mediated detectable phenotype or whether they are at risk of suffering from such a condition at a subsequent time.

Expression levels in nucleic acid samples from affected and unaffected individuals is determined by performing Northern blots using detectable probes derived from the PG1 gene or the PG1 cDNA. A variety of conventional Northern blotting procedures is used to detect and quantitate PG1 expression and the frequencies of the various transcription species of PG1, including those disclosed in Current Protocols in Molecular Biology, John Wiley 503 Sons, Inc. 1997 and Sambrook et al. Molecular Cloning: A Laboratory Manual, Second Edition, Cold Spring Harbor Laboratory Press, 1989.

Alternatively, PG1 expression levels is determined as described in Example 15, below.

EXAMPLE 15

Expression levels and patterns of PG1 is analyzed by solution hybridization with long probes as described in International Patent Application No. WO 97/05277. Briefly, the PG1 cDNA or the PG1 genomic DNA described above, or fragments thereof, is inserted at a cloning site immediately downstream of a bacteriophage (13, T7 or SP6) RNA polymerase promoter to produce antisense RNA. Preferably, the PG1 insert comprises at least 100 or more consecutive nucleotides of the genomic DNA sequence of SEQ ID NO: 1 or the cDNA sequences of SEQ ID NO: 3. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formnamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of PG1 gene expression may also be performed using arrays as described in Sections II and X,. As used here, the term array means an arrangement of a plurality of nucleic acids of sufficient length to permit specific detection of expression of PG1 mRNAs capable of hybridizing thereto. For example, the arrays may contain a plurality of nucleic acids derived from genes whose expression levels are to be assessed. The arrays may include the PG1 genomic DNA of SEQ ID NO: 179, the PG1 cDNA of SEQ ID NO:3 or the sequences complementary thereto or fragments thereof. The array may contain some or all of the known alternative splice or transcription species of PG1, including the species in SEQ ID NOs: 3, and 112–124 to determine the relative frequency of particular transcription species. Alternatively, the array may contain polynucleotides which overlap all of the potential splice junctions, including, for example SEQ ID NOs: 137–178, so that the frequency of particular splice junctions can be determined and correlated with traits or used in diagnostics just as expressions levels are. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments is more than 500 nucleotides in length.

For example, quantitative analysis of PG1 gene expression is performed with a complementary DNA microarray as described by Schena et al. (Science 270:467–470, 1995; Proc. Natl. Acad. Sci. U.S.A. 93:10614–10619, 1996). Full length PG1 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of PG1 gene expression may also be performed with full length PG1 cDNAs or fragments thereof in complementary DNA arrays as described by Pietu et al. (Genome Research 6:492–503, 1996). The full length PG1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the PG1 genomic DNA, the PG1 cDNA, or fragments thereof can be done through high density nucleotide arrays as described by Lockhart et al. (Nature Biotechnology 14: 1675–1680, 1996) and Sosnowsky et al. (Proc. Natl. Acad. Sci. 94:1119–1123, 1997). Oligonucleotides of 15–50 nucleotides from the sequences of the PG1 genomic DNA of SEQ ID NO: 179, the PG1 cDNA of SEQ ID NO: 3, 112–124 or the sequences complementary thereto, are synthesized directly on the chip (Lockhart et al., supra) or synthesized and then addressed to the chip (Sosnowski et al., supra).

PG1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94:1119–1123)., the dyes or labeling compounds are detected and quantified. Duplicate hybridizations are performed. Comparative analysis of the intensity of the signal originating from cDNA probes on the same target oligonucleotide in different cDNA samples indicates a differential expression of PG1 mRNA.

The above methods may also be used to determine whether an individual exhibits a PG1 expression pattern associated with cancer, prostate cancer or other diseases. In such methods, nucleic acid samples from the individual are assayed for PG1 expression as described above. If a PG1 expression pattern associated with cancer, prostate cancer, or another disease is observed, an appropriate diagnosis is rendered and appropriate therapeutic techniques which target the PG1 gene or protein is applied.

The above methods may also be applied using allele specific probes to determine whether an individual possesses a PG1 allele associated with cancer, prostate cancer, or another disease. In such approaches, one or more allele specific oligonucleotides containing polymorphic nucleotides in the PG1 gene which are associated with prostate cancer are fixed to a microarray. The array is contacted with a nucleic acid sample from the individual being tested under conditions which permit allele specific hybridization of the sample nucleic acid to the allele specific PG1 probes. Hybridization of the sample nucleic acid to one or more of the allele specific PG1 probes indicates that the individual suffers from prostate cancer caused by the PG1 gene or that the individual is at risk for developing prostate cancer at a subsequent time. Alternatively, any of the genotyping methods described in Section X is utilized.

Use of the Biallelic Markers Of The Invention In Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids. The trait analyzed using the present diagnostics is any detectable trait, cancer, prostate cancer or another disease, a response to an anti-cancer, or anti-prostate cancer, or side effects to an anti-cancer or anti-prostate cancer agent. Diagnostics, which analyze and predict response to a drug or side effects to a drug, is used to determine whether an individual should be treated with a particular drug. For example, if the diagnostic indicates a likelihood that an individual will respond positively to treatment with a particular drug, the drug is administered to the individual. Conversely, if the diagnostic indicates that an individual is likely to respond negatively to treatment with a particular drug, an alternative course of treatment is prescribed. A negative response is defined as either the absence of an efficacious response or the presence of toxic side effects.

Clinical drug trials represent another application for the markers of the present invention. One or more markers indicative of response to an anti-cancer or anti-prostate cancer agent or to side effects to an anti-cancer or anti-prostate cancer agent is identified using the methods described in Section XI, below. Thereafter, potential participants in clinical trials of such an agent is screened to identify those individuals most likely to respond favorably to the drug and exclude those likely to experience side effects. In that way, the effectiveness of drug treatment is measured in individuals who respond positively to the drug, without lowering the measurement as a result of the inclusion of individuals who are unlikely to respond positively in the study and without risking undesirable safety problems. Preferably, in such diagnostic methods, a nucleic acid sample is obtained from the individual and this sample is genotyped using methods described in Section X.

Another aspect of the present invention relates to a method of determining whether an individual is at risk of developing a trait or whether an individual expresses a trait as a consequence of possessing a particular trait-causing allele. The present invention relates to a method of determining whether an individual is at risk of developing a plurality of traits or whether an individual expresses a plurality of traits as a result of possessing a particular trait-causing allele. These methods involve obtaining a nucleic acid sample from the individual and determining whether the nucleic acid sample contains one or more alleles of one or more biallelic markers indicative of a risk of developing the trait or indicative that the individual expresses the trait as a result of possessing a particular trait-causing allele.

As described herein, the diagnostics is based on a single biallelic marker or a group of biallelic markers.

VI. ASSAYING THE PG1 PROTEIN FOR INVOLVEMENT IN RECEPTOR/LIGAND INTERACTIONS

The expressed PG1 protein or portion thereof is evaluated for involvement in receptor/ligand interactions as described in Example 16 below.

EXAMPLE 16

The proteins encoded by the PG1 gene or a portion thereof may also be evaluated for their involvement in receptor/ligand interactions. Numerous assays for such involvement are familiar to those skilled in the art including the assays disclosed in the following references: Chapter 7.28 (Measurement of Cellular Adhesion under Static Conditions 7.28.1–7.28.22) in Current Protocols in Immunology, J. E. Coligan et al. Eds. Greene Publishing Associates and Wiley-Interscience; Takai et al., *Proc. Natl. Acad. Sci.* USA 84:6864–6868, 1987; Bierer et al., J. Exp. Med. 168:1145–1156, 1988; Rosenstein et al., J. Exp. Med. 169:149–160, 1989; Stoltenborg et al., J. Immunol. Methods 175:59–68, 1994; Stitt et al., Cell 80:661–670, 1995; Gyuris et al., Cell 75:791–803, 1993.

For example, the proteins of the present invention may demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as sclectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The PG1 protein or portions thereof described above is used in drug screening procedures to identify molecules which are agonists, antagonists, or inhibitors of PG1 activity. The PG1 protein or portion thereof used in such analyses is free in solution or linked to a solid support. Alternatively, PG1 protein or portions thereof can be expressed on a cell surface. The cell may naturally express the PG1 protein or portion thereof or, alternatively, the cell may express the PG1 protein or portion thereof from an expression vector such as those described below. In one method of drug screening, eukaryotic or prokaryotic host cells which are stably transformed with recombinant polynucleotides in order to express the PG1 protein or a portion thereof are used in conventional competitive binding assays or standard direct binding assays. For example, the formation of a complex between the PG1 protein or a portion thereof and the agent being tested is measured in direct binding assays. Alternatively, the ability of a test agent to prevent formation of a complex between the PG1 protein or a portion thereof and a known ligand is measured.

Alternatively, the high throughput screening techniques disclosed in the published PCT application WO 84/03564, is used. In such techniques, large numbers of small peptides to be tested for PG1 binding activity are synthesized on a surface and affixed thereto. The test peptides are contacted with the PG1 protein or a portion thereof, followed by a wash step. The amount of PG1 protein or portion thereof which binds to the test compound is quantitated using conventional techniques.

In some methods, PG1 protein or a portion thereof is fixed to a surface and contacted with a test compound. After a washing step, the amount of test compound which binds to the PG1 protein or portion thereof is measured.

In another approach, the three dimensional structure of the PG1 protein or a portion thereof may be determined and used for rational drug design.

Alternatively, the PG1 protein or a portion thereof is expressed in a host cell using expression vectors such as those described herein. The PG1 protein or portion thereof is an isotype which is associated with prostate cancer or an isotype which is not associated with prostate cancer. The cells expressing the PG1 protein or portion thereof are contacted with a series of test agents and the effects of the test agents on PG1 activity are measured. Test agents which modify PG1 activity is employed in therapeutic treatments.

The above procedures may also be applied to evaluate mutant PG1 proteins responsible for a detectable phenotype.
Identification of Proteins which Interact with the PG1 Protein Proteins which interact with the PG1 protein is identified as described in Example 17, below.

EXAMPLE 17

Proteins which interact with the PG1 protein or a portion thereof, is identified using two hybrid systems such as the Matchmaker Two Hybrid System 2 (Catalog No. K1604–1, Clontech). As described in the manual accompanying the Matchmaker Two Hybrid System 2 (Catalog No. K1604-1, Clontech), nucleic acids encoding the PG1 protein or a portion thereof, are inserted into an expression vector such that they are in frame with DNA encoding the DNA binding domain of the yeast transcriptional activator GAL4. cDNAs in a cDNA library which encode proteins which might interact with the polypeptides encoded by the nucleic acids encoding the PG1 protein or a portion thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the nucleic acid inserts.

Alternatively, the system described in Lustig et al., Methods in Enzymology 283: 83–99 (1997), is used for identifying molecules which interact with the PG1 protein or a portion thereof. In such systems, in vitro transcription reactions are performed on vectors containing an insert encoded the PG1 protein or a portion thereof cloned downstream of a promoter which drives in vitro transcription. The resulting mRNA is introduced into Xenopus laevis oocytes. The oocytes are then assayed for a desired activity.

Alternatively, the in vitro transcription products produced as described above is translated in vitro. The in vitro translation products can be assayed for a desired activity or for interaction with a known polypeptide.

The system described in U.S. Pat. No. 5,654,150 may also be used to identify molecules which interact with the PG1 protein or a portion thereof. In this system, pools of cDNAs are transcribed and translated in vitro and the reaction products are assayed for interaction with a known polypeptide or antibody.

Proteins or other molecules interacting with the PG1 protein or portions thereof can be found by a variety of additional techniques. In one method, affinity columns containing the PG1 protein or a portion thereof can be constructed. In some versions of this method the affinity column contains chimeric proteins in which the PG1 protein or a portion thereof is fused to glutathione S-transferase. A mixture of cellular proteins or pool of expressed proteins as described above is applied to the affinity column. Proteins interacting with the polypeptide attached to the column can then be isolated and analyzed on 2-D electrophoresis gel as described in Ramunsen et al. Electrophoresis, 18, 588–598 (1997). Alternatively, the proteins retained on the affinity column can be purified by electrophoresis based methods and sequenced. The same method can be used to isolate antibodies, to screen phage display products, or to screen phage display human antibodies.

Proteins interacting with the PG1 protein or portions thereof can also be screened by using an Optical Biosensor as described in Edwards et Leatherbarrow, Analytical Biochemistry, 246, 1–6 (1997). The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred nanometers from the sensor surface). In these screening assays, the target molecule can be the PG1 protein or a portion thereof and the test sample can be a collection of proteins extracted from tissues or cells, a pool of expressed proteins, combinatorial peptide and/or chemical libraries, or phage displayed peptides. The tissues or cells from which the test proteins are extracted can originate from any species.

In other methods, a target protein is immobilized and the test population is the PG1 protein or a portion thereof.

To study the interaction of the PG1 protein or a portion thereof with drugs, the microdialysis coupled to HPLC method described by Wang et al., Chromatographia, 44, 205–208(1997) or the affinity capillary electrophoresis method described by Busch et al., J. Chromatogr. 777:311–328 (1997).

The above procedures may also be applied to evaluate mutant PG1 proteins responsible for a detectable phenotype.

VII. PRODUCTION OF ANTIBODIES AGAINST PG1 POLYPEPTIDES

Any PG1 polypeptide or whole protein (SEQ ID NOs: 4, 5, 70, 74, 125–136) whether human, mouse or mammalian is used to generate antibodies capable of specifically binding to expressed PG1 protein or fragments thereof as described in Example 16, below. The antibodies is capable of binding the full length PG1 protein. PG1 proteins which result from naturally occurring mutant, particularly functional mutants of PG1, including SEQ ID NO: 70, which may used in the production of antibodies. The present invention also contemplates the use of polypeptides comprising a contiguous stretch of at least 6 amino acids, preferably at least 8 to 10 amino acids, more preferably at least 12, 15, 20, 25, 50, or 100 amino acids of any PG1 protein in the manufacture of antibodies. In a preferred embodiment the contiguous stretch of amino acids comprises the site of a mutation or functional mutation, including a deletion, addition, swap or truncation of the amino acids in the PG1 protein sequence. For instance, polypeptides that contain either the Arg and His residues at amino acid position 184, and polypeptides that contain either the Arg or Ile residue at amino acid position 293 of the SEQ ID NO: 4 in said contiguous stretch are particularly preferred embodiments of the invention and useful in the manufacture of antibodies to detect the presence and absence of these mutations. Similarly, polypeptides with a carboxy terminus at position 228 is a particularly preferred embodiment of the invention and useful in the manufacture of antibodies to detect the presence and absence of the mutation shown in SEQ ID NOs: 69 and 70. Similarly, polypeptides that that contain an peptide sequences of 8, 10, 12, 15, or 25 amino acids encoded over a naturally-occurring splice junction (the point at which two human PG1 exon (SEQ ID NOs: 100–111) are covalently linked) in said contiguous stretch are particularly preferred embodiments and useful in the manufacture of antibodies to detect the presence, localization, and quantity of the various protein products of the PG1 alternative splice species.

Alternatively, the antibodies is screened so as to isolate those which are capable of binding an epitope-containing fragment of at least 8, 10, 12, 15, 20, 25, or 30 amino acids of a human, mouse, or mammalian PG1 protein, preferably a sequence selected from SEQ ID NOs: 4, 5, 70, 74, or 125–136.

Antibodies may also be generated which are capable of specifically binding to a given isoform of the PG1 protein. For example, the antibodies is capable of specifically binding to an isoform of the PG1 protein which causes prostate cancer or another detectable phenotype which has been obtained as described above and expressed from an expression vector as described above. Alternatively, the antibodies is capable of binding to an isoform of the PG1 protein which does not cause prostate cancer. Such antibodies is used in diagnostic assays in which protein samples from an individual are evaluated for the presence of an isoform of the PG1 protein which causes cancer or another detectable phenotype using techniques such as Western blotting or ELISA assays.

Non-human animals or mammals, whether wild-type or transgenic, which express a different species of PG1 than the one to which antibody binding is desired, and animals which do not express PG1 (i.e. an PG1 knock out animal as described in Section VIII.) are particularly useful for preparing antibodies. PG1 knock out animals will recognize all or most of the exposed regions of PG1 as foreign antigens, and therefore produce antibodies with a wider array of PG1 epitopes. The humoral immune system of animals which produce a species of PG1 that resembles the antigenic sequence will preferentially recognize the differences between the animal's native PG1 species and the antigen sequence, and produce antibodies to these unique sites in the antigen sequence.

Preferred Antibodies That Bind PG-1 Polypeptides of the Invention

Any PG-1 polypeptide or whole protein may be used to generate antibodies capable of specifically binding to an expressed PG-1 protein or fragments thereof as described.

One antibody composition of the invention is capable of specifically binding or specifically bind to the variant of the PG-1 protein of SEQ ID No 4. For an antibody composition to specifically bind to a first variant of PG-1, it must demonstrate at least a 5%, 10%, 15%, 20%, 25%, 50%, or 100% greater binding affinity for a full length first variant of the PG-1 protein than for a full length second variant of the PG-1 protein in an ELISA, RIA, or other antibody-based binding assay.

In a preferred embodiment, the invention concerns antibody compositions, either polyclonal or monoclonal, capable of selectively binding, or selectively bind to an epitope-containing a polypeptide comprising a contiguous span of at least 6 amino acids, preferably at least 8 to 10 amino acids, more preferably at least 12, 15, 20, 25, 30, 40, 50, or 100 amino acids of SEQ ID No 4, wherein said epitope comprises at least 1, 2, 3, or 5 of the amino acid positions 1–26, 295–302, and 333–353.

The invention also concerns a purified or isolated antibody capable of specifically binding to a mutated PG-1 protein or to a fragment or variant thereof comprising an epitope of the mutated PG-1 protein. In another preferred embodiment, the present invention concerns an antibody capable of binding to a polypeptide comprising at least 10 consecutive amino acids of a PG-1 protein and including at least one of the amino acids which can be encoded by the trait causing mutations.

In a preferred embodiment, the invention concerns the use in the manufacture of antibodies of a polypeptide comprising a contiguous span of at least 6 amino acids, preferably at least 8 to 10 amino acids, more preferably at least 12, 15, 20, 25, 30, 40, 50, or 100 amino acids of SEQ ID No 4, wherein said contiguous span comprises at least 1, 2, 3, or 5 of the amino acid positions 1–26, 295–302, and 333–353.

EXAMPLE 18

Substantially pure protein or polypeptide is isolated from transfected or transformed cells containing an expression vector encoding the PG1 protein or a portion thereof as described in Example 11. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the PG1 protein or a portion thereof can be prepared from murine hybridomas according to the classical method of Kohler, G. and Milstein, C., Nature 256:495 (1975) or derivative methods thereof. Also see Harlow, E., and D. Lane. 1988. Antibodies A Laboratory Manual. Cold Spring Harbor Laboratory. pp. 53–242.

Briefly, a mouse is repetitively inoculated with a few micrograms of the PG1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, N.Y. Section 21–2.

B. Polyclonal Antibody Production by Immunization

Polyclonal antiserum containing antibodies to heterogeneous epitopes in the PG1 protein or a portion thereof can be prepared by immunizing suitable non-human animal with the PG1 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for PG1 concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

VIII. VECTORS AND THE USES OF POLYNUCLEOTIDES IN CELLS, ANIMALS, AND HUMANS

The nucleic acids of the invention include expression vectors, amplification vectors, PCR-suitable polynucleotide primers, and vectors which are suitable for the introduction of a polynucleotide of the invention into an embryonic stem cells for the production of transgenic non-human animals. In addition, vectors which are suitable for the introduction of a polynucleotide of the invention into cells, organs and individuals, including human individuals, for the purposes of gene therapy to reduce the severity of or prevent genetic diseases associated with functional mutations in PG1 genes are encompassed by the present invention. Functional mutations in PG1 genes which are suitable as targets for the gene therapy and transgenic vectors and methods of the invention include, but are not limited to, mutations in the coding region of the PG1 gene which affect the amino acid sequence of the PG1 gene's product, mutations in the promoter or other regulatory regions which affect the levels of PG1 expression, mutations in the PG1 splice sites which affect length of the PG1 gene product or the relative frequency of PG1 alternative splicing species, and any other mutation which in any way affects the level or quality of PG1 expression or activity. The gene therapy methods can be achieved by targeting vectors and method for changing a mutant PG1 gene into a wild-type PG1 gene in a embryonic stem cell or somatic cell. Alternatively, the present invention also encompasses methods and vectors for introducing the expression of wild-type PG1 sequences without the disruption of any mutant PG1 which already reside in the cell, organ or individual.

The invention also embodies amplification vectors, which comprise a polynucleotide of the invention, and an origin of replication. Preferably, such amplification vectors further comprise restriction endonuclease sites flanking the polynucleotide, so as to facilitate cleavage and purification of the polynucleotides from the remainder of the amplification vector, and a selectable marker, so as to facilitate amplification of the amplification vector. Most preferably, the restriction endonuclease sites in the amplification vector are situated such that cleavage at those site would result in no other amplification vector fragments of a similar size.

Thus, such an amplification vector is transfected into a host cell compatible with the origin of replication of said amplification vector, wherein the host cell is a prokaryotic or eukaryotic cell, preferably a mammalian, insect, yeast, or bacterial cell, most preferably an Escherichia coli cell. The resulting transfected host cells is grown by culture methods known in the art, preferably under selection compatible with the selectable marker (e.g., antibiotics). The amplification vectors can be isolated and purified by methods known in the art (e.g., standard plasmid prep procedures). The polynucleotide of the invention can be cleaved with restriction enzymes that specifically cleave at the restriction endonuclease sites flanking the polynucleotide, and the double-stranded polynucleotide fragment purified by techniques known in the art, including gel electrophoresis.

Alternatively linear polynucleotides comprising a polynucleotide of the invention is amplified by PCR. The PCR method is well known in the art and described in, e.g., U.S. Pat. Nos. 4,683,195 and 4,683,202 and Saiki, R et al. 1988. Science 239:487–491, and European patent applications 86302298.4, 86302299.2 and 87300203.4, as well as Methods in Enzymology 1987 155:335–350.

The polynucleotides of the invention can also be derivatized in various ways, including those appropriate for facilitating transfection and/or gene therapy. The polynucleotides can be derivatized by attaching a nuclear localization signal to it to improve targeted delivery to the nucleus. One well-characterized nuclear localization signal is the heptapeptide PKKKRKV (pro-lys-lys-lys-arg-lys-val). Preferably, in the case of polynucleotides in the form of a closed circle, the nuclear localization signal is attached via a modified loop nucleotide or spacer that forms a branching structure.

If it is to be used in vivo, the polynucleotide of the invention is derivatized to include ligands and/or delivery vehicles which provide dispersion through the blood, targeting to specific cell types, or permit easier transit of cellular barriers. Thus, the polynucleotides of the invention is linked or combined with any targeting or delivery agent known in the art, including but not limited to, cell penetration enhancers, lipofectin, liposomes, dendrimers, DNA intercalators, and nanoparticles. In particular, nanoparticles for use in the delivery of the polynucleotides of the invention are particles of less than about 50 nanometers diameter, nontoxic, non-antigenic, and comprised of albumin and surfactant, or iron as in the nanoparticle particle technology of SynGenix. In general the delivery vehicles used to target the polynucleotides of the invention may further comprise any cell specific or general targeting agents known in the art, and will have a specific trapping efficiency to the target cells or organs of from about 5 to about 35%.

The polynucleotides of the invention is used ex vivo in a gene therapy method for obtaining cells or organs which produce wild-type PG1 or PG1 proteins which have been selectively mutated. The cells are created by incubation of the target cell with one or more of the above-described polynucleotides under standard conditions for uptake of nucleic acids, including electroporation or lipofection. In practicing an ex vivo method of treating cells or organs, the concentration of polynucleotides of the invention in a solution prepare to treat target cells or organs is from about 0.1 to about 100 µM, preferably 0.5 to 50 µM, most preferably from 1 to 10 µM.

Alternatively, the oligonucleotides can be modified or co-administered for targeted delivery to the nucleus. Improved oligonucleotide stability is expected in the nucleus due to: (1) lower levels of DNases and RNases; and (2) higher oligonucleotide concentrations due to lower total volume.

Alternatively, the polynucleotides of the invention can be covalently bonded to biotin to form a biotin-polynucleotide prodrug by methods known in the art, and co-administered with a receptor ligand bound to avidin or receptor specific antibody bound to avidin, wherein the receptor is capable of causing uptake of the resulting polynucleotide-biotin-avidin complex into the cells. Receptors that cause uptake are known to those of skill in the art.

The invention encompasses vectors which are suitable for the introduction of a polynucleotide of the invention into an embryonic stem cell for the production of transgenic non-human animals, which in turn result in the expression of recombinant PG1 in the transgenic animal. Any appropriate vector system can be used for the introduction and expression of PG1 in transgenic animals, including for example yeast artificial chromosomes (YAC), bacterial artificial chromosomes (BAC), bacteriophage P1, and other vectors known in the art which are able to accommodate sufficiently large inserts to encode the PG1 protein or desired fragments thereof. Selected alterations, additions and deletions in the PG1 gene may optionally be achieved by site-directed mutagenesis. Once an appropriate vector system is chosen, the site-directed mutagenesis process may then be conducted by techniques well known in the art, and the fragment be returned and ligated to the larger vector from which it was cleaved. For site directed mutagenesis methods see, for example, Kunkel, T. 1985. Proc. Natl. Acad. Sci. U.S.A. 82:488; Bandeyar, M. et al. 1988. Gene 65: 129–133; Nelson, M., and M. McClelland 1992. Methods Enzymol. 216:279–303; Weiner, M. 1994. Gene 151: 119–123; Costa, G. and M. Weiner. 1994. Nucleic Acids Res. 22: 2423; Hu, G. 1993. DNA and Cell Biology 12:763–770; and Deng, W. and J. Nickoff. 1992. Anal. Biochem. 200:81.

Briefly, the transgenic technology used herein involves the inactivation, addition or replacement of a portion of the PG1 gene or the entire gene. For example the present technology includes the addition of PG1 genes with or without the inactivation of the non-human animal's native PG1 genes, as described in the preceding two paragraphs and in the Examples. The invention also encompasses the use of vectors, and the vectors themselves which target and modify an existing human PG1 gene in a stem cell, whether it is contained in a non-human animal cell where it was previously introduced into the germ line by transgenic technology or it is a native PG1 gene in a human pluripotent or somatic cell. This transgene technology usually relies on homologous recombination in a pluripotent cell that is capable of differentiating into germ cell tissue. A DNA construct that encodes an altered region of the non-human animal's PG1 gene that contains, for instance a stop codon to destroy expression, is introduced into the nuclei of embryonic stem cells. Preferably mice are used for this transgenic work. In a portion of the cells, the introduced DNA recombines with the endogenous copy of the cell's gene, replacing it with the altered copy. Cells containing the newly engineered genetic alteration are injected in a host embryo of the same species as the stem cell, and the embryo is reimplanted into a recipient female. Some of these embryos develop into chimeric individuals that posses germ cells entirely derived from the mutant cell line. Therefore, by breeding the chimeric progeny it is possible to obtain a new strain containing the introduced genetic alteration. See Capecchi 1989. Science. 244:1288–1292 for a review of this procedure.

The present invention encompasses the polynucleotides described herein, as well as the methods for making these polynucleotides including the method for creating a mutation in a human PG1 gene. In addition, the present invention encompasses cells which comprise the polynucleotides of the invention, including but not limited to amplification host cells comprising amplification vectors of the invention. Furthermore the present invention comprises the embryonic stem cells and transgenic non-human animals and mammals described herein which comprise a gene encoding a human PG1 protein.

DNA Construct that Enables Directing Temporal and Spatial Gene Expression in Recombinant host Cells and in Transgenic Animals.

In order to study the physiological and phenotype consequences of a lack of synthesis of the PG1 protein, both at the cellular level and at the multi-cellular organism level, in particular as regards to disorders related to abnormal cell proliferation, notably cancers, the invention also encompasses DNA constructs and recombinant vectors enabling a conditional expression of a specific allele of the PG1 genomic sequence or cDNA and also of a copy of this genomic sequence or cDNA harboring substitutions, deletions, or additions of one or more bases as regards to the PG1 nucleotide sequence of SEQ ID NOs: 3, 112–125, 179, 182–184, or a fragment thereof, these base substitutions, deletions or additions being located either in an exon, an intron or a regulatory sequence, but preferably in a 5'-regulatory sequence of a mammalian PG1 gene, more preferably SEQ ID NO: 180 or in an exon of the PG1 genomic sequence or within the PG1 cDNA of SEQ ID NOs 3, 112–125, or 184.

A first preferred DNA construct is based on the tetracycline resistance operon tet from *E. coli* transposon Tn 110 for controlling the PG1 gene expression, such as described by Gossen M. et al., 1992, Proc. Natl. Acad. Sci. USA, 89: 5547–5551; Gossen M. et al., 1995, Science, 268: 1766–1769; and Furth P.A. et al., 1994, Proc. Natl Acad. Sci USA, 91: 9302–9306. Such a DNA construct contains seven tet operator sequences from Tn10 (tetop) that are fused to either a minimal promoter or a 5'-regulatory sequence of the PG1 gene, said minimal promoter or said PG1 regulatory sequence being operably linked to a polynucleotide of interest that codes either for a sense or an antisense oligonucleotide or for a polypeptide, including a PG1 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP 16 of herpes simplex virus, placed under the control of a promoter, such as the HCMVIE1 enhancer/ promoter or the MMTV-LTR. Indeed, a preferred DNA construct of the invention will comprise both the polynucleotide containing the tet operator sequences and the polynucleotide containing a sequence coding for the tTA or the rTA repressor.

In the specific embodiment wherein the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised of a PG1 sequence preferably a PG1 genomic sequence; (b) a nucleotide sequence comprising a positive selection marker, such as the marker for neomycin resistance (neo); and (c) a second nucleotide sequence that comprised of a PG1 sequence preferably a PG1 genomic sequence, and is located on the genome downstream the first PG1 nucleotide sequence (a).

In a preferred embodiment, this DNA construct also comprises a negative selection marker located upstream the nucleotide sequence (a) or downstream the nucleotide sequence (b). Preferably, the negative selection marker consists of the thymidine kinase (tk) gene (Thomas K. R. et al., 1986, Cell, 44: 419–428), the hygromycin beta gene (Te Riele et al., 1990, Nature, 348: 649–651), the hprt gene (Van der Lugt et al., 1991, Gene, 105: 263–267; and Reid L. H. et al., 1990, *Proc. Natl. Acad. Sci.* USA, 87: 4299–4303) or the Diphteria toxin A fragment (Dt-A) gene (Nada S. et al., 1993, Cell, 73: 1125–1135; Yagi T. et al., 1990, Proc. Natl. Acad. Sci. USA, 87: 9918–9922). Preferably, the positive selection marker is located within a PG1 exon sequence so as to interrupt the sequence encoding a PG1 protein.

These replacement vectors are described for example by Thomas K. R. et al., 1986, Cell, 44: 419–428; Thomas K. R. et al., 1987, Cell, 51: 503–512; Mansour S. L. et al., 1988, Nature, 336: 348–352; and Koller et al., 1992, Annu. Rev. Immunol., 10: 705–30.

The first and second nucleotide sequences (a) and (c) is located at any point within a PG1 regulatory sequence, an intronic sequence, an exon sequence or a sequence containing both regulatory and/or intronic and/or exon sequences. The length of nucleotide sequences (a) and (c) is determined empirically by one of ordinary skill in the art. Nucleotide sequences (a) and (c) or any length are specifically contemplated in the present invention, however, lengths ranging from 1 kb to 50 kb, preferably from 1 kb to 10 kb, more preferably from 2 kb to 6 kb and most preferably from 2 kb to 4 kb are normally used.

DNA Constructs Allowing Homologous Recombination: Cre-loxP System.

These new DNA constructs make use of the site-specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986, Nucleic Acids Res., 14: 2287–2300). The recombination by the Cre enzyme between two loxP sites having an identical orientation leads to the deletion of the DNA fragment.

The Cre-loxP system used in combination with a homologous recombination technique has been first described by Gu H. et al., 1993, Cell, 73: 1155–1164; and Gu H. et al., 1994, Science, 265: 103–106. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant host cell. The recombinase enzyme is brought at the desired time either by (a) incubating the recombinant host cells in a culture medium containing this enzyme, by injecting the Cre enzyme directly into the desired cell, such as described by Araki K. et al., 1995, Proc. Natl. Acad. Sci. U.S.A, 92: 160–164; or by lipofection of the enzyme into the cells, such as described by Baubonis et al., 1993, Nucleic Acids Res., 21: 2025–2029; (b) transfecting the cell host with a vector comprising the Cre coding sequence operably linked to a promoter functional in the recombinant cell host, which promoter being optionally inducible, said vector being introduced in the recombinant cell host, such as described by Gu H. et al., 1993, Cell, 73: 1155–1164; and Sauer B. et al., 1988, *Proc. Natl. Acad. Sci.* USA, 85: 5166–5170; (c) introducing in the genome of the host cell a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu H. et al., 1994, Science, 265: 103–106.

In the specific embodiment wherein the vector containing the sequence to be inserted in the PG1 gene by homologous recombination is constructed in such a way that selectable markers are flanked by loxP sites of the same orientation, it is possible, by treatment by the Cre enzyme, to eliminate the selectable markers while leaving the PG1 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou Y. R. et al., 1994, Curr. Biol., 4: 1099–1103.

Thus, a third preferred DNA construct of the invention comprises, from 5'-end to 3'-end: (a) a first nucleotide sequence that is comprised of a PG1 sequence, preferably a PG1 genomic sequence; (b) a nucleotide sequence comprising a polynucleotide encoding a positive selection marker, such as the marker for neomycin resistance (neo), said nucleotide sequence comprising additionally two sequences defining a site recognized by a recombinase, such as a loxP site, the two sites being placed in the same orientation; and (c) a second nucleotide sequence that is comprised of a PG1 sequence, preferably a PG1 genomic sequence, and is located on the genome downstream of the first PG1 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu H. et al., 1994, Science, 265: 103–106.

The presence of the Cre enzyme within the genome of the recombinant cell host may result of the breeding of two transgenic animals, the first transgenic animal bearing the PG1-derived sequence of interest containing the loxP sites as described above and the second transgenic animal bearing the Cre coding sequence operably linked to a suitable promoter sequence, such as described by Gu H. et al., 1994, Science, 265: 103–106. Spatio-temporal control of the Cre enzyme expression may also be achieved with an adenovirus based vector that contains the Cre gene thus allowing infection of cells, or in vivo infection of organs, for delivery of the Cre enzyme, such as described by Anton M. et al., 1995, J. Virol., 69: 4600–4606; and Kanegae Y. et al., 1995, Nucl. Acids Res., 23: 3816–3821.

The DNA constructs described above is used to introduce a desired nucleotide sequence of the invention, preferably a PG1 genomic sequence or a PG1 cDNA sequence, and most preferably an altered copy of a PG1 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination).

Nuclear Antisense DNA Constructs

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu Z. et al., 1994, *Proc. Natl. Acad. Sci.* USA, 91: 4528–4262. In a preferred embodiment, these PG1 antisense polynucleotides also comprise, within the ribozyme cassette, a histone stem-loop structure to stabilize cleaved transcripts against 3'–5' exonucleolytic degradation, such as described by Eckner R. et al., 1991, EMBO J., 10: 3513–3522.

Expression Vectors

The polynucleotides of the invention also include expression vectors. Expression vector systems, control sequences and compatible host are known in the art. For a review of these systems see, for example, U.S. Pat. No. 5,350,671, columns 45–48. Any of the standard methods known to those skilled in the art for the insertion of DNA fragments into a vector is used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of a polypeptide, peptide or derivative, or analogs thereof encoded by a polynucleotide sequence in SEQ ID NOs: 3, 69, 100–112, or 179–184 is regulated by a second nucleic acid sequence so that the protein or peptide is expressed in a host transformed with the recombinant DNA molecule. For example, expression of a protein or peptide is controlled by any promoter/enhancer element known in the art. Promoters which is used to control expression include, but are not limited to, the CMV promoter, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the beta-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., 1983, Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase 1 gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1: 161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (deadhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Other suitable vectors, particularly for the expression of genes in mammalian cells, is selected from the group of vectors consisting of P1 bacteriophages, and bacterial artificial chromosomes (BACs). These types of vectors may contain large inserts ranging from about 80–90 kb (P1 bacteriophage) to about 300 kb (BACs).

P1 Bacteriophage

The construction of P1 bacteriophage vectors such as p158 or p158/neo8 are notably described by Sternberg N. L., 1992, Trends Genet., 8: 1–16; and Sternberg N. L., 1994, Mamm. Genome, 5: 397–404. Recombinant P1 clones comprising PG1 nucleotide sequences is designed for inserting large polynucleotides of more than 40 kb (Linton M.F. et al., 1993, J. Clin. Invest., 92: 3029–3037). To generate P1 DNA for transgenic experiments, a preferred protocol is the protocol described by McCormick et al., 1994, Genet. Anal. Tech. Appl., 11: 158–164. Briefly, *E. coli* (preferably strain NS3529) harboring the P1 plasmid are grown overnight in a suitable broth medium containing 25 μg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising PG1 nucleotide sequences in a transgenic animal, typically in transgenic mice, it is desirable to remove vector sequences from the P1 DNA fragment, for example by cleaving the P1 DNA at rare-cutting sites within the PI polylinker (SfiI, NotI or SalI). The P1 insert is then purified from vector sequences on a pulsed-field agarose gel, using methods similar using methods similar to those originally reported for the isolation of DNA from YACs (Schedl A. et al., 1993, Nature, 362: 258–261; and Peterson et al., 1993, Proc. Natl. Acad. Sci. USA, 90: 7593–7597). At this stage, the resulting purified insert DNA can be concentrated, if necessary, on a Millipore Ultrafree-MC Filter Unit (Millipore, Bedford, Mass., USA-30,000 molecular weight limit) and then dialyzed against microinjection buffer (10 mM Tris-HCl, pH 7.4; 250 μM EDTA) containing 100 mMNaCl, 30 μM spermine, 70 μM spermidine on a microdyalisis membrane (type VS, 0.025 μM from Millipore). The intactness of the purified P1 DNA insert is assessed by electrophoresis on 1% agarose (Sea Kem GTG; FMC Bio-products) pulse-field gel and staining with ethidium bromide.

Bacterial Artificial Chromosomes (BACs)

The bacterial artificial chromosome (BAC) cloning system (Shizuya et al., 1992, Proc. Natl. Acad. Sci. USA, 89: 8794–8797) has been developed to stably maintain large fragments of genomic DNA (100–100 kb) in *E. coli*. A preferred BAC vector consists of pBeloBAC11 vector that has been described Kim U. J., et al., 1996, Genomics, 34: 213–218. BAC libraries are prepared with this vector using size-selected genomic DNA that has been partially digested using enzymes that permit ligation into either the Bam HI or Hind III sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC 11 vector is linearized by treatment of the BAC vector with the commercially available enzyme lambda terminase that leads to the cleavage at the unique cosN site, but this cleavage method results in a full length BAC clone containing both the insert DNA and the BAC sequences.

Host Cells

The PG1 gene expression in human cells is rendered defective, or alternatively it is proceeded with the insertion of a PG1 genomic or cDNA sequence with the replacement of the PG1 gene counterpart in the genome of an animal cell by a PG1 polynucleotide according to the invention. These genetic alterations is generated by homologous recombination events using specific DNA constructs that have been previously described.

One kind of host cell that is used are mammal zygotes, such as murine zygotes. For example, murine zygotes may undergo microinjection with a purified DNA molecule of interest, for example a purified DNA molecule that has previously been adjusted to a concentration range from 1 ng/ml -for BAC inserts-3 ng/μl -for P1 bacteriophage inserts- in 10 mM Tris-HCl, pH 7.4, 250 μM EDTA containing 100 mM NaCl, 30 μM spermine, and 70 μM spermidine. When the DNA to be microinjected has a large size, polyamines and high salt concentrations can be used in order to avoid mechanical breakage of this DNA, as described by Schedl et al., 1993, Nucleic Acids Res., 21: 4783–4787.

Anyone of the polynucleotides of the invention, including the DNA constructs described herein, is introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-El4TG2a (ATCC No. CRL-1821), ES-D3 (ATCC No. CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells consist of primary embryonic fibroblasts that are established from tissue of day 13-day 14 embryos of virtually any mouse strain, that are maintained in culture, such as described by Abbondanzo S. J. et al., 1993, Methods in Enzymology, Academic Press, New York, pp. 803–823; and are inhibited in growth by irradiation, such as described by Robertson E., 1987, Embryo-derived stem cell lines. E. J. Robertson Ed. Teratocarcinomas and embrionic stem cells: a practical approach. IRL Press, Oxford, pp. 71, or by the presence of an inhibitory concentration of LIF, such as described by Pease S. and William R. S., 1990, Exp. Cell. Res., 190: 209–211.

Transgenic Animals

The terms "transgenic animals" or "host animals" are used herein designate non-human animals that have their genome genetically and artificially manipulated so as to include one of the nucleic acids according to the invention. Preferred animals are non-human mammals and include those belonging to a genus selected from Mus (e.g. mice), Rattus (e.g. rats) and Oryctogalus (e.g. rabbits) which have their genome artificially and genetically altered by the insertion of a nucleic acid according to the invention.

The transgenic animals of the invention all include within a plurality of their cells a cloned recombinant or synthetic DNA sequence, more specifically one of the purified or isolated nucleic acids comprising a PG1 coding sequence, a PG1 regulatory polynucleotide or a DNA sequence encoding an antisense polynucleotide such as described in the present specification.

Preferred transgenic animals according to the invention contains in their somatic cells and/or in their germ line cells a polynucleotide selected from the following group of polynucleotides:

a) non-native, purified or isolated nucleic acid encoding a PG1 polypeptide, or a polypeptide fragment or variant thereof.

b) a non-native, purified or isolated nucleic comprising at least 8 consecutive nucleotides of the nucleotide sequence SEQ ID NOs: 179, 182, or 183, a nucleotide sequence complementary; in some embodiments, the length of the fragments can range from at least 8, 10, 15, 20 or 30 to 200 nucleotides, preferably from at least 10 to 50 nucleotides, more preferably from at least 40 to 50 nucleotides of SEQ ID NOs: 179, 182, or 183, or the sequence complementary thereto. In some embodiments, the fragments may comprise more than 200 nucleotides of SEQ ID NOs: 179, 182, or 183, or the sequence complementary thereto.

c) a non-native, purified or isolated nucleic acid comprising at least 8 consecutive nucleotides of the nucleotide sequence SEQ ID NOs: 3, 69, 112–125 or 184, a sequence complementary thereto or a variant thereof; In some embodiments, the length of the fragments can range from at least 8, 10, 15, 20 or 30 to 200 nucleotides, preferably from at least 10 to 50 nucleotides, more preferably from at least 40 to 50 nucleotides of SEQ ID NOs: 3, 69, 112–125 or 184, or the sequence complementary thereto. In some embodiments, the fragments may comprise more than 200 nucleotides of SEQ ID NOs: 3, 69, 112–125 or 184, or the sequence complementary thereto.

d) a non-native, purified or isolated nucleic acid comprising a nucleotide sequence selected from the group of SEQ ID NOs: 100 to 111, a sequence complementary thereto or a fragment or a variant thereof.

e) a non-native, purified or isolated nucleic acid comprising a combination of at least two polynucleotides selected from the group consisting of SEQ ID NOs: 100 to 111, or the sequences complementary thereto wherein the polynucleotides are arranged within the nucleic acid, from the 5' end to the 3' end of said nucleic acid, in the same order than in SEQ NOs: 179, 182, or 183.

f) a non-native, purified or isolated nucleic acid comprising the nucleotide sequence SEQ ID NO: 180, or the sequences complementary thereto or a biologically active fragment or variant of the nucleotide sequence of SEQ ID NO: 180, or the sequence complementary thereto.

g) a non-native, purified or isolated nucleic acid comprising the nucleotide sequence SEQ ID NO: 181, or the sequence complementary thereto or a biologically active fragment or variant of the nucleotide sequence of SEQ ID NO: 181 or the sequence complementary thereto.

h) a polynucleotide consisting of:
  (1) a nucleic acid comprising a regulatory polynucleotide of SEQ ID NO: 180 or the sequences complementary thereto or a biologically active fragment or variant thereof
  (2) a polynucleotide encoding a desired polypeptide or nucleic acid.
  (3) Optionally, a nucleic acid comprising a regulatory polynucleotide of SEQ NO: 181, or the sequence complementary thereto or a biologically active fragment or variant thereof.

i) a DNA construct as described previously in the present specification.

The transgenic animals of the invention thus contain specific sequences of exogenous genetic material or "non-native" such as the nucleotide sequences described above in detail.

In a first preferred embodiment, these transgenic animals is good experimental models in order to study the diverse pathologies related to cell differentiation, in particular concerning the transgenic animals within the genome of which has been inserted one or several copies of a polynucleotide encoding a native PG1 protein, or alternatively a mutant PG1 protein.

In a second preferred embodiment, these transgenic animals may express a desired polypeptide of interest under the control of the regulatory polynucleotides of the PG1 gene, leading to good yields in the synthesis of this protein of interest, and eventually a tissue specific expression of this protein of interest.

The design of the transgenic animals of the invention is made according to the conventional techniques well known from the one skilled in the art. For more details regarding the production of transgenic animals, and specifically transgenic mice, it is referred to Sandou et al. (1994) and also to U.S. Pat. Nos. 4,873,191, issued Oct. 10, 1989, U.S. Pat. No. 5,464,764 issued Nov. 7, 1995 and U.S. Pat. No. 5,789,215, issued Aug. 4, 1998, these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a PG1 coding sequence, a PG1 regulatory polynucleotide or a DNA sequence encoding a PG1 antisense polynucleotide such as described in the present specification.

A recombinant polynucleotide of the invention is inserted into an embryonic or ES stem cell line. The insertion is preferably made using electroporation, such as described by Thomas K. R. et al., 1987, Cell, 51: 503–512. The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that is used according to the invention is described by Mansour S. L. et al., 1988, Nature, 336: 348–352.

Then, the positive cells are isolated, cloned and injected into 3.5 days old blastocysts from mice, such as described by Bradley A., 1987, Production and analysis of chimaeric mice. In: E. J. Robertson (Ed.), Teratocarcinomas and embryonic stem cells: A practical approach. IRL Press, Oxford, pp.113. The blastocysts are then inserted into a female host animal and allowed to grow to term.

Alternatively, the positive ES cells are brought into contact with embryos at the 2.5 days old 8–16 cell stage (morulae) such as described by Wood S. A. et al., 1993, Proc. Natl. Acad. Sci. USA, 90: 4582–4585; or by Nagy A. et al., 1993, *Proc. Natl. Acad. Sci*. USA, 90: 8424–8428. The ES cells being internalized to colonize extensively the blastocyst including the cells which will give rise to the germ line. The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein.

Recombinant cell lines is established in vitro from cells obtained from any tissue of a transgenic animal according to the invention, for example by transfection of primary cell cultures with vectors expressing onc-genes such as SV40 large T antigen, as described by Chou J. Y., 1989, Mol. Endocrinol., 3: 1511–1514; and Shay J. W. et al., 1991, Biochem. Biophys. Acta, 1072: 1–7.

Functional Analysis of the PG1 Poplypeptides In Transgenic Animals

Using different BACs that contain the PG1 gene, we performed FISH experiment on the adenocarcinoma prostatic cell line PC3. Only one signal could be detected showing that this region of chromosome 8 is hemizygous in this tumoral cell line.

To study the function of PG1, it is inactivate by homologous recombination in the remaining allele of PG1 in the PC3 cell line. To inactivate the remaining PG1 allele, a knock-out targeting vector is generated by inserting two genomic DNA fragments of 3.0 and 4.3 kb (that correspond to a sequence upstream of the PG1 promoter and to part of intron 1, respectively) in the pKO Scrambler Neo T.K. vector (Lexicon ref V1901). Since the targeting vector contains the neomycine resistance gene as well as the Tk gene, homologous recombination is selected by adding geneticin and FIAU to the medium. The promoter, the transcriptional start site, and the first ATG contained in exon 1 on the recombinant allele is deleted by homologous recombination between the targeting vector and the remaining PG1 allele. Accordingly, no coding transcripts is initiated from the recombinant allele. The parental PC3 cells as well as cells hemizygous for the null allele are assessed for their phenotype, their growth rate in liquid culture, their ability to grow in agar (anchorage-independent growth) as well as their ability to form tumors and metastasis when injected subcutaneously in nude mice.

To determine the function of PG1 in the animal, and to generate an animal model for prostate tumorigenesis, mice in which tissue specific inactivation of the PG1 alleles can be induced are generated. For this purpose, the Cre-loxP system is utilized as described above to allow chromosome engineering to be perform directly in the animal.

First, to generate mice with a conditional null allele, two loxP sites are introduced in the murine genome, the first one 5' to the PG1 promoter and the second one 3' to the PG1 exon 1. Alternatively, to generate subtle mutations or to specifically mutate some isoforms, the loxP sites are introduced so that they flank any of the given exons or any potential set of exons. It is important to note that a functional PG1 messenger can be transcribed from these alleles until a recombination is triggered between the loxP sites by the Cre enzyme.

Second, to generate the inducer mice, the Cre gene is introduced in the mouse genome under the control of a tissue specific promoter, for example under the control of the PSA (prostate specific antigen) promoter.

Finally, tissue specific inactivation of the PG1 gene are induced by generating mice containing the Cre transgene that are homozygous for the recombinant PG1 allele.

Gene Therapy

The present invention also comprises the use of the PG1 genomic DNA sequence of SEQ ID NO: 179, the PG1 cDNA of SEQ ID NO: 3, or nucleic acid encoding a mutant PG1 protein responsible for a detectable phenotype in gene therapy strategies, including antisense and triple helix strategies as described in Examples 19 and 20, below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid is incorporated in a ribozyme capable of specifically cleaving the target mRNA.

EXAMPLE 19

Preparation and Use of Antisense Oligonucleotides

The antisense nucleic acid molecules to be used in gene therapy is either DNA or RNA sequences. They may comprise a sequence complementary to the sequence of the PG1 genomic DNA of SEQ ID NO: 179, the PG1 cDNA of SEQ ID NO: 3, or a nucleic acid encoding a PG1 protein responsible for a detectable phenoytpe. The antisense nucleic acids should have a length and melting temperature sufficient to permit formation of an intracellular duplex having sufficient stability to inhibit the expression of the PG1 mRNA in the duplex. Strategies for designing antisense nucleic acids suitable for use in gene therapy are disclosed in Green et al., Ann. Rev. Biochem. 55:569–597 (1986) and Izant and Weintraub, Cell 36:1007–1015 (1984).

In some strategies, antisense molecules are obtained by reversing the orientation of the PG1 coding region with respect to a promoter so as to transcribe the opposite strand from that which is normally transcribed in the cell. The antisense molecules is transcribed using in vitro transcription systems such as those which employ T7 or SP6 polymerase to generate the transcript. Another approach involves transcription of PG1 antisense nucleic acids in vivo by operably linking DNA containing the antisense sequence to a promoter in an expression vector.

Alternatively, oligonucleotides which are complementary to the strand of the PG1 gene normally transcribed in the cell is synthesized in vitro. Thus, the antisense PG1 nucleic acids are complementary to the PG1 mRNA and are capable of hybridizing to the mRNA to create a duplex. In some embodiments, the PG1 antisense sequences may contain modified sugar phosphate backbones to increase stability and make them less sensitive to RNase activity. Examples of modifications suitable for use in antisense strategies are described by Rossi et al., Pharmacol. Ther. 50(2):245–254, (1991).

Various types of antisense oligonucleotides complementary to the sequence of the PG1 genomic DNA of SEQ ID NO: 179, the PG1 cDNA of SEQ ID NO: 3, or a nucleic acid encoding a PG1 protein responsible for a detectable phenoytpe is used. In one preferred embodiment, stable and semi-stable antisense oligonucleotides as described in International Application No. PCT WO94/23026, are used to inhibit the expression of the PG1 gene. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides described in International Application No. WO 95/04141, are used to inhibit expression of the PG1 gene.

In yet another preferred embodiment, the covalently cross-linked antisense oligonucleotides described in International Application No. WO 96/31523, are used to inhibit expression of the PG1 gene. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, may also be used to inhibit the expression of the PG1 gene. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, are used to inhibit the expression of the PG1 gene. These ligated oligonucleotide "dumbbells" contain the binding site for a transcription factor which binds to the PG1 promoter and inhibits expression of the gene under control of the transcription factor by sequestering the factor.

Use of the closed antisense oligonucleotides disclosed in International Application No. WO 92/19732, is also contemplated. Because these molecules have no free ends, they are more resistant to degradation by exonucleases than are conventional oligonucleotides. These oligonucleotides is multifunctional, interacting with several regions which are not adjacent to the target mRNA.

The appropriate level of antisense nucleic acids required to inhibit PG1 gene expression is determined using in vitro expression analysis. The antisense molecule is introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector is any of a variety of expression vectors known in the art, including retroviral or viral vectors, vectors capable of extrachromosomal replication, or integrating vectors. The vectors is DNA or RNA.

The PG1 antisense molecules are introduced onto cell samples at a number of different concentrations preferably between $1 \times 10^{-10}$M to $1 \times^{-4}$M. Once the minimum concentration that can adequately control gene expression is identified, the optimized dose is translated into a dosage suitable for use in vivo. For example, an inhibiting concentration in culture of $1 \times 10^{31}$ $^7$ translates into a dose of approximately 0.6 mg/kg bodyweight. Levels of oligonucleotide approaching 100 mg/kg bodyweight or higher is possible after testing the toxicity of the oligonucleotide in laboratory animals. It is additionally contemplated that cells from the vertebrate are removed, treated with the antisense oligonucleotide, and reintroduced into the vertebrate.

It is further contemplated that the PG1 antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, antibody-mediated tests such as RIAs and ELISA, functional assays, or radiolabeling are used to determine the effectiveness of antisense inhibition on PG1 expression.

The PG1 cDNA, the PG1 genomic DNA, and the PG1 alleles of the present invention may also be used in gene therapy approaches based on intracellular triple helix formation. Triple helix oligonucleotides are used to inhibit transcription from a genome. They are particularly useful for studying alterations in cell activity as it is associated with a particular gene. The PG1 cDNA, PG1 genomic DNA, or PG1 allele of the present invention or, more preferably, a portion of those sequences, can be used to inhibit gene expression in individuals suffering from prostate cancer or another detectable phenotype or individuals at risk for developing prostate cancer or another detectable phenotype at a later date as a result of their PG1 genotype. Similarly, a portion of the PG1 cDNA, the PG1 genomic DNA, or the PG1 alleles can be used to study the effect of inhibiting PG1 transcription within a cell. Traditionally, homopurine sequences were considered the most useful for triple helix strategies, such as those described in Example 20, below. However, homopyrimidine sequences can also inhibit gene expression. Such homopyrimidine oligonucleotides bind to the major groove at homopurine:homopyrimidine sequences. Thus, both types of sequences from the PG1 cDNA, the PG1 genomic DNA, and the PG1 alleles are contemplated within the scope of this invention.

EXAMPLE 20

The sequences of the PG1 cDNA, the PG1 genomic DNA, and the PG1 alleles are scanned to identify 10-mer to 20-mer homopyrimidine or homopurine stretches which could be used in triple-helix based strategies for inhibiting PG1 expression. Following identification of candidate homopyrimidine or homopurine stretches, their efficiency in inhibiting PG1 expression is assessed by introducing varying amounts of oligonucleotides containing the candidate sequences into tissue culture cells which express the PG1 gene. The oligonucleotides is prepared on an oligonucleotide synthesizer or they is purchased commercially from a company specializing in custom oligonucleotide synthesis, such as GENSET, Paris, France.

The oligonucleotides is introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced PG1 expression using techniques such as Northern blotting, RNase protection assays, or PCR based strategies to monitor the transcription levels of the PG1 gene in cells which have been treated with the oligonucleotide.

The oligonucleotides which are effective in inhibiting gene expression in tissue culture cells may then be introduced in vivo using the techniques described above and in Example 19 at a dosage calculated based on the in vitro results, as described in Example 19.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245:967–971 (1989).

Alternatively, the PG1 cDNA, the PG1 genomic DNA, and the PG1 alleles of the present invention is used in gene therapy approaches in which expression of the PG1 protein is beneficial, as described in Example 21 below.

EXAMPLE 21

The PG1 cDNA, the PG1 genomic DNA, and the PG1 alleles of the present invention may also be used to express the PG1 protein or a portion thereof in a host organism to produce a beneficial effect. In such procedures, the PG1 protein is transiently expressed in the host organism or stably expressed in the host organism. The expressed PG1 protein is used to treat conditions resulting from a lack of PG1 expression or conditions in which augmentation of existing levels of PG1 expression is beneficial.

A nucleic acid encoding the PG1 proteins of SEQ ID NO: 4, SEQ ID NO:5, or a PG1 allele is introduced into the host organism. The nucleic acid is introduced into the host organism using a variety of techniques known to those of skill in the art. For example, the nucleic acid is injected into the host organism as naked DNA such that the encoded PG1 protein is expressed in the host organism, thereby producing a beneficial effect.

Alternatively, the nucleic acid encoding the PG1 proteins of SEQ ID NO: 4, SEQ ID NO: 5, or a PG1 allele is cloned into an expression vector downstream of a promoter which is active in the host organism. The expression vector is any of the expression vectors designed for use in gene therapy, including viral or retroviral vectors.

The expression vector is directly introduced into the host organism such that the PG1 protein is expressed in the host organism to produce a beneficial effect. In another approach, the expression vector is introduced into cells in vitro. Cells containing the expression vector are thereafter selected and introduced into the host organism, where they express the PG1 protein to produce a beneficial effect.

IX. ISOLATION OF PG1 cDNA FROM NONHUMAN MAMMALS

The present invention encompasses mammalian PG1 sequences including genomic and cDNA sequences, as well as polypeptide sequences. The present invention also encompasses the use of PG1 genomic and cDNA sequences of the invention, including SEQ ID NOs: 179, 3, 182, and 183, in methods of isolating and characterizing PG1 nucleotide sequences derived from nonhuman mammals, in addition to sequences derived from human sequences. The human and mouse PG1 nucleic acid sequences of the invention can be used to construct primers and probes for amplifing and identifing PG1 genes in other nonhuman animals particularly mammals. The primers and probes used to identify nonhuman PG1 sequences is selected and used for the isolation of nonhuman PG1 utilizing the same techniques described above in Examples 4, 5, 6, 12 and 13.

In addition, sequence analysis of other homologous proteins is used to optimize the sequences of these primers and probes. As described above in the Analysis of the PG1 Protein Sequence, three boxes of homology were identified in the structure of the PG1 protein product when compared to proteins from a diverse range of organisms. See FIG. 9. Using the assumption that the nucleotide sequences for these homologous proteins also show a high degree of homology, it is possible to construct primers that are specific for the PCR amplification of PG1 cDNA in nonhuman mammals.

EXAMPLE 22

The primers BOXIed: AATCATCAAAGCACAGT-TGACTGGAT (SEQ ID NO: 77) and BOXIIIer: ATAAAC-CACCGTAACATCATAAATTGCATCTAA (SEQ ID NO: 78) were designed as PCR primers from the human PG1 sequences after comparison with the sequence homologies of FIG. 9. The BOXIed (SEQ ID NO: 77) and BOXIIIer (SEQ ID NO: 78) primers were used to amplify a mouse PG1 cDNA sequence from mouse liver marathon-ready cDNA (Clontech) under the conditions described above in Example 4. This PCR reaction yielded a product of approximately 400 base pairs, the boxI-boxIII fragment, which was subjected to automated dideoxy terminator sequencing and electrophoresed on ABI 377 sequencers as described above. Sequence analysis confirmed very high homology to human PG1 both at the nucleic acid and protein levels.

Primers were designed for RACE analysis using the 400 base pair boxI-boxIII fragment. Further sequence information was obtained using 5' and 3' RACE reactions on mouse liver marathon cDNA using two sets of these nested PCR primers: moPG1 RACE5.350: AATCAAAAGCAACGT-GAGTGGC (SEQ ID NO: 94) and moPG1 RACE5.276: GCAAATGCCTGACTGGCTGA (SEQ ID NO: 93) for the 5' RACE reaction and moPG1RACE3.18: CTGCCAGA-CAGGATGCCCTA (SEQ ID NO: 90) and moPG1RACE3.63: ACAAGTTAAAATGGCTTCCGCTG (SEQ ID NO: 91) for the 3' RACE reaction. The PCR products of the RACE reactions were sequenced by primer walking using the following primers: moPGrace3S473: GAGATAAAAG ATAGGTTGCT CA (SEQ ID NO: 79); moPGrace3S526: AAGAAACAAA TTTCCTGGG (SEQ ID NO: 80); moPGrace3S597: TCTTGGGGAG TTTGACTG (SEQ ID NO: 81); moPGrace5R323: GAC-CCCGGTG TAGTTCT (SEQ ID NO: 82); moPGrace5R372: CAGTAAAGCC GGTCGTC (SEQ ID NO: 83); moPGrace5R444: CAGGCCAGCA GGTAGGT (SEQ ID NO: 84); moPGrace5R492: AGCAGGTAGC GCATAGAGT (SEQ ID NO: 85).

Again a high degree of homology between the mouse sequence obtained from the primer walking and the human PG1 sequence was observed. An additional pair of nested primers were designed and utilized to further extend the 3' mouse PG1 sequence in yet another RACE reaction, moPG3RACE2: TGGGCACCTG GTTGTATGGA (SEQ ID NO: 95) and moPG3RACE2n: TCCTTGGCTG CCTGTG-GTTT (SEQ ID NO:96). The PCR product of this final RACE reaction was also sequenced by primer walking using the following primers: moPG1RACE3R94: CAAATG-CATG TTGGCTGT (SEQ ID NO: 92); moPG3RACES20: GATGGCTACA CATTGTATCAC (SEQ ID NO: 97); moPG3RACES5: TCCTGAATTA AATAAGGAGT TTTC (SEQ ID NO: 98); moPG3RACES90: GTTTGTTATT AAAGCATAAG CAAG (SEQ ID NO: 99).

The overlap in the 5' RACE, boxI-boxIII, and 3' RACE fragments allowed a single contiguous coding sequence for the mouse PG1 ortholog to be generated alignment of the three fragments. Primers were chosen from near the 5' and 3' ends of this predicted contiguous sequence (contig) in order to confirm the existence of such a transcript. PCR amplification was performed again on mouse liver marathon-ready cDNA (Clontech) with the chosen primers, moPG15: TGGCGAGCCGAGAGGATG (SEQ ID NO: 87) and moPG13LR2: GGAAACAATGTGATACAATGTG-TAGCC (SEQ ID NO: 86) under the PCR conditions described above in Example 4. The resulting PCR product was a roughly 1.2 kb DNA molecule and was shown to have an identical sequence to that of the deduced contig. Finally modified versions of the moPG15 and moPG13LR2 primers with the addition of EcoRI and BamHI sites, moPG1 SEc-oRI: CGTGAATTCTGGCGAGCCGAGAGGATG (SEQ ID NO: 89) and moPG1 SBam 1: CGTGGATCCGGAAA-CAATGTGATACAATGTGTAGCC (SEQ ID NO: 88) were used to obtain a PCR product that could be cloned into a pSKBluescript plasmid (Stratagene) cleaved with EcoRI and BamHI restriction enzymes. The mouse PG1 cDNA in the resulting construct was subjected to automated dideoxy terminator sequencing and electrophoresed on ABI 377 sequencers as described above. The sequence for mouse PG1 cDNA is reported in SEQ ID NO: 72, and the deduced amino acid sequence corresponding to the cDNA is reported in SEQ ID NO: 74.

EXAMPLE 23

A mouse BAC library was constructed by the cloning of BamHI partially digested DNA of pluripotent embryonic stem cells, cell line ES-El 4TG2a (ATCC CRL–1 821) into pBeloBACII vector plasmid. Approximately fifty-six thousand clones with an average inset 30 size of 120 kb were picked individually and pooled for PCR screening as described above for human BAC library screening. These pools were screened with STS g34292 derived from the region of the mouse PG1 transcript corresponding to exon 6 of the human gene. The upstream and downstream primers defining this STS are: upstream amplification primer for g34292: ATTAAAACACGTACTGACACCA (SEQ ID NO: 75), and downstream amplification primer for g34292: AGT-CATGGAT GGTGGATTT (SEQ ID NO: 76). BAC CO281H06 tested positive for hybridizing to g34292. This BAC was isolated and sequenced by sub-cloning into pGen-Del sequencing vector. The resulting partial genomic sequence for mouse PG1 is reported in SEQ ID NO: 73. This process was repeated and the resulting partial genomic sequences for mouse PG1 is reported in SEQ ID NOs: 182 and 183.

Other mammalian PG1 cDNA and genomic sequences can be isolated by the methods of the present invention. PG1 genes in mammalian species have a region of at least 100, preferably 200, more preferably 500 nucleotides in each mammal's most abundant transcription species which has at least 75%, preferably 85%, more preferably 95% sequence homology to the most abundant human or mouse cDNA species (SEQ ID NO: 3). PG1 proteins in mammalian species have a region of at least 40, preferably 90, more preferably 160 amino acids in the deduced amino acid sequence of the most abundant PG1 transcirption species which has at least 75%, preferably 85%, more preferably 95% sequence homology to the deduced amino acid sequence of the most abundant human or mouse translations species (SEQ ID NO: 4 or 74).

X. METHODS FOR GENOTYPING AN INDIVIDUAL FOR BIALLELIC MARKERS

Methods are provided to genotype a biological sample for one or more biallelic markers of the present invention, all of which is performed in vitro. Such methods of genotyping comprise determining the identity of a nucleotide at an PG1-related biallelic marker by any method known in the art. These methods find use in genotyping case-control populations in association studies as well as individuals in the context of detection of alleles of biallelic markers which, are known to be associated with a given trait, in which case both copies of the biallelic marker present in individual's genome are determined so that an individual is classified as homozygous or heterozygous for a particular allele.

These genotyping methods can be performed nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

X.A. Source of DNA for Genotyping

Any source of nucleic acids, in purified or non-purified form, can be utilized as the starting nucleic acid, provided it contains or is suspected of containing the specific nucleic acid sequence desired. DNA or RNA is extracted from cells, tissues, body fluids. As for the source of genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. While nucleic acids for use in the genotyping methods of the invention can be derived from any mammalian source, the test subjects and individuals from which nucleic acid samples are taken are generally understood to be human.

X.B. Amplification Of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers is used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention.

Amplification of DNA is achieved by any method known in the art. The established PCR (polymerase chain reaction) method or by developments thereof or alternatives.

Amplification methods which can be utilized herein include but are not limited to Ligase Chain Reaction (LCR) as described in EP A 320 308 and EP A 439 182, Gap LCR (Wolcott, M. J., Clin. Mcrobiol. Rev. 5:370–186), the so-called "NASBA" or "3 SR" technique described in Guatelli J. C. et al. (*Proc. Natl. Acad. Sci. USA* 87:1874–1878, 1990) and in Compton J. (*Nature* 350:91–92, 1991), Q-beta amplification as described in European Patent Application no 4544610, strand displacement amplification as described in Walker et al. (*Clin. Chem.* 42:9–13, 1996) and EP A 684 315 and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate–3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall R.L. et al. (PCR *Methods and Applications* 4:80–84, 1994). AGLCR is a modification of GLCR that allows the amplification of RNA.

Some of these amplification methods are particularly suited for the detection of single nucleotide polymorphisms and allow the simultaneous amplification of a target sequence and the identification of the polymorphic nucleotide as it is further described in X.C.

The PCR technology is the preferred amplification technique used in the present invention. A variety of PCR techniques are familiar to those skilled in the art. For a review of PCR technology, see Molecular Cloning to Genetic Engineering White, B. A. Ed. in *Methods in Molecular Biology* 67: Humana Press, Totowa (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention. Primers can be prepared by any suitable method. As for example, direct chemical synthesis by a method such as the phosphodiester method of Narang S. A. et al. (*Methods Enzymol*. 68:90–98, 1979), the phosphodiester method of Brown E. L. et al. (*Methods Enzymol*. 68:109–151, 1979), the diethylphosphoramidite method of Beaucage et al. (*Tetrahedron Lett*. 22:1859–1862, 1981) and the solid support method described in EP 0 707 592.

In some embodiments the present invention provides primers for amplifing a DNA fragment containing one or more biallelic markers of the present invention. It will be appreciated that the amplification primers listed in the present specification are merely exemplary and that any other set of primers which produce amplification products containing one or more biallelic markers of the present invention.

The primers are selected to be substantially complementary to the different strands of each specific sequence to be amplified. The length of the primers of the present invention can range from 8 to 100 nucleotides, preferably from 8 to 50, 8 to 30 or more preferably 8 to 25 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature ™ of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions is empirically determined by one of skill in the art.

The spacing of the primers determines the length of the segment to be amplified. In the context of the present invention amplified segments carrying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers is any sequence which allow the specific amplification of any DNA fragment carrying the markers. Amplification primers is labeled or immobilized on a solid support as described in Section II.

X.C. Methods of Genotyping DNA Samples for Biallelic Markers

Any method known in the art can be used to identify the nucleotide present at a biallelic marker site. Since the biallelic marker allele to be detected has been identified and specified in the present invention, detection will prove routine for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods.

Methods well-known to those skilled in the art that can be used to detect biallelic polymorphisms include methods such as, conventional dot blot analyzes, single strand conformational polymorphism analysis (SSCP) described by Orita et al. (*Proc. NatL. Acad. Sci. U.S.A* 86:27776–2770, 1989), denaturing gradient gel electrophoresis (DGGE), heteroduplex analysis, mismatch cleavage detection, and other conventional techniques as described in Sheffield, V.C. et al. (*Proc. Natl. Acad. Sci.* USA 49:699–706, 1991), White et al. (*Genomics* 12:301–306, 1992), Grompe, M. et al. (*Proc. Natl. Acad. Sci.* USA 86:5855–5892, 1989) and Grompe, M. (*Nature Genetics* 5:111–117, 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, allele-specific amplification assay, or hybridization assay. The following is a description of some preferred methods. A highly preferred method is the microsequencing technique. The term "sequencing assay" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. Methods for sequencing DNA using either the dideoxy-mediated method (Sanger method) or the Maxam-Gilbert method are widely known to those of ordinary skill in the art. Such methods are for example disclosed in Maniatis et al. (Molecular Cloning, A Laboratory Manual, Cold Spring Harbor Press, Second Edition, 1989). Alternative approaches include hybridization to high-density DNA probe arrays as described in Chee et al. (Science 274, 610, 1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis.

The polymorphism detection in a pooled sample is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies.

Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously.

Different approaches can be used to detect the nucleotide added to the microsequencing primer. A homogeneous phase detection method based on fluorescence resonance energy transfer has been described by Chen and Kwok (*Nucleic Acids Research* 25:347–353 1997) and Chen et al. (*Proc. Natl. Acad. Sci. USA* 94/20 10756–10761,1997). In this method amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer is analyzed by MALDI-TOF Mass Spectrometry. The base at the polymorphic site is identified by the mass added onto the microsequencing primer (see Haff L. A. and Smirnov I. P., *Genome Research*, 7:378–388, 1997).

Microsequencing is achieved by the established microsequencing method or by developments or derivatives thereof. Alternative methods include several solid-phase microsequencing techniques. The basic microsequencing protocol is the same as described previously, except that the method is conducted as a heterogenous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner oligonucleotides or templates is attached to a solid support in a high-density format. In such solid phase microsequencing reactions, incorporated ddNTPs can be radiolabeled (Syvänen, *Clinica Chimica Acta* 226:225–236, 1994) or linked to fluorescein (Livak and Hainer, *Human Mutation* 3:379–385,1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., *Clin. Chem.* 39/11 2282–2287, 1993) or biotinylated ddNTP and horseradish peroxidase-conjugated streptavidin with o-phenylenediamine as a substrate (WO 92/15712). As yet another alternative solid-phase microsequencing procedure, Nyren et al. (*Analytical Biochemistry* 208:171–175, 1993) described a method relying on the detection of DNA polymerase activity by an enzymatic luminometric inorganic pyrophosphate detection assay (ELIDA).

Pastinen et al. (*Genome research* 7:606–614, 1997) describe a method for multiplex detection of single nucleotide polymorphism in which the solid phase minisequencing principle is applied to an oligonucleotide array format. High-density arrays of DNA probes attached to a solid support (DNA chips) are further described in X.C.5.

In one aspect the present invention provides polynucleotides and methods to genotype one or more biallelic markers of the present invention by performing a microsequencing assay. It will be appreciated that any primer having a 3' end immediately adjacent to the polymorphic nucleotide is used. However, polynucleotides comprising at least 8, 12, 15, 20, 25, or 30 consecutive nucleotides of the sequence immediately adjacent to the biallelic marker and having a 3' terminus immediately upstream of the corresponding biallelic marker are well suited for determining the identity of a nucleotide at biallelic marker site.

Similarly, it will be appreciated that microsequencing analysis is performed for any biallelic marker or any combination of biallelic markers of the present invention.

Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in X.B.

Allele Specific Amplification

Discrimination between the two alleles of a biallelic marker can also be achieved by allele specific amplification, a selective strategy, whereby one of the alleles is amplified without amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Designing the appropriate allele-specific primer and the corresponding assay conditions are well with the ordinary skill in the art.

Ligation/amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and is advantageously combined with PCR as described by Nickerson D.A. et al. (*Proc. Natl. Acad. Sci. U.S.A.* 87:8923–8927, 1990). In this method, PCR is used to achieve the exponential amplification of target DNA, which is then detected using OLA.

Other methods which are particularly suited for the detection of single nucleotide polymorphism include LCR (ligase chain reaction), Gap LCR (GLCR) which are described above in X.B. As mentioned above LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

2) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay is used including Southern hybridization, Northern hybridization, dot blot hybridization and solid-phase hybridization (see Sambrook et al., Molecular Cloning—A Laboratory Manual, Second Edition, Cold Spring Harbor Press, N.Y., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms.

Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., Molecular Cloning—A Laboratory Manual, Second Edition, Cold Spring Harbor Press, N.Y., 1989). Stringent conditions are sequence dependent and will be different in different circumstances. Generally, stringent conditions are selected to be about 5° C. lower than the thermal melting point ™ for the specific sequence at a defmed ionic strength and pH. By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5–20 ×10$^6$ cpm of $^{32}$P-labeled probe. Alternatively, the hybridization step can be performed at 65° C.in the presence of SSC buffer, 1×SSC corresponding to 0.15 M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C.for 45 min. Alternatively, filter washes can be performed in a solution containing 2×SSC and 0.1% SDS, or 0.5×SSC and 0.1% SDS, or 0.1 ×SSC and 0.1% SDS at 68° C.for 15 minute intervals. Following the wash steps, the hybridized probes are detectable by autoradiography. By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of high and intermediate stringency which is used are well known in the art and as cited in Sambrook et al. (Molecular Cloning—A Laboratory Manual, Second Edition, Cold Spring Harbor Press, N.Y., 1989) and Ausubel et al. (Current Protocols in Molecular Biology, Green Publishing Associates and Wiley Interscience, N.Y., 1989).

Although such hybridizations can be performed in solution, it is preferred to employ a solid-phase hybridization assay. The target DNA comprising a biallelic marker of the present invention is amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps is employed to wash away excess target DNA or probe. Standard heterogeneous assay formats are suitable for detecting the hybrids using the labels present on the primers and probes.

Two recently developed assays allow hybridization-based allele discrimination with no need for separations or washes (see Landegren U. et al., *Genome Research*, 8:769–776, 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., *Nature Genetics*, 9:341–342, 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., *Nature Biotechnology*, 16:49–53, 1998).

The polynucleotides provided herein can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. The GC content in the probes of the invention usually ranges between 10 and 75%, preferably between 35 and 60%, and more preferably between 40 and 55%. The length of these probes can range from 10, 15, 20, or 30 to at least 100 nucleotides, preferably from 10 to 50, more preferably from 18 to 35 nucleotides. A particularly preferred probe is 25 nucleotides in length. Preferably the biallelic marker is within 4 nucleotides of the center of the polynucleotide probe. In particularly preferred probes the biallelic marker is at the center of said polynucleotide. Shorter probes may lack specificity for a target nucleic acid sequence and generally require cooler temperatures to form sufficiently stable hybrid complexes with the template. Longer probes are expensive to produce and can sometimes self-hybridize to form hairpin structures. Methods for the synthesis of oligonucleotide probes have been described above and can be applied to the probes of the present invention.

Preferably the probes of the present invention are labeled or immobilized on a solid support. Labels and solid supports are further described in II. Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

The probes of the present invention are useful for a number of purposes. They can be used in Southern hybridization to genomic DNA or Northern hybridization to mRNA. The probes can also be used to detect PCR amplification products. By assaying the hybridization to an allele specific probe, one can detect the presence or absence of a biallelic marker allele in a given sample.

High-Throughput parallel hybridizations in array format are specifically encompassed within "hybridization assays" and are described below.

Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., *Nature Genetics*, 14(4):441–447, 1996; Shoemaker et al., *Nature Genetics*, 14(4):450–456, 1996; Kozal et al., *Nature Medicine*, 2:753–759, 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP785280 describes a tiling strategy for the detection of single nucleotide polymorphisms. Briefly, arrays may generally be "tiled" for a large number of specific polymorphisms. By "tiling" is generally meant the synthesis of a defmed set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific, identified biallelic marker sequences. In particular the array is tiled to include a number of detection blocks, each detection block being specific for a specific biallelic marker or a set of biallelic markers. For example, a detection block is tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning is carried out as described in PCT application No. WO 92/10092 and WO 95/11995 and U.S. Pat. No. No. 5,424,186.

5) Integrated Systems

Another technique, which is used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection.

XI. METHODS OF GENETIC ANALYSIS USING THE BIALLELIC MARKERS OF THE PRESENT INVENTION

The methods available for the genetic analysis of complex traits fall into different categories (see Lander and Schork, *Science*, 265, 2037–2048, 1994). In general, the biallelic markers of the present invention find use in any method known in the art to demonstrate a statistically significant correlation between a genotype and a phenotype. The biallelic markers is used in linkage analysis and in allele-sharing methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention is conducted on any scale. The whole set of biallelic markers of the present invention or any subset of biallelic markers of the present invention is used. In some embodiments, any additional set of genetic markers including a biallelic marker of the present invention is used. As mentioned above, it should be noted that the biallelic markers of the present invention is included in any complete or partial genetic map of the human genome. These different uses are specifically contemplated in the present invention and claims.

XI.A. Linkage Analysis

Until recently, the identification of genes linked with detectable traits has mainly relied on a statistical approach called linkage analysis. Linkage analysis involves proposing a model to explain the inheritance pattern of phenotypes and genotypes observed in a pedigree. Linkage analysis is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offspring of all families. Those that co-segregate with the trait are tracked. After pooling data from all families, statistical methods are used to determine the likelihood that the marker and the trait are segregating independently in all families. As a result of the statistical analysis, one or several regions having a high probability of harboring a gene linked to the trait are selected as candidates for further analysis. The result of linkage analysis is considered as significant (i.e. there is a high probability that the region contains a gene involved in a detectable trait) when the chance of independent segregation of the marker and the trait is lower than 1 in 1000 (expressed as a LOD score >3). Generally, the length of the candidate region identified as having a LOD score of greater than 3 using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). About 100 pathological trait-causing genes were discovered using linkage analysis over the last 10 years. In most of these cases, the majority of affected individuals had affected relatives and the detectable trait was rare in the general population (frequencies less than 0.1%). In about 10 cases, such as Alzheimer's Disease, breast cancer, and Type II diabetes, the detectable trait was more common but the allele associated with the detectable trait was rare in the affected population. Thus, the alleles associated with these traits were not responsible for the trait in all sporadic cases.

Linkage analysis suffers from a variety of drawbacks. First, linkage analysis is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, linkage analysis approaches have proven difficult when applied to complex genetic traits, such as those due to the combined action of multiple genes and/or environmental factors. In such cases, too large an effort and cost are needed to recruit the adequate number of affected families required for applying linkage analysis to these situations, as recently discussed by Risch, N. and Merikangas, K. (*Science*, 273:1516–1517, 1996). Finally, linkage analysis cannot be applied to the study of traits for which no large informative families are available. Typically, this will be the case in any attempt to identify trait-causing alleles involved in sporadic cases, such as alleles associated with positive or negative responses to drug treatment.

XI.B. Allele-Sharing Methods

Whereas linkage analysis involves proposing a model to explain the inheritance pattern of phenotypes and genotypes in a pedigree, allele-sharing methods are not based on constructing a model, but rather on rejecting a model (see Lander and Schork, *Science*, 265, 2037–2048, 1994). More specifically, one tries to prove that the inheritance pattern of a chromosomal region is not consistent with random Mendelian segregation by showing that affected relatives inherit identical copies of the region more often than expected by chance. Because allele-sharing methods are nonparametric (that is, assume no model for the inheritance of the trait), they tend to be more useful for the analysis of complex traits than linkage analysis. Affected relatives should show excess allele sharing even in the presence of incomplete penetrance and polygenic inheritance. Allele-Sharing methods involve studying affected relatives in a pedigree to determine how often a particular copy of a chromosomal region is shared identical-by-descent (IBD), that is, is inherited from a common ancestor within the pedigree. The frequency of IBD sharing at a locus can then be compared with random expectation. Affected sib pair analysis is a well-known special case and is the simplest form of this method.

However, as allele-sharing methods analyze affected relatives, they tend to be of limited value in the genetic analysis of drug responses or in the analysis of side effects to treatments. This type of analysis is impractical in such cases due to the lack of availability of familial cases. In fact, the likelihood of having more than one individual in a family being exposed to the same drug at the same time is very low.

XI.C. Association Studies

The present invention comprises methods for identifying one or several genes among a set of candidate genes that are associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention is incorporated in any map of genetic markers of the human genome in order to perform genome-wide association studies. Methods to generate a high-density map of biallelic markers has been described in U.S. Provisional Patent application serial No. 60/082,614. The biallelic markers of the present invention may further be incorporated in any map of a specific candidate region of the genome (a specific chromosome or a specific chromosomal region for example).

As mentioned above, association studies is conducted within the general population and are not limited to studies performed on related individuals in affected families. Linkage disequilibrium and association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies and Linkage Disequilibrium mapping methods using the biallelic markers of the present invention can therefore be used to refine the location of a trait causing allele in a candidate region identified by Linkage Analysis or by Allele-Sharing methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention and claims.

1) Case-control Populations (Inclusion Criteria)

Association studies do not concern familial inheritance and do not involve the analysis of large family pedigrees but compare the prevalence of a particular genetic marker, or a set of markers, in case-control populations. They are case-control studies based on comparison of unrelated case (affected or trait positive) individuals and unrelated control (random or unaffected or trait negative) individuals. The control group is composed of individuals chosen randomly or of unaffected (trait negative) individuals, preferably the control group is composed of unaffected or trait negative individuals. Further, the control group is preferably both ethnically- and age-matched to the case population. In the following "trait positive population", "case population" and "affected population" are used interchangeably.

An important step in the dissection of complex traits using association studies is the choice of case-control populations (see Lander and Schork, *Science*, 265, 2037–2048, 1994). Narrowing the definition of the disease and restricting the patient population to extreme phenotypes allows one to work with a trait that is more nearly Mendelian in its inheritance pattern and more likely to be homogeneous (patients suffer from the disease for the same genetic reasons). Therefore, a major step in the choice of case-control populations is the clinical definition of a given trait or phenotype. Four criteria are often useful: clinical phenotype, age at onset, family history and severity. Preferably, in order to perform efficient and significant association studies, such as those described herein, the trait under study should preferably follow a bimodal distribution in the population under study, presenting two clear non-overlapping phenotypes (trait positive and trait negative). Nevertheless, even in the absence of such bimodal distribution (as may in fact be the case for more complex genetic traits), any genetic trait may still be analyzed by the association method proposed here by carefully selecting the individuals to be included in the trait positive and trait negative phenotypic groups. The selection procedure involves selecting individuals at opposite ends of the non-bimodal phenotype spectra of the trait under study, so as to include in these trait positive and trait negative populations individuals which clearly represent extreme, preferably non-overlapping phenotypes. This is particularly useful for continuous or quantitative traits (such as blood pressure for example). Selection of individuals at extreme ends of the trait distribution increases the ability to analyze these complex traits. The definition of the inclusion criteria for the case-control populations is an important aspect of association studies. The selection of those drastically different but relatively uniform phenotypes enables efficient comparisons in association studies and the possible detection of marked differences at the genetic level, provided that the sample sizes of the populations under study are significant enough.

Preferably, case-control populations to be included in association studies such as those proposed in the present invention consist of phenotypically homogeneous populations of individuals each representing 100% of the corresponding phenotype if the trait distribution is bimodal. If the trait distribution is non-bimodal, trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and selected among individuals exhibiting non-overlapping phenotypes. In some embodiments, the trait positive and trait negative groups consist of individuals exhibiting the extreme phenotypes within the studied population. The clearer the difference between the two trait phenotypes, the greater the probability of detecting an association with biallelic markers.

In preferred embodiments, a first group of between 50 and 300 trait positive individuals, preferably about 100 individuals, are recruited according to their phenotypes. A similar number of trait negative individuals are included in such studies.

In the present invention, typical examples of inclusion criteria include a diagnosis of cancer or prostate cancer or the evaluation of the response to anti-cancer or anti-prostate cancer agent or side effects to treatment with anti-cancer or anti-prostate cancer agents.

Suitable examples of association studies using biallelic markers including the biallelic markers of the present invention, are studies involving the following populations:

a case population suffering from a form of cancer and a healthy unaffected control population, or a case population suffering from a form of prostate cancer and a healthy unaffected control population, or a case population treated with anticancer agents suffering from side-effects resulting from the treatment and a control population treated with the same agents showing no side-effects, or a case population treated with anti-prostate cancer agents suffering from side-effects resulting from the treatment and a control population treated with the same agents showing no side-effects, or a case population treated with anti-cancer agents showing a beneficial response and a control population treated with same agents showing no beneficial response, or a case population treated with anti-prostate cancer agents showing a beneficial response and a control population treated with same agents showing no beneficial response.

2) Determining the Frequency of an Allele in Case-Control Populations

Allelic frequencies of the biallelic markers in each of the populations can be determined using one of the methods described above under the in Section X. under the heading "Methods for genotyping an individual for biallelic markers", or any genotyping procedure suitable for this intended purpose. The frequency of a biallelic marker allele in a population can be determined by genotyping pooled samples or individual samples. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

3) Determining the Frequency of a Haplotype in Case-Control Populations

The gametic phase of haplotypes is usually unknown when diploid individuals are heterozygous at more than one locus. Different strategies for inferring haplotypes is used to partially overcome this difficulty (see Excoffier L. and Slatkin M., *Mol Biol Evol.*, 12(5): 921–927, 1995). One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al., *Nucleic Acids Res.*, 17:2503–2516, 1989; Wu et al., *Proc. Nati. Acad. Sci. USA*, 86:2757, 1989) or by isolation of single chromosome by limit dilution followed by PCR amplification (see Ruano et al., *Proc. Natl. Acad. Sci. USA*, 87:6296–6300, 1990). Further, multiple haplotypes can sometimes be inferred using genealogical information in families (Perlin et al., *Am. J. Hum. Genet.*, 55:777–787, 1994). A sample is haplotyped for sufficiently close biallelic markers by double PCR amplification of specific alleles (Sarkar, G. and Sommer S. S., *Biotechniques*, 1991). These approaches are not entirely satisfying either because of their technical complexity, the additional cost they entail, their lack of generalization at a large scale, or the possible biases they introduce. To overcome these difficulties, an algorithm based on Hardy-Weinberg equilibrium (random mating) to infer the phase of PCR-amplified DNA genotypes introduced by Clark A. G. (*MoL Biol. EvoL.*, 7:111–122, 1990) is used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Any other method known in the art to determine the frequency of a haplotype in a population is used. Preferably, an expectation-maximization (EM) algorithm (Dempster et al., *J. R. Stat. Soc.*, 39B: 1–38, 1977) leading to maximum-likelihood estimates of haplotype frequencies under the assumption of Hardy-Weinberg proportions is used (see Excoffier L. and Slatkin M., *Mol. Biol. Evol.*, 12(5): 921–927, 1995). The EM algorithm is used to estimate haplotype frequencies in the case when only genotype data from unrelated individuals are available. The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical methods".

4) Genetic Analysis Based on Linkage Disequilibrium

Linkage disequilibrium is the non-random association of alleles at two or more loci and represents a powerful tool for genetic mapping of complex traits (see Jorde L. B., *Am. J. Hum. Genet.*, 56:11–14, 1995). Biallelic markers, because they are densely spaced in the human genome and can be genotyped in large numbers, are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombinations occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations.

The pattern or curve of disequilibrium between disease and marker loci will exhibit a single maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provide powerful tools for fine-scale mapping. Different methods to calculate linkage disequilibrium are described below under the heading "Statistical Methods". Moreover, association studies as a method of mapping genetic traits rely on the phenomenon of linkage disequilibrium.

3) Association Studies

As mentioned above, the occurrence of pairs of specific alleles at different loci on the same chromosome is not random, and the deviation from random is called linkage disequilibrium. If a specific allele in a given gene is directly involved in causing a particular trait, its frequency will be statistically increased in an affected (trait positive) population when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular allele's region. Association studies focus on population frequencies. Case-control populations can be genotyped for biallelic markers to identify associations that narrowly locate a trait causing allele. Moreover, any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Association Analysis

The general strategy to perform association studies using biallelic markers derived from a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (the associated allele is the trait causing allele), or more likely the associated allele is in linkage disequilibrium with the trait causing allele. The specific characteristics of the associated allele with respect to the candidate gene function usually gives further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker.

Association studies are usually run in two successive steps. In a first phase, the frequencies of a reduced number of biallelic markers from one or several candidate genes are determined in the trait positive and trait negative populations. In a second phase of the analysis, the identity of the candidate gene and the position of the genetic loci responsible for the given trait is further refined using a higher density of markers from the relevant gene. However, if the candidate gene under study is relatively small in length, as it is the case for many of the candidate genes analyzed included in the present invention, a single phase is sufficient to establish significant associations.

Haplotype Analysis

As described above, when a chromosome carrying a disease allele first appears in a population as a result of either mutation or migration, the mutant allele necessarily resides on a chromosome having a unique set of linked markers: the ancestral haplotype. This haplotype can be tracked through populations and its statistical association with a given trait can be analyzed. The statistical power of association studies is increased by complementing single point (allelic) association studies with multi-point association studies also called haplotype studies. Thus, a haplotype association study allows one to define the frequency and the type of the ancestral carrier haplotype. A haplotype analysis is important in that it increases the statistical significance of an analysis involving individual markers. Indeed, by performing an association study with a set of biallelic markers, it increases the value of the results obtained through the study, allowing false positive and/or negative data that may result from the single marker studies to be eliminated.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals which should be subjected to this analysis to obtain statistically significant results usually ranges between 30 and 300, with a preferred number of individuals ranging between 50 and 150. The same considerations apply to the number of random control or unaffected individuals used in the study. The results of this first analysis provide haplotype frequencies in case-control populations, the relative risk for an individual carrying a given haplotype of being affected with the given trait under study and the estimated p value for each evaluated haplotype.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis, similar to those described in further details within the present invention. Preferably, genotyping typing is performed using the microsequencing technique.

Methods to test for association between a trait and a biallelic marker allele or a haplotype of biallelic marker alleles are described below.

XI.D. STATISTICAL METHODS

In general, any method known in the art to test whether a trait and a genotype show a statistically significant correlation is used.

Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., *Mathematical and Statistical Methods for Genetic Analysis*, Springer, N.Y., 1997; Weir, B. S., *Genetic data Analysis* II: *Methods for Discrete population genetic Data*, Sinauer Assoc., Inc., Sunderland, Mass., USA, 1996) Preferably, maximum-likelihood haplotype frequencies are computed using an Expectation- Maximization (EM) algorithm (see Dempster et al., *J. R. Stat. Soc.*, 39B:1–38, 1977; Excoffier L. and Slatkin M., *Mol. Biol. Evol.*, 12(5): 921–927, 1995). This procedure is an iterative process aiming at obtaining maximum-likelihood estimates of haplotype frequencies from multi-locus genotype data when the gametic phase is unknown. Haplotype estimations are usually performed by applying the EM algorithm using for example the EM-HAPLO program (Hawley M. E. et al., *Am. J Phys. Anthropol.*, 18:104, 1994) or the Arlequin program (Schneider et al., *Arlequin: a software for population genetics data analysis*, University of Geneva, 1997). The EM algorithm is a generalized iterative maximum likelihood approach to estimation and is briefly described below.

In the following part of this text, phenotypes will refer to multi-locus genotypes with unknown phase. Genotypes will refer to known-phase multi-locus genotypes.

Suppose a sample of N unrelated individuals typed for K markers. The data observed are the unknown-phase K-locus phenotypes that can categorized in F different phenotypes. Suppose that we have H underlying possible haplotypes (in case of K biallelic markers, $H=2^K$). For phenotype j, suppose that cj genotypes are possible. We thus have the following equation $$P_j = \sum_{i=1}^{c_j} pr(genotype_i) = \sum_{i=1}^{c_j} pr(h_k, h_l) \quad \text{Equation 1}$$

where Pj is the probability of the phenotype j, hk and hl are the two haplotypes constituent the genotype i. Under the Hardy-Weinberg equilibrium, pr(hk, hl) becomes:

$Pr(h_k,h_l)=pr(h_k)^2$ if $h_k=h_l$, $pr(h_k,h_l)=2pr(h_k) \cdot pr(h_l)$ if $h_k \neq h_l$.

Equation 2

The successive steps of the E-M algorithm can be described as follows: Starting with initial values of the of haplotypes frequencies, noted, $p_1^{(0)}, p_2^{(0)}, \ldots p_T^{(0)}$. these initial values serve to estimate the genotype frequencies (Expectation step) and then estimate another set of haplotype frequencies (Maximization step): $p_1^{(1)}, p_2^{(1)}, \ldots p_T^{(1)}$. these two steps are iterated until change in the sets of haplotypes frequency are very small.

A stop criterion can be that the maximum difference between haplotype frequencies between two iterations is less than $10^{-7}$. These values can be adjusted according to the desired precision of estimations.

In detail, at a given iteration s, the Expectation step consists in calculating the genotypes frequencies by the following equation:

$$pr(genotype_i)^{(s)} = pr(phenotype_j) \cdot$$

$$pr(genoptype_i | phenoptype_j)^{(s)}$$

$$= \frac{n_j}{N} \cdot \frac{pr(h_k, h_l)^{(s)}}{P_j^{(s)}}$$

Equation 3 where genotype i occurs in phenotype j, and where hk and hl constitute genotype i. Each probability are derived according to equations 1 and 2 above.

Then the Maximization step simply estimates another set of haplotype frequencies given the genotypes frequencies. This approach is also known as gene-counting method (Smith, *Ann. Hum. Genet.*, 21:254–276, 1957).

$$p_t^{(s+1)} = \frac{1}{2} \sum_{j=1}^{F} \sum_{i=1}^{c_j} \delta_{it} \cdot pr(genotype_i)^{(s)} \quad \text{Equation 4}$$

where $\delta_{it}$ it is an indicator variable which count the number of time haplotype t in genotype i. It takes the values of 0, 1 or 2.

To ensure that the estimation finally obtained are the maximum-likelihood estimations several values of departures are required. The estimations obtained are compared and if they differ the estimations leading to the best likelihood are kept. The term "haplotype determination method" is used to refer to all methods for determinin haplotypes known in the art including expectation-maximization algorithms.

Methods to Calculate Linkage Disequilibrium Between Markers

A number of methods can be used to calculate linkage disequilibrium between any two genetic positions, in practice, linkage disequilibrium is measured by applying a statistical association test to haplotype data taken from a population. Linkage disequilibrium between any pair of biallelic markers comprising at least one of the biallelic markers of the present invention $(M_i, M_j)$ can be calculated for every allele combination $(M_{i1}, M_{j1}; M_{i1}, M_{j2}; M_{i2}, M_{j1}$ and $M_{i2}, M_{j2})$, according to the Piazza formula: $\Delta M_{ik}, M_{j1} = \sqrt{\theta 4} - \sqrt{(\theta 4 + \theta 3)(\theta 4 + \theta 2)}$, where: $\theta 4 = --$=frequency of genotypes not having allele k at $M_i$ and not having allele 1 at $M_j$ $\theta 3 = -+$=frequency of genotypes not having allele k at $M_i$ and having allele 1 at $M_j$ $\theta 2 = +-$=frequency of genotypes having allele k at $M_i$ and not having allele 1 at $M_j$ Linkage disequilibrium (LD) between pairs of biallelic markers (Mi, Mj) can also be calculated for every allele combination $(M_{i1}, M_{j1}; M_{i1}, M_{j2}; M_{i2}, M_{j1}$ and $M_{i2}, M_{j2})$, according to the maximum-likelihood estimate (MLE) for delta (the composite linkage disequilibrium coefficient), as described by Weir (B. S. Weir, *Genetic Data Analysis*, Sinauer Ass. Eds, 1996). This formula allows linkage disequilibrium between alleles to be estimated when only genotype, and not haplotype, data are available. This LD composite test makes no assumption for random mating in the sampled population, and thus seems to be more appropriate than other LD tests for genotypic data.

Another means of calculating the linkage disequilibrium between markers is as follows. For a couple of biallelic markers, Mi $(a_i/b_i)$ and Mj $(a_j/b_j)$, fitting the Hardy-Weinberg equilibrium, one can estimate the four possible haplotype frequencies in a given population according to the approach described above.

The estimation of gametic disequilibrium between ai and aj is simply:

$D_{aiaj} = pr(haplotype(a_i, a_j)) - pr(a_i) \cdot pr(a_j)$.

Where pr(ai) is the probability of allele ai and aj is the probability of allele aj. and where pr(haplotype (ai, aj)) is estimated as in Equation 3 above. For a couple of biallelic marker only one measure of disequilibrium is necessary to describe the association between Mi and Mj.

Then a normalized value of the above is calculated as follows:

D'aiaj=Daiaj/max(pr(ai)·pr(aj),pr(bi)·(bj)) with Daiaj<0

D'aiaj=Daiaj/max(pr(bi)·pr(aj),pr(ai)·(bj)) with Daiaj>0

The skilled person will readily appreciate that other LD calculation methods can be used without undue experimentation.

Linkage disequilibrium among a set of biallelic markers having an adequate heterozygosity rate can be determined by genotyping between 50 and 1000 unrelated individuals, preferably between 75 and 200, more preferably around 100.

Testing for Association

Methods for determining the statistical significance of a correlation between a phenotype and a genotype, in this case an allele at a biallelic marker or a haplotype made up of such alleles, is determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype is used. Preferably the statistical test employed is a chi square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1\times10^{-2}$ or less, more preferably about $1\times10^{-4}$ or less, for a single biallelic marker analysis and about $1\times10^{-1}$ or less, still more preferably $1\times10^{-6}$ or less and most preferably of about $1\times10^{-8}$ or less, for a haplotype analysis involving several markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and cancer and prostate cancer can be revealed and used for diagnosis and drug screening purposes.

Using the method described above and evaluating the associations for single marker alleles or for haplotypes permits an estimation of the risk a corresponding carrier has to develop a given trait, and particularly in the context of the present invention, a disease, preferably cancer, more preferably prostate cancer. Significance thresholds of relative risks are to be adapted to the reference sample population used.

In this regard, among all the possible marker combinations or haplotypes which are evaluated to determine the significance of their association with a given trait, for example a form of cancer or prostate cancer, a response to treatment with anti-cancer or anti-prostate cancer agents or side effects related to treatment with anti-cancer or anti-prostate cancer agents, it is believed that those displaying a coefficient of relative risk above 1, preferably about 5 or more, preferably of about 7 or more are indicative of a "significant risk" for the individuals carrying the identified haplotype to develop the given trait. It is difficult to evaluate accurately quantified boundaries for the so-called "significant risk". Indeed, and as it has been demonstrated previously, several traits observed in a given population are multifactorial in that they are not only the result of a single genetic predisposition but also of other factors such as environmental factors or the presence of further, apparently unrelated, haplotype associations. Thus, the evaluation of a significant risk must take these parameters into consideration in order to, in a certain manner, weigh the potential importance of external parameters in the development of a given trait. Without wishing to be bound to any invariable model or theory based on the above statistical analyses, the inventors believe that a "significant risk" to develop a given trait is evaluated differently depending on the trait under consideration.

It will of course be understood by practitioners skilled in the treatment or diagnosis of cancer and prostate cancer that the present invention does not intend to provide an absolute identification of individuals who could be at risk of developing a particular form of cancer or who will or will not respond or exhibit side effects to treatment with anti-cancer or anti-prostate cancer agents but rather to indicate a certain degree or likelihood of developing a disease or of observing in a given individual a response or a side effect to treatment with a particular agent or set of agents.

However, this information is extremely valuable as it can, in certain circumstances, be used to initiate preventive treatments or to allow an individual carrying a significant haplotype to foresee warning signs such as minor symptoms. In the case of cancer, the knowledge of a potential predisposition, even if this predisposition is not absolute, might contribute in a very significant manner to treatment, or allow for suggestions in changes in diet or the reduction of risky behaviors, e.g. smoking. Similarly, a diagnosed predisposition to a potential side effect could immediately direct the physician toward a treatment, for which such side effects have not been observed during clinical trials.

Phenotypic Randomization

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated between 50 and 200 times, preferably between 75 and 125 times. The repeated iterations allow the determination of the percentage of obtained haplotypes with a significant p-value level below about $1\times10^{-3}$.

EXAMPLE 24

Detailed Association Studies

The initial association studies between the 8p23 locus and prostate cancer described in Section I.D. were repeated at a higher level of sophistication.

Collection of DNA Samples from Affected and Non-Affected Individuals

Prostate cancer patients were recruited according to clinical inclusion criteria based on pathological or radical prostatectomy records as described above in Section I. However, the pool of individuals suffering from prostate cancer described in Section I was augmented from the original 185 individuals to a range of between 275 and 491 individuals depending on the marker tested. Similarly, the control pool of non-diseased individuals described in Section I was augmented from the original 104 individuals to a range of between 130 and 313 individuals depending on the marker tested.

Genotyping Affected and Control Individuals

As for Section I.D., allelic frequencies of the biallelic markers in each population were determined by performing microsequencing reactions on amplified fragments obtained by genomic PCR performed on the DNA samples from each individual as described in Example 5.

Association Studies

Association results were obtained using markers spanning a 650 kb region of the 8p28 locus around PG1 both using single point analysis and haplotyping studies. See FIG. 16. As compared with the earlier representation of the initial association results for this region shown in FIG. 2, FIG. 16 is to scale, since the entire region has now been sequenced. In addition, more markers were generated around the association peak in the area of PG1; each of which has been tested in single point analysis (hence the density of data within this subregion). The haplotyping curve in FIG. 16 represents, for each marker considered, the maximum p-value for haplotypes obtained using this marker and any number from all markers harbored by the same BAC and being in Hardy Weindeberg Disequilibrium with said marker.

The data presented in FIG. 16 shows a strong association between this specific region within 8p23 locus, especially in the area that has been identified as being the PG1 gene, and prostate cancer. The maximum p-value in single point analysis, for the PG1 sub-region, is $3.10^{-3}$, while outside of the PG1 subregion, most of the p-values obtained for single point associations are less significant than $1.10^{-1}$. The maximum p-value obtained for haplotyping studies is the one obtained for a marker inside PG1's BAC, and equals $3.10^{-6}$.

FIG. 17 is a graph showing an enlarged view of the single point association results within a 160 kb region comprising the PG1 gene. Markers involved in this enlargement were all located on BAC B0463F0 1 (see FIG. 16), except marker 4–14, which lies in very close proximity, on BAC B0189E08. FIG. 17 shows all of the markers which made up the maximum haplotype shown in FIG. 16. Some of these markers were later revealed to lie within the promoter, exonic or intronic regions of the PG1 gene. The markers outside the gene were all informative biallelic markers with a least frequent allele present at a frequency of more than 20%, while markers within the gene were a mix of such informative markers and markers whose least frequent allele's frequency is less than 20%. These data confirm and narrow the previous peak of association values seen in FIG. 16, to a 40 kb harboring the PG1 gene. Significant associations are obtained for markers starting at the promoter site with marker No. 99–1485, and ending at the 3' UTR site with marker No. 5–66.

FIG. 18A is a graph showing an enlarged view of the single point association results of 40 kb within the PG1 gene. These data confirm that seven markers within the PG1 gene have one allele associated with prostate cancer, with p-values all similar and more significant than $1.10^{-2}$, specifically markers 99-622 ; 4-77 ; 4-71; 4-73 ; 99-598 ; 99-576 ; 4-66. FIG. 18B is a table listing the location of markers within PG1 gene, the two possible alleles at each site. For each marker, the disease-associated allele is indicated first; its frequencies in cases and controls as well as the difference between both are shown ; the odd-ratio and the p-value of each individual marker association are also shown.

The data in FIGS. 17, 18A, and 18B demonstrate that the markers in the PG1 gene have an association with prostate cancer that is valid, and exhibits similar significance values, regardless whether the considered cases are sporadic or familial cases. Therefore, some PG1 alleles must be general risk factors for any type of prostate cancer, whether familial or sporadic. The fact that several p-values for associated alleles are around $1.10^{-2}$ suggests that all these markers are in linkage disequilibrium to one another, and can all be used individually to assess PG1 associated prostate cancer susceptibility risk. The prostate cancer associated alleles of the 7 markers discussed above, all exhibit an odd-ratio of about 1.5, which means for each of them that an individual carrying such allele has 1.5 more chances to be susceptible to prostate cancer than not.

In order to confirm the significance of the association results found for markers on the BAC harboring PG1, we a novel statistical method was performed as described in provisional patent application serial no. 60/107,986, filed Nov. 10, 1998, the specification of which is incorporated herein.

Haplotype Analysis

The results of a haplotype analysis study using 4 markers (marker Nos. 4-14, 99-217, 4-66 and 99-221)) within the 160 kb region shown in FIG. 17 are shown in FIG. 19A. These 4 markers have each been shown to be strongly associated with prostate cancer, i.e. with p-values more significant than $1.10^{-3}$ on approximately 150 cases and 130 controls. All haplotypes using 2, 3, or 4 markers among the 4 above cited were analyzed using 491 case patients and 317 control individuals. FIG. 19A shows the most significant haplotypes obtained, as well as the individual odd-ratios for each. Haplotype 11 is the most significant (p-value of ca. $3.10^{-6}$), and is related to haplotype 5, shown in FIG. 4 in that three of the four marker alleles (4-14 C, 99-217 T and 99-221 A) are common to both haplotypes, and both cover a similar region. Differences in p-values are explained both by the addition of markers and of more case or control individuals. Haplotype 11 has an highly informative odd-ratio (of above 3); it is present in 3% of the controls and almost 10% of the cases.

FIG. 19B is a table showing the segmented haplotyping results according to the age of the subjects, and whether the prostate cancer cases were sporadic or familial, using the same markers 4 markers and the same individuals as were used to generate the results in FIG. 19A. FIG. 19B shows equivalent results for all segments of the population analyzed, demonstrating that the PG1 associated alleles are general risk factors for prostate cancer, regardless of the age of onset of the disease.

The haplotyping results and odd ratios for all of the combinations of the 7 markers (99-622; 4-77; 4-71; 4-7 ; 99-598; 99-576; and 4-66) within PG1 gene that were shown in FIG. 18 to have p-values more significant than $1 \times 10^{-2}$ were computed. A portion of these data are shown in FIG. 20. All of the 2-, 3-, 4-, 5-, 6—and 7-marker haplotypes were tested. FIG. 20 identifies for each x-marker haplotype category, the most significant haplotype. Among all these, the most significant haplotype is the two-marker haplotype 1, which shows a p-value of approximately $6.10^{-5}$, with an odd ratio of 2. The frequency of haplotype 1 among the control individuals is 15%, while it is 26% among the case patients. It is worth noting that these frequencies are very similar for all haplotypes presented on FIG. 20. It will thus be sufficient to test this two marker haplotype for prognosis/diagnosis on risk patients, as opposed to having a more complex test of a haplotype comprising 3 or more makers.

Finally, FIG. 21 is a graph showing the distribution of statistical significance, as measured by Chi-square values, for each series of possible x-marker haplotypes, (x=2, 3 or 4) using all of the 19 markers found in PG1 gene. These data confirm that testing 2-marker haplotypes within PG1 is sufficient because the testing 3- or 4-marker haplotypes does not increase the statistical relevance of the analysis.

EXAMPLE 25

Attributable Risk

Attributable risk describes the proportion of individuals in a population exhibiting a phenotype due to exposure to a particular factor. For further discussion of attributable risk values, see Holland, Bart K, Probability without Equations—Conceptsfor Clinicians; The Johns Hopkins University Press, pp. 88-90. In the present case the phenotype examined was prostate cancer, and the exposure was either one single allele of an individual PG1-related marker, or a haplotype thereof in an individual's genome. The formula used for calculating attributable risk values in the present study was the following:

$$AR = P_E(RR-1)/[P_E(RR-1)+1], \text{ where:}$$

AR was the attributable risk of allele or haplotype;

$P_E$ was the frequency of exposure to allele or haplotype within the population at large, in the present study a random male Caucasian population ; and RR was the relative risk, in the present study relative risk is approximated with the odd-ratio, because of the relatively low incidence of prostate cancer in populations at large (values for the odd ratios are found in FIGS. 18B and 20). In this case, PE was estimated using a dominant transmission model for prostate cancer:

$P_E = (N_{AA} + N_{AB})/N$, where:

$N_{AA}$ was the number of homozygous individuals harboring the disease associated allele or haplotype within a given random population, and $N_{AB}$ was the number of heterozygous individuals is said random population. $N_{AA}$ and $N_{AB}$ were calculated using the allele frequencies in the random population as indicated in FIGS. 18B and 20, and N was the number of individuals in total random population.

We calculated the attributable risks of disease-associated alleles for markers within PG1 gene and presented these results in FIG. 18B. In FIG. 20, the attributable risk for the two-marker haplotypes present in the figure as shown as well. These data demonstrate that disease-associated alleles of PG1 are present in approximately 20% of prostate cancer patients in the Caucasian population at large, and therefor represent prognostic tools of significant value.

XII. COMPUTER-RELATED EMBODIMENTS

As used herein the term "nucleic acid codes of the invention" encompass the nucleotide sequences comprising, consisting essentially of, or consisting of any one of the following: a) a contiguous span of at least 12, 15, 18, 20, 25, 30, 35, 40, 50, 60, 70, 80, 90, 100, 150, 200, 500, or 1000 nucleotides of SEQ ID No 179, wherein said contiguous span comprises at least 1, 2, 3, 5, 10, or 25 of the following nucleotide positions of SEQ ID No 179: 1–2324, 2852–2936, 3204–3249, 3456–3572, 3899–4996, 5028–6086, 6310–8710, 9136–11170, 11534–12104, 12733–13163, 13206–14150, 14191–14302, 14338–14359, 14788–15589, 16050–16409, 16440–21718, 21959–22007, 22086–23057, 23488–23712, 23832–24099, 24165–24376, 24429–24568, 24607–25096, 25127–25269, 25300–27576, 27612–29217, 29415–30776, 30807–30986, 31628–32658, 32699–36324, 36772–39149, 39184–40269, 40580–40683, 40844–41048, 41271–43539, 43570–47024, 47510–48065, 48192–49692, 49723–50174, 52626–53599, 54516–55209, and 55666–56146; b) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, 10, or 25 of the following nucleotide positions of SEQ ID No 3: 1–280, 651–690, 3315–4288, and 5176–5227; and c) anucleotide sequence complementary to either one of the preceding nucleotide sequences.

The "nucleic acid codes of the invention" further encompass nucleotide sequences homologous to: a) a contiguous span of at least 12, 15, 18, 20, 25, 30, 35, 40, 50, 60, 70, 80, 90, 100, 150, 200, 500, or 1000 nucleotides of SEQ ID No 179, wherein said contiguous span comprises at least 1, 2, 3, 5, 10, or 25 of the following nucleotide positions of SEQ ID No 179: 1–2324, 2852–2936, 3204–3249, 3456–3572, 3899–4996, 5028–6086, 6310–8710, 9136–11170, 11534–12104, 12733–13163, 13206–14150, 14191–14302, 14338–14359, 14788–15589, 16050–16409, 16440–21718, 21959–22007, 22086–23057, 23488–23712, 23832–24099, 24165–24376, 24429–24568, 24607–25096, 25127–25269, 25300–27576, 27612–29217, 29415–30776, 30807–30986, 31628–32658, 32699–36324, 36772–39149, 39184–40269, 40580–40683, 40844–41048, 41271–43539, 43570–47024, 47510–48065, 48192–49692, 49723–50174, 52626–53599, 54516–55209, and 55666–56146; b) a contiguous span of at least 12, 15, 18, 20, 25, 30, 35, 40, 50, 60, 70, 80, 90, 100, 150, 200, 500, or 1000 nucleotides of SEQ ID No 3 or the complements thereof, wherein said contiguous span comprises at least 1, 2, 3, 5, 10, or 25 of the following nucleotide positions of SEQ ID No 3: 1–280, 651–690, 3315–4288, and 5176–5227; and, c) sequences complementary to all of the preceding sequences. Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. Biochemistry, $3^{rd}$ edition. W. H Freeman & Co., New York) or in any other format or code which records the identity of the nucleotides in a sequence.

As used herein the term "polypeptide codes of the invention" encompass the polypeptide sequences comprising a contiguous span of at least 6, 8, 10, 12, 15, 20, 25, 30, 40, 50, or 100 amino acids of SEQ ID No 4, wherein said contiguous span includes at least 1, 2, 3, or 5 of the amino acid positions 1–26, 295–302, and 333–353. It will be appreciated that the polypeptide codes of the invention can be represented in the traditional single character format or three letter format (See the inside back cover of Stryer, Lubert. Biochemistry, $3^{rd}$ edition. W. H Freeman & Co., New York) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the present invention include systems, particularly computer systems which store and manipulate the sequence information described herein. One example of a computer system 100 is illustrated in block diagram form in FIG. 22. As used herein, "a computer system" refers to the hardware components, software components, and data storage components used to analyze the nucleotide sequences of the nucleic acid codes of the invention or the amino acid sequences of the polypeptide codes of the invention. In one embodiment, the computer system 100 is a Sun Enterprise 1000 server (Sun Microsystems, Palo Alto, Calif. The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of the nucleic acid codes of the invention or the amino acid sequences of the polypeptide codes of the invention (such as search tools, compare tools, and modeling tools etc.) may reside in main memory 115 during execution.

In some embodiments, the computer system 100 may further comprise a sequence comparer for comparing the above-described nucleic acid codes of the invention or the polypeptide codes of the invention stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

FIG. 23 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR OR SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

FIG. 24 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256.

The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms The method may be implemented by the computer systems described above and the method illustrated in FIG. 24. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

FIG. 25 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence.

If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of the invention. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to defme the structurally conserved regions in that family. This protein modeling technique also uses the known three-dimensional structure of a homologous protein to approximate the structure of the polypeptide codes of the invention. (See e.g., Srinivasan, et al., U.S. Pat. No. 5,557, 535 issued September 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszodi et al., Proteins:Structure, Function, and Genetics, Supplement 1:38–42 (1997)).

The results of the molecular modeling analysis may then be used in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattem (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al., 1990, J. Mol. Biol. 215(3):403–410), FASTA (Pearson and Lipman, 1988, Proc. Natl. Acad. Sci. USA 85(8):2444–2448), FASTDB (Brutlag et al. Comp. App. Biosci.

6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Although this invention has been described in terms of certain preferred embodiments, other embodiments which will be apparent to those of ordinary skill in the art in view of the disclosure herein are also within the scope of this invention. Accordingly, the scope of the invention is intended to be defmed only by reference to the appended claims. All documents cited herein are incorporated herein by reference in their entirety.

What is claimed is:

1. A composition comprising a purified or isolated polypeptide, wherein said polypeptide comprises a contiguous span of at least 8 amino acids of SEQ ID NO: 4.

2. A composition comprising a purified or isolated polypeptide, wherein said polypeptide comprises a contiguous span of at least 8 amino acids of SEQ ID NO: 5.

3. A composition comprising a purified or isolated polypeptide, wherein said polypeptide comprises a contiguous span of at least 8 amino acids of SEQ ID NO: 70.

4. The composition of claim 1, wherein said polypeptide comprises a contigious span of at least 10 amino acids of SEQ ID NO: 4.

5. The composition of claim 1, wherein said polypeptide comprises a contiguous span of at least 20 amino acids of SEQ ID NO: 4.

6. The composition of claim 1, wherein said polypeptide comprises a contiguous span of at least 50 amino acids of SEQ ID NO: 4.

7. The composition of claim 1, wherein said polypeptide comprises a contiguous span of at least 100 amino acids of SEQ ID NO: 4.

8. The composition of claim 2, wherein said polypeptide comprises a contiguous span of at least 10 amino acids of SEQ ID NO: 5.

9. The composition of claim 2, wherein said polypeptide comprises a contiguous span of at least 20 amino acids of SEQ ID NO: 5.

10. The composition of claim 2, wherein said polypeptide comprises a contiguous span of at least 50 amino acids of SEQ ID NO: 5.

11. The composition of claim 2, wherein said polypeptide comprises a contiguous span of at least 100 amino acids of SEQ ID NO: 5.

12. The composition of claim 3, wherein said polypeptide comprises a contiguous span of at least 10 amino acids of SEQ ID NO: 70.

13. The composition of claim 3, wherein said polypeptide comprises a contiguous span of at least 20 amino acids of SEQ ID NO: 70.

14. The composition of claim 3, wherein said polypeptide comprises a contiguous span of at least 50 amino acids of SEQ ID NO: 70.

15. The composition of claim 2, wherein said polypeptide comprises a contiguous span of at least 100 amino acids of SEQ ID NO: 70.

16. The composition of claim 1, wherein said polypeptide comprises either an Arginine or an Isoleucine residue in said contiguous span at an amino acid position that corresponds to amino acid postion 293 of SEQ. ID NO: 4.

17. The composition of claim 1, wherein said polypeptide comprises either an Arginine or an Hisitidine residue in said contiguous span at an amino acid position that corresponds to amino acid position 184 of SEQ. ID. No: 4.

18. The composition of claim 1, wherein said polypeptide comprises at least one of the contiguous spans of SEQ. ID. No. 4 selected from the group consisting of amino acids 1–26, 295–302, and 333–353.

19. The composition of claim 1, wherein said polypeptide comprises the sequence of SEQ. ID. No. 4.

20. The composition of claim 1, wherein said polypeptide comprises the sequence of SEQ. ID. No. 5.

21. The composition of claim 1, wherein said polypeptide comprises the sequence of SEQ. ID. No. 70.

* * * * *

SEQUENCE LISTING

```
<160> NUMBER OF SEQ ID NOS: 578

<210> SEQ ID NO 1
<211> LENGTH: 56516
<212> TYPE: DNA
<213> ORGANISM: Homo sapiens
<220> FEATURE:
<221> NAME/KEY: promoter
<222> LOCATION: 1629..1870
<223> OTHER INFORMATION: identification  method  Proscan
<220> FEATURE:
<221> NAME/KEY: misc_feature
<222> LOCATION: 1998..2000
<223> OTHER INFORMATION: potential start codon
<220> FEATURE:
<221> NAME/KEY: exon
<222> LOCATION: 2001..2216
<223> OTHER INFORMATION: exon1
<220> FEATURE:
<221> NAME/KEY: misc_feature
<222> LOCATION: 2031..2033
<223> OTHER INFORMATION: ATG
<220> FEATURE:
<221> NAME/KEY: misc_feature
<222> LOCATION: 11694..14332
<223> OTHER INFORMATION: Tyr  Phos
<220> FEATURE:
<221> NAME/KEY: primer_bind
<222> LOCATION: 11930..11947
<223> OTHER INFORMATION: upstream  amplification  primer  4-77  SEQ
      ID42
<220> FEATURE:
<221> NAME/KEY: allele
<222> LOCATION: 12057..12103
<223> OTHER INFORMATION: polymorphic  fragment  4-77  SEQ  ID24
<220> FEATURE:
<221> NAME/KEY: primer_bind
<222> LOCATION: 12339..12358
<223> OTHER INFORMATION: downstream  amplification  primer  4-77  SEQ
      ID51,  complement
<220> FEATURE:
<221> NAME/KEY: primer_bind
<222> LOCATION: 13547..13564
<223> OTHER INFORMATION: upstream  amplification  primer  4-73  SEQ
      ID64
<220> FEATURE:
<221> NAME/KEY: allele
<222> LOCATION: 13657..13703
<223> OTHER INFORMATION: polymorphic  fragment  4-73  SEQ  ID58
<220> FEATURE:
<221> NAME/KEY: primer_bind
```

```
<222> LOCATION: 13962..13981
<223> OTHER INFORMATION: downstream  amplification  primer  4-73  SEQ
      ID67,  complement
<220> FEATURE:
<221> NAME/KEY: exon
<222> LOCATION: 18196..18265
<223> OTHER INFORMATION: exon  2
<220> FEATURE:
<221> NAME/KEY: exon
<222> LOCATION: 23717..23832
<223> OTHER INFORMATION: exon  3
<220> FEATURE:
<221> NAME/KEY: exon
<222> LOCATION: 25571..25660
<223> OTHER INFORMATION: exon  4
<220> FEATURE:
<221> NAME/KEY: primer_bind
<222> LOCATION: 34216..34234
<223> OTHER INFORMATION: upstream  amplification  primer  99-217  SEQ
      ID43
<220> FEATURE:
<221> NAME/KEY: allele
<222> LOCATION: 34469..34515
<223> OTHER INFORMATION: polymorphic  fragment  99-217  SEQ  ID25
<220> FEATURE:
<221> NAME/KEY: primer_bind
<222> LOCATION: 34625..34645
<223> OTHER INFORMATION: downstream  amplification  primer  99-217  SEQ
      ID52,  complement
<220> FEATURE:
<221> NAME/KEY: exon
<222> LOCATION: 34669..34759
<223> OTHER INFORMATION: exon  5
<220> FEATURE:
<221> NAME/KEY: exon
<222> LOCATION: 40688..40846
<223> OTHER INFORMATION: exon  6
<220> FEATURE:
<221> NAME/KEY: exon
<222> LOCATION: 48070..48193
<223> OTHER INFORMATION: exon  7
<220> FEATURE:
<221> NAME/KEY: exon
<222> LOCATION: 50182..54523
<223> OTHER INFORMATION: exon  8
<220> FEATURE:
<221> NAME/KEY: primer_bind
<222> LOCATION: 51149..51168
<223> OTHER INFORMATION: upstream  amplification  primer  4-65  SEQ
      ID65
<220> FEATURE:
<221> NAME/KEY: allele
<222> LOCATION: 51448..51494
<223> OTHER INFORMATION: polymorphic  fragment  4-65  SEQ  ID59
<220> FEATURE:
<221> NAME/KEY: primer_bind
<222> LOCATION: 51482..51499
<223> OTHER INFORMATION: downstream  amplification  primer  4-65  SEQ
      ID68,  complement
<220> FEATURE:
<221> NAME/KEY: primer_bind
<222> LOCATION: 51596..51613
<223> OTHER INFORMATION: upstream  amplification  primer  4-67  SEQ
      ID44
<220> FEATURE:
<221> NAME/KEY: allele
<222> LOCATION: 51612..51658
<223> OTHER INFORMATION: polymorphic  fragment  4-67  SEQ  ID26
<220> FEATURE:
<221> NAME/KEY: primer_bind
<222> LOCATION: 51996..52015
<223> OTHER INFORMATION: downstream  amplification  primer  4-67  SEQ
      ID53,  complement
<220> FEATURE:
<221> NAME/KEY: polyA_signal
<222> LOCATION: 54445..54450
<223> OTHER INFORMATION: AATAAA

<400> SEQUENCE: 1
```

-continued

```
gtggatctgt gactgttcgc aggaagagag gagcgggagc aggacagaca ataactgata        60
gtcaggagct gggtttggag ataaagaggg aacaagagaa agttaagttc tgtgttttca       120
tggcaaacat tgcacaaaag tttacaactt cgtgactaac agtaatctgg ggtgattcac       180
aacaaattta cacataaaca catatttact gactttatac acagcaatcc taacgtgaac       240
acagaacctg ctttatcttt tcgcacactg ttctagtgta gagatgtctg gtctcagtta       300
aagaaagcat aaggagcatt agttgtgcac actgtccaca cccgtgactt ttttccacca       360
gtactaaacc tagtgcttct tacagtacag ggcaatgaca gccacagaaa gagagaagct       420
ccttttactg tgtaatgctt cctgctggcc ttcaaatact tgttacttga gagatctcca       480
ttcacctggc tttgtcccca aaggtcatca tctaccaatg atgttgttat ttgatgttaa       540
tcatgtataa agaaagtagc taccatcctg gccctgatta gaacttccca ctgaaatacc       600
gtcctgccta aaggtagcac aggtttccat atggtggtg gtggggaggg ggcgggaata       660
tatatatata tatatatata tatatatatg gtaaagcatt cggcattctt ttaaagtaca       720
actatccttg aaaagggtta catattaaac cattttttacc acagccaaag gggaggagaa       780
agatccaaaa gtcctgtgga tctgctttaa catcaataaa acagttatcc acccttcgta       840
gcttttagtg aaggctacaa aagtatgctt tttatggatt acacatgtgc acgcaactac       900
tttaattact acagaaaaaa acgaggctcc ttattaaaaa aaaatcagaa acaagtccaa       960
cagactctga ggaaatgaag caagagtgaa ttctgaaaag gtctaataaa cagtatggaa      1020
atatccttgt gggattgttc ttcagctatg cataaacatg taattatcat cattactgtg      1080
atggggaaaa acacggaccc taattctgaa acaccctggt agcgagagac gggcaggagg      1140
ggctgctgcg cactcagagc ggaggctgag gaggcggcgt ccccttgcaa aggactggca      1200
gtgagcagat ggggacactc gagctgcccc gcgacctggg ccgagctgcc tacaacctgg      1260
gcccaggtgc ctgcaagaat tagacctccg ataacgttaa cacccacttt ctcactgctc      1320
taattgtgtg catcccggcg cccagggct tgtgagcagc aggtgcgcgt tccaggcagc      1380
tccagcgacc cttaaacctg accgcgcgca cgtccggccc gagggagcag aacaagaggc      1440
acccggaccc tcctccggcc agcacccacc ttcacccagt tccgtcagtc gccaccacct      1500
cccttcccgc gtccgcagcc ggcccagctg gggagcatgc gcagtggccg gagccgggtt      1560
gcccgcgcca cagcaggtag ctgtactgca actgtcggcc caaaccaacc aatcaagaga      1620
cgtgttattg ccgccgaggt ggaactatgg caacgggcga ccaatcagaa ggcgcgttgt      1680
tgccgcggag cccctgccc cggcaggggg atgtggcgat gggtgagggt catgggtgt       1740 gagcatccct gagccatcga tccgggaggg ccgcgggttc ccttgctttg ccgccgggag      1800
cggcgcacgc agccccgcac tcgcctaccc ggccccgggc ggcggcgcgg cccatgcggc      1860
tgggggcgga ggctgggagc gggtggcggg cgcggcggcc cgggcccggg cggtgattgg      1920
ccgcctgctg gccgcgactg aggcccggga ggcggcggg gagcgcaggc ggagctcgct      1980
gccgccgagc tgagaagatg ctgctgtccc tggtgctcca cacgtactcc atgcgctacc      2040
tgctgcccag cgtcgtgctc ctgggcacgg cgcccaccta cgtgttggcc tggggggtct      2100
ggcggctgct ctccgccttc ctgccgccc gcttctacca agcgctggac gaccggctgt      2160
actgcgtcta ccagagcatg gtgctcttct tcttcgagaa ttacaccggg gtccaggtga      2220
gccgcctccc gctcccgggt ctcggcgtcc acccgagctc ccggggcgc ggacctctcc      2280 gctcccccac agctggcgag ggtcacccgg ccggcccggc ggacccagca cggagagcac      2340
```

-continued

```
gtgccgcctc cccgccttcc tctccgcatg cttcctgccg ttctgccgag atcgctctct    2400
aggaagctgt ggctgcgtcg tcctgaggct acgagtggga cccgccgccc ctttccccgc    2460
ccctcgcctg ggtctgatgc tgcttagcaa agtgggtgca gatgcacgtt ttaaataata    2520
gggcacgcgt ttagcagttt ctggcctttg gtccaaagag gtggtcatgt tggaacagat    2580
cggagacgtc tacactccga agtgcgcttt tacagtgacc tcttgaaaca gaagtacaat    2640
tcggtcttgt gttctttccc ctggacaagt gaaagctggg cgaagaaatg aatacatttg    2700
ttaaccgtag aagcctaact agatacaatt cttgccaact ttaactgggc ttgaatgtgt    2760
gggtgatctg ttgtctgatt actttctttc tgttactgtt tctctgtaga gattggattc    2820
gtagattaaa cttgagaaac aaaccataaa agtggaaggc cctctttaac agtaggtatt    2880
tgaagtgtta taaaaaaaaa aaaggtgaat ttttctttta tttctcagtt tgaaagaaca    2940
gctttattct tggttattcc taatgtccac ctagtcctct tttactttc ttggtagggt     3000 tagggtggca tggggaaatg ggacggtatc attttgtctt tttaactttt tttttttcca    3060
cctacagcag ctgtttttac cctgtggtca gtcaggtact atatttagtt tgcagttgca    3120
ctgctgatcg acccttgatg gccccagttg gaagttgttt gggggaagg aactaggaga     3180 ggccagggcc tccatttaaa ccagtgtctg taagtgtctc cttggaagga aaaaagata     3240 ctgttccagg tcatggtttc ctggtagttg acgtttaaaa tgggcctcat ttaaaaattt    3300
caataattca ggctaatttt ttcccttat atggtaactc caccaagttt gtctaaatgt     3360
atgattttta tcatgattaa gttttactt ccacatcatg tgacaactgg cctgggatgg     3420
gatataagct cagaacacaa agtcattcac ctgttaaaaa aataattcta tctgtggcgg    3480
gttatgttat ttttgttcaa agaggacaca atatgatgca gaatacacca ttgaaggatt    3540
ttttggtttg gcaagttctt attttttta atggctgtaa aacctagcag tgtttctgaa     3600
attgcatacc ttacctgatg ttcagagatc cgatttactt cttgatttcc cagcaagtga    3660
ttttgaaaac atttaatcta atcattcccc ccaccgtctg ttcaaatcaa aggaagtggc    3720
atccagcact aattttcatg catttatgaa aggatgcctg aggacccta agtataattc     3780 aaaattttgt ttaatgtgtg ttccttgatg aagttcttta ggagtcgtag aacgaactga    3840
ttgcccactg atcatcaaat gcaagttatg aacatttaat aaaaatttaa aaccaagagt    3900
ttcttgttcc tgcattttta tttttattgt atggagggga caaataatta ttttctgttt    3960
agtaacagag cagggtattt tgaatttatt agggtctttt tctgcagtct gggtttcctg    4020
tgtacacaaa gctacctttc aatatttttt attgtttctg ttaagattaa atcaatagag    4080
gaataaatag ctatcttcaa acataagacc caaaggaaaa agatttatag tgatgttctg    4140
tcaccttatt ttttacctgt gactttgtac cattaacttt gtcactgaga tgttttgatt    4200 aaaatttta gcttgctttt cttgttttgt taggacactc ttttttttctt gaattgtttt    4260 tatcagcttt cgtttgcaag gctagtgatg attctcttgt tctgtataaa gtattgttga    4320
ctcatttctg aagggagttt tagtaattta agaggttata agttttttaaa taaaggtttt   4380 attaatttat atatattaaa gaggcatttt aaaataaaat ttttttaaa tgacatttt     4440 acacctttca actctaggtt taaaaaataa gtggttcaca gtagttcttg cagaagaata    4500
ttttctttta catagaattt ttaagctgaa gagaagtagt agtaggtcca tgagatttat    4560
gatctgtgct tggcaggtaa acctgcttcc aacaaattta gttggatttt tcttggattc    4620
tgggtaaata ccttttcctt ccccagtttc actacttat tttcatatgt atctctgaga     4680
tagagaaata tttcagtcag tgctgctaaa attgttcctt ataactcgtt tatccttta    4740
```

```
ggtccttcca gaatctctca ttggtactga aactcaaatg ggtactttct tcaccattta   4800
tttctttaga ataagtaata agaatttat aagctttttt atatttcacg taatttgaga   4860
ctattgaaaa tccagttaag tctctctact gtgttgagag gcattgattc aagtacctgt   4920
gttactttcc tgtgctgcca aaacagatca cctcaaacta agcggcttaa aataatagaa   4980
cttaagttct cgtgattctg gaggccagca ctttgaaatc aaggtgtagg ctcaattta   5040
ctccctctgg aggccctagg gggaatctgt tcttgtgggt ttcaacttct ggtgactggt   5100
ggcattcctt ggcttgggggc cccatcactt caacctctgc cttacagtcc ttgctgccac   5160
ctcttctgtc tcacatctca ctctcccttt ctcttagaag gatgcttgtc attgggttta   5220
gagcccacct ggatattccg ggatgatctc ttcatctcaa gatccttaat tataactgca   5280
aagagccttt tccaaataa gaaacattc acaggttcca gggcttagga tgtggacaca   5340
ttttttgagg ggctgcccctt cattccccca caacaatgaa ctccatagtt ctgcctattc   5400
agtattttgt agttatttcg tagtttaact tgccttattt ctttaggtat ttacgtatta   5460
aagcatttg gtctctgctt tctttaacag agaacctggt tttctgtaat aagtttactt   5520
actttcccat aatctttag tttcttattt acagattac cttcacatat cccttaagta   5580
gaacatttga ttaactgttt tattttcgga acaaatctgc attctgtata ataaccaact   5640
tattcatatt tcggtattct tttaattctt atctgattct gaaattacca tcttgtgatt   5700
atatatatat atatatggaa ataactgaaa tcttgataaa ttaaaggtga tataacttct   5760
aagacaatta attatgtatg atgtggtgaa tatactggtg ttttggtttgt ttgccactta   5820
aaagccctat ctataggata ggaagtaact tgaatgtgga atgcttagag actcagagta   5880
agaggccgta tatatatcct tgagctggag tttaaggaaa acttatggga aattaaaagg   5940
aaagttggag tactgacaga ggattgcgta ggactcatga aaaaggaatg aagttacctt   6000
aaattctatc atcgtgagtt aacgtgaaac tagatttatg ttagtttata gcctagaatt   6060
ctatcctagg aatctagata tatcctaaat gttgagatag ctgcataaac aataactgta   6120
atcgttatga taaataatga caaatctttt tagcatgttt tgtgaagctg ataaatgtta   6180
ataggatgtc ttcaaatgtc agaattcttt tttctttgct tctttttaa aaaatttctt   6240
ttccccccatt cctatgcaat acactgaaaa ctgatcattg aaatttgtag gccaaaaaat   6300
taatcaacac gtaatagatt ggggtttggg ttttttgag tcagggtctt cttctgtcac   6360
ccaggctctg gtgcggtggc accatcatgg ctcattgcag cctgtgaatgc ctgggttcaa   6420
gtgatcctcc ggagtagctg ccgtgccatt atttctagct aattttaaa agttttgta   6480
gaaatggggt ctttctgtgt tgcccaggct ggtcttgaat tcctggcctc aggtgatcct   6540
tctgccttgg cctcccaaag tgctgggatt acaggtgtga ccaccatgc ctagcccta   6600
ataaatattc taattaccga tttatcttgc ttaaatcagt tggtaacact tggaatttac   6660
ttcagaatat attttacatt agtggctctg actgctaatt ccccttctc caaatgctaa   6720
tgtaatataa caataaaatg cacagttctt aagtttat aaaataaaca ggttttcagt   6780
tgacctgctt taagtgtaaa atagtgtgaa aaacacaaga agaagataa agaatttaag   6840
attttgacat ttctctaata tgcccttaac ttctccaagg attcatactt ttttttgtaa   6900
gacagaatct cacactgttg cccaaaccag aggtgcagtg gtgcagtctc cactcactgc   6960
aacctctgcc cccgggctca gcggtcctc ccacctcagc ctcctgagta gctgggacta   7020
caggtacaca gcaccatgcc cagctaattt tttttttgg tatttttag tggggggtaga   7080
```

```
gacgagattt tgccatattg cccagtctgg ttttgagctc ctgggctcaa gtgatccgtc   7140
cttgatccac catgcttagc tgattcatac tcttaactga acattgttc caagtttctc    7200
agaaacagtc aaggctttt atctagagaa catttataac tggatctttc tttgtgtagc    7260
actgattcat caaactaatc ctaaactcct aatgagttaa atttatattc tgaatcttgc   7320
tgtaaaagca gccattcatt agaatgaaac atgtttactt agaattggag aagggagctt   7380
ataagtcatc tagtctactc cctttatga cacttctaca ttctttctgc acttctgcca    7440
aaatgttgcc cagcgtcgtc tctgatacct atagtcctaa caagaatatg aatcataact   7500
tgtatcctta attttactct tctctgctta tttgccattc atgtgaagac cttaaataga   7560
tcttaaattg cttccttcac tttagctgag agtgacagga ctgtgtaggt gtgggtgtgt   7620
ttctgcattt gcttatttaa gcaggataat aaaaactttt actataggaa attaaacatt   7680
tcccaatcaa atacaattcc agtctaacac aattaaattc tggttaggga actgcttaac   7740
ttactagact tataggaaaa tactaaaaaa atgtaactag aactctattt ttacacttta   7800
taaatataaa cctctgtgaa caaaccagtt atttcaggtt gcatttgtgt atagttttt    7860
aatgcctgat ttttctattt taaaatcaca gatgcaatta tacattcaaa cactgccaca   7920
atactttgag aaagttaaag ttttccctac tcctacactg cgtacacctt tcctaggtac   7980
atcccagttt ggtgtgtaac tttagatttc ttccaagagc ttttgagtaa gtgttttgaat 8040
tgtgggaagg ttctttagtt aaatgaactt cttacagatc agtttttag tacagtagca    8100
cgaaatatac ctgcatacct atggggtatac ctctgtgcca ttacgatgga aggcacggga  8160
aaacagcact ccgtatatac ctagtttact ttccctcttt tgtatatttg tctgattttg   8220
tggagctgat gcttctcaag tggaatcaga agttaacttt tcctttacta ttttctcatt   8280
ttattatggt ttcttaacta gaggttgatg ttagtggttg gaccattcaa tagtaagtaa   8340
tgacttttca gtaagggatc tctagaaccc agatcccctta attcctgcaa tattcccgtg  8400
tgtacattgt tccaggtgct gtcctgggta ccaagggata caatgtttga tagacaatgt   8460
acctgccatt atggaggtca cattctagtg tgggaagaca aacaataaca agaaaatgaa   8520
aatttactgt gccatgccag gttgtttagc ctggtgggtg agaggtaggg gtttggaaaa   8580
tcttactgag caagtgacat ttgtgtggag ctctgtaaaa gggccagctt ggaaggtaat   8640
gtagtcatcc aggtgagaaa tgatggttag gggagtggaa agagtggatg ttaagattga   8700
aaagaattcc aaatctattt tagtggtagc tgatagggct ttgtgattga atgtggagga   8760
aaaagaagag ggtgggttag taacacactc agtcgcagtt agtgagtgct gctgtgtgca   8820
agtattgttc tattatgtaa ataattccat ctttacaaag taggcaccat tcttcctctt   8880
ttacagacaa ggaaaaggga cacccatgg ttcacatctg tagtagccta gccaggagtt    8940
tcaggcactt attttctgaa gatgctctgc ctggcaatgt ggttatattg gttgaaatga   9000
gaccccctac tttcaaggta ttcatctagg aaagacatga actgccaatt acaatatagg   9060
ataacactga aattagagac gtgtttatta actttgccat acagaggtaa agtaactctt   9120
taaagtaact ctttgcttgg gttagtggag aaggctataa aaattacttg gagtttttac   9180
tttgaacatg cgtaattaac atggaatgtt tagggaaaag aggttttcaa ttgataacat   9240
aataaacatg aggagtttga agcatggcat tcaaggtttt ctaaattctg ccccggttaa   9300
cttttccatt cgttggtttc attctagtct agcttttcct tctgggccgc ccctccccac   9360
attagaccgc tcctctctgg aattccaact caagcccttg cttttctcca tctgtcatga   9420
tgttaccccca tctcattgtc agggtaactt ttatgtaata ttaacatata taatactgat  9480
```

```
ataacattag catattttaa tgtatggatc atctcctctg caacattgta acctcttgga   9540
gatggcaata atgggaagaa tgacttgatt ttacttttc ttttaacaaa atggtggag    9600 tagtctgggc acggtgtggc tcatgcctgt aatcccagca ttttgggagg ccaaggaggg   9660
tggatcactt gaggtcaggc attcgagacc agtctggcca acattgtgaa accccatctc   9720
taccaaaaaa atacaaacac ttactgggca tggtggtgtg tgcctgtagt cctagctact   9780
caggaggctg aggtgggaga atcacttgaa catgggaggt agaggctcca gcttgggcga   9840
cagagtgaga ccctgtctca aaagaaaaaa aaggtaaaag gccaggtgc ggaggctcac    9900 gctggtaatc caagcacttt gggaggctga ggcaatggat cacctgaggt cgggagttcg   9960
agatcagcct gaccaacatg gagaaacccc ttctctacta aaatacaaa attagccggg   10020 cgtggtggtg cctgcctgta atctaagcta catgggaggc tgaggcagga gaatcacttg   10080
aacccaggag acagaggttg tggtgagcca agatggcacc attgcactcc cgactgggca   10140
acaagagcga aattccgtct caaacaaac aaacaaacaa acaaaacag agagaaaagg     10200 cagagtactc tagggaattc tagtctgtgt ttctgtggaa atgtatatga atctcacttt   10260
taagggatgg agattttga atggcataac tagttgataa gttttgctct aacagggtac    10320
ccaagtctag tgagtccgat tcattctttc cttaaataga tgaaggagga agaaacatga   10380 ctccacccctc aagagtaagg cagaatgagc aaagtcagag aagttaaaaa agaattctca  10440
cgcagccagc agtgcagaga aaccttggtt tagttgtgaa tcaaaaccag acttttttgt   10500 aattttttgag cctatgcaat tctccaaggt tttatgttgt ttcttctgtt tctctgtagg  10560
caccagaaat caaaaccccca aataagaaag tgttacttga agattttaga gtacttattt   10620
gtgtataagt gtaagtgata tttggaagac gactttactg cgctcctcca gcttggcatg   10680
agaattccag gggcggaaag aaaggagggt gatggtacct ggaaaggaga gtcatgttaa   10740
gtcccagcca catattaagt gctaaccacc tactgttaaa aggtgtaatg ttctagactg   10800
acaaaataca tagtctctac cgtaaagtaa cacataattt agcagtgcag aaagatgtca   10860
cttaaaagaa aacttgaata tatgctgaga tagttcacaa attaaagaaa tgaacaaaga   10920
actgaggaaa taaaggagga atacaactgt gtccaaatga atacttaact gggtgggagc   10980
tgttgcatat gtaagcaggt ggttcaccta aaagttggat gtaacgtagt taacgccagc   11040
tcttggtgca cttacatatt gcattgcttc cgggcttaat ttgtgttcat ataggaataa   11100
attttttgtt ggtttttaat tttactcctt gtaattccgt ggttgatatt caaagtgaaa   11160
aaaattacat aagcttctaa tatatgagaa gtcttctcac ttgacatttt ttatttggaa   11220
tttttgcaga gagtagtttt gtcacagtca aaagattttg ggatcttgca gtgagaaacc   11280
taggtgtaat tcctatttct ctgccattcc gtatgtcatc tggattaagt gtcaacttct   11340
cagtctcaag attctcgtcc ttaaatgaa tacttttgt catgctattt tgaagacaaa     11400
atgagataat acgtgaaact gcctagctca gtgaatggta catcatagat actcagaaaa   11460
aacacaccct ctaaaataag aacagtacca aaagacagga tgtaaaataa gggcagtacc   11520
aaaagacaca tgcatgctga gtgtatgaga aagaactttg tggccttctt gggtggcaca   11580
ggccatggca gttccacagc atgacgtggt tgctgtgggt ggtagagcag acatgccgct   11640
ccccgtcact gcctggcttt gatgcttgct ttcttcagct gagaggacgc agctgtgata   11700
tgaaggtctt gtgtgtacag tcgtgacctc acatttccaa tttcctgctg gcagaaccca   11760
cagtctacaa cgtacgagca ccagagttga cgtgagacag acagcataca gaggcttgta   11820
```

```
acatccttct ggaaaacact gtgtaagctt tcagtgcgaa taaacatgat cagtggcaag    11880
ttctgttaga tgtagtctgc aagcatcctg attttactgg gcaagactat gttgatttac    11940
aggcggctga tgattccatg gatagcccac tactagtatt ttcacaaatt tcacaagaca    12000
ttcttactgg aagattgccc tgttcttatg atactgctgc ccttttagct tcatttgctg    12060
ttcagactaa acttggagac tacagtcagt cagagaactt gctaggccac ctctcaggtt    12120
attctttcat tcctgatcat cctcaaaatt ttgaaaaaga aattgtaaaa attacatcag    12180
caacatatag gcttatgtcc ttgagaagca gcagttaatt acctaaacac agcaagtacc    12240
ttagaactct gtggagttga attgcactat gcaagggatc aagtaacaat aaaattatga    12300
ttggaatgat gtcaagagga attctgtattt ataacaggct atgaatgagt acctttccat    12360
ggtcgaagat tgtaaaaatt tgttttaagt gcaaacagtt ttttattcag ctttgaaaat    12420
gacttgcata atctggagaa agattatca ggatttaata tggtgaatta tatggcatgt    12480
aaacatttgt ggaaagcaag tttagaacat cacatattct tctgtttgga cagaccactt    12540
ccaactagaa agaatttttt tgcacattat tttacattag gttcaaaatt cctaatgcat    12600
ggtgggagaa ctgaagttca gttagttcag tatggcaaag aaaaggcaaa taaagacaga    12660
ctacttgcag gatcctcaag taagccattg acgtggaaat taatagtttg ggaagtagta    12720
ggcaggaatt caatatctga tgaaaagatt agaaacataa agccttccat cacaattccc    12780
acccggaaca ggaattccta ctcatcaaaa ttctgcattc atacaagagg gaacctgatt    12840
atgaccatct tctgttggtc atttggtaga ttatgtggtt cacacttctt ccaaatattt    12900
gcaaatcaga catcaccatt atcagcacaa gctaatagca tcattctgga atcatcacta    12960
ttacaggaca cccctggaga tgggtagcct ccagctttac cacccaaaca agctaagaaa    13020
aactgttgga accaaattca ttatttacat tttcaacaag atctggaaga tcatattaat    13080
gaaacgttga tgttctatct tctcttaaaa aatctgctcc taatggtggt attctacatg    13140
ataatcgtgt tctaatccga gtgaacctga cgaaaatgga aggtttggag tcaatgcaaa    13200 ggggggatatg atcagaagat gtctgtgatc gtgtcctgag aagcaccagg aacacctttg    13260
acctcagtga ctctcgattg aagagaagac caagttgtat tgatcagtgg ttgggacttt    13320
acagaacaca cccatgattg ggttgtcctg cttttaaag ccaactgtga gagacattct    13380
ggggaactca tgcttctagt tctacctatg ctgcatatga tgtagtggaa gaagtgctag    13440
aaaatgagac agacttccag tacattctgg agaaagcccc actagatagt gtccaccagg    13500
atgaccatgt gctgtgggag tcagtgatcc agctaaccga gggcttatcg ctggaacatt    13560
ctggacacaa tttgatcaac ttatcaaaaa aaacttgga atgacaattt ctggtgccag    13620
attaccttag aacctttgca aaaatagata gagatagttt tccttatgat gttacatggc    13680 ttattttttaa aggtaatgaa aactacatca gtgtaattcc agcatcataa gtcagaacag    13740
tgcttgtcaa ggggcgttac cacacacttg aacagatttt tggcagatga cttgggaaca    13800
aggctcctcc atgtttgtaa tgttgaccac acaagttgaa tgtggcagag ttaaatgacc    13860
ccaatattgg ccagaaccca caggaagttc atcctatgga tgctaccaag ccttctgcca    13920
ctgagaagaa ggaagcactg tctttatctt caggaagatc acactgctgt taaccaaga    13980 gaaaaattag agagtcatca atcacgcaga tccagtacag agggtggcct gaccatggag    14040
accctgatga ttcagtgact ttctggattt tgttttttcat atgcaaaata agagggctag    14100
caaggaaaaa cccccttgttg tttcttgcag tgctggagtt ggaagaacca gcgttcttaa    14160
tactatggaa acagccatgt gtctcattga tctcattgaa tgcagtcagc cagtttattc    14220
```

```
actagacatg gtaagaacaa tgagagagca gtgagccgtg atggtccaaa cacctagtca    14280
ttacagtttt gcgtgtgaag tactattttg aaagcttatg aagaaggctt tgctgaagaa    14340
agcaaaagga aaaaagaac tttgtcatct gttaggttcc atttattgca tgataattgt    14400
gtttgtattg attattgggc aagtagctgt ttgctatttt gatcttattt cagaagggca    14460
taataatttt actattcaat gaaacgtttt aaacgggta gaaaaagact agttttgta     14520 tgctttacag cagaaatctt ataatgatta actggtaata tatttcgttg cataaaaat    14580 acatttaaaa gttcaagtaa ttataaacat tgtaaattgt atatgtaatc atattgaaat    14640
tgaaattctt tatagctgta cttctgtgta atcaaagact ggggagagat agactagcta    14700
gctctttctc ttatccatta atcacttaac agagttttga ataaaaagtt ccatttcatg    14760
ggataagaat aatgacaggt taacctattt tagttggtta ctatgttcta ggtgttgtat    14820
gaagtagttt acatagtttc actgatttca ctacaatccc aggaggagta gttactatta    14880
ttacactcat tttacaggca agaaatagg tttggagggg ttgggtgttt tgcccaagtt     14940
ctcatcgtaa aatgacagat gaggattcaa attcaagtct taattgaagt ccattacttt    15000
agaacctacc tcttagtggc tcttatgtta cagtataagg gagagcagac tgttccttta    15060
cccttgtagg gtagctaggg cttgtgaatt aagagactga ttaacaggag aagaggcata    15120 cacatttat tgacgttagt attttacat gcacagggaa ggagggtttt attttattt      15180 ttatttttat ctttattta aagagacagg ggtcttgctg tgttgccagg ctggactca     15240 aactcctgaa gccaagcgat tcttctgctt gagattcctg agtagcaggg actataggtg    15300
tgctcctctg tgcttggcta aagaagggt ttgtatgtga tttttaacaa aggctgataa     15360
attgtgaaga agtgactagt caaggagaa gaggatttca gctcccaggg gtggtaaatt     15420
gtgggaagat gactaggaaa tgtatagtaa taaggtttgc tatgcaggtt tattttgcca    15480
gtttctggtc tcctaataag ggacagggaa acacctttac agatggaaat tcatatcacc    15540
tttccacagg gaaatttatg tcctgcctta ggcagttagg ggaagggcag agaattcttc    15600
ctgtatctgc tgtgtctcag gtgccttcag ctcaaaataa tccttatgcc aaagtagcat    15660
atttgggtgt ggcatattct ctgatctctt tcaacagcat catctatact taacaacagc    15720
aaaagttttt tttaaaaaat catgtttcaa gatttgcatg tggaagacaa atggacatga    15780
ttgagataaa tgaagaatat atatttttta acaaagaatg ctgtatattt atgtctctgt    15840
gacattgtgt tatggaggct aaggtgttaa gcatgtgatt actttagatg ccgtatgact    15900
acctgttttt aagattaaaa aagaatcaat aggcagttta tatgcatggg agcaagttaa    15960
aaacaacaca gatgtgatga aggcgaggtg aaactggtcc gcatctaatt caggccttct    16020
cctgaaagcc agtgtgtgca agataaataa gtttgtttga cgaaagcaga ataactagtt    16080
tgtcctttgt gatgaagata gttattcaga aatcatttt attggctacc tctgaattaa     16140
taaatgaaaa gagaaatttt tttttctgta ggggatgtct gatgagttct taaaaagtgg    16200
atgaacctga aattatcatg aacaagcaat tataatgaac ttaaaattac ttaaagagtt    16260
atgaaaaaca aaaagaaaag ccgtatgttt tcttgtgcct tatttgaag tgacaaatta     16320 tttgcagggt acatttgtag acggaactaa tgtgatttaa aaaatgagta ctagatttac    16380
agaatgatgc ctttaaaaag tcactggtgc actttaatta ttttattat gtttattctg     16440 aaactaccct tattttgaaa atgaggtata gctttgccta ctggtgacaa aagtgtaaat    16500
aattcagtaa acatctgtta aaaaccagct tggtgctagg ctcttggggt agaaaactga    16560
```

```
tcaggccatt gaggagctca tagtccctaa ggggctgggg acttgtcatt aggtgtgcag    16620
tgtgttctgg atgctcctga aggagtgtgg gcaggtgcgc accaccatgc ctggctaatc    16680
tttttataat tatgtagaga cagggtctgg ctgtgctgcc catgctgggt ttgaacttct    16740
gggcttaaga gatcttccct ccctgcccct accgaccccg cccgcccact ccacctcagc    16800
ctccccaaag cactgggatt gcaggcatgg gccactatgc ctgggctgtg caaaactttt    16860
aaatcagtgc atactcaatg gtcttgatgc aattctggct tgttggtaag agaatgggga    16920
tttactcaca agccacgatg tcacttttaa ctctgaacag atcaagctat tggtattact    16980
catttatgtc atcgataaac tttatgaata aaaactcatt gtgcaaatat ttaaacatac    17040
tacatacata gcactgtgca gtttctaagg aaagtaatgg aaacctttgt cacatccctg    17100
gcttccagaa ctttatgtta tctaagtgca tttgtctgca agttgttgg gttaattgcc    17160 cctttctttc ttctctttt aagatattaa taaatagtgt catgaccaaa agataatcct    17220
tatggacaag atagatctaa aaagccttag ctaatttata atcttgcata atccatgatg    17280
acaagatgca gaaacaaaaa tgcccagaat aaaaacttag caccattagc agccatttcc    17340
ttttaagtct ttacaagtat actcccagtt tcttgaaaaa tttattctaa aatatgtaag    17400
acacacaaaa cagcagaagg actaatacag gtacatcgaa cacctgtgtg cctaccgccc    17460
agtttaaaaa taaactggaa tgatgtttct ctcatactta cagaataaag ttttaatctt    17520
tagcatggaa ttcaaaagac ttctgccatt ccagttcaga gccacccttc tggtctcctt    17580
gctcctcagc cgcgacactg cccatgtacc caacaggcct ccagggttac tgcttccatt    17640
cgttcttatt ctcatgaaca ttttccttca tctcatctgc cagaatccta cctaataata    17700
ctcctgctct gcagtttaca gttctttaaa attaaaaaag gttgtgtacc ctttagtgtc    17760
ctgaaaaaag aaaaaacaaa tttaaaacct taaaaggta ccatattttc atagtatttg    17820
cgttatgtct cattacagtt cctgtggaca tgtctgtctc ttttactaga ttgattgtgg    17880
gctctttgaa ggaagatata tcttatgaac agtgttttat atattgttag caatcaatga    17940
atgcttgcta tattttctc atgaggatat tgattattct attttaattt attaccnnnn    18000
nnntgtacta tacataactg ctttctgtac ctgagctatt tatgatctct gaggctcctg    18060
tgagaaatct aattttgtt aatcatggat ggaaatattc acaacatcat tcgtcagttt    18120
cttcacattg tcttcctttg tatattacag atgttttaaa atatcaaagt aatgtttttt    18180
tgttttatct tttagatatt gctatatgga gatttgccaa aaaataaaga aaatataata    18240
tatttagcaa atcatcaaag cacaggtttg tatttcattt gcatgaaacc taggtttttc    18300
tacagatggc acatgggcat tcaaaatacc gttcttatat ttaaatgaag tgggtttttt    18360
aaaacagcaa ttttctgtgc agatattaca cctgttcttg tattttgtg attttacttt    18420 ttggaaagtc agaaacttga aagctatgaa ttttcctaaa cttaccttct ccctctgttg    18480
gatgtaagta agctatcttc ttacttgctt gctttgtttt tcctttgtgt agctctttaa    18540
agagtgtatt cattcttttt gtaagtgatg tttctagaag tagcattggt gggtcgaagt    18600
gtgtatacat tttacatttt tgattgctaa gctgcagaaa agctgtattg gtatgtaagt    18660
actcgtttcc ttactatgct cgtcatttct agtgtctgct cttcctttcc ttcttcaaat    18720
gggtttggtt taattctagt tgctactgtt ccatcagagg aattgcagag aactggtctt    18780
caaaacagtg cagtatatac tttaggtgaa gatacttcta aaaaccttg tattttgagg    18840 taattctaga gtcccaagaa tttgcaaaaa gagtacattg tcagcaatat ttttcccaat    18900
ggtgacatct aatataact gtagcacagt agcagaatca ggaaattgtc attgggtaag    18960
```

```
gtacttttta attctccaaa taattcagcc ctccaaaaaa atcccacttc ttatgttttc    19020
aaacctgtag ctactttga tgcgtacttc ctaaattgca tttttattac tttaaaaaat    19080
ataataccta gaagctcaaa gctggaaaca gcctgatcaa tatagtactc ttaagctaaa    19140
aacaacctga tcaatatagt actcttaggg aaatcactta tgcctgtggc ttttttaaa    19200 ttttcttcct gtcagctgtc tcttcatgat tttgtggttt ttattactgc ttataccata    19260
gatgaggtat agaaagtaaa agaagttaaa atgcatttt ctcaatttag tgaattaatg    19320
attacattca gatttatagg acaagggttg aagctancaa ggggttgata ggaatcttga    19380
tgtatctgag tattttcccc aactttatta catgactggt tcagactatt ttatctaatt    19440
acatttcact cttggcagaa atagcaaaac agtcaaccaa tggtcaatgc tgctgagaac    19500
tctggcctgt gcagacatat tggctgtttt acttctaata ccattctgct tttcctgtcc    19560
tgctgctgat ggatgtttct tccaggtttt aaatatcaaa caaagggat ctgtgggccc    19620 agtacaggga atggctcttg atagatttga ttttcctgca tttcctttat tttgatccag    19680
tgttaatttc atgtagagtt gtctgtttaa caggattctc ttaaaattcc ttcttcagtt    19740
tacctgccag cttttctttg tccaggtttc agtatgaact ccactcgatt aatagagctc    19800
tctagtagtg acttgtggag tgggttctct gaacatttct ggaagtgttg ctgatagtga    19860
taatattgat cactagtact gttaatttgt gtgcttacta catgttggct tttatatgta    19920
ttccttcaga ttaaggactt ctagaaaaca tccatgaaaa aacagattaa aaaaacaat    19980 tctgcatgta tttgggacta gaaggtacta tgggaaggat aatcttcata ctcagaccat    20040
actgacctga atttcattta tcagtttaga gaaccacttc cccttccctt caccctacct    20100
ccgagtgcct gtgactttgt atcaccgctc tggcaccaca tcctcatccc agcaggattt    20160
gggaaggctg cttttgaaa gccttttaaa attctgtaag ttgagaaaat actaggggaa    20220 tgatttaaa tttctttaga attacaggct ttagtcagta tatgacagag ccttttccta    20280
gaaaaatgtg catataaaaa tttgcatgta gttttagggt ttcagagacc cctaaagcct    20340
atccatagac gtggttcatt gtctgattgt gtttaggtac ccttctaaaa ccctttgag    20400 atgttaggaa tcacaacaga gtatctctga aaatgtaatt agcggaaaga acatttcaaa    20460
gactgttgtt ctgcttagac tttctagttt gtcttctgcc aggcttgccg gaataaatga    20520
gtttcctggc ctgatactca aaagaattga catttaaatt agtctctctc ttcccttgtt    20580
ttcgcttgac acatccttgt ctctacattc tgtctctgtc tctgttagct tatttctctc    20640
tcgagtcagc aggatatagt ggctgttatt tcttcccctt atccttcaac gatctacttt    20700
tgacaacact ttgcctttt tttttgaga tggagtttca ctcttgttgc ccaggctggg    20760
tgtaatggtg caatctcagc tcactgcaac ctttgcctcc cgggttcaag ccattttcct    20820
gcctcagcct cccgagtagc tgggattaca gacatgcacc accacgcctg gctaattttg    20880
tattttcagt agagatgggg tttcaccatg ttggtcaggc tggtcttgaa ctcctgacct    20940
caggtgatct gcctgcctcg gcctcccaaa gtgcagggat tacaggcgtg agccactgtg    21000
ccctgcctgc tatttgcctt tttaatctca tgaaatgttc tcttttcttg gctgaagtgt    21060
cacttttctt gttgaacagc atgcgtggtg agtagaatgt tataaaagg gatgactttt    21120 ggagttagag agacccaggt tcctgttcgg cattgcagaa atgctgttct gcaataggct    21180
gtgtgtcagt gggcaaatta cttatctctc agagccttat tggtaaggtg tgagtgatag    21240
ctcctttcag gcaccttaca gaggctgtct cctaatcctg gtagcgtacc tggctcatag    21300
```

```
atggcattta aaagtggttg tgatgacagt catagctcac cattagcata gcgctggatc    21360
catggcaggg aagcgctgca catgcagtat ctcttggact acacagggcc ctcatgaatt    21420
aggaactgct gtttcatgag gatagggatg aggaaattag acttgctgcc cctcactgcc    21480
ttccactcct ctcctccaag ttaatgggaa ctatgactct gctttggctt gattgccatg    21540
gaagattctc acacagccaa atttattgct atcttagtta aattatgcca gaacacaaaa    21600
tatgaagtta ttgtcaaagt aatataatct cagctgtaac tgagatagtc agaaactgtc    21660
tgtaatctga tgtcctatct gaaggtagc tgagaataaa caagaaataa agagaattca    21720
gtagcaaata ttggtgacac aaagctttta tattttgact agttaagcta gttcttaaat    21780
gtttccacta aaatattcaa gtttaagggc atagcccagg gcagcttatt atgaacatga    21840
tgtattttgg aaatcttaca ctttctctta aaagttcttg ggagggcat gtgaggccat    21900 aatataacca taaaaccatt tgttttaaaa taaaacccat ttttaaaatt cttccaaata    21960
aaaaaattat tgcaggaaaa aatgctaaac ctggtttta actttgtacg ccaactatat    22020
ttccaagatg tgctgtagcc tggtaaccat acagaaccat acagaattag ttctcagaat    22080
ttattgtctg cttacttttg catttggtac aggtataaca gggtcgatta tatggtttct    22140
aagacatgac tagaaagaaa tatgtttatc agttattatt tcttccatct aaattagaag    22200
gggctaggga gagggcttca acaggaattt atatacttta gagaaaagtg atcattgata    22260
gcccaatagt atagatatct caacccaata acacaggttg tgtctgtctc tgggatcata    22320
cactgtaggg gagaatcttt gcaagcaaca ttctacttat agggagccat aacaaaagtt    22380
tcatatgtat aataattata agtcttaagt catcaagaaa aagttaactt gtgaatgata    22440
atccctgatt aaaagagag atgtataata atggataaga gattttctt ggttaatttt    22500 tagtattaaa atggctaaat cttctttggg atattctgac tagtatggtg cattgtctaa    22560
tagatttccc atagctgaga gctaatcatc ttgtaatctg tggaaaactg tcctctttgg    22620
ctaaaacttt attgtaattc ctctaaatcc tcagcttta ttttctacag actttttttt    22680
ttttttaaca tttccttcct ctgactcact ccttttgttc tcattttcat ggcctgagaa    22740
catgggtgat gatagaatta ttcttttcac agattaacag ttttcttttc gagtatcgtt    22800
gagctcatgt gtgtattaac tagagaagtc tcccttacat ttcatttta tgttttcttt    22860 ctcatcagga gatagtttgt agccattac tttcaaatcc aagtttctgc ggttcttaag    22920
acctgtatca tttgtctcct gaatttcact tcatttcctc tttaaaccat gtcctctgtt    22980
tcccatcttc tgcacccact tgccacttc ctgtttgttt aattggcaag ggccactctc    23040
tgtgttggaa atttttcttt tttgaaagct caactaacaa cttctaggaa gtttttatt    23100 gctactgtta tcaattcata ccatcttacc cttgttttg caacccttg ttaataacat    23160 atttatttaa ctatagttat tagcagtctg agatcatttt acttggttac ataaggagca    23220
catatatcta cccagcatca ttgtaaggca tgtgagacct ttgtttgatt gctgtcctaa    23280
cctagtaccg agtcctaaaa actcattagt agaagatgaa gtgtccttgc cttttgctga    23340
acatatatat acacactgaa tatttagtgg caattcatag ttgcatttgg ccatttttg    23400 tttataattt ccccttttctc attaaaaaaa ctttgttttc tagactttag gatttagaga    23460
agctcatttt gttccataca catgctgctg ttggattatt taggtatttt gtgactgtat    23520
tttatctttg aaataaaaag cctttcaaga aatgcaaaaa aaaaaagctc aaaaaacaga    23580
aaatgtatat tttttaaata tctcagatag atttaaagaa attttaaaca tcctaatcat    23640
agtacttttg aagcccattc atagtacaac ctgtgaagag cctcatgtac gcgctaactg    23700
```

-continued

```
ggtcctgtct ctgcagttga ctggattgtt gctgacatct tggccatcag gcagaatgcg    23760
ctaggacatg tgcgctacgt gctgaaagaa gggttaaaat ggctgccatt gtatgggtgt    23820
tactttgctc aggtaacttg tttccatgct tttctctcta tatatgtagt ttataaattt    23880
tttttttttt ttttggagac agtctcactt tattgctcag gctgagtgca gtggtgtgaa    23940
cacagctcac tgcagccttg acctctgggg ctcaagtgaa cctcctgcct ctgcctccca    24000
agtagttggg accgtagtgc ccaccatcat gcccggctaa attttctatt ttttgtagag    24060 atggggtct cgctgtgttg cccaggctgg tcttggactc aagcaatctg cctgtctcag    24120
cctaccaaaa tgctggatta taggtgtgaa ctgccatacc caaccctata aaatgttat     24180 attttaaaat ttaacaatat acttcatgtg aatgtatggt tttaaaatg ggtttaatag     24240 tttattctca gttgaagtaa ttttgtttgg cattttagt ggtgtgtatt tatatacgtc     24300
tgattatcca tatgcggttt tccttcagca tctgtgggga ttggttttag aaccaccaca    24360
gataccaaaa tctaaggtgt tcaagaccct catatagaat gggatagtat ttgcatataa    24420
cctgtgcact actttaaatc atctctagat tacttataat atctaataca ttataaatgc    24480
catgtaaatg gttgttatac ttttatttttt atttgtatta ttttaattgt tatattattt   24540 ttaatttta tttgttcaca tatttttgat ctgtgatttg ttgaatctgc agatgtggaa     24600
ctcatggatg tgaagggcca gctgcagtaa aatgaaagag caaaaatgca aatgtacaaa    24660
gttcaaacaa ataggaaatt taaaggcata gaatttgata ggcaattaca ttaaactgtt    24720
gataacagta attagtgatc tgtatgatat taaaaaaaaa aagcaaactg tatatataaa    24780
acttactttc tccagttctg gaggctagac atccaagatc aaggtgttga cagggttagt    24840
ttctcccaag gcctctctcc caggcttgca gacagcatcc ttcttcctgt gtcctcaggt    24900 ggttttttttc cctgtgccca agcacccctg gcactgcttc ctcttcttag aaggactagt   24960
tacactggat gactaatcct tctacagaga ctgctaaggt cccactctga ggccctttt     25020 taaccttaat taccacctct aagtccctct ctctgaatac agtcacagtg ggaactatta    25080 gggcttagt agactgattt gggggaacac acttctgtcc gtaacagtgc cacataaata     25140
tctttagcag gattgatttt ttaaaatccc taaagatcgt gagtattgac atgttaagga    25200 cgcttttttag tgactctgta ataagtgggt ggaagaattg ggagttaaat ccatctgatg   25260
gatcaggttt tttattttta aaatgtgta tttaagaaag aaagcatttt catttttaact    25320 gccaacaaaa ctaaacttca tgtgttttcc aatacagtgt cacatgcagt tttttttgaat   25380 tatgttgaga caaggcaatt ttcagctaaa tgttctttag aagctaatgt ttgaagatat    25440
taaatataga ttaaattctg aaatgtagtt ttcattctgt acttttttgca agagaagttg   25500 ccttttttgat gactctggcc aattgttatt ttaaaagtaa atgctctttc tcccgatttg   25560
attgtggcag catggaggaa tctatgtaaa gcgcagtgcc aaatttaacg agaaagagat    25620
gcgaaacaag ttgcagagct acgtggacgc aggaactcca gtaagagcct acccgttttt    25680 attttttctta ccagctctca gtttctaaat ttaagaatta aattaaaatc taagaattgt   25740
tttgacaatg tattttccca tgtgtaatta ctaattcagg gttatgctga ggtaacagaa    25800
accctctatg tacaggtagg caggtttttc agccatcaga aagattgctg taaacaacta    25860
ggtcctttgc tggtcagtgg accttaaaga ggaataaaaa gagcatttgg tgtcgttcag    25920
agtctataaa tagaactaac tgcatttttaa cctgacattt aagctagttt acaagctcat   25980
cttacttctt gtcttcttta gtatcagatt tggttttaga agcagcaact gttttctgtt    26040
```

```
agtgcaaatt ttgaatgtct tacatgtaca gaaaaaccaa aaaaggatga atctctacaa   26100
atgttaaatc attcagtgta aataatattt tataaaactt tattccacaa aagtggggag   26160
agttcaatct gctttgtata gaatgctgat tgctgccaaa ggcttttccc ctggttccct   26220
ccggagacaa agcaccatga tcaccggggc gacttgggct ttctctttca gtacatgaca   26280
tgtgctcaga agcttagctc gtgtgcacag gctttccctt tcctttctgg ctccctccct   26340
ctgtcttccc tcctctcctc ttgccctccc ctcaccaggg gtcctgggca gcagctggag   26400
ctcatggtga aggaagaatt cttcatggtc agctggcgaa gtgcctggtg tgagcattgt   26460
ttattcacat gcctcttcta ggtgttttta cattagaaca ttgcatctgt tttgggcatg   26520
tgttgggtga cagaagcaga atggaatgag atgaacagtg accctttatc ctgttatagc   26580
taacccttga gaaccaagct tggtgtcttc aaagggtctg tttagtctga aacagtgtgg   26640
tgaatttggg cagaattgtg gtcattgcat gtaggtctcc aaaagacaga ataagttggt   26700
aatatggttt atcgactttt tacaaaaaaa atttaaaaat catgaattta taccttaaaa   26760
tgtccatccc acttctctcc cagctgtcca gtcaccccag caatggatga ctgctgtgga   26820
gttccttctg tgtcctgctg tgggcattgt atatatgaag caaatgaaga tagctgcctt   26880
ttgggtgatg ttggcatcct atgcacagtg gtcccttgct tttttgcccc catgaatata   26940
gctgccagtg gcgctagggc tgaaaaaatc agctctttac acttgtcatg tgtcttgttt   27000
atgtggctgc cttcgtgagt ttcttcttgt ttttggtttg cagcagttta agtatcatat   27060
atctgagtgt catttaaaaa ttttttacctg gattggtcct ctgagcttgg atctatgatt   27120
tggtgtctgt tattaatttt ggaaatttct ttgctcttat ttccttaaat attattccta   27180
ccccagtctt tcttctccag ttatgttttgt gttggttcat ttctcgctgt tctttagttc   27240
ttagatgcat tattcgtttt ttgttggttt tttttttaaat tttttttttt acgccccctc   27300
cctttttcct ttttgtgtta cattttggat aatttctgtt gacccacctt tgagttcatg   27360
gattcttcct ttggctgtgt tgagtctact ggtgagccag tttaaggcac tcttcatctc   27420
tgctactgcg tgtttcattc ctcacatttc cctttgaccc tgtttcatag tttccatctc   27480
tgtgctagtg tatctatctg atcataaagc ttagtcacgt tttccagttg aacctttatc   27540
attttattat acttgcagtt ctcttaaatt ccctgcttga taattccaac atctgggcca   27600
tatctgagtc tgcaaatttt gattacttta tctcttcaga ttgtgcttta tcttgccttt   27660
gtcatacttc ctaagatttt gcctaacgct gggcctttt tgtaagacag gagaaatgga   27720
ggcaagttgt cttgatacct ggaaatggat agacttgtct ttctgcttgg cttttagtgt   27780
tgaggagtgg agtcagtcca ctgaggaggt gcactgcatt tgggttttgc tcatgtgctt   27840
tttctcacag cttcaggttt ctgtagaact cattactttg tttgtaggtt ggggatgtcc   27900
tcccgctaga gcttttcctc agtgtctatt tcacactcag cgttttcaca tagcaccttg   27960
gagtggctct cttctttatg cctttcccca ctatacttct tggatacttg ttactgaact   28020
ctcgctagtt tggtggtaga aggagaggga agggaagtgt cttttcattc ttagggagaa   28080
tctcagggat ggagccttct ctgatcctgc cttgcttctg gctgtaagtc tgtgcccagt   28140
atgtattcct gcctttacta agagtttttc cctgttctct tcacccagcc tcatcgagta   28200
ttcatccgtg ccccatgggt agcagggttt tgttgcccct gttcatcagt ttcaggctgc   28260
tgttccatag gaaaggtaga aagaaggatg tgggctgggc cctgagccct tcccacaggg   28320
ctgcttttcc ctcccacaag cctacatcca gtcttccctg accgcagtgt gtttttcttt   28380
ttctttgtct tgtgagtaca caggaggtct gtgggtcgag cctgtgaaat gtgctgcatt   28440
```

```
ctccttgtgt ctgtagccca ggggttcgtc tgttccactg gctcatactt ggctttctgc   28500
aaaattgata aaattttag ctaaattctt tttactggta tctgttacat tggcccccaa    28560
ctaaacaacc acttgcatct tgtttctcct ttgagttttc catctttcct tagacttttg   28620
ggttagttgg ttgccttgca accttgcagc tctctgaagg gtctaagaaa agtcatgaat   28680
ctacagcttg tcagtgttgt tgttgttgta gggttggcag tagtattcct tcagcattct   28740
acatacttaa tggaagccgc ctcccatttt tggttaataa atttcaaaac ttggaacaat   28800
gttagattta caaaaacgtc agaaagaaca gagtgttcct gtttattctt tatatagctt   28860
tttttttttt tttttttttt gagttggagt ctcggtctgt cacccaggct ggagtgcagt   28920
ggcacgatct tggctcactg caacctctgc ctcacgggtt caagcaatct cctgcctcag   28980
cctcctgagt agctgggatt acaggcgtgc accgccatgc ccggctaatt tttgtatttt   29040
tagtagagac agggtttcac catgttggcc aggctggtct cgaactcctg acctcttgat   29100
ccgcccgcct cggccccccca cagtgctggg attataggtg tgagccacca cgcccagcct   29160
tcttcatcta gctttaacat ctaatgttga catcttacat aacatggtat atatttgtca   29220
aaactaagaa ataaacattg gtaccacact attaattgta ctacagattt ttattcagac   29280
tttaccaggt ttttccactaa tgtccttttt ctgttctaaa atacaatcca gaatagatac   29340
aaatccattc aacttcagtg ttttaaatta ttgttttca ttatatgaag tgctgtgtgg   29400
tttttgtcaa atctgttatt ttggttttaa tcttcaagct tgtctttgtt tcttaagtg   29460 ataaaggcat aatttaaaag gtgtgttggg ttatttcagt gcctaaagtc ttgtctgagt   29520
cacttgtttt ctgctgttct tgcttatggt actttctttc cttgtttgct ttgttatctt   29580
cctttgctgc tggctgtgtt tggttaagtt atttgtggaa atcagttgaa gcctcaggtg   29640
ggagtgtctt tctccggaga acatttctac ctgttttagc tgggccccctt aaggctcctc   29700 tagcgtgggc cccacccaaa cgagattctg agttgaaggt gaactgagcc attcaggcag   29760
tgcagccagg gttgcagatg cacgtgagac ctgctcacct ctcatttact ttcaccctga   29820
gagtagagcc tttggtgttt cgttcacttg tctgattctc tcttcacagt tctattagaa   29880
ggtccatggg ttttggtttc tgtgcccttc atcttatgag tcttgtaaat caaagttctg   29940
ttttatgctt acttctgctt tactgtgttt gcttaatttc agtcttaaca tcttgccaac   30000
tcttgggtac ttttaaaata atgttatatc cagcttttta agttgttttc agtaggaagg   30060
ttgattcaaa taacctagtc tggttatggg ctacgagaat agcctccctg ttttttgtgg   30120
gcaaaattcc agcctttat gttcctagcg cagtgtggat aacagactgg caggttcaag   30180
aggccgtgct gagcagcttt cactgtaagg tcactgtccc aggtcgggtt tctaagaatc   30240
tggatggttg tttcatttct taatatgtac gccctgtgag agcggataca tcttgctcag   30300
gttcttatga ttcttttgtt tctgaaggtg aattaagtaa gtgacatggt agaatatgtt   30360
aagtcaactt tcgtgtggct tactagttct catgaatcta ttccatgatt gtatcagttc   30420
ttattcagta ttagtattta agaaatgcag aattttgttt caaaaatat atttgtatta    30480 taagttgtga agaaatacat ctccataatt attgctggga caatacagta ttttcttaag   30540
gaacttattg gttgtggatg caaatgaagc atatttgta taaaaataac taatagaagt   30600
cattttgtta gactatgagc tagtaaaact tatggcacaa acatggagac ttaacacttt   30660
ttcttccagc tttcacttaa gttccttttc agataggagg cagcctggtg gataagagta   30720
ttggttttga aattagattc aggtttaaat cccagatctt ctgtttaatc tttattttat   30780
```

```
ttcaggtaga ttttctggat aacttgctat agcttatacg tcagtacttg ccacttcaat    30840
tttatgttat ggagagacgg cttctttcct taaacctcac gaaccaacct ctgctagctt    30900
ctaagttttt tcctgccact tctttacctc tctcagcctt cagagaatta agggagtta    30960 gggccttgct ctggattagg atttgcttta agggagtgtt gtggctggtt tgatgtttta    31020
tctagagcac tcaaactttc tccatatcag caataaggct gttttgcttt ctaatcattc    31080
atgtgttcag tgaagtagca cttttaattc tctttaagaa cttttccttt gcatccgcaa    31140
cttggctgtt tagtggaaag gacctagctt ttgacctacc ttggctttca atataccttc    31200
ctcactaagc catttctagc tattgatgta aagtgagaga catgcaactc ttccttcac    31260 tggaacgctt agcagccatt gtagggttat taattggcct aatttcaata ttgttgtgtc    31320
tcagggaata gggaaaccca aggggcggta gagagaaaga gagacaggag aacaggccat    31380
cattggagca gtcagaacac acgacatt tatcaattaa atttgtcatc ttatatgggt     31440
gcaattcatg gcaccccccaa acaattacaa tagtaacatc agagatcaca gatcacaata    31500
acagatataa taatatgaaa tattgtgaga ttaccgaaat atgacacaga gacgtgaggt    31560
gagcacatac tgttggaaaa atggcaccaa tagacttgct cgatgcaggg ttgtcataaa    31620
ccttcaatgg gaaaaaaatg caatttccgt gaagctcagt aaagcgaagc atgataaaat    31680
gagatgagcc tgtcactcct aagaatgttc ctgtacaagt ttttgcatc tgttacttac     31740 cttttcctat ttgtgaatag tatcttttt gagtacgtgt gttttttat ttttatacat      31800 ttatatgtat cttttgaaga acatacttt aagcttaatt tattgatttt ttttctctca     31860
taatttccac ttttgtatc ctatttaaga agtccttgcc aaacttaagg ttgctaagat     31920
tttctccttt gttttcttct ggaaatttta gagttttgct tttacattta gttctaggat    31980
ttatttataa ttaatgtttt catatggtgt aagatcgaag ttcatattt tttaatatag     32040 gtaaccatca ctatagaaaa gattatttcc ccccaatgtt tgaaataagt agactgaata    32100
tagatgggtc tgttatccct agatcaatgg agcatttgtt ctgttatatt gatctatata    32160
tatatatcct tatgccaata ccatactgtc ttaataatgc ttgctttgca gtaagttttt    32220
aaatagtgta gttgtcttct aaatttgttc tttcttttca agttgtttt ggctatttta     32280 ggttttttgc atttctgtgt gaattataga attagctcga caatttctac ccaaagtttg    32340
tgggcttttc attttgattg tattgaagat atagatgaat ttgggaagaa ttgatataac    32400
aggattgaat ctttggattc atgaacgtag cctgcatttg tttacttagg tcttcttttat   32460 ttatctcagt gtgttttgta gtttaatgta cagatttgca catcttttgc cagatatatc    32520
cctaagaatt tcagttttg atactattgt agatgacatt taaaaaaatt tcaagttttt     32580
gtttgttgac ctaggcatat atttgacttt ttaatatact aaccttgcta aacttattta    32640
tcatctagta acttacaaaa tatattcctt aggatttcct acataaacaa tcatgtcatt    32700
gttttagaaa taacagtttt actttgtcct ttttaatctt gatggctttt atttcttttt    32760
cttgctaaat tttctggcta gacctcctag tacagccttg actagaactg gtgtgaggga    32820
aatcctttcc atattcctca tctttaggga aaagcactca ttctttatc cattctttag     32880 ttcctagccc cattgccctt cctaaatttt ttctcatcat tttccttcat cacaccttgt    32940
tctttttctt tgcaatcata tcatgatatg taacgacatg tttttattta tctgtttaat    33000
gtatttcttt tcctcacttg tccatgaagg gaaggaccat atgtgttgtt atcctttgtg    33060
cagttcctgg aacataataa gtatataaga aatagtttct gaattagctg tgaatgaatt    33120
catgccttcc tgctgtctgt caatgttctt ttaaattaaa catctaagac agcaaataat    33180
```

-continued

```
accacatgag ttattaacct gagaaataat cgttttattt ataaatgact gagttgaaag    33240
ctgatagccc acagtaattg ctttcatggc tttgaatata aaccttactg ttacaaaaca    33300
cattttcatg aaaatgaatg tgtggtgttt ggaactagct ttaatgtttg tcttcctgtt    33360
tttccttcta gttgctataa tataataagg aattttgtat gttttttccta attgtaccca   33420 cttttctaca ttttcttaac agatctggtg aatcttcatt attaaatata attatacata    33480
taaattattg tttaataata atattaatta ttaaaaataa tataaattat taaatataaa    33540
gatacatata atattatctg ttaatttcta agttaggtgt gggttctgaa gactattata    33600
tgaatgaaca aaaagcttgc atatttgcgt ggaagctgaa agtacgaaat ttttagatac    33660
cattatacca gtatctaaag aaaaaattca gtaccacata ggttttttaag taggagctgt   33720 atgatcatag gtcatccaga tgaaggaagg cttctgtacc agacgtacag aggtagacag    33780
tgttgtctga gtactgtctg agatctggca agaatgaatc caataaacgt agttttctcc    33840
catgagctcc tgtcttgttt cctgtattct gtttgtattt gaaaagattt ggtgtgcata    33900
acttattttt gtcttttggc tgtcaatcaa agttattagt gtagttttg taactcagtt     33960 ctcaagctag gagtttttgc tgtataattt taatgtttct gttttttactt tcctaagcag   34020 ataagcgtaa aaacttagac taattgatta cttattaaac gtccagcttg atattcttct    34080
ttatattatt ttagtttcag tttatataac aaatgaggtt tcttataaat aaaatttaaa    34140
atgcactaaa ggagctgtgt gaaataggaa ttctgtgtga agcttttgaa tgtgaacatt    34200
tagaacgttt cacatggtgg gaatttacta tatgattttc atcaaatgag gtactttta    34260 gtgttggtac ttaacgatac tgatttctaa aatttgtatt tctaaaaatg acgtattaca    34320
ggatctgaaa gggcaaaaac tcattgaggc tttgtatgag tcagcgtttc atggcctatt    34380
tttaattagt gaattattag catataatta gaaatgtttt tagattcttc atggctgacc    34440
taccaatgaa tgtagcactg catttaaaat atagttcacg ttatgttcat acttaattgt    34500
tgcattttgt ttgcccctct tgaaacgaag gtcacatgta aataaatata cattttctcc    34560
tactgtagga aatactctgt tagcattagt aggtttagct ttttaggtt aacaataaca     34620 aaaacaaagc tcacacaaaa taaaccaaat ttgctctatg tcccacagat gtatcttgtg    34680
atttttccag aaggtacaag gtataatcca gagcaaacaa aagtccttc agctagtcag     34740 gcatttgctg cccaacgtgg taagtaaaaa tttgagtgtt tgaacaaata attttcaaag    34800
ataataacat ttttagtttt tcttcctgga aaagatactt ttgttttaca gttgaaggaa    34860
tgaatgtatt cattccttga attagtgtac atattatctc ttaggaaatg aagtttcttc    34920
tccttaattc actttcatgc tattattaca tatatctgag aaattaagtt gaagtgcttg    34980
ttacgataca tattcttgtg ccatggattt atttaaaatc tatctaagta catgattatg    35040
tagatggaag cttttttctac agtgtatggg ttatatgtaa tggagcttct gttttgtaag   35100
atgacagacc taagttggag tccaaactcg tacttttatt agctgtatgg ttgcaacttg    35160
gaagttgtgt aatgttgctg agcttgcttc ttcatctctt aaaagaacat atgccttata   35220
agtagatcta aatctgtgtg aggattagat tagaaaatat gtcaagtttc tattggagaa    35280
gttacacaaa gttggtccac agtgcttgga agctgttaat gtcttcaaca atggtaatgt   35340
tcttaatatc catattttag aaaattgaat aattggtaca ccaataagct atgcaattta   35400
accaaattgg gaagtataca gaaaacagtg gctatgctat gttcttagag gtgtctttga   35460
agcttgactg tgatttagtg tgtgatctcc atatgttgat agtcactcac tgagcaaata   35520
```

```
ccttgttggt gacattacag cagggcctat gacagtgctg tctaatggaa ctttctgcaa    35580
taatggtaaa gttcttcatc tgttctgtcc agtgtgctgg ctcctaccaa tgtggttttt    35640
gagcattcaa catgtgacta gtgcatgaaa ctaattttta attttattta attttagttt    35700
aattaaaaat aaggggagt ttttacaagg tgcttacaag agcagatatg tcataggtat    35760
atgacatcat ttgtaacagt acttttaaaa aatgccagtt tgttttaaa cacatgtcct    35820 attaagtaag gagtgtttca gaataggagg gttcagttgg tctccccatc tgccagctct    35880
cttttgactt tcattgcttc ctctgtctaa tagacatgac gttctgtcat ttcagttgct    35940
cttttgcaat gccattgtct cttttgccct tttcacattt attaaacaga acaaaacaaa    36000
aaccactctc gaatctgtag tctacctttg ttgtaagcac ttttccagt actcactctg    36060 ccctcaattt gttttggtct gatttgaaat tctctcccta gacttctgtg gggctgttct    36120
ccattatcct cccaactctc tggcgattac ttcctagcct ccttccagc ctctttctgc    36180 ttcatttctc cctgctacat gtgttatttc cagtgtcagg ttttggtgtt tgattaattt    36240
cactttttgt ttctcatggt ggccttcctc taaatccatg gctttagcca tcgtttcctt    36300
gactgctgat gactcgcaaa agcttcctcc cctccatgtc tctctgccta actctggacc    36360
catttgtaca attgtccatt agagagcttc gcttgactgg cccaaaagga tgtctcaaac    36420
tcagcatatt gaagatagaa tttatccttc catgcataca ctcatatttc ttgtcttggt    36480
aactccatca ttcagttttt ttgcctaagt tttattcaca aaaagaacaa attgatagca    36540
gttgcatacc tcttatagga aacttagaca tggaggaaga agctgttcag atggggtcct    36600
gcagaagtgc aggcactgtg gtaatattta aacttttctc agctgttcga aggggttttgt   36660 tttaactaat tttccttaga cttgttttag gtatttggct ttctaatggt tataagggat    36720
gtggaattaa atgtatctta atctgccacc tggacccatt aaagtaagcc cctatggtgg    36780
tttttttttt taattgccat ggttaaaacc atagttgcta gcgaaggtga catacttaag    36840 cttttttgaac tctcttaaaa gaaaacagaa atttaatgat gtgtctataa tggcaaacca    36900
gatacctaga atttccatgt tattcatagg gtgaataaca ctggcgattg tagagatttg    36960
agagttcttt caaaacagga gaacaaaggg aataagctac aaagcaattt ttttctttgt    37020
agacttaact gaataaaaat tattttatg tctcaaacat catatgaaca aatttagttg    37080
gcaaatggca agctaataat attttataat ataggatatt aatatactta atattacaaa    37140
agtgcttcat aattagaaaa gacataaact agaaaaatgg gaaagggca tgaataagaa    37200 attcaagaga tacaaatgac ccacacactt gaacaaatgt ttattctttc tcataatcaa    37260
agaagtagaa attaaatgaa tactttgaag ccaacttctg agaaagcata gcaaacaaga    37320
aagctagtgc tcagctttgt gtggtaacgg cactctcgct cttaagaagg tgtgtttgct    37380
ccctgtggct gctctcaggc agggccacaa acttggtggc ttaaaacacc acagatttct    37440
tctcttacat ttgagaagtc tgaaatgggt cttactcagc tgaaatcaag gtgttggcag    37500
ggctgcagtc ctttgtggag gcttgggggg atcttgttct cctgtacggg gtcctgtgct    37560
tggttcgggg tcctgtgctt ggtctgggat cctgtgcttg gttcgaggtc ctgtgctggg    37620
tccagtgctc tgcttttacc accttgaagt tcatctggaa atggcactgg ctcgcccaca    37680
ccatatagct gactctggtt ctccctcctc ctcactcgct ctaaacctgt gttttttggct   37740 gatttctaat ctctctttcc ttggcccttc tgcagcttgc agggccttct gcagctcttg    37800
tctgccccag ccccggggtc tgcccatccc agtgctgggc tgttctgttc ctgccctgcc    37860
tttcctcagc ccttggcaac cctgtttgtt ttctcccttc cttagcagtg gagaacatcg    37920
```

```
taagatcaat gctgactgcc ttctgcagcc aagccaggcc atttcatttc agccgagcca    37980
agtctgtgtg gagcagttct tttatttttc tccttttgac tacctcatgg ttttcacgga    38040
tttttgttct cttcacattc aaggatttt tgctttcaga aagttatatt tctctggaaa     38100
gagtgcaccc aatatccctt ttgatttcaa aatcttaatg tggagtctct tgacttggat    38160
ttctttggaa gaaactgctg aagctgccat gtctaagaag aaaactttgg agaaaaattt    38220
tcttcttaga catggcaacg tcaacagttt ctaagctctt gattccgtct accctgtctc    38280
catcgttgcc tcagtcatct gccttacttc tctgcagggg tttctcccag cttgcaaatg    38340
tactccaatt ctgaaataac taagtctata gctgtgcaaa gagaagtctg ggccccttgc    38400
tttcttgtgt ttgactccat ccactctcca gaaatgaatc ccacttctca cttaaccact    38460
gacctccaaa gcatcgtatc atttgtgtca gttgtcatat ttgttaactt tcacataact    38520
tttgacatta tttatacctt tataaccagg aaataatttt aactttattg tagaaataaa    38580
caatggagta taatttttct tgttgaagat aaatatcacc tcctcttcct ttaaacatct    38640
cttccctttg tttttgtatt acattggttt cccccctttt tttatttcct gggttgtcgt    38700
attccctgtt attatttta ccttttttttt tttaatgtgg atgtttccgg agtctgtatt     38760
tcttgccttt tcatcttctg ccctttatta ttctcagcca ctgccattac ttcagttatc    38820
cattcccatg gtttccacat gcttagcttc ggttgattct tgccatttta cagaccatat    38880
ttccaactac ttctagaatg tttttgttcct tcagcctcag tatgcccaat ttgaactcat   38940
gttctctctc cccccttcttt cttccttctt tctttcgctc tctctcccctt ccttcttttc   39000 tttccctccc tcccttttctt ccttccctca ctcgttctct cttgcttgct tgctttctct   39060
cctctctctc ttttctttct gcnnnnnnnn nnnattcttc tccctccctc tcttccttct    39120
ctcccccact cccaacttc caggctaaag cagtcctcct gagtagttag gactacagac     39180
atacacgtgc caccgcgccc agctccgtgt tctctttgtt tccctgcctc ctgctcttcc    39240
acttatcttt gcatggcagg tgggtgcacg caggcatgct ctgcatgtct tcctcttggc    39300 cattccccctt ctagttatgg tgtggcttta tctacgcgtt ctggagcaga agcctagtca   39360
caaagctatt ttttttaaaac attcatgata attcatttcc ttttatgttt taaaaatact   39420
agctttctgt ctttatttcc ttactaactt acttggatgc cagtaattag ttgttttagt    39480
gaacaccaca gagtgatatt ttgaaacttt ggacttcata aagttggatg agctccagta    39540
gcaaagaagg aagtgttaac tagtttaact gacaaataaa tgcttcccag cttggtgtgc    39600
gattgagatt tttgttgcaa gtttgtgaat caatttaact gccctgcc tgggactaa       39660 agtcagatac gtgcttgtgg gaatctttgt ctttcccaca ccaccctgca ttttaaaacc    39720
tcttgtgtgg gacagtccca ccatgtaata gctgttcttc cttactcagc tactttccct    39780
ccagagaggc cagtagaaaa tctagactag tttttatag tctattttca tgtcacttat     39840
tgagagctac tgttttctgt taaattgtca gtaaatattt taatcaagga aaagggaggc    39900
aataggaagg agagaagaac aaatccttaa ccctagtagg aacctaatga atgggatttg    39960
ttctggataa ttgcagtagt cccccagcta aagaaccttt taaaaatatg tcagatatac    40020
ccaagaggat tgaaatcgta tgttcataca aaagcttgtt cacctgcagc cttcatatgc    40080
aattcctatg aatgttcata gcagcattat tcataatagc caaagtatgg atgcaaccca    40140
aatgtccatg aagcaattaa taggtaaaca aaatgtgatc tgttcacaca gtggaatact    40200
aactattcag ccataaaaag gaatgaagca ctgagtcctg cagccacaca gatgaacctc    40260
```

```
agatccatgc tgagcgaaag aagccagaaa caggaggcca tgtgctgtgt gactgtattt    40320
ctaggaaatc ttgagtcacc atgggcaaga tgctatcacc tttgttcagt ggccagaagc    40380
gagggcacta atatttaccc ttgccggggt ctactagatt gaagcgtttc cgctaggcca    40440
taaacttcca acacggtgac ttgtacatgt agatatttga tcaatatata gcaaatgaat    40500
attgatttaa acagaaaaag gcaagtgaga gtgctttcta aacttagagc cctaaatata    40560
tgaggttgtg gaattaatag attctgttgt gtgtgtttga gggaatttaa aaataattta    40620
gatgttaaac agtatattgt ggaggtgttt tgtaactaat taatgacggc actgaattga    40680
cttctaggcc ttgcagtatt aaaacatgtg ctaacaccac gaataaaggc aactcacgtt    40740
gcttttgatt gcatgaagaa ttatttagat gcaatttatg atgttacggt ggtttatgaa    40800
gggaaagacg atggagggca gcgaagagag tcaccgacca tgacgggtaa gtgtgttcac    40860
gcacctgaaa tgcctgtaca cggtatatac agtgcacatg tttatgtaga attcagtttt    40920
acaaagtagg ttaagtgtac ttttttcctc cattacattt acccggtata tttttcaaga    40980
tgttattaag atgtaacagt ggagatttca ttagtcctgc aaagtgtggt atttcttggc    41040
tgtcgtgtga gtcctgtgga ctcaccaatt atcattaatc cagcctcttt ctactcaaag    41100
ttcacactta aaaggaaagc tctgtaaaag ggaggaagac gtgaagaagg agcacgcctg    41160
gcagtactga gtgcacgtta ttagtcagtg ctgcccttttt gctgtatttt tcgtaaaata    41220
tttattaaat ttgggtgtca ttgtgacaag aagaaatgca gttaagtgtg accttttttt    41280
ttccccaaac atgttaggtt ttaagaacct ttgagctatt gtcagatata accagaaaaa    41340
aatagaattt taagtgagca ggataactta gttaaactaa ccaaacatag tgttagctgt    41400
tagagaaatg taaacatgga aataggcaaa cagggaagtg tgtggagttt ctgtttcctt    41460
ttcaaaatat ctgtttgagc tggggttgag agagaacact aggcttcatg gggttttttt    41520
gtttttcgtt ttttgttttg agacaagagt ttcgctctgt cgcccaggct ggagtgcagt    41580
ggcgcaatct tggctcactg caacctccgc ctcccacgtt cacacgattc tcctgcctta    41640
gcctcctgag tagctggaac tacatgcgtg tgccaccatg catgactaat atttgtattt    41700
ttagtagata tgggatttca ccttgttggc caggctggtc tcaaactcct tacctcaggt    41760
gatccacgca cctcggcctc ccaaatgagc tttgtgtttt tacctcatca gctgtttggg    41820
gttgagccac tatgtatgtc agtgtgcttg tatcagtagg atctactgag ggcagatgtt    41880
caaaatatga gcctccagca cgttttacat ggaaaccctc acctgaagca ttcgtctgaa    41940
gttgatgtgc cttggaaatt ttatagagta atattttttaa ctacaacaaa acatttataa    42000
aagtagacat tattaaagca ttcagaagtg agcaaggata gaaattattc tgcccaacct    42060
tacacgtagg ccttctagac gtagtactgt gcaccgttac attatctaac actgtctgtg    42120
tgtcatcttt ggatgttagg gattttttcca aagttcagtg agattatagt tgtcaaatga    42180
ttagtctgtt aaataatgat aagatgaggg tcactcaggt tttaaaagaa aagctctttg    42240
actgaaagag agagcagctg tctactgcag aaagttaggg agggaggctg gaggagtgag    42300
gcccaggggc tagctagtat aaaaattggt tatggtcgaa ggaaaaaaaa atgtaacata    42360
tttatatctg aaagatgatt gttctcataa ttgtatataa cacagagtaa ttgtaaagta    42420
gaaaactaag gtgttttcta ttttagatgt aaatgtttag aatatgtaat gcatcagttt    42480
aaaaattaaa actgtacgaa atgcacagtg aaacgtcttc cttgctttcc accctgctac    42540
ctggccttcc cttctccttc ctagcgataa ccagttttct taatttgttg tgcgttgtat    42600
gtgcaaattt aagtatatct tcttattcta ccatccctcc cttcttacag aaaagtggca    42660
```

```
tattaatatt tttctctttt aaactatcga aggagttact tacctatttt tgcatttcaa  42720
aacagacagt tcatcaagat tgtcgttggt ttattaaaca tagtttaaga ttaaacaagt  42780
gtttataacc aatgaaaaac agatagactc cccataataa ccttgtttaa atgctgctac  42840
ttttatcatg tcccctcctg tctaagaacc ccttggttca gcagagctca tgggtaaggc  42900
cagcctctgt tgcctgccat cggaggaatg cgttccagcc gtgatctctg ccttgccttc  42960
gcttcctcct gtgctgtgcc gtgaagcctc ggccgtggtg aagctggctg actgagtcct  43020
cctgcacccc atgcatattc agtagttgaa ggctttgtgt ggccaatcct gctttccaca  43080
ggaaaccacc ctctcttttg ttgccctcat ccaaggctac tgttctccca gagtgacagg  43140
cggcaccttt cccagcatag cactgtgcct tctcctgccc ctgctcttgc agtactgctg  43200
tggcactgat ggcgtgtgtt acagtgctgg cacttagcac agggctctgc ctttctctct  43260
tcccagccgc atcataagtg ccttgaggaa gccaaaacct tctgtgagtt gcattgcctg  43320
ggttccaacc tcccactgcc ctgcttatcc tctgctacat gtgagctgac tgtggctttg  43380
gggtggtcac tgcctatgtg tattcattac aaattgtctc cttttgaaag attgacctttt  43440
ctgacttacc cagataccat aaagaaaata aaatcttatc acttcagtca aggataaagt  43500
atttctgaat taaaggaaaa atacaccaga gtaaaatcaa gactgaaaga caaactggga  43560
aattatttgc aacctagatc atagaaaagg ggtcatttcc ttcttgcgta aagtgcactt  43620
acaaattgat aagaagatga ctgataacta gaaagaaaaa tgggtaaaga acaacaatag  43680
acatttcaca tttaacctca ttcatgataa ggtaagtgca aatgaaaact acaggggata  43740
cctttttttt tttttaatcc attagattgg caaacatccc aaggtttgat cataggctca  43800
gtgggtgaga tttaagtatt atcaggcatt tttatacttt gctgttagga atgcaatgta  43860
gtacaaacct ttgtagaagt tgctttggaa atgtctctca gatgtacaaa tgcattcaca  43920
ttttagattt agcattcccg ctttctgaga cattattcaa catgtatacg tgtgcacata  43980
agatataata ataacacgtt tttccttcta gtgtgttgct tttaacctgt agcttgaaaa  44040
aactctgctt tcattgtttt tttttgtttt ctgtcactgg ctcagccctg ctttcaattg  44100
tttatatgaa ttgatgggtg ttctggtctg gttataatct actttagttt aagagtcact  44160
ttaaattata tgacatctga tataagttgt gttaggtaga aaattctgta acttggaata  44220
ctgtaagtac tttgtggcca catttcatta gtattaaata ttatctctat atatagtagg  44280
ctatttaata ttcatatttt atgatgcaat taagaaaataa ttttttttctg aagttggtag  44340
attgttgata tgccatggcc cagtgtttct caaagcattc tgggggatca ctgtttgtca  44400
gaattagctg cagtgattgt tgaacatgca gggcctctgc tccactccac gttgctacca  44460
ggacgctctg caggtgagag ctgggaagct gtagaagctg cagtgctaac aaatgctaca  44520
ggaattcttg tagtcacctt catgaggtct tatgttgagg agaggcagcc agtagtgtcc  44580
cttgtccttc ccgttttatg gtgtaagttt cattttaagg gaggtataaa tcaaagccca  44640
cctgggcatt ctctcatggt tcactgcttc ttgtaatcat ggaagatgtc attgcggcag  44700
agacgaaaca gtgtagtttg attactattg attttttttt aattattttt ctgaagtggc  44760
tgttgtaatg taataaattg tgtgcttaag gacaaccttt ggtattctat ttgagtattg  44820
tgtatgatcc tagttaagtt ttttctacca gtattttcat attacaacat atttactttc  44880
catttctatt aatatttta tatttaaagt atggaggccg ggcacagtgg ctcacgcgtg  44940
taatcccagc attttgggat gctgaggcgg gtggatcaca aggtcaggag ttctagacca  45000
```

```
gcgtgaccaa cacggtgaaa tcccatctct actaaaaata caaaaattag ccgggcacag  45060
tggtaggcac ctgtaattcc agctactcag gaggctgagg taggagaatc acttgaatcc  45120
gggaggcagc agttgcagtg agctaagatc gtgccactgg actctagcct ggctgacaga  45180
gcaagaatcc gcctaaaaaa aaagggatca gggaagaggg gattacagat aacccaaaga  45240
agaaggaaaa atctccacaa gttcacctgt ccagcggtaa ccccaatttg gatattttcc  45300
tttaacaatt tggatatttt cctttaaatc ctctttttta taatgtctat atgttggaga  45360
gagtatgtgc ctttacgtat tttttaaaga tgagatttct gtgtgtgtct atatctcctg  45420
ttcttcatat tttcttgtgt gttataaaca gctgtacatg tcagtatata tacttccgta  45480
acttttttt aaaggctata tagtgttcat tgatgtgatt taacagcagt tatctccccg  45540
gcttcatctt gttggaatgt gggtcctgtg tgttgccttc agagcaaatg gggcttggtt  45600
ttgcagcaag tagacctgtg acctgtacga atagttggaa gactttctct attacccaag  45660
cgtatcagta tactttagtg cctactagaa atttatgggt agaaaaacaa taatatctta  45720
gagtatttt tcctagattc cctaaggtgc tataggggtga tttttactca tgtaacatga  45780
actatgcttc aactaagata gttttgcaa atgtggatat ataagtactt tattaaaccct  45840
ataggaagta tttataccac ttatttcctc ccttcagtgt tagaacctcc taaatggcat  45900
ttgacattga actgctttcc actttgtcgc atgctcctct cattgtccct acctgggtcc  45960
tgaaccttag ggacttggct gttatagccc caccatggct acgctgggcc ttggtcgtct  46020
ctgagactta gtttcttcat cttacaagga gataataaca gccctgcct gcgtagaatt  46080
gcagagatca aatgaaataa ttaacatact caaaagcatg ccgtaaacac attctgagca  46140
catgtacgtt ttaggaaaaa caaaaggacc catgcacatt tcggagtgct tttgtctcag  46200
cagcactgcc tcttcttcca aagctgacgt cttagtagag gccctgccac gtcctgagca  46260
ctgtactcca cgaagcattc tatttctgac attcgaaatg cagtctgttc catcttcctt  46320
acaatctgta tgccagcact tgaaataccg ggtatctgca gtgttgacca ggtgattact  46380
taattatgga aatgttgagg tggagatcta gataattcag tgaaggcagg aaaattggtg  46440
tcggaatctg tcttttttatg tgtcagaaat agaaataaga tagggtgaga agtaatttgt  46500
ggctaaaaca ctataatagc taacacatag tgcatactgt gtgccaagca ctcctgtagg  46560
tgcttgaaat cttctattat tattatccct actttatag cttgcaccct taggcacaga  46620
gaggcggaca gttgtccaag gttaccccag aggtggagat ccaggctacc tgactccacc  46680
atgtgtgctc ttccctaggg cacagttgtg ctgctaaaaa tactttttaa gcagttcttt  46740
gattattcag atgatagtac tgtaggaaaa ttaagacaaa aataatgaaa aattaaaatc  46800
tttatttag tgttttgcac atgtattatt aaagccagtt tactcctgga agtgtgtaag  46860
aatacagggt attttttgatc acctaaatgc tgcatgttac taagagctcg acactgaagt  46920
caagaagagc agttgcagag agtacttagc aaaaacggga agtgtgtggg gttgaaggag  46980
caaagacaag tcttcctcgg acggtggagt gtagaattca tcatttctca gaacacgtct  47040
ttgaacgcat tttcaatttg aggccaaagg tctcagcctc ccactcggca tacctcccta  47100
ccttagtcag ctcttaaatc ttaggaatat ttcctttgttc ttcaaggaac ttaaatatgt  47160
taacattctt acctgtccac agggagcccc ctacaaagaa gggagtttct agtctccgtt  47220
ctttcttgga ataaataata gcctcatacc ttgtgcaatc gaggctgaaa aagactgtct  47280
cctttttttca aataagcaag tcttagaaac tacagttgtt tacagggctc atggctattc  47340
cacagtaata atttttggttc ttttaccaat tatataatat gttaaaatat ggcaagtatc  47400
```

```
aggaaagcaa ggagtggcaa tgattagaaa ccaatggcca agttagagag gagggggcaat   47460 tgctccccca agtttgttgt ggctgtgtag cagtcagtga cgagaagctg tgtgtcaggc   47520
gacaagcaaa gttgaggatt atcaggcgcc tgtgagtgcc cagctgtgtg ccaggtcagg   47580
aggtgccatc gtgagccaga ccagcttcct ctcggcccct gtggagctcg cagtctggtg   47640
gggaggcagc agtcaccatg gtgacaggtg acacactagg atggggctgg tggtggtagg   47700
catttgcggg tcccttcaga gaggtgagta tggacttaga ggaggctcca gcttcctatt   47760
cctgggctgt ctatagcact aaaagttgtc acatgaaaaa taacatttgg tactattgat   47820
ttaacttaat gacttatgta attgtagttg acttagaaat tataacatgc tcttctactt   47880
cagcttgaaa cccccaacca ccagtttata atcctttttt tttaactttt gtttattttt   47940
cctaaggaat ctgtactttt tcttcatttt acaactttt ttgtcctgtt accttatttt   48000
catttttact ttatatgacc atgagttcta aaatagtaaa aaaaagaat tattttgtt   48060 ctttgttaga atttctctgc aaagaatgtc caaaaattca tattcacatt gatcgtatcg   48120
acaaaaaaga tgtcccagaa gaacaagaac atatgagaag atggctgcat gaacgtttcg   48180
aaatcaaaga taagtgagta acaacagttc cagcacttcc ggaacttcgg ttcaactaga   48240
tttcagtata gtcaacaatt tgaaaccaat gtaaatggtt atattgtctc aagaatacat   48300
tttataaatt caaatcaaat tttatgcatg tctgatcgtg ttttaaactt tacttgtaca   48360
aatcagtcta aaagaacttg ttacagtggg cccatctact tgcattgata gtatttcttg   48420
gacaatacta cgtgataaca tagcaaatta aattaaaaac aacaacaaac acacaaaaaa   48480
actttccagt gtcagatgcc cggacctacc tgtcaggtca cataaagtgg tgttactgtg   48540
tgaggtctgg ctgttgggcc agtgtgcgca gaaaagcaag ggaggggtag aggactatgc   48600
ggacgtgcag gtggacatga tgctgttata tttgttggaa atagaagggg gcagttgaca   48660
gcgttatatc caaagtgtct tctgtggtta attatattca gaaattttag ccaattgttt   48720
tattctctaa atatgtactt tctgctcaag aaactatcat tgttcttctt ttccttgttt   48780
tacagtacag tgtttttaat taaccctcct gggttaactt taccaggtga aaatgattaa   48840
aagtgtaata ggttaacaat gaaactttaa gcttctattt ttcattgact cttaactgta   48900
catgatgtaa tgtattcagc gagccattca ggaccacttt ggcccatgga agaaatttaa   48960
aagtaagatc tacatgtatt gacatgaaaa tatgttctca gaaaaaagac taatgtattt   49020
aatgtcctac ttattttata agtatttaga atacctctgg acattttaaa acaatgatta   49080
ttgctagggt gtgtgattta taaagcaata gaagcgcttt cccttctgt ttgtgtttta   49140 gattattata tcgggtatgt tctgctatca taactttaca aatcttatgt aatatgggaa   49200
aatgagttaa ctatgctgtt ttccttcttt tacctgcctt tctaattctg tgggaataaa   49260 ggcgttttg agacagccca ggtgtagtga gcagtccata tccatggatt ccacattcat   49320
ggattccacc aagcacagac caaaaatact cagaaaaaaa ggggctggc tgtggtggct   49380 catgcatgta atcccagcac tttgggaggc taaggcaggc aaattgcttg agcccagaag   49440
ttcaagacag cctgggcaac atggcaaaac cctgtctcta cagaaaatac aaaaattagc   49500
caggcgtgca cctgtagtcc cagctactca ggaggccgag gtgcgaggat cacctgagcc   49560
tggaaggttg agactgcagt gagctatcat tgtgccaact ccagcctggt aacagagtgc   49620 ctttttcaa aaaaaaaaa aaaaaggat ttgggaggat atgcatatgt tatattcaaa   49680
tacatgccat tttattcata tatcagggac ttgagcatcc tttgatcttg gtctctgccg   49740
```

```
ggtatcctgg gaccagcccc ctgtcgatac agagggaccg ctgtctaaga accgctggtc   49800
ctatctttga cttctggcgg aataggagct ccatgtaaaa aggaggagaa gctgcagcgg   49860
gttattagcc atttgtgagt caggtcactg taaaacttta tcaaaagttt aaaagacaaa   49920
aagcatcctc ataaaatgcc ttaaaaccac ctgttgaaat attacatata caattcatgt   49980
atactaatca tagagcatat taaagatatt ttagaagact agaaacttct attaaaccaa   50040
gtttctggat gtttccgtat tcatccttat tttccaggga cctgcataac ttttccagcg   50100
tgtaatagct acctgattga tattttttga attgaaatac tgaagtgact aaaatctaaa   50160
cttttttccat tctggccata ggatgcttat agaatttat gagtcaccag atccagaaag   50220
aagaaaaaga tttcctggga aaagtgttaa ttccaaatta agtatcaaga agactttacc   50280
atcaatgttg atcttaagtg gtttgactgc aggcatgctt atgaccgatg ctggaaggaa   50340
gctgtatgtg aacacctgga tatatggaac cctacttggc tgcctgtggg ttactattaa   50400
agcatagaca agtagctgtc tccagacagt gggatgtgct acattgtcta tttttggcgg   50460
ctgcacatga catcaaattg tttcctgaat ttattaagga gtgtaaataa agccttgttg   50520
attgaagatt ggataataga atttgtgacg aaagctgata tgcaatggtc ttgggcaaac   50580
ataccctggtt gtacaacttt agcatcgggg ctgctggaag ggtaaaagct aaatggagtt   50640
tctcctgctc tgtccatttc ctatgaacta atgacaactt gagaaggctg ggaggattgt   50700
gtattttgca agtcagatgg ctgcattttt gagcattaat ttgcagcgta tttcactttt   50760
tctgttattt tcaatttatt acaacttgac agctccaagc tcttattact aaagtatta   50820
gtatcttgca gctagttaat atttcatctt ttgcttattt ctacaagtca gtgaaataaa   50880
ttgtatttag gaagtgtcag gatgttcaaa ggaaagggta aaaagtgttc atggggaaaa   50940
agctctgttt agcacatgat tttattgtat tgcgttatta gctgatttta ctcattttat   51000
atttgcaaaa taaatttcta atatttattg aaattgctta atttgcacac cctgtacaca   51060
cagaaaatgg tataaaatat gagaacgaag tttaaaattg tgactctgat tcattatagc   51120
agaactttaa atttcccagc ttttttgaaga tttaagctac gctattagta cttcccttg   51180
tctgtgccat aagtgcttga aaacgttaag gttttctgtt ttgttttgtt tttttaatat   51240
caaaagagtc ggtgtgaacc ttggttggac cccaagttca caagattttt aaggtgatga   51300
gagcctgcag acattctgcc tagatttact agcgtgtgcc ttttgcctgc ttctctttga   51360
tttcacagaa tattcattca gaagtcgcgt ttctgtagtg tggtggattc ccactgggct   51420
ctggtccttc ccttggatcc cgtcagtggt gctgctcagc ggcttgcacg tagacttgct   51480
aggaagaaat gcagagccag cctgtgctgc ccactttcag agttgaactc tttaagccct   51540
tgtgagtggg cttccaccagc tactgcagag gcattttgca tttgtctgtg tcaagaagtt   51600
caccttctca agccagtgaa atacagactt aattcgtcat gactgaacga atttgtttat   51660
ttcccattag gtttagtgga gctacacatt aatatgtatc gccttagagc aagagctgtg   51720
ttccaggaac cagatcacga tttttagcca tggaacaata tatcccatgg gagaagacct   51780
ttcagtgtga actgttctat ttttgtgtta taatttaaac ttcgatttcc tcatagtcct   51840
ttaagttgac atttctgctt actgctactg gattttgct gcagaaatat atcagtggcc   51900
cacattaaac ataccagttg gatcatgata agcaaaatga aagaaataat gattaaggga   51960
aaattaagtg actgtgttac actgcttctc ccatgccaga gaataaactc tttcaagcat   52020
catctttgaa gagtcgtgtg gtgtgaattg gtttgtgtac attagaatgt atgcacacat   52080
ccatggacac tcaggatata gttggcctaa taatcggggc atgggtaaaa cttatgaaaa   52140
```

```
tttcctcatg ctgaattgta attttctctt acctgtaaag taaaatttag atcaattcca    52200
tgtctttgtt aagtacaggg atttaatata ttttgaatat aatgggtatg ttctaaattt    52260
gaactttgag aggcaatact gttggaatta tgtggattct aactcatttt aacaaggtag    52320
cctgacctgc ataagatcac ttgaatgtta ggtttcatag aactatacta atcttctcac    52380
aaaaggtcta taaaatacag tcgttgaaaa aaattttgta tcaaaatgtt tggaaaatta    52440
gaagcttctc cttaacctgt attgatactg acttgaatta ttttctaaaa ttaagagccg    52500
tatacctacc tgtaagtctt ttcacatatc atttaaactt ttgtttgtat tattactgat    52560
ttacagctta gttattaatt tttctttata agaatgccgt cgatgtgcat gcttttatgt    52620
ttttcagaaa agggtgtgtt tggatgaaag taaaaaaaaa aataaaatct ttcactgtct    52680
ctaatggctg tgctgtttaa catttttttga ccctaaaatt caccaacagt ctcccagtac    52740
ataaaatagg cttaatgact ggccctgcat tcttcacaat attttttccct aagctttgag    52800 caaagtttta aaaaaataca ctaaaataat caaaactgtt aagcagtata ttagtttggt    52860
tatataaatt catctgcaat ttataagatg catggccgat gttaatttgc ttggcaattc    52920
tgtaatcatt aagtgatctc agtgaaacat gtcaaatgcc ttaaattaac taagttggtg    52980
aataaaagtg ccgatctggc taactcttac accatacata ctgatagttt ttcatatgtt    53040
tcatttccat gtgattttta aaatttagag tggcaacaat tttgcttaat atgggttaca    53100
taagctttat ttttccttt gttcataatt atattctttg aataggtctg tgtcaatcaa    53160
gtgatctaac tagactgatc atagatagaa ggaaataagg ccaagttcaa gaccagcctg    53220
ggcaacatat cgagaacctg tctacaaaaa aattaaaaaa aattagccag gcatggtggc    53280
gtacactgag tagtttgtcc cagctactcg ggagggtgag gtgggaggat cgcttcagcc    53340
caggaggttg agattgcagt gagccatgga cataccactg cactcagcc taggtaacag    53400 cacgagaccc caactcttag aaaatgaaaa ggaaatatag aaatataaaa tttgcttatt    53460
atagacacac agtaactccc agatatgtac cacaaaaaat gtgaaaagag agagaaatgt    53520
ctaccaaagc agtattttgt gtgtataatt gcaagcgcat agtaaaataa ttttaacctt    53580 aatttgttttt tagtagtgtt tagattgaag attgagtgaa atattttctt ggcagatatt    53640
ccgtatctgg tggaaagcta caatgcaatg tcgttgtagt tttgcatggc ttgctttata    53700
aacaagattt tttctccctc cttttgggcc agttttcatt acgagtaact cacactttt    53760 gattaaagaa cttgaaatta cgttatcact tagtataatt gacattatat agagactatg    53820
taacatgcaa tcattagaat caaaattagt actttggtca aaatatttac aacattcaca    53880
tacttgtcaa atattcatgt aattaactga atttaaaacc ttcaactatt atgaagtgct    53940
cgtctgtaca atcgctaatt tactcagttt agagtagcta caactcttcg atactatcat    54000
caatatttga catcttttcc aatttgtgta tgaaaagtaa atctattcct gtagcaactg    54060
gggagtcata tatgaggtca aagacatata ccttgttatt ataatatgta tactataata    54120
atagctggtt atcctgagca ggggaaaagg ttatttttag gaaaaccact tcaaatagaa    54180
agctgaagta cttctaatat actgagggaa gtataatatg tggaacaaac tctcaacaaa    54240
atgtttattg atgttgatga aacagatcag tttttccatc cggattatta ttggttcatg    54300 atttatatg tgaatatgta agatatgttc tgcaatttta taaatgttca tgtctttttt    54360
taaaaaaggt gctattgaaa ttctgtgtct ccagcaggca agaatacttg actaactctt    54420
tttgtctctt tatggtatt tcagaataaa gtctgacttg tgttttgag attattggtg    54480
```

-continued

```
cctcattaat tcagcaataa aggaaaatat gcatctcaaa aattggtgat aaaaagttat    54540
ttcttgtata tgtgataaag tttacatgtt gtgtatatat gttgtattgc caaatacggc    54600
tattaaatac tacgtcatat tttaaaggtt cagtttgtag tgatagtaaa caagcagtgc    54660
actaagcctc ttgcgggcat catctcatct cactgtcatc acaaacccca tgccacagcg    54720
tagcttgacc actaaaagta atgcatctgc aagcatactg ccaggttttg gatagtttgt    54780
accaacagtt accttatcaa ggtaaatccc agactctaaa agagttggtg ctgtgtcact    54840
acatgcataa cttaaataa atttcctgcc gggcgcggtg gctcacgcct gtaatcccag    54900
cagtttggga ggccgaggca gtggatcac ttgaggtcag gagtttgaga ccagcctggc    54960
caacgtggtg aaaccctgtc tctactaaaa atacaaaaat tagccaggcg tgtggtggca    55020
ggcacctgta atcccagcta cttgggagga tgaggcagga gaatcatttg aatcctgcag    55080
gcggaggttg cagtgagcca agatggcgtc attgcactcc agcctgggcg acaagagcga    55140
gactccgtat taaaaaaaaa aaaaaaaaaa aaaaaaatt cctctcctgt ttgagctttc    55200
ccttacctgt aaagagggga gaatatgtat ttacttcaaa gagttcaggg aaatgactct    55260
cactagtttg agattctagg tataaaaata cattcttata taattttaac accaatgtga    55320
gagattatta ttcttgctaa accaattcag ttttatttgc tgtctaaaat gtgtgaataa    55380
gtaattgtcc attattttct gaagtgtttt ggaactcaac acatgattgt gaggaggatt    55440
tgttgctaaa catctttctg gttattcaag ctcgtgtata ctgtgctctg ttgagacatg    55500
cagagttact ttctgtctgg gtcacaggtc agttcttgat agttttcgga caattaacca    55560
gttttcattt gcccatgacc acctttattc ttttcctca actgcaccca tctttataa    55620
ggtctttcag tttattgcag agaagatggt ggagaaaagc cggaattccc acccaccgct    55680
gccatcccca tgttttatca ttggctagag tggaaaatag cagtaactac tgtgagagat    55740
catttgttta tataatggaa acaaagatga ggaaagaacc tggcttagat cagagaactg    55800
atgtatttag attcttttt tttttttttt taagacggag tgttgctctg ttgcccagac    55860
tggagtacag tggctcaatc tcggctcact gcaacctcca tttccctggt tcaagcaatt    55920
atcctgcctc agcctcccaa gtatttggga ttacaggcgt gttccaccac acctggctaa    55980
ttttttgtat tttagtaga gacggggttt cgccatgttg gccaggctgg tctcgaaatc    56040
ctgacctcag atgatccacc cgccttggcc tcccaaagtg ctgggattac aggcgcgagc    56100
caccgcgcct ggcccaatgt atttggattc ttaaagaaca ctttcaaatt aaatatcagt    56160
tgaagagaac tagaactaaa gaatttctgt gtcaaactgt ttagcaaatg taagtagaag    56220
ctgggagatg tgtcctggaa tgaatgaata catcagtaaa ataccatacg tatgttatga    56280
tgttattgtt tccttgcctt ggttgatttg gttttactgt gaaataattt tcaatataga    56340
attgtgatcg ttggaatttg gtcatctact agaaaatgag aaagaagtta atagctatct    56400
tccttaaaga tttctgaggt tgggattaag gtagtgttcc caaggtgttc taaaacggca    56460
gcgagagctg tgcactcact tcacaaattt gaattcctgc tctgtgttag gcgctg       56516
```

<210> SEQ ID NO 2
<211> LENGTH: 23
<212> TYPE: DNA
<213> ORGANISM: Homo sapiens

<400> SEQUENCE: 2
ggtcgtccag cgcttggtag aag    23

-continued

```
<210> SEQ ID NO 3
<211> LENGTH: 5227
<212> TYPE: DNA
<213> ORGANISM: Homo sapiens
<220> FEATURE:
<221> NAME/KEY: polyA_signal
<222> LOCATION: 5180..5186
<223> OTHER INFORMATION: AATAAA

<400> SEQUENCE: 3
```

| | | |
|---|---|---|
| ctgctgtccc tggtgctcca cacgtactcc atg cgc tac ctg ctg ccc agc gtc<br>                                         Met Arg Tyr Leu Leu Pro Ser Val<br>                                          1               5 | 54 |
| gtg ctc ctg ggc acg gcg ccc acc tac gtg ttg gcc tgg ggg gtc tgg<br>Val Leu Leu Gly Thr Ala Pro Thr Tyr Val Leu Ala Trp Gly Val Trp<br>         10                  15                  20 | 102 |
| cgg ctc ctc tcc gcc ttc ctg ccc gcc cgc ttc tac caa gcg ctg gac<br>Arg Leu Leu Ser Ala Phe Leu Pro Ala Arg Phe Tyr Gln Ala Leu Asp<br> 25                  30                  35                  40 | 150 |
| gac cgg ctc tac tgc gtc tac cag agc atg gtg ctc ttc ttc ttc gag<br>Asp Arg Leu Tyr Cys Val Tyr Gln Ser Met Val Leu Phe Phe Phe Glu<br>                 45                  50                  55 | 198 |
| aat tac acc ggg gtc cag ata ttg cta tat gga gat ttg cca aaa aat<br>Asn Tyr Thr Gly Val Gln Ile Leu Leu Tyr Gly Asp Leu Pro Lys Asn<br>             60                  65                  70 | 246 |
| aaa gaa aat ata ata tat tta gca aat cat caa agc aca gtt gac tgg<br>Lys Glu Asn Ile Ile Tyr Leu Ala Asn His Gln Ser Thr Val Asp Trp<br>         75                  80                  85 | 294 |
| att gtt gct gac atc ttg gcc atc agg cag aat gcg cta gga cat gtg<br>Ile Val Ala Asp Ile Leu Ala Ile Arg Gln Asn Ala Leu Gly His Val<br>     90                  95                 100 | 342 |
| cgc tac gtg ctg aaa gaa ggg tta aaa tgg ctg cca ttg tat ggg tgt<br>Arg Tyr Val Leu Lys Glu Gly Leu Lys Trp Leu Pro Leu Tyr Gly Cys<br>105                 110                 115                 120 | 390 |
| tac ttt gct cag cat gga gga atc tat gta aag cgc agt gcc aaa ttt<br>Tyr Phe Ala Gln His Gly Gly Ile Tyr Val Lys Arg Ser Ala Lys Phe<br>                125                 130                 135 | 438 |
| aac gag aaa gag atg cga aac aag ttg cag agc tac gtg gac gca gga<br>Asn Glu Lys Glu Met Arg Asn Lys Leu Gln Ser Tyr Val Asp Ala Gly<br>            140                 145                 150 | 486 |
| act cca atg tat ctt gtg att ttt cca gaa ggt aca agg tat aat cca<br>Thr Pro Met Tyr Leu Val Ile Phe Pro Glu Gly Thr Arg Tyr Asn Pro<br>        155                 160                 165 | 534 |
| gag caa aca aaa gtc ctt tca gct agt cag gca ttt gct gcc caa cgt<br>Glu Gln Thr Lys Val Leu Ser Ala Ser Gln Ala Phe Ala Ala Gln Arg<br>    170                 175                 180 | 582 |
| ggc ctt gca gta tta aaa cat gtg cta aca cca cga ata aag gca act<br>Gly Leu Ala Val Leu Lys His Val Leu Thr Pro Arg Ile Lys Ala Thr<br>185                 190                 195                 200 | 630 |
| cac gtt gct ttt gat tgc atg aag aat tat tta gat gca att tat gat<br>His Val Ala Phe Asp Cys Met Lys Asn Tyr Leu Asp Ala Ile Tyr Asp<br>                205                 210                 215 | 678 |
| gtt acg gtg gtt tat gaa ggg aaa gac gat gga ggg cag cga aga gag<br>Val Thr Val Val Tyr Glu Gly Lys Asp Asp Gly Gly Gln Arg Arg Glu<br>            220                 225                 230 | 726 |
| tca ccg acc atg acg gaa ttt ctc tgc aaa gaa tgt cca aaa att cat<br>Ser Pro Thr Met Thr Glu Phe Leu Cys Lys Glu Cys Pro Lys Ile His<br>        235                 240                 245 | 774 |
| att cac att gat cgt atc gac aaa aaa gat gtc cca gaa gaa caa gaa<br>Ile His Ile Asp Arg Ile Asp Lys Lys Asp Val Pro Glu Glu Gln Glu<br>    250                 255                 260 | 822 |

-continued

```
cat atg aga aga tgg ctg cat gaa cgt ttc gaa atc aaa gat aag atg       870
His Met Arg Arg Trp Leu His Glu Arg Phe Glu Ile Lys Asp Lys Met
265                 270                 275                 280 ctt ata gaa ttt tat gag tca cca gat cca gaa aga aga aaa aga ttt       918
Leu Ile Glu Phe Tyr Glu Ser Pro Asp Pro Glu Arg Arg Lys Arg Phe
                285                 290                 295 cct ggg aaa agt gtt aat tcc aaa tta agt atc aag aag act tta cca       966
Pro Gly Lys Ser Val Asn Ser Lys Leu Ser Ile Lys Lys Thr Leu Pro
            300                 305                 310 tca atg ttg atc tta agt ggt ttg act gca ggc atg ctt atg acc gat      1014
Ser Met Leu Ile Leu Ser Gly Leu Thr Ala Gly Met Leu Met Thr Asp
        315                 320                 325 gct gga agg aag ctg tat gtg aac acc tgg ata tat gga acc cta ctt      1062
Ala Gly Arg Lys Leu Tyr Val Asn Thr Trp Ile Tyr Gly Thr Leu Leu
    330                 335                 340 ggc tgc ctg tgg gtt act att aaa gca tag acaagtagct gtctccagac        1112
Gly Cys Leu Trp Val Thr Ile Lys Ala
345                 350 agtgggatgt gctacattgt ctattttggg cggctgcaca tgacatcaaa ttgtttcctg    1172
aatttattaa ggagtgtaaa taaagccttg ttgattgaag attggataat agaatttgtg    1232
acgaaagctg atatgcaatg gtcttgggca aacatacctg gttgtacaac tttagcatcg    1292
gggctgctgg aagggtaaaa gctaaatgga gtttctcctg ctctgtccat ttcctatgaa    1352
ctaatgacaa cttgagaagg ctgggaggat tgtgtatttt gcaagtcaga tggctgcatt    1412
tttgagcatt aatttgcagc gtatttcact ttttctgtta ttttcaattt attacaactt    1472
gacagctcca agctcttatt actaaagtat ttagtatctt gcagctagtt aatatttcat    1532
cttttgctta tttctacaag tcagtgaaat aaattgtatt taggaagtgt caggatgttc    1592
aaaggaaagg gtaaaagtg ttcatgggga aaagctctg tttagcacat gattttattg      1652
tattgcgtta ttagctgatt ttactcattt tatatttgca aaataaattt ctaatattta    1712
ttgaaattgc ttaatttgca caccctgtac acacagaaaa tggtataaaa tatgagaacg    1772
aagtttaaaa ttgtgactct gattcattat agcagaactt taaatttccc agcttttga    1832 agatttaagc tacgctatta gtacttccct ttgtctgtgc cataagtgct tgaaaacgtt    1892
aaggttttct gttttgtttt gttttttaa tatcaaaaga gtcggtgtga accttggttg     1952
gaccccaagt tcacaagatt tttaaggtga tgagagcctg cagacattct gcctagattt    2012
actagcgtgt gccttttgcc tgcttctctt tgatttcaca gaatattcat tcagaagtcg    2072
cgtttctgta gtgtggtgga ttcccactgg gctctggtcc ttcccttgga tcccgtcagt    2132
ggtgctgctc agcggcttgc acgtagactt gctaggaaga aatgcagagc cagcctgtgc    2192
tgcccacttt cagagttgaa ctctttaaag cccttgtgag tgggcttcac cagctactgc    2252
agaggcattt tgcatttgtc tgtgtcaaga agttcacctt ctcaagccag tgaaatacag    2312
acttaattcg tcatgactga acgaatttgt ttatttccca ttaggtttag tggagctaca    2372
cattaatatg tatcgcctta gagcaagagc tgtgttccag gaaccagatc acgatttta     2432 gccatggaac aatatatccc atgggagaag acctttcagt gtgaactgtt ctattttgt     2492 gttataattt aaacttcgat ttcctcatag tcctttaagt tgacatttct gcttactgct    2552
actggatttt tgctgcagaa atatatcagt ggcccacatt aaacatacca gttggatcat    2612
gataagcaaa atgaaagaaa taatgattaa gggaaaatta agtgactgtg ttacactgct    2672
tctcccatgc cagagaataa actctttcaa gcatcatctt tgaagagtcg tgtggtgtga    2732
attggtttgt gtacattaga atgtatgcac acatccatgg acactcagga tatagttggc    2792
```

-continued

```
ctaataatcg gggcatgggt aaaacttatg aaaatttcct catgctgaat tgtaattttc    2852
tcttacctgt aaagtaaaat ttagatcaat tccatgtctt tgttaagtac agggatttaa    2912
tatattttga atataatggg tatgttctaa atttgaactt tgagaggcaa tactgttgga    2972
attatgtgga ttctaactca ttttaacaag gtagcctgac ctgcataaga tcacttgaat    3032
gttaggtttc atagaactat actaatcttc tcacaaaagg tctataaaat acagtcgttg    3092
aaaaaaattt tgtatcaaaa tgtttggaaa attagaagct tctccttaac ctgtattgat    3152
actgacttga attattttct aaaattaaga gccgtatacc tacctgtaag tcttttcaca    3212
tatcatttaa acttttgttt gtattattac tgatttacag cttagttatt aattttttctt   3272 tataagaatg ccgtcgatgt gcatgctttt atgtttttca gaaagggtg tgtttggatg     3332 aaagtaaaaa aaaaaataaa atctttcact gtctctaatg gctgtgctgt ttaacatttt    3392
ttgaccctaa aattcaccaa cagtctccca gtacataaaa taggcttaat gactggccct    3452
gcattcttca caatattttt ccctaagctt tgagcaaagt tttaaaaaaa tacactaaaa    3512
taatcaaaac tgttaagcag tatattagtt tggttatata aattcatctg caatttataa    3572
gatgcatggc cgatgttaat ttgcttggca attctgtaat cattaagtga tctcagtgaa    3632
acatgtcaaa tgccttaaat taactaagtt ggtgaataaa agtgccgatc tggctaactc    3692
ttacaccata catactgata gttttttcata tgtttcattt ccatgtgatt tttaaaattt   3752
agagtggcaa caattttgct taatatgggt tacataagct ttattttttc ctttgttcat    3812
aattatattc tttgaatagg tctgtgtcaa tcaagtgatc taactagact gatcatagat    3872
agaaggaaat aaggccaagt tcaagaccag cctgggcaac atatcgagaa cctgtctaca    3932
aaaaaattaa aaaaaattag ccaggcatgg tggcgtacac tgagtagttt gtcccagcta    3992
ctcgggaggg tgaggtggga ggatcgcttc agcccaggag gttgagattg cagtgagcca    4052
tggacatacc actgcactac agcctaggta acagcacgag accccaactc ttagaaaatg    4112
aaaaggaaat atagaaatat aaaatttgct tattatagac acacagtaac tcccagatat    4172
gtaccacaaa aaatgtgaaa agagagagaa atgtctacca aagcagtatt ttgtgtgtat    4232
aattgcaagc gcatagtaaa ataatttttaa ccttaatttg ttttttagtag tgtttagatt   4292 gaagattgag tgaaatattt tcttggcaga tattccgtat ctggtggaaa gctacaatgc    4352
aatgtcgttg tagttttgca tggcttgctt tataaacaag attttttctc cctccttttg    4412
ggccagtttt cattacgagt aactcacact ttttgattaa agaacttgaa attacgttat    4472
cacttagtat aattgacatt atatagagac tatgtaacat gcaatcatta gaatcaaaat    4532
tagtactttg gtcaaaatat ttacaacatt cacatacttg tcaaatattc atgtaattaa    4592
ctgaatttaa aaccttcaac tattatgaag tgctcgtctg tacaatcgct aatttactca    4652
gtttagagta gctacaactc ttcgatacta tcatcaatat ttgacatctt ttccaatttg    4712
tgtatgaaaa gtaaatctat tcctgtagca actggggagt catatatgag gtcaaagaca    4772
tataccttgt tattataata tgtatactat aataatagct ggttatcctg agcaggggaa    4832 aaggttatt ttaggaaaac cacttcaaat agaaagctga agtacttcta atatactgag     4892
ggaagtataa tatgtggaac aaactctcaa caaaatgttt attgatgttg atgaaacaga    4952 tcagttttc catccggatt attattggtt catgatttta tatgtgaata tgtaagatat      5012
gttctgcaat tttataaatg ttcatgtctt tttttaaaaa aggtgctatc gaattctgt     5072 gtctccagca ggcaagaata cttgactaac tcttttttgtc tctttatggt attttcagaa   5132
```

```
taaagtctga cttgtgtttt tgagattatt ggtgcctcat taattcagca ataaaggaaa      5192
atatgcattt caaaaanaaa aaaaaaaaaa aaaaa                                 5227
```

```
<210> SEQ ID NO 4
<211> LENGTH: 353
<212> TYPE: PRT
<213> ORGANISM: Homo sapiens
<220> FEATURE:
<221> NAME/KEY: HELIX
<222> LOCATION: 1..33
<223> OTHER INFORMATION: Rao  and  Argos   identification  method,
      potential  helix
<220> FEATURE:
<221> NAME/KEY: HELIX
<222> LOCATION: 4..20
<223> OTHER INFORMATION: Klein,  Kanehisa  and  DeLisi  identification
      method,  potential  helix
<220> FEATURE:
<221> NAME/KEY: HELIX
<222> LOCATION: 4..24
<223> OTHER INFORMATION: Eisenberg,  Schwarz,  Komarony,  Wall
      identification  method,  potential  helix
<220> FEATURE:
<221> NAME/KEY: MYRISTATE
<222> LOCATION: 12..16
<223> OTHER INFORMATION: Prosite  match
<220> FEATURE:
<221> NAME/KEY: HELIX
<222> LOCATION: 50..70
<223> OTHER INFORMATION: Eisenberg,  Schwarz,  Komarony,  Wall
      identification  method,  potential  helix
<220> FEATURE:
<221> NAME/KEY: CARBOHYD
<222> LOCATION: 57..59
<223> OTHER INFORMATION: Prosite  match
<220> FEATURE:
<221> NAME/KEY: HELIX
<222> LOCATION: 76..96
<223> OTHER INFORMATION: Eisenberg,  Schwarz,  Komarony,  Wall
      identification  method, potential  helix
<220> FEATURE:
<221> NAME/KEY: PHOSPHORYLATION
<222> LOCATION: 78
<223> OTHER INFORMATION: potential  Tyrosine  kinase  site,  Prosite
      match
<220> FEATURE:
<221> NAME/KEY: PHOSPHORYLATION
<222> LOCATION: 84
<223> OTHER INFORMATION: potential  caseine  kinase  II  site,  Prosite
      match
<220> FEATURE:
<221> NAME/KEY: SITE
<222> LOCATION: 94..115
<223> OTHER INFORMATION: potential  Leucine  zipper  site,  Prosite
      match
<220> FEATURE:
<221> NAME/KEY: MYRISTATE
<222> LOCATION: 119..123
<223> OTHER INFORMATION: potential  site,  Prosite  match
<220> FEATURE:
<221> NAME/KEY: PHOSPHORYLATION
<222> LOCATION: 133
<223> OTHER INFORMATION: potential  protein  kinase  C,  Prosite  match
<220> FEATURE:
<221> NAME/KEY: PHOSPHORYLATION
<222> LOCATION: 147
<223> OTHER INFORMATION: potential  caseine  kinase  II  site,  Prosite
      match
<220> FEATURE:
<221> NAME/KEY: PHOSPHORYLATION
<222> LOCATION: 194
<223> OTHER INFORMATION: potential  protein  kinase  C,  Prosite  match
<220> FEATURE:
<221> NAME/KEY: PHOSPHORYLATION
<222> LOCATION: 215
<223> OTHER INFORMATION: potential  Tyrosine  kinase  site,  Prosite
      match
```

```
<220> FEATURE:
<221> NAME/KEY: SULFATATION
<222> LOCATION: 221
<223> OTHER INFORMATION: Prosite  match
<220> FEATURE:
<221> NAME/KEY: PHOSPHORYLATION
<222> LOCATION: 233
<223> OTHER INFORMATION: potential  cAMP  and  cGMP  dependant  protein
      kinase  site,  Prosite  match
<220> FEATURE:
<221> NAME/KEY: PHOSPHORYLATION
<222> LOCATION: 235
<223> OTHER INFORMATION: potential  caseine  kinase  II  site,  Prosite
      match
<220> FEATURE:
<221> NAME/KEY: PHOSPHORYLATION
<222> LOCATION: 306
<223> OTHER INFORMATION: potential  protein  kinase  C,  Prosite  match
<220> FEATURE:
<221> NAME/KEY: HELIX
<222> LOCATION: 310..330
<223> OTHER INFORMATION: Eisenberg,  Schwarz,  Komarony,  Wall
      identification  method,  potential  helix
<220> FEATURE:
<221> NAME/KEY: MYRISTATE
<222> LOCATION: 319..323
<223> OTHER INFORMATION: Prosite  match
<220> FEATURE:
<221> NAME/KEY: MYRISTATE
<222> LOCATION: 323..327
<223> OTHER INFORMATION: Prosite  match
<220> FEATURE:
<221> NAME/KEY: AMIDATION
<222> LOCATION: 329
<223> OTHER INFORMATION: Prosite  match
<220> FEATURE:
<221> NAME/KEY: HELIX
<222> LOCATION: 333..353
<223> OTHER INFORMATION: Eisenberg,  Schwarz,  Komarony,  Wall
      identification  method,  potential  helix
<220> FEATURE:
<221> NAME/KEY: MYRISTATE
<222> LOCATION: 341..345
<223> OTHER INFORMATION: Prosite  match
<220> FEATURE:
<221> NAME/KEY: PHOSPHORYLATION
<222> LOCATION: 350
<223> OTHER INFORMATION: potential  protein  kinase  C,  Prosite  match

<400> SEQUENCE: 4

Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45

Ser Met Val Leu Phe Phe Phe Glu Asn Tyr Thr Gly Val Gln Ile Leu
    50                  55                  60

Leu Tyr Gly Asp Leu Pro Lys Asn Lys Glu Asn Ile Ile Tyr Leu Ala
65                  70                  75                  80

Asn His Gln Ser Thr Val Asp Trp Ile Val Ala Asp Ile Leu Ala Ile
                85                  90                  95

Arg Gln Asn Ala Leu Gly His Val Arg Tyr Val Leu Lys Glu Gly Leu
            100                 105                 110

Lys Trp Leu Pro Leu Tyr Gly Cys Tyr Phe Ala Gln His Gly Gly Ile
        115                 120                 125

Tyr Val Lys Arg Ser Ala Lys Phe Asn Glu Lys Glu Met Arg Asn Lys
    130                 135                 140

Leu Gln Ser Tyr Val Asp Ala Gly Thr Pro Met Tyr Leu Val Ile Phe
```

```
145                 150                 155                 160
Pro Glu Gly Thr Arg Tyr Asn Pro Glu Gln Thr Lys Val Leu Ser Ala
                165                 170                 175

Ser Gln Ala Phe Ala Ala Gln Arg Gly Leu Ala Val Leu Lys His Val
            180                 185                 190

Leu Thr Pro Arg Ile Lys Ala Thr His Val Ala Phe Asp Cys Met Lys
        195                 200                 205

Asn Tyr Leu Asp Ala Ile Tyr Asp Val Thr Val Val Tyr Glu Gly Lys
        210                 215                 220

Asp Asp Gly Gly Gln Arg Arg Glu Ser Pro Thr Met Thr Glu Phe Leu
225                 230                 235                 240

Cys Lys Glu Cys Pro Lys Ile His Ile His Ile Asp Arg Ile Asp Lys
                245                 250                 255

Lys Asp Val Pro Glu Gln Glu His Met Arg Arg Trp Leu His Glu
                260                 265                 270

Arg Phe Glu Ile Lys Asp Lys Met Leu Ile Glu Phe Tyr Glu Ser Pro
        275                 280                 285

Asp Pro Glu Arg Arg Lys Arg Phe Pro Gly Lys Ser Val Asn Ser Lys
        290                 295                 300

Leu Ser Ile Lys Lys Thr Leu Pro Ser Met Leu Ile Leu Ser Gly Leu
305                 310                 315                 320

Thr Ala Gly Met Leu Met Thr Asp Ala Gly Arg Lys Leu Tyr Val Asn
                325                 330                 335

Thr Trp Ile Tyr Gly Thr Leu Leu Gly Cys Leu Trp Val Thr Ile Lys
                340                 345                 350

Ala

<210> SEQ ID NO 5
<211> LENGTH: 364
<212> TYPE: PRT
<213> ORGANISM: Homo sapiens

<400> SEQUENCE: 5

Met Leu Leu Ser Leu Val Leu His Thr Tyr Ser Met Arg Tyr Leu Leu
1               5                   10                  15

Pro Ser Val Val Leu Leu Gly Thr Ala Pro Thr Tyr Val Leu Ala Trp
                20                  25                  30

Gly Val Trp Arg Leu Leu Ser Ala Phe Leu Pro Ala Arg Phe Tyr Gln
            35                  40                  45

Ala Leu Asp Asp Arg Leu Tyr Cys Val Tyr Gln Ser Met Val Leu Phe
        50                  55                  60

Phe Phe Glu Asn Tyr Thr Gly Val Gln Ile Leu Leu Tyr Gly Asp Leu
65                  70                  75                  80

Pro Lys Asn Lys Glu Asn Ile Ile Tyr Leu Ala Asn His Gln Ser Thr
                85                  90                  95

Val Asp Trp Ile Val Ala Asp Ile Leu Ala Ile Arg Gln Asn Ala Leu
            100                 105                 110

Gly His Val Arg Tyr Val Leu Lys Glu Gly Leu Lys Trp Leu Pro Leu
        115                 120                 125

Tyr Gly Cys Tyr Phe Ala Gln His Gly Gly Ile Tyr Val Lys Arg Ser
        130                 135                 140

Ala Lys Phe Asn Glu Lys Glu Met Arg Asn Lys Leu Gln Ser Tyr Val
145                 150                 155                 160

Asp Ala Gly Thr Pro Met Tyr Leu Val Ile Phe Pro Glu Gly Thr Arg
```

```
            165                 170                 175
Tyr Asn Pro Glu Gln Thr Lys Val Leu Ser Ala Ser Gln Ala Phe Ala
            180                 185                 190

Ala Gln Arg Gly Leu Ala Val Leu Lys His Val Leu Thr Pro Arg Ile
            195                 200                 205

Lys Ala Thr His Val Ala Phe Asp Cys Met Lys Asn Tyr Leu Asp Ala
            210                 215                 220

Ile Tyr Asp Val Thr Val Val Tyr Glu Gly Lys Asp Asp Gly Gly Gln
225                 230                 235                 240

Arg Arg Glu Ser Pro Thr Met Thr Glu Phe Leu Cys Lys Glu Cys Pro
            245                 250                 255

Lys Ile His Ile His Ile Asp Arg Ile Asp Lys Lys Asp Val Pro Glu
            260                 265                 270

Glu Gln Glu His Met Arg Arg Trp Leu His Glu Arg Phe Glu Ile Lys
            275                 280                 285

Asp Lys Met Leu Ile Glu Phe Tyr Glu Ser Pro Asp Pro Glu Arg Arg
            290                 295                 300

Lys Arg Phe Pro Gly Lys Ser Val Asn Ser Lys Leu Ser Ile Lys Lys
305                 310                 315                 320

Thr Leu Pro Ser Met Leu Ile Leu Ser Gly Leu Thr Ala Gly Met Leu
            325                 330                 335

Met Thr Asp Ala Gly Arg Lys Leu Tyr Val Asn Thr Trp Ile Tyr Gly
            340                 345                 350

Thr Leu Leu Gly Cys Leu Trp Val Thr Ile Lys Ala
            355                 360

<210> SEQ ID NO 6
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: primer oligonucleotide GC1.5p.1

<400> SEQUENCE: 6
ctgtccctgg tgctccacac gtactc                                      26

<210> SEQ ID NO 7
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: primer oligonucleotide GC1.5p.2

<400> SEQUENCE: 7
tggtgctcca cacgtactcc atgcgc                                      26

<210> SEQ ID NO 8
<211> LENGTH: 27
<212> TYPE: DNA
<213> ORGANISM: Homo Sapiens
<220> FEATURE:
<221> NAME/KEY: misc_feature
<222> LOCATION: 1..27
<223> OTHER INFORMATION: primer oligonucleotide pg15RACE196

<400> SEQUENCE: 8
caatatctgg accccggtgt aattctc                                     27
```

```
<210> SEQ ID NO 9
<211> LENGTH: 34
<212> TYPE: DNA
<213> ORGANISM: Homo Sapiens
<220> FEATURE:
<221> NAME/KEY: misc_feature
<222> LOCATION: 1..34
<223> OTHER INFORMATION: primer oligonucleotide GC1.3p

<400> SEQUENCE: 9
cttgcctgct ggagacacag aatttcgata gcac                              34

<210> SEQ ID NO 10
<211> LENGTH: 24
<212> TYPE: DNA
<213> ORGANISM: Homo Sapiens
<220> FEATURE:
<221> NAME/KEY: misc_feature
<222> LOCATION: 1..24
<223> OTHER INFORMATION: primer oligonucleotide PGRT32

<400> SEQUENCE: 10
tttttttttt ttttttttg aaat                                          24

<210> SEQ ID NO 11
<211> LENGTH: 6
<212> TYPE: PRT
<213> ORGANISM: Homo sapiens
<220> FEATURE:
<221> NAME/KEY: SITE
<222> LOCATION: 160..165
<223> OTHER INFORMATION: box2 from SEQID4, present in AF003136,
      P33333, P26647, U89336, U56417, AB005623.

<400> SEQUENCE: 11

Phe Pro Glu Gly Thr Arg
1               5

<210> SEQ ID NO 12
<211> LENGTH: 6
<212> TYPE: PRT
<213> ORGANISM: Homo sapiens
<220> FEATURE:
<221> NAME/KEY: SITE
<222> LOCATION: 129..134
<223> OTHER INFORMATION: box2 from Z72511

<400> SEQUENCE: 12

Phe Pro Glu Gly Thr Asp
1               5

<210> SEQ ID NO 13
<211> LENGTH: 6
<212> TYPE: PRT
<213> ORGANISM: Homo sapiens
<220> FEATURE:
<221> NAME/KEY: SITE
<222> LOCATION: 223..228
<223> OTHER INFORMATION: box2 from P38226, Z49770

<400> SEQUENCE: 13

Phe Pro Glu Gly Thr Asn
1               5

<210> SEQ ID NO 14
<211> LENGTH: 6
<212> TYPE: PRT
```

```
<213> ORGANISM: Homo sapiens
<220> FEATURE:
<221> NAME/KEY: SITE
<222> LOCATION: 90..95
<223> OTHER INFORMATION: box2 from Z49860 and Z29518

<400> SEQUENCE: 14

Phe Val Glu Gly Thr Arg
1               5

<210> SEQ ID NO 15
<211> LENGTH: 9
<212> TYPE: PRT
<213> ORGANISM: Homo sapiens
<220> FEATURE:
<221> NAME/KEY: SITE
<222> LOCATION: 211..219
<223> OTHER INFORMATION: box3 from SEQID4, present in AF003136

<400> SEQUENCE: 15

Leu Asp Ala Ile Tyr Asp Val Thr Val
1               5

<210> SEQ ID NO 16
<211> LENGTH: 9
<212> TYPE: PRT
<213> ORGANISM: Homo sapiens
<220> FEATURE:
<221> NAME/KEY: SITE
<222> LOCATION: 204..212
<223> OTHER INFORMATION: box3 from Z72511

<400> SEQUENCE: 16

Val Glu Tyr Ile Tyr Asp Ile Thr Ile
1               5

<210> SEQ ID NO 17
<211> LENGTH: 9
<212> TYPE: PRT
<213> ORGANISM: Homo sapiens
<220> FEATURE:
<221> NAME/KEY: SITE
<222> LOCATION: 271..279
<223> OTHER INFORMATION: box3 from P38226

<400> SEQUENCE: 17

Ile Glu Ser Leu Tyr Asp Ile Thr Ile
1               5

<210> SEQ ID NO 18
<211> LENGTH: 9
<212> TYPE: PRT
<213> ORGANISM: Homo sapiens
<220> FEATURE:
<221> NAME/KEY: SITE
<222> LOCATION: 265..273
<223> OTHER INFORMATION: box3 from Z49770

<400> SEQUENCE: 18

Leu Asp Ala Ile Tyr Asp Val Thr Ile
1               5

<210> SEQ ID NO 19
<211> LENGTH: 9
<212> TYPE: PRT
<213> ORGANISM: Homo sapiens
<220> FEATURE:
<221> NAME/KEY: SITE
<222> LOCATION: 138..146
```

```
<223> OTHER INFORMATION: box3  fromZ49860

<400> SEQUENCE: 19

Val Pro Ala Ile Tyr Asp Met Thr Val
1               5

<210> SEQ ID NO 20
<211> LENGTH: 9
<212> TYPE: PRT
<213> ORGANISM: Homo sapiens
<220> FEATURE:
<221> NAME/KEY: SITE
<222> LOCATION: 218..226
<223> OTHER INFORMATION: box3  from  Z29518

<400> SEQUENCE: 20

Val Pro Ala Ile Tyr Asp Thr Thr Val
1               5

<210> SEQ ID NO 21
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-123
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-123.mis1
<220> FEATURE:
<221> NAME/KEY: primer_bind
<222> LOCATION: 25..47
<223> OTHER INFORMATION: complement potential microsequencing oligo
      99-123.mis2

<400> SEQUENCE: 21
tttctcatcc tcacacctca ctgcgccect cctgaaccca ctcctttt                   47

<210> SEQ ID NO 22
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-26
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-26.mis1
<220> FEATURE:
<221> NAME/KEY: primer_bind
<222> LOCATION: 25..47
<223> OTHER INFORMATION: complement potential microsequencing oligo
      4-26.mis2

<400> SEQUENCE: 22
ccctgtnaga cacgtcctgt atcgttgttg agatgggaaa gtgcatc                    47

<210> SEQ ID NO 23
<211> LENGTH: 47
```

```
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14
<220> FEATURE:
<221> NAME/KEY: allele
<222> LOCATION: 24
<223> OTHER INFORMATION: polymorphic base T
<220> FEATURE:
<221> NAME/KEY: primer_bind
<222> LOCATION: 1..23
<223> OTHER INFORMATION: potential microsequencing oligo 4-14.mis1
<220> FEATURE:
<221> NAME/KEY: primer_bind
<222> LOCATION: 25..47
<223> OTHER INFORMATION: complement potential microsequencing oligo
      4-14.mis2

<400> SEQUENCE: 23
gcagggagca gaccagacat gatttgttct agtctagctg attcata                47

<210> SEQ ID NO 24
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-77, extracted from SEQ
      ID1 12057 12103
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-77.mis1
<220> FEATURE:
<221> NAME/KEY: primer_bind
<222> LOCATION: 25..47
<223> OTHER INFORMATION: complement potential microsequencing oligo
      4-77.mis2

<400> SEQUENCE: 24
gctgttcaga ctaaacttgg agactacagt cagtcagaga acttgct                47

<210> SEQ ID NO 25
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-217, extracted from SEQ
      ID1 34469 34515
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-217.mis1
<220> FEATURE:
<221> NAME/KEY: primer_bind
<222> LOCATION: 25..47
<223> OTHER INFORMATION: complement potential microsequencing oligo
      99-217.mis2

<400> SEQUENCE: 25
atatagttca cgttatgttc atacttaatt gttgcatttt gtttgcc                47
```

<210> SEQ ID NO 26
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-67, extracted from SEQ
      ID1 51612 51658
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-67.mis1
<220> FEATURE:
<221> NAME/KEY: primer_bind
<222> LOCATION: 25..47
<223> OTHER INFORMATION: complement potential microsequencing oligo
      4-67.mis2

<400> SEQUENCE: 26
gccagtgaaa tacagactta attcgtcatg actgaacgaa tttgttt                47

<210> SEQ ID NO 27
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-213
<220> FEATURE:
<221> NAME/KEY: allele
<222> LOCATION: 24
<223> OTHER INFORMATION: polymorphic base T
<220> FEATURE:
<221> NAME/KEY: primer_bind
<222> LOCATION: 1..23
<223> OTHER INFORMATION: potential microsequencing oligo 99-213.mis1
<220> FEATURE:
<221> NAME/KEY: primer_bind
<222> LOCATION: 25..47
<223> OTHER INFORMATION: complement potential microsequencing oligo
      99-213.mis2

<400> SEQUENCE: 27
ccttagcatt caagcccctg agctctggtg ttgtccaccc ctggggg                47

<210> SEQ ID NO 28
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-221
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-221.mis1
<220> FEATURE:
<221> NAME/KEY: primer_bind
<222> LOCATION: 25..47
<223> OTHER INFORMATION: complement potential microsequencing oligo
      99-221.mis2

<400> SEQUENCE: 28
agcttgagaa accagaaaag ccaaaaggag gctcctacca catgggt        47

<210> SEQ ID NO 29
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-135
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-135.mis1
<220> FEATURE:
<221> NAME/KEY: primer_bind
<222> LOCATION: 25..47
<223> OTHER INFORMATION: complement potential microsequencing oligo
      99-135.mis2

<400> SEQUENCE: 29
agtcactata tctatgttta atgaagatag aaagagatgc agaaatg        47

<210> SEQ ID NO 30
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-123, variant version of
      SEQ ID21
<220> FEATURE:
<221> NAME/KEY: allele
<222> LOCATION: 24
<223> OTHER INFORMATION: base T ; C in SEQ ID21
<220> FEATURE:
<221> NAME/KEY: primer_bind
<222> LOCATION: 1..23
<223> OTHER INFORMATION: potential microsequencing oligo 99-123.mis1
<220> FEATURE:
<221> NAME/KEY: primer_bind
<222> LOCATION: 25..47
<223> OTHER INFORMATION: complement potential microsequencing oligo
      99-123.mis2

<400> SEQUENCE: 30
tttctcatcc tcacacctca ctgtgcccct cctgaaccca ctccttt        47

<210> SEQ ID NO 31
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-26, variant version of
      SEQ ID22
<220> FEATURE:
<221> NAME/KEY: allele
<222> LOCATION: 24
<223> OTHER INFORMATION: base A ; G in SEQ ID22
<220> FEATURE:
<221> NAME/KEY: primer_bind
<222> LOCATION: 1..23
<223> OTHER INFORMATION: potential microsequencing oligo 4-26.mis1
<220> FEATURE:
<221> NAME/KEY: primer_bind

```
<222> LOCATION: 25..47
<223> OTHER INFORMATION: complement potential microsequencing oligo
      4-26.mis2

<400> SEQUENCE: 31
ccctgtnaga cacgtcctgt atcattgttg agatgggaaa gtgcatc                 47

<210> SEQ ID NO 32
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14, variant version of
      SEQ ID23
<220> FEATURE:
<221> NAME/KEY: allele
<222> LOCATION: 24
<223> OTHER INFORMATION: base C ; T in SEQ ID23
<220> FEATURE:
<221> NAME/KEY: primer_bind
<222> LOCATION: 1..23
<223> OTHER INFORMATION: potential microsequencing oligo 4-14.mis1
<220> FEATURE:
<221> NAME/KEY: primer_bind
<222> LOCATION: 25..47
<223> OTHER INFORMATION: complement potential microsequencing oligo
      4-14.mis2

<400> SEQUENCE: 32 gcaggagca gaccagacat gatctgttct agtctagctg attcata                  47

<210> SEQ ID NO 33
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-77, variant version of
      SEQ ID24
<220> FEATURE:
<221> NAME/KEY: allele
<222> LOCATION: 24
<223> OTHER INFORMATION: base G ; C in SEQ ID24
<220> FEATURE:
<221> NAME/KEY: primer_bind
<222> LOCATION: 1..23
<223> OTHER INFORMATION: potential microsequencing oligo 4-77.mis1
<220> FEATURE:
<221> NAME/KEY: primer_bind
<222> LOCATION: 25..47
<223> OTHER INFORMATION: complement potential microsequencing oligo
      4-77.mis2

<400> SEQUENCE: 33
gctgttcaga ctaaacttgg agagtacagt cagtcagaga acttgct                 47

<210> SEQ ID NO 34
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-217, variant version of
      SEQ ID25
<220> FEATURE:
<221> NAME/KEY: allele
<222> LOCATION: 24
<223> OTHER INFORMATION: base T ; C in SEQ ID25
<220> FEATURE:
```

```
<221> NAME/KEY: primer_bind
<222> LOCATION: 1..23
<223> OTHER INFORMATION: potential microsequencing oligo 99-217.mis1
<220> FEATURE:
<221> NAME/KEY: primer_bind
<222> LOCATION: 25..47
<223> OTHER INFORMATION: complement potential microsequencing oligo
      99-217.mis2

<400> SEQUENCE: 34
atatagttca cgttatgttc atatttaatt gttgcatttt gtttgcc              47

<210> SEQ ID NO 35
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-67, variant version of
      SEQ ID26
<220> FEATURE:
<221> NAME/KEY: allele
<222> LOCATION: 24
<223> OTHER INFORMATION: base T ; C in SEQ ID26
<220> FEATURE:
<221> NAME/KEY: primer_bind
<222> LOCATION: 1..23
<223> OTHER INFORMATION: potential microsequencing oligo 4-67.mis1
<220> FEATURE:
<221> NAME/KEY: primer_bind
<222> LOCATION: 25..47
<223> OTHER INFORMATION: complement potential microsequencing oligo
      4-67.mis2

<400> SEQUENCE: 35
gccagtgaaa tacagactta atttgtcatg actgaacgaa tttgttt              47

<210> SEQ ID NO 36
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-213, variant version of
      SEQ ID27
<220> FEATURE:
<221> NAME/KEY: allele
<222> LOCATION: 24
<223> OTHER INFORMATION: base C ; T in SEQ ID27
<220> FEATURE:
<221> NAME/KEY: primer_bind
<222> LOCATION: 1..23
<223> OTHER INFORMATION: potential microsequencing oligo 99-213.mis1
<220> FEATURE:
<221> NAME/KEY: primer_bind
<222> LOCATION: 25..47
<223> OTHER INFORMATION: complement potential microsequencing oligo
      99-213.mis2

<400> SEQUENCE: 36
ccttagcatt caagcccctg agccctggtg ttgtccaccc ctgggg              47

<210> SEQ ID NO 37
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-221, variant version of
      SEQ ID28
```

```
<220> FEATURE:
<221> NAME/KEY: allele
<222> LOCATION: 24
<223> OTHER INFORMATION: base C ; A in SEQ ID28
<220> FEATURE:
<221> NAME/KEY: primer_bind
<222> LOCATION: 1..23
<223> OTHER INFORMATION: potential microsequencing oligo 99-221.mis1
<220> FEATURE:
<221> NAME/KEY: primer_bind
<222> LOCATION: 25..47
<223> OTHER INFORMATION: complement potential microsequencing oligo
      99-221.mis2

<400> SEQUENCE: 37
agcttgagaa accagaaaag ccacaaggag gctcctacca catgggt            47

<210> SEQ ID NO 38
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-135, variant version of
      SEQ ID29
<220> FEATURE:
<221> NAME/KEY: allele
<222> LOCATION: 24
<223> OTHER INFORMATION: base G ; A in SEQ ID29
<220> FEATURE:
<221> NAME/KEY: primer_bind
<222> LOCATION: 1..23
<223> OTHER INFORMATION: potential microsequencing oligo 99-135.mis1
<220> FEATURE:
<221> NAME/KEY: primer_bind
<222> LOCATION: 25..47
<223> OTHER INFORMATION: complement potential microsequencing oligo
      99-135.mis2

<400> SEQUENCE: 38
agtcactata tctatgttta atggagatag aaagagatgc agaaatg            47

<210> SEQ ID NO 39
<211> LENGTH: 18
<212> TYPE: DNA
<213> ORGANISM: Homo Sapiens
<220> FEATURE:
<221> NAME/KEY: misc-feature
<222> LOCATION: 1..18
<223> OTHER INFORMATION: upstream amplification primer 99-123-PU

<400> SEQUENCE: 39
aaagccagga ctagaagg            18

<210> SEQ ID NO 40
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer 4-26-PU

<400> SEQUENCE: 40
tacagccctg taagacac            18

<210> SEQ ID NO 41
<211> LENGTH: 18
<212> TYPE: DNA
<213> ORGANISM: Homo Sapiens
```

```
<220> FEATURE:
<221> NAME/KEY: misc_feature
<222> LOCATION: 1..18
<223> OTHER INFORMATION: upstream amplification primer 4-14-PU

<400> SEQUENCE: 41
tctaacctct catccaac                                                 18

<210> SEQ ID NO 42
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer 4-77-PU,
      extracted from SEQ ID1 11930 11947

<400> SEQUENCE: 42
tgttgattta caggcggc                                                 18

<210> SEQ ID NO 43
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer 99-217-PU,
      extracted from SEQ ID1 34216 34234

<400> SEQUENCE: 43
ggtgggaatt tactatatg                                                19

<210> SEQ ID NO 44
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer 4-67-PU,
      extracted from SEQ ID1 51596 51613

<400> SEQUENCE: 44
aagttcacct tctcaagc                                                 18

<210> SEQ ID NO 45
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: upstream amplification primer 99-213-PU

<400> SEQUENCE: 45
atactggcag cgtgtgcttc                                               20

<210> SEQ ID NO 46
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer 99-221-PU

<400> SEQUENCE: 46
```

```
cccttttcct tcactgttc                                                    19
```

<210> SEQ ID NO 47
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer 99-135-PU

<400> SEQUENCE: 47

```
tggaagttgt tattgccc                                                     18
```

<210> SEQ ID NO 48
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer 99-123-RP

<400> SEQUENCE: 48

```
tattcagaaa ggagtggg                                                     18
```

<210> SEQ ID NO 49
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer 4-26-RP

<400> SEQUENCE: 49

```
tgaggactgc taggaaag                                                     18
```

<210> SEQ ID NO 50
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer 4-14-RP

<400> SEQUENCE: 50

```
gactgtatcc tttgatgcac                                                   20
```

<210> SEQ ID NO 51
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer 4-77-RP,
      extracted from SEQ ID1 12339 123 58 complement

<400> SEQUENCE: 51

```
ggaaaggtac tcattcatag                                                   20
```

<210> SEQ ID NO 52
<211> LENGTH: 21
<212> TYPE: DNA
<213> ORGANISM: Homo Sapiens

```
<220> FEATURE:
<221> NAME/KEY: misc_feature
<222> LOCATION: 1..21
<223> OTHER INFORMATION: downstream amplification primer 99-217-RP,
      extracted from SEQ ID1 34625 34645 complement

<400> SEQUENCE: 52
gtttattttg tgtgagcttt g                                        21

<210> SEQ ID NO 53
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer 4-67-RP,
      extracted from SEQ ID1 51996 520 15 complement

<400> SEQUENCE: 53
tgaaagagtt tattctctgg                                          20

<210> SEQ ID NO 54
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer 99-213-RP

<400> SEQUENCE: 54
ttattgcccc acatgcttga g                                        21

<210> SEQ ID NO 55
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer 99-221-RP

<400> SEQUENCE: 55
tcattcgtct ggctaggtc                                           19

<210> SEQ ID NO 56
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer 99-135-RP

<400> SEQUENCE: 56
aaacacctcc cattgtgc                                            18

<210> SEQ ID NO 57
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1482
<220> FEATURE:
<221> NAME/KEY: allele
<222> LOCATION: 24
```

```
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-1482.mis1
<220> FEATURE:
<221> NAME/KEY: primer_bind
<222> LOCATION: 25..47
<223> OTHER INFORMATION: complement potential microsequencing oligo
      99-1482.mis2

<400> SEQUENCE: 57
agtgaagtct gaggggggaaa aatcaaccct atagagggaa ggatctg                    47

<210> SEQ ID NO 58
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-73, extracted from SED
      ID1 13657 13703
<220> FEATURE:
<221> NAME/KEY: allele
<222> LOCATION: 24
<223> OTHER INFORMATION: polymorphic base C in PG1 (13680) SEQ ID1
<220> FEATURE:
<221> NAME/KEY: primer_bind
<222> LOCATION: 1..23
<223> OTHER INFORMATION: potential microsequencing oligo 4-73.mis1
<220> FEATURE:
<221> NAME/KEY: primer_bind
<222> LOCATION: 25..47
<223> OTHER INFORMATION: complement potential microsequencing oligo
      4-73.mis2

<400> SEQUENCE: 58
gttttcctta tgatgttaca tggcttattt ttaaaggtaa tgaaaac                     47

<210> SEQ ID NO 59
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-65, extracted from SEQ
      ID1 51448 51494
<220> FEATURE:
<221> NAME/KEY: allele
<222> LOCATION: 24
<223> OTHER INFORMATION: polymorphic base T in PG1 (51471) SEQ ID1
<220> FEATURE:
<221> NAME/KEY: primer_bind
<222> LOCATION: 1..23
<223> OTHER INFORMATION: potential microsequencing oligo 4-65.mis1
<220> FEATURE:
<221> NAME/KEY: primer_bind
<222> LOCATION: 25..47
<223> OTHER INFORMATION: complement potential microsequencing oligo
      4-65.mis2

<400> SEQUENCE: 59
ggtgctgctc agcggcttgc acgtagactt gctaggaaga aatgcag                     47

<210> SEQ ID NO 60
<211> LENGTH: 47
<212> TYPE: DNA
<213> ORGANISM: Homo Sapiens
<220> FEATURE:
<221> NAME/KEY: allele
<222> LOCATION: 1..47
```

```
<223> OTHER INFORMATION: polymorphic fragment 99-1482, variant version
      of SEQ ID57
<220> FEATURE:
<221> NAME/KEY: allele
<222> LOCATION: 24
<223> OTHER INFORMATION: base A ; C in SEQ ID57
<220> FEATURE:
<221> NAME/KEY: primer_bind
<222> LOCATION: 1..23
<223> OTHER INFORMATION: potential microsequencing oligo 99-1482.mis1
<220> FEATURE:
<221> NAME/KEY: primer_bind
<222> LOCATION: 25..47
<223> OTHER INFORMATION: complement potential microsequencing oligo
      99-1482.mis2

<400> SEQUENCE: 60
agtgaagtct gaggggggaaa aataaaccct atagagggaa ggatctg                  47

<210> SEQ ID NO 61
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-73, variant version of
      SEQ ID58
<220> FEATURE:
<221> NAME/KEY: allele
<222> LOCATION: 24
<223> OTHER INFORMATION: base G ; C in SEQ ID58
<220> FEATURE:
<221> NAME/KEY: primer_bind
<222> LOCATION: 1..23
<223> OTHER INFORMATION: potential microsequencing oligo 4-73.mis1
<220> FEATURE:
<221> NAME/KEY: primer_bind
<222> LOCATION: 25..47
<223> OTHER INFORMATION: complement potential microsequencing oligo
      4-73.mis2

<400> SEQUENCE: 61
gttttcctta tgatgttaca tgggttattt ttaaaggtaa tgaaaac                   47

<210> SEQ ID NO 62
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-65, variant version of
      SEQ ID59
<220> FEATURE:
<221> NAME/KEY: allele
<222> LOCATION: 24
<223> OTHER INFORMATION: base C ; T in SEQ ID59
<220> FEATURE:
<221> NAME/KEY: primer_bind
<222> LOCATION: 1..23
<223> OTHER INFORMATION: potential microsequencing oligo 4-65.mis1
<220> FEATURE:
<221> NAME/KEY: primer_bind
<222> LOCATION: 25..47
<223> OTHER INFORMATION: complement potential microsequencing oligo
      4-65.mis2

<400> SEQUENCE: 62
ggtgctgctc agcggcttgc acgcagactt gctaggaaga aatgcag                   47

<210> SEQ ID NO 63
<211> LENGTH: 21
```

```
<212> TYPE: DNA
<213> ORGANISM: Homo Sapiens
<220> FEATURE:
<221> NAME/KEY: misc_feature
<222> LOCATION: 1..21
<223> OTHER INFORMATION: upstream amplification primer 99-1482-PU

<400> SEQUENCE: 63
atcaaatcag tgaagtctga g                                                 21

<210> SEQ ID NO 64
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer 4-73-PU,
      extracted from SEQ ID1 13547 13564

<400> SEQUENCE: 64
atcgctggaa cattctgg                                                     18

<210> SEQ ID NO 65
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: upstream amplification primer 4-65-PU,
      extracted from SEQ ID1 51149 51168

<400> SEQUENCE: 65
gatttaagct acgctattag                                                   20

<210> SEQ ID NO 66
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer 99-1482-RP

<400> SEQUENCE: 66
acaaatctat ataaggctgg                                                   20

<210> SEQ ID NO 67
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer 4-73-RP,
      extracted from SEQ ID1 13962 13981 complement

<400> SEQUENCE: 67
ctcttggtta aacagcagtg                                                   20

<210> SEQ ID NO 68
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer 4-65-RP,
``` extracted from SEQ ID1 51482 51499 complement

<400> SEQUENCE: 68

```
tggctctgca tttcttcc                                                18
```

<210> SEQ ID NO 69
<211> LENGTH: 5226
<212> TYPE: DNA
<213> ORGANISM: Homo sapiens

<400> SEQUENCE: 69

| ctgctgtccc tggtgctcca cacgtactcc | atg cgc tac ctg ctg ccc agc gtc | 54 |
| | Met Arg Tyr Leu Leu Pro Ser Val | |
| | 1           5                    | |

| gtg ctc ctg ggc acg gcg ccc acc tac gtg ttg gcc tgg ggg gtc tgg | 102 |
| Val Leu Leu Gly Thr Ala Pro Thr Tyr Val Leu Ala Trp Gly Val Trp | |
|  10              15                  20                         | |

| cgg ctg ctc tcc gcc ttc ctg ccc gcc cgc ttc tac caa gcg ctg gac | 150 |
| Arg Leu Leu Ser Ala Phe Leu Pro Ala Arg Phe Tyr Gln Ala Leu Asp | |
| 25              30                  35                  40      | |

| gac cgg ctc tac tgc gtc tac cag agc atg gtg ctc ttc ttc ttc gag | 198 |
| Asp Arg Leu Tyr Cys Val Tyr Gln Ser Met Val Leu Phe Phe Phe Glu | |
|             45                  50                  55          | |

| aat tac acc ggg gtc cag ata ttg cta tat gga gat ttg cca aaa aat | 246 |
| Asn Tyr Thr Gly Val Gln Ile Leu Leu Tyr Gly Asp Leu Pro Lys Asn | |
|         60                  65                  70              | |

| aaa gaa aat ata ata tat tta gca aat cat caa agc aca gtt gac tgg | 294 |
| Lys Glu Asn Ile Ile Tyr Leu Ala Asn His Gln Ser Thr Val Asp Trp | |
|     75                  80                  85                  | |

| att gtt gct gac atc ttg gcc atc agg cag aat gcg cta gga cat gtg | 342 |
| Ile Val Ala Asp Ile Leu Ala Ile Arg Gln Asn Ala Leu Gly His Val | |
|  90                  95                 100                     | |

| cgc tac gtg ctg aaa gaa ggg tta aaa tgg ctg cca ttg tat ggg tgt | 390 |
| Arg Tyr Val Leu Lys Glu Gly Leu Lys Trp Leu Pro Leu Tyr Gly Cys | |
| 105             110                 115                     120 | |

| tac ttt gct cag cat gga gga atc tat gta aag cgc agt gcc aaa ttt | 438 |
| Tyr Phe Ala Gln His Gly Gly Ile Tyr Val Lys Arg Ser Ala Lys Phe | |
|             125                 130                 135         | |

| aac gag aaa gag atg cga aac aag ttg cag agc tac gtg gac gca gga | 486 |
| Asn Glu Lys Glu Met Arg Asn Lys Leu Gln Ser Tyr Val Asp Ala Gly | |
|         140                 145                 150             | |

| act cca atg tat ctt gtg att ttt cca gaa ggt aca agg tat aat cca | 534 |
| Thr Pro Met Tyr Leu Val Ile Phe Pro Glu Gly Thr Arg Tyr Asn Pro | |
|     155                 160                 165                 | |

| gag caa aca aaa gtc ctt tca gct agt cag gca ttt gct gcc caa cgt | 582 |
| Glu Gln Thr Lys Val Leu Ser Ala Ser Gln Ala Phe Ala Ala Gln Arg | |
| 170                 175                 180                     | |

| ggc ctt gca gta tta aaa cat gtg cta aca cca cga ata aag gca act | 630 |
| Gly Leu Ala Val Leu Lys His Val Leu Thr Pro Arg Ile Lys Ala Thr | |
| 185                 190                 195                 200 | |

| cac gtt gct ttt gat tgc atg aag aat tat tta gat gca att tat gat | 678 |
| His Val Ala Phe Asp Cys Met Lys Asn Tyr Leu Asp Ala Ile Tyr Asp | |
|                 205                 210                 215     | |

| gtt acg gtg gtt tat gaa ggg aaa gac gat gga ggg tag cgaagagagt | 727 |
| Val Thr Val Val Tyr Glu Gly Lys Asp Asp Gly Gly                 | |
|             220                 225                             | |

| caccgaccat gacggaattt ctctgcaaag aatgtccaaa aattcatatt cacattgatc | 787 |

| gtatcgacaa aaaagatgtc ccagaagaac aagaacatat gagaagatgg ctgcatgaac | 847 |

| gtttcgaaat caaagataag atgcttatag aattttatga gtcaccagat ccagaaagaa | 907 |

```
gaaaaagatt tcctgggaaa agtgttaatt ccaaattaag tatcaagaag actttaccat    967
caatgttgat cttaagtggt ttgactgcag gcatgcttat gaccgatgct ggaaggaagc   1027
tgtatgtgaa cacctggata tatggaaccc tacttggctg cctgtgggtt actattaaag   1087
catagacaag tagctgtctc cagacagtgg gatgtgctac attgtctatt tttggcggct   1147
gcacatgaca tcaaattgtt tcctgaattt attaaggagt gtaaataaag ccttgttgat   1207
tgaagattgg ataatagaat ttgtgacgaa agctgtatg caatggtctt gggcaaacat   1267
acctggttgt acaactttag catcggggct gctggaaggg taaaagctaa atggagtttc   1327
tcctgctctg tccatttcct atgaactaat gacaacttga gaaggctggg aggattgtgt   1387
attttgcaag tcagatggct gcattttga gcattaattt gcagcgtatt tcacttttc   1447
tgttattttc aatttattac aacttgacag ctccaagctc ttattactaa agtatttagt   1507
atcttgcagc tagttaatat ttcatctttt gcttatttct acaagtcagt gaaataaatt   1567
gtatttagga agtgtcagga tgttcaaagg aaagggtaaa aagtgttcat ggggaaaaag   1627
ctctgtttag cacatgattt tattgtattg cgttattagc tgatttact cattttatat   1687
ttgcaaaata aatttctaat atttattgaa attgcttaat ttgcacaccc tgtacacaca   1747
gaaaatggta taaatatga gaacgaagtt taaaattgtg actctgattc attatagcag   1807
aactttaaat ttcccagctt tttgaagatt taagctacgc tattagtact tcccttgtc   1867
tgtgccataa gtgcttgaaa acgttaaggt tttctgtttt gttttgtttt tttaatatca   1927
aaagagtcgg tgtgaacctt ggttggaccc caagttcaca agatttttaa ggtgatgaga   1987
gcctgcagac attctgccta gatttactag cgtgtgcctt ttgcctgctt ctctttgatt   2047
tcacagaata ttcattcaga agtcgcgttt ctgtagtgtg gtggattccc actgggctct   2107
ggtccttccc ttggatcccg tcagtggtgc tgctcagcgg cttgcacgta gacttgctag   2167
gaagaaatgc agagccagcc tgtgctgccc actttcagag ttgaactctt taagcccttg   2227
tgagtgggct tcaccagcta ctgcagaggc attttgcatt tgtctgtgtc aagaagttca   2287
ccttctcaag ccagtgaaat acagacttaa ttcgtcatga ctgaacgaat tgtttattt   2347
cccattaggt ttagtggagc tacacattaa tatgtatcgc cttagagcaa gagctgtgtt   2407
ccaggaacca gatcacgatt tttagccatg gaacaatata tcccatggga gaagaccttt   2467
cagtgtgaac tgttctatt ttgtgttata atttaaactt cgatttcctc atagtccttt   2527
aagttgacat ttctgcttac tgctactgga tttttgctgc agaaatatat cagtggccca   2587
cattaaacat accagttgga tcatgataag caaaatgaaa gaaataatga ttaagggaaa   2647
attaagtgac tgtgttacac tgcttctccc atgccagaga ataaactctt tcaagcatca   2707
tctttgaaga gtcgtgtggt gtgaattggt ttgtgtacat tagaatgtat gcacacatcc   2767
atggacactc aggatatagt tggcctaata atcggggcat gggtaaaact tatgaaaatt   2827
tcctcatgct gaattgtaat tttctcttac ctgtaaagta aaatttagat caattccatg   2887
tctttgttaa gtacagggat ttaatatatt ttgaatataa tgggtatgtt ctaaatttga   2947
actttgagag gcaatactgt tggaattatg tggattctaa ctcatttaa caaggtagcc   3007
tgacctgcat aagatcactt gaatgttagg tttcatagaa ctatactaat cttctcacaa   3067
aaggtctata aaatacagtc gttgaaaaaa attttgtatc aaaatgtttg gaaaattaga   3127
agcttctcct taacctgtat tgatactgac ttgaattatt ttctaaaatt aagagccgta   3187
tacctacctg taagtctttt cacatatcat ttaaacttt gtttgtatta ttactgattt   3247
```

-continued

```
acagcttagt tattaatttt tctttataag aatgccgtcg atgtgcatgc ttttatgttt    3307
ttcagaaaag ggtgtgtttg gatgaaagta aaaaaaaaaa taaaatcttt cactgtctct    3367
aatggctgtg ctgtttaaca ttttttgacc ctaaaattca ccaacagtct cccagtacat    3427
aaaataggct taatgactgg ccctgcattc ttcacaatat ttttccctaa gctttgagca    3487 aagtttttaaa aaaatacact aaaataatca aaactgttaa gcagtatatt agtttggtta    3547
tataaattca tctgcaattt ataagatgca tggccgatgt taatttgctt ggcaattctg    3607
taatcattaa gtgatctcag tgaaacatgt caaatgcctt aaattaacta agttggtgaa    3667
taaaagtgcc gatctggcta actcttacac catacatact gatagttttt catatgtttc    3727
atttccatgt gatttttaaa atttagagtg caacaatttt tgcttaatat gggttacata    3787
agctttattt tttcctttgt tcataattat attctttgaa taggtctgtg tcaatcaagt    3847
gatctaacta gactgatcat agatagaagg aaataaggcc aagttcaaga ccagcctggg    3907
caacatatcg agaacctgtc tacaaaaaaa ttaaaaaaaa ttagccaggc atggtggcgt    3967
acactgagta gtttgtccca gctactcggg agggtgaggt gggaggatcg cttcagccca    4027
ggaggttgag attgcagtga gccatggaca taccactgca ctacagccta ggtaacagca    4087
cgagacccca actcttagaa aatgaaaagg aaatatagaa atataaaatt tgcttattat    4147
agacacacag taactcccag atatgtacca caaaaaatgt gaaagagag agaaatgtct    4207 accaaagcag tattttgtgt gtataattgc aagcgcatag taaaataatt ttaaccttaa    4267
tttgttttta gtagtgttta gattgaagat tgagtgaaat attttcttgg cagatattcc    4327
gtatctggtg gaaagctaca atgcaatgtc gttgtagttt tgcatggctt gctttataaa    4387
caagattttt tctccctcct tttgggccag ttttcattac gagtaactca cacttttga    4447 ttaaagaact tgaaattacg ttatcactta gtataattga cattatatag agactatgta    4507
acatgcaatc attagaatca aaattagtac tttggtcaaa atatttacaa cattcacata    4567
cttgtcaaat attcatgtaa ttaactgaat ttaaaacctt caactattat gaagtgctcg    4627
tctgtacaat cgctaattta ctcagtttag agtagctaca actcttcgat actatcatca    4687
atatttgaca tcttttccaa tttgtgtatg aaaagtaaat ctattcctgt agcaactggg    4747
gagtcatata tgaggtcaaa gacatatacc ttgttattat aatatgtata ctataataat    4807
agctggttat cctgagcagg ggaaaaggtt atttttagga aaaccacttc aaatagaaag    4867
ctgaagtact tctaatatac tgagggaagt ataatatgtg gaacaaactc tcaacaaaat    4927
gtttattgat gttgatgaaa cagatcagtt tttccatccg gattattatt ggttcatgat    4987
tttatatgtg aatatgtaag atatgttctg caattttata aatgttcatg tcttttttta    5047
aaaaaggtgc tatcgaaatt ctgtgtctcc agcaggcaag aatacttgac taactctttt    5107
tgtctcttta tggtattttc agaataaagt ctgacttgtg ttttttgagat tattggtgcc    5167 tcattaattc agcaataaag gaaaatatgc atttcaaaaa naaaaaaaaa aaaaaaaa     5226
```

<210> SEQ ID NO 70
<211> LENGTH: 228
<212> TYPE: PRT
<213> ORGANISM: Homo sapiens

<400> SEQUENCE: 70

```
Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
            20                  25                  30
```

```
Ala Arg Phe Tyr Gln Ala Leu Asp Asp Arg Leu Tyr Cys Val Tyr Gln
         35                  40                  45

Ser Met Val Leu Phe Phe Phe Glu Asn Tyr Thr Gly Val Gln Ile Leu
 50                  55                  60

Leu Tyr Gly Asp Leu Pro Lys Asn Lys Glu Asn Ile Ile Tyr Leu Ala
 65                  70                  75                  80

Asn His Gln Ser Thr Val Asp Trp Ile Val Ala Asp Ile Leu Ala Ile
                 85                  90                  95

Arg Gln Asn Ala Leu Gly His Val Arg Tyr Val Leu Lys Glu Gly Leu
                100                 105                 110

Lys Trp Leu Pro Leu Tyr Gly Cys Tyr Phe Ala Gln His Gly Gly Ile
            115                 120                 125

Tyr Val Lys Arg Ser Ala Lys Phe Asn Glu Lys Glu Met Arg Asn Lys
        130                 135                 140

Leu Gln Ser Tyr Val Asp Ala Gly Thr Pro Met Tyr Leu Val Ile Phe
145                 150                 155                 160

Pro Glu Gly Thr Arg Tyr Asn Pro Glu Gln Thr Lys Val Leu Ser Ala
                165                 170                 175

Ser Gln Ala Phe Ala Ala Gln Arg Gly Leu Ala Val Leu Lys His Val
                180                 185                 190

Leu Thr Pro Arg Ile Lys Ala Thr His Val Ala Phe Asp Cys Met Lys
            195                 200                 205

Asn Tyr Leu Asp Ala Ile Tyr Asp Val Thr Val Tyr Glu Gly Lys
        210                 215                 220

Asp Asp Gly Gly
225

<210> SEQ ID NO 71
<211> LENGTH: 158
<212> TYPE: DNA
<213> ORGANISM: Homo sapiens

<400> SEQUENCE: 71
gccttgcagt attaaaacat gtgctaacac cacgaataaa ggcaactcac gttgcttttg      60
attgcatgaa gaattattta gatgcaattt atgatgttac ggtggtttat gaagggaaag    120
acgatggagg gtagcgaaga gagtcaccga ccatgacg                             158

<210> SEQ ID NO 72
<211> LENGTH: 1381
<212> TYPE: DNA
<213> ORGANISM: Mus musculus
<220> FEATURE:
<221> NAME/KEY: misc_binding
<222> LOCATION: 608..629
<223> OTHER INFORMATION: amplification   primer  g34292.pu
<220> FEATURE:
<221> NAME/KEY: misc_binding
<222> LOCATION: 740..758
<223> OTHER INFORMATION: amplification   primer  g34292.rp

<400> SEQUENCE: 72
gagccgagag gatgctgctg tccctggtgc tccacacgta ctct atg cgc tac ctg       56
                                              Met Arg Tyr Leu
                                                1 ctc ccc agc gtc ctg ttg ctg ggc tcg gcg ccc acc tac ctg ctg gcc       104
Leu Pro Ser Val Leu Leu Leu Gly Ser Ala Pro Thr Tyr Leu Leu Ala
  5                  10                  15                  20 tgg acg ctg tgg cgg gtg ctc tcc gcg ctg atg ccc gcc cgc ctg tac       152
```

```
                                                                         -continued Trp Thr Leu Trp Arg Val Leu Ser Ala Leu Met Pro Ala Arg Leu Tyr
             25                  30                  35 cag cgc gtg gac gac cgg ctt tac tgc gtc tac cag aac atg gtg ctc            200
Gln Arg Val Asp Asp Arg Leu Tyr Cys Val Tyr Gln Asn Met Val Leu
             40                  45                  50 ttc ttc ttc gag aac tac acc ggg gtc cag ata ttg cta tat gga gat            248
Phe Phe Phe Glu Asn Tyr Thr Gly Val Gln Ile Leu Leu Tyr Gly Asp
         55                  60                  65 ttg cca aaa aat aaa gaa aat gta ata tat cta gcg aat cat caa agc            296
Leu Pro Lys Asn Lys Glu Asn Val Ile Tyr Leu Ala Asn His Gln Ser
     70                  75                  80 aca gtt gac tgg att gtt gcg gac atg ctg gct gcc aga cag gat gcc            344
Thr Val Asp Trp Ile Val Ala Asp Met Leu Ala Ala Arg Gln Asp Ala
 85                  90                  95                 100 cta gga cat gtg cgc tac gta ctg aaa gac aag tta aaa tgg ctt ccg            392
Leu Gly His Val Arg Tyr Val Leu Lys Asp Lys Leu Lys Trp Leu Pro
                105                 110                 115 ctg tat ggg ttc tac ttt gct cag cat gga gga att tat gta aaa cga            440
Leu Tyr Gly Phe Tyr Phe Ala Gln His Gly Gly Ile Tyr Val Lys Arg
            120                 125                 130 agt gcc aaa ttt aat gat aaa gaa atg aga agc aag ctg cag agc tat            488
Ser Ala Lys Phe Asn Asp Lys Glu Met Arg Ser Lys Leu Gln Ser Tyr
        135                 140                 145 gtg aac gca gga aca ccg atg tat ctt gtg att ttc cca gag gga aca            536
Val Asn Ala Gly Thr Pro Met Tyr Leu Val Ile Phe Pro Glu Gly Thr
    150                 155                 160 agg tat aat gca aca tac aca aaa ctc ctt tca gcc agt cag gca ttt            584
Arg Tyr Asn Ala Thr Tyr Thr Lys Leu Leu Ser Ala Ser Gln Ala Phe
165                 170                 175                 180 gct gct cag cgg ggc ctt gca gta tta aaa cac gta ctg aca cca aga            632
Ala Ala Gln Arg Gly Leu Ala Val Leu Lys His Val Leu Thr Pro Arg
                185                 190                 195 ata aag gcc act cac gtt gct ttt gat tct atg aag agt cat tta gat            680
Ile Lys Ala Thr His Val Ala Phe Asp Ser Met Lys Ser His Leu Asp
            200                 205                 210 gca att tat gat gtc aca gtg gtt tat gaa ggg aat gag aaa ggt tca            728
Ala Ile Tyr Asp Val Thr Val Val Tyr Glu Gly Asn Glu Lys Gly Ser
        215                 220                 225 gga aaa tac tca aat cca cca tcc atg act gag ttt ctc tgc aaa cag            776
Gly Lys Tyr Ser Asn Pro Pro Ser Met Thr Glu Phe Leu Cys Lys Gln
    230                 235                 240 tgc cca aaa ctt cat att cac ttt gat cgt ata gac aga aat gaa gtt            824
Cys Pro Lys Leu His Ile His Phe Asp Arg Ile Asp Arg Asn Glu Val
245                 250                 255                 260 cca gag gaa caa gaa cac atg aaa aag tgg ctt cat gag cgc ttt gag            872
Pro Glu Glu Gln Glu His Met Lys Lys Trp Leu His Glu Arg Phe Glu
                265                 270                 275 ata aaa gat agg ttg ctc ata gag ttc tat gat tca cca gat cca gaa            920
Ile Lys Asp Arg Leu Leu Ile Glu Phe Tyr Asp Ser Pro Asp Pro Glu
            280                 285                 290 aga aga aac aaa ttt cct ggg aaa agt gtt cat tcc aga cta agt gtg            968
Arg Arg Asn Lys Phe Pro Gly Lys Ser Val His Ser Arg Leu Ser Val
        295                 300                 305 aag aag act tta cct tca gtg ttg atc ttg ggg agt ttg act gcg gtc           1016
Lys Lys Thr Leu Pro Ser Val Leu Ile Leu Gly Ser Leu Thr Ala Val
    310                 315                 320 atg ctg atg acg gag tcc gga agg aaa ctg tac atg ggc acc tgg ttg           1064
Met Leu Met Thr Glu Ser Gly Arg Lys Leu Tyr Met Gly Thr Trp Leu
325                 330                 335                 340
```

| | |
|---|---|
| tat gga acc ctc ctt ggc tgc ctg tgg ttt gtt att aaa gca taa<br>Tyr Gly Thr Leu Leu Gly Cys Leu Trp Phe Val Ile Lys Ala<br>                  345                       350                     355 | 1109 |
| gcaagtagca ggctgcagtc acagtctctt attgatggct acacattgta tcacattgtt | 1169 |
| tcctgaatta aataaggagt tttcttgttg ttgtttttt tgttttgttt tgttctgttt | 1229 |
| taagccttga tgatngnncn cnnnnnnnnn ncnantcnng ngaccacagc caacatgcat | 1289 |
| ttgatttggg gcaaacacat gtggcttttc aggtgctggg gttgctggag acatggaagc | 1349 |
| taagtggagt ttatgctgtt tttttttttt tt | 1381 |

<210> SEQ ID NO 73
<211> LENGTH: 15766
<212> TYPE: DNA
<213> ORGANISM: Mus musculus
<220> FEATURE:
<221> NAME/KEY: exon
<222> LOCATION: 52..121
<223> OTHER INFORMATION: exon2
<220> FEATURE:
<221> NAME/KEY: exon
<222> LOCATION: 682..797
<223> OTHER INFORMATION: exon3
<220> FEATURE:
<221> NAME/KEY: exon
<222> LOCATION: 2628..2717
<223> OTHER INFORMATION: exon4
<220> FEATURE:
<221> NAME/KEY: exon
<222> LOCATION: 7834..7924
<223> OTHER INFORMATION: exon5
<220> FEATURE:
<221> NAME/KEY: exon
<222> LOCATION: 9804..9965
<223> OTHER INFORMATION: exon6
<220> FEATURE:
<221> NAME/KEY: exon
<222> LOCATION: 11404..11527
<223> OTHER INFORMATION: exon7
<220> FEATURE:
<221> NAME/KEY: exon
<222> LOCATION: 13539..14035
<223> OTHER INFORMATION: exon8
<220> FEATURE:
<221> NAME/KEY: misc_feature
<222> LOCATION: 13762..13764
<223> OTHER INFORMATION: stop codon
<220> FEATURE:
<221> NAME/KEY: polyA_signal
<222> LOCATION: 13835..13839
<223> OTHER INFORMATION: AATAAA  potential

<400> SEQUENCE: 73

| | |
|---|---|
| tttttttttt ttaattgtca aagtcatgat tctttttgtt ttctcttta gatattgcta | 60 |
| tatggagatt tgccaaaaaa taagaaaat gtaatatatc tagcgaatca tcaaagcaca | 120 |
| ggtttgtatt tcatttgatg aaatttgggt ttttctagaa atggtaaatg agcattaata | 180 |
| tgtacacaca catacacaca aacacacata tgtacacaca catatgtttt aaagacagga | 240 |
| tttcatgtga cccagaatgg cctcatactc tctgagtagc tgagaatgat tttaagcttg | 300 |
| tgacacacct gccttcatct ccaaggtaca ggaattgcag gtgctttctt tgnnnnnnnn | 360 |
| nntttttttt tttgagtttt ggggagggg tatatttttt aatgtgtctg tagttggctt | 420 |
| tgttttaagc attttaatca tactttattt ttaaaaaac taaaagcttt tttaaggcta | 480 |
| ggtcttgcta tgtggcccta gtgttcctgg gacttgctct gtacaccggg ttgactctga | 540 |
| gcctgtgcgc cttctgcctc tgcctccata gttagattct caggacatgt tacaaagact | 600 |
| gtgctgtgaa gatgagtttt tgttcctggg agggaaggtt ggagctgact tgtgaggtac | 660 |

```
tgacttgggt ctgccttaca gttgactgga ttgttgcgga catgctggct gccagacagg      720
atgccctagg acatgtgcgc tacgtactga aagacaagtt aaaatggctt ccgctgtatg      780
ggttctactt tgctcaggta aactttgtct ttgcccttttt atttcaaact taacaccatt    840
taatgaaact atatctgatt tttttgttta tgtgtttgtt ttatggtacc cgtgattgaa      900
catggggtca tatgtgtgct actgagtgac agccttagtt cagacatttt ttaaagcgac     960
ttttactagt attttattt agaattctat atgtgtgcac atgcatatgt gtgcttgtgt     1020
gcacacgtgg atgcatgtga ggtcgaagga caattttcag tacaagtgtg agtgtcactt     1080
tttaggcacc ttccactctt attttgagac agtctcctag acctttgctg agttgcccag     1140
gctagccggc cagtgagccc tgggcatcta ccggtctctg cctccttacc tttacttagg     1200
ttacaagtgt gtgctgctac gcccagctgt ttactagatt ctaggatcc aaatgtgggt    1260 cctcgtaact tgtgagacaa gtactttcca aactgagcca cctccctagc tcttcttcac     1320
ggttcctgat ggtgtgtgtc tagatggctg gttgtccgta tatttaagtc cagtagcaga     1380
aatacaaata cctaggagtc caatagaaag ctacaagtgc agaattgaca atcggtaatg     1440
ttcggaaatt gattcaaaag tagttagtga gtgacagaca ggagctaaaa gcagactctg     1500
agctcagagt gtgaagtgtg gagaaatgtg ttttctcaca gttctgaagg ctgaaagtct     1560
ccccaaggtc aggatgtggg tggtactgct gtctcccaan cacccacctc tttggattat     1620
agactgcagc cttctccctg tgttctgagc cggcctttcc cacatgtgga catccttggt     1680
gggtgttcca ccagcagggc ctcagctagt gcccttattt cacttaactg taatgatttt     1740
cttaaagacc ctgtctccat acacagtcac tgtggaagct gaagcttcaa tgtaagagtt     1800
aaggggggag ggggaaattt agtccataat ggtgtcacac caatctctgt agctgagtcc     1860
atgattcagt tctttaaagg ctctgagtgt agacattatc ttaattattt tgcccattta     1920
tgtattatct ttaatttatt ttatgtaact gaatgcctgt gtatatatgt ttctggttcc     1980
tagtccatat tttaattcct taaggatgg aggtgtagac ttttgtcttt ttaattttct     2040
atccttccct cctggcctcc tgtggcctct tttacgtatt tattatttt aatttatttt      2100 atgtgtttga gtgttttgta tctatgcatt cctggggccc atggaggtca gaaaacaca      2160 ttaggtggcc tacaactgag ttatgggtgg tttgtgacca tggggtgctg ggacttgatc     2220
accagtctct gagaagactc gtgtctgctg agccttctct ccagtcctgg gagtgtggat     2280
attttaagga tactttttaat tgacttggtg aatgacagta gaaaatcaat gagttaggat     2340
ccatcggaaa aagcttttga actaaatctt ttaaagagaa atatttttaa gtgctaacaa     2400
aattaaatgt gtatttttcca tgatgcagtt ttacttgggc tctgtagaaa taggattttc     2460
aggtacatat tgtatatata gttggcaata tttaaatact aactgtcgct tgagttctga     2520
aatgtagttt tatgttttttt actcattagg agtacagttg ccttaataac tacggagatt     2580
agttattaaa gaataattgc tcttcttttt tcttttctgt gtaccagcat ggaggaattt     2640
atgtaaaacg aagtgccaaa tttaatgata agaaatgag agcaagctg cagagctatg      2700 tgaacgcagg aacaccggta agtgcgcccg cttttattcc tcaaggcagg ttaagaagtt     2760
aagttcttaa gtcattttga aaatatatta ccccatgtgg agcaatggaa ctggttcggg     2820
gttttgttga gataagctgt cctctggccg tgaggtaaga ttgctgcagg tgattgtaag     2880
gtttctcctg agtaacagtc agcatgggct cgggacgggc aagggcaggc cttagtgtgc     2940
agaggatgga gctcactgaa gccccaaaga gttagtcttc acatgagatt cagttctaga     3000
```

```
agaagttaaa ttgctttctt tctgtgtaaa tttggatttt tattgtagaa attaaagttt    3060
gttttctttt aaaacaaaca caaacccaga gcaaagagtc tcctagtgaa gagtcattcc    3120
gtgtcagtat tttacacaac tgttttctg  taaaggggga aaaagaattc aaatcttctc    3180
tttcaagaat gctgactgct gccaactgcc tctccccgtg gcccctctct gtatagacag    3240
gcatagctat ggtgaggact tgggcggctc ttgtctttct cctctctctg cttctctacc    3300 cttctctcg  tgcctccac  ttaccaggcc ctgggaagct acacaccagg caacagtgac    3360
cagggcctcg gcctgggctt cgaccaatta ctagagcaga aacagcagca gctgcagtgt    3420
tgttttgtgc tgtgcactgt attaggttgt gttttcatca cctttgggtt ttgtgatgtt    3480
ttgatgaagt cctggtacca ttctagtttt tacattctgg gtagatagag tttattcaag    3540
gtctcaaggc atatgaatgg aagagctcct ctttacagcc attcgtgtag catgcataac    3600
tgctcttctg tattctctct agtgtctttt tttttgtgtg tgaatctgat gtcttgttat    3660
tcacctacaa tgtggagtaa tggtcataaa catataaagt acttatgcct ttatctgcca    3720
aattgtattt aactttcag  cttttaatat aacttttat  ataataatta atttatttta    3780 aaaaaattg  aataccagcc tgttatagtg gcatatgcct gtgttcctag cactcaggag    3840 acaaggcag  aagtgtgaga acttcagact catactcagc tatatacaag accccaaatt    3900
tgtgctagat tctgcagtac agccatgagt gtccccatct tagagggaga tcgctcatcc    3960
ttgtgctgtt ctttaagtct taccctgcaa cccactgtaa gtacactctt gctcacagtc    4020
ctttagaatc tcacactctt tctctttaca gacaccatgt cattgcccac tttattattt    4080
atctgatgtc tacaaagatt atgaaagaga aacttgtatg cattctgtgt aaagtacttg    4140
acacaaataa tagtattcaa gaatgacttc ttaaatgaac actgaatgaa tagtttgttc    4200 taatttttt  gatcaacaaa tcaaaaaata tttagattaa atatctaaga tacaaagcat    4260
aataccacat gaatcattaa agtgagtaat caatcttata agtgactgac cctaaaactc    4320
atagacatta ataattgctt tcattgctta gatataaact ttattgatta atacgttctc    4380
atgaaagtgg ttcttggaag gttctggaaa cgaaaatatt tttcttactg cttttttctt    4440
ctagtaactg attgaatttt tctgcagttc cataaagcat ctggtcaatt gctattatcc    4500
aatatgagga tatataacaa agtattgatt tttaaatttg gcggtgataa gacaagactg    4560
ggcgtgtgaa tgagggggtc tctgtttctt gtcccttctc ttgggttctt ttccttttgt    4620
tggtttgcct tctccagctg ctatgtgatg ggttctgatt atcttattat atcttatttt    4680
gttatttttc attgttatct cttagaagcc aacatgttat atcacctcca ctcccaccat    4740
taggtgtnct cacaaatacc ccaagctaaa caaccacatc atgtcatgtt nctgtatact    4800
tccataagtg ttgttaactc tactgactct tgtgagcagg cccaattggc tttatcccta    4860
gctgggtgac ctgggttcct ccccaacacc ataccgtcca tcaaactgag tccttttcca    4920
agcacacacc agatactgct catctgagga ctcttctcat ccacctaagg actgcctgct    4980
cctcggcaga aagggcctct agtcccatac ccttacgccc tcaccaatgc cttaggaaca    5040
tgtgctcaat gcccctgtgg gtcatttccg tttacagtag ggaaatttgc ctgataactt    5100
gcagcacacc tataaagagg ccttgcttgc tctcatattt agctggagaa gataatgtac    5160
tcaccaactc cactctatgc aacccagtct gctctgccca tgccagtcag acgtgaatct    5220
tacacctgga ttcagattga tgaatctaca acatcaccca ctccatgctt ccttctaaat    5280
cagcagttct agcctgaatg acagatgcta cccaagtctc atctagttag ccctgtccgg    5340
agtaaccctg accttgagga ttagaccagg atgcacatcc tgcaccagtt cccttttgtcc   5400
```

```
acctgacttc atcccacccg ggccatagcc catgctcagg ctccaccctc catgcacaaa    5460
gctggctttt ccagcttcct tcacctgtat cagacacaaa tagcaaaagg ggtccacgtg    5520
cctaggtccc atcacaagac catgtgcggt agtttggaaa acagtctcca cttgaggctc    5580
agatagnttg gaatcttggc tctcatgtag ttgtactgat tagatcagtt taggaagtat    5640 gaccttntg gaaagaacat ataactggga ggggctttga gatgtaaagg ccccacacaa    5700
ttcctagttc aaactntact gcctgctcaa agcttgaggc atgaactctc actgttcctg    5760
atgtcatggt tcctgtctgc ttccacaatt ccctatcatt aggggtccct ttccttcctg    5820
gaattttaag tataaataaa cncttcttn taaaacaaca agaacaacaa atctgacnct    5880
gataatggat tttaaggcgt cttctctgga taagaaaaaa aaagaatat atttgcatag    5940 gtgctgtatt acttttgtca ttggtataac ctgactggaa gcaacttaaa ggaagaagaa    6000
tgtatcttga tttgtagatt aagagcacca tgactaagaa ggcatagcag cacaggtgca    6060
ccagcaagaa cataggctgc tagctcagat ctctgtagat atgggaacag ggcaggaagc    6120
tagtagtcta taaacctcag gacccatccc atggagttcc ttgtcttcca gtgatgtcct    6180
gtgtcttaaa gtttcacagt tcccacagca gcacctgccg tctgggaacc aacctgtggt    6240
ggatatttta caacgtgata ggcatatttt gtctctagcc ctgtaggttt atagccatcc    6300
tatacttcag tttatctagt ccacctcagt ctgatggtct tatagttcca acacttcaaa    6360
actacaaagt cttaagggcc atgggctcgg gtttattaga gcagtaacac ctctactagc    6420
tttctgtgtt acccactcct cttaaggtct ggttgaaatc ctaataggaa gcagcttgag    6480
aggagggttt attgtggccc atactttgtt ggtacattct atcatgcaag ggtggcactg    6540
tgatacagcc gaggccatcc gaggatggta ctgttggctt acatctgggt gggacaggaa    6600
atggtaattc tcaaggccca cctgcttggt gacttctttc agttaagccc catactctaa    6660
atcctctaca acctcccaac ataatgccac cagctgggga tcagctgttg acagtgctgg    6720
cccaggggag cagtttaaat ccagaccagg ggacctgaaa acagagaact gcagaggggc    6780
tgtgggactt tataccagct ttgcagacaa atcacggcat ttctttgtga gcttggttca    6840
taaacaaata tatattctcc tataggctcc tttagtgggt gtttcatatc cacaaatttg    6900
ttcagaaaaa cactgtgttt tatgctagct gtgtaggaga taataccgct gggagtcact    6960
tgagcatgga taagtgacat agttcgtcct catgagtccc tgtcctgttt ctgtattatg    7020
tttacttgat gagtttagtt tgtcagttgg ccaccaatta aaaagtatca tttattttt    7080 tttacaatac tcagttctca agttaggagt tttgttatta tatggcttca atattcacat    7140
tttaaccttt ccaggagtta agtataaaaa cttatatcaa ctgttgactt agtaaatatc    7200
tattacagat actatattct tcttagttta tatcatgaat atgaggttgc ttaaagtaag    7260
tgatgtaaaa tacactaggg gatgcttata aaatggaatg ttgtgagttt tttgaaacac    7320
gagtactaaa ttcataagtt tttaaatagt tacactgtta gcttcagtac tgctagatac    7380
atgtctataa tggctgaaga gtggagcttg gatattataa gtgtactctg tatattcatg    7440
cagacatata gcagattcca ctagtatgtg tggttaatat gtgctaataa aaatttaata    7500
caaaagtcat gttttattac tgggaaccag aggggttggt tgtgctgatt ttaagtcagt    7560
gactattagc atattctaag aaacagtttt naggatttta aagattggct ttaccataaa    7620
tgtagagcta tgttttacta taatccatat tatggtcggc cttaattcaa tctctgcagt    7680
ttggttactc tgctcaaagt gaaggtcatt tataaatgat acacattttc tcaccatagg    7740
```

```
aaatactacc tggccaataa cagagttaga attgctaaat tgatggtacc aacaatggac      7800
tcaacacaaa ctaaagttta tttatgccca cagatgtatc ttgtgatttt cccagaggga      7860
acaaggtata atgcaacata cacaaaactc ctttcagcca gtcaggcatt tgctgctcag      7920
cggggtaagt aaagatttaa ctgtattcag aaaaacactt ttttaagaag agtgatcttt      7980
gtttccttca gagtcatact aaagaatatg cgtttcttgt aagagctaag tgagagaata      8040
tccgatcttc tacagagtta ggtatattct tattagtctg tgtctgagag gttagagacg      8100
caggcttgct atggcacatt tcccatgctg tgaattgagt taaaaatgta ggtaaatgat      8160
atccccaaga aagtatactt ttnggagtga ctcagtataa agcctggtgt tataacataa      8220
acacgcacgt gcggatgtat atgtagcaca tatgtaaaca caggtatatg canttgtaat      8280
aagaaagtgg aggtcggggc ccactgcagg caagtctttt agtgatgctg agctaatgct      8340
gagaggtaga aagaccaaga aggctggagt tgctcattcg gcaaaggtca gagctcactg      8400
tgtgccataa ctcgagtgtt ctgtctccct tttgatacag ttttcttgtt tttaattatt      8460
agtttttaca attatcccat aaaatgtggg ctcattgtgg tcatcgtttt cataaagtcc      8520
ttcaagtata cacccagcaa gtatctaaat acactgggaa gaatcagtca gctgatggct      8580
tgaagtttca ggacatctag tgccacatca tgcttcagaa ccgacctgca cttagtcagg      8640
gtcatattca tgccacgtga agacgagagg aggccatgcc gtctgactta ggatggaaat      8700
ttccttcgag caaacacgaa cgggctaggt cttagttata ggcatagtgt ctgtggttat      8760
actaggcaga cattagtgga ctgggtgtta gaaggtacaa acaggcaaga atttgctgta      8820
gatttgtttc cctcatgtgt tgacaccaca tctaacctgc ttttttgagct tctagtccta      8880 ataatctcat aaaaatactg gttgaaccag aaatggtgtt gcaaagctat gatcccagct      8940
cctgggatct agggtgggag gatcataaat ttgaggccag cttgggtctg tcttagagaa      9000 aaagaaaaa taaaaagtct ggtcaaggta acatggagcc tggaagtttc acagggtgat      9060
tctgtaaagg tcctgagaca agatggcctc tagtggcgaa tgacttagct gacaangaaa      9120
actttcccag cttggttgac ttttcagact tcatacaagt ttgtgaataa attacactcc      9180
ttctgccctt gggactgaac tcagatatgt ggttgtggga atggctttct ttcccacacc      9240
accctgcatt ttaaaaattc ttctgtagac agtcccacca tcctgtagct gttcttcctt      9300
atgtcgccac tttccctgga gagaggcagt gcagacttca acccgcttct ccctagtcgc      9360
tgttcatagc acatcgaaag acctagtgct tcctgtgaaa ttgtaagtac atcctggagt      9420
ccaggagagg aggaagccga acagagtgga gggaatgctg agttctgtcc taagaaagac      9480
tgcgtgctta gcaagatgct gctgctctcc tgtcgtgtct ttcttgtcag aacttatcaa      9540
agagaaggct cgcagtgggt cataatcttc ccaaggacca gccttccag cttctcgcag       9600 catatctcat tcatgtagat gtttaatgga tatgtgtcaa tggggttgac ctaagtgaga      9660
tggcaatgta tgtgagcatt ctaggtgtga ggttatggca ttaaacttta atttccgtct      9720
atttgtggta gttgataagt aatttagatg ttgactttca tgtattccta attatgacca      9780
cattgaatct acctgctttc taggccttgc agtattaaaa cacgtactga caccaagaat      9840
aaaggccact cacgttgctt ttgattctat gaagagtcat ttagatgcaa tttatgatgt      9900
cacagtggtt tatgaaggga atgagaaagg ttcaggaaaa tactcaaatc caccatccat      9960
gactggtaag tccgtatttc catagaagct gaatagtaca tggtacaggt aagataaact     10020
cttgttttgt cgctttgctt agcttggttc agtttggttt tcagtagagg gttccactat     10080
gaagctctgg ctggccggga actcactatg tagaccaagc tggccttggg ctccactaca     10140
```

```
cccagcacca atcacccact cttatncttt tatgcntttt tgttttgct ttgagctttc    10200 tttataacat gtttgggaag gacattgtca ttatttacaa gaagaaatat ggtcttttcc    10260
caacatgcta gaatttaaag actcagaact cttgcctttg tcagtgacaa agtgagaatg    10320
gctgtgaagt gacgtggctt tgagtgagaa tagttcaggt aactatagcc acagactcaa    10380
catttgaaca tgggaacagg tgagaacgga gtgatggaag attctggccc ctttcagaga    10440
attcatttta gagagagatg agagtagtaa ggaagagaga agagagagac gtggtatttt    10500
gctgcagact aaagagatct cttataatcg cagtactaag gaggaagaag cagaagatga    10560
tgactacagg gccaggctga acaatctagt aaaatcctaa gtcaggaagt cagggctgag    10620
gtgcagctca gtaggagagt tgttgtctgc cctacacaag gcctggattt agctcccagt    10680
agcaacgaag ggaggcgagg gtgggcaaaa tcgaacactt actcttggag actcccttta    10740
tgaatattac cacactccag taaatactct ccagagattt cagatgagat tctgcttcct    10800
ggtaaacagg aggccaagaa tattatgtca cactgaacat gggatggaag acatgttctg    10860
aggaatgtct gcactccagt gtgatgaaga cttgaagttt agggacattt tccctccctg    10920
gccccactca ccccatctgt attgagtatt cccctagtgc tcatctttat ttgtatgtta    10980
actttcagga aggggaagca gattgatatt caaacccagc cagttttctt aaatactttg    11040
tggatgggat tggctttgac agtaaatgag gaaatgtaaa atgtaaaaga ttctaatttt    11100 taatattta aaggtgaggt tttctgttag tacgcagagt gagaggtttc ttactgatgt    11160
ctgcgtacct agaggaagga tggctacttc tccaaggctt gctgttagaa gtcagtgaca    11220
tgggcttaac aagagatatg tgctaatgag gttttaattt cagcttaata ctgcaaatca    11280
taagtgcata gctttattgt tttaaattct tttagtctta atgtttcatt tttaccataa    11340
gttactttgt ataatcacaa attctaaact agtaagacgt gaaattttct tcttctttgt    11400
tagagtttct ctgcaaacag tgcccaaaac ttcatattca ctttgatcgt atagacagaa    11460
atgaagttcc agaggaacaa gaacacatga aaaagtggct tcatgagcgc tttgagataa    11520
aagataggta agtggtaaga gctccagcat ttagaaagtg cagttcaacc aaatttact    11580 ctcagatcct gcttgaaagg agtcttttta tcttcattat ttagtaaata ctaatcatac    11640
ctgcatagac aagaccacat atacttaaat gtagcatgtt tcatggtgcg ttacccttgt    11700
ttaacaatta agtttaacat cctacatcag tttgcctgtt gatttctgta ccatgacaac    11760
tcaacacagc gatgcgttta ttccaaagtc gatagcacag caaaagtgaa actaaagtct    11820
gtattgtttc aagaatgctt tttgtgaact cgggttaaat cttattctat cctttcgtgt    11880
tcacattgta cattttcatg agtcactata aaaatcatga catggtggcc tacctgcagt    11940
gtttgctgga cagtaggctg ctgtgtgata agagcctttc ctcttcagct acacggggga    12000
cacgaggctt tgggggttcaa gactgaagca cgggtgagca caacaccttt gtgttgtggg    12060
aaggaaggga attgttcttt tcataatgaa attgtcccct ttcttgagtt agtagaaagt    12120
attacaagga tagagagttg aaatgaagct ttatattaga tttatgcctt gtgttgtcac    12180
gtgtttctac ctgacataac ttttcaaccc agccgctcag gattattttg atgatgggaa    12240
caatgtaaga aggcctatgt atcggtaact cactgttgta gctctgtgga ancggntcnn    12300
caggcagtag ggacgcttct gtgcttttgt gcctgtcctg ctgttagaat cttacagagg    12360
aggatgaatg aatgacccctt tttatttctc ttgtctgctt ttctaatttt atgggaataa    12420
gaacttttgg taggtctctg tcactggcct cttgttgtga agagacacct tgagcaaagc    12480
```

-continued

```
aactcttctg agagaaagca tttagttggg gaattcctta cagcttcaga ggttgagttc    12540
gttttcatca tgctgaggac agggaggcac tcaggcagga gaagtagttg agagccacat    12600
tctgatctac aggcagagag agacagactg agcctggcat gggttcttgg aacctcaaag    12660
cctctcatcc ctaccccatc tcccgacccc tatacacact tcctccaaca aggctacacc    12720
ttctaatcct tcttaaagag tcaccacatc cagcgactaa gcattcagat atgtgaacct    12780
gtcggagcct ttcttactca gatcacctca ggaggaaaac tcctatgcta taagaatttc    12840
ttttctttcg catctttgaa agcttgtttt tgtgtgatta gatcctggcc tcacacatgc    12900
tcggcaatca ttttactgtt gagctccagc ctcagccgtt ttcattggct tatgggatgc    12960
gagccatggg agagaagcta gaaggccttt cgttttatga gtcgggttgg tggaaccact    13020
tacagatgga agatttacaa acaaaaatga agctggggcc atcaaggctc agcactcgct    13080
gctcttccag agagttcagg ttcatttctc agtaaccaca tggtggcttt gtaaatgtaa    13140
cttcatattc aatgaccctg acaccctctt ctggcctctg tgggcaccag acacaatcat    13200
ggtatacaga cacacacact agccaacacc catctacata aaagtatata anacatatct    13260
ttatcttaaa aatccccgaa gtcctcatta aatatcttag atccccgccg tgttttgatt    13320
tttgtttccc acgtggtgag gatataatat catgtccaaa ctgtaaggag tgaatgccct    13380
cccgtgcctc tcggacacct ctgcactcat ccaagttttc taaggagctg tacttgctca    13440
gcaagtactc aatacctaat aaatggttta tgtttgtttc aacaccaaaa atgtccaaaa    13500
ctgaaagatc aattctgttg ttttccttct ggccataggt tgctcataga gttctatgat    13560
tcaccagatc cagaaagaag aaacaaattt cctgggaaaa gtgttcattc cagactaagt    13620
gtgaagaaga ctttaccttc agtgttgatc ttggggagtt tgactgcggt catgctgatg    13680
acggagtccg gaaggaaact gtacatgggc acctggttgt atggaaccct ccttggctgc    13740
ctgtggtttt ttattaaagc ataagcaagt agcaggctgc agtcacagtc tcttattgat    13800
ggctacacat tgtatcacat tgtttcctga attaaataag gagttttctt gttgttgttt    13860
ttttgtttt gttttgttct gttttaagcc ttgatgattg aacactggat aaagtagagt    13920
ttgtgaccac agccaacatg catttgattt ggggcaaaca catgtggctt tcaggtgct    13980
ggggttgctg gagacatgga agctaagtgg agtttatgct gntttttttt ttttttttnaa    14040
tgttttcatg aattaatgtc cacttgtaaa gattattgga tactttctgt aattcagaag    14100
gttgtatttt aacactagtt tgcagtatgt ttcgctatat tggttatctt ccatttgact    14160
acttggcagc tcagactctt aatactaaag tattttacat tttgaagcta tgtgatactg    14220
gttttttgtt gttgttgttg ttgttaattt ctgaaagtca atgaaagaca ctgtaatgat    14280
gcgttaagat gttccaagaa aaaggtgaga attattcatg gcaaaaaaga tctgtctagt    14340
gtatattttt attatattgc tctatttagc taattttctt tatatttgca aaataatgaa    14400
cattttaat atttattaaa atgcttgatt tgcataccc cgattctaca gagaataatg    14460
tgtaaagtgt cagaatagac ttgaagctct gctgtgactc agtctccttt gtcagagctt    14520
ctagtagccc agctactgag ctgctttgtt agtacctcca gcacctgagc cgttaagtac    14580
ttataaatgc aagggacccg ttatcttcat atcggaatag acatgaacag agctctaagg    14640
cgatgaaagt ctgccagcat cctctctgtc ctcgcacgtg ccttctgcct ggctccattt    14700
gctttggcac tgcgttcgat ctagagtgta ggtgctcact gcttatttca gccctggctc    14760
tgtggttttg tgtcctccag tggtgctgtt cactgttggg gtgcaggtgg tgctgccctg    14820
actcagaggg gcagctccct ggctcctgag ggtgagcctt cttggctact acagaagtat    14880
```

-continued

```
tgtgcgtttg tgtatggcaa gaaccatcag gattggataa atgtgttatt tctctttgat    14940
ttccatggag ccacactgtt ggtacatgtc ccctgtgaac agagctacct ttcaggagca    15000
catcatactg tcgtgagtca cggcacggtg tgtcctgtga agaggcttt tctaacgtgt     15060
gatttgccgt gtttctatgt tgtgatttaa gcgtgattgc ctactagtca ttcaaggtaa    15120
catttctgca aatttcatac agatttttgt cacaaaatta ctataccaat gatctagttg    15180
aaatagacca attgaatcac aataaataat ttttttttaat tgagggaaaa tttgcttctt   15240
gttttttcaa agccagaaaa cgagccattt caaacatctt tgaagagtca tgtgctgtca    15300
cttgttttct atgtgttagt gtctatattc atgtatggat acacatgaac atgtatattc    15360
atacacacac gccaatagaa tataacagcc taaaaacaat ccagcttgtg tatcatgtta    15420
ctgtgctgaa ttgtaatggt ttttacttac aaagtgaggc taaaatcgat ttcatgtctt    15480
tgttaaatac gttttttttca gcaatcctat tagagcttat tttgaccaga tcaaaataag    15540
tacaagttca gagactttaa atatggctga ggtctagagc gatagctcag tagttaggaa    15600
cacatgccac tctttcaagg gcttcagttc ccagcactca tatggaggct cacagaaggc    15660
tggaattcca gcttcatgga attggacaca tcctctagct tccatggatc tgtctgtctg    15720
tctctccctt ctctctctct ctctctctct ctctctctct ctctct                   15766
```

<210> SEQ ID NO 74
<211> LENGTH: 354
<212> TYPE: PRT
<213> ORGANISM: Mus musculus

<400> SEQUENCE: 74

```
Met Arg Tyr Leu Leu Pro Ser Val Leu Leu Gly Ser Ala Pro Thr
 1               5                  10                  15

Tyr Leu Leu Ala Trp Thr Leu Trp Arg Val Leu Ser Ala Leu Met Pro
                20                  25                  30

Ala Arg Leu Tyr Gln Arg Val Asp Asp Arg Leu Tyr Cys Val Tyr Gln
            35                  40                  45

Asn Met Val Leu Phe Phe Glu Asn Tyr Thr Gly Val Gln Ile Leu
        50                  55                  60

Leu Tyr Gly Asp Leu Pro Lys Asn Lys Glu Asn Val Ile Tyr Leu Ala
65                  70                  75                  80

Asn His Gln Ser Thr Val Asp Trp Ile Val Ala Asp Met Leu Ala Ala
                85                  90                  95

Arg Gln Asp Ala Leu Gly His Val Arg Tyr Val Leu Lys Asp Lys Leu
            100                 105                 110

Lys Trp Leu Pro Leu Tyr Gly Phe Tyr Phe Ala Gln His Gly Gly Ile
        115                 120                 125

Tyr Val Lys Arg Ser Ala Lys Phe Asn Asp Lys Glu Met Arg Ser Lys
    130                 135                 140

Leu Gln Ser Tyr Val Asn Ala Gly Thr Pro Met Tyr Leu Val Ile Phe
145                 150                 155                 160

Pro Glu Gly Thr Arg Tyr Asn Ala Thr Tyr Thr Lys Leu Leu Ser Ala
                165                 170                 175

Ser Gln Ala Phe Ala Ala Gln Arg Gly Leu Ala Val Leu Lys His Val
            180                 185                 190

Leu Thr Pro Arg Ile Lys Ala Thr His Val Ala Phe Asp Ser Met Lys
        195                 200                 205

Ser His Leu Asp Ala Ile Tyr Asp Val Thr Val Val Tyr Glu Gly Asn
```

-continued

```
                210                 215                 220
Glu Lys Gly Ser Gly Lys Tyr Ser Asn Pro Pro Ser Met Thr Glu Phe
225                 230                 235                 240

Leu Cys Lys Gln Cys Pro Lys Leu His Ile His Phe Asp Arg Ile Asp
                245                 250                 255

Arg Asn Glu Val Pro Glu Gln Glu His Met Lys Lys Trp Leu His
                260                 265                 270

Glu Arg Phe Glu Ile Lys Asp Arg Leu Leu Ile Glu Phe Tyr Asp Ser
                275                 280                 285

Pro Asp Pro Glu Arg Arg Asn Lys Phe Pro Gly Lys Ser Val His Ser
                290                 295                 300

Arg Leu Ser Val Lys Lys Thr Leu Pro Ser Val Leu Ile Leu Gly Ser
305                 310                 315                 320

Leu Thr Ala Val Met Leu Met Thr Glu Ser Gly Arg Lys Leu Tyr Met
                325                 330                 335

Gly Thr Trp Leu Tyr Gly Thr Leu Leu Gly Cys Leu Trp Phe Val Ile
                340                 345                 350

Lys Ala

<210> SEQ ID NO 75
<211> LENGTH: 22
<212> TYPE: DNA
<213> ORGANISM: Mus Musculus
<220> FEATURE:
<221> NAME/KEY: misc_feature
<222> LOCATION: 1..22
<223> OTHER INFORMATION: amplification oligonucleotide g34292.pu

<400> SEQUENCE: 75
attaaaacac gtactgacac ca                                              22

<210> SEQ ID NO 76
<211> LENGTH: 19
<212> TYPE: DNA
<213> ORGANISM: Mus Musculus
<220> FEATURE:
<221> NAME/KEY: misc_feature
<222> LOCATION: 1..19
<223> OTHER INFORMATION: amplification oligonucleotide g34292.rp

<400> SEQUENCE: 76
agtcatggat ggtggattt                                                  19

<210> SEQ ID NO 77
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: amplification oligonucleotide BOXIed

<400> SEQUENCE: 77
aatcatcaaa gcacagttga ctggat                                          26

<210> SEQ ID NO 78
<211> LENGTH: 33
<212> TYPE: DNA
<213> ORGANISM: Homo Sapiens
<220> FEATURE:
<221> NAME/KEY: misc_feature
<222> LOCATION: 1..33
<223> OTHER INFORMATION: amplification oligonucleotide BOXIIIer
```

```
<400> SEQUENCE: 78
ataaaccacc gtaacatcat aaattgcatc taa                                    33

<210> SEQ ID NO 79
<211> LENGTH: 22
<212> TYPE: DNA
<213> ORGANISM: Mus Musculus
<220> FEATURE:
<221> NAME/KEY: misc_feature
<222> LOCATION: 1..22
<223> OTHER INFORMATION: sequencing oligonucleotide moPGrace3S473

<400> SEQUENCE: 79
gagataaaag ataggttgct ca                                                22

<210> SEQ ID NO 80
<211> LENGTH: 19
<212> TYPE: DNA
<213> ORGANISM: Mus Musculus
<220> FEATURE:
<221> NAME/KEY: misc_feature
<222> LOCATION: 1..19
<223> OTHER INFORMATION: sequencing oligonucleotide moPGrace3S526

<400> SEQUENCE: 80
aagaaacaaa tttcctggg                                                    19

<210> SEQ ID NO 81
<211> LENGTH: 18
<212> TYPE: DNA
<213> ORGANISM: Mus Musculus
<220> FEATURE:
<221> NAME/KEY: misc_feature
<222> LOCATION: 1..18
<223> OTHER INFORMATION: sequencing oligonucleotide moPGrace3S597

<400> SEQUENCE: 81
tcttggggag tttgactg                                                     18

<210> SEQ ID NO 82
<211> LENGTH: 18
<212> TYPE: DNA
<213> ORGANISM: Mus Musculus
<220> FEATURE:
<221> NAME/KEY: misc_feature
<222> LOCATION: 1..18
<223> OTHER INFORMATION: sequencing oligonucleotide moPGrace5R323

<400> SEQUENCE: 82
gaccccggtg tagttctc                                                     18

<210> SEQ ID NO 83
<211> LENGTH: 17
<212> TYPE: DNA
<213> ORGANISM: Mus Musculus
<220> FEATURE:
<221> NAME/KEY: misc_feature
<222> LOCATION: 1..17
<223> OTHER INFORMATION: sequencing oligonucleotide moPGrace5R372

<400> SEQUENCE: 83
cagtaaagcc ggtcgtc                                                      17

<210> SEQ ID NO 84
<211> LENGTH: 17
<212> TYPE: DNA
```

<213> ORGANISM: Mus Musculus
<220> FEATURE:
<221> NAME/KEY: misc_feature
<222> LOCATION: 1..17
<223> OTHER INFORMATION: sequencing oligonucleotide moPGrace5R444

<400> SEQUENCE: 84
caggccagca ggtaggt     17

<210> SEQ ID NO 85
<211> LENGTH: 19
<212> TYPE: DNA
<213> ORGANISM: Mus Musculus
<220> FEATURE:
<221> NAME/KEY: misc_feature
<222> LOCATION: 1..19
<223> OTHER INFORMATION: sequencing oligonucleotide moPGrace5R492

<400> SEQUENCE: 85
agcaggtagc gcatagagt     19

<210> SEQ ID NO 86
<211> LENGTH: 27
<212> TYPE: DNA
<213> ORGANISM: Mus Musculus
<220> FEATURE:
<221> NAME/KEY: misc_feature
<222> LOCATION: 1..27
<223> OTHER INFORMATION: amplification oligonucleotide moPG13LR2

<400> SEQUENCE: 86
ggaaacaatg tgatacaatg tgtagcc     27

<210> SEQ ID NO 87
<211> LENGTH: 18
<212> TYPE: DNA
<213> ORGANISM: Mus Musculus
<220> FEATURE:
<221> NAME/KEY: misc_feature
<222> LOCATION: 1..18
<223> OTHER INFORMATION: amplification oligonucleotide moPG15

<400> SEQUENCE: 87
tggcgagccg agaggatg     18

<210> SEQ ID NO 88
<211> LENGTH: 36
<212> TYPE: DNA
<213> ORGANISM: Mus Musculus
<220> FEATURE:
<221> NAME/KEY: misc_feature
<222> LOCATION: 1..36
<223> OTHER INFORMATION: amplification oligonucleotide moPG15Bam1

<400> SEQUENCE: 88
cgtggatccg gaaacaatgt gatacaatgt gtagcc     36

<210> SEQ ID NO 89
<211> LENGTH: 27
<212> TYPE: DNA
<213> ORGANISM: Mus Musculus
<220> FEATURE:
<221> NAME/KEY: misc_feature
<222> LOCATION: 1..27
<223> OTHER INFORMATION: amplification oligonucleotide moPG15Eco1

<400> SEQUENCE: 89
cgtgaattct ggcgagccga gaggatg     27

```
<210> SEQ ID NO 90
<211> LENGTH: 20
<212> TYPE: DNA
<213> ORGANISM: Mus Musculus
<220> FEATURE:
<221> NAME/KEY: misc_feature
<222> LOCATION: 1..20
<223> OTHER INFORMATION: amplification oligonucleotide moPG1RACE3.18

<400> SEQUENCE: 90
ctgccagaca ggatgcccta                                              20

<210> SEQ ID NO 91
<211> LENGTH: 23
<212> TYPE: DNA
<213> ORGANISM: Mus Musculus
<220> FEATURE:
<221> NAME/KEY: misc_feature
<222> LOCATION: 1..23
<223> OTHER INFORMATION: amplification oligonucleotide moPG1RACE3.63

<400> SEQUENCE: 91
acaagttaaa atggcttccg ctg                                          23

<210> SEQ ID NO 92
<211> LENGTH: 18
<212> TYPE: DNA
<213> ORGANISM: Mus Musculus
<220> FEATURE:
<221> NAME/KEY: misc_feature
<222> LOCATION: 1..18
<223> OTHER INFORMATION: sequencing oligonucleotide moPG1RACE3R94

<400> SEQUENCE: 92
caaatgcatg ttggctgt                                                18

<210> SEQ ID NO 93
<211> LENGTH: 20
<212> TYPE: DNA
<213> ORGANISM: Mus Musculus
<220> FEATURE:
<221> NAME/KEY: misc_feature
<222> LOCATION: 1..20
<223> OTHER INFORMATION: amplification oligonucleotide moPG1RACE5.276

<400> SEQUENCE: 93
gcaaatgcct gactggctga                                              20

<210> SEQ ID NO 94
<211> LENGTH: 22
<212> TYPE: DNA
<213> ORGANISM: Mus Musculus
<220> FEATURE:
<221> NAME/KEY: misc_feature
<222> LOCATION: 1..22
<223> OTHER INFORMATION: amplification oligonucleotide moPG1RACE5.350

<400> SEQUENCE: 94
aatcaaaagc aacgtgagtg gc                                           22

<210> SEQ ID NO 95
<211> LENGTH: 20
<212> TYPE: DNA
<213> ORGANISM: Mus Musculus
<220> FEATURE:
<221> NAME/KEY: misc_feature
<222> LOCATION: 1..20
```

```
<223> OTHER INFORMATION: amplification oligonucleotide moPG3RACE2

<400> SEQUENCE: 95
tgggcacctg gttgtatgga                                            20

<210> SEQ ID NO 96
<211> LENGTH: 20
<212> TYPE: DNA
<213> ORGANISM: Mus Musculus
<220> FEATURE:
<221> NAME/KEY: misc_feature
<222> LOCATION: 1..20
<223> OTHER INFORMATION: amplification oligonucleotide moPG3RACE2n

<400> SEQUENCE: 96
tccttggctg cctgtggttt                                            20

<210> SEQ ID NO 97
<211> LENGTH: 21
<212> TYPE: DNA
<213> ORGANISM: Mus Musculus
<220> FEATURE:
<221> NAME/KEY: misc_feature
<222> LOCATION: 1..21
<223> OTHER INFORMATION: sequencing oligonucleotide moPG3RACES20

<400> SEQUENCE: 97
gatggctaca cattgtatca c                                          21

<210> SEQ ID NO 98
<211> LENGTH: 24
<212> TYPE: DNA
<213> ORGANISM: Mus Musculus
<220> FEATURE:
<221> NAME/KEY: misc_feature
<222> LOCATION: 1..24
<223> OTHER INFORMATION: sequencing oligonucleotide moPG3RACES5

<400> SEQUENCE: 98
tcctgaatta aataaggagt tttc                                       24

<210> SEQ ID NO 99
<211> LENGTH: 24
<212> TYPE: DNA
<213> ORGANISM: Mus Musculus
<220> FEATURE:
<221> NAME/KEY: misc_feature
<222> LOCATION: 1..24
<223> OTHER INFORMATION: sequencing oligonucleotide moPG3RACES90

<400> SEQUENCE: 99
gtttgttatt aaagcataag caag                                       24

<210> SEQ ID NO 100
<211> LENGTH: 216
<212> TYPE: DNA
<213> ORGANISM: Homo sapiens

<400> SEQUENCE: 100
ctgctgtccc tggtgctcca cacgtactcc atgcgctacc tgctgcccag cgtcgtgctc    60
ctgggcacgg cgcccaccta cgtgttggcc tgggggtct ggcggctgct ctccgccttc   120
ctgcccgccc gcttctacca agcgctggac gaccggctgt actgcgtcta ccagagcatg   180
gtgctcttct tcttcgagaa ttacaccggg gtccag                            216
```

```
<210> SEQ ID NO 101
<211> LENGTH: 70
<212> TYPE: DNA
<213> ORGANISM: Homo sapiens

<400> SEQUENCE: 101
atattgctat atggagattt gccaaaaaat aaagaaaata taatatattt agcaaatcat      60
caaagcacag                                                           70

<210> SEQ ID NO 102
<211> LENGTH: 116
<212> TYPE: DNA
<213> ORGANISM: Homo sapiens

<400> SEQUENCE: 102
ttgactggat tgttgctgac atcttggcca tcaggcagaa tgcgctagga catgtgcgct      60
acgtgctgaa agaagggtta aaatggctgc cattgtatgg gtgttacttt gctcag        116

<210> SEQ ID NO 103
<211> LENGTH: 90
<212> TYPE: DNA
<213> ORGANISM: Homo sapiens

<400> SEQUENCE: 103
catggaggaa tctatgtaaa gcgcagtgcc aaatttaacg agaaagagat gcgaaacaag      60
ttgcagagct acgtggacgc aggaactcca                                      90

<210> SEQ ID NO 104
<211> LENGTH: 91
<212> TYPE: DNA
<213> ORGANISM: Homo sapiens

<400> SEQUENCE: 104
atgtatcttg tgattttttcc agaaggtaca aggtataatc cagagcaaac aaaagtcctt    60
tcagctagtc aggcatttgc tgcccaacgt g                                    91

<210> SEQ ID NO 105
<211> LENGTH: 159
<212> TYPE: DNA
<213> ORGANISM: Homo sapiens

<400> SEQUENCE: 105
gccttgcagt attaaaacat gtgctaacac cacgaataaa ggcaactcac gttgcttttg      60
attgcatgaa gaattattta gatgcaattt atgatgttac ggtggtttat gaagggaaag     120
acgatggagg gcagcgaaga gagtcaccga ccatgacgg                            159

<210> SEQ ID NO 106
<211> LENGTH: 124
<212> TYPE: DNA
<213> ORGANISM: Homo sapiens

<400> SEQUENCE: 106
aatttctctg caaagaatgt ccaaaaattc atattcacat tgatcgtatc gacaaaaaag      60
atgtcccaga agaacaagaa catatgagaa gatggctgca tgaacgtttc gaatcaaag     120 ataa                                                                 124

<210> SEQ ID NO 107
<211> LENGTH: 4342
<212> TYPE: DNA
```

```
<213> ORGANISM: Homo sapiens
<220> FEATURE:
<221> NAME/KEY: polyA_signal
<222> LOCATION: 325..330
<223> OTHER INFORMATION: AATAAA  potential
<220> FEATURE:
<221> NAME/KEY: polyA_signal
<222> LOCATION: 694..699
<223> OTHER INFORMATION: AATAAA  potential
<220> FEATURE:
<221> NAME/KEY: polyA_signal
<222> LOCATION: 828..833
<223> OTHER INFORMATION: AATAAA  potential
<220> FEATURE:
<221> NAME/KEY: polyA_signal
<222> LOCATION: 1821..1826
<223> OTHER INFORMATION: AATAAA  potential
<220> FEATURE:
<221> NAME/KEY: polyA_signal
<222> LOCATION: 2480..2485
<223> OTHER INFORMATION: AATAAA  potential
<220> FEATURE:
<221> NAME/KEY: polyA_signal
<222> LOCATION: 2800..2805
<223> OTHER INFORMATION: AATAAA  potential
<220> FEATURE:
<221> NAME/KEY: polyA_signal
<222> LOCATION: 4264..4269
<223> OTHER INFORMATION: AATAAA  potential
<220> FEATURE:
<221> NAME/KEY: polyA_signal
<222> LOCATION: 4320..4315
<223> OTHER INFORMATION: AATAAA

<400> SEQUENCE: 107
gatgcttata gaattttatg agtcaccaga tccagaaaga agaaaaagat ttcctgggaa      60
aagtgttaat tccaaattaa gtatcaagaa gactttacca tcaatgttga tcttaagtgg     120
tttgactgca ggcatgctta tgaccgatgc tggaaggaag ctgtatgtga acacctggat     180
atatggaacc ctacttggct gcctgtgggt tactattaaa gcatagacaa gtagctgtct     240
ccagacagtg ggatgtgcta cattgtctat ttttggcggc tgcacatgac atcaaattgt     300
ttcctgaatt tattaaggag tgtaaataaa gccttgttga ttgaagattg gataatagaa     360
tttgtgacga aagctgatat gcaatggtct tgggcaaaca tacctggttg tacaacttta     420
gcatcggggc tgctggaagg gtaaaagcta aatggagttt ctcctgctct gtccatttcc     480
tatgaactaa tgacaacttg agaaggctgg gaggattgtg tattttgcaa gtcagatggc     540
tgcatttttg agcattaatt tgcagcgtat ttcacttttt ctgttatttt caatttatta     600
caacttgaca gctccaagct cttattacta agtatttag tatcttgcag ctagttaata     660
tttcatcttt tgcttatttc tacaagtcag tgaaataaat tgtatttagg aagtgtcagg     720
atgttcaaag gaaagggtaa aaagtgttca tggggaaaaa gctctgttta gcacatgatt     780
ttattgtatt gcgttattag ctgattttac tcattttata tttgcaaaat aaatttctaa     840
tatttattga aattgcttaa tttgcacacc ctgtacacac agaaatggt ataaaatatg      900 agaacgaagt ttaaaattgt gactctgatt cattatagca gaactttaaa tttcccagct     960
ttttgaagat ttaagctacg ctattagtac ttcccttgt ctgtgccata agtgcttgaa     1020
aacgttaagg ttttctgttt tgttttgttt ttttaatatc aaaagagtcg gtgtgaacct    1080
tggttggacc ccaagttcac aagattttta aggtgatgag agcctgcaga cattctgcct    1140
agatttacta gcgtgtgcct tttgcctgct tctctttgat ttcacagaat attcattcag    1200
aagtcgcgtt tctgtagtgt ggtggattcc cactgggctc tggtccttcc cttggatccc    1260
gtcagtggtg ctgctcagcg gcttgcacgt agacttgcta ggaagaaatg cagagccagc    1320
```

```
ctgtgctgcc cactttcaga gttgaactct ttaagccctt gtgagtgggc ttcaccagct    1380
actgcagagg cattttgcat ttgtctgtgt caagaagttc accttctcaa gccagtgaaa    1440
tacagactta attcgtcatg actgaacgaa tttgtttatt tcccattagg tttagtggag    1500
ctacacatta atatgtatcg ccttagagca agagctgtgt tccaggaacc agatcacgat    1560
ttttagccat ggaacaatat atcccatggg agaagacctt tcagtgtgaa ctgttctatt    1620
tttgtgttat aatttaaact tcgatttcct catagtcctt taagttgaca tttctgctta    1680
ctgctactgg attttgctg cagaaatata tcagtggccc acattaaaca taccagttgg     1740
atcatgataa gcaaaatgaa agaaataatg attaagggaa aattaagtga ctgtgttaca    1800
ctgcttctcc catgccagag aataaactct ttcaagcatc atctttgaag agtcgtgtgg    1860
tgtgaattgg tttgtgtaca ttagaatgta tgcacacatc catggacact caggatatag    1920
ttggcctaat aatcggggca tgggtaaaac ttatgaaaat ttcctcatgc tgaattgtaa    1980
ttttctctta cctgtaaagt aaaatttaga tcaattccat gtctttgtta agtacaggga    2040
tttaatatat tttgaatata atgggtatgt tctaaatttg aactttgaga ggcaatactg    2100
ttggaattat gtggattcta actcatttta acaaggtagc ctgacctgca taagatcact    2160
tgaatgttag gtttcataga actatactaa tcttctcaca aaaggtctat aaaatacagt    2220
cgttgaaaaa aattttgtat caaaatgttt ggaaaattag aagcttctcc ttaacctgta    2280
ttgatactga cttgaattat tttctaaaat taagagccgt atacctacct gtaagtctttt   2340 tcacatatca tttaaacttt tgtttgtatt attactgatt tacagcttag ttattaattt    2400
ttctttataa gaatgccgtc gatgtgcatg cttttatgtt tttcagaaaa gggtgtgttt    2460
ggatgaaagt aaaaaaaaaa ataaaatctt tcactgtctc taatggctgt gctgtttaac    2520 atttttgac cctaaaattc accaacagtc tcccagtaca taaaataggc ttaatgactg     2580
gccctgcatt cttcacaata ttttttccta agctttgagc aaagttttaa aaaaatacac    2640
taaaataatc aaaactgtta agcagtatat tagtttggtt atataaattc atctgcaatt    2700
tataagatgc atggccgatg ttaatttgct tggcaattct gtaatcatta agtgatctca    2760
gtgaaacatg tcaaatgcct taaattaact aagttggtga ataaaagtgc cgatctggct    2820
aactcttaca ccatacatac tgatagtttt tcatatgttt catttccatg tgattttaa    2880 aatttagagt ggcaacaatt ttgcttaata tgggttacat aagctttatt ttttcctttg    2940
ttcataatta tattctttga ataggtctgt gtcaatcaag tgatctaact agactgatca    3000
tagatagaag gaaataaggc caagttcaag accagcctgg gcaacatatc gagaacctgt    3060
ctacaaaaaa attaaaaaaa attagccagg catggtggcg tacactgagt agtttgtccc    3120
agctactcgg gagggtgagg tgggaggatc gcttcagccc aggaggttga gattgcagtg    3180
agccatggac ataccactgc actacagcct aggtaacagc acgagacccc aactcttaga    3240
aaatgaaaag gaaatataga aatataaaat ttgcttatta tagcacaca gtaactccca     3300 gatatgtacc acaaaaaatg tgaaagagag agaaatgtc taccaaagca gtattttgtg     3360
tgtataattg caagcgcata gtaaaataat tttaaccttta atttgttttt agtagtgttt   3420
agattgaaga ttgagtgaaa tattttcttg gcagatattc cgtatctggt ggaaagctac    3480
aatgcaatgt cgttgtagtt ttgcatggct tgctttataa acaagatttt ttctccctcc    3540
ttttgggcca gttttcatta cgagtaactc acacttttg attaaagaac ttgaaattac     3600
gttatcactt agtataattg acattatata gagactatgt aacatgcaat cattagaatc    3660
```

| | | | |
|---|---|---|---|
| aaaattagta | ctttggtcaa | aatatttaca | acattcacat acttgtcaaa tattcatgta | 3720 |
| attaactgaa | tttaaaacct | tcaactatta | tgaagtgctc gtctgtacaa tcgctaattt | 3780 |
| actcagttta | gagtagctac | aactcttcga | tactatcatc aatatttgac atcttttcca | 3840 |
| atttgtgtat | gaaaagtaaa | tctattcctg | tagcaactgg ggagtcatat atgaggtcaa | 3900 |
| agacatatac | cttgttatta | taatatgtat | actataataa tagctggtta tcctgagcag | 3960 |
| gggaaaaggt | tattttagg | aaaaccactt | caaatagaaa gctgaagtac ttctaatata | 4020 |
| ctgagggaag | tataatatgt | ggaacaaact | ctcaacaaaa tgtttattga tgttgatgaa | 4080 |
| acagatcagt | ttttccatcc | ggattattat | tggttcatga ttttatatgt gaatatgtaa | 4140 |
| gatatgttct | gcaattttat | aaatgttcat | gtcttttttt aaaaaaggtg ctattgaaat | 4200 |
| tctgtgtctc | cagcaggcaa | gaatacttga | ctaactcttt ttgtctcttt atggtatttt | 4260 |
| cagaataaag | tctgacttgt | gtttttgaga | ttattggtgc ctcattaatt cagcaataaa | 4320 |
| ggaaaatatg | catctcaaaa | at | | 4342 |

<210> SEQ ID NO 108
<211> LENGTH: 62
<212> TYPE: DNA
<213> ORGANISM: Homo sapiens

<400> SEQUENCE: 108
agattggatt cgtagattaa acttgagaaa caaaccataa aagtggaagg ccctctttaa       60
ca                                                                     62

<210> SEQ ID NO 109
<211> LENGTH: 86
<212> TYPE: DNA
<213> ORGANISM: Homo sapiens

<400> SEQUENCE: 109 gagatgggg tctcgctgtg ttgcccaggc tggtcttgga ctcaagcaat ctgcctgtct        60
cagcctacca aaatgctgga ttatag                                           86

<210> SEQ ID NO 110
<211> LENGTH: 116
<212> TYPE: DNA
<213> ORGANISM: Homo sapiens

<400> SEQUENCE: 110
gctaaagcag tcctcctgag tagttaggac tacagacata cacgtgccac cgcgcccagc       60
tccgtgttct ctttgtttcc ctgcctcctg ctcttccact tatctttgca tggcag          116

<210> SEQ ID NO 111
<211> LENGTH: 45
<212> TYPE: DNA
<213> ORGANISM: Homo sapiens

<400> SEQUENCE: 111
ggaaagacga tggagggcag cgaagagagt caccgaccat gacgg                      45

<210> SEQ ID NO 112
<211> LENGTH: 5138
<212> TYPE: DNA
<213> ORGANISM: Homo sapiens
<220> FEATURE:
<221> NAME/KEY: CDS
<222> LOCATION: 31..264
<221> NAME/KEY: polyA_signal

```
<222> LOCATION: 5111..5116
<223> OTHER INFORMATION: AATAAA

<400> SEQUENCE: 112
ctgctgtccc tggtgctcca cacgtactcc atg cgc tac ctg ctg ccc agc gtc         54
                                   Met Arg Tyr Leu Leu Pro Ser Val
                                    1               5 gtg ctc ctg ggc acg gcg ccc acc tac gtg ttg gcc tgg ggg gtc tgg        102
Val Leu Leu Gly Thr Ala Pro Thr Tyr Val Leu Ala Trp Gly Val Trp
     10              15                  20 cgg ctg ctc tcc gcc ttc ctg ccc gcc cgc ttc tac caa gcg ctg gac        150
Arg Leu Leu Ser Ala Phe Leu Pro Ala Arg Phe Tyr Gln Ala Leu Asp
 25              30                  35                  40 gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
                 45                  50                  55 aat tac acc ggg gtc cag ttg act gga ttg ttg ctg aca tct tgg cca        246
Asn Tyr Thr Gly Val Gln Leu Thr Gly Leu Leu Leu Thr Ser Trp Pro
             60                  65                  70 tca ggc aga atg cgc tag gacatgtgcg ctacgtgctg aaagaagggt               294
Ser Gly Arg Met Arg
             75 taaaatggct gccattgtat gggtgttact ttgctcagca tggaggaatc tatgtaaagc      354 gcagtgccaa atttaacgag aaagagatgc gaaacaagtt gcagagctac gtggacgcag      414 gaactccaat gtatcttgtg attttccag aaggtacaag gtataatcca gagcaaacaa       474 aagtcctttc agctagtcag gcatttgctg cccaacgtgg ccttgcagta ttaaaacatg      534 tgctaacacc acgaataaag gcaactcacg ttgcttttga ttgcatgaag aattatttag      594 atgcaatttta tgatgttacg gtggtttatg aagggaaaga cgatggaggg cagcgaagag     654 agtcaccgac catgacggaa tttctctgca aagaatgtcc aaaaattcat attcacattg      714 atcgtatcga caaaaaagat gtcccagaag aacaagaaca tatgagaaga tggctgcatg      774 aacgtttcga atcaaagat aagatgctta tagaatttta tgagtcacca gatccagaaa       834 gaagaaaaag atttcctggg aaaagtgtta attccaaatt aagtatcaag aagactttac      894 catcaatgtt gatcttaagt ggtttgactg caggcatgct tatgaccgat gctggaagga     954 agctgtatgt gaacacctgg atatatggaa ccctacttgg ctgcctgtgg gttactatta     1014 aagcatagac aagtagctgt ctccagacag tgggatgtgc tacattgtct atttttggcg    1074 gctgcacatg acatcaaatt gtttcctgaa tttattaagg agtgtaaata aagccttgtt    1134 gattgaagat tggataatag aatttgtgac gaaagctgat atgcaatggt cttgggcaaa    1194 catacctggt tgtacaactt tagcatcggg gctgctggaa gggtaaaagc taatggagt     1254 ttctcctgct ctgtccattt cctatgaact aatgacaact tgagaaggct gggaggattg    1314 tgtattttgc aagtcagatg gctgcatttt tgagcattaa tttgcagcgt atttcacttt    1374 ttctgttatt ttcaatttat tacaacttga cagctccaag ctcttattac taaagtattt    1434 agtatcttgc agctagttaa tatttcatct tttgcttatt tctacaagtc agtgaaataa    1494 attgtattta ggaagtgtca ggatgttcaa aggaaagggt aaaaagtgtt catggggaaa    1554 aagctctgtt tagcacatga ttttattgta ttgcgttatt agctgatttt actcattta     1614 tatttgcaaa ataaatttct aatatttatt gaaattgctt aatttgcaca ccctgtacac    1674 acagaaaatg gtataaaata tgagaacgaa gtttaaaatt gtgactctga ttcattatag    1734 cagaacttta aatttcccag cttttgaag atttaagcta cgctattagt acttcccttt     1794
```

-continued

```
gtctgtgcca taagtgcttg aaaacgttaa ggttttctgt tttgttttgt tttttaata    1854
tcaaaagagt cggtgtgaac cttggttgga ccccaagttc acaagatttt taaggtgatg   1914
agagcctgca gacattctgc ctagatttac tagcgtgtgc cttttgcctg cttctctttg   1974
atttcacaga atattcattc agaagtcgcg tttctgtagt gtggtggatt cccactgggc   2034
tctggtcctt cccttggatc ccgtcagtgg tgctgctcag cggcttgcac gtagacttgc   2094
taggaagaaa tgcagagcca gcctgtgctg cccactttca gagttgaact ctttaagccc   2154
ttgtgagtgg gcttcaccag ctactgcaga ggcattttgc atttgtctgt gtcaagaagt   2214
tcaccttctc aagccagtga aatacagact taattcgtca tgactgaacg aatttgttta   2274
tttcccatta ggtttagtgg agctacacat taatatgtat cgccttagag caagagctgt   2334
gttccaggaa ccagatcacg atttttagcc atggaacaat atatcccatg ggagaagacc   2394
tttcagtgtg aactgttcta tttttgtgtt ataatttaaa cttcgatttc ctcatagtcc   2454
tttaagttga catttctgct tactgctact ggattttgc tgcagaaata tatcagtggc    2514
ccacattaaa cataccagtt ggatcatgat aagcaaaatg aaagaaataa tgattaaggg   2574
aaaattaagt gactgtgtta cactgcttct cccatgccag agaataaact ctttcaagca   2634
tcatctttga agagtcgtgt ggtgtgaatt ggtttgtgta cattagaatg tatgcacaca   2694
tccatggaca ctcaggatat agttggccta ataatcgggg catgggtaaa acttatgaaa   2754
atttcctcat gctgaattgt aattttctct tacctgtaaa gtaaaattta gatcaattcc   2814
atgtctttgt taagtacagg gatttaatat attttgaata taatgggtat gttctaaatt   2874
tgaactttga gaggcaatac tgttggaatt atgtggattc taactcatt taacaaggta    2934
gcctgacctg cataagatca cttgaatgtt aggtttcata gaactatact aatcttctca   2994
caaaaggtct ataaaataca gtcgttgaaa aaatttttgt atcaaaatgt ttggaaaatt   3054
agaagcttcc ccttaacctg tattgatact gacttgaatt attttctaaa attaagagcc   3114
gtatacctac ctgtaagtct tttcacatat catttaaact tttgtttgta ttattactga   3174
tttacagctt agttattaat ttttcttat aagaatgccg tcgatgtgca tgcttttatg    3234
ttttcagaa aagggtgtgt ttggatgaaa gtaaaaaaaa aataaaaatc tttcactgtc    3294
tctaatggct gtgctgttta acatttttg accctaaaat tcaccaacag tctcccagta    3354
cataaaatag gcttaatgac tggccctgca ttcttcacaa tattttccc taagctttga    3414
gcaaagtttt aaaaaaatac actaaaataa tcaaaactgt taagcagtat attagtttgg   3474
ttatataaat tcatctgcaa tttataagat gcatggccga tgttaatttg cttggcaatt   3534
ctgtaatcat taagtgatct cagtgaaaca tgtcaaatgc cttaaattaa ctaagttggt   3594
gaataaaagt gccgatctgg ctaactctta caccatacat actgatagtt tttcatatgt   3654
ttcatttcca tgtgattttt aaaatttaga gtggcaacaa ttttgcttaa tatgggttac   3714
ataagcttta ttttttcctt tgttcataat tatattcttt gaataggtct gtgtcaatca   3774
agtgatctaa ctagactgat catagataga aggaaataag gccaagttca agaccagcct   3834
gggcaacata tcgagaacct gtctacaaaa aaattaaaaa aaattagcca ggcatggtgg   3894
cgtacactga gtagtttgtc ccagctactc gggagggtga ggtgggagga tcgcttcagc   3954
ccaggaggtt gagattgcag tgagccatgg acataccact gcactacagc ctaggtaaca   4014
gcacgagacc ccaactctta gaaaatgaaa aggaaatata gaaatataaa atttgcttat   4074
tatagacaca cagtaactcc cagatatgta ccacaaaaaa tgtgaaaaga gagagaaatg   4134
tctaccaaag cagtattttg tgtgtataat tgcaagcgca tagtaaaata attttaacct   4194
```

| | |
|---|---|
| taatttgttt ttagtagtgt ttagattgaa gattgagtga aatatttct tggcagatat | 4254 |
| tccgtatctg gtggaaagct acaatgcaat gtcgttgtag ttttgcatgg cttgctttat | 4314 |
| aaacaagatt ttttctccct ccttttgggc cagttttcat tacgagtaac tcacactttt | 4374 |
| tgattaaaga acttgaaatt acgttatcac ttagtataat tgacattata tagagactat | 4434 |
| gtaacatgca atcattagaa tcaaaattag tactttggtc aaaatattta caacattcac | 4494 |
| atacttgtca aatattcatg taattaactg aatttaaaac cttcaactat tatgaagtgc | 4554 |
| tcgtctgtac aatcgctaat ttactcagtt tagagtagct acaactcttc gatactatca | 4614 |
| tcaatatttg acatcttttc caatttgtgt atgaaaagta aatctattcc tgtagcaact | 4674 |
| ggggagtcat atatgaggtc aaagacatat accttgttat tataatatgt atactataat | 4734 |
| aatagctggt tatcctgagc aggggaaaag gttatttta ggaaaaccac ttcaaataga | 4794 |
| aagctgaagt acttctaata tactgaggga agtataaat gtggaacaaa ctctcaacaa | 4854 |
| aatgtttatt gatgttgatg aaacagatca gttttccat ccggattatt attggttcat | 4914 |
| gattttatat gtgaatatgt aagatatgtt ctgcaattt ataaatgttc atgtcttttt | 4974 |
| ttaaaaaagg tgctattgaa attctgtgtc tccagcaggc aagaatactt gactaactct | 5034 |
| ttttgtctct ttatggtatt ttcagaataa agtctgactt gtgttttga gattattggt | 5094 |
| gcctcattaa ttcagcaata aaggaaaata tgcatctcaa aaat | 5138 |

<210> SEQ ID NO 113
<211> LENGTH: 5224
<212> TYPE: DNA
<213> ORGANISM: Homo sapiens
<220> FEATURE:
<221> NAME/KEY: CDS
<222> LOCATION: 31..264
<221> NAME/KEY: polyA_signal
<222> LOCATION: 5197..5202
<223> OTHER INFORMATION: AATAAA

<400> SEQUENCE: 113

| | |
|---|---|
| ctgctgtccc tggtgctcca cacgtactcc atg cgc tac ctg ctg ccc agc gtc<br>                                               Met Arg Tyr Leu Leu Pro Ser Val<br>                                                1               5 | 54 |
| gtg ctc ctg ggc acg gcg ccc acc tac gtg ttg gcc tgg ggg gtc tgg<br>Val Leu Leu Gly Thr Ala Pro Thr Tyr Val Leu Ala Trp Gly Val Trp<br>    10               15               20 | 102 |
| cgg ctg ctc tcc gcc ttc ctg ccc gcc cgc ttc tac caa gcg ctg gac<br>Arg Leu Leu Ser Ala Phe Leu Pro Ala Arg Phe Tyr Gln Ala Leu Asp<br>25                30               35               40 | 150 |
| gac cgg ctg tac tgc gtc tac cag agc atg gtg ctc ttc ttc ttc gag<br>Asp Arg Leu Tyr Cys Val Tyr Gln Ser Met Val Leu Phe Phe Phe Glu<br>                  45               50               55 | 198 |
| aat tac acc ggg gtc cag ttg act gga ttg ttg ctg aca tct tgg cca<br>Asn Tyr Thr Gly Val Gln Leu Thr Gly Leu Leu Leu Thr Ser Trp Pro<br>              60               65               70 | 246 |
| tca ggc aga atg cgc tag gacatgtgcg ctacgtgctg aaagaagggt<br>Ser Gly Arg Met Arg<br>        75 | 294 |
| taaaatggct gccattgtat gggtgttact ttgctcagga gatggggtc tcgctgtgtt | 354 |
| gcccaggctg gtcttggact caagcaatct gcctgtctca gcctaccaaa atgctggatt | 414 |
| atagcatgga ggaatctatg taaagcgcag tgccaaattt aacgagaaag agatgcgaaa | 474 |
| caagttgcag agctacgtgg acgcaggaac tccaatgtat cttgtgattt ttccagaagg | 534 |

```
tacaaggtat aatccagagc aaacaaaagt cctttcagct agtcaggcat ttgctgccca      594
acgtggcctt gcagtattaa acatgtgct aacaccacga ataaaggcaa ctcacgttgc       654
ttttgattgc atgaagaatt atttagatgc aatttatgat gttacggtgg tttatgaagg     714
gaaagacgat ggagggcagc gaagagagtc accgaccatg acggaatttc tctgcaaaga    774
atgtccaaaa attcatattc acattgatcg tatcgacaaa aaagatgtcc cagaagaaca    834
agaacatatg agaagatggc tgcatgaacg tttcgaaatc aaagataaga tgcttataga   894
atttatgag tcaccagatc cagaaagaag aaaaagattt cctgggaaaa gtgttaattc     954
caaattaagt atcaagaaga ctttaccatc aatgttgatc ttaagtggtt tgactgcagg   1014
catgcttatg accgatgctg gaaggaagct gtatgtgaac acctggatat atggaaccct   1074
acttggctgc ctgtgggtta ctattaaagc atagacaagt agctgtctcc agacagtggg   1134
atgtgctaca ttgtctattt ttggcggctg cacatgacat caaattgttt cctgaattta   1194
ttaaggagtg taaataaagc cttgttgatt gaagattgga aatagaatt tgtgacgaaa    1254
gctgatatgc aatggtcttg gcaaacata cctggttgta caactttagc atcgggctg     1314
ctggaagggt aaaagctaaa tggagtttct cctgctctgt ccatttccta tgaactaatg   1374
acaacttgag aaggctggga ggattgtgta ttttgcaagt cagatggctg catttttgag   1434
cattaatttg cagcgtattt cacttttct gttattttca atttattaca acttgacagc    1494
tccaagctct tattactaaa gtatttagta tcttgcagct agttaatatt tcatcttttg   1554
cttatttcta caagtcagtg aaataaattg tatttaggaa gtgtcaggat gttcaaagga   1614
aagggtaaaa agtgttcatg gggaaaaagc tctgtttagc acatgatttt attgtattgc   1674
gttattagct gattttactc attttatatt tgcaaaataa atttctaata tttattgaaa   1734
ttgcttaatt tgcacaccct gtacacacag aaaatggtat aaaatatgag aacgaagttt   1794
aaaattgtga ctctgattca ttatagcaga actttaaatt tcccagcttt ttgaagattt   1854
aagctacgct attagtactt cccttgtct gtgccataag tgcttgaaaa cgttaaggtt    1914
ttctgttttg ttttgttttt ttaatatcaa aagagtcggt gtgaaccttg gttggacccc   1974
aagttcacaa gatttttaag gtgatgagag cctgcagaca ttctgcctag atttactagc   2034
gtgtgccttt tgcctgcttc tctttgattt cacagaatat tcattcagaa gtcgcgtttc   2094
tgtagtgtgg tggattccca ctgggctctg gtccttccct tggatcccgt cagtggtgct   2154
gctcagcggc ttgcacgtag acttgctagg aagaaatgca gagccagcct gtgctgccca   2214
ctttcagagt tgaactcttt aagcccttgt gagtgggctt caccagctac tgcagaggca   2274
ttttgcattt gtctgtgtca agaagttcac cttctcaagc cagtgaaata cagacttaat   2334
tcgtcatgac tgaacgaatt tgtttatttc ccattaggtt tagtggagct acacattaat   2394
atgtatcgcc ttagagcaag agctgtgttc caggaaccag atcacgattt ttagccatgg   2454
aacaatatat cccatgggag aagacctttc agtgtgaact gttctatttt tgtgttataa   2514
tttaaacttc gatttcctca tagtcccttta agttgacatt tctgcttact gctactggat  2574
ttttgctgca gaaatatatc agtggcccac attaaacata ccagttggat catgataagc   2634
aaaatgaaag aaataatgat taagggaaaa ttaagtgact gtgttacact gcttctccca   2694
tgccagagaa taaactcttt caagcatcat ctttgaagag tcgtgtggtg tgaattggtt   2754
tgtgtacatt agaatgtatg cacacatcca tggacactca ggatatagtt ggcctaataa   2814
tcggggcatg ggtaaaactt atgaaaattt cctcatgctg aattgtaatt ttctcttacc   2874
tgtaaagtaa aatttagatc aattccatgt ctttgttaag tacagggatt taatatattt   2934
```

```
tgaatataat gggtatgttc taaatttgaa ctttgagagg caatactgtt ggaattatgt    2994
ggattctaac tcattttaac aaggtagcct gacctgcata agatcacttg aatgttaggt    3054
ttcatagaac tatactaatc ttctcacaaa aggtctataa aatacagtcg ttgaaaaaaa    3114
ttttgtatca aaatgtttgg aaaattagaa gcttctcctt aacctgtatt gatactgact    3174
tgaattattt tctaaaatta agagccgtat acctacctgt aagtcttttc acatatcatt    3234
taaacttttg tttgtattat tactgattta cagcttagtt attaatttt ctttataaga     3294
atgccgtcga tgtgcatgct tttatgtttt tcagaaaagg gtgtgtttgg atgaaagtaa    3354
aaaaaaaaat aaaatctttc actgtctcta atggctgtgc tgtttaacat tttttgaccc    3414
taaaattcac caacagtctc ccagtacata aaataggctt aatgactggc cctgcattct    3474
tcacaatatt tttccctaag ctttgagcaa agttttaaaa aaatacacta aataatcaa     3534
aactgttaag cagtatatta gtttggttat ataaattcat ctgcaattta taagatgcat    3594
ggccgatgtt aatttgcttg gcaattctgt aatcattaag tgatctcagt gaaacatgtc    3654
aaatgcctta aattaactaa gttggtgaat aaaagtgccg atctggctaa ctcttacacc    3714
atacatactg atagtttttc atatgtttca tttccatgtg attttttaaaa tttagagtgg   3774
caacaatttt gcttaatatg ggttacataa gctttattt ttccttttgtt cataattata    3834
ttctttgaat aggtctgtgt caatcaagtg atctaactag actgatcata gatagaagga    3894
aataaggcca agttcaagac cagcctgggc aacatatcga gaacctgtct acaaaaaaat   3954
taaaaaaaat tagccaggca tggtggcgta cactgagtag tttgtcccag ctactcggga    4014
gggtgaggtg ggaggatcgc ttcagcccag gaggttgaga ttgcagtgag ccatggacat    4074
accactgcac tacagcctag gtaacagcac gagacccccaa ctcttagaaa atgaaaagga   4134
aatatagaaa tataaaattt gcttattata gacacacagt aactcccaga tatgtaccac    4194
aaaaaatgtg aaaagagaga gaaatgtcta ccaaagcagt attttgtgtg tataattgca    4254
agcgcatagt aaaataattt taaccttaat ttgttttag tagtgtttag attgaagatt     4314
gagtgaaata ttttcttggc agatattccg tatctggtgg aaagctacaa tgcaatgtcg    4374
ttgtagtttt gcatggcttg ctttataaac aagatttttt ctccctcctt ttgggccagt    4434
tttcattacg agtaactcac acttttgat taaagaactt gaaattacgt tatcacttag     4494
tataattgac attatataga gactatgtaa catgcaatca ttagaatcaa aattagtact    4554
ttggtcaaaa tatttacaac attcacatac ttgtcaaata ttcatgtaat taactgaatt    4614
taaaccttc aactattatg aagtgctcgt ctgtacaatc gctaatttac tcagtttaga     4674
gtagctacaa ctcttcgata ctatcatcaa tatttgacat cttttccaat ttgtgtatga    4734
aaagtaaatc tattcctgta gcaactgggg agtcatatat gaggtcaaag acatatacct    4794
tgttattata atatgtatac tataataata gctggttatc ctgagcaggg gaaaaggtta    4854
tttttaggaa aaccacttca aatagaaagc tgaagtactt ctaatatact gagggaagta    4914
taatatgtgg aacaaactct caacaaaatg tttattgatg ttgatgaaac agatcagtttt   4974
ttccatccgg attattattg gttcatgatt ttatatgtga atatgtaaga tatgttctgc    5034
aattttataa atgttcatgt cttttttaa aaaggtgct attgaaattc tgtgtctcca     5094
gcaggcaaga atacttgact aactcttttt gtctctttat ggtattttca gaataaagtc    5154
tgacttgtgt ttttgagatt attggtgcct cattaattca gcaataaagg aaaatatgca    5214
tctcaaaaat                                                           5224
```

<210> SEQ ID NO 114
<211> LENGTH: 4863
<212> TYPE: DNA
<213> ORGANISM: Homo sapiens
<220> FEATURE:
<221> NAME/KEY: CDS
<222> LOCATION: 31..747
<221> NAME/KEY: polyA_signal
<222> LOCATION: 4836..4841
<223> OTHER INFORMATION: AATAAA

<400> SEQUENCE: 114

```
ctgctgtccc tggtgctcca cacgtactcc atg cgc tac ctg ctg ccc agc gtc         54
                                 Met Arg Tyr Leu Leu Pro Ser Val
                                  1               5 gtg ctc ctg ggc acg gcg ccc acc tac gtg ttg gcc tgg ggg gtc tgg         102
Val Leu Leu Gly Thr Ala Pro Thr Tyr Val Leu Ala Trp Gly Val Trp
 10              15                  20 cgg ctg ctc tcc gcc ttc ctg ccc gcc cgc ttc tac caa gcg ctg gac         150
Arg Leu Leu Ser Ala Phe Leu Pro Ala Arg Phe Tyr Gln Ala Leu Asp
 25                  30                  35                  40 gac cgg ctg tac tgc gtc tac cag agc atg gtg ctc ttc ttc ttc gag         198
Asp Arg Leu Tyr Cys Val Tyr Gln Ser Met Val Leu Phe Phe Phe Glu
                 45                  50                  55 aat tac acc ggg gtc cag cat gga gga atc tat gta aag cgc agt gcc         246
Asn Tyr Thr Gly Val Gln His Gly Gly Ile Tyr Val Lys Arg Ser Ala
             60                  65                  70 aaa ttt aac gag aaa gag atg cga aac aag ttg cag agc tac gtg gac         294
Lys Phe Asn Glu Lys Glu Met Arg Asn Lys Leu Gln Ser Tyr Val Asp
         75                  80                  85 gca gga act cca atg tat ctt gtg att ttt cca gaa ggt aca agg tat         342
Ala Gly Thr Pro Met Tyr Leu Val Ile Phe Pro Glu Gly Thr Arg Tyr
     90                  95                 100 aat cca gag caa aca aaa gtc ctt tca gct agt cag gca ttt gct gcc         390
Asn Pro Glu Gln Thr Lys Val Leu Ser Ala Ser Gln Ala Phe Ala Ala
105                 110                 115                 120 caa cgt gaa ttt ctc tgc aaa gaa tgt cca aaa att cat att cac att         438
Gln Arg Glu Phe Leu Cys Lys Glu Cys Pro Lys Ile His Ile His Ile
                125                 130                 135 gat cgt atc gac aaa aaa gat gtc cca gaa gaa caa gaa cat atg aga         486
Asp Arg Ile Asp Lys Lys Asp Val Pro Glu Glu Gln Glu His Met Arg
            140                 145                 150 aga tgg ctg cat gaa cgt ttc gaa atc aaa gat aag atg ctt ata gaa         534
Arg Trp Leu His Glu Arg Phe Glu Ile Lys Asp Lys Met Leu Ile Glu
        155                 160                 165 ttt tat gag tca cca gat cca gaa aga aga aaa aga ttt cct ggg aaa         582
Phe Tyr Glu Ser Pro Asp Pro Glu Arg Arg Lys Arg Phe Pro Gly Lys
    170                 175                 180 agt gtt aat tcc aaa tta agt atc aag aag act tta cca tca atg ttg         630
Ser Val Asn Ser Lys Leu Ser Ile Lys Lys Thr Leu Pro Ser Met Leu
185                 190                 195                 200 atc tta agt ggt ttg act gca ggc atg ctt atg acc gat gct gga agg         678
Ile Leu Ser Gly Leu Thr Ala Gly Met Leu Met Thr Asp Ala Gly Arg
                205                 210                 215 aag ctg tat gtg aac acc tgg ata tat gga acc cta ctt ggc tgc ctg         726
Lys Leu Tyr Val Asn Thr Trp Ile Tyr Gly Thr Leu Leu Gly Cys Leu
            220                 225                 230 tgg gtt act att aaa gca tag acaagtagct gtctccagac agtgggatgt           777
Trp Val Thr Ile Lys Ala
                235 gctacattgt ctattttggg cggctgcaca tgacatcaaa ttgtttcctg aatttattaa      837
```

```
ggagtgtaaa taaagccttg ttgattgaag attggataat agaatttgtg acgaaagctg    897
atatgcaatg gtcttgggca aacatacctg gttgtacaac tttagcatcg ggctgctgg     957
aagggtaaaa gctaaatgga gtttctcctg ctctgtccat ttcctatgaa ctaatgacaa   1017
cttgagaagg ctgggaggat tgtgtatttt gcaagtcaga tggctgcatt tttgagcatt   1077
aatttgcagc gtatttcact ttttctgtta ttttcaattt attacaactt gacagctcca   1137
agctcttatt actaaagtat ttagtatctt gcagctagtt aatatttcat cttttgctta   1197
tttctacaag tcagtgaaat aaattgtatt taggaagtgt caggatgttc aaaggaaagg   1257
gtaaaaagtg ttcatgggga aaaagctctg tttagcacat gattttattg tattgcgtta   1317
ttagctgatt ttactcattt tatatttgca aaataaattt ctaatattta ttgaaattgc   1377
ttaatttgca caccctgtac acacagaaaa tggtataaaa tatgagaacg aagtttaaaa   1437
ttgtgactct gattcattat agcagaactt taaatttccc agcttttga agatttaagc    1497
tacgctatta gtacttccct ttgtctgtgc cataagtgct tgaaaacgtt aaggttttct   1557
gttttgtttt gttttttttaa tatcaaaaga gtcggtgtga accttggttg accccaagt   1617
tcacaagatt tttaaggtga tgagagcctg cagacattct gcctagattt actagcgtgt   1677
gccttttgcc tgcttctctt tgatttcaca gaatattcat tcagaagtcg cgttctgta    1737
gtgtggtgga ttcccactgg gctctggtcc ttcccttgga tcccgtcagt ggtgctgctc   1797
agcggcttgc acgtagactt gctaggaaga aatgcagagc cagcctgtgc tgcccacttt   1857
cagagttgaa ctctttaagc ccttgtgagt gggcttcacc agctactgca gaggcatttt   1917
gcatttgtct gtgtcaagaa gttcaccttc tcaagccagt gaaatacaga cttaattcgt   1977
catgactgaa cgaatttgtt tatttcccat taggtttagt ggagctacac attaatatgt   2037
atcgccttag agcaagagct gtgttccagg aaccagatca cgattttttag ccatggaaca   2097
atatatccca tgggagaaga cctttcagtg tgaactgttc tattttttgtg ttataattta   2157
aacttcgatt tcctcatagt cctttaagtt gacatttctg cttactgcta ctggattttt   2217
gctgcagaaa tatatcagtg gcccacatta acataccag ttggatcatg ataagcaaaa    2277
tgaaagaaat aatgattaag ggaaaattaa gtgactgtgt tacactgctt ctcccatgcc   2337
agagaataaa ctcttttcaag catcatcttt gaagagtcgt gtggtgtgaa ttggtttgtg   2397
tacattagaa tgtatgcaca catccatgga cactcaggat atagttggcc taataatcgg   2457
ggcatgggta aaacttatga aaatttcctc atgctgaatt gtaattttct cttacctgta   2517
aagtaaaatt tagatcaatt ccatgtcttt gttaagtaca gggatttaat atattttgaa   2577
tataatgggt atgttctaaa tttgaacttt gagaggcaat actgttggaa ttatgtggat   2637
tctaactcat tttaacaagg tagcctgacc tgcataagat cacttgaatg ttaggtttca   2697
tagaactata ctaatcttct cacaaaaggt ctataaaata cagtcgttga aaaaaatttt   2757
gtatcaaaat gtttggaaaa ttagaagctt ctccttaacc tgtattgata ctgacttgaa   2817
ttattttcta aaattaagag ccgtatacct acctgtaagt cttttcacat atcatttaaa   2877
cttttgtttg tattattact gatttacagc ttagttatta attttttcttt ataagaatgc   2937
cgtcgatgtg catgctttta tgttttttcag aaaagggtgt gtttggatga agtaaaaaa    2997
aaaaataaaa tctttcactg tctctaatgg ctgtgctgtt aacattttt tgaccctaaa    3057
attcaccaac agtctcccag tacataaaat aggcttaatg actggccctg cattcttcac   3117
aatattttc cctaagcttt gagcaaagtt ttaaaaaaat acactaaaat aatcaaaact    3177
```

```
gttaagcagt atattagttt ggttatataa attcatctgc aatttataag atgcatggcc    3237
gatgttaatt tgcttggcaa ttctgtaatc attaagtgat ctcagtgaaa catgtcaaat    3297
gccttaaatt aactaagttg gtgaataaaa gtgccgatct ggctaactct tacaccatac    3357
atactgatag ttttcatat gtttcatttc catgtgattt ttaaaattta gagtggcaac     3417
aattttgctt aatatgggtt acataagctt tattttttcc tttgttcata attatattct    3477
ttgaataggt ctgtgtcaat caagtgatct aactagactg atcatagata aaggaaata     3537 aggccaagtt caagaccagc ctgggcaaca tatcgagaac ctgtctacaa aaaaattaaa    3597
aaaaattagc caggcatggt ggcgtacact gagtagtttg tcccagctac tcgggagggt    3657
gaggtgggag gatcgcttca gcccaggagg ttgagattgc agtgagccat ggacatacca    3717
ctgcactaca gcctaggtaa cagcacgaga ccccaactct tagaaaatga aaggaaata    3777 tagaaatata aaatttgctt attatagaca cacagtaact cccagatatg taccacaaaa    3837
aatgtgaaaa gagagagaaa tgtctaccaa agcagtattt tgtgtgtata attgcaagcg    3897
catagtaaaa taattttaac cttaatttgt tttagtagt gtttagattg aagattgagt     3957
gaaatatttt cttggcagat attccgtatc tggtggaaag ctacaatgca atgtcgttgt    4017
agttttgcat ggcttgcttt ataaacaaga tttttctcc ctccttttgg gccagttttc     4077
attacgagta actcacactt tttgattaaa gaacttgaaa ttacgttatc acttagtata    4137
attgacatta tatagagact atgtaacatg caatcattag aatcaaaatt agtactttgg    4197
tcaaaatatt tacaacattc acatacttgt caaatattca tgtaattaac tgaatttaaa    4257
accttcaact attatgaagt gctcgtctgt acaatcgcta atttactcag tttagagtag    4317
ctacaactct tcgatactat catcaatatt tgacatcttt tccaatttgt gtatgaaaag    4377
taaatctatt cctgtagcaa ctggggagtc atatatgagg tcaaagacat ataccttgtt    4437
attataatat gtatactata ataatagctg gttatcctga gcaggggaaa aggttatttt    4497
taggaaaacc acttcaaata gaaagctgaa gtacttctaa tatactgagg gaagtataat    4557
atgtggaaca aactctcaac aaaatgttta ttgatgttga tgaaacagat cagtttttcc    4617
atccggatta ttattggttc atgatttat atgtgaatat gtaagatatg ttctgcaatt     4677
ttataaatgt tcatgtcttt ttttaaaaaa ggtgctattg aaattctgtg tctccagcag    4737
gcaagaatac ttgactaact cttttgtct ctttatggta ttttcagaat aaagtctgac     4797
ttgtgttttt gagattattg gtgcctcatt aattcagcaa taaggaaaa tatgcatctc     4857 aaaaat                                                                4863
```

<210> SEQ ID NO 115
<211> LENGTH: 5022
<212> TYPE: DNA
<213> ORGANISM: Homo sapiens
<220> FEATURE:
<221> NAME/KEY: CDS
<222> LOCATION: 31..906
<221> NAME/KEY: polyA_signal
<222> LOCATION: 4995..5000
<223> OTHER INFORMATION: AATAAA

<400> SEQUENCE: 115

```
ctgctgtccc tggtgctcca cacgtactcc atg cgc tac ctg ctg ccc agc gtc      54
                                 Met Arg Tyr Leu Leu Pro Ser Val
                                   1               5 gtg ctc ctg ggc acg gcg ccc acc tac gtg ttg gcc tgg ggg gtc tgg      102
Val Leu Leu Gly Thr Ala Pro Thr Tyr Val Leu Ala Trp Gly Val Trp
     10                  15                  20
```

```
cgg ctg ctc tcc gcc ttc ctg ccc gcc cgc ttc tac caa gcg ctg gac    150
Arg Leu Leu Ser Ala Phe Leu Pro Ala Arg Phe Tyr Gln Ala Leu Asp
 25              30                  35                  40 gac cgg ctg tac tgc gtc tac cag agc atg gtg ctc ttc ttc ttc gag    198
Asp Arg Leu Tyr Cys Val Tyr Gln Ser Met Val Leu Phe Phe Phe Glu
                 45                  50                  55 aat tac acc ggg gtc cag cat gga gga atc tat gta aag cgc agt gcc    246
Asn Tyr Thr Gly Val Gln His Gly Gly Ile Tyr Val Lys Arg Ser Ala
             60                  65                  70 aaa ttt aac gag aaa gag atg cga aac aag ttg cag agc tac gtg gac    294
Lys Phe Asn Glu Lys Glu Met Arg Asn Lys Leu Gln Ser Tyr Val Asp
         75                  80                  85 gca gga act cca atg tat ctt gtg att ttt cca gaa ggt aca agg tat    342
Ala Gly Thr Pro Met Tyr Leu Val Ile Phe Pro Glu Gly Thr Arg Tyr
     90                  95                  100 aat cca gag caa aca aaa gtc ctt tca gct agt cag gca ttt gct gcc    390
Asn Pro Glu Gln Thr Lys Val Leu Ser Ala Ser Gln Ala Phe Ala Ala
105                 110                 115                 120 caa cgt ggc ctt gca gta tta aaa cat gtg cta aca cca cga ata aag    438
Gln Arg Gly Leu Ala Val Leu Lys His Val Leu Thr Pro Arg Ile Lys
                125                 130                 135 gca act cac gtt gct ttt gat tgc atg aag aat tat tta gat gca att    486
Ala Thr His Val Ala Phe Asp Cys Met Lys Asn Tyr Leu Asp Ala Ile
            140                 145                 150 tat gat gtt acg gtg gtt tat gaa ggg aaa gac gat gga ggg cag cga    534
Tyr Asp Val Thr Val Val Tyr Glu Gly Lys Asp Asp Gly Gly Gln Arg
                155                 160                 165 aga gag tca ccg acc atg acg gaa ttt ctc tgc aaa gaa tgt cca aaa    582
Arg Glu Ser Pro Thr Met Thr Glu Phe Leu Cys Lys Glu Cys Pro Lys
        170                 175                 180 att cat att cac att gat cgt atc gac aaa aaa gat gtc cca gaa gaa    630
Ile His Ile His Ile Asp Arg Ile Asp Lys Lys Asp Val Pro Glu Glu
185                 190                 195                 200 caa gaa cat atg aga aga tgg ctg cat gaa cgt ttc gaa atc aaa gat    678
Gln Glu His Met Arg Arg Trp Leu His Glu Arg Phe Glu Ile Lys Asp
                205                 210                 215 aag atg ctt ata gaa ttt tat gag tca cca gat cca gaa aga aga aaa    726
Lys Met Leu Ile Glu Phe Tyr Glu Ser Pro Asp Pro Glu Arg Arg Lys
            220                 225                 230 aga ttt cct ggg aaa agt gtt aat tcc aaa tta agt atc aag aag act    774
Arg Phe Pro Gly Lys Ser Val Asn Ser Lys Leu Ser Ile Lys Lys Thr
        235                 240                 245 tta cca tca atg ttg atc tta agt ggt ttg act gca ggc atg ctt atg    822
Leu Pro Ser Met Leu Ile Leu Ser Gly Leu Thr Ala Gly Met Leu Met
250                 255                 260 acc gat gct gga agg aag ctg tat gtg aac acc tgg ata tat gga acc    870
Thr Asp Ala Gly Arg Lys Leu Tyr Val Asn Thr Trp Ile Tyr Gly Thr
                265                 270                 275                 280 cta ctt ggc tgc ctg tgg gtt act att aaa gca tag acaagtagct         916
Leu Leu Gly Cys Leu Trp Val Thr Ile Lys Ala
            285                 290 gtctccagac agtgggatgt gctacattgt ctattttggg cggctgcaca tgacatcaaa    976
ttgtttcctg aatttattaa ggagtgtaaa taaagccttg ttgattgaag attggataat    1036
agaatttgtg acgaaagctg atatgcaatg gtcttgggca acatacctg gttgtacaac    1096 tttagcatcg gggctgctgg aagggtaaaa gctaaatgga gtttctcctg ctctgtccat    1156
ttcctatgaa ctaatgacaa cttgagaagg ctgggaggat tgtgtatttt gcaagtcaga    1216
```

```
tggctgcatt tttgagcatt aatttgcagc gtatttcact ttttctgtta ttttcaattt    1276
attacaactt gacagctcca agctcttatt actaaagtat ttagtatctt gcagctagtt    1336
aatatttcat cttttgctta tttctacaag tcagtgaaat aaattgtatt taggaagtgt    1396
caggatgttc aaaggaaagg gtaaaaagtg ttcatgggga aaaagctctg tttagcacat    1456
gattttattg tattgcgtta ttagctgatt ttactcattt tatatttgca aaataaattt    1516
ctaatattta ttgaaattgc ttaatttgca caccctgtac acacagaaaa tggtataaaa    1576
tatgagaacg aagtttaaaa ttgtgactct gattcattat agcagaactt taaatttccc    1636 agcttttga agatttaagc tacgctatta gtacttccct ttgtctgtgc cataagtgct    1696
tgaaaacgtt aaggttttct gttttgtttt gttttttttaa tatcaaaaga gtcggtgtga    1756
accttggttg gaccccaagt tcacaagatt tttaaggtga tgagagcctg cagacattct    1816
gcctagattt actagcgtgt gccttttgcc tgcttctctt tgatttcaca gaatattcat    1876
tcagaagtcg cgtttctgta gtgtggtgga ttcccactgg gctctggtcc ttcccttgga    1936
tcccgtcagt ggtgctgctc agcggcttgc acgtagactt gctaggaaga aatgcagagc    1996
cagcctgtgc tgcccacttt cagagttgaa ctctttaagc ccttgtgagt gggcttcacc    2056
agctactgca gaggcatttt gcatttgtct gtgtcaagaa gttcaccttc tcaagccagt    2116
gaaatacaga cttaattcgt catgactgaa cgaatttgtt tatttcccat taggtttagt    2176
ggagctacac attaatatgt atcgccttag agcaagagct gtgttccagg aaccagatca    2236 cgattttttag ccatggaaca atatatccca tgggagaaga cctttcagtg tgaactgttc    2296 tattttttgtg ttataattta aacttcgatt tcctcatagt cctttaagtt gacatttctg    2356
cttactgcta ctggattttt gctgcagaaa tatatcagtg gcccacatta aacataccag    2416
ttggatcatg ataagcaaaa tgaaagaaat aatgattaag ggaaaattaa gtgactgtgt    2476
tacactgctt ctcccatgcc agagaataaa ctctttcaag catcatcttt gaagagtcgt    2536
gtggtgtgaa ttggtttgtg tacattagaa tgtatgcaca catccatgga cactcaggat    2596
atagttggcc taataatcgg ggcatgggta aaacttatga aaatttcctc atgctgaatt    2656 gtaatttttct cttacctgta aagtaaaatt tagatcaatt ccatgtcttt gttaagtaca    2716
gggatttaat atattttgaa tataatgggt atgttctaaa tttgaacttt gagaggcaat    2776
actgttggaa ttatgtggat tctaactcat tttaacaagg tagcctgacc tgcataagat    2836
cacttgaatg ttaggtttca tagaactata ctaatcttct cacaaaaggt ctataaaata    2896
cagtcgttga aaaaaatttt gtatcaaaat gtttggaaaa ttagaagctt ctccttaacc    2956
tgtattgata ctgacttgaa ttattttcta aaattaagag ccgtatacct acctgtaagt    3016
cttttcacat atcatttaaa cttttgtttg tattattact gatttacagc ttagttatta    3076 attttttcttt ataagaatgc cgtcgatgtg catgctttta tgttttttcag aaaagggtgt    3136 gtttggatga agtaaaaaa aaaaataaaa tctttcactg tctctaatgg ctgtgctgtt    3196
taacattttt tgaccctaaa attccaccaac agtctcccag tacataaaat aggcttaatg    3256
actggccctg cattcttcac aatatttttc cctaagcttt gagcaaagtt ttaaaaaaat    3316
acactaaaat aatcaaaact gttaagcagt atattagttt ggttatataa attcatctgc    3376
aatttataag atgcatggcc gatgttaatt tgcttggcaa ttctgtaatc attaagtgat    3436
ctcagtgaaa catgtcaaat gccttaaatt aactaagttg gtgaataaaa gtgccgatct    3496
ggctaactct tacaccatac atactgatag ttttttcatat gtttcatttc catgtgatttt   3556 ttaaaattta gagtggcaac aattttgctt aatatggggtt acataagctt tatttttttcc   3616
```

-continued

```
tttgttcata attatattct ttgaataggt ctgtgtcaat caagtgatct aactagactg    3676
atcatagata gaaggaaata aggccaagtt caagaccagc ctgggcaaca tatcgagaac    3736
ctgtctacaa aaaaattaaa aaaaattagc caggcatggt ggcgtacact gagtagtttg    3796
tcccagctac tcgggagggt gaggtgggag gatcgcttca gcccaggagg ttgagattgc    3856
agtgagccat ggacatacca ctgcactaca gcctaggtaa cagcacgaga ccccaactct    3916
tagaaaatga aaaggaaata tagaaatata aatttgctt attatagaca cacagtaact     3976
cccagatatg taccacaaaa aatgtgaaaa gagagagaaa tgtctaccaa agcagtatttt   4036 tgtgtgtata attgcaagcg catagtaaaa taattttaac cttaatttgt ttttagtagt    4096
gtttagattg aagattgagt gaaatatttt cttggcagat attccgtatc tggtggaaag    4156
ctacaatgca atgtcgttgt agttttgcat ggcttgcttt ataaacaaga tttttctcc     4216 ctccttttgg gccagttttc attacgagta actcacactt tttgattaaa gaacttgaaa    4276
ttacgttatc acttagtata attgacatta tatagagact atgtaacatg caatcattag    4336
aatcaaaatt agtactttgg tcaaaatatt tacaacattc acatacttgt caaatattca    4396
tgtaattaac tgaatttaaa accttcaact attatgaagt gctcgtctgt acaatcgcta    4456
atttactcag tttagagtag ctacaactct tcgatactat catcaatatt tgacatcttt    4516
tccaatttgt gtatgaaaag taaatctatt cctgtagcaa ctggggagtc atatatgagg    4576
tcaaagacat atccttgtt attataatat gtatactata ataatagctg ttatcctga     4636 gcagggaaa aggttatttt taggaaaacc acttcaaata gaaagctgaa gtacttctaa     4696
tatactgagg gaagtataat atgtggaaca aactctcaac aaaatgttta ttgatgttga    4756
tgaaacagat cagttttcc atccggatta ttattggttc atgattttat atgtgaatat     4816
gtaagatatg ttctgcaatt ttataaatgt tcatgtctttt ttttaaaaaa ggtgctattg    4876
aaattctgtg tctccagcag gcaagaatac ttgactaact cttttttgtct ctttatggta   4936 ttttcagaat aaagtctgac ttgtgttttt gagattattg gtgcctcatt aattcagcaa    4996
taaaggaaaa tatgcatctc aaaaat                                         5022
```

```
<210> SEQ ID NO 116
<211> LENGTH: 4932
<212> TYPE: DNA
<213> ORGANISM: Homo sapiens
<220> FEATURE:
<221> NAME/KEY: CDS
<222> LOCATION: 31..816
<221> NAME/KEY: polyA_signal
<222> LOCATION: 4905..4910
<223> OTHER INFORMATION: AATAAA

<400> SEQUENCE: 116
ctgctgtccc tggtgctcca cacgtactcc atg cgc tac ctg ctg ccc agc gtc        54
                                   Met Arg Tyr Leu Leu Pro Ser Val
                                   1               5 gtg ctc ctg ggc acg gcg ccc acc tac gtg ttg gcc tgg ggg gtc tgg        102
Val Leu Leu Gly Thr Ala Pro Thr Tyr Val Leu Ala Trp Gly Val Trp
    10              15                  20 cgg ctg ctc tcc gcc ttc ctg ccc gcc cgc ttc tac caa gcg ctg gac        150
Arg Leu Leu Ser Ala Phe Leu Pro Ala Arg Phe Tyr Gln Ala Leu Asp
25              30                  35                  40 gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
            45                  50                  55
```

-continued

| | | |
|---|---|---|
| aat tac acc ggg gtc cag atg tat ctt gtg att ttt cca gaa ggt aca<br>Asn Tyr Thr Gly Val Gln Met Tyr Leu Val Ile Phe Pro Glu Gly Thr<br>                60                       65                   70 | 246 |
| agg tat aat cca gag caa aca aaa gtc ctt tca gct agt cag gca ttt<br>Arg Tyr Asn Pro Glu Gln Thr Lys Val Leu Ser Ala Ser Gln Ala Phe<br>        75                     80                     85 | 294 |
| gct gcc caa cgt ggc ctt gca gta tta aaa cat gtg cta aca cca cga<br>Ala Ala Gln Arg Gly Leu Ala Val Leu Lys His Val Leu Thr Pro Arg<br>90                       95                     100 | 342 |
| ata aag gca act cac gtt gct ttt gat tgc atg aag aat tat tta gat<br>Ile Lys Ala Thr His Val Ala Phe Asp Cys Met Lys Asn Tyr Leu Asp<br>105                 110                 115               120 | 390 |
| gca att tat gat gtt acg gtg gtt tat gaa ggg aaa gac gat gga ggg<br>Ala Ile Tyr Asp Val Thr Val Val Tyr Glu Gly Lys Asp Asp Gly Gly<br>                 125                    130                135 | 438 |
| cag cga aga gag tca ccg acc atg acg gaa ttt ctc tgc aaa gaa tgt<br>Gln Arg Arg Glu Ser Pro Thr Met Thr Glu Phe Leu Cys Lys Glu Cys<br>            140                    145                   150 | 486 |
| cca aaa att cat att cac att gat cgt atc gac aaa aaa gat gtc cca<br>Pro Lys Ile His Ile His Ile Asp Arg Ile Asp Lys Lys Asp Val Pro<br>155                 160                 165 | 534 |
| gaa gaa caa gaa cat atg aga aga tgg ctg cat gaa cgt ttc gaa atc<br>Glu Glu Gln Glu His Met Arg Arg Trp Leu His Glu Arg Phe Glu Ile<br>        170                     175                   180 | 582 |
| aaa gat aag atg ctt ata gaa ttt tat gag tca cca gat cca gaa aga<br>Lys Asp Lys Met Leu Ile Glu Phe Tyr Glu Ser Pro Asp Pro Glu Arg<br>185                 190                 195               200 | 630 |
| aga aaa aga ttt cct ggg aaa agt gtt aat tcc aaa tta agt atc aag<br>Arg Lys Arg Phe Pro Gly Lys Ser Val Asn Ser Lys Leu Ser Ile Lys<br>                 205                    210               215 | 678 |
| aag act tta cca tca atg ttg atc tta agt ggt ttg act gca ggc atg<br>Lys Thr Leu Pro Ser Met Leu Ile Leu Ser Gly Leu Thr Ala Gly Met<br>            220                    225                   230 | 726 |
| ctt atg acc gat gct gga agg aag ctg tat gtg aac acc tgg ata tat<br>Leu Met Thr Asp Ala Gly Arg Lys Leu Tyr Val Asn Thr Trp Ile Tyr<br>        235                     240                   245 | 774 |
| gga acc cta ctt ggc tgc ctg tgg gtt act att aaa gca tag<br>Gly Thr Leu Leu Gly Cys Leu Trp Val Thr Ile Lys Ala<br>        250                     255                   260 | 816 |
| acaagtagct gtctccagac agtgggatgt gctacattgt ctattttgg cggctgcaca | 876 |
| tgacatcaaa ttgtttcctg aatttattaa ggagtgtaaa taaagccttg ttgattgaag | 936 |
| attggataat agaatttgtg acgaaagctg atatgcaatg gtcttgggca acatacctg | 996 |
| gttgtacaac tttagcatcg gggctgctgg aagggtaaaa gctaaatgga gtttctcctg | 1056 |
| ctctgtccat ttcctatgaa ctaatgacaa cttgagaagg ctgggaggat tgtgtatttt | 1116 |
| gcaagtcaga tggctgcatt tttgagcatt aatttgcagc gtatttcact tttttctgtta | 1176 |
| ttttcaattt attacaactt gacagctcca agctcttatt actaaagtat ttagtatctt | 1236 |
| gcagctagtt aatatttcat cttttgctta tttctacaag tcagtgaaat aaattgtatt | 1296 |
| taggaagtgt caggatgttc aaaggaaagg gtaaaaagtg ttcatgggga aaaagctctg | 1356 |
| tttagcacat gattttattg tattgcgtta ttagctgatt ttactcattt tatatttgca | 1416 |
| aaataaattt ctaatattta ttgaaattgc ttaatttgca caccctgtac acacagaaaa | 1476 |
| tggtataaaa tatgagaacg aagtttaaaa ttgtgactct gattcattat agcagaactt | 1536 |
| taaatttccc agcttttga agatttaagc tacgctatta gtacttccct ttgtctgtgc | 1596 |
| cataagtgct tgaaaacgtt aaggttttct gttttgtttt gtttttttaa tatcaaagaa | 1656 |

```
gtcggtgtga accttggttg gaccccaagt tcacaagatt tttaaggtga tgagagcctg   1716
cagacattct gcctagattt actagcgtgt gccttttgcc tgcttctctt tgatttcaca   1776
gaatattcat tcagaagtcg cgtttctgta gtgtggtgga ttcccactgg gctctggtcc   1836
ttcccttgga tcccgtcagt ggtgctgctc agcggcttgc acgtagactt gctaggaaga   1896
aatgcagagc cagcctgtgc tgcccacttt cagagttgaa ctctttaagc ccttgtgagt   1956
gggcttcacc agctactgca gaggcatttt gcatttgtct gtgtcaagaa gttcaccttc   2016
tcaagccagt gaaatacaga cttaattcgt catgactgaa cgaatttgtt tatttcccat   2076
taggtttagt ggagctacac attaatatgt atcgccttag agcaagagct gtgttccagg   2136
aaccagatca cgatttttag ccatggaaca atatatccca tgggagaaga cctttcagtg   2196
tgaactgttc tattttgtg ttataattta aacttcgatt tcctcatagt cctttaagtt   2256
gacatttctg cttactgcta ctggattttt gctgcagaaa tatatcagtg gcccacatta   2316
aacataccag ttggatcatg ataagcaaaa tgaaagaaat aatgattaag ggaaaattaa   2376
gtgactgtgt tacactgctt ctcccatgcc agagaataaa ctctttcaag catcatcttt   2436
gaagagtcgt gtggtgtgaa ttggtttgtg tacattagaa tgtatgcaca catccatgga   2496
cactcaggat atagttggcc taataatcgg ggcatgggta aaacttatga aaatttcctc   2556
atgctgaatt gtaatttct cttacctgta aagtaaaatt tagatcaatt ccatgtctt   2616 gttaagtaca gggatttaat atattttgaa tataatgggg atgttctaaa tttgaacttt   2676
gagaggcaat actgttggaa ttatgtggat tctaactcat tttaacaagg tagcctgacc   2736
tgcataagat cacttgaatg ttaggtttca tagaactata ctaatcttct cacaaaaggt   2796
ctataaaata cagtcgttga aaaaaatttt gtatcaaaat gtttggaaaa ttagaagctt   2856
ctccttaacc tgtattgata ctgacttgaa ttattttcta aaattaagag ccgtatacct   2916
acctgtaagt cttttcacat atcatttaaa cttttgtttg tattattact gatttacagc   2976
ttagttatta attttctttt ataagaatgc cgtcgatgtg catgctttta tgtttttcag   3036
aaaagggtgt gtttggatga aagtaaaaaa aaaaataaaa tctttcactg tctctaatgg   3096
ctgtgctgtt taacattttt tgaccctaaa attcaccaac agtctcccag tacataaaat   3156
aggcttaatg actggccctg cattcttcac aatattttc cctaagcttt gagcaaagtt   3216
ttaaaaaaat acactaaaat aatcaaaact gttaagcagt atattagttt ggttatataa   3276
attcatctgc aatttataag atgcatggcc gatgttaatt tgcttggcaa ttctgtaatc   3336
attaagtgat ctcagtgaaa catgtcaaat gccttaaatt aactaagttg gtgaataaaa   3396
gtgccgatct ggctaactct tacaccatac atactgatag ttttttcatat gtttcatttc   3456 catgtgattt ttaaaattta gagtggcaac aattttgctt aatatgggtt acataagctt   3516 tatttttcc tttgttcata attatattct ttgaataggt ctgtgtcaat caagtgatct   3576
aactagactg atcatagata gaaggaaata aggccaagtt caagaccagc ctgggcaaca   3636
tatcgagaac ctgtctacaa aaaattaaa aaaattagc caggcatggt ggcgtacact   3696
gagtagtttg tcccagctac tcgggagggt gaggtgggag gatcgcttca gcccaggagg   3756
ttgagattgc agtgagccat ggacatacca ctgcactaca gcctaggtaa cagcacgaga   3816
ccccaactct tagaaaatga aaaggaaata tagaaatata aatttgctt attatagaca   3876 cacagtaact cccagatatg taccacaaaa atgtgaaaa gagagagaaa tgtctaccaa   3936
agcagtattt tgtgtgtata attgcaagcg catagtaaaa taattttaac cttaatttgt   3996
```

```
ttttagtagt gtttagattg aagattgagt gaaatatttt cttggcagat attccgtatc    4056
tggtggaaag ctacaatgca atgtcgttgt agttttgcat ggcttgcttt ataaacaaga    4116
ttttttctcc ctccttttgg gccagttttc attacgagta actcacactt tttgattaaa    4176
gaacttgaaa ttacgttatc acttagtata attgacatta tatagagact atgtaacatg    4236
caatcattag aatcaaaatt agtactttgg tcaaaatatt tacaacattc acatacttgt    4296
caaatattca tgtaattaac tgaatttaaa accttcaact attatgaagt gctcgtctgt    4356
acaatcgcta atttactcag tttagagtag ctacaactct tcgatactat catcaatatt    4416
tgacatcttt tccaatttgt gtatgaaaag taaatctatt cctgtagcaa ctggggagtc    4476
atatatgagg tcaaagacat ataccttgtt attataatat gtatactata ataatagctg    4536
gttatcctga gcaggggaaa aggttatttt taggaaaacc acttcaaata gaaagctgaa    4596
gtacttctaa tatactgagg gaagtataat atgtggaaca aactctcaac aaaatgttta    4656
ttgatgttga tgaaacagat cagttttttcc atccggatta ttattggttc atgattttat    4716
atgtgaatat gtaagatatg ttctgcaatt ttataaatgt tcatgtcttt ttttaaaaaa    4776
ggtgctattg aaattctgtg tctccagcag gcaagaatac ttgactaact cttttttgtct    4836 ctttatggta ttttcagaat aaagtctgac ttgtgttttt gagattattg gtgcctcatt    4896
aattcagcaa taaggaaaa tatgcatctc aaaaat                               4932

<210> SEQ ID NO 117
<211> LENGTH: 4682
<212> TYPE: DNA
<213> ORGANISM: Homo sapiens
<220> FEATURE:
<221> NAME/KEY: CDS
<222> LOCATION: 31..303
<221> NAME/KEY: polyA_signal
<222> LOCATION: 4655..4660
<223> OTHER INFORMATION: AATAAA

<400> SEQUENCE: 117
ctgctgtccc tggtgctcca cacgtactcc atg cgc tac ctg ctg ccc agc gtc        54
                                 Met Arg Tyr Leu Leu Pro Ser Val
                                  1               5 gtg ctc ctg ggc acg gcg ccc acc tac gtg ttg gcc tgg ggg gtc tgg       102
Val Leu Leu Gly Thr Ala Pro Thr Tyr Val Leu Ala Trp Gly Val Trp
     10                  15                  20 cgg ctg ctc tcc gcc ttc ctg ccc gcc cgc ttc tac caa gcg ctg gac       150
Arg Leu Leu Ser Ala Phe Leu Pro Ala Arg Phe Tyr Gln Ala Leu Asp
25                  30                  35                  40 gac cgg ctg tac tgc gtc tac cag agc atg gtg ctc ttc ttc ttc gag       198
Asp Arg Leu Tyr Cys Val Tyr Gln Ser Met Val Leu Phe Phe Phe Glu
                 45                  50                  55 aat tac acc ggg gtc cag aat ttc tct gca aag aat gtc caa aaa ttc       246
Asn Tyr Thr Gly Val Gln Asn Phe Ser Ala Lys Asn Val Gln Lys Phe
             60                  65                  70 ata ttc aca ttg atc gta tcg aca aaa aag atg tcc cag aag aac aag       294
Ile Phe Thr Leu Ile Val Ser Thr Lys Lys Met Ser Gln Lys Asn Lys
         75                  80                  85 aac ata tga gaagatggct gcatgaacgt ttcgaaatca aagataagat                343
Asn Ile
    90 gcttatagaa ttttatgagt caccagatcc agaaagaaga aaaagatttc ctgggaaaag     403 tgttaattcc aaattaagta tcaagaagac tttaccatca atgttgatct taagtggttt     463 gactgcaggc atgcttatga ccgatgctgg aaggaagctg tatgtgaaca cctggatata     523
```

-continued

```
tggacccta cttggctgcc tgtgggttac tattaaagca tagacaagta gctgtctcca    583
gacagtggga tgtgctacat tgtctatttt tggcggctgc acatgacatc aaattgtttc    643
ctgaatttat taaggagtgt aaataaagcc ttgttgattg aagattggat aatagaattt    703
gtgacgaaag ctgatatgca atggtcttgg gcaaacatac ctggttgtac aactttagca    763
tcggggctgc tggaagggta aaagctaaat ggagtttctc ctgctctgtc catttcctat    823
gaactaatga caacttgaga aggctgggag gattgtgtat tttgcaagtc agatggctgc    883
atttttgagc attaatttgc agcgtatttc acttttctg ttattttcaa tttattacaa    943
cttgacagct ccaagctctt attactaaag tatttagtat cttgcagcta gttaatattt   1003
catcttttgc ttatttctac aagtcagtga ataaattgt atttaggaag tgtcaggatg   1063
ttcaaaggaa agggtaaaaa gtgttcatgg ggaaaaagct ctgtttagca catgatttta   1123
ttgtattgcg ttattagctg attttactca ttttatattt gcaaataaa tttctaatat   1183 ttattgaaat tgcttaattt gcacaccctg tacacacaga aaatggtata aatatgaga   1243 acgaagttta aaattgtgac tctgattcat tatagcagaa cttaaattt cccagctttt   1303 tgaagattta agctacgcta ttagtacttc cctttgtctg tgccataagt gcttgaaaac   1363
gttaaggttt tctgttttgt tttgttttt taatatcaaa agagtcggtg tgaaccttgg   1423
ttggacccca agttcacaag attttaagg tgatgagagc ctgcagacat tctgcctaga   1483
tttactagcg tgtgcctttt gcctgcttct ctttgatttc acagaatatt cattcagaag   1543
tcgcgtttct gtagtgtggt ggattcccac tgggctctgg tccttccctt ggatcccgtc   1603
agtggtgctc ctcagcggct tgcacgtaga cttgctagga agaaatgcag agccagcctg   1663
tgctgcccac tttcagagtt gaactcttta agcccttgtg agtgggcttc accagctact   1723
gcagaggcat tttgcatttg tctgtgtcaa gaagttcacc ttctcaagcc agtgaaatac   1783
agacttaatt cgtcatgact gaacgaattt gtttatttcc cattaggttt agtggagcta   1843
cacattaata tgtatcgcct tagagcaaga gctgtgttcc aggaaccaga tcacgatttt   1903
tagccatgga acaatatatc ccatgggaga agacctttca gtgtgaactg ttctattttt   1963
gtgttataat ttaaacttcg atttcctcat agtcctttaa gttgacattt ctgcttactg   2023
ctactggatt tttgctgcag aaatatatca gtggcccaca ttaaacatac cagttggatc   2083
atgataagca aaatgaaaga aataatgatt aagggaaaat taagtgactg tgttacactg   2143
cttctcccat gccagagaat aaactctttc aagcatcatc tttgaagagt cgtgtggtgt   2203
gaattggttt gtgtacatta gaatgtatgc acacatccat ggacactcag gatatagttg   2263
gcctaataat cggggcatgg gtaaaactta tgaaaatttc ctcatgctga attgtaattt   2323
tctcttacct gtaaagtaaa atttagatca attccatgtc tttgttaagt acagggattt   2383
aatatatttt gaatataatg ggtatgttct aaatttgaac tttgagaggc aatactgttg   2443
gaattatgtg gattctaact cattttaaca aggtagcctg acctgcataa gatcacttga   2503
atgttaggtt tcatagaact atactaatct tctcacaaaa ggtctataaa atacagtcgt   2563
tgaaaaaaat tttgtatcaa aatgtttgga aaattagaag cttctcctta acctgtattg   2623
atactgactt gaattatttt ctaaaattaa gagccgtata cctacctgta agtcttttca   2683
catatcattt aaacttttgt ttgtattatt actgatttac agcttagtta ttaatttttc   2743
tttataagaa tgccgtcgat gtgcatgctt ttatgttttt cagaaaaggg tgtgtttgga   2803
tgaaagtaaa aaaaaaaata aaatctttca ctgtctctaa tggctgtgct gtttaacatt   2863
```

-continued

```
ttttgaccct aaaattcacc aacagtctcc cagtacataa aataggctta atgactggcc    2923
ctgcattctt cacaatattt ttccctaagc tttgagcaaa gttttaaaaa aatacactaa    2983
aataatcaaa actgttaagc agtatattag tttggttata taaattcatc tgcaatttat    3043
aagatgcatg gccgatgtta atttgcttgg caattctgta atcattaagt gatctcagtg    3103
aaacatgtca aatgccttaa attaactaag ttggtgaata aaagtgccga tctggctaac    3163
tcttacacca tacatactga tagttttca tatgtttcat ttccatgtga tttttaaaat    3223
ttagagtggc aacaattttg cttaatatgg gttacataag cttattttt tcctttgttc    3283 ataattatat tctttgaata ggtctgtgtc aatcaagtga tctaactaga ctgatcatag    3343
atagaaggaa ataaggccaa gttcaagacc agcctgggca acatatcgag aacctgtcta    3403
caaaaaaatt aaaaaaaatt agccaggcat ggtggcgtac actgagtagt ttgtcccagc    3463
tactcgggag ggtgaggtgg gaggatcgct tcagcccagg aggttgagat tgcagtgagc    3523
catggacata ccactgcact acagcctagg taacagcacg agaccccaac tcttagaaaa    3583
tgaaaaggaa atatagaaat ataaaatttg cttattatag acacacagta actcccagat    3643
atgtaccaca aaaatgtga aagagagag aaatgtctac caaagcagta ttttgtgtgt    3703
ataattgcaa gcgcatagta aaataatttt aaccttaatt tgtttttagt agtgtttaga    3763
ttgaagattg agtgaaatat tttcttggca gatattccgt atctggtgga aagctacaat    3823
gcaatgtcgt tgtagttttg catggcttgc tttataaaca agatttttc tccctccttt    3883 tgggccagtt ttcattacga gtaactcaca cttttgatt aaagaacttg aaattacgtt    3943
atcacttagt ataattgaca ttatatagag actatgtaac atgcaatcat tagaatcaaa    4003
attagtactt tggtcaaaat atttacaaca ttcacatact tgtcaaatat tcatgtaatt    4063
aactgaattt aaaaccttca actattatga agtgctcgtc tgtacaatcg ctaatttact    4123
cagtttagag tagctacaac tcttcgatac tatcatcaat atttgacatc ttttccaatt    4183
tgtgtatgaa aagtaaatct attcctgtag caactgggga gtcatatatg aggtcaaaga    4243 catataccttgttattataa tatgtatact ataataatag ctggttatcc tgagcagggg    4303
aaaaggttat ttttaggaaa accacttcaa atagaaagct gaagtacttc taatatactg    4363
agggaagtat aaatatgtgga acaaactctc aacaaaatgt ttattgatgt tgatgaaaca    4423
gatcagtttt tccatccgga ttattattgg ttcatgattt tatatgtgaa tatgtaagat    4483
atgttctgca attttataaa tgttcatgtc tttttttaaa aaaggtgcta ttgaaattct    4543
gtgtctccag caggcaagaa tacttgacta actcttttg tctctttatg gtattttcag    4603
aataaagtct gacttgtgtt tttgagatta ttggtgcctc attaattcag caataaagga    4663
aaatatgcat ctcaaaaat                                                 4682
```

<210> SEQ ID NO 118
<211> LENGTH: 4558
<212> TYPE: DNA
<213> ORGANISM: Homo sapiens
<220> FEATURE:
<221> NAME/KEY: CDS
<222> LOCATION: 31..237
<221> NAME/KEY: polyA_signal
<222> LOCATION: 4531..4536
<223> OTHER INFORMATION: AATAAA

<400> SEQUENCE: 118

```
ctgctgtccc tggtgctcca cacgtactcc atg cgc tac ctg ctg ccc agc gtc       54
                                 Met Arg Tyr Leu Leu Pro Ser Val
                                  1               5
```

-continued

```
gtg ctc ctg ggc acg gcg ccc acc tac gtg ttg gcc tgg ggg gtc tgg        102
Val Leu Leu Gly Thr Ala Pro Thr Tyr Val Leu Ala Trp Gly Val Trp
 10                  15                  20 cgg ctg ctc tcc gcc ttc ctg ccc gcc cgc ttc tac caa gcg ctg gac        150
Arg Leu Leu Ser Ala Phe Leu Pro Ala Arg Phe Tyr Gln Ala Leu Asp
 25                  30                  35                  40 gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
                 45                  50                  55 aat tac acc ggg gtc cag gat gct tat aga att tta tga gtcaccagat         247
Asn Tyr Thr Gly Val Gln Asp Ala Tyr Arg Ile Leu
             60                  65 ccagaaagaa gaaaaagatt tcctgggaaa agtgttaatt ccaaattaag tatcaagaag      307
actttaccat caatgttgat cttaagtggt ttgactgcag gcatgcttat gaccgatgct      367
ggaaggaagc tgtatgtgaa cacctggata tatggaaccc tacttggctg cctgtgggtt      427
actattaaag catagacaag tagctgtctc cagacagtgg gatgtgctac attgtctatt      487
tttggcggct gcacatgaca tcaaattgtt tcctgaattt attaaggagt gtaaataaag      547
ccttgttgat tgaagattgg ataatagaat ttgtgacgaa agctgatatg caatggtctt      607
gggcaaacat acctggttgt acaactttag catcggggct gctggaaggg taaaagctaa      667
atggagtttc tcctgctctg tccatttcct atgaactaat gacaacttga gaaggctggg      727
aggattgtgt attttgcaag tcagatggct gcattttga gcattaattt gcagcgtatt       787
tcacttttc tgttattttc aatttattac aacttgacag ctccaagctc ttattactaa       847
agtatttagt atcttgcagc tagttaatat ttcatctttt gcttatttct acaagtcagt      907
gaaataaatt gtatttagga agtgtcagga tgttcaaagg aaagggtaaa aagtgttcat      967
ggggaaaaag ctctgtttag cacatgattt tattgtattg cgttattagc tgattttact     1027
cattttatat ttgcaaaata aatttctaat atttattgaa attgcttaat ttgcacaccc     1087
tgtacacaca gaaaatggta taaaatatga gaacgaagtt taaaattgtg actctgattc     1147
attatagcag aactttaaat ttcccagctt tttgaagatt taagctacgc tattagtact     1207
tcccttgtc tgtgccataa gtgcttgaaa acgttaaggt tttctgtttt gttttgtttt      1267
tttaatatca aaagagtcgg tgtgaacctt ggttggaccc caagttcaca agattttaa      1327
ggtgatgaga gcctgcagac attctgccta gatttactag cgtgtgcctt ttgcctgctt     1387
ctctttgatt tcacagaata ttcattcaga agtcgcgttt ctgtagtgtg gtggattccc     1447
actgggctct ggtccttccc ttggatcccg tcagtggtgc tgctcagcgg cttgcacgta     1507
gacttgctag gaagaaatgc agagccagcc tgtgctgccc actttcagag ttgaactctt     1567
taagcccttg tgagtgggct tcaccagcta ctgcagaggc attttgcatt tgtctgtgtc     1627
aagaagttca ccttctcaag ccagtgaaat acagacttaa ttcgtcatga ctgaacgaat     1687
ttgtttattt cccattaggt ttagtggagc tacacattaa tatgtatcgc cttagagcaa     1747
gagctgtgtt ccaggaacca gatcacgatt tttagccatg gaacaatata tcccatggga    1807
gaagaccttt cagtgtgaac tgttctattt ttgtgttata atttaaactt cgatttcctc    1867
atagtccttt aagttgacat ttctgcttac tgctactgga ttttttgctgc agaaatatat   1927
cagtggccca cattaaacat accagttgga tcatgataag caaaatgaaa gaaataatga    1987
ttaagggaaa attaagtgac tgtgttacac tgcttctccc atgccagaga ataaactctt    2047
tcaagcatca tctttgaaga gtcgtgtggt gtgaattggt ttgtgtacat tagaatgtat    2107
```

```
gcacacatcc atggacactc aggatatagt tggcctaata atcggggcat gggtaaaact   2167
tatgaaaatt tcctcatgct gaattgtaat tttctcttac ctgtaaagta aaatttagat   2227
caattccatg tctttgttaa gtacaggat ttaatatatt ttgaatataa tgggtatgtt   2287
ctaaatttga actttgagag gcaatactgt tggaattatg tggattctaa ctcattttaa   2347
caaggtagcc tgacctgcat aagatcactt gaatgttagg tttcatagaa ctatactaat   2407
cttctcacaa aagtctata aaatacagtc gttgaaaaaa attttgtatc aaaatgtttg   2467
gaaaattaga agcttctcct taacctgtat tgatactgac ttgaattatt ttctaaaatt   2527
aagagccgta tacctacctg taagtctttt cacatatcat ttaaactttt gtttgtatta   2587
ttactgattt acagcttagt tattaatttt tctttataag aatgccgtcg atgtgcatgc   2647
ttttatgttt ttcagaaaag ggtgtgtttg gatgaaagta aaaaaaaaaa taaaatcttt   2707
cactgtctct aatggctgtg ctgtttaaca ttttttgacc ctaaaattca ccaacagtct   2767
cccagtacat aaaataggct taatgactgg ccctgcattc ttcacaatat ttttccctaa   2827
gctttgagca aagttttaaa aaatacact aaaataatca aaactgttaa gcagtatatt    2887
agtttggtta tataaattca tctgcaattt ataagatgca tggccgatgt taatttgctt   2947
ggcaattctg taatcattaa gtgatctcag tgaaacatgt caaatgcctt aaattaacta   3007
agttggtgaa taaaagtgcc gatctggcta actcttacac catacatact gatagttttt   3067
catatgtttc atttccatgt gattttaaa atttagagtg gcaacaattt tgcttaatat   3127
gggttacata agctttattt tttcctttgt tcataattat attctttgaa taggtctgtg   3187
tcaatcaagt gatctaacta gactgatcat agatagaagg aaataaggcc aagttcaaga   3247
ccagcctggg caacatatcg agaacctgtc tacaaaaaaa ttaaaaaaaa ttagccaggc   3307
atggtggcgt acactgagta gtttgtccca gctactcggg agggtgaggt gggaggatcg   3367
cttcagccca ggaggttgag attgcagtga gccatggaca taccactgca ctacagccta   3427
ggtaacagca cgagacccca actcttagaa aatgaaaagg aaatatagaa atataaaatt   3487
tgcttattat agacacacag taactcccag atatgtacca caaaaaatgt gaaagagag    3547
agaaatgtct accaaagcag tattttgtgt gtataattgc aagcgcatag taaaataatt   3607
ttaaccttaa tttgttttta gtagtgttta gattgaagat tgagtgaaat attttcttgg   3667
cagatattcc gtatctggtg gaaagctaca atgcaatgtc gttgtagttt tgcatggctt   3727
gctttataaa caagattttt tctccctcct tttgggccag ttttcattac gagtaactca   3787
cacttttttga ttaaagaact tgaaattacg ttatcactta gtataattga cattatatag   3847
agactatgta acatgcaatc attagaatca aaattagtac tttggtcaaa atatttacaa   3907
cattcacata cttgtcaaat attcatgtaa ttaactgaat ttaaaacctt caactattat   3967
gaagtgctcg tctgtacaat cgctaattta ctcagtttag agtagctaca actcttcgat   4027
actatcatca atatttgaca tcttttccaa tttgtgtatg aaaagtaaat ctattcctgt   4087
agcaactggg gagtcatata tgaggtcaaa gacatatacc ttgttattat aatatgtata   4147
ctataataat agctggttat cctgagcagg ggaaaaggtt attttttagga aaccacttc   4207
aaatagaaag ctgaagtact tctaatatac tgagggaagt ataatatgtg gaacaaactc   4267
tcaacaaaat gtttattgat gttgatgaaa cagatcagtt tttccatccg gattattatt   4327
ggttcatgat tttatatgtg aatatgtaag atatgttctg caattttata aatgttcatg   4387
tcttttttta aaaaggtgc tattgaaatt ctgtgtctcc agcaggcaag aatacttgac    4447
taactctttt tgtctctttta tggtattttc agaataaagt ctgacttgtg tttttgagat   4507
```

-continued

```
tattggtgcc tcattaattc agcaataaag gaaaatatgc atctcaaaaa t            4558

<210> SEQ ID NO 119
<211> LENGTH: 5270
<212> TYPE: DNA
<213> ORGANISM: Homo sapiens
<220> FEATURE:
<221> NAME/KEY: CDS
<222> LOCATION: 31..231
<221> NAME/KEY: polyA_signal
<222> LOCATION: 5243..5248
<223> OTHER INFORMATION: AATAAA

<400> SEQUENCE: 119
ctgctgtccc tggtgctcca cacgtactcc atg cgc tac ctg ctg ccc agc gtc      54
                                Met Arg Tyr Leu Leu Pro Ser Val
                                 1               5 gtg ctc ctg ggc acg gcg ccc acc tac gtg ttg gcc tgg ggg gtc tgg     102
Val Leu Leu Gly Thr Ala Pro Thr Tyr Val Leu Ala Trp Gly Val Trp
    10                  15                  20 cgg ctg ctc tcc gcc ttc ctg ccc gcc cgc ttc tac caa gcg ctg gac     150
Arg Leu Leu Ser Ala Phe Leu Pro Ala Arg Phe Tyr Gln Ala Leu Asp
25                  30                  35                  40 gac cgg ctg tac tgc gtc tac cag agc atg gtg ctc ttc ttc ttc gag     198
Asp Arg Leu Tyr Cys Val Tyr Gln Ser Met Val Leu Phe Phe Phe Glu
                45                  50                  55 aat tac acc ggg gtc cag aga ttg gat tcg tag attaaacttg agaaacaaac   251
Asn Tyr Thr Gly Val Gln Arg Leu Asp Ser
                60                  65 cataaaagtg gaaggccctc tttaacaata ttgctatatg gagatttgcc aaaaaataaa   311
gaaaatataa tatatttagc aaatcatcaa agcacagttg actggattgt tgctgacatc   371
ttggccatca ggcagaatgc gctaggacat gtgcgctacg tgctgaaaga agggttaaaa   431
tggctgccat tgtatgggtg ttactttgct cagcatggag gaatctatgt aaagcgcagt   491
gccaaattta acgagaaaga gatgcgaaac aagttgcaga gctacgtgga cgcaggaact   551
ccaatgtatc ttgtgatttt tccagaaggt acaaggtata atccagagca aacaaaagtc   611
ctttcagcta gtcaggcatt tgctgcccaa cgtggccttg cagtattaaa acatgtgcta   671
acaccacgaa taaaggcaac tcacgttgct tttgattgca tgaagaatta tttagatgca   731
atttatgatg ttacggtggt ttatgaaggg aaagacgatg gagggcagcg aagagagtca   791
ccgaccatga cggaatttct ctgcaaagaa tgtccaaaaa ttcatattca cattgatcgt   851
atcgacaaaa aagatgtccc agaagaacaa gaacatatga aagatggct gcatgaacgt   911 ttcgaaatca agataagat gcttatagaa ttttatgagt caccagatcc agaaagaaga   971 aaagattct ctgggaaaag tgttaattcc aaattaagta tcaagaagac tttaccatca  1031
atgttgatct taagtggttt gactgcaggc atgcttatga ccgatgctgg aaggaagctg  1091
tatgtgaaca cctggatata tggaacccta cttggctgcc tgtgggttac tattaaagca  1151
tagacaagta gctgtctcca gacagtggga tgtgctacat tgtctatttt tggcggctgc  1211
acatgacatc aaattgtttc ctgaatttat taaggagtgt aaataaagcc ttgttgattg  1271
aagattggat aatagaattt gtgacgaaag ctgatatgca atggtcttgg gcaaacatac  1331
ctggttgtac aactttagca tcggggctgc tggaagggta aaagctaaat ggagtttctc  1391
ctgctctgtc catttcctat gaactaatga caacttgaga aggctgggag gattgtgtat  1451
tttgcaagtc agatggctgc attttgagc attaatttgc agcgtatttc acttttttctg  1511
```

```
ttattttcaa tttattacaa cttgacagct ccaagctctt attactaaag tatttagtat     1571
cttgcagcta gttaatattt catcttttgc ttatttctac aagtcagtga aataaattgt     1631
atttaggaag tgtcaggatg ttcaaaggaa agggtaaaaa gtgttcatgg ggaaaaagct     1691
ctgtttagca catgatttta ttgtattgcg ttattagctg attttactca ttttatattt     1751
gcaaaataaa tttctaatat ttattgaaat tgcttaattt gcacaccctg tacacacaga     1811
aaatggtata aaatatgaga acgaagttta aaattgtgac tctgattcat tatagcagaa     1871
cttaaatttt cccagctttt tgaagattta agctacgcta ttagtacttc cctttgtctg     1931
tgccataagt gcttgaaaac gttaaggttt tctgttttgt tttgttttt taatatcaaa      1991 agagtcggtg tgaaccttgg ttggacccca agttcacaag attttaagg tgatgagagc      2051 ctgcagacat tctgcctaga tttactagcg tgtgccttt gcctgcttct ctttgatttc      2111
acagaatatt cattcagaag tcgcgtttct gtagtgtggt ggattcccac tgggctctgg     2171
tccttccctt ggatcccgtc agtggtgctg ctcagcggct tgcacgtaga cttgctagga    2231
agaaatgcag agccagcctg tgctgcccac tttcagagtt gaactcttta agcccttgtg    2291
agtgggcttc accagctact gcagaggcat tttgcatttg tctgtgtcaa gaagttcacc    2351
ttctcaagcc agtgaaatac agacttaatt cgtcatgact gaacgaattt gtttatttcc    2411
cattaggttt agtggagcta cacattaata tgtatcgcct tagagcaaga gctgtgttcc    2471
aggaaccaga tcacgatttt tagccatgga acaatatatc ccatgggaga agacctttca    2531
gtgtgaactg ttctattttt gtgttataat ttaaacttcg atttcctcat agtcctttaa    2591
gttgacattt ctgcttactg ctactggatt tttgctgcag aaatatatca gtggcccaca    2651
ttaaacatac cagttggatc atgataagca aaatgaaaga aataatgatt aagggaaaat    2711
taagtgactg tgttacactg cttctcccat gccagagaat aaactctttc aagcatcatc    2771
tttgaagagt cgtgtggtgt gaattggttt gtgtacatta aatgtatgc acacatccat     2831 ggacactcag gatatagttg gcctaataat cggggcatgg gtaaaactta tgaaaatttc    2891
ctcatgctga attgtaattt tctcttacct gtaaagtaaa atttagatca attccatgtc    2951
tttgttaagt acagggattt aatatatttt gaatataatg ggtatgttct aaatttgaac    3011
tttgagaggc aatactgttg gaattatgtg gattctaact catttaaca aggtagcctg     3071 acctgcataa gatcacttga atgttaggtt tcatagaact atactaatct tctcacaaaa    3131
ggtctataaa atacagtcgt tgaaaaaaat tttgtatcaa aatgtttgga aaattagaag    3191
cttctcctta acctgtattg atactgactt gaattatttt ctaaaattaa gagccgtata    3251
cctacctgta agtcttttca catatcattt aaacttttgt ttgtattatt actgatttac    3311
agcttagtta ttaatttttc tttataagaa tgccgtcgat gtgcatgctt ttatgttttt    3371
cagaaaaggg tgtgtttgga tgaaagtaaa aaaaaaaata aaatctttca ctgtctctaa    3431
tggctgtgct gtttaacatt ttttgaccct aaaattcacc aacagtctcc cagtacataa    3491
aataggctta atgactggcc ctgcattctt cacaatattt ttccctaagc tttgagcaaa    3551
gttttaaaaa aatacactaa aataatcaaa actgttaagc agtatattag tttggttata    3611
taaattcatc tgcaatttat aagatgcatg gccgatgtta atttgcttgg caattctgta    3671
atcattaagt gatctcagtg aaacatgtca aatgccttaa attaactaag ttggtgaata    3731
aaagtgccga tctggctaac tcttacacca tacatactga tagttttttca tatgtttcat   3791 ttccatgtga tttttaaaat ttagagtggc aacaattttg cttaatatgg gttacataag    3851 ctttatttt tcctttgttc ataattatat tctttgaata ggtctgtgtc aatcaagtga     3911
```

```
tctaactaga ctgatcatag atagaaggaa ataaggccaa gttcaagacc agcctgggca    3971
acatatcgag aacctgtcta caaaaaaatt aaaaaaaatt agccaggcat ggtggcgtac    4031
actgagtagt ttgtcccagc tactcgggag ggtgaggtgg gaggatcgct tcagcccagg    4091
aggttgagat tgcagtgagc catggacata ccactgcact acagcctagg taacagcacg    4151
agaccccaac tcttagaaaa tgaaaggaa atatagaaat ataaaatttg cttattatag     4211
acacacagta actcccagat atgtaccaca aaaatgtga aaagagagag aaatgtctac     4271
caaagcagta ttttgtgtgt ataattgcaa gcgcatagta aaataatttt aaccttaatt    4331 tgttttttagt agtgtttaga ttgaagattg agtgaaatat tttcttggca gatattccgt   4391
atctggtgga aagctacaat gcaatgtcgt tgtagtttg catggcttgc tttataaaca     4451 agatttttc tccctccttt tgggccagtt ttcattacga gtaactcaca cttttgatt      4511 aaagaacttg aaattacgtt atcacttagt ataattgaca ttatatagag actatgtaac    4571
atgcaatcat tagaatcaaa attagtactt tggtcaaaat atttacaaca ttcacatact    4631
tgtcaaatat tcatgtaatt aactgaattt aaaaccttca actattatga agtgctcgtc    4691
tgtacaatcg ctaatttact cagtttagag tagctacaac tcttcgatac tatcatcaat    4751
atttgacatc ttttccaatt tgtgtatgaa aagtaaatct attcctgtag caactgggga    4811
gtcatatatg aggtcaaaga catatacctt gttattataa tatgtatact ataataatag    4871
ctggttatcc tgagcagggg aaaaggttat ttttaggaaa accacttcaa atagaaagct    4931
gaagtacttc taatatactg agggaagtat aatatgtgga acaaactctc aacaaaatgt    4991
ttattgatgt tgatgaaaca gatcagtttt tccatccgga ttattattgg ttcatgattt    5051
tatatgtgaa tatgtaagat atgttctgca attttataaa tgttcatgtc ttttttaaa    5111 aaaggtgcta ttgaaattct gtgtctccag caggcaagaa tacttgacta actctttttg    5171
tctctttatg gtattttcag aataaagtct gacttgtgtt tttgagatta ttggtgcctc    5231
attaattcag caataaagga aaatatgcat ctcaaaaat                           5270
```

<210> SEQ ID NO 120
<211> LENGTH: 5002
<212> TYPE: DNA
<213> ORGANISM: Homo sapiens
<220> FEATURE:
<221> NAME/KEY: CDS
<222> LOCATION: 31..324
<221> NAME/KEY: polyA_signal
<222> LOCATION: 4975..4980
<223> OTHER INFORMATION: AATAAA

<400> SEQUENCE: 120

```
ctgctgtccc tggtgctcca cacgtactcc atg cgc tac ctg ctg ccc agc gtc         54
                                Met Arg Tyr Leu Leu Pro Ser Val
                                 1               5 gtg ctc ctg ggc acg gcg ccc acc tac gtg ttg gcc tgg ggg gtc tgg         102
Val Leu Leu Gly Thr Ala Pro Thr Tyr Val Leu Ala Trp Gly Val Trp
        10                  15                  20 cgg ctc ctc tcc gcc ttc ctg ccc gcc cgc ttc tac caa gcg ctg gac         150
Arg Leu Leu Ser Ala Phe Leu Pro Ala Arg Phe Tyr Gln Ala Leu Asp
 25                  30                  35                  40 gac cgg ctg tac tgc gtc tac cag agc atg gtg ctc ttc ttc ttc gag         198
Asp Arg Leu Tyr Cys Val Tyr Gln Ser Met Val Leu Phe Phe Phe Glu
                 45                  50                  55 aat tac acc ggg gtc cag ata ttg cta tat gga gat ttg cca aaa aat         246
Asn Tyr Thr Gly Val Gln Ile Leu Leu Tyr Gly Asp Leu Pro Lys Asn
```

```
                    60              65              70
aaa gaa aat ata ata tat tta gca aat cat caa agc aca gat gta tct    294
Lys Glu Asn Ile Ile Tyr Leu Ala Asn His Gln Ser Thr Asp Val Ser
         75                  80                  85 tgt gat ttt tcc aga agg tac aag gta taa tccagagcaa acaaaagtcc      344
Cys Asp Phe Ser Arg Arg Tyr Lys Val
         90                  95 tttcagctag tcaggcattt gctgcccaac gtggccttgc agtattaaaa catgtgctaa  404
caccacgaat aaaggcaact cacgttgctt tgattgcat gaagaattat ttagatgcaa   464
tttatgatgt tacggtggtt tatgaaggga agacgatgg agggcagcga agagagtcac   524
cgaccatgac ggaatttctc tgcaaagaat gtccaaaaat tcatattcac attgatcgta  584
tcgacaaaaa agatgtccca agaacaag aacatatgag aagatggctg catgaacgtt    644
tcgaaatcaa agataagatg cttatagaat tttatgagtc accagatcca gaaagaagaa  704
aaagatttcc tgggaaaagt gttaattcca aattaagtat caagaagact ttaccatcaa  764
tgttgatctt aagtggtttg actgcaggca tgcttatgac cgatgctgga aggaagctgt   824
atgtgaacac ctggatatat ggaaccctac ttggctgcct gtgggttact attaaagcat   884
agacaagtag ctgtctccag acagtgggat gtgctacatt gtctattttt ggcggctgca   944
catgacatca aattgtttcc tgaatttatt aaggagtgta aataaagcct tgttgattga  1004
agattggata tagaatttg tgacgaaagc tgatatgcaa tggtcttggg caaacatacc   1064
tggttgtaca actttagcat cggggctgct ggaagggtaa aagctaaatg gagtttctcc  1124
tgctctgtcc atttcctatg aactaatgac aacttgagaa ggctgggagg attgtgtatt  1184
ttgcaagtca gatggctgca ttttgagca ttaatttgca cgtatttca cttttctgt    1244 tattttcaat ttattacaac ttgacagctc caagctctta ttactaaagt atttagtatc  1304
ttgcagctag ttaatatttc atcttttgct tatttctaca agtcagtgaa ataaattgta   1364
tttaggaagt gtcaggatgt tcaaaggaaa gggtaaaaag tgttcatggg gaaaaagctc   1424
tgtttagcac atgattttat tgtattgcgt tattagctga ttttactcat tttatatttg   1484
caaaataaat ttctaatatt tattgaaatt gcttaatttg cacaccctgt acacacagaa   1544
aatggtataa aatatgagaa cgaagtttaa aattgtgact ctgattcatt atagcagaac   1604
tttaaatttc ccagcttttt gaagatttaa gctacgctat tagtacttcc ctttgtctgt   1664
gccataagtg cttgaaaacg ttaaggtttt ctgttttgtt ttgttttttt aatatcaaaa   1724
gagtcggtgt gaaccttggt tggaccccaa gttcacaaga ttttaaggt gatgagagcc    1784 tgcagacatt ctgcctagat ttactagcgt gtgccttttg cctgcttctc tttgatttca   1844
cagaatattc attcagaagt cgcgtttctg tagtgtggtg gattcccact gggctctggt   1904
ccttcccttg gatcccgtca gtggtgctgc tcagcggctt gcacgtagac ttgctaggaa   1964
gaaatgcaga gccagcctgt gctgcccact ttcagagttg aactctttaa gcccttgtga   2024
gtgggcttca ccagctactg cagaggcatt tgcatttgt ctgtgtcaag aagttcacct    2084
tctcaagcca gtgaaataca gacttaattc gtcatgactg aacgaatttg tttatttccc   2144
attaggttta gtggagctac acattaatat gtatcgcctt agagcaagag ctgtgttcca   2204
ggaaccagat cacgattttt agccatggaa caatatatcc catgggagaa gacctttcag   2264
tgtgaactgt tctatttttg tgttataatt taaacttcga tttcctcata gtcctttaag   2324
ttgacatttc tgcttactgc tactggattt ttgctgcaga aatatatcag tggcccacat   2384
taaacatacc agttggatca tgataagcaa aatgaaagaa ataatgatta agggaaaatt   2444
```

```
aagtgactgt gttacactgc ttctcccatg ccagagaata aactctttca agcatcatct   2504
ttgaagagtc gtgtggtgtg aattggtttg tgtacattag aatgtatgca cacatccatg   2564
gacactcagg atatagttgg cctaataatc ggggcatggg taaaacttat gaaaatttcc   2624
tcatgctgaa ttgtaatttt ctcttacctg taaagtaaaa tttagatcaa ttccatgtct   2684
ttgttaagta cagggattta atatattttg aatataatgg gtatgttcta aatttgaact   2744
ttgagaggca atactgttgg aattatgtgg attctaactc atttttaacaa ggtagcctga   2804
cctgcataag atcacttgaa tgttaggttt catagaacta tactaatctt ctcacaaaag   2864
gtctataaaa tacagtcgtt gaaaaaaatt ttgtatcaaa atgtttggaa aattagaagc   2924
ttctccttaa cctgtattga tactgacttg aattattttc taaaattaag agccgtatac   2984
ctacctgtaa gtcttttcac atatcattta aacttttgtt tgtattatta ctgatttaca   3044
gcttagttat taatttttct ttataagaat gccgtcgatg tgcatgcttt tatgtttttc   3104
agaaaagggt gtgtttggat gaaagtaaaa aaaaaaataa aatctttcac tgtctctaat   3164
ggctgtgctg tttaacatt tttgaccta aaattcacca acagtctccc agtacataaa   3224
ataggcttaa tgactggccc tgcattcttc acaatatttt tccctaagct ttgagcaaag   3284
ttttaaaaaa atacactaaa ataatcaaaa ctgttaagca gtatattagt ttggttatat   3344
aaattcatct gcaatttata agatgcatgg ccgatgttaa tttgcttggc aattctgtaa   3404
tcattaagtg atctcagtga aacatgtcaa atgccttaaa ttaactaagt tggtgaataa   3464
aagtgccgat ctggctaact cttacaccat acatactgat agttttttcat atgtttcatt   3524
tccatgtgat ttttaaaatt tagagtggca acaattttgc ttaatatggg ttacataagc   3584
tttatttttt cctttgttca taattatatt ctttgaatag gtctgtgtca atcaagtgat   3644
ctaactagac tgatcataga tagaaggaaa taaggccaag ttcaagacca gcctgggcaa   3704
catatcgaga acctgtctac aaaaaaatta aaaaaaatta gccaggcatg gtggcgtaca   3764
ctgagtagtt tgtcccagct actcgggagg gtgaggtggg aggatcgctt cagcccagga   3824
ggttgagatt gcagtgagcc atggacatac cactgcacta cagcctaggt aacagcacga   3884
gaccccaact cttagaaaat gaaaggaaa tatagaaata taaaatttgc ttattataga   3944
cacacagtaa ctcccagata tgtaccacaa aaaatgtgaa aagagagaga aatgtctacc   4004
aaagcagtat tttgtgtgta taattgcaag cgcatagtaa aataattta accttaattt   4064
gttttagta gtgtttagat tgaagattga gtgaaatatt tcttggcag atattccgta   4124
tctggtggaa agctacaatg caatgtcgtt gtagttttgc atggcttgct ttataaacaa   4184
gattttttct ccctccttt gggccagttt tcattacgag taactcacac ttttgatta   4244
aagaacttga aattacgtta tcacttagta taattgacat tatatagaga ctatgtaaca   4304
tgcaatcatt agaatcaaaa ttagtacttt ggtcaaaata tttacaacat tcacatactt   4364
gtcaaatatt catgtaatta actgaattta aaaccttcaa ctattatgaa gtgctcgtct   4424
gtacaatcgc taatttactc agtttagagt agctacaact cttcgatact atcatcaata   4484
tttgacatct tttccaattt gtgtatgaaa agtaaatcta ttcctgtagc aactggggag   4544
tcatatatga ggtcaaagac atataccttg ttattataat atgtatacta taataatagc   4604
tggttatcct gagcagggga aaaggttatt tttaggaaaa ccacttcaaa tagaaagctg   4664
aagtacttct aatatactga gggaagtata atatgtggaa caaactctca acaaaatgtt   4724
tattgatgtt gatgaaacag atcagttttt ccatccggat tattattggt tcatgatttt   4784
```

-continued

```
atatgtgaat atgtaagata tgttctgcaa ttttataaat gttcatgtct ttttttaaaa    4844
aaggtgctat tgaaattctg tgtctccagc aggcaagaat acttgactaa ctcttttttgt   4904 ctctttatgg tattttcaga ataaagtctg acttgtgttt ttgagattat tggtgcctca    4964
ttaattcagc aataaaggaa aatatgcatc tcaaaaat                            5002
```

<210> SEQ ID NO 121
<211> LENGTH: 4958
<212> TYPE: DNA
<213> ORGANISM: Homo sapiens
<220> FEATURE:
<221> NAME/KEY: CDS
<222> LOCATION: 31..579
<221> NAME/KEY: polyA_signal
<222> LOCATION: 4931..4936
<223> OTHER INFORMATION: AATAAA

<400> SEQUENCE: 121

```
ctgctgtccc tggtgctcca cacgtactcc atg cgc tac ctg ctg ccc agc gtc         54
                                Met Arg Tyr Leu Leu Pro Ser Val
                                  1               5 gtg ctc ctg ggc acg gcg ccc acc tac gtg ttg gcc tgg ggg gtc tgg         102
Val Leu Leu Gly Thr Ala Pro Thr Tyr Val Leu Ala Trp Gly Val Trp
 10              15                  20 cgg ctg ctc tcc gcc ttc ctg ccc gcc cgc ttc tac caa gcg ctg gac        150
Arg Leu Leu Ser Ala Phe Leu Pro Ala Arg Phe Tyr Gln Ala Leu Asp
25              30                  35                  40 gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
                45                  50                  55 aat tac acc ggg gtc cag ata ttg cta tat gga gat ttg cca aaa aat        246
Asn Tyr Thr Gly Val Gln Ile Leu Leu Tyr Gly Asp Leu Pro Lys Asn
         60                  65                  70 aaa gaa aat ata ata tat tta gca aat cat caa agc aca gtt gac tgg        294
Lys Glu Asn Ile Ile Tyr Leu Ala Asn His Gln Ser Thr Val Asp Trp
     75                  80                  85 att gtt gct gac atc ttg gcc atc agg cag aat gcg cta gga cat gtg        342
Ile Val Ala Asp Ile Leu Ala Ile Arg Gln Asn Ala Leu Gly His Val
 90                  95                  100 cgc tac gtg ctg aaa gaa ggg tta aaa tgg ctg cca ttg tat ggg tgt        390
Arg Tyr Val Leu Lys Glu Gly Leu Lys Trp Leu Pro Leu Tyr Gly Cys
105                 110                 115                 120 tac ttt gct cag cat gga gga atc tat gta aag cgc agt gcc aaa ttt        438
Tyr Phe Ala Gln His Gly Gly Ile Tyr Val Lys Arg Ser Ala Lys Phe
                125                 130                 135 aac gag aaa gag atg cga aac aag ttg cag agc tac gtg gac gca gga        486
Asn Glu Lys Glu Met Arg Asn Lys Leu Gln Ser Tyr Val Asp Ala Gly
            140                 145                 150 act cca aat ttc tct gca aag aat gtc caa aaa ttc ata ttc aca ttg        534
Thr Pro Asn Phe Ser Ala Lys Asn Val Gln Lys Phe Ile Phe Thr Leu
        155                 160                 165 atc gta tcg aca aaa aag atg tcc cag aag aac aag aac ata tga            579
Ile Val Ser Thr Lys Lys Met Ser Gln Lys Asn Lys Asn Ile
    170                 175                 180 gaagatggct gcatgaacgt ttcgaaatca aagataagat gcttatagaa ttttatgagt       639
caccagatcc agaaagaaga aaaagatttc ctgggaaaag tgttaattcc aaattaagta      699
tcaagaagac tttaccatca atgttgatct taagtggttt gactgcaggc atgcttatga      759
ccgatgctgg aaggaagctg tatgtgaaca cctggatata tggaacccta cttggctgcc      819
tgtgggttac tattaaagca tagacaagta gctgtctcca gacagtggga tgtgctacat      879
```

```
tgtctatttt tggcggctgc acatgacatc aaattgtttc ctgaatttat taaggagtgt    939
aaataaagcc ttgttgattg aagattggat aatagaattt gtgacgaaag ctgtatatgca   999 atggtcttgg gcaaacatac ctggttgtac aactttagca tcggggctgc tggaagggta   1059
aaagctaaat ggagtttctc ctgctctgtc catttcctat gaactaatga caacttgaga   1119
aggctgggag gattgtgtat tttgcaagtc agatggctgc attttttgagc attaatttgc   1179 agcgtatttc acttttttctg ttattttcaa tttattacaa cttgacagct ccaagctctt   1239
attactaaag tatttagtat cttgcagcta gttaatattt catcttttgc ttatttctac    1299
aagtcagtga aataaattgt atttaggaag tgtcaggatg ttcaaaggaa agggtaaaaa    1359
gtgttcatgg ggaaaaagct ctgtttagca catgatttta ttgtattgcg ttattagctg    1419
attttactca ttttatattt gcaaaataaa tttctaatat ttattgaaat tgcttaattt    1479
gcacaccctg tacacacaga aaatggtata aaatatgaga acgaagttta aaattgtgac    1539
tctgattcat tatagcagaa ctttaaattt cccagctttt tgaagattta agctacgcta    1599
ttagtacttc cctttgtctg tgccataagt gcttgaaaac gttaaggttt ctgttttgt    1659 tttgtttttt taatatcaaa agagtcggtg tgaaccttgg ttggacccca agttcacaag    1719
atttttaagg tgatgagagc ctgcagacat tctgcctaga tttactagcg tgtgcctttt    1779
gcctgcttct ctttgatttc acagaatatt cattcagaag tcgcgtttct gtagtgtggt    1839
ggattcccac tgggctctgg tccttccctt ggatcccgtc agtggtgctg ctcagcggct    1899
tgcacgtaga cttgctagga agaaatgcag agccagcctg tgctgcccac tttcagagtt    1959
gaactcttta agcccttgtg agtgggcttc accagctact gcagaggcat tttgcatttg    2019
tctgtgtcaa gaagttcacc ttctcaagcc agtgaaatac agacttaatt cgtcatgact    2079
gaacgaattt gtttatttcc cattaggttt agtggagcta cacattaata tgtatcgcct    2139
tagagcaaga gctgtgttcc aggaaccaga tcacgatttt tagccatgga acaatatatc    2199
ccatgggaga agacctttca gtgtgaactg ttctattttt gtgttataat ttaaacttcg    2259
atttcctcat agtcctttaa gttgacattt ctgcttactg ctactggatt tttgctgcag    2319
aaatatatca gtgggcccaca ttaaacatac cagttggatc atgataagca aaatgaaaga    2379
aataatgatt aagggaaaat taagtgactg tgttacactg cttctcccat gccagagaat    2439
aaactctttc aagcatcatc tttgaagagt cgtgtggtgt gaattggttt gtgtacatta    2499
gaatgtatgc acacatccat ggacactcag gatatagttg gcctaataat cggggcatgg    2559
gtaaaactta tgaaaatttc ctcatgctga attgtaattt tctcttacct gtaaagtaaa    2619
atttagatca attccatgtc tttgttaagt acagggattt aatatatttt gaatataatg    2679
ggtatgttct aaatttgaac tttgagaggc aatactgttg gaattatgtg gattctaact    2739
cattttaaca aggtagcctg acctgcataa gatcacttga atgttaggtt tcatagaact    2799
atactaatct tctcacaaaa ggtctataaa atacagtcgt tgaaaaaaat tttgtatcaa    2859
aatgtttgga aaattagaag cttctcctta acctgtattg atactgactt gaattatttt    2919
ctaaaattaa gagccgtata cctacctgta agtcttttca catatcattt aaacttttgt    2979
ttgtattatt actgatttac agcttagtta ttaatttttc tttataagaa tgccgtcgat    3039
gtgcatgctt ttatgttttt cagaaagggg tgtgtttgga tgaaagtaaa aaaaaaata    3099 aaatctttca ctgtctctaa tggctgtgct gtttaacatt ttttgaccct aaaattcacc    3159
aacagtctcc cagtacataa aataggctta atgactggcc ctgcattctt cacaatattt    3219
```

-continued

| | |
|---|---|
| ttccctaagc tttgagcaaa gttttaaaaa aatacactaa aataatcaaa actgttaagc | 3279 |
| agtatattag tttggttata taaattcatc tgcaatttat aagatgcatg gccgatgtta | 3339 |
| atttgcttgg caattctgta atcattaagt gatctcagtg aaacatgtca aatgccttaa | 3399 |
| attaactaag ttggtgaata aaagtgccga tctggctaac tcttacacca tacatactga | 3459 |
| tagtttttca tatgtttcat ttccatgtga tttttaaaat ttagagtggc aacaattttg | 3519 |
| cttaatatgg gttacataag ctttattttt tcctttgttc ataattatat tctttgaata | 3579 |
| ggtctgtgtc aatcaagtga tctaactaga ctgatcatag atagaaggaa ataaggccaa | 3639 |
| gttcaagacc agcctgggca acatatcgag aacctgtcta caaaaaatt aaaaaaaatt | 3699 |
| agccaggcat ggtggcgtac actgagtagt ttgtcccagc tactcgggag ggtgaggtgg | 3759 |
| gaggatcgct tcagcccagg aggttgagat tgcagtgagc catggacata ccactgcact | 3819 |
| acagcctagg taacagcacg agaccccaac tcttagaaaa tgaaaaggaa atatagaaat | 3879 |
| ataaaatttg cttattatag acacacagta actcccagat atgtaccaca aaaaatgtga | 3939 |
| aaagagagag aaatgtctac caaagcagta ttttgtgtgt ataattgcaa gcgcatagta | 3999 |
| aaataatttt aaccttaatt tgtttttagt agtgtttaga ttgaagattg agtgaaatat | 4059 |
| tttcttggca gatattccgt atctggtgga aagctacaat gcaatgtcgt tgtagttttg | 4119 |
| catggcttgc tttataaaca agattttttc tccctccttt tgggccagtt ttcattacga | 4179 |
| gtaactcaca cttttgatt aaagaacttg aaattacgtt atcacttagt ataattgaca | 4239 |
| ttatatagag actatgtaac atgcaatcat tagaatcaaa attagtactt tggtcaaaat | 4299 |
| atttacaaca ttcacatact tgtcaaatat tcatgtaatt aactgaattt aaaaccttca | 4359 |
| actattatga agtgctcgtc tgtacaatcg ctaatttact cagtttagag tagctacaac | 4419 |
| tcttcgatac tatcatcaat atttgacatc ttttccaatt tgtgtatgaa aagtaaatct | 4479 |
| attcctgtag caactgggga gtcatatatg aggtcaaaga catataccctt gttattataa | 4539 |
| tatgtatact ataataatag ctggttatcc tgagcagggg aaaaggttat ttttaggaaa | 4599 |
| accacttcaa atagaaagct gaagtacttc taatatactg agggaagtat aatatgtgga | 4659 |
| acaaactctc aacaaaatgt ttattgatgt tgatgaaaca gatcagtttt tccatccgga | 4719 |
| ttattattgg ttcatgattt tatatgtgaa tatgtaagat atgttctgca attttataaa | 4779 |
| tgttcatgtc ttttttttaaa aaaggtgcta ttgaaattct gtgtctccag caggcaagaa | 4839 |
| tacttgacta actcttttg tctctttatg gtattttcag aataaagtct gacttgtgtt | 4899 |
| tttgagatta ttggtgcctc attaattcag caataaagga aaatatgcat ctcaaaaat | 4958 |

<210> SEQ ID NO 122
<211> LENGTH: 5094
<212> TYPE: DNA
<213> ORGANISM: Homo sapiens
<220> FEATURE:
<221> NAME/KEY: CDS
<222> LOCATION: 31..978
<221> NAME/KEY: polyA_signal
<222> LOCATION: 5067..5072
<223> OTHER INFORMATION: AATAAA

<400> SEQUENCE: 122

```
ctgctgtccc tggtgctcca cacgtactcc atg cgc tac ctg ctg ccc agc gtc        54
                                 Met Arg Tyr Leu Leu Pro Ser Val
                                  1               5 gtg ctc ctg ggc acg gcg ccc acc tac gtg ttg gcc tgg ggg gtc tgg        102
Val Leu Leu Gly Thr Ala Pro Thr Tyr Val Leu Ala Trp Gly Val Trp
     10              15                  20
```

```
cgg ctg ctc tcc gcc ttc ctg ccc gcc cgc ttc tac caa gcg ctg gac    150
Arg Leu Leu Ser Ala Phe Leu Pro Ala Arg Phe Tyr Gln Ala Leu Asp
 25              30                  35                  40 gac cgg ctg tac tgc gtc tac cag agc atg gtg ctc ttc ttc ttc gag    198
Asp Arg Leu Tyr Cys Val Tyr Gln Ser Met Val Leu Phe Phe Phe Glu
                 45                  50                  55 aat tac acc ggg gtc cag ata ttg cta tat gga gat ttg cca aaa aat    246
Asn Tyr Thr Gly Val Gln Ile Leu Leu Tyr Gly Asp Leu Pro Lys Asn
             60                  65                  70 aaa gaa aat ata ata tat tta gca aat cat caa agc aca gtt gac tgg    294
Lys Glu Asn Ile Ile Tyr Leu Ala Asn His Gln Ser Thr Val Asp Trp
     75                  80                  85 att gtt gct gac atc ttg gcc atc agg cag aat gcg cta gga cat gtg    342
Ile Val Ala Asp Ile Leu Ala Ile Arg Gln Asn Ala Leu Gly His Val
 90                  95                  100 cgc tac gtg ctg aaa gaa ggg tta aaa tgg ctg cca ttg tat ggg tgt    390
Arg Tyr Val Leu Lys Glu Gly Leu Lys Trp Leu Pro Leu Tyr Gly Cys
105                 110                 115                 120 tac ttt gct cag cat gga gga atc tat gta aag cgc agt gcc aaa ttt    438
Tyr Phe Ala Gln His Gly Gly Ile Tyr Val Lys Arg Ser Ala Lys Phe
                125                 130                 135 aac gag aaa gag atg cga aac aag ttg cag agc tac gtg gac gca gga    486
Asn Glu Lys Glu Met Arg Asn Lys Leu Gln Ser Tyr Val Asp Ala Gly
            140                 145                 150 act cca atg tat ctt gtg att ttt cca gaa ggt aca agg tat aat cca    534
Thr Pro Met Tyr Leu Val Ile Phe Pro Glu Gly Thr Arg Tyr Asn Pro
        155                 160                 165 gag caa aca aaa gtc ctt tca gct agt cag gca ttt gct gcc caa cgt    582
Glu Gln Thr Lys Val Leu Ser Ala Ser Gln Ala Phe Ala Ala Gln Arg
    170                 175                 180 ggg aaa gac gat gga ggg cag cga aga gag tca ccg acc atg acg gaa    630
Gly Lys Asp Asp Gly Gly Gln Arg Arg Glu Ser Pro Thr Met Thr Glu
185                 190                 195                 200 ttt ctc tgc aaa gaa tgt cca aaa att cat att cac att gat cgt atc    678
Phe Leu Cys Lys Glu Cys Pro Lys Ile His Ile His Ile Asp Arg Ile
                205                 210                 215 gac aaa aaa gat gtc cca gaa gaa caa gaa cat atg aga aga tgg ctg    726
Asp Lys Lys Asp Val Pro Glu Glu Gln Glu His Met Arg Arg Trp Leu
            220                 225                 230 cat gaa cgt ttc gaa atc aaa gat aag atg ctt ata gaa ttt tat gag    774
His Glu Arg Phe Glu Ile Lys Asp Lys Met Leu Ile Glu Phe Tyr Glu
        235                 240                 245 tca cca gat cca gaa aga aga aaa aga ttt cct ggg aaa agt gtt aat    822
Ser Pro Asp Pro Glu Arg Arg Lys Arg Phe Pro Gly Lys Ser Val Asn
    250                 255                 260 tcc aaa tta agt atc aag aag act tta cca tca atg ttg atc tta agt    870
Ser Lys Leu Ser Ile Lys Lys Thr Leu Pro Ser Met Leu Ile Leu Ser
265                 270                 275                 280 ggt ttg act gca ggc atg ctt atg acc gat gct gga agg aag ctg tat    918
Gly Leu Thr Ala Gly Met Leu Met Thr Asp Ala Gly Arg Lys Leu Tyr
                285                 290                 295 gtg aac acc tgg ata tat gga acc cta ctt ggc tgc ctg tgg gtt act    966
Val Asn Thr Trp Ile Tyr Gly Thr Leu Leu Gly Cys Leu Trp Val Thr
            300                 305                 310 att aaa gca tag acaagtagct gtctccagac agtgggatgt gctacattgt       1018
Ile Lys Ala
        315 ctatttttgg cggctgcaca tgacatcaaa ttgtttcctg aatttattaa ggagtgtaaa  1078
```

```
taaagccttg ttgattgaag attggataat agaatttgtg acgaaagctg atatgcaatg   1138
gtcttgggca acatacctg gttgtacaac tttagcatcg gggctgctgg aagggtaaaa   1198
gctaaatgga gtttctcctg ctctgtccat ttcctatgaa ctaatgacaa cttgagaagg   1258
ctgggaggat tgtgtatttt gcaagtcaga tggctgcatt tttgagcatt aatttgcagc   1318
gtatttcact ttttctgtta ttttcaattt attacaactt gacagctcca agctcttatt   1378
actaaagtat ttagtatctt gcagctagtt aatatttcat cttttgctta tttctacaag   1438
tcagtgaaat aaattgtatt taggaagtgt caggatgttc aaaggaaagg gtaaaaagtg   1498
ttcatgggga aaaagctctg tttagcacat gatttttattg tattgcgtta ttagctgatt   1558
ttactcattt tatatttgca aaataaattt ctaatattta ttgaaattgc ttaatttgca   1618
caccctgtac acacagaaaa tggtataaaa tatgagaacg aagtttaaaa ttgtgactct   1678
gattcattat agcagaactt taaatttccc agcttttttga agatttaagc tacgctatta   1738
gtacttccct ttgtctgtgc cataagtgct tgaaaacgtt aaggttttct gttttgtttt   1798
gttttttttaa tatcaaaaga gtcggtgtga accttggttg gaccccaagt tcacaagatt   1858
tttaaggtga tgagagcctg cagacattct gcctagattt actagcgtgt gccttttgcc   1918
tgcttctctt tgatttcaca gaatattcat tcagaagtcg cgtttctgta gtgtggtgga   1978
ttcccactgg gctctggtcc ttcccttgga tcccgtcagt ggtgctgctc agcggcttgc   2038
acgtagactt gctaggaaga aatgcagagc cagcctgtgc tgcccacttt cagagttgaa   2098
ctctttaagc ccttgtgagt gggcttcacc agctactgca gaggcatttt gcatttgtct   2158
gtgtcaagaa gttcaccttc tcaagccagt gaaatacaga cttaattcgt catgactgaa   2218
cgaatttgtt tatttcccat taggtttagt ggagctacac attaatatgt atcgccttag   2278
agcaagagct gtgttccagg aaccagatca cgattttttag ccatggaaca atatatccca   2338
tgggagaaga cctttcagtg tgaactgttc tatttttgtg ttataattta aacttcgatt   2398
tcctcatagt cctttaagtt gacatttctg cttactgcta ctggattttt gctgcagaaa   2458
tatatcagtg gcccacatta acataccag ttggatcatg ataagcaaaa tgaaagaaat   2518
aatgattaag ggaaaattaa gtgactgtgt tacactgctt ctcccatgcc agagaataaa   2578
ctctttcaag catcatcttt gaagagtcgt gtggtgtgaa ttggtttgtg tacattagaa   2638
tgtatgcaca catccatgga cactcaggat atagttggcc taataatcgg ggcatgggta   2698
aaacttatga aaatttcctc atgctgaatt gtaattttct cttacctgta aagtaaaatt   2758
tagatcaatt ccatgtcttt gttaagtaca gggatttaat atattttgaa tataatgggt   2818
atgttctaaa tttgaacttt gagaggcaat actgttggaa ttatgtggat tctaactcat   2878
tttaacaagg tagcctgacc tgcataagat cacttgaatg ttaggtttca tagaactata   2938
ctaatcttct cacaaaaggt ctataaaata cagtcgttga aaaaattttt gtatcaaaat   2998
gtttggaaaa ttagaagctt ctccttaacc tgtattgata ctgacttgaa ttattttcta   3058
aaattaagag ccgtatacct acctgtaagt cttttcacat atcatttaaa cttttgtttg   3118
tattattact gatttacagc ttagttatta attttttcttt ataagaatgc cgtcgatgtg   3178
catgctttta tgttttttcag aaagggtgt gtttggatga agtaaaaaa aaaaataaaa   3238
tctttcactg tctctaatgg ctgtgctgtt taacattttt tgaccctaaa attcaccaac   3298
agtctcccag tacataaaat aggcttaatg actggccctg cattcttcac aatattttttc   3358
cctaagcttt gagcaaagtt ttaaaaaaat acactaaaat aatcaaaact gttaagcagt   3418
atattagttt ggttatataa attcatctgc aatttataag atgcatggcc gatgttaatt   3478
```

```
tgcttggcaa ttctgtaatc attaagtgat ctcagtgaaa catgtcaaat gccttaaatt    3538
aactaagttg gtgaataaaa gtgccgatct ggctaactct tacaccatac atactgatag    3598
tttttcatat gtttcatttc catgtgattt ttaaaattta gagtggcaac aattttgctt    3658
aatatgggtt acataagctt tatttttttcc tttgttcata attatattct ttgaataggt    3718
ctgtgtcaat caagtgatct aactagactg atcatagata gaaggaaata aggccaagtt    3778
caagaccagc ctgggcaaca tatcgagaac ctgtctacaa aaaaattaaa aaaaattagc    3838
caggcatggt ggcgtacact gagtagtttg tcccagctac tcgggagggt gaggtgggag    3898
gatcgcttca gcccaggagg ttgagattgc agtgagccat ggacatacca ctgcactaca    3958
gcctaggtaa cagcacgaga ccccaactct tagaaaatga aaaggaaata tagaaatata    4018
aaatttgctt attatagaca cacagtaact cccagatatg taccacaaaa aatgtgaaaa    4078
gagagagaaa tgtctaccaa agcagtattt tgtgtgtata attgcaagcg catagtaaaa    4138 taatttttaac cttaatttgt ttttagtagt gtttagattg aagattgagt gaaatatttt    4198
cttggcagat attccgtatc tggtggaaag ctacaatgca atgtcgttgt agttttgcat    4258
ggcttgcttt ataaacaaga tttttctcc ctccttttgg gccagttttc attacgagta    4318
actcacactt tttgattaaa gaacttgaaa ttacgttatc acttagtata attgacatta    4378
tatagagact atgtaacatg caatcattag aatcaaaatt agtactttgg tcaaaatatt    4438
tacaacattc acatacttgt caaatattca tgtaattaac tgaatttaaa accttcaact    4498
attatgaagt gctcgtctgt acaatcgcta atttactcag tttagagtag ctacaactct    4558
tcgatactat catcaatatt tgacatcttt tccaatttgt gtatgaaaag taaatctatt    4618
cctgtagcaa ctggggagtc atatatgagg tcaaagacat ataccttgtt attataatat    4678
gtatactata ataatagctg gttatcctga gcagggaaa aggttatttt taggaaaacc    4738
acttcaaata gaaagctgaa gtacttctaa tatactgagg gaagtataat atgtggaaca    4798
aactctcaac aaaatgttta ttgatgttga tgaaacagat cagttttttcc atccggatta    4858 ttattggttc atgattttat atgtgaatat gtaagatatg ttctgcaatt ttataaatgt    4918
tcatgtcttt ttttaaaaaa ggtgctattg aaattctgtg tctccagcag gcaagaatac    4978
ttgactaact cttttttgtct ctttatggta ttttcagaat aaagtctgac ttgtgttttt    5038
gagattattg gtgcctcatt aattcagcaa taaggaaaa tatgcatctc aaaaat        5094
```

<210> SEQ ID NO 123
<211> LENGTH: 5049
<212> TYPE: DNA
<213> ORGANISM: Homo sapiens
<220> FEATURE:
<221> NAME/KEY: CDS
<222> LOCATION: 31..933
<221> NAME/KEY: polyA_signal
<222> LOCATION: 5022..5027
<223> OTHER INFORMATION: AATAAA

<400> SEQUENCE: 123

```
ctgctgtccc tggtgctcca cacgtactcc atg cgc tac ctg ctg ccc agc gtc        54
                                  Met Arg Tyr Leu Leu Pro Ser Val
                                   1               5 gtg ctc ctg ggc acg gcg ccc acc tac gtg ttg gcc tgg ggg gtc tgg       102
Val Leu Leu Gly Thr Ala Pro Thr Tyr Val Leu Ala Trp Gly Val Trp
     10              15                  20 cgg ctc ctc tcc gcc ttc ctg ccc gcc cgc ttc tac caa gcg ctg gac       150
Arg Leu Leu Ser Ala Phe Leu Pro Ala Arg Phe Tyr Gln Ala Leu Asp
```

```
              25                  30                  35                  40
gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
                        45                  50                  55 aat tac acc ggg gtc cag ata ttg cta tat gga gat ttg cca aaa aat        246
Asn Tyr Thr Gly Val Gln Ile Leu Leu Tyr Gly Asp Leu Pro Lys Asn
            60                  65                  70 aaa gaa aat ata ata tat tta gca aat cat caa agc aca gtt gac tgg        294
Lys Glu Asn Ile Ile Tyr Leu Ala Asn His Gln Ser Thr Val Asp Trp
        75                  80                  85 att gtt gct gac atc ttg gcc atc agg cag aat gcg cta gga cat gtg        342
Ile Val Ala Asp Ile Leu Ala Ile Arg Gln Asn Ala Leu Gly His Val
    90                  95                  100 cgc tac gtg ctg aaa gaa ggg tta aaa tgg ctg cca ttg tat ggg tgt        390
Arg Tyr Val Leu Lys Glu Gly Leu Lys Trp Leu Pro Leu Tyr Gly Cys
105                 110                 115                 120 tac ttt gct cag cat gga gga atc tat gta aag cgc agt gcc aaa ttt        438
Tyr Phe Ala Gln His Gly Gly Ile Tyr Val Lys Arg Ser Ala Lys Phe
                125                 130                 135 aac gag aaa gag atg cga aac aag ttg cag agc tac gtg gac gca gga        486
Asn Glu Lys Glu Met Arg Asn Lys Leu Gln Ser Tyr Val Asp Ala Gly
            140                 145                 150 act cca atg tat ctt gtg att ttt cca gaa ggt aca agg tat aat cca        534
Thr Pro Met Tyr Leu Val Ile Phe Pro Glu Gly Thr Arg Tyr Asn Pro
        155                 160                 165 gag caa aca aaa gtc ctt tca gct agt cag gca ttt gct gcc caa cgt        582
Glu Gln Thr Lys Val Leu Ser Ala Ser Gln Ala Phe Ala Ala Gln Arg
    170                 175                 180 gaa ttt ctc tgc aaa gaa tgt cca aaa att cat att cac att gat cgt        630
Glu Phe Leu Cys Lys Glu Cys Pro Lys Ile His Ile His Ile Asp Arg
185                 190                 195                 200 atc gac aaa aaa gat gtc cca gaa gaa caa gaa cat atg aga aga tgg        678
Ile Asp Lys Lys Asp Val Pro Glu Glu Gln Glu His Met Arg Arg Trp
                205                 210                 215 ctg cat gaa cgt ttc gaa atc aaa gat aag atg ctt ata gaa ttt tat        726
Leu His Glu Arg Phe Glu Ile Lys Asp Lys Met Leu Ile Glu Phe Tyr
            220                 225                 230 gag tca cca gat cca gaa aga aga aaa aga ttt cct ggg aaa agt gtt        774
Glu Ser Pro Asp Pro Glu Arg Arg Lys Arg Phe Pro Gly Lys Ser Val
        235                 240                 245 aat tcc aaa tta agt atc aag aag act tta cca tca atg ttg atc tta        822
Asn Ser Lys Leu Ser Ile Lys Lys Thr Leu Pro Ser Met Leu Ile Leu
    250                 255                 260 agt ggt ttg act gca ggc atg ctt atg acc gat gct gga agg aag ctg        870
Ser Gly Leu Thr Ala Gly Met Leu Met Thr Asp Ala Gly Arg Lys Leu
265                 270                 275                 280 tat gtg aac acc tgg ata tat gga acc cta ctt ggc tgc ctg tgg gtt        918
Tyr Val Asn Thr Trp Ile Tyr Gly Thr Leu Leu Gly Cys Leu Trp Val
                285                 290                 295 act att aaa gca tag acaagtagct gtctccagac agtgggatgt gctacattgt        973
Thr Ile Lys Ala
            300 ctatttttgg cggctgcaca tgacatcaaa ttgtttcctg aatttattaa ggagtgtaaa     1033 taaagccttg ttgattgaag attggataat agaatttgtg acgaaagctg atatgcaatg     1093 gtcttgggca aacatacctg gttgtacaac tttagcatcg gggctgctgg aagggtaaaa     1153 gctaaatgga gtttctcctg ctctgtccat ttcctatgaa ctaatgacaa cttgagaagg     1213 ctgggaggat tgtgtatttt gcaagtcaga tggctgcatt tttgagcatt aatttgcagc     1273
```

```
gtatttcact ttttctgtta ttttcaattt attacaactt gacagctcca agctcttatt    1333
actaaagtat ttagtatctt gcagctagtt aatatttcat cttttgctta tttctacaag    1393
tcagtgaaat aaattgtatt taggaagtgt caggatgttc aaaggaaagg gtaaaaagtg    1453
ttcatgggga aaaagctctg tttagcacat gattttattg tattgcgtta ttagctgatt    1513
ttactcattt tatatttgca aaataaattt ctaatattta ttgaaattgc ttaatttgca    1573
caccctgtac acacagaaaa tggtataaaa tatgagaacg aagtttaaaa ttgtgactct    1633
gattcattat agcagaactt taaatttccc agctttttga agatttaagc tacgctatta    1693
gtacttccct ttgtctgtgc cataagtgct tgaaaacgtt aaggttttct gttttgtttt    1753 gttttttttaa tatcaaaaga gtcggtgtga accttggttg gacccccaagt tcacaagatt    1813 tttaaggtga tgagagcctg cagacattct gcctagattt actagcgtgt gccttttgcc    1873
tgcttctctt tgatttcaca gaatattcat tcagaagtcg cgtttctgta gtgtggtgga    1933
ttcccactgg gctctggtcc ttcccttgga tcccgtcagt ggtgctgctc agcggcttgc    1993
acgtagactt gctaggaaga aatgcagagc cagcctgtgc tgcccacttt cagagttgaa    2053
ctctttaagc ccttgtgagt gggcttcacc agctactgca gaggcatttt gcatttgtct    2113
gtgtcaagaa gttcaccttc tcaagccagt gaaatacaga cttaattcgt catgactgaa    2173
cgaatttgtt tatttcccat taggtttagt ggagctacac attaatatgt atcgccttag    2233
agcaagagct gtgttccagg aaccagatca cgatttttag ccatggaaca atatatccca    2293
tgggagaaga cctttcagtg tgaactgttc tattttttgtg ttataattta aacttcgatt    2353
tcctcatagt cctttaagtt gacatttctg cttactgcta ctggattttt gctgcagaaa    2413
tatatcagtg gcccacatta aacataccag ttggatcatg ataagcaaaa tgaaagaaat    2473
aatgattaag ggaaaattaa gtgactgtgt tacactgctt ctcccatgcc agagaataaa    2533
ctctttcaag catcatcttt gaagagtcgt gtggtgtgaa ttggtttgtg tacattagaa    2593
tgtatgcaca catccatgga cactcaggat atagttggcc taataatcgg ggcatgggta    2653
aaacttatga aaatttcctc atgctgaatt gtaatttttct cttacctgta aagtaaaatt    2713
tagatcaatt ccatgtcttt gttaagtaca gggatttaat atattttgaa tataatgggt    2773
atgttctaaa tttgaacttt gagaggcaat actgttggaa ttatgtggat tctaactcat    2833
tttaacaagg tagcctgacc tgcataagat cacttgaatg ttaggtttca tagaactata    2893
ctaatcttct cacaaaaggt ctataaaata cagtcgttga aaaaaatttt gtatcaaaat    2953
gtttggaaaa ttagaagctt ctccttaacc tgtattgata ctgacttgaa ttatttttcta    3013 aaattaagag ccgtatacct acctgtaagt cttttcacat atcatttaaa cttttgtttg    3073
tattattact gatttacagc ttagttatta attttttcttt ataagaatgc cgtcgatgtg    3133
catgctttta tgttttttcag aaaagggtgt gtttggatga aagtaaaaaa aaaaataaaa    3193
tctttcactg tctctaatgg ctgtgctgtt taacattttt tgaccctaaa attcaccaac    3253
agtctcccag tacataaaat aggcttaatg actggccctg cattcttcac aatattttttc    3313 cctaagcttt gagcaaagtt ttaaaaaaat acactaaaat aatcaaaact gttaagcagt    3373
atattagttt ggtatataaa attcatctgc aatttataag atgcatggcc gatgttaatt    3433
tgcttggcaa ttctgtaatc attaagtgat ctcagtgaaa catgtcaaat gccttaaatt    3493
aactaagttg gtgaataaaa gtgccgatct ggctaactct tacaccatac atactgatag    3553
tttttcatat gtttcatttc catgtgattt ttaaaattta gagtggcaac aatttttgctt    3613
```

```
aatatgggtt acataagctt tatttttttcc tttgttcata attatattct ttgaataggt    3673
ctgtgtcaat caagtgatct aactagactg atcatagata gaaggaaata aggccaagtt    3733
caagaccagc ctgggcaaca tatcgagaac ctgtctacaa aaaaattaaa aaaaattagc    3793
caggcatggt ggcgtacact gagtagtttg tcccagctac tcgggagggt gaggtgggag    3853
gatcgcttca gcccaggagg ttgagattgc agtgagccat ggacatacca ctgcactaca    3913
gcctaggtaa cagcacgaga ccccaactct tagaaaatga aaggaaata tagaaatata     3973 aaatttgctt attatagaca cacagtaact cccagatatg taccacaaaa aatgtgaaaa    4033
gagagagaaa tgtctaccaa agcagtattt tgtgtgtata attgcaagcg catagtaaaa    4093
taattttaac cttaatttgt ttttagtagt gtttagattg aagattgagt gaaatatttt    4153
cttggcagat attccgtatc tggtggaaag ctacaatgca atgtcgttgt agttttgcat    4213
ggcttgcttt ataaacaaga ttttttctcc ctccttttgg gccagttttc attacgagta    4273
actcacactt tttgattaaa gaacttgaaa ttacgttatc acttagtata attgacatta    4333
tatagagact atgtaacatg caatcattag aatcaaaatt agtactttgg tcaaaatatt    4393
tacaacattc acatacttgt caaatattca tgtaattaac tgaattttaaa accttcaact   4453 attatgaagt gctcgtctgt acaatcgcta atttactcag tttagagtag ctacaactct    4513
tcgatactat catcaatatt tgacatcttt tccaatttgt gtatgaaaag taaatctatt    4573
cctgtagcaa ctggggagtc atatatgagg tcaaagacat ataccttgtt attataatat    4633
gtatactata ataatagctg gttatcctga gcaggggaaa aggttatttt taggaaaacc    4693
acttcaaata gaaagctgaa gtacttctaa tatactgagg gaagtataat atgtggaaca    4753
aactctcaac aaaatgttta ttgatgttga tgaaacagat cagttttttcc atccggatta   4813 ttattggttc atgattttat atgtgaatat gtaagatatg ttctgcaatt ttataaatgt    4873
tcatgtcttt ttttaaaaaa ggtgctattg aaattctgtg tctccagcag gcaagaatac    4933
ttgactaact cttttttgtct ctttatggta ttttcagaat aaagtctgac ttgtgttttt   4993
gagattattg gtgcctcatt aattcagcaa taaggaaaa tatgcatctc aaaaat         5049
```

```
<210> SEQ ID NO 124
<211> LENGTH: 5324
<212> TYPE: DNA
<213> ORGANISM: Homo sapiens
<220> FEATURE:
<221> NAME/KEY: CDS
<222> LOCATION: 31..588
<221> NAME/KEY: polyA_signal
<222> LOCATION: 5297..5302
<223> OTHER INFORMATION: AATAAA

<400> SEQUENCE: 124
```

```
ctgctgtccc tggtgctcca cacgtactcc atg cgc tac ctg ctg ccc agc gtc         54
                                 Met Arg Tyr Leu Leu Pro Ser Val
                                  1               5 gtg ctc ctg ggc acg gcg ccc acc tac gtg ttg gcc tgg ggg gtc tgg         102
Val Leu Leu Gly Thr Ala Pro Thr Tyr Val Leu Ala Trp Gly Val Trp
     10                  15                  20 cgg ctg ctc tcc gcc ttc ctg ccc gcc cgc ttc tac caa gcg ctg gac        150
Arg Leu Leu Ser Ala Phe Leu Pro Ala Arg Phe Tyr Gln Ala Leu Asp
 25                  30                  35                  40 gac cgg ctg tac tgc gtc tac cag agc atg gtg ctc ttc ttc ttc gag        198
Asp Arg Leu Tyr Cys Val Tyr Gln Ser Met Val Leu Phe Phe Phe Glu
                 45                  50                  55 aat tac acc ggg gtc cag ata ttg cta tat gga gat ttg cca aaa aat        246
```

```
Asn Tyr Thr Gly Val Gln Ile Leu Leu Tyr Gly Asp Leu Pro Lys Asn
         60                  65                  70 aaa gaa aat ata ata tat tta gca aat cat caa agc aca gtt gac tgg      294
Lys Glu Asn Ile Ile Tyr Leu Ala Asn His Gln Ser Thr Val Asp Trp
             75                  80                  85 att gtt gct gac atc ttg gcc atc agg cag aat gcg cta gga cat gtg      342
Ile Val Ala Asp Ile Leu Ala Ile Arg Gln Asn Ala Leu Gly His Val
         90                  95                 100 cgc tac gtg ctg aaa gaa ggg tta aaa tgg ctg cca ttg tat ggg tgt      390
Arg Tyr Val Leu Lys Glu Gly Leu Lys Trp Leu Pro Leu Tyr Gly Cys
105                 110                 115                 120 tac ttt gct cag cat gga gga atc tat gta aag cgc agt gcc aaa ttt      438
Tyr Phe Ala Gln His Gly Gly Ile Tyr Val Lys Arg Ser Ala Lys Phe
                125                 130                 135 aac gag aaa gag atg cga aac aag ttg cag agc tac gtg gac gca gga      486
Asn Glu Lys Glu Met Arg Asn Lys Leu Gln Ser Tyr Val Asp Ala Gly
            140                 145                 150 act cca atg tat ctt gtg att ttt cca gaa ggt aca agg tat aat cca      534
Thr Pro Met Tyr Leu Val Ile Phe Pro Glu Gly Thr Arg Tyr Asn Pro
        155                 160                 165 gag caa aca aaa gtc ctt tca gct agt cag gca ttt gct gcc caa cgt      582
Glu Gln Thr Lys Val Leu Ser Ala Ser Gln Ala Phe Ala Ala Gln Arg
    170                 175                 180 ggc taa agcagtcctc ctgagtagtt aggactacag acatacacgt gccaccgcgc       638
Gly
185 ccagctccgt gttctctttg tttccctgcc tcctgctctt ccacttatct ttgcatggca    698 ggccttgcag tattaaaaca tgtgctaaca ccacgaataa aggcaactca cgttgctttt    758 gattgcatga agaattattt agatgcaatt tatgatgtta cggtggttta tgaagggaaa    818 gacgatggag ggcagcgaag agagtcaccg accatgacgg aatttctctg caaagaatgt    878 ccaaaaattc atattcacat tgatcgtatc gacaaaaaag atgtcccaga gaacaagaa     938 catatgagaa gatggctgca tgaacgtttc gaaatcaaag ataagatgct atagaatttt    998 tatgagtcac cagatccaga aagaagaaaa agatttcctg ggaaaagtgt taattccaaa    1058 ttaagtatca agaagacttt accatcaatg ttgatcttaa gtggtttgac tgcaggcatg    1118 cttatgaccg atgctggaag gaagctgtat gtgaacacct ggatatatgg aaccctactt    1178 ggctgcctgt gggttactat taaagcatag acaagtagct gtctccagac agtgggatgt    1238 gctacattgt ctattttgg cggctgcaca tgacatcaaa ttgtttcctg aatttattaa     1298 ggagtgtaaa taaagccttg ttgattgaag attggataat agaatttgtg acgaaagctg    1358 atatgcaatg gtcttgggca acatacctg gttgtacaac tttagcatcg gggctgctgg     1418 aagggtaaaa gctaaatgga gtttctcctg ctctgtccat ttcctatgaa ctaatgacaa    1478 cttgagaagg ctgggaggat tgtgtatttt gcaagtcaga tggctgcatt tttgagcatt    1538 aatttgcagc gtatttcact ttttctgtta ttttcaattt attacaactt gacagctcca    1598 agctcttatt actaaagtat ttagtatctt gcagctagtt aatatttcat cttttgctta    1658 tttctacaag tcagtgaaat aaattgtatt taggaagtgt caggatgttc aaaggaaagg    1718 gtaaaaagtg ttcatgggga aaaagctctg tttagcacat gatttattg tattgcgtta     1778 ttagctgatt ttactcattt tatatttgca aaataaattt ctaatattta ttgaaattgc    1838 ttaatttgca caccctgtac acacagaaaa tggtataaaa tatgagaacg aagtttaaaa    1898 ttgtgactct gattcattat agcagaactt taaatttccc agcttttga agatttaagc     1958
```

```
tacgctatta gtacttccct ttgtctgtgc cataagtgct tgaaaacgtt aaggttttct    2018
gttttgtttt gttttttttaa tatcaaaaga gtcggtgtga accttggttg gacccccaagt    2078 tcacaagatt tttaaggtga tgagagcctg cagacattct gcctagattt actagcgtgt    2138
gccttttgcc tgcttctctt tgatttcaca gaatattcat tcagaagtcg cgtttctgta    2198
gtgtggtgga ttcccactgg gctctggtcc ttcccttgga tcccgtcagt ggtgctgctc    2258
agcggcttgc acgtagactt gctaggaaga aatgcagagc cagcctgtgc tgcccacttt    2318
cagagttgaa ctctttaagc ccttgtgagt gggcttcacc agctactgca gaggcatttt    2378
gcatttgtct gtgtcaagaa gttccccttc tcaagccagt gaaatacaga cttaattcgt    2438
catgactgaa cgaatttgtt tatttcccat taggtttagt ggagctacac attaatatgt    2498
atcgccttag agcaagagct gtgttccagg aaccagatca cgattttttag ccatggaaca    2558 atatatccca tgggagaaga cctttcagtg tgaactgttc tattttttgtg ttataattta    2618 aacttcgatt tcctcatagt cctttaagtt gacatttctg cttactgcta ctggattttt    2678
gctgcagaaa tatatcagtg gcccacatta aacataccag ttggatcatg ataagcaaaa    2738
tgaaagaaat aatgattaag ggaaaattaa gtgactgtgt tacactgctt ctcccatgcc    2798
agagaataaa ctcttttcaag catcatcttt gaagagtcgt gtggtgtgaa ttggtttgtg    2858
tacattagaa tgtatgcaca catccatgga cactcaggat atagttggcc taataatcgg    2918
ggcatgggta aaacttatga aaatttcctc atgctgaatt gtaattttct cttacctgta    2978
aagtaaaatt tagatcaatt ccatgtcttt gttaagtaca gggatttaat atattttgaa    3038
tataatgggt atgttctaaa tttgaacttt gagaggcaat actgttgaa ttatgtggat    3098 tctaactcat tttaacaagg tagcctgacc tgcataagat cacttgaatg ttaggtttca    3158
tagaactata ctaatcttct cacaaaaggt ctataaaata cagtcgttga aaaaaatttt    3218
gtatcaaaat gtttggaaaaa ttagaagctt ctccttaacc tgtattgata ctgacttgaa    3278
ttattttcta aaattaagag ccgtatacct acctgtaagt cttttcacat atcatttaaa    3338
cttttgtttg tattattact gatttacagc ttagttatta atttttcttt ataagaatgc    3398
cgtcgatgtg catgctttta tgttttttcag aaaagggtgt gtttggatga aagtaaaaaa    3458
aaaaataaaa tctttcactg tctctaatgg ctgtgctgtt taacattttt tgaccctaaa    3518
attcaccaac agtctcccag tacataaaat aggcttaatg actggccctg cattcttcac    3578
aatatttttc cctaagcttt gagcaaagtt ttaaaaaaat acactaaaat aatcaaaact    3638
gttaagcagt atattagttt ggttatataa attcatctgc aatttataag atgcatggcc    3698
gatgttaatt tgcttggcaa ttctgtaatc attaagtgat ctcagtgaaa catgtcaaat    3758
gccttaaatt aactaagttg gtgaataaaa gtgccgatct ggctaactct tacaccatac    3818
atactgatag ttttttcatat gtttcatttc catgtgattt ttaaaattta gagtggcaac    3878
aattttgctt aaatatgggtt acataagctt tattttttcc tttgttcata attatattct    3938
ttgaataggt ctgtgtcaat caagtgatct aactagactg atcatagata gaaggaaata    3998
aggccaagtt caagaccagc ctgggcaaca tatcgagaac ctgtctacaa aaaaattaaa    4058
aaaaattagc caggcatggt ggcgtacact gagtagtttg tcccagctac tcgggagggt    4118
gaggtgggag gatcgcttca gcccaggagg ttgagattgc agtgagccat ggacatacca    4178
ctgcactaca gcctaggtaa cagcacgaga ccccaactct tagaaaatga aaaggaaata    4238
tagaaatata aaatttgctt attatagaca cacagtaact cccagatatg taccacaaaa    4298
aatgtgaaaa gagagagaaa tgtctaccaa agcagtattt tgtgtgtata attgcaagcg    4358
```

```
catagtaaaa taattttaac cttaatttgt ttttagtagt gtttagattg aagattgagt    4418
gaaatatttt cttggcagat attccgtatc tggtggaaag ctacaatgca atgtcgttgt    4478
agttttgcat ggcttgcttt ataaacaaga ttttttctcc ctccttttgg gccagttttc    4538
attacgagta actcacactt tttgattaaa gaacttgaaa ttcgttatc acttagtata     4598 attgacatta tatagagact atgtaacatg caatcattag aatcaaaatt agtactttgg    4658
tcaaaatatt tacaacattc acatacttgt caaatattca tgtaattaac tgaatttaaa    4718
accttcaact attatgaagt gctcgtctgt acaatcgcta atttactcag tttagagtag    4778
ctacaactct tcgatactat catcaatatt tgacatcttt tccaatttgt gtatgaaaag    4838
taaatctatt cctgtagcaa ctggggagtc atatatgagg tcaaagacat ataccttgtt    4898
attataatat gtatactata ataatagctg gttatcctga gcaggggaaa aggttatttt    4958
taggaaaacc acttcaaata gaaagctgaa gtacttctaa tatactgagg gaagtataat    5018
atgtggaaca aactctcaac aaaatgttta ttgatgttga tgaaacagat cagttttcc    5078 atccggatta ttattggttc atgattttat atgtgaatat gtaagatatg ttctgcaatt    5138
ttataaatgt tcatgtcttt ttttaaaaaa ggtgctattg aaattctgtg tctccagcag    5198
gcaagaatac ttgactaact cttttgtct ctttatggta ttttcagaat aaagtctgac     5258
ttgtgttttt gagattattg gtgcctcatt aattcagcaa taaggaaaaa tatgcatctc    5318
aaaaat                                                                5324

<210> SEQ ID NO 125
<211> LENGTH: 77
<212> TYPE: PRT
<213> ORGANISM: Homo sapiens

<400> SEQUENCE: 125

Met Arg Tyr Leu Leu Pro Ser Val Val Leu Leu Gly Thr Ala Pro Thr
1               5                  10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45

Ser Met Val Leu Phe Phe Phe Glu Asn Tyr Thr Gly Val Gln Leu Thr
    50                  55                  60

Gly Leu Leu Leu Thr Ser Trp Pro Ser Gly Arg Met Arg
65                  70                  75

<210> SEQ ID NO 126
<211> LENGTH: 238
<212> TYPE: PRT
<213> ORGANISM: Homo sapiens
<220> FEATURE:
<221> NAME/KEY: SITE
<222> LOCATION: 98..103
<223> OTHER INFORMATION: Box  II

<400> SEQUENCE: 126

Met Arg Tyr Leu Leu Pro Ser Val Val Leu Leu Gly Thr Ala Pro Thr
1               5                  10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45
```

```
Ser Met Val Leu Phe Phe Glu Asn Tyr Thr Gly Val Gln His Gly
    50              55                  60

Gly Ile Tyr Val Lys Arg Ser Ala Lys Phe Asn Glu Lys Glu Met Arg
65              70                  75                  80

Asn Lys Leu Gln Ser Tyr Val Asp Ala Gly Thr Pro Met Tyr Leu Val
                85                  90                  95

Ile Phe Pro Glu Gly Thr Arg Tyr Asn Pro Glu Gln Thr Lys Val Leu
                100                 105                 110

Ser Ala Ser Gln Ala Phe Ala Ala Gln Arg Glu Phe Leu Cys Lys Glu
            115                 120                 125

Cys Pro Lys Ile His Ile His Ile Asp Arg Ile Asp Lys Lys Asp Val
        130                 135                 140

Pro Glu Glu Gln Glu His Met Arg Arg Trp Leu His Glu Arg Phe Glu
145                 150                 155                 160

Ile Lys Asp Lys Met Leu Ile Glu Phe Tyr Glu Ser Pro Asp Pro Glu
                165                 170                 175

Arg Arg Lys Arg Phe Pro Gly Lys Ser Val Asn Ser Lys Leu Ser Ile
                180                 185                 190

Lys Lys Thr Leu Pro Ser Met Leu Ile Leu Ser Gly Leu Thr Ala Gly
            195                 200                 205

Met Leu Met Thr Asp Ala Gly Arg Lys Leu Tyr Val Asn Thr Trp Ile
        210                 215                 220

Tyr Gly Thr Leu Leu Gly Cys Leu Trp Val Thr Ile Lys Ala
225                 230                 235

<210> SEQ ID NO 127
<211> LENGTH: 291
<212> TYPE: PRT
<213> ORGANISM: Homo sapiens
<220> FEATURE:
<221> NAME/KEY: SITE
<222> LOCATION: 98..103
<223> OTHER INFORMATION: Box II
<220> FEATURE:
<221> NAME/KEY: SITE
<222> LOCATION: 149..157
<223> OTHER INFORMATION: Box III

<400> SEQUENCE: 127

Met Arg Tyr Leu Leu Pro Ser Val Val Leu Leu Gly Thr Ala Pro Thr
1               5                   10                  15

Tyr Val Leu Ala Trp Gly Val Trp Arg Leu Leu Ser Ala Phe Leu Pro
                20                  25                  30

Ala Arg Phe Tyr Gln Ala Leu Asp Asp Arg Leu Tyr Cys Val Tyr Gln
            35                  40                  45

Ser Met Val Leu Phe Phe Glu Asn Tyr Thr Gly Val Gln His Gly
    50              55                  60

Gly Ile Tyr Val Lys Arg Ser Ala Lys Phe Asn Glu Lys Glu Met Arg
65              70                  75                  80

Asn Lys Leu Gln Ser Tyr Val Asp Ala Gly Thr Pro Met Tyr Leu Val
                85                  90                  95

Ile Phe Pro Glu Gly Thr Arg Tyr Asn Pro Glu Gln Thr Lys Val Leu
                100                 105                 110

Ser Ala Ser Gln Ala Phe Ala Ala Gln Arg Gly Leu Ala Val Leu Lys
            115                 120                 125

His Val Leu Thr Pro Arg Ile Lys Ala Thr His Val Ala Phe Asp Cys
        130                 135                 140
```

-continued

```
Met Lys Asn Tyr Leu Asp Ala Ile Tyr Asp Val Thr Val Tyr Glu
145                 150                 155                 160

Gly Lys Asp Asp Gly Gly Gln Arg Arg Glu Ser Pro Thr Met Thr Glu
                165                 170                 175

Phe Leu Cys Lys Glu Cys Pro Lys Ile His Ile His Ile Asp Arg Ile
            180                 185                 190

Asp Lys Lys Asp Val Pro Glu Glu Gln Glu His Met Arg Arg Trp Leu
        195                 200                 205

His Glu Arg Phe Glu Ile Lys Asp Lys Met Leu Ile Glu Phe Tyr Glu
    210                 215                 220

Ser Pro Asp Pro Glu Arg Arg Lys Arg Phe Pro Gly Lys Ser Val Asn
225                 230                 235                 240

Ser Lys Leu Ser Ile Lys Lys Thr Leu Pro Ser Met Leu Ile Leu Ser
                245                 250                 255

Gly Leu Thr Ala Gly Met Leu Met Thr Asp Ala Gly Arg Lys Leu Tyr
            260                 265                 270

Val Asn Thr Trp Ile Tyr Gly Thr Leu Leu Gly Cys Leu Trp Val Thr
        275                 280                 285

Ile Lys Ala
    290
```

<210> SEQ ID NO 128
<211> LENGTH: 261
<212> TYPE: PRT
<213> ORGANISM: Homo sapiens
<220> FEATURE:
<221> NAME/KEY: SITE
<222> LOCATION: 68..73
<223> OTHER INFORMATION: Box II
<220> FEATURE:
<221> NAME/KEY: SITE
<222> LOCATION: 119..127
<223> OTHER INFORMATION: Box III

<400> SEQUENCE: 128

```
Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
                20                  25                  30

Ala Arg Phe Tyr Gln Ala Leu Asp Asp Arg Leu Tyr Cys Val Tyr Gln
            35                  40                  45

Ser Met Val Leu Phe Phe Phe Glu Asn Tyr Thr Gly Val Gln Met Tyr
        50                  55                  60

Leu Val Ile Phe Pro Glu Gly Thr Arg Tyr Asn Pro Glu Gln Thr Lys
65                  70                  75                  80

Val Leu Ser Ala Ser Gln Ala Phe Ala Ala Gln Arg Gly Leu Ala Val
                85                  90                  95

Leu Lys His Val Leu Thr Pro Arg Ile Lys Ala Thr His Val Ala Phe
            100                 105                 110

Asp Cys Met Lys Asn Tyr Leu Asp Ala Ile Tyr Asp Val Thr Val Val
        115                 120                 125

Tyr Glu Gly Lys Asp Asp Gly Gly Gln Arg Arg Glu Ser Pro Thr Met
    130                 135                 140

Thr Glu Phe Leu Cys Lys Glu Cys Pro Lys Ile His Ile His Ile Asp
145                 150                 155                 160

Arg Ile Asp Lys Lys Asp Val Pro Glu Glu Gln Glu His Met Arg Arg
                165                 170                 175
```

```
Trp Leu His Glu Arg Phe Glu Ile Lys Asp Lys Met Leu Ile Glu Phe
            180                 185                 190

Tyr Glu Ser Pro Asp Pro Glu Arg Arg Lys Arg Phe Pro Gly Lys Ser
        195                 200                 205

Val Asn Ser Lys Leu Ser Ile Lys Lys Thr Leu Pro Ser Met Leu Ile
    210                 215                 220

Leu Ser Gly Leu Thr Ala Gly Met Leu Met Thr Asp Ala Gly Arg Lys
225                 230                 235                 240

Leu Tyr Val Asn Thr Trp Ile Tyr Gly Thr Leu Leu Gly Cys Leu Trp
                245                 250                 255

Val Thr Ile Lys Ala
            260

<210> SEQ ID NO 129
<211> LENGTH: 90
<212> TYPE: PRT
<213> ORGANISM: Homo sapiens

<400> SEQUENCE: 129

Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45

Ser Met Val Leu Phe Phe Glu Asn Tyr Thr Gly Val Gln Asn Phe
    50                  55                  60

Ser Ala Lys Asn Val Gln Lys Phe Ile Phe Thr Leu Ile Val Ser Thr
65                  70                  75                  80

Lys Lys Met Ser Gln Lys Asn Lys Asn Ile
                85                  90

<210> SEQ ID NO 130
<211> LENGTH: 68
<212> TYPE: PRT
<213> ORGANISM: Homo sapiens

<400> SEQUENCE: 130

Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45

Ser Met Val Leu Phe Phe Glu Asn Tyr Thr Gly Val Gln Asp Ala
    50                  55                  60

Tyr Arg Ile Leu
65

<210> SEQ ID NO 131
<211> LENGTH: 66
<212> TYPE: PRT
<213> ORGANISM: Homo sapiens

<400> SEQUENCE: 131

Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
```

-continued

```
                 20                  25                  30

Ala Arg Phe Tyr Gln Ala Leu Asp Asp Arg Leu Tyr Cys Val Tyr Gln
             35                  40                  45

Ser Met Val Leu Phe Phe Phe Glu Asn Tyr Thr Gly Val Gln Arg Leu
     50                  55                  60

Asp Ser
65

<210> SEQ ID NO 132
<211> LENGTH: 97
<212> TYPE: PRT
<213> ORGANISM: Homo sapiens
<220> FEATURE:
<221> NAME/KEY: SITE
<222> LOCATION: 81..83
<223> OTHER INFORMATION: Box  I

<400> SEQUENCE: 132

Met Arg Tyr Leu Leu Pro Ser Val Val Leu Gly Thr Ala Pro Thr
 1               5                  10                  15

Tyr Val Leu Ala Trp Gly Val Trp Arg Leu Leu Ser Ala Phe Leu Pro
             20                  25                  30

Ala Arg Phe Tyr Gln Ala Leu Asp Asp Arg Leu Tyr Cys Val Tyr Gln
             35                  40                  45

Ser Met Val Leu Phe Phe Phe Glu Asn Tyr Thr Gly Val Gln Ile Leu
     50                  55                  60

Leu Tyr Gly Asp Leu Pro Lys Asn Lys Glu Asn Ile Ile Tyr Leu Ala
65                   70                  75                  80

Asn His Gln Ser Thr Asp Val Ser Cys Asp Phe Ser Arg Tyr Lys
                 85                  90                  95

Val

<210> SEQ ID NO 133
<211> LENGTH: 182
<212> TYPE: PRT
<213> ORGANISM: Homo sapiens
<220> FEATURE:
<221> NAME/KEY: SITE
<222> LOCATION: 81..83
<223> OTHER INFORMATION: Box  I

<400> SEQUENCE: 133

Met Arg Tyr Leu Leu Pro Ser Val Val Leu Gly Thr Ala Pro Thr
 1               5                  10                  15

Tyr Val Leu Ala Trp Gly Val Trp Arg Leu Leu Ser Ala Phe Leu Pro
             20                  25                  30

Ala Arg Phe Tyr Gln Ala Leu Asp Asp Arg Leu Tyr Cys Val Tyr Gln
             35                  40                  45

Ser Met Val Leu Phe Phe Phe Glu Asn Tyr Thr Gly Val Gln Ile Leu
     50                  55                  60

Leu Tyr Gly Asp Leu Pro Lys Asn Lys Glu Asn Ile Ile Tyr Leu Ala
65                   70                  75                  80

Asn His Gln Ser Thr Val Asp Trp Ile Val Ala Asp Ile Leu Ala Ile
                 85                  90                  95

Arg Gln Asn Ala Leu Gly His Val Arg Tyr Val Leu Lys Glu Gly Leu
                100                 105                 110

Lys Trp Leu Pro Leu Tyr Gly Cys Tyr Phe Ala Gln His Gly Gly Ile
            115                 120                 125
```

-continued

Tyr Val Lys Arg Ser Ala Lys Phe Asn Glu Lys Glu Met Arg Asn Lys
            130                 135                 140

Leu Gln Ser Tyr Val Asp Ala Gly Thr Pro Asn Phe Ser Ala Lys Asn
145                 150                 155                 160

Val Gln Lys Phe Ile Phe Thr Leu Ile Val Ser Thr Lys Lys Met Ser
                165                 170                 175

Gln Lys Asn Lys Asn Ile
            180

<210> SEQ ID NO 134
<211> LENGTH: 315
<212> TYPE: PRT
<213> ORGANISM: Homo sapiens
<220> FEATURE:
<221> NAME/KEY: SITE
<222> LOCATION: 81..83
<223> OTHER INFORMATION: Box I
<220> FEATURE:
<221> NAME/KEY: SITE
<222> LOCATION: 160..165
<223> OTHER INFORMATION: Box II

<400> SEQUENCE: 134

Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
                20                  25                  30

Ala Arg Phe Tyr Gln Ala Leu Asp Asp Arg Leu Tyr Cys Val Tyr Gln
                35                  40                  45

Ser Met Val Leu Phe Phe Phe Glu Asn Tyr Thr Gly Val Gln Ile Leu
50                  55                  60

Leu Tyr Gly Asp Leu Pro Lys Asn Lys Glu Asn Ile Ile Tyr Leu Ala
65                  70                  75                  80

Asn His Gln Ser Thr Val Asp Trp Ile Val Ala Asp Ile Leu Ala Ile
                85                  90                  95

Arg Gln Asn Ala Leu Gly His Val Arg Tyr Val Leu Lys Glu Gly Leu
                100                 105                 110

Lys Trp Leu Pro Leu Tyr Gly Cys Tyr Phe Ala Gln His Gly Gly Ile
                115                 120                 125

Tyr Val Lys Arg Ser Ala Lys Phe Asn Glu Lys Glu Met Arg Asn Lys
            130                 135                 140

Leu Gln Ser Tyr Val Asp Ala Gly Thr Pro Met Tyr Leu Val Ile Phe
145                 150                 155                 160

Pro Glu Gly Thr Arg Tyr Asn Pro Glu Gln Thr Lys Val Leu Ser Ala
                165                 170                 175

Ser Gln Ala Phe Ala Ala Gln Arg Gly Lys Asp Asp Gly Gly Gln Arg
                180                 185                 190

Arg Glu Ser Pro Thr Met Thr Glu Phe Leu Cys Lys Glu Cys Pro Lys
            195                 200                 205

Ile His Ile His Ile Asp Arg Ile Asp Lys Lys Asp Val Pro Glu Glu
            210                 215                 220

Gln Glu His Met Arg Arg Trp Leu His Glu Arg Phe Glu Ile Lys Asp
225                 230                 235                 240

Lys Met Leu Ile Glu Phe Tyr Glu Ser Pro Asp Pro Glu Arg Arg Lys
                245                 250                 255

Arg Phe Pro Gly Lys Ser Val Asn Ser Lys Leu Ser Ile Lys Lys Thr
                260                 265                 270

-continued

```
Leu Pro Ser Met Leu Ile Leu Ser Gly Leu Thr Ala Gly Met Leu Met
            275                 280                 285

Thr Asp Ala Gly Arg Lys Leu Tyr Val Asn Thr Trp Ile Tyr Gly Thr
        290                 295                 300

Leu Leu Gly Cys Leu Trp Val Thr Ile Lys Ala
305                 310                 315

<210> SEQ ID NO 135
<211> LENGTH: 300
<212> TYPE: PRT
<213> ORGANISM: Homo sapiens
<220> FEATURE:
<221> NAME/KEY: SITE
<222> LOCATION: 81..83
<223> OTHER INFORMATION: Box  I
<220> FEATURE:
<221> NAME/KEY: SITE
<222> LOCATION: 160..165
<223> OTHER INFORMATION: Box  II

<400> SEQUENCE: 135

Met Arg Tyr Leu Leu Pro Ser Val Val Leu Gly Thr Ala Pro Thr
1               5                  10                  15

Tyr Val Leu Ala Trp Gly Val Trp Arg Leu Leu Ser Ala Phe Leu Pro
            20                  25                  30

Ala Arg Phe Tyr Gln Ala Leu Asp Asp Arg Leu Tyr Cys Val Tyr Gln
        35                  40                  45

Ser Met Val Leu Phe Phe Glu Asn Tyr Thr Gly Val Gln Ile Leu
    50                  55                  60

Leu Tyr Gly Asp Leu Pro Lys Asn Lys Glu Asn Ile Ile Tyr Leu Ala
65                  70                  75                  80

Asn His Gln Ser Thr Val Asp Trp Ile Val Ala Asp Ile Leu Ala Ile
                85                  90                  95

Arg Gln Asn Ala Leu Gly His Val Arg Tyr Val Leu Lys Glu Gly Leu
            100                 105                 110

Lys Trp Leu Pro Leu Tyr Gly Cys Tyr Phe Ala Gln His Gly Gly Ile
        115                 120                 125

Tyr Val Lys Arg Ser Ala Lys Phe Asn Glu Lys Glu Met Arg Asn Lys
    130                 135                 140

Leu Gln Ser Tyr Val Asp Ala Gly Thr Pro Met Tyr Leu Val Ile Phe
145                 150                 155                 160

Pro Glu Gly Thr Arg Tyr Asn Pro Glu Gln Thr Lys Val Leu Ser Ala
                165                 170                 175

Ser Gln Ala Phe Ala Ala Gln Arg Glu Phe Leu Cys Lys Glu Cys Pro
            180                 185                 190

Lys Ile His Ile His Ile Asp Arg Ile Asp Lys Lys Asp Val Pro Glu
        195                 200                 205

Glu Gln Glu His Met Arg Arg Trp Leu His Glu Arg Phe Glu Ile Lys
    210                 215                 220

Asp Lys Met Leu Ile Glu Phe Tyr Glu Ser Pro Asp Pro Glu Arg Arg
225                 230                 235                 240

Lys Arg Phe Pro Gly Lys Ser Val Asn Ser Lys Leu Ser Ile Lys Lys
                245                 250                 255

Thr Leu Pro Ser Met Leu Ile Leu Ser Gly Leu Thr Ala Gly Met Leu
            260                 265                 270

Met Thr Asp Ala Gly Arg Lys Leu Tyr Val Asn Thr Trp Ile Tyr Gly
        275                 280                 285
```

```
Thr Leu Leu Gly Cys Leu Trp Val Thr Ile Lys Ala
    290             295             300
```

<210> SEQ ID NO 136
<211> LENGTH: 185
<212> TYPE: PRT
<213> ORGANISM: Homo sapiens
<220> FEATURE:
<221> NAME/KEY: SITE
<222> LOCATION: 81..83
<223> OTHER INFORMATION: Box I
<220> FEATURE:
<221> NAME/KEY: SITE
<222> LOCATION: 160..165
<223> OTHER INFORMATION: Box II

<400> SEQUENCE: 136

```
Met Arg Tyr Leu Leu Pro Ser Val Val Leu Gly Thr Ala Pro Thr
1               5                   10                  15

Tyr Val Leu Ala Trp Gly Val Trp Arg Leu Leu Ser Ala Phe Leu Pro
                20                  25                  30

Ala Arg Phe Tyr Gln Ala Leu Asp Asp Arg Leu Tyr Cys Val Tyr Gln
            35                  40                  45

Ser Met Val Leu Phe Phe Phe Glu Asn Tyr Thr Gly Val Gln Ile Leu
50                      55                  60

Leu Tyr Gly Asp Leu Pro Lys Asn Lys Glu Asn Ile Ile Tyr Leu Ala
65                  70                  75                  80

Asn His Gln Ser Thr Val Asp Trp Ile Val Ala Asp Ile Leu Ala Ile
                85                  90                  95

Arg Gln Asn Ala Leu Gly His Val Arg Tyr Val Leu Lys Glu Gly Leu
            100                 105                 110

Lys Trp Leu Pro Leu Tyr Gly Cys Tyr Phe Ala Gln His Gly Gly Ile
        115                 120                 125

Tyr Val Lys Arg Ser Ala Lys Phe Asn Glu Lys Glu Met Arg Asn Lys
    130                 135                 140

Leu Gln Ser Tyr Val Asp Ala Gly Thr Pro Met Tyr Leu Val Ile Phe
145                 150                 155                 160

Pro Glu Gly Thr Arg Tyr Asn Pro Glu Gln Thr Lys Val Leu Ser Ala
                165                 170                 175

Ser Gln Ala Phe Ala Ala Gln Arg Gly
                180                 185
```

<210> SEQ ID NO 137
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: amplification oligonucleotide PG1ASe13

<400> SEQUENCE: 137
accggggtcc agttgactg                                            19

<210> SEQ ID NO 138
<211> LENGTH: 17
<212> TYPE: DNA
<213> ORGANISM: Homo Sapiens
<220> FEATURE:
<221> NAME/KEY: misc_feature
<222> LOCATION: 1..17
<223> OTHER INFORMATION: amplification oligonucleotide PG1ASe14

<400> SEQUENCE: 138
cggggtccag catggag                                              17

<210> SEQ ID NO 139
<211> LENGTH: 16
<212> TYPE: DNA
<213> ORGANISM: Homo Sapiens
<220> FEATURE:
<221> NAME/KEY: misc_feature
<222> LOCATION: 1..16
<223> OTHER INFORMATION: amplification oligonucleotide PG1ASe15

<400> SEQUENCE: 139
ccggggtcca ggcctt                                               16

<210> SEQ ID NO 140
<211> LENGTH: 16
<212> TYPE: DNA
<213> ORGANISM: Homo Sapiens
<220> FEATURE:
<221> NAME/KEY: misc_feature
<222> LOCATION: 1..16
<223> OTHER INFORMATION: amplification oligonucleotide PG1ASe16

<400> SEQUENCE: 140
cggggtccag gccttg                                               16

<210> SEQ ID NO 141
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: amplification oligonucleotide PG1ASe17

<400> SEQUENCE: 141
accggggtcc agaatttctc t                                         21

<210> SEQ ID NO 142
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: amplification oligonucleotide PG1ASe18

<400> SEQUENCE: 142
cggggtccag gatgcttat                                            19

<210> SEQ ID NO 143
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: amplification oligonucleotide PG1ASe24

<400> SEQUENCE: 143
aatcatcaaa gcacagcatg gag                                       23

<210> SEQ ID NO 144
<211> LENGTH: 28
<212> TYPE: DNA
<213> ORGANISM: Homo Sapiens

```
<220> FEATURE:
<221> NAME/KEY: misc_feature
<222> LOCATION: 1..28
<223> OTHER INFORMATION: amplification oligonucleotide PG1ASe25

<400> SEQUENCE: 144
caaatcatca aagcacagat gtatcttg                                28

<210> SEQ ID NO 145
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: amplification oligonucleotide PG1ASe26

<400> SEQUENCE: 145
atcaaagcac aggccttgca                                         20

<210> SEQ ID NO 146
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: amplification oligonucleotide PG1ASe27

<400> SEQUENCE: 146
agcaaatcat caaagcacag aatttc                                  26

<210> SEQ ID NO 147
<211> LENGTH: 28
<212> TYPE: DNA
<213> ORGANISM: Homo Sapiens
<220> FEATURE:
<221> NAME/KEY: misc_feature
<222> LOCATION: 1..28
<223> OTHER INFORMATION: amplification oligonucleotide PG1ASe28

<400> SEQUENCE: 147
atcatcaaag cacaggatgc ttatagaa                                28

<210> SEQ ID NO 148
<211> LENGTH: 31
<212> TYPE: DNA
<213> ORGANISM: Homo Sapiens
<220> FEATURE:
<221> NAME/KEY: misc_feature
<222> LOCATION: 1..31
<223> OTHER INFORMATION: amplification oligonucleotide PG1ASe35

<400> SEQUENCE: 148
gtgttacttt gctcagatgt atcttgtgat t                            31

<210> SEQ ID NO 149
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: amplification oligonucleotide PG1ASe36

<400> SEQUENCE: 149
tactttgctc aggccttgca gta                                     23
```

```
<210> SEQ ID NO 150
<211> LENGTH: 27
<212> TYPE: DNA
<213> ORGANISM: Homo Sapiens
<220> FEATURE:
<221> NAME/KEY: misc_feature
<222> LOCATION: 1..27
<223> OTHER INFORMATION: amplification oligonucleotide PG1ASe37

<400> SEQUENCE: 150
gggtgttact tgctcagaa tttctct                                    27

<210> SEQ ID NO 151
<211> LENGTH: 29
<212> TYPE: DNA
<213> ORGANISM: Homo Sapiens
<220> FEATURE:
<221> NAME/KEY: misc_feature
<222> LOCATION: 1..29
<223> OTHER INFORMATION: amplification oligonucleotide PG1ASe38

<400> SEQUENCE: 151
ggtgttactt tgctcaggat gcttataga                                 29

<210> SEQ ID NO 152
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: amplification oligonucleotide PG1ASe46

<400> SEQUENCE: 152
caggaactcc agccttgcag                                           20

<210> SEQ ID NO 153
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: amplification oligonucleotide PG1ASe47

<400> SEQUENCE: 153
caggaactcc aaatttctct gca                                       23

<210> SEQ ID NO 154
<211> LENGTH: 25
<212> TYPE: DNA
<213> ORGANISM: Homo Sapiens
<220> FEATURE:
<221> NAME/KEY: misc_feature
<222> LOCATION: 1..25
<223> OTHER INFORMATION: amplification oligonucleotide PG1ASe48

<400> SEQUENCE: 154
cgcaggaact ccagatgctt ataga                                     25

<210> SEQ ID NO 155
<211> LENGTH: 22
<212> TYPE: DNA
<213> ORGANISM: Homo Sapiens
<220> FEATURE:
<221> NAME/KEY: misc_feature
<222> LOCATION: 1..22
<223> OTHER INFORMATION: amplification oligonucleotide PG1ASe57
```

```
<400> SEQUENCE: 155
ctgcccaacg tgaatttctc tg                                    22

<210> SEQ ID NO 156
<211> LENGTH: 22
<212> TYPE: DNA
<213> ORGANISM: Homo Sapiens
<220> FEATURE:
<221> NAME/KEY: misc_feature
<222> LOCATION: 1..22
<223> OTHER INFORMATION: amplification oligonucleotide PG1ASe58

<400> SEQUENCE: 156
gcccaacgtg gatgcttata ga                                    22

<210> SEQ ID NO 157
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: amplification oligonucleotide PG1ASe68

<400> SEQUENCE: 157
cgaccatgac gggatgctta tag                                   23

<210> SEQ ID NO 158
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: amplification oligonucleotide PG1ASe1X

<400> SEQUENCE: 158
ccggggtcca gagattgga                                        19

<210> SEQ ID NO 159
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: amplification oligonucleotide PG1ASeX2

<400> SEQUENCE: 159
aaagtggaag gccctcttta acaata                                26

<210> SEQ ID NO 160
<211> LENGTH: 25
<212> TYPE: DNA
<213> ORGANISM: Homo Sapiens
<220> FEATURE:
<221> NAME/KEY: misc_feature
<222> LOCATION: 1..25
<223> OTHER INFORMATION: amplification oligonucleotide PG1Ae1b3

<400> SEQUENCE: 160
gccctcttta acattgactg gattg                                 25

<210> SEQ ID NO 161
<211> LENGTH: 24
<212> TYPE: DNA
```

```
<213> ORGANISM: Homo Sapiens
<220> FEATURE:
<221> NAME/KEY: misc_feature
<222> LOCATION: 1..24
<223> OTHER INFORMATION: amplification oligonucleotide PG1Ae1b4

<400> SEQUENCE: 161
gccctcttta acacatggag gaat                                          24

<210> SEQ ID NO 162
<211> LENGTH: 28
<212> TYPE: DNA
<213> ORGANISM: Homo Sapiens
<220> FEATURE:
<221> NAME/KEY: misc_feature
<222> LOCATION: 1..28
<223> OTHER INFORMATION: amplification oligonucleotide PG1Ae1b5

<400> SEQUENCE: 162
ggccctcttt aacaatgtat cttgtgat                                      28

<210> SEQ ID NO 163
<211> LENGTH: 25
<212> TYPE: DNA
<213> ORGANISM: Homo Sapiens
<220> FEATURE:
<221> NAME/KEY: misc_feature
<222> LOCATION: 1..25
<223> OTHER INFORMATION: amplification oligonucleotide PG1Ae1b6

<400> SEQUENCE: 163
gccctcttta acagccttgc agtat                                         25

<210> SEQ ID NO 164
<211> LENGTH: 25
<212> TYPE: DNA
<213> ORGANISM: Homo Sapiens
<220> FEATURE:
<221> NAME/KEY: misc_feature
<222> LOCATION: 1..25
<223> OTHER INFORMATION: amplification oligonucleotide PG1Ae1b7

<400> SEQUENCE: 164
ggccctcttt aacaaatttc tctgc                                         25

<210> SEQ ID NO 165
<211> LENGTH: 28
<212> TYPE: DNA
<213> ORGANISM: Homo Sapiens
<220> FEATURE:
<221> NAME/KEY: misc_feature
<222> LOCATION: 1..28
<223> OTHER INFORMATION: amplification oligonucleotide PG1Ae1b8

<400> SEQUENCE: 165
gaaggccctc tttaacagat gcttatag                                      28

<210> SEQ ID NO 166
<211> LENGTH: 26
<212> TYPE: DNA
<213> ORGANISM: Homo Sapiens
<220> FEATURE:
<221> NAME/KEY: misc_feature
<222> LOCATION: 1..26
<223> OTHER INFORMATION: amplification oligonucleotide PG1Ae3b4

<400> SEQUENCE: 166
atgctggatt atagcatgga ggaatc                                        26
```

<210> SEQ ID NO 167
<211> LENGTH: 31
<212> TYPE: DNA
<213> ORGANISM: Homo Sapiens
<220> FEATURE:
<221> NAME/KEY: misc_feature
<222> LOCATION: 1..31
<223> OTHER INFORMATION: amplification oligonucleotide PG1Ae3b5

<400> SEQUENCE: 167
caaaatgctg gattatagat gtatcttgtg a                           31

<210> SEQ ID NO 168
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: amplification oligonucleotide PG1Ae3b6

<400> SEQUENCE: 168
tgctggatta taggccttgc agt                                    23

<210> SEQ ID NO 169
<211> LENGTH: 28
<212> TYPE: DNA
<213> ORGANISM: Homo Sapiens
<220> FEATURE:
<221> NAME/KEY: misc_feature
<222> LOCATION: 1..28
<223> OTHER INFORMATION: amplification oligonucleotide PG1Ae3b7

<400> SEQUENCE: 169
tgctggatta tagaatttct ctgcaaag                               28

<210> SEQ ID NO 170
<211> LENGTH: 30
<212> TYPE: DNA
<213> ORGANISM: Homo Sapiens
<220> FEATURE:
<221> NAME/KEY: misc_feature
<222> LOCATION: 1..30
<223> OTHER INFORMATION: amplification oligonucleotide PG1Ae3b8

<400> SEQUENCE: 170
ccaaaatgct ggattatagg atgcttatag                             30

<210> SEQ ID NO 171
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: amplification oligonucleotide PG1Ae5b6

<400> SEQUENCE: 171
tatctttgca tggcagcctt g                                      21

<210> SEQ ID NO 172
<211> LENGTH: 23
<212> TYPE: DNA
<213> ORGANISM: Homo Sapiens
<220> FEATURE:
<221> NAME/KEY: misc_feature
<222> LOCATION: 1..23

-continued

```
<223> OTHER INFORMATION: amplification oligonucleotide PG1Ae5b7

<400> SEQUENCE: 172
ctttgcatgg caaatttctc tgc                                          23

<210> SEQ ID NO 173
<211> LENGTH: 27
<212> TYPE: DNA
<213> ORGANISM: Homo Sapiens
<220> FEATURE:
<221> NAME/KEY: misc_feature
<222> LOCATION: 1..27
<223> OTHER INFORMATION: amplification oligonucleotide PG1Ae5b8

<400> SEQUENCE: 173
ttatctttgc atggcagatg cttatag                                      27

<210> SEQ ID NO 174
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: amplification oligonucleotide PG1Ae56b

<400> SEQUENCE: 174
ctgcccaacg tgggaaagac                                              20

<210> SEQ ID NO 175
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: amplification oligonucleotide PG1Ae46b

<400> SEQUENCE: 175
gcaggaactc caggaaagac g                                            21

<210> SEQ ID NO 176
<211> LENGTH: 25
<212> TYPE: DNA
<213> ORGANISM: Homo Sapiens
<220> FEATURE:
<221> NAME/KEY: misc_feature
<222> LOCATION: 1..25
<223> OTHER INFORMATION: amplification oligonucleotide PG1Ae36b

<400> SEQUENCE: 176
tgttactttg ctcagggaaa gacga                                        25

<210> SEQ ID NO 177
<211> LENGTH: 22
<212> TYPE: DNA
<213> ORGANISM: Homo Sapiens
<220> FEATURE:
<221> NAME/KEY: misc_feature
<222> LOCATION: 1..22
<223> OTHER INFORMATION: amplification oligonucleotide PG1Ae26b

<400> SEQUENCE: 177
atcaaagcac agggaaagac ga                                           22

<210> SEQ ID NO 178
<211> LENGTH: 19
```

```
<212> TYPE: DNA
<213> ORGANISM: Homo Sapiens
<220> FEATURE:
<221> NAME/KEY: misc_feature
<222> LOCATION: 1..19
<223> OTHER INFORMATION: amplification oligonucleotide PG1Ae16b

<400> SEQUENCE: 178
ccggggtcca gggaaagac                                                     19

<210> SEQ ID NO 179
<211> LENGTH: 56520
<212> TYPE: DNA
<213> ORGANISM: Homo sapiens
<220> FEATURE:
<221> NAME/KEY: exon
<222> LOCATION: 2001..2216
<223> OTHER INFORMATION: exon1
<220> FEATURE:
<221> NAME/KEY: exon
<222> LOCATION: 18196..18265
<223> OTHER INFORMATION: exon2
<220> FEATURE:
<221> NAME/KEY: exon
<222> LOCATION: 23716..23831
<223> OTHER INFORMATION: exon3
<220> FEATURE:
<221> NAME/KEY: exon
<222> LOCATION: 25570..25659
<223> OTHER INFORMATION: exon4
<220> FEATURE:
<221> NAME/KEY: exon
<222> LOCATION: 34668..34758
<223> OTHER INFORMATION: exon5
<220> FEATURE:
<221> NAME/KEY: exon
<222> LOCATION: 40685..40843
<223> OTHER INFORMATION: exon6
<220> FEATURE:
<221> NAME/KEY: exon
<222> LOCATION: 48067..48190
<223> OTHER INFORMATION: exon7
<220> FEATURE:
<221> NAME/KEY: exon
<222> LOCATION: 50179..54519
<223> OTHER INFORMATION: exon8
<220> FEATURE:
<221> NAME/KEY: polyA_signal
<222> LOCATION: 54493..54498
<223> OTHER INFORMATION: AATAAA
<220> FEATURE:
<221> NAME/KEY: primer_bind
<222> LOCATION: 1991..2008
<223> OTHER INFORMATION: upstream amplification primer 5-63
<220> FEATURE:
<221> NAME/KEY: primer_bind
<222> LOCATION: 2505..2525
<223> OTHER INFORMATION: downstream amplification primer 5-63 ,
      complement
<220> FEATURE:
<221> NAME/KEY: primer_bind
<222> LOCATION: 4091..4111
<223> OTHER INFORMATION: downstream amplification primer 99-622
<220> FEATURE:
<221> NAME/KEY: primer_bind
<222> LOCATION: 4528..4546
<223> OTHER INFORMATION: upstream amplification primer 99-622 ,
      complement
<220> FEATURE:
<221> NAME/KEY: primer_bind
<222> LOCATION: 5475..5495
<223> OTHER INFORMATION: downstream amplification primer 99-621
<220> FEATURE:
<221> NAME/KEY: primer_bind
<222> LOCATION: 5927..5947
<223> OTHER INFORMATION: upstream amplification primer 99-621 ,
      complement
```

```
<220> FEATURE:
<221> NAME/KEY: primer_bind
<222> LOCATION: 8127..8144
<223> OTHER INFORMATION: downstream amplification primer 99-619
<220> FEATURE:
<221> NAME/KEY: primer_bind
<222> LOCATION: 8560..8578
<223> OTHER INFORMATION: upstream amplification primer 99-619 ,
      complement
<220> FEATURE:
<221> NAME/KEY: primer_bind
<222> LOCATION: 11622..11639
<223> OTHER INFORMATION: upstream amplification primer 4-76
<220> FEATURE:
<221> NAME/KEY: primer_bind
<222> LOCATION: 12018..12037
<223> OTHER INFORMATION: downstream amplification primer 4-76 ,
      complement
<220> FEATURE:
<221> NAME/KEY: primer_bind
<222> LOCATION: 11930..11947
<223> OTHER INFORMATION: upstream amplification primer 4-77
<220> FEATURE:
<221> NAME/KEY: primer_bind
<222> LOCATION: 12339..12358
<223> OTHER INFORMATION: downstream amplification primer 4-77 ,
      complement
<220> FEATURE:
<221> NAME/KEY: primer_bind
<222> LOCATION: 12915..12932
<223> OTHER INFORMATION: upstream amplification primer 4-71
<220> FEATURE:
<221> NAME/KEY: primer_bind
<222> LOCATION: 13317..13334
<223> OTHER INFORMATION: downstream amplification primer 4-71 ,
      complement
<220> FEATURE:
<221> NAME/KEY: primer_bind
<222> LOCATION: 13216..13233
<223> OTHER INFORMATION: upstream amplification primer 4-72
<220> FEATURE:
<221> NAME/KEY: primer_bind
<222> LOCATION: 13617..13636
<223> OTHER INFORMATION: downstream amplification primer 4-72 ,
      complement
<220> FEATURE:
<221> NAME/KEY: primer_bind
<222> LOCATION: 13547..13564
<223> OTHER INFORMATION: upstream amplification primer 4-73
<220> FEATURE:
<221> NAME/KEY: primer_bind
<222> LOCATION: 13962..13981
<223> OTHER INFORMATION: downstream amplification primer 4-73 ,
      complement
<220> FEATURE:
<221> NAME/KEY: primer_bind
<222> LOCATION: 15994..16011
<223> OTHER INFORMATION: downstream amplification primer 99-610
<220> FEATURE:
<221> NAME/KEY: primer_bind
<222> LOCATION: 16463..16480
<223> OTHER INFORMATION: upstream amplification primer 99-610 ,
      complement
<220> FEATURE:
<221> NAME/KEY: primer_bind
<222> LOCATION: 17304..17324
<223> OTHER INFORMATION: downstream amplification primer 99-609
<220> FEATURE:
<221> NAME/KEY: primer_bind
<222> LOCATION: 17814..17832
<223> OTHER INFORMATION: upstream amplification primer 99-609 ,
      complement
<220> FEATURE:
<221> NAME/KEY: primer_bind
<222> LOCATION: 18008..18027
<223> OTHER INFORMATION: upstream amplification primer 4-90
<220> FEATURE:
<221> NAME/KEY: primer_bind
<222> LOCATION: 18423..18442
```

-continued

```
<223> OTHER INFORMATION: downstream amplification primer 4-90 ,
      complement
<220> FEATURE:
<221> NAME/KEY: primer_bind
<222> LOCATION: 18699..18716
<223> OTHER INFORMATION: downstream amplification primer 99-607
<220> FEATURE:
<221> NAME/KEY: primer_bind
<222> LOCATION: 19164..19182
<223> OTHER INFORMATION: upstream amplification primer 99-607 ,
      complement
<220> FEATURE:
<221> NAME/KEY: primer_bind
<222> LOCATION: 22589..22609
<223> OTHER INFORMATION: downstream amplification primer 99-602
<220> FEATURE:
<221> NAME/KEY: primer_bind
<222> LOCATION: 23111..23129
<223> OTHER INFORMATION: upstream amplification primer 99-602 ,
      complement
<220> FEATURE:
<221> NAME/KEY: primer_bind
<222> LOCATION: 25098..25118
<223> OTHER INFORMATION: downstream amplification primer 99-600
<220> FEATURE:
<221> NAME/KEY: primer_bind
<222> LOCATION: 25657..25674
<223> OTHER INFORMATION: upstream amplification primer 99-600 ,
      complement
<220> FEATURE:
<221> NAME/KEY: primer_bind
<222> LOCATION: 26537..26557
<223> OTHER INFORMATION: downstream amplification primer 99-598
<220> FEATURE:
<221> NAME/KEY: primer_bind
<222> LOCATION: 27022..27040
<223> OTHER INFORMATION: upstream amplification primer 99-598 ,
      complement
<220> FEATURE:
<221> NAME/KEY: primer_bind
<222> LOCATION: 32262..32281
<223> OTHER INFORMATION: downstream amplification primer 99-592
<220> FEATURE:
<221> NAME/KEY: primer_bind
<222> LOCATION: 32823..32841
<223> OTHER INFORMATION: upstream amplification primer 99-592 ,
      complement
<220> FEATURE:
<221> NAME/KEY: primer_bind
<222> LOCATION: 34215..34233
<223> OTHER INFORMATION: upstream amplification primer 99-217
<220> FEATURE:
<221> NAME/KEY: primer_bind
<222> LOCATION: 34624..34644
<223> OTHER INFORMATION: downstream amplification primer 99-217 ,
      complement
<220> FEATURE:
<221> NAME/KEY: primer_bind
<222> LOCATION: 34473..34491
<223> OTHER INFORMATION: upstream amplification primer 5-47
<220> FEATURE:
<221> NAME/KEY: primer_bind
<222> LOCATION: 34916..34936
<223> OTHER INFORMATION: downstream amplification primer 5-47 ,
      complement
<220> FEATURE:
<221> NAME/KEY: primer_bind
<222> LOCATION: 34702..34722
<223> OTHER INFORMATION: downstream amplification primer 99-589
<220> FEATURE:
<221> NAME/KEY: primer_bind
<222> LOCATION: 35182..35200
<223> OTHER INFORMATION: upstream amplification primer 99-589 ,
      complement
<220> FEATURE:
<221> NAME/KEY: primer_bind
<222> LOCATION: 39591..39611
<223> OTHER INFORMATION: upstream amplification primer 99-12899
<220> FEATURE:
```

-continued

```
<221> NAME/KEY: primer_bind
<222> LOCATION: 39971..39991
<223> OTHER INFORMATION: downstream amplification primer 99-12899 ,
      complement
<220> FEATURE:
<221> NAME/KEY: primer_bind
<222> LOCATION: 40531..40549
<223> OTHER INFORMATION: upstream amplification primer 4-12
<220> FEATURE:
<221> NAME/KEY: primer_bind
<222> LOCATION: 40932..40950
<223> OTHER INFORMATION: downstream amplification primer 4-12 ,
      complement
<220> FEATURE:
<221> NAME/KEY: primer_bind
<222> LOCATION: 40629..40649
<223> OTHER INFORMATION: downstream amplification primer 99-582
<220> FEATURE:
<221> NAME/KEY: primer_bind
<222> LOCATION: 41058..41078
<223> OTHER INFORMATION: upstream amplification primer 99-582 ,
      complement
<220> FEATURE:
<221> NAME/KEY: primer_bind
<222> LOCATION: 45729..45746
<223> OTHER INFORMATION: downstream amplification primer 99-576
<220> FEATURE:
<221> NAME/KEY: primer_bind
<222> LOCATION: 46186..46203
<223> OTHER INFORMATION: upstream amplification primer 99-576 ,
      complement
<220> FEATURE:
<221> NAME/KEY: primer_bind
<222> LOCATION: 47879..47896
<223> OTHER INFORMATION: upstream amplification primer 4-13
<220> FEATURE:
<221> NAME/KEY: primer_bind
<222> LOCATION: 48217..48236
<223> OTHER INFORMATION: downstream amplification primer 4-13 ,
      complement
<220> FEATURE:
<221> NAME/KEY: primer_bind
<222> LOCATION: 48902..48922
<223> OTHER INFORMATION: upstream amplification primer 99-12903
<220> FEATURE:
<221> NAME/KEY: primer_bind
<222> LOCATION: 49331..49351
<223> OTHER INFORMATION: downstream amplification primer 99-12903 ,
      complement
<220> FEATURE:
<221> NAME/KEY: primer_bind
<222> LOCATION: 49830..49848
<223> OTHER INFORMATION: upstream amplification primer 5-56
<220> FEATURE:
<221> NAME/KEY: primer_bind
<222> LOCATION: 50271..50290
<223> OTHER INFORMATION: downstream amplification primer 5-56 ,
      complement
<220> FEATURE:
<221> NAME/KEY: primer_bind
<222> LOCATION: 50172..50189
<223> OTHER INFORMATION: upstream amplification primer 4-61
<220> FEATURE:
<221> NAME/KEY: primer_bind
<222> LOCATION: 50573..50591
<223> OTHER INFORMATION: downstream amplification primer 4-61 ,
      complement
<220> FEATURE:
<221> NAME/KEY: primer_bind
<222> LOCATION: 50541..50560
<223> OTHER INFORMATION: upstream amplification primer 4-62
<220> FEATURE:
<221> NAME/KEY: primer_bind
<222> LOCATION: 50940..50959
<223> OTHER INFORMATION: downstream amplification primer 4-62 ,
      complement
<220> FEATURE:
<221> NAME/KEY: primer_bind
<222> LOCATION: 50555..50572
```

```
<223> OTHER INFORMATION: upstream amplification primer 4-63
<220> FEATURE:
<221> NAME/KEY: primer_bind
<222> LOCATION: 50964..50983
<223> OTHER INFORMATION: downstream amplification primer 4-63 ,
      complement
<220> FEATURE:
<221> NAME/KEY: primer_bind
<222> LOCATION: 50774..50792
<223> OTHER INFORMATION: upstream amplification primer 4-64
<220> FEATURE:
<221> NAME/KEY: primer_bind
<222> LOCATION: 51183..51202
<223> OTHER INFORMATION: downstream amplification primer 4-64 ,
      complement
<220> FEATURE:
<221> NAME/KEY: primer_bind
<222> LOCATION: 51146..51165
<223> OTHER INFORMATION: upstream amplification primer 4-65
<220> FEATURE:
<221> NAME/KEY: primer_bind
<222> LOCATION: 51479..51496
<223> OTHER INFORMATION: downstream amplification primer 4-65 ,
      complement
<220> FEATURE:
<221> NAME/KEY: primer_bind
<222> LOCATION: 51593..51610
<223> OTHER INFORMATION: upstream amplification primer 4-67
<220> FEATURE:
<221> NAME/KEY: primer_bind
<222> LOCATION: 29734..29744
<223> OTHER INFORMATION: upstream amplification primer 4-67 ,
      complement
<220> FEATURE:
<221> NAME/KEY: primer_bind
<222> LOCATION: 51167..51185
<223> OTHER INFORMATION: upstream amplification primer 5-50
<220> FEATURE:
<221> NAME/KEY: primer_bind
<222> LOCATION: 51667..51687
<223> OTHER INFORMATION: downstream amplification primer 5-50 ,
      complement
<220> FEATURE:
<221> NAME/KEY: primer_bind
<222> LOCATION: 51387..51403
<223> OTHER INFORMATION: upstream amplification primer 5-71
<220> FEATURE:
<221> NAME/KEY: primer_bind
<222> LOCATION: 51826..51843
<223> OTHER INFORMATION: downstream amplification primer 5-71 ,
      complement
<220> FEATURE:
<221> NAME/KEY: primer_bind
<222> LOCATION: 51772..51789
<223> OTHER INFORMATION: upstream amplification primer 5-30
<220> FEATURE:
<221> NAME/KEY: primer_bind
<222> LOCATION: 52199..52217
<223> OTHER INFORMATION: downstream amplification primer 5-30 ,
      complement
<220> FEATURE:
<221> NAME/KEY: primer_bind
<222> LOCATION: 51850..51867
<223> OTHER INFORMATION: upstream amplification primer 5-58
<220> FEATURE:
<221> NAME/KEY: primer_bind
<222> LOCATION: 52382..52400
<223> OTHER INFORMATION: downstream amplification primer 5-58 ,
      complement
<220> FEATURE:
<221> NAME/KEY: primer_bind
<222> LOCATION: 52507..52527
<223> OTHER INFORMATION: upstream amplification primer 5-53
<220> FEATURE:
<221> NAME/KEY: primer_bind
<222> LOCATION: 52997..53017
<223> OTHER INFORMATION: downstream amplification primer 5-53 ,
      complement
<220> FEATURE:
```

-continued

```
<221> NAME/KEY: primer_bind
<222> LOCATION: 52703..52721
<223> OTHER INFORMATION: upstream amplification primer 5-60
<220> FEATURE:
<221> NAME/KEY: primer_bind
<222> LOCATION: 53142..53162
<223> OTHER INFORMATION: downstream amplification primer 5-60 ,
      complement
<220> FEATURE:
<221> NAME/KEY: primer_bind
<222> LOCATION: 53001..53018
<223> OTHER INFORMATION: upstream amplification primer 5-68
<220> FEATURE:
<221> NAME/KEY: primer_bind
<222> LOCATION: 53521..53538
<223> OTHER INFORMATION: downstream amplification primer 5-68 ,
      complement
<220> FEATURE:
<221> NAME/KEY: primer_bind
<222> LOCATION: 53459..53476
<223> OTHER INFORMATION: upstream amplification primer 5-66
<220> FEATURE:
<221> NAME/KEY: primer_bind
<222> LOCATION: 53920..53940
<223> OTHER INFORMATION: downstream amplification primer 5-66 ,
      complement
<220> FEATURE:
<221> NAME/KEY: primer_bind
<222> LOCATION: 54202..54220
<223> OTHER INFORMATION: upstream amplification primer 5-62
<220> FEATURE:
<221> NAME/KEY: primer_bind
<222> LOCATION: 54681..54701
<223> OTHER INFORMATION: downstream amplification primer 5-62 ,
      complement

<400> SEQUENCE: 179
gtggatctgt gactgttcgc aggaagagag gagcgggagc aggacagaca ataactgata      60
gtcaggagct gggtttggag ataaagaggg aacaagagaa agttaagttc tgtgttttca     120
tggcaaacat tgcacaaaag tttacaactt cgtgactaac agtaatctgg ggtgattcac     180
aacaaattta cacataaaca catatttact gactttatac acagcaatcc taacgtgaac     240
acagaacctg ctttatcttt tcgcacactg ttctagtgta gagatgtctg gtctcagtta     300
aagaaagcat aaggagcatt agttgtgcac actgtccaca cccgtgactt ttttccacca     360
gtactaaacc tagtgcttct tacagtacag ggcaatgaca gccacagaaa gagagaagct     420 cctttactg tgtaatgctt cctgctggcc ttcaaatact tgttacttga gagatctcca     480
ttcacctggc tttgtcccca aaggtcatca tctaccaatg atgttgttat ttgatgttaa     540
tcatgtataa agaaagtagc taccatcctg gccctgatta gaacttccca ctgaaatacc     600
gtcctgccta aaggtagcac aggtttccat tatggtggtg gtggggaggg ggcgggaata     660
tatatatata tatatatata tatatatatg gtaaagcatt cggcattctt ttaaagtaca     720
actatccttg aaaagggtta catattaaac cattttttacc acagccaaag gggaggagaa     780
agatccaaaa gtcctgtgga tctgctttaa catcaataaa acagttatcc acccttcgta     840
gcttttagtg aaggctacaa aagtatgctt tttatggatt acacatgtgc acgcaactac     900
tttaattact acagaaaaaa acgaggctcc ttattaaaaa aaaatcagaa acaagtccaa     960
cagactctga ggaaatgaag caagagtgaa ttctgaaaag gtctaataaa cagtatgaaa    1020
atatccttgt gggattgttc ttcagctatg cataaacatg taattatcat cattactgtg    1080
atggggaaaa acacggaccc taattctgaa acaccctggt agcgagagac gggcaggagg    1140
ggctgctgcg cactcagagc ggaggctgag gaggcggcgt cccccttgcaa aggactggca    1200 gtgagcagat ggggacactc gagctgcccc gcgacctggg ccgagctgcc tacaacctgg    1260
```

```
gcccaggtgc ctgcaagaat tagacctccg ataacgttaa cacccacttt ctcactgctc    1320
taattgtgtg catcccggcg cccagggget tgtgagcagc aggtgcgcgt tccaggcagc    1380
tccagcgacc cttaaacctg accgcgcgca cgtccgcccc gagggagcag aacaagaggc    1440
acccggaccc tcctccggcc agcacccacc ttcacccagt tccgtcagtc gccaccacct    1500
cccttcccgc gtccgcagcc ggcccagctg gggagcatgc gcagtggccg gagccgggtt    1560
gcccgcgcca cagcaggtag ctgtactgca actgtcggcc caaaccaacc aatcaagaga    1620
cgtgttattg ccgccgaggt ggaactatgg caacgggcga ccaatcagaa ggcgcgttgt    1680
tgccgcggag cccctgccc cggcagggg atgtggcgat gggtgagggt catggggtgt    1740
gagcatccct gagccatcga tccgggaggg ccgcgggttc ccttgctttg ccgccgggag    1800
cggcgcacgc agccccgcac tcgcctaccc ggccccgggc ggcggcgcgg cccatgcggc    1860
tggggggcgga ggctgggagc gggtggcggg cgcggcggcc cggccccggg cggtgattgg    1920
ccgcctgctg ccgcgactg aggcccggga ggcgggcggg gagcgcaggc ggagctcgct    1980
gccgccgagc tgagaagatg ctgctgtccc tggtgctcca cacgtactcc atgcgctacc    2040
tgctgcccag cgtcgtgctc ctgggcacgg cgcccaccta cgtgttggcc tggggggtct    2100
ggcggctgct ctccgccttc ctgcccgccc gcttctacca agcgctggac gaccggctgt    2160
actgcgtcta ccagagcatg gtgctcttct tcttcgagaa ttacaccggg gtccaggtga    2220
gccgcctccc gctcccgggt ctcggcgtcc acccgagctc ccgggggcgc ggacctctcc    2280
gctcccccac agctggcgag ggtcacccgg ccggcccggc ggacccagca cggagagcac    2340
gtgccgcctc cccgccttcc tctccgcatg cttcctgccg ttctgccgag atcgctctct    2400
aggaagctgt ggctgcgtcg tcctgaggct acgagtggga cccgccgccc ctttccccgc    2460
ccctcgcctg ggtctgatgc tgcttagcaa agtgggtgca gatgcacgtt ttaaataata    2520
gggcacgcgt ttagcagttt ctggcctttg gtccaaagag gtggtcatgt tggaacagat    2580
cggagacgtc tacactccga agtgcgcttt tacagtgacc tcttgaaaca gaagtacaat    2640
tcggtcttgt gttctttccc ctggacaagt gaaagctggg cgaagaaatg aatacatttg    2700
ttaaccgtag aagcctaact agatacaatt cttgccaact ttaactgggc ttgaatgtgt    2760
gggtgatctg ttgtctgatt actttctttc tgttactgtt tctctgtaga gattggattc    2820
gtagattaaa cttgagaaac aaaccataaa agtggaaggc cctctttaac agtaggtatt    2880
tgaagtgtta taaaaaaaa aaaggtgaat ttttctttta tttctcagtt tgaaagaaca    2940
gctttattct tggttattcc taatgtccac ctagtcctct tttactttc ttggtagggt    3000
tagggtggca tggggaaatg ggacggtatc attttgtctt tttaactttt ttttttcca    3060
cctacagcag ctgtttttac cctgtggtca gtcaggtact atatttagtt tgcagttgca    3120
ctgctgatcg acccttgatg gccccagttg gaagttgttt gggggaagg aactaggaga    3180
ggccagggcc tccatttaaa ccagtgtctg taagtgtctc cttggaagga aaaaagata    3240
ctgttccagg tcatggtttc ctggtagttg acgtttaaaa tgggcctcat ttaaaaattt    3300
caataattca ggctaatttt ttcccttat atggtaactc caccaagttt gtctaaatgt    3360
atgattttta tcatgattaa gttttttactt ccacatcatg tgacaactgg cctgggatgg    3420
gatataagct cagaacacaa agtcattcac ctgttaaaaa aataattcta tctgtggcgg    3480
gttatgttat ttttgttcaa agaggacaca atatgatgca gaatacacca ttgaaggatt    3540
ttttggtttg gcaagttctt attttttaa atggctgtaa aacctagcag tgtttctgaa    3600
```

-continued

| | |
|---|---|
| attgcatacc ttacctgatg ttcagagatc cgatttactt cttgatttcc cagcaagtga | 3660 |
| ttttgaaaac atttaatcta atcattcccc ccaccgtctg ttcaaatcaa aggaagtggc | 3720 |
| atccagcact aattttcatg catttatgaa aggatgcctg aggaccctta agtataattc | 3780 |
| aaaattttgt ttaatgtgtg ttccttgatg aagttcttta ggagtcgtag aacgaactga | 3840 |
| ttgcccactg atcatcaaat gcaagttatg aacatttaat aaaaatttaa aaccaagagt | 3900 |
| ttcttgttcc tgcattttta tttttattgt atggagggga caaataatta ttttctgttt | 3960 |
| agtaacagag cagggtattt tgaatttatt agggtctttt tctgcagtct gggtttcctg | 4020 |
| tgtacacaaa gctacctttc aatattttt attgtttctg ttaagattaa atcaatagag | 4080 |
| gaataaatag ctatcttcaa acataagacc caaggaaaaa agatttatag tgatgttctg | 4140 |
| tcaccttatt ttttacctgt gactttgtac cattaacttt gtcactgaga tgttttgatt | 4200 |
| aaaattttta gcttgctttt cttgttttgt taggacactc ttttttttctt gaattgtttt | 4260 |
| tatcagcttt cgtttgcaag gctagtgatg attctcttgt tctgtataaa gtattgttga | 4320 |
| ctcatttctg aagggagttt tagtaattta agaggttata agttttttaaa taaaaggttt | 4380 |
| attaatttat atatattaaa gaggcatttt aaaataaaat ttttttttaaa tgacattttt | 4440 |
| acacctttca actctaggtt taaaaaataa gtggttcaca gtagttcttg cagaagaata | 4500 |
| ttttctttta catagaattt ttaagctgaa gagaagtagt agtaggtcca tgagatttat | 4560 |
| gatctgtgct tggcaggtaa acctgcttcc aacaaattta gttggatttt tcttggattc | 4620 |
| tgggtaaata ccttttttctt ccccagtttc actactttat tttcatatgt atctctgaga | 4680 |
| tagagaaata tttcagtcag tgctgctaaa attgttcctt ataactcgtt tatccttta | 4740 |
| ggtccttcca gaatctctca ttggtactga aactcaaatg ggtactttct tcaccattta | 4800 |
| tttctttaga ataagtaata agaattttat aagcttttt atatttcacg taatttgaga | 4860 |
| ctattgaaaa tccagttaag tctctctact gtgttgagag gcattgattc aagtacctgt | 4920 |
| gttactttcc tgtgctgcca aaacagatca cctcaaacta agcggcttaa aataatagaa | 4980 |
| cttaagttct cgtgattctg gaggccagca cttttgaaatc aaggtgtagg ctcaatttta | 5040 |
| ctccctctgg aggccctagg gggaatctgt tcttgtgggt ttcaacttct ggtgactggt | 5100 |
| ggcattcctt ggcttggggc cccatcactt caacctctgc cttacagtcc ttgctgccac | 5160 |
| ctcttctgtc tcacatctca ctctcccttt ctcttagaag gatgcttgtc attgggttta | 5220 |
| gagcccacct ggatattccg ggatgatctc ttcatctcaa gatccttaat tataactgca | 5280 |
| aagagccttt ttccaaataa gaaaacattc acaggttcca gggcttagga tgtggacaca | 5340 |
| tttttttgagg ggctgccctt cattccccca caacaatgaa ctccatagtt ctgcctattc | 5400 |
| agtattttgt agttatttcg tagtttaact tgccttatt ctttaggtat ttacgtatta | 5460 |
| aagcattttg gtctctgctt tctttaacag agaacctggt tttctgtaat aagtttactt | 5520 |
| actttcccat aatcttttag tttcttattt acagatttac cttcacatat cccttaagta | 5580 |
| gaacatttga ttaactgttt tattttcgga acaaatctgc attctgtata ataaccaact | 5640 |
| tattcatatt tcggtattct tttaattctt atctgattct gaaattacca tcttgtgatt | 5700 |
| atatatatat atatatggaa ataactgaaa tcttgataaa ttaaaggtga tataacttct | 5760 |
| aagacaatta attatgtatg atgtggtgaa tatactggtg tttggtttgt ttgccactta | 5820 |
| aaagccctat ctataggata ggaagtaact tgaatgtgga atgctagag actcagagta | 5880 |
| agaggccgta tatatatcct tgagctggag tttaaggaaa acttatggga aattaaaagg | 5940 |
| aaagttggag tactgacaga ggattgcgta ggactcatga aaaaggaatg aagttacctt | 6000 |

```
aaattctatc atcgtgagtt aacgtgaaac tagatttatg ttagtttata gcctagaatt    6060
ctatcctagg aatctagata tatcctaaat gttgagatag ctgcataaac aataactgta    6120
atcgttatga taaataatga caaatctttt tagcatgttt tgtgaagctg ataaatgtta    6180
ataggatgtc ttcaaatgtc agaattcttt tttctttgct tcttttttaa aaaatttctt    6240
ttcccccatt cctatgcaat acactgaaaa ctgatcattg aaatttgtag gccaaaaaat    6300
taatcaacac gtaatagatt ggggtttggg ttttttttgag tcagggtctt cttctgtcac    6360
ccaggctctg gtgcggtggc accatcatgg ctcattgcag ccttgaatgc ctgggttcaa    6420
gtgatcctcc ggagtagctg ccgtgccatt atttctagct aattttttaaa agttttttgta    6480 gaaatggggt ctttctgtgt tgcccaggct ggtcttgaat tcctggcctc aggtgatcct    6540
tctgccttgg cctcccaaag tgctgggatt acaggtgtga gccaccatgc ctagccccta    6600
ataaatattc taattaccga tttatcttgc ttaaatcagt tggtaacact tggaatttac    6660
ttcagaatat atttttacatt agtggctctg actgctaatt cccccttctc caaatgctaa    6720
tgtaatataa caataaaatg cacagttctt aagtttatat aaaataaaca ggttttcagt    6780
tgacctgctt taagtgtaaa atagtgtgaa aaacacaaga aagaagataa agaatttaag    6840
attttgacat ttctctaata tgcccttaac ttctccaagg attcatactt tttttttgtaa    6900 gacagaatct cacactgttg cccaaaccag aggtgcagtg gtgcagtctc cactcactgc    6960
aacctctgcc cccgggctca gcggtcctc ccacctcagc ctcctgagta gctgggacta    7020
caggtacaca gcaccatgcc cagctaattt tttttttttgg tatttttttag tgggggtaga    7080 gacgagattt tgccatattg cccagtctgg ttttgagctc ctgggctcaa gtgatccgtc    7140
cttgatccac catgcttagc tgattcatac tcttaactga acattgttc caagtttctc    7200 agaaacagtc aaggctttt atctagagaa catttataac tggatctttc tttgtgtagc    7260
actgattcat caaactaatc ctaaactcct aatgagttaa atttatattc tgaatcttgc    7320
tgtaaaagca gccattcatt agaatgaaac atgtttactt agaattggag aagggagctt    7380
ataagtcatc tagtctactc cctttttatga cacttctaca ttctttctgc acttctgcca    7440
aaatgttgcc cagcgtcgtc tctgatacct atagtcctaa caagaatatg aatcatacct    7500
tgtatcctta atttttactct tctctgctta tttgccattc atgtgaagac cttaaataga    7560
tcttaaattg cttccttcac tttagctgag agtgacagga ctgtgtaggt gtgggtgtgt    7620
ttctgcattt gcttatttaa gcaggataat aaaaactttt actataggaa attaaacatt    7680
tcccaatcaa atacaattcc agtctaacac aattaaattc tggttaggga actgcttaac    7740
ttactagact tataggaaaa tactaaaaaa atgtaactag aactctattt ttacacttta    7800
taaatataaa cctctgtgaa caaaccagtt atttcaggtt gcatttgtgt atagtttttt    7860
aatgcctgat ttttctattt taaaatcaca gatgcaatta tacattcaaa cactgccaca    7920
atactttgag aaagttaaag ttttccctac tcctacactg cgtacacctt tcctaggtac    7980
atcccagttt ggtgtgtaac tttagatttc ttccaagagc ttttgagtaa gtgtttgaat    8040
tgtgggaagg ttcttagtt aaatgaactt cttacagatc agttttttag tacagtagca    8100
cgaaatatac ctgcatacct atggggatac ctctgtgcca ttacgatgga aggcacggga    8160
aaacagcact ccgtatatac ctagtttact ttccctcttt tgtatatttg tctgattttg    8220
tggagctgat gcttctcaag tggaatcaga agttaacttt tcctttacta ttttctcatt    8280
ttattatggt ttcttaacta gaggttgatg ttagtggttg gaccattcaa tagtaagtaa    8340
```

```
tgacttttca gtaagggatc tctagaaccc agatccctta attcctgcaa tattcccgtg   8400
tgtacattgt tccaggtgct gtcctgggta ccaagggata caatgtttga tagacaatgt   8460
acctgccatt atggaggtca cattctagtg tgggaagaca aacaataaca agaaaatgaa   8520
aatttactgt gccatgccag gttgtttagc ctggtgggtg agaggtaggg gtttggaaaa   8580
tcttactgag caagtgacat ttgtgtggag ctctgtaaaa gggccagctt ggaaggtaat   8640
gtagtcatcc aggtgagaaa tgatggttag gggagtggaa agagtggatg ttaagattga   8700
aaagaattcc aaatctattt tagtggtagc tgatagggct ttgtgattga atgtggagga   8760 aaagaagag ggtgggttag taacacactc agtcgcagtt agtgagtgct gctgtgtgca   8820
agtattgttc tattatgtaa ataattccat ctttacaaag taggcaccat tcttcctctt   8880
ttacagacaa ggaaaaggga acacccatgg ttcacatctg tagtagccta gccaggagtt   8940
tcaggcactt attttctgaa gatgctctgc ctggcaatgt ggttatattg gttgaaatga   9000
gaccccctac tttcaaggta ttcatctagg aaagacatga actgccaatt acaatatagg   9060
ataacactga aattagagac gtgtttatta actttgccat acagaggtaa agtaactctt   9120
taaagtaact ctttgcttgg gttagtggag aaggctataa aaattacttg gagttttttac  9180 tttgaacatg cgtaattaac atggaatgtt tagggaaaag aggttttcaa ttgataacat   9240
aataaacatg aggagtttga agcatggcat tcaaggtttt ctaaattctg ccccggttaa   9300
cttttccatt cgttggtttc attctagtct agcttttcct tctgggccgc cctccccac    9360 attagaccgc tcctctctgg aattccaact caagcccttg cttttctcca tctgtcatga   9420
tgttacccca tctcattgtc agggtaactt ttatgtaata ttaacatata taatactgat   9480
ataacattag catattttaa tgtatggatc atctcctctg caacattgta acctcttgga   9540
gatggcaata atgggaagaa tgacttgatt ttactttttc ttttaacaaa aatggtggag   9600
tagtctgggc acgtgtggc tcatgcctgt aatcccagca ttttgggagg ccaaggaggg   9660
tggatcactt gaggtcaggc attcgagacc agtctggcca acattgtgaa accccatctc   9720
taccaaaaaa atacaaacac ttactgggca tggtggtgtg tgcctgtagt cctagctact   9780
caggaggctg aggtgggaga atcacttgaa catgggaggt agaggctcca gcttgggcga   9840
cagagtgaga ccctgtctca aagaaaaaa aaggtaaaag ggccaggtgc ggaggctcac   9900
gctggtaatc caagcacttt gggaggctga ggcaatggat cacctgaggt cgggagttcg   9960
agatcagcct gaccaacatg gagaaacccc ttctctacta aaaatacaaa attagccggg  10020
cgtggtggtg cctgcctgta atctaagcta catgggaggc tgaggcagga gaatcacttg  10080
aacccaggag acagaggttg tggtgagcca agatggcacc attgcactcc cgactgggca  10140
acaagagcga aattccgtct caaaacaaac aaacaaacaa aacaaaacag agagaaaagg  10200
cagagtactc tagggaattc tagtctgtgt ttctgtggaa atgtatatga atctcacttt  10260
taagggatgg agattttga atggcataac tagttgataa gttttgctct aacagggtac  10320
ccaagtctag tgagtccgat tcattctttc cttaaataga tgaaggagga agaaacatga  10380
ctccaccctc aagagtaagg cagaatgagc aaagtcagag aagttaaaaa agaattctca  10440
cgcagccagc agtgcagaga aaccttggtt tagttgtgaa tcaaaaccag tactttttgt  10500 aattttttgag cctatgcaat tctccaaggt tttatgttgt ttcttctgtt tctctgtagg  10560
caccagaaat caaaacccca aataagaaag tgttacttga agatttttaga gtacttattt  10620 gtgtataagt gtaagtgata tttggaagac gactttactg cgctcctcca gcttggcatg  10680
agaattccag gggcggaaag aaaggagggt gatggtacct ggaaaggaga gtcatgttaa  10740
```

```
gtcccagcca catattaagt gctaaccacc tactgttaaa aggtgtaatg ttctagactg   10800
acaaaataca tagtctctac cgtaaagtaa cacataattt agcagtgcag aaagatgtca   10860
cttaaaagaa aacttgaata tatgctgaga tagttcacaa attaaagaaa tgaacaaaga   10920
actgaggaaa taaaggagga atacaactgt gtccaaatga atacttaact gggtgggagc   10980
tgttgcatat gtaagcaggt ggttcaccta aaagttggat gtaacgtagt taacgccagc   11040
tcttggtgca cttacatatt gcattgcttc cgggcttaat ttgtgttcat ataggaataa   11100
attttttgtt ggtttttaat tttactcctt gtaattccgt ggttgatatt caaagtgaaa   11160
aaaattacat aagcttctaa tatatgagaa gtcttctcac ttgacatttt ttatttggaa   11220
tttttgcaga gagtagtttt gtcacagtca aaagattttg ggatcttgca gtgagaaacc   11280
taggtgtaat tcctatttct ctgccattcc gtatgtcatc tggattaagt gtcaacttct   11340
cagtctcaag attctcgtcc ttaaatggaa tacttttgt catgctattt tgaagacaaa   11400
atgagataat acgtgaaact gcctagctca gtgaatggta catcatagat actcagaaaa   11460
aacacaccct ctaaaataag aacagtacca aagacagga tgtaaaataa gggcagtacc   11520
aaaagacaca tgcatgctga gtgtatgaga aagaactttg tggccttctt gggtggcaca   11580
ggccatggca gttccacagc atgacgtggt tgctgtgggt ggtagagcag acatgccgct   11640
ccccgtcact gcctggcttt gatgcttgct ttcttcagct gagaggacgc agctgtgata   11700
tgaaggtctt gtgtgtacag tcgtgacctc acatttccaa tttcctgctg gcagaaccca   11760
cagtctacaa cgtacgagca ccagagttga cgtgagacag acagcataca gaggcttgta   11820
acatccttct ggaaaacact gtgtaagctt tcagtgcgaa taaacatgat cagtggcaag   11880
ttctgttaga tgtagtctgc aagcatcctg attttactgg gcaagactat gttgatttac   11940
aggcggctga tgattccatg gatagcccac tactagtatt ttcacaaatt tcacaagaca   12000
ttcttactgg aagattgccc tgttcttatg atactgctgc cctttagct tcatttgctg   12060 ttcagactaa acttggagac tacagtcagt cagagaactt gctaggccac ctctcaggtt   12120
attctttcat tcctgatcat cctcaaaatt ttgaaaaga aattgtaaaa attacatcag   12180
caacatatag gcttatgtcc ttgagaagca gcagttaatt acctaaacac agcaagtacc   12240
ttagaactct gtggagttga attgcactat gcaagggatc aagtaacaat aaaattatga   12300
ttggaatgat gtcaagagga attctgattt ataacaggct atgaatgagt accttccat   12360 ggtcgaagat tgtaaaaatt tgttttaagt gcaaacagtt ttttattcag ctttgaaaat   12420
gacttgcata aatctggaga aagattatca ggatttaata tggtgaatta tatggcatgt   12480
aaacatttgt ggaaagcaag tttagaacat cacatattct tctgtttgga cagaccactt   12540
ccaactagaa agaatttttt tgcacattat tttacattag gttcaaaatt cctaatgcat   12600
ggtgggagaa ctgaagttca gttagttcag tatggcaaag aaaaggcaaa taagacaga   12660 ctacttgcag gatcctcaag taagccattg acgtggaaat taatagtttg ggaagtagta   12720
ggcaggaatt caatatctga tgaaaagatt agaaacataa agccttccat cacaattccc   12780
acccggaaca ggaattccta ctcatcaaaa ttctgcattc atacaagagg gaacctgatt   12840
atgaccatct tctgttggtc atttggtaga ttatgtggtt cacacttctt ccaaatattt   12900
gcaaatcaga catcaccatt atcagcacaa gctaatagca tcattctgga atcatcacta   12960
ttacaggaca cccctggaga tgggtagcct ccagctttac cacccaaaca agctaagaaa   13020
aactgttgga accaaattca ttatttacat tttcaacaag atctggaaga tcatattaat   13080
```

```
gaaacgttga tgttctatct tctcttaaaa aatctgctcc taatggtggt attctacatg    13140
ataatcgtgt tctaatccga gtgaacctga cgaaaatgga aggtttggag tcaatgcaaa    13200
gggggatatg atcagaagat gtctgtgatc gtgtcctgag aagcaccagg aacacctttg    13260
acctcagtga ctctcgattg aagagaagac caagttgtat tgatcagtgg ttgggacttt    13320
acagaacaca cccatgattg ggttgtcctg ctttttaaag ccaactgtga gagacattct    13380
ggggaactca tgcttctagt tctacctatg ctgcatatga tgtagtggaa gaagtgctag    13440
aaaatgagac agacttccag tacattctgg agaaagcccc actagatagt gtccaccagg    13500
atgaccatgt gctgtgggag tcagtgatcc agctaaccga gggcttatcg ctggaacatt    13560
ctggacacaa tttgatcaac ttatcaaaaa aaacttgga atgacaattt ctggtgccag    13620
attaccttag aacctttgca aaatagata gagatagttt tccttatgat gttacatggc    13680
ttatttttaa aggtaatgaa aactacatca gtgtaattcc agcatcataa gtcagaacag    13740
tgcttgtcaa ggggcgttac cacacacttg aacagatttt tggcagatga cttgggaaca    13800
aggctcctcc atgtttgtaa tgttgaccac acaagttgaa tgtggcagag ttaaatgacc    13860
ccaatattgg ccagaaccca caggaagttc atcctatgga tgctaccaag ccttctgcca    13920
ctgagaagaa ggaagcactg tctttatctt caggaagatc acactgctgt ttaaccaaga    13980
gaaaaattag agagtcatca atcacgcaga tccagtacag agggtggcct gaccatggag    14040
accctgatga ttcagtgact ttctggattt tgttttcat atgcaaaata agagggctag    14100
caaggaaaaa cccccttgttg tttcttgcag tgctggagtt ggaagaacca gcgttcttaa    14160
tactatggaa acagccatgt gtctcattga tctcattgaa tgcagtcagc cagtttattc    14220
actagacatg gtaagaacaa tgagagagca gtgagccgtg atggtccaaa cacctagtca    14280 ttacagttttt gcgtgtgaag tactattttg aaagcttatg aagaaggctt tgctgaagaa    14340
agcaaaagga aaaaagaac tttgtcatct gttaggttcc atttattgca tgataattgt    14400
gtttgtattg attattgggc aagtagctgt ttgctatttt gatcttattt cagaagggca    14460
taataatttt actattcaat gaaacgtttt aaacggggta gaaaaagact agttttttgta    14520 tgctttacag cagaaatctt ataatgatta actggtaata tatttcgttg gcataaaaat    14580
acatttaaaa gttcaagtaa ttataaacat tgtaaattgt atatgtaatc atattgaaat    14640
tgaaattctt tatagctgta cttctgtgta atcaaagact ggggagagat agactagcta    14700
gctctttctc ttatccatta atcacttaac agagttttga ataaaaagtt ccatttcatg    14760
ggataagaat aatgacaggt taacctatt tagttggtta ctatgttcta ggtgttgtat    14820
gaagtagttt acatagtttc actgatttca ctacaatccc aggaggagta gttactatta    14880
ttacactcat tttacaggca aagaaatagg tttggagggg ttgggtgttt tgcccaagtt    14940
ctcatcgtaa aatgacagat gaggattcaa attcaagtct taattgaagt ccattacttt    15000
agaacctacc tcttagtggc tcttatgtta cagtataagg gagagcagac tgttcccttta    15060 cccttgtagg gtagctaggg cttgtgaatt aagagactga ttaacaggag aagaggcata    15120
cacattttat tgacgttagt attttacat gcacagggaa ggagggtttt atttttattt    15180 ttattttat ctttattta aagagacagg ggtcttgctg tgttgccagg gctggactca    15240
aactcctgaa gccaagcgat tcttctgctt gagattcctg agtagcaggg actataggtg    15300
tgctcctctg tgcttggcta agaaggggt ttgtatgtga ttttaacaa aggctgataa    15360 attgtgaaga agtgactagt caaggagaa gaggattca gctcccaggg gtggtaaatt    15420
gtgggaagat gactaggaaa tgtatagtaa taaggtttgc tatgcaggtt tattttgcca    15480
```

```
gtttctggtc tcctaataag ggacagggaa acacctttac agatggaaat tcatatcacc   15540
tttccacagg gaaatttatg tcctgcctta ggcagttagg ggaagggcag agaattcttc   15600
ctgtatctgc tgtgtctcag gtgccttcag ctcaaaataa tccttatgcc aaagtagcat   15660
atttgggtgt ggcatattct ctgatctctt tcaacagcat catctatact taacaacagc   15720
aaaagttttt tttaaaaaat catgtttcaa gatttgcatg tggaagacaa atggacatga   15780
ttgagataaa tgaagaatat atattttta acaaagaatg ctgtatattt atgtctctgt    15840
gacattgtgt tatggaggct aaggtgttaa gcatgtgatt actttagatg ccgtatgact   15900
acctgttttt aagattaaaa aagaatcaat aggcagtttta tatgcatggg agcaagttaa  15960
aaacaacaca gatgtgatga aggcgaggtg aaactggtcc gcatctaatt caggccttct   16020
cctgaaagcc agtgtgtgca agataaataa gtttgtttga cgaaagcaga ataactagtt   16080 tgtccttttgt gatgaagata gttattcaga aatcattttt attggctacc tctgaattaa  16140
taaatgaaaa gagaaatttt tttttctgta ggggatgtct gatgagttct taaaaagtgg   16200
atgaacctga aattatcatg aacaagcaat tataatgaac ttaaaattac ttaaagagtt   16260
atgaaaaaca aaagaaaag ccgtatgttt tcttgtgcct tattttgaag tgacaaatta    16320
tttgcagggt acatttgtag acggaactaa tgtgatttaa aaaatgagta ctagatttac   16380
agaatgatgc ctttaaaaag tcactggtgc actttaatta ttttatttat gtttattctg   16440
aaactacctt tattttgaaa atgaggtata gctttgccta ctggtgacaa aagtgtaaat   16500
aattcagtaa acatctgtta aaaaccagct tggtgctagg ctcttggggt agaaaactga   16560
tcaggccatt gaggagctca tagtccctaa ggggctgggg acttgtcatt aggtgtgcag   16620
tgtgttctgg atgctcctga aggagtgtgg gcaggtgcgc accaccatgc ctggctaatc   16680
tttttataat tatgtagaga cagggtctgg ctgtgctgcc catgctgggt ttgaacttct   16740
gggcttaaga gatcttccct ccctgccct accgaccccg cccgcccact ccacctcagc    16800
ctccccaaag cactgggatt gcaggcatgg gccactatgc ctgggctgtg caaaactttt   16860
aaatcagtgc atactcaatg gtcttgatgc aattctggct tgttggtaag agaatgggga   16920
tttactcaca agccacgatg tcacttttaa ctctgaacag atcaagctat tggtattact   16980
catttatgtc atcgataaac tttatgaata aaaactcatt gtgcaaatat ttaaacatac   17040
tacatacata gcactgtgca gtttctaagg aaagtaatgg aaacctttgt cacatccctg   17100
gcttccagaa ctttatgtta tctaagtgca tttgtctgca aagttgttgg gttaattgcc   17160
cctttcttct ttctctttttt aagatattaa taaatagtgt catgaccaaa agataatcct  17220
tatggacaag atagatctaa aaagccttag ctaatttata atcttgcata atccatgatg   17280
acaagatgca gaaacaaaaa tgcccagaat aaaaacttag caccattagc agccatttcc   17340
ttttaagtct ttacaagtat actcccagtt tcttgaaaaa tttattctaa aatatgtaag   17400
acacacaaaa cagcagaagg actaatacag gtacatcgaa cacctgtgtg cctaccgccc   17460
agtttaaaaa taaactggaa tgatgtttct ctcatactta cagaataaag ttttaatctt   17520
tagcatggaa ttcaaaagac ttctgccatt ccagttcaga gccaccctc tggtctcctt    17580 gctcctcagc cgcgacactg cccatgtacc caacaggcct ccagggttac tgcttccatt   17640
cgttcttatt ctcatgaaca ttttccttca tctcatctgc cagaatccta cctaataata   17700
ctcctgctct gcagtttaca gttctttaaa attaaaaaag gttgtgtacc ctttagtgtc   17760
ctgaaaaaag aaaaaacaaa tttaaaacct taaaaggta ccatatttttc atagtatttg    17820
```

-continued

```
cgttatgtct cattacagtt cctgtggaca tgtctgtctc ttttactaga ttgattgtgg    17880
gctctttgaa ggaagatata tcttatgaac agtgttttat atattgttag caatcaatga    17940
atgcttgcta tattttctc atgaggatat tgattattct atttaattt attaccgtta     18000 acctgtacta tacataactg ctttctgtac ctgagctatt tatgatctct gaggctcctg    18060
tgagaaatct aattttgtt aatcatggat ggaaatattc acaacatcat tcgtcagttt    18120
cttcacattg tcttcctttg tatattacag atgttttaaa atatcaaagt aatgtttttt    18180
tgttttatct tttagatatt gctatatgga gatttgccaa aaaataaaga aaatataata    18240
tatttagcaa atcatcaaag cacaggtttg tatttcattt gcatgaaacc taggtttttc    18300
tacagatggc acatgggcat tcaaaatacc gttcttatat ttaaatgaag tgggtttttt    18360
aaaacagcaa ttttctgtgc agatattaca cctgttcttg tattttgtg atttactttt     18420 ttggaaagtc agaaacttga aagctatgaa ttttcctaaa cttaccttct ccctctgttg    18480
gatgtaagta agctatcttc ttacttgctt gctttgtttt tcctttgtgt agctctttaa    18540
agagtgtatt cattctttt gtaagtgatg tttctagaag tagcattggt gggtcgaagt      18600
gtgtatacat tttacatttt tgattgctaa gctgcagaaa agctgtattg gtatgtaagt    18660
actcgtttcc ttactatgct cgtcatttct agtgtctgct cttcctttcc ttcttcaaat    18720
gggtttggtt taattctagt tgctactgtt ccatcagagg aattgcagag aactggtctt    18780
caaaacagtg cagtatatac tttaggtgaa gatacttcta aaacctttg tattttgagg     18840 taattctaga gtcccaagaa tttgcaaaaa gagtacattg tcagcaatat ttttcccaat    18900
ggtgacatct taatataact gtagcacagt agcagaatca ggaaattgtc attgggtaag    18960
gtacttttta attctccaaa taattcagcc ctccaaaaaa atcccacttc ttatgttttc    19020
aaacctgtag ctactttga tgcgtacttc ctaaattgca ttttattac tttaaaaaat      19080 ataaccta gaagctcaaa gctggaaaca gcctgatcaa tatagtactc ttaagctaaa      19140
aacaacctga tcaatatagt actcttaggg aaatcactta tgcctgtggc ttttttaaa    19200 ttttcttcct gtcagctgtc tcttcatgat tttgtggttt ttattactgc ttataccata    19260
gatgaggtat agaaagtaaa agaagttaaa atgcattttt ctcaatttag tgaattaatg    19320
attacattca gatttatagg acaagggttg aagctacaag gggttgatag gaatcttgat    19380
gtatctgagt attttcccca actttattac atgactggtt cagactattt tatctaatta    19440
catttcactc ttggcagaaa tagcaaaaca gtcaaccaat ggtcaatgct gctgagaact    19500
ctggcctgtg cagacatatt ggctgtttta cttctaatac cattctgctt ttcctgtcct    19560
gctgctgatg gatgtttctt ccaggttta aatatcaaac aaaagggatc tgtgggccca     19620
gtacagggaa tggctcttga tagatttgat tttcctgcat ttcctttatt ttgatccagt    19680 gttaattca tgtagagttg tctgtttaac aggattctct taaaattcct tcttcagttt     19740
acctgccagc ttttctttgt ccaggtttca gtatgaactc cactcgatta atagagctct    19800
ctagtagtga cttgtggagt gggttctctg aacatttctg gaagtgttgc tgatagtgat    19860
aatattgatc actagtactg ttaatttgtg tgcttactac atgttggctt ttatatgtat    19920
tccttcagat taaggacttc tagaaaacat ccatgaaaaa acagattaaa aaaacaatt    19980 ctgcatgtat ttgggactag aaggtactat gggaaggata atcttcatac tcagaccata    20040
ctgacctgaa tttcatttat cagtttagag aaccacttcc ccttcccttc acctacctc    20100 cgagtgcctg tgactttgta tcaccgctct ggcaccacat cctcatccca gcaggatttg    20160
ggaaggctgc ttttgaaag cctttaaaa ttctgtaagt tgagaaaata ctaggggaat      20220
```

```
gattttaaat ttctttagaa ttacaggctt tagtcagtat atgacagagc cttttcctag  20280
aaaaatgtgc atataaaaat ttgcatgtag ttttagggtt tcagagaccc ctaaagccta  20340
tccatagacg tggttcattg tctgattgtg tttaggtacc cttctaaaac ccttttgaga  20400
tgttaggaat cacaacagag tatctctgaa aatgtaatta gcggaaagaa catttcaaag  20460
actgttgttc tgcttagact ttctagtttg tcttctgcca ggcttgccgg aataaatgag  20520
tttcctggcc tgatactcaa aagaattgac atttaaatta gtctctctct tcccttgttt  20580
tcgcttgaca catccttgtc tctacattct gtctctgtct ctgttagctt atttctctct  20640
cgagtcagca ggatatagtg gctgttattt cttcccctta tccttcaacg atctactttt  20700
gacaacactt tgcctttttt tttttgagat ggagtttcac tcttgttgcc caggctgggt  20760
gtaatggtgc aatctcagct cactgcaacc tttgcctccc gggttcaagc cattttcctg  20820
cctcagcctc ccgagtagct gggattacag acatgccacca ccacgcctgg ctaattttgt  20880
attttcagta gagatggggt ttcaccatgt tggtcaggct ggtcttgaac tcctgacctc  20940
aggtgatctg cctgcctcgg cctcccaaag tgcaggatt acaggcgtga gccactgtgc  21000
cctgcctgct atttgccttt ttaatctcat gaaatgttct cttttcttgg ctgaagtgtc  21060
acttttcttg ttgaacagca tgcgtggtga gtagaatgtt ataaaaggg atggactttg  21120 gagttagaga gacccaggtt cctgttcggc attgcagaaa tgctgttctg caataggctg  21180
tgtgtcagtg gcaaattac ttatctctca gagccttatt ggtaaggtgt gagtgatagc  21240
tcctttcagg caccttacag aggctgtctc ctaatcctgg tagcgtacct ggctcataga  21300
tggcatttaa aagtggttgt gatgacagtc atagctcacc attagcatag cgctggatcc  21360
atggcaggga agcgctgcac atgcagtatc tcttggacta cacagggccc tcatgaatta  21420
ggaactgctg tttcatgagg atagggatga ggaaattaga cttgctgccc ctcactgcct  21480
tccactcctc tcctccaagt taatgggaac tatgactctg ctttggcttg attgccatgg  21540
aagattctca cacagccaaa tttattgcta tcttagttaa attatgccag aacacaaaat  21600
atgaagttat tgtcaaagta atataatctc agctgtaact gagatagtca gaaactgtct  21660
gtaatctgat gtcctatctg aaaggtagct gagaataaac aagaaataaa gagaattcag  21720
tagcaaatat tggtgacaca aagctttat atttttgacta gttaagctag ttcttaaatg  21780
tttccactaa aatattcaag tttaagggca tagcccaggg cagcttatta tgaacatgat  21840
gtattttgga aatcttacac tttctcttaa aagttcttgg gaggggcatg tgaggccata  21900
atataaccat aaaaccattt gttttaaaat aaaacccatt tttaaaattc ttccaaataa  21960
aaaaattatt gcaggaaaaa atgctaaacc tggttttaa ctttgtacgc caactatatt  22020
tccaagatgt gctgtagcct ggtaaccata cagaaccata cagaattagt tctcagaatt  22080
tattgtctgc ttacttttgc atttggtaca ggtataacag ggtcgattat atggtttcta  22140
agacatgact agaaagaaat atgtttatca gttattattt cttccatcta aattagaagg  22200
ggctagggag agggcttcaa caggaattta tatacttag agaaaagtga tcattgatag  22260
cccaatagta tagatatctc aacccaataa cacaggttgt gtctgtctct gggatcatac  22320
actgtagggg agaatctttg caagcaacat tctacttata gggagccata acaaaagttt  22380
catatgtata ataattataa gtcttaagtc atcaagaaaa agttaacttg tgaatgataa  22440
tccctgatta aaaagagaga tgtataataa tggataagag attttcttg gttaattttt  22500 agtattaaaa tggctaaatc ttctttggga tattctgact agtatggtgc attgtctaat  22560
```

```
agatttccca tagctgagag ctaatcatct tgtaatctgt ggaaaactgt cctctttggc    22620
taaaacttta ttgtaattcc tctaaatcct cagcttttat tttctacaga cttttttttt    22680
tttttaacat ttccttcctc tgactcactc cttttgttct cattttcatg gcctgagaac    22740
atgggtgatg atagaattat tcttttcaca gattaacagt tttcttttcg agtatcgttg    22800
agctcatgtg tgtattaact agagaagtct cccttacatt tcatttttat gttttctttc    22860
tcatcaggag atagtttgta gccatttact ttcaaatcca agtttctgcg gttcttaaga    22920
cctgtatcat ttgtctcctg aatttcactt catttcctct ttaaaccatg tcctctgttt    22980
cccatcttct gcacccactt tgccacttcc tgtttgttta attggcaagg gccactctct    23040
gtgttggaaa ttttttcttt ttgaaagctc aactaacaac ttctaggaag ttttttattg    23100
ctactgttat caattcatac catcttaccc ttgttttttgc aaccctttgt taataacata    23160
tttatttaac tatagttatt agcagtctga gatcatttta cttggttaca taaggagcac    23220
atatatctac ccagcatcat tgtaaggcat gtgagacctt tgtttgattg ctgtcctaac    23280
ctagtaccga gtcctaaaaa ctcattagta gaagatgaag tgtccttgcc ttttgctgaa    23340
catatatata cacactgaat atttagtggc aattcatagt tgcatttggc catttttttgt    23400 ttataatttc ccctttctca ttaaaaaaac tttgttttct agactttagg atttagagaa    23460
gctcattttg ttccatacac atgctgctgt tggattattt aggtattttg tgactgtatt    23520
ttatctttga aataaaaagc ctttcaagaa atgcaaaaaa aaaagctca aaaacagaa    23580 aatgtatatt ttttaaatat ctcagataga tttaagaaa ttttaaacat cctaatcata    23640
gtacttttga agcccattca tagtacaacc tgtgaagagc ctcatgtacg cgctaactgg    23700
gtcctgtctc tgcagttgac tggattgttg ctgacatctt ggccatcagg cagaatgcgc    23760
taggacatgt gcgctacgtg ctgaaagaag ggttaaaatg gctgccattg tatgggtgtt    23820
actttgctca ggtaacttgt ttccatgctt ttctctctat atatgtagtt tataaatttt    23880
tttttttttt tttggagaca gtctcacttt attgctcagg ctgagtgcag tggtgtgaac    23940
acagctcact gcagccttga cctctggggc tcaagtgaac ctcctgcctc tgcctcccaa    24000
gtagttggga ccgtagtgcc caccatcatg cccggctaaa ttttctattt tttgtagaga    24060
tgggggtctc gctgtgttgc ccaggctggt cttggactca agcaatctgc ctgtctcagc    24120
ctaccaaaat gctggattat aggtgtgaac tgccataccc aaccctataa aaatgttata    24180
ttttaaaatt taacaatata cttcatgtga atgtatggtt tttaaaatgg gtttaatagt    24240
ttattctcag ttgaagtaat tttgtttggc attttttagtg gtgtgtattt atatacgtct    24300
gattatccat atgcggtttt ccttcagcat ctgtggggat tggttttaga accaccacag    24360
ataccaaaat ctaaggtgtt caagaccctc atatagaatg ggatagtatt tgcatataac    24420
ctgtgcacta ctttaaatca tctctagatt acttataata tctaatacat tataaatgcc    24480
atgtaaatgg ttgttatact ttatttttta tttgtattat tttaattgtt atattatttt    24540
taatttttat ttgttcacat attttttgatc tgtgatttgt tgaatctgca gatgtggaac    24600
tcatggatgt gaagggccag ctgcagtaaa atgaaagagc aaaaatgcaa atgtacaaag    24660
ttcaaacaaa taggaaattt aaaggcatag aatttgatag gcaattacat taaactgttg    24720
ataacagtaa ttagtgatct gtatgatatt aaaaaaaaaa agcaaactgt atatataaaa    24780
cttactttct ccagttctgg aggctagaca tccaagatca aggtgttgac agggttagtt    24840
tctcccaagg cctctctccc aggcttgcag acagcatcct tcttcctgtg tcctcaggtg    24900 gttttttttcc ctgtgcccaa gcaccccctgg cactgcttcc tcttcttaga aggactagtt    24960
```

```
acactggatg actaatcctt ctacagagac tgctaaggtc ccactctgag gcccttttt    25020 aaccttaatt accacctcta agtccctctc tctgaataca gtcacagtgg aactattag    25080 ggctttagta gactgatttg ggggaacaca cttctgtccg taacagtgcc acataaatat    25140
ctttagcagg attgattttt taaaatccct aaagatcgtg agtattgaca tgttaaggac    25200 gcttttagt gactctgtaa taagtgggtg gaagaattgg gagttaaatc catctgatgg     25260
atcaggtttt ttatttttaa aaatgtgtat ttaagaaaga aagcattttc attttaactg    25320
ccaacaaaac taaacttcat gtgttttcca atacagtgtc acatgcagtt tttttgaatt    25380
atgttgagac aaggcaattt tcagctaaat gttctttaga agctaatgtt tgaagatatt    25440
aaatatagat taaattctga aatgtagttt tcattctgta cttttttgcaa gagaagttgc   25500 ctttttgatg actctggcca attgttattt taaaagtaaa tgctctttct cccgatttga    25560
ttgtggcagc atggaggaat ctatgtaaag cgcagtgcca aatttaacga gaaagagatg    25620
cgaaacaagt tgcagagcta cgtggacgca ggaactccag taagagccta cccgttttta    25680
tttttcttac cagctctcag tttctaaatt taagaattaa attaaaatct aagaattgtt    25740
ttgacaatgt attttcccat gtgtaattac taattcaggg ttatgctgag gtaacagaaa   25800
ccctctatgt acaggtaggc aggttttca gccatcagaa agattgctgt aaacaactag    25860
gtcctttgct ggtcagtgga ccttaaagag gaataaaaag agcatttggt gtcgttcaga    25920
gtctataaat agaactaact gcattttaac ctgacattta agctagttta caagctcatc    25980
ttacttcttg tcttctttag tatcagattt ggttttagaa gcagcaactg ttttctgtta    26040
gtgcaaattt tgaatgtctt acatgtacag aaaaaccaaa aaaggatgaa tctctacaaa    26100
tgttaaatca ttcagtgtaa ataatatttt ataaaacttt attccacaaa agtggggaga    26160
gttcaatctg ctttgtatag aatgctgatt gctgccaaag gcttttcccc tggttccctc    26220
cggagacaaa gcaccatgat caccggggcg acttgggctt tctctttcag tacatgacat    26280
gtgctcagaa gcttagctcg tgtgcacagg ctttcccttt cctttctggc tccctccctc    26340
tgtcttccct cctctcctct gccctcccc tcaccagggg tcctgggcag cagctggagc    26400
tcatggtgaa ggaagaattc ttcatggtca gctggcgaag tgcctggtgt gagcattgtt    26460
tattcacatg cctcttctag gtgttttac attagaacat tgcatctgtt ttgggcatgt    26520
gttgggtgac agaagcagaa tggaatgaga tgaacagtga ccctttatcc tgttatagct    26580
aacccttgag aaccaagctt ggtgtcttca aagggtctgt ttagtctgaa acagtgtggt    26640
gaatttgggc agaattgtgg tcattgcatg taggtctcca aaagacagaa taagttggta    26700
atatggttta tcgactttt acaaaaaaaa tttaaaaatc atgaatttat accttaaaat    26760
gtccatccca cttctctccc agctgtccag tcaccccagc aatggatgac tgctgtggag    26820
ttccttctgt gtcctgctgt gggcattgta tatatgaagc aaatgaagat agctgccttt    26880
tgggtgatgt tggcatccta tgcacagtgg tcccttgctt ttttgccccc atgaatatag    26940
ctgccagtgg cgctagggct gaaaaaatca gctctttaca cttgtcatgt gtcttgttta    27000
tgtggctgcc ttcgtgagtt tcttcttgtt tttggtttgc agcagtttaa gtatcatata    27060
tctgagtgtc atttaaaaat ttttacctgg attggtcctc tgagcttgga tctatgattt    27120
ggtgtctgtt attaattttg gaaatttctt tgctcttatt tccttaaata ttattcctac    27180
cccagtcttt cttctccagt tatgtttgtg ttggttcatt tctcgctgtt ctttagttct    27240
tagatgcatt attcgttttt tgttggtttt tttttaaatt ttttttttta cgcccctcc    27300
```

```
cttttttctt tttgtgttac attttggata atttctgttg acccacctttt gagttcatgg   27360 attcttcctt tggctgtgtt gagtctactg gtgagccagt ttaaggcact cttcatctct   27420
gctactgcgt gtttcattcc tcacatttcc ctttgaccct gtttcatagt ttccatctct   27480
gtgctagtgt atctatctga tcataaagct tagtcacgtt ttccagttga acctttatca   27540
ttttattata cttgcagttc tcttaaattc cctgcttgat aattccaaca tctgggccat   27600
atctgagtct gcaaattttg attactttat ctcttcagat tgtgctttat cttgcctttg   27660
tcatacttcc taagattttg cctaacgctg ggcctttttt gtaagacagg agaaatggag   27720
gcaagttgtc ttgatacctg gaaatggata gacttgtctt tctgcttggc ttttagtgtt   27780
gaggagtgga gtcagtccac tgaggaggtg cactgcattt gggttttgct catgtgcttt   27840
ttctcacagc ttcaggtttc tgtagaactc attactttgt ttgtaggttg gggatgtcct   27900
cccgctagag cttttcctca gtgtctattt cacactcagc gttttcacat agcaccttgg   27960
agtggctctc ttctttatgc ctttccccac tatacttctt ggatacttgt tactgaactc   28020
tcgctagttt ggtggtagaa ggagagggaa gggaagtgtc ttttcattct tagggagaat   28080 ctcagggggtg gagccttctc tgatcctgcc ttgcttctgg ctgtaagtct gtgcccagta   28140
tgtattcctg cctttactaa gagttttttcc ctgttctctt cacccagcct catcgagtat   28200
tcatccgtgc cccatgggta gcagggtttt gttgcccctg ttcatcagtt tcaggctgct   28260
gttccatagg aaaggtagaa agaaggatgt gggctgggcc ctgagcccct cccacagggc   28320
tgcttttccc tcccacaagc ctacatccag tcttccctga ccgcagtgtg ttttcttttt   28380
tctttgtctt gtgagtacac aggaggtctg tgggtcgagc ctgtgaaatg tgctgcattc   28440
tccttgtgtc tgtagcccag gggttcgtct gttccactgg ctcatacttg gctttctgca   28500
aaattgataa aattttttagc taaattcttt ttactggtat ctgttacatt ggccccccaac   28560 taaacaacca cttgcatctt gtttctcctt tgagttttcc atctttcctt agacttttgg   28620
gttagttggt tgccttgcaa ccttgcagct ctctgaaggg tctaagaaaa gtcatgaatc   28680
tacagcttgt cagtgttgtt gttgttgtag ggttggcagt agtattcctt cagcattcta   28740
catacttaat ggaagccgcc tcccattttt ggttaataaa tttcaaaact tggaacaatg   28800
ttagatttac aaaaacgtca gaaagaacag agtgttcctg tttattcttt atatagcttt   28860
tttttttttt ttttttttttg agttggagtc tcggtctgtc acccaggctg gagtgcagtg   28920
gcacgatctc ggctcactgc aacctctgcc tcacgggttc aagcaatctc ctgcctcagc   28980
ctcctgagta gctgggatta caggcgtgca ccgccatgcc cggctaattt ttgtattttt   29040
agtagagaca gggtttcacc atgttggcca ggctggtctc gaactcctga cctcttgatc   29100
cgcccgcctc ggcccccccac agtgctggga ttataggtgt gagccaccac gcccagcctt   29160
cttcatctag ctttaacatc taatgttgac atcttacata acatggtata tatttgtcaa   29220
aactaagaaa taaacattgg taccacacta ttaattgtac tacagatttt tattcagact   29280
ttaccaggtt ttccactaat gtccttttc tgttctaaaa tacaatccag aatagataca   29340
aatccattca acttcagtgt ttttaaattat tgtttttcat tatatgaagt gctgtgtggt   29400
ttttgtcaaa tctgttattt tggttttaat cttcaagctt gtctttgttt ctttaagtga   29460
taaaggcata atttaaaagg tgtgttgggt tatttcagtg cctaaagtct tgtctgagtc   29520
acttgttttc tgctgttctt gcttatggta cttttctttcc ttgtttgctt tgttatcttc   29580
ctttgctgct ggctgtgttt ggttaagtta tttgtggaaa tcagttgaag cctcaggtgg   29640
gagtgtcttt ctccggagaa catttctacc tgttttagct gggcccctta aggctcctct   29700
```

-continued

```
agcgtgggcc ccacccaaac gagattctga gttgaaggtg aactgagcca ttcaggcagt    29760
gcagccaggg ttgcagatgc acgtgagacc tgctcacctc tcatttactt tcaccctgag    29820
agtagagcct ttggtgtttc gttcacttgt ctgattctct cttcacagtt ctattagaag    29880
gtccatgggt tttggtttct gtgcccttca tcttatgagt cttgtaaatc aaagttctgt    29940
tttatgctta cttctgcttt actgtgtttg cttaatttca gtcttaacat cttgccaact    30000
cttgggtact tttaaaataa tgttatatcc agctttttaa gttgttttca gtaggaaggt    30060
tgattcaaat aacctagtct ggttatgggc tacgagaata gcctccctgt tttttgtggg    30120
caaaattcca gccttttatg ttcctagcgc agtgtggata acagactggc aggttcaaga    30180
ggccgtgctg agcagctttc actgtaaggt cactgtccca ggtcgggttt ctaagaatct    30240
ggatggttgt ttcatttctt aatatgtacg ccctgtgaga gcggatacat cttgctcagg    30300
ttcttatgat tcttttgttt ctgaaggtga attaagtaag tgacatggta gaatatgtta    30360
agtcaacttt cgtgtggctt actagttctc atgaatctat tccatgattg tatcagttct    30420
tattcagtat tagtatttaa gaaatgcaga attttgtttc aaaaaatata tttgtattat    30480
aagttgtgaa gaaatacatc tccataatta ttgctgggac aatacagtat tttcttaagg    30540
aacttattgg ttgtggatgc aaatgaagca tatttgtgat aaaaataact aatagaagtc    30600
attttgttag actatgagct agtaaaactt atggcacaaa catggagact taacactttt    30660
tcttccagct ttcacttaag ttccttttca gataggaggc agcctggtgg ataagagtat    30720
tggttttgaa attagattca ggtttaaatc ccagatcttc tgtttaatct ttatttt att    30780 tcaggtagat tttctggata acttgctata gcttatacgt cagtacttgc cacttcaatt    30840
ttatgttatg gagagacggc ttctttcctt aaacctcacg aaccaacctc tgctagcttc    30900
taagtttttt cctgccactt ctttacctct ctcagccttc agagaattaa agggagttag    30960
ggccttgctc tggattagga tttgctttaa gggagtgttg tggctggttt gatgttttat    31020
ctagagcact caaactttct ccatatcagc aataaggctg ttttgctttc taatcattca    31080
tgtgttcagt gaagtagcac ttttaattct ctttaagaac ttttcctttg catccgcaac    31140
ttggctgttt agtggaaagg acctagcttt tgacctacct tggctttcaa catccttcc    31200 tcactaagcc atttctagct attgatgtaa agtgagagac atgcaactct tcctttcact    31260
ggaacgctta gcagccattg tagggttatt aattggccta atttcaatat tgttgtgtct    31320
cagggaatag ggaaacccaa ggggcggtag agagaaagag agacaggaga acaggccatc    31380
attggagcag tcagaacaca cacgacattt atcaattaaa tttgtcatct tatatgggtg    31440
caattcatgg caccccaaa caattacaat agtaacatca gagatcacag atcacaataa    31500
cagatataat aatatgaaat attgtgagat taccgaaata tgacacagag acgtgaggtg    31560
agcacatact gttggaaaaa tggcaccaat agacttgctc gatgcagggt tgtcataaac    31620
cttcaatggg aaaaaaatgc aatttccgtg aagctcagta aagcgaagca tgataaaatg    31680
agatgagcct gtcactccta agaatgttcc tgtacaagtt ttttgcatct gttacttacc    31740
ttttcctatt tgtgaatagt atctttttg agtacgtgtg tttttttatt tttatacatt    31800
tatatgtatc ttttgaagaa catacttta agcttaattt attgattttt tttctctcat    31860
aatttccact ttttgtatcc tatttaagaa gtccttgcca aacttaaggt tgctaagatt    31920
ttctcctttg ttttcttctg gaatttttag agttttgctt ttcatttag ttctaggatt    31980 tatttataat taatgttttc atatggtgta agatcgaagt tcatattttt ttaatatagg    32040
```

```
taaccatcac tatagaaaag attatttccc cccaatgttt gaaataagta gactgaatat   32100
agatgggtct gttatcccta gatcaatgga gcatttgttc tgttatattg atctatatat   32160
atatatcctt atgccaatac catactgtct taataatgct tgctttgcag taagttttta   32220
aatagtgtag ttgtcttcta aatttgttct ttcttttcaa agttgttttg gctattttag   32280
gttttttgca tttctgtgtg aattatagaa ttagctcgac aatttctacc caagtttgt    32340 gggcttttca ttttgattgt attgaagata tagatgaatt tgggaagaat tgatataaca   32400
ggattgaatc tttggattca tgaacgtagc ctgcatttgt ttacttaggt cttctttatt   32460
tatctcagtg tgttttgtag tttaatgtac agatttgcac atcttttgcc agatatatcc   32520
ctaagaattt cagtttttga tactattgta gatgacattt aaaaaaattt caagtttttg   32580
tttgttgacc taggcatata tttgactttt taatatacta accttgctaa acttatttat   32640
catctagtaa cttacaaaat atattcctta ggatttccta cataaacaat catgtcattg   32700
ttttagaaat aacagtttta ctttgtcctt tttaatcttg atggctttta tttcttttc    32760 ttgctaaatt ttctggctag acctcctagt acagccttga ctagaactgg tgtgagggaa   32820
atcctttcca tattcctcat ctttagggaa aagcactcat tcttttatcc attctttagt   32880
tcctagcccc attgccctto ctaaatttttt tctcatcatt ttccttcatc acccttgtt   32940 cttttctttt gcaatcatat catgatatgt aacgacatgt ttttatttat ctgtttaatg   33000
tatttctttt cctcacttgt ccatgaaggg aaggaccata tgtgttgtta tcctttgtgc   33060
agttcctgga acataataag tatataagaa atagtttctg aattagctgt gaatgaattc   33120
atgccttcct gctgtctgtc aatgttcttt taaattaaac atctaagaca gcaaataata   33180
ccacatgagt tattaacctg agaaataatc gttttattta taaatgactg agttgaaagc   33240
tgatagccca cagtaattgc tttcatggct ttgaatataa accttactgt tacaaaacac   33300
attttcatga aaatgaatgt gtggtgtttg gaactagctt taatgtttgt cttcctgttt   33360
ttccttctag ttgctataat ataataagga attttgtatg ttttttcctaa ttgtacccac   33420 ttttctacat tttcttaaca gatctggtga atcttcatta ttaaatataa ttatacatat   33480
aaattattgt ttaataataa tattaattat taaaaataat ataattatt aaatataaag    33540 atacatataa tattatctgt taatttctaa gttaggtgtg ggttctgaag actattatat   33600
gaatgaacaa aaagcttgca tatttgcgtg gaagctgaaa gtacgaaatt tttagatacc   33660
attataccag tatctaaaga aaaaattcag taccacatag gttttttaagt aggagctgta   33720 tgatcatagg tcatccagat gaaggaaggc ttctgtacca gacgtacaga ggtagacagt   33780
gttgtctgag tactgtctga gatctggcaa gaatgaatcc aataaacgta gttttctccc   33840
atgagctcct gtcttgtttc ctgtattctg tttgtatttg aaaagatttg gtgtgcataa   33900
cttatttttg tcttttggct gtcaatcaaa gttattagtg tagttttgtt aactcagttc   33960
tcaagctagg agttttttgct gtataatttt aatgtttctg ttttttacttt cctaagcaga   34020 taagcgtaaa aacttagact aattgattac ttattaaacg tccagcttga tattcttctt   34080
tatattattt tagtttcagt ttatataaca aatgaggttt cttataaata aaatttaaaa   34140
tgcactaaag gagctgtgtg aaataggaat tctgtgtgaa gcttttgaat gtgaacattt   34200
agaacgtttc acatggtggg aatttactat atgattttca tcaaatgagg tactttttag   34260
tgttggtact taacgatact gatttctaaa atttgtattt ctaaaaatga cgtattacag   34320
gatctgaaag ggcaaaaact cattgaggct ttgtatgagt cagcgtttca tggcctattt   34380
ttaattagtg aattattagc atataattag aaatgttttt agattcttca tggctgacct   34440
```

```
accaatgaat gtagcactgc atttaaaata tagttcacgt tatgttcata cttaattgtt    34500
gcattttgtt tgcccctctt gaaacgaagg tcacatgtaa ataaatatac attttctcct    34560
actgtaggaa atactctgtt agcattagta ggtttagctt ttttaggtta acaataacaa    34620
aaacaaagct cacacaaaat aaaccaaatt tgctctatgt cccacagatg tatcttgtga    34680
tttttccaga aggtacaagg tataatccag agcaaacaaa agtcctttca gctagtcagg    34740
catttgctgc ccaacgtggt aagtaaaaat ttgagtgttt gaacaaataa ttttcaaaga    34800
taataacatt tttagttttt cttcctggaa agatacttt tgttttacag ttgaaggaat     34860
gaatgtattc attccttgaa ttagtgtaca tattatctct taggaaatga agtttcttct    34920
ccttaattca ctttcatgct attattacat atatctgaga aattaagttg aagtgcttgt    34980
tacgatacat attcttgtgc catggattta tttaaaatct atctaagtac atgattatgt    35040
agatggaagc ttttctaca gtgtatgggt tatatgtaat ggagcttctg ttttgtaaga    35100
tgacagacct aagttggagt ccaaactcgt acttttatta gctgtatggt tgcaacttgg    35160
aagttgtgta atgttgctga gcttgcttct tcatctctta aaagaacata tgccttataa    35220
gtagatctaa atctgtgtga ggattagatt agaaaatatg tcaagtttct attggagaag    35280
ttacacaaag ttggtccaca gtgcttggaa gctgttaatg tcttcaacaa tggtaatgtt    35340
cttaatatcc atattttaga aaattgaata attggtacac caataagcta tgcaatttaa    35400
ccaaattggg aagtatacag aaaacagtgg ctatgctatg ttcttagagg tgtctttgaa    35460
gcttgactgt gatttagtgt gtgatctcca tatgttgata gtcactcact gagcaaatac    35520
cttgttggtg acattacagc agggcctatg acagtgctgt ctaatggaac tttctgcaat    35580
aatggtaaag ttcttcatct gttctgtcca gtgtgctggc tcctaccaat gtggtttttg    35640
agcattcaac atgtgactag tgcatgaaac taattttaa ttttatttaa ttttagttta    35700
attaaaaata aggggagtt tttacaaggt gcttacaaga gcagatatgt cataggtata    35760
tgacatcatt tgtaacagta cttttaaaaa atgccagttt gttttaaac acatgtccta    35820 ttaagtaagg agtgcttcag aataggaggg ttcagttggt ctccccatct gccagctctc    35880
ttttgacttt cattgcttcc tctgtctaat agacatgacg ttctgtcatt tcagttgctc    35940
ttttgcaatg ccattgtctc ttttgcccct ttcacattta ttaaacagaa caaaacaaaa    36000
accactctcg aatctgtagt ctacctttgt tgtaagcact ttttccagta ctcactctgc    36060
cctcaatttg ttttggtctg atttgaaatt ctctccctag acttctgtgg ggctgttctc    36120
cattatcctc ccaactctct ggcgattact tcctagcctc cttccagcc tcttctgct     36180 tcatttctcc ctgctacatg tgttatttcc agtgtcaggt tttggtgttt gattaatttc    36240 acttttgtt tctcatggtg gccttcctct aaatccatgg ctttagccat cgtttccttg    36300
actgctgatg actcgcaaaa gcttcctccc ctccatgtct ctctgcctaa ctctggaccc    36360
atttgtacaa ttgtccatta gagagcttcg cttgactggc ccaaaaggat gtctcaaact    36420
cagcatattg aagatagaat ttatccttcc atgcatacac tcatatttct tgtcttggta    36480
actccatcat tcagtttttt tgcctaagtt ttattcacaa aaagaacaaa ttgatagcag    36540
ttgcatacct cttataggaa acttagacat ggaggaagaa gctgttcaga tggggtcctg    36600
cagaagtgca ggcactgtgg taatatttaa acttttctca gctgttcgaa gggttttgtt    36660
ttaactaatt ttccttagac ttgttttagg tatttggctt tctaatggtt ataagggatg    36720
tggaattaaa tgtatcttaa tctgccacct ggacccatta agtaagccc ctatggtggt     36780
```

```
tttttttttt aattgccatg gttaaaacca tagttgctag cgaaggtgac atacttaagc   36840
tttttgaact ctcttaaaag aaaacagaaa tttaatgatg tgtctataat ggcaaaccag   36900
atacctagaa tttccatgtt attcataggg tgaataacac tggcgattgt agagatttga   36960
gagttctttc aaaacaggag aacaaaggga ataagctaca aagcaatttt tttctttgta   37020
gacttaactg aataaaaatt atttttatgt ctcaaacatc atatgaacaa atttagttgg   37080
caaatggcaa gctaataata ttttataata taggatatta atatacttaa tattacaaaa   37140
gtgcttcata attagaaaag acataaacta gaaaatgggg aaaagggcat gaataagaaa   37200
ttcaagagat acaaatgacc cacacacttg aacaaatgtt tattctttct cataatcaaa   37260
gaagtagaaa ttaaatgaat actttgaagc caacttctga gaaagcatag caaacaagaa   37320
agctagtgct cagctttgtg tggtaacggc actctcgctc ttaagaaggt gtgtttgctc   37380
cctgtggctg ctctcaggca gggccacaaa cttggtggct taaaacacca cagatttctt   37440
ctcttacatt tgagaagtct gaaatgggtc ttactcagct gaaatcaagg tgttggcagg   37500
gctgcagtcc tttgtggagg cttggggggga tcttgttctc ctgtacgggg tcctgtgctt   37560
ggttcggggt cctgtgcttg gtctgggatc ctgtgcttgg ttcgaggtcc tgtgctgggt   37620
ccagtgctct gcttttacca ccttgaagtt catctggaaa tggcactggc tcgcccacac   37680
catatagctg actctggttc tccctcctcc tcactcgctc taaacctgtg ttttttggctg   37740
atttctaatc tctctttcct tggcccttct gcagcttgca gggccttctg cagctcttgt   37800
ctgccccagc cccggggtct gcccatccca gtgctgggct gttctgttcc tgccctgcct   37860
ttcctcagcc cttggcaacc ctgtttgttt tctcccttcc ttagcagtgg agaacatcgt   37920
aagatcaatg ctgactgcct tctgcagcca agccaggcca tttcatttca gccgagccaa   37980
gtctgtgtgg agcagttctt ttatttttct cctttgact acctcatggt tttcacggat   38040
ttttgttctc ttcacattca aggatttttt gctttcagaa agttatattt ctctggaaag   38100
agtgcaccca atatccttt tgatttcaaa atcttaatgt ggagtctctt gacttggatt   38160
tctttggaag aaactgctga agctgccatg tctaagaaga aaactttgga gaaaaatttt   38220
cttcttagac atggcaacgt caacagtttc taagctcttg attccgtcta ccctgtctcc   38280
atcgttgcct cagtcatctg ccttacttct ctgcaggggt ttctcccagc ttgcaaatgt   38340
actccaattc tgaaataact aagtctatag ctgtgcaaag agaagtctgg gccccttgct   38400
ttcttgtgtt tgactccatc cactctccag aaatgaatcc cacttctcac ttaaccactg   38460
acctccaaag catcgtatca tttgtgtcag ttgtcatatt tgttaacttt cacataactt   38520
ttgacattat ttataccttt ataaccagga ataattttta actttattgt agaaataaac   38580
aatggagtat aattttttctt gttgaagata aatatcacct cctcttcctt taaacatctc   38640
ttcccttttgt ttttgtatta cattggtttc cccccttttt ttatttcctg ggttgtcgta   38700
ttccctgtta ttatttttac cttttttttt ttaatgtgga tgtttccgga gtctgtattt   38760
cttgcctttt catcttctgc cctttattat tctcagccac tgccattact tcagttatcc   38820
attcccatgg tttccacatg cttagcttcg gttgattctt gccatttttac agaccatatt   38880
tccaactact tctagaatgt tttgttcctt cagcctcagt atgcccaatt tgaactcatg   38940
ttctctctcc cccttctttc ttccttcttt ctttcgctct ctctcccttc cttcttttct   39000
ttccctccct cccttcttc cttccctcac tcgttctctc ttgcttgctt gctttctctc   39060
ctctctctct tttctttctg ctttctttct attcttctcc ctccctctct tccttctctc   39120
ccccactccc caacttccag gctaaagcag tcctcctgag tagttaggac tacagacata   39180
```

```
cacgtgccac cgcgcccagc tccgtgttct ctttgtttcc ctgcctcctg ctcttccact   39240
tatctttgca tggcaggtgg gtgcacgcag gcatgctctg catgtcttcc tcttggccat   39300
tccccttcta gttatggtgt ggctttatct acgcgttctg gagcagaagc ctagtcacaa   39360
agctattttt ttaaaacatt catgataatt catttccttt tatgttttaa aaatactagc   39420
tttctgtctt tatttcctta ctaacttact tggatgccag taattagttg ttttagtgaa   39480
caccacagag tgatattttg aaactttgga cttcataaag ttggatgagc tccagtagca   39540
aagaaggaag tgttaactag tttaactgac aaataaatgc ttcccagctt ggtgtgcgat   39600
tgagattttt gttgcaagtt tgtgaatcaa tttaactgcc cctgccctgg ggactaaagt   39660
cagatacgtg cttgtgggaa tctttgtctt tcccacacca ccctgcattt taaaacctct   39720
tgtgtgggac agtcccacca tgtaatagct gttcttcctt actcagctac tttccctcca   39780
gagaggccag tagaaaatct agactagttt tttatagtct attttcatgt cacttattga   39840
gagctactgt tttctgttaa attgtcagta aatattttaa tcaaggaaaa gggaggcaat   39900
aggaaggaga gaagaacaaa tccttaaccc tagtaggaac ctaatgaatg ggatttgttc   39960
tggataattg cagtagtccc ccagctaaag aacctttttaa aaatatgtca gatatacccca   40020 agaggattga aatcgtatgt tcatacaaaa gcttgttcac ctgcagcctt catatgcaat   40080
tcctatgaat gttcatagca gcattattca taatagccaa agtatggatg caacccaaat   40140
gtccatgaag caattaatag gtaaacaaaa tgtgatctgt tcacacagtg gaatactaac   40200
tattcagcca taaaaggaa tgaagcactg agtcctgcag ccacacagat gaacctcaga   40260
tccatgctga gcgaaagaag ccagaaacag gaggccatgt gctgtgtgac tgtatttcta   40320
ggaaatcttg agtcaccatg ggcaagatgc tatcacctt gttcagtggc cagaagcgag   40380
ggcactaata tttaccccttg ccggggtcta ctagattgaa gcgtttccgc taggccataa   40440
acttccaaca cggtgacttg tacatgtaga tatttgatca atatatagca aatgaatatt   40500
gatttaaaca gaaaaaggca agtgagagtg cttctaaac ttagagcccct aaatatatga   40560 ggttgtggaa ttaatagatt ctgttgtgtg tgtttgaggg aatttaaaaa taatttagat   40620
gttaaacagt atattgtgga ggtgttttgt aactaattaa tgacggcact gaattgactt   40680
ctaggccttg cagtattaaa acatgtgcta acaccacgaa taaaggcaac tcacgttgct   40740
tttgattgca tgaagaatta tttagatgca atttatgatg ttacggtggt ttatgaaggg   40800
aaagacgatg gagggcagcg aagagagtca ccgaccatga cgggtaagtg tgttcacgca   40860
cctgaaatgc ctgtacacgg tatatacagt gcacatgttt atgtagaatt cagttttaca   40920
aagtaggtta agtgtacttt tttcctccat tacatttacc cggtatattt ttcaagatgt   40980
tattaagatg taacagtgga gatttcatta gtcctgcaaa gtgtggtatt tcttggctgt   41040
cgtgtgagtc ctgtggactc accaattatc attaatccag cctctttcta ctcaaagttc   41100
acacttaaaa ggaaagctct gtaaagggga ggaagacgtg aagaaggagc acgcctggca   41160
gtactgagtg cacgttatta gtcagtgctg ccctttttgct gtattttcg taaaatattt   41220 attaaatttg ggtgtcattg tgacaagaag aaatgcagtt aagtgtgacc ttttttttc   41280 cccaaacatg ttaggtttta agaacctttg agctattgtc agatataacc agaaaaaaat   41340
agaattttaa gtgagcagga taacttagtt aaactaacca aacatagtgt tagctgttag   41400
agaaatgtaa acatggaaat aggcaaacag ggaagtgtgt ggagtttctg tttccttttc   41460
aaaatatctg tttgagctgg ggttgagaga gaacactagg cttcatgggg ttttttttgtt   41520
```

-continued

| | | | | |
|---|---|---|---|---|
| tttcgttttt | tgttttgaga | caagagtttc | gctctgtcgc | ccaggctgga gtgcagtggc | 41580 |
| gcaatcttgg | ctcactgcaa | cctccgcctc | ccacgttcac | acgattctcc tgccttagcc | 41640 |
| tcctgagtag | ctggaactac | atgcgtgtgc | caccatgcat | gactaatatt tgtatttta | 41700 |
| gtagatatgg | gatttcacct | tgttggccag | gctggtctca | aactccttac ctcaggtgat | 41760 |
| ccacgcacct | cggcctccca | aatgagcttt | gtgttttac | ctcatcagct gtttggggtt | 41820 |
| gagccactat | gtatgtcagt | gtgcttgtat | cagtaggatc | tactgagggc agatgttcaa | 41880 |
| aatatgagcc | tccagcacgt | tttacatgga | accctcacc | tgaagcattc gtctgaagtt | 41940 |
| gatgtgcctt | ggaaatttta | tagagtaata | ttttaacta | caacaaaaca tttataaaag | 42000 |
| tagacattat | taaagcattc | agaagtgagc | aaggatagaa | attattctgc ccaaccttac | 42060 |
| acgtaggcct | tctagacgta | gtactgtgca | ccgttacatt | atctaacact gtctgtgtgt | 42120 |
| catctttgga | tgttagggat | ttttccaaag | ttcagtgaga | ttatagttgt caaatgatta | 42180 |
| gtctgttaaa | taatgataag | atgagggtca | ctcaggtttt | aaagaaaag ctctttgact | 42240 |
| gaaagagaga | gcagctgtct | actgcagaaa | gttaggagg | gaggctggag gagtgaggcc | 42300 |
| cagggctag | ctagtataaa | aattggttat | ggtcgaagga | aaaaaaatg taacatattt | 42360 |
| atatctgaaa | gatgattgtt | ctcataattg | tatataacac | agagtaattg taaagtagaa | 42420 |
| aactaaggtg | tttttcattt | tagatgtaaa | tgtttagaat | atgtaatgca tcagtttaaa | 42480 |
| aattaaaact | gtacgaaatg | cacagtgaaa | cgtcttcctt | gctttccacc ctgctacctg | 42540 |
| gccttcctt | ctccttccta | gcgataacca | gttttcttaa | tttgttgtgc gttgtatgtg | 42600 |
| caaatttaag | tatatcttct | tattctacca | tccctcctt | cttacagaaa agtggcatat | 42660 |
| taatattttt | ctcttttaaa | ctatcgaagg | agttacttac | ctatttttgc atttcaaaac | 42720 |
| agacagttca | tcaagattgt | cgttggttta | ttaaacatag | tttaagatta aacaagtgtt | 42780 |
| tataaccaat | gaaaacaga | tagactcccc | ataataacct | tgtttaaatg ctgctacttt | 42840 |
| tatcatgtcc | cctcctgtct | aagaacccct | tggttcagca | gagctcatgg gtaaggccag | 42900 |
| cctctgttgc | ctgccatcgg | aggaatgcgt | tccagccgtg | atctctgcct tgccttcgct | 42960 |
| tcctcctgtg | ctgtgccgtg | aagcctcggc | cgtggtgaag | ctggctgact gagtcctcct | 43020 |
| gcacccatg | catattcagt | agttgaaggc | tttgtgtggc | caatcctgct ttccacagga | 43080 |
| aaccaccctc | tcttttgttg | ccctcatcca | aggctactgt | tctcccagag tgacaggcgg | 43140 |
| cacctttccc | agcatagcac | tgtgccttct | cctgccctg | ctcttgcagt actgctgtgg | 43200 |
| cactgatggc | gtgtgttaca | gtgctggcac | ttagcacagg | gctctgcctt tctctcttcc | 43260 |
| cagccgcatc | ataagtgcct | tgaggaagcc | aaaaccttct | gtgagttgca ttgcctgggt | 43320 |
| tccaacctcc | cactgccctg | cttatcctct | gctacatgtg | agctgactgt ggctttgggg | 43380 |
| tggtcactgc | ctatgtgtat | tcattacaaa | ttgtctcctt | ttgaaagatt gacctttctg | 43440 |
| acttacccag | ataccataaa | gaaataaaa | tcttatcact | tcagtcaagg ataaagtatt | 43500 |
| tctgaattaa | aggaaaaata | caccagagta | aaatcaagac | tgaaagacaa actgggaaat | 43560 |
| tatttgcaac | ctagatcata | gaaaagggt | catttccttc | ttgcgtaaag tgcacttaca | 43620 |
| aattgataag | aagatgactg | ataactagaa | agaaaaatgg | gtaaagaaca acaatagaca | 43680 |
| tttcacattt | aacctcattc | atgataaggt | aagtgcaaat | gaaaactaca ggggatacct | 43740 |
| ttttttttt | ttaatccatt | agattggcaa | acatcccaag | gtttgatcat aggctcagtg | 43800 |
| ggtgagattt | aagtattatc | aggcattttt | atactttgct | gttaggaatg caatgtagta | 43860 |
| caaacctttg | tagaagttgc | tttggaaatg | tctctcagat | gtacaaatgc attcacattt | 43920 |

```
tagatttagc attcccgctt tctgagacat tattcaacat gtatacgtgt gcacataaga    43980
tataataata acacgttttt ccttctagtg tgttgctttt aacctgtagc ttgaaaaaac    44040
tctgctttca ttgttttttt ttgttttctg tcactggctc agccctgctt tcaattgttt    44100
atatgaattg atgggtgttc tggtctggtt ataatctact ttagtttaag agtcacttta    44160
aattatatga catctgatat aagttgtgtt aggtagaaaa ttctgtaact tggaatactg    44220
taagtacttt gtggccacat ttcattagta ttaaatatta tctctatata tagtaggcta    44280
tttaatattc atattttatg atgcaattaa gaaataattt ttttctgaag ttggtagatt    44340
gttgatatgc catggcccag tgtttctcaa agcattctgg gggatcactg tttgtcagaa    44400
ttagctgcag tgattgttga acatgcaggg cctctgctcc actccacgtt gctaccagga    44460
cgctctgcag gtgagagctg ggaagctgta gaagctgcag tgctaacaaa tgctacagga    44520
attcttgtag tcaccttcat gaggtcttat gttgaggaga ggcagccagt agtgtccctt    44580
gtccttcccg ttttatggtg taagtttcat tttaagggag gtataaatca aagcccacct    44640
gggcattctc tcatggttca ctgcttcttg taatcatgga agatgtcatt gcggcagaga    44700
cgaaacagtg tagtttgatt actattgatt ttttttttaat tattttttctg aagtggctgt    44760
tgtaatgtaa taaattgtgt gcttaaggac aacctttggt attctatttg agtattgtgt    44820
atgatcctag ttaagttttt tctaccagta ttttcatatt acaacatatt tactttccat    44880
ttctattaat atttttatat ttaaagtatg gaggccgggc acagtggctc acgcgtgtaa    44940
tcccagcatt ttgggatgct gaggcgggtg gatcacaagg tcaggagttc tagaccagcg    45000
tgaccaacac ggtgaaatcc catctctact aaaaatacaa aaattagccg ggcacagtgg    45060
taggcacctg taattccagc tactcaggag gctgaggtag gagaatcact tgaatccggg    45120
aggcagcagt tgcagtgagc taagatcgtg ccactggact ctagcctggc tgacagagca    45180
agaatccgcc taaaaaaaaa gggatcaggg aagagdggat tacagataac ccaaagaaga    45240
aggaaaaatc tccacaagtt cacctgtcca gcggtaaccc caatttggat attttccttt    45300
aacaatttgg atattttcct ttaaatcctc tttttttataa tgtctatatg ttggagagag    45360
tatgtgcctt tacgtatttt ttaaagatga gatttctgtg tgtgtctata tctcctgttc    45420
ttcatatttt cttgtgtgtt ataaacagct gtacatgtca gtatatatac ttccgtaact    45480
tttttttaaa ggctatatag tgttcattga tgtgatttaa cagcagttat ctccccggct    45540
tcatcttgtt ggaatgtggg tcctgtgtgt tgccttcaga gcaaatgggg cttggttttg    45600
cagcaagtag acctgtgacc tgtacgaata gttggaagac tttctctatt acccaagcgt    45660
atcagtatac tttagtgcct actagaaatt tatgggtaga aaaacaataa tatcttagag    45720
tatttttttcc tagattccct aaggtgctat agggtgattt ttactcatgt aacatgaact    45780
atgcttcaac taagatagtt tttgcaaatg tggatatata agtactttat taaacctata    45840
ggaagtattt ataccactta tttcctccct tcagtgttag aacctcctaa atggcatttg    45900
acattgaact gctttccact ttgtcgcatg ctcctctcat tgtccctacc tgggtcctga    45960
accttaggga cttggctgtt atagccccac catggctacg ctgggccttg gtcgtctctg    46020
agacttagtt tcttcatctt acaaggagat aataacagcc cctgcctgcg tagaattgca    46080
gagatcaaat gaaataatta acatactcaa aagcatgccg taaacacatt ctgagcacat    46140
gtacgtttta ggaaaaacaa aaggacccat gcacatttcg gagtgctttt gtctcagcag    46200
cactgcctct tcttccaaag ctgacgtctt agtagaggcc ctgccacgtc ctgagcactg    46260
```

```
tactccacga agcattctat ttctgacatt cgaaatgcag tctgttccat cttccttaca    46320
atctgtatgc cagcacttga aataccgggt atctgcagtg ttgaccaggt gattacttaa    46380
ttatggaaat gttgaggtgg agatctagat aattcagtga aggcaggaaa attggtgtcg    46440
gaatctgtct ttttatgtgt cagaaataga aataagatag ggtgagaagt aatttgtggc    46500
taaaacacta taatagctaa cacatagtgc atactgtgtg ccaagcactc ctgtaggtgc    46560
ttgaaatctt ctattattat tatccctact ttatagactt gcacccttag gcacagagag    46620
gcggacagtt gtccaaggtt accccagagg tggagatcca ggctacctga ctccaccatg    46680
tgtgctcttc cctagggcac agttgtgctg ctaaaaatac tttttaagca gttctttgat    46740
tattcagatg atagtactgt aggaaaatta agacaaaaat aatgaaaaat taaaatcttt    46800
attttagtgt tttgcacatg tattattaaa gccagtttac tcctggaagt gtgtaagaat    46860
acagggtatt tttgatcacc taaatgctgc atgttactaa gagctcgaca ctgaagtcaa    46920
gaagagcagt tgcagagagt acttagcaaa acgggaagt gtgtggggtt gaaggagcaa    46980
agacaagtct tcctcggacg gtggagtgta gaattcatca tttctcagaa cacgtctttg    47040
aacgcatttt caatttgagg ccaaaggtct cagcctccca ctcggcatac ctccctacct    47100
tagtcagctc ttaaatctta ggaatatttc tttgttcttc aaggaactta aatatgttaa    47160
cattcttacc tgtccacagg gagcccccta caaagaaggg agtttctagt ctccgttctt    47220
tcttggaata aataatagcc tcataccttg tgcaatcgag gctgaaaaag actgtctcct    47280 ttttttcaaat aagcaagtct tagaaactac agttgtttac agggctcatg gctattccac    47340
agtaataatt ttggttcttt taccaattat ataatatgtt aaaatatggc aagtatcagg    47400
aaagcaagga gtggcaatga ttagaaacca atggccaagt tagagaggag gggcaattgc    47460 tccccccaagt ttgttgtggc tgtgtagcag tcagtgacga gaagctgtgt gtcaggcgac    47520
aagcaaagtt gaggattatc aggcgcctgt gagtgcccag ctgtgtgcca ggtcaggagg    47580
tgccatcgtg agccagacca gcttcctctc ggcccctgtg gagctcgcag tctggtgggg    47640
aggcagcagt caccatggtg acaggtgaca cactaggatg gggctggtgg tggtaggcat    47700
ttgcgggtcc cttcagagag gtgagtatgg acttagagga ggctccagct tcctattcct    47760
gggctgtcta tagcactaaa agttgtcaca tgaaaaataa catttggtac tattgattta    47820
acttaatgac ttatgtaatt gtagttgact tagaaattat aacatgctct tctacttcag    47880
cttgaaaccc ccaaccacca gtttataatc cttttttttt aacttttgtt tattttttcct    47940 aaggaatctg tacttttttct tcatttaca acttttttttg tcctgttacc ttattttcat    48000
ttttacttta tatgaccatg agttctaaaa tagtaaaaaa aaagaattat ttttgttctt    48060
tgttagaatt tctctgcaaa gaatgtccaa aaattcatat tcacattgat cgtatcgaca    48120
aaaaagatgt cccagaagaa caagaacata tgagaagatg gctgcatgaa cgtttcgaaa    48180
tcaaagataa gtgagtaaca acagttccag cacttccgga acttcggttc aactagattt    48240
cagtatagtc aacaatttga aaccaatgta aatggttata ttgtctcaag aatacatttt    48300
ataaattcaa atcaaatttt atgcatgtct gatcgtgttt taaactttac ttgtacaaat    48360
cagtctaaaa gaacttgtta cagtgggccc atctacttgc attgatagta tttcttggac    48420
aatactacgt gataacatag caaattaaat taaaacaac aacaaacaca caaaaaaact    48480
ttccagtgtc agatgcccgg acctacctgt caggtcacat aaagtggtgt tactgtgtga    48540
ggtctggctg ttgggccagt gtgcgcagaa agcaagggaa ggggtagagg actatgcgga    48600
cgtgcaggtg gacatgatgc tgttatattt gttggaaata gaagggggca gttgacagcg    48660
```

```
ttatatccaa agtgtcttct gtggttaatt atattcagaa attttagcca attgttttat    48720
tctctaaata tgtactttct gctcaagaaa ctatcattgt tcttcttttc cttgttttac    48780
agtacagtgt ttttaattaa ccctcctggg ttaactttac caggtgaaaa tgattaaaag    48840
tgtaataggt taacaatgaa actttaagct tctattttc attgactctt aactgtacat     48900
gatgtaatgt attcagcgag ccattcagga ccactttggc ccatggaaga aatttaaaag    48960
taagatctac atgtattgac atgaaaatat gttctcagaa aaaagactaa tgtatttaat    49020
gtcctactta ttttataagt atttagaata cctctggaca ttttaaaaca atgattattg    49080
ctagggtgtg tgatttataa agcaatagaa gcgctttccc tttctgtttg tgttttagat    49140
tattatatcg ggtatgttct gctatcataa ctttacaaat cttatgtaat atgggaaaat    49200
gagttaacta tgctgttttc cttcttttac ctgcctttct aattctgtgg gaataaaggc    49260
gtttttgaga cagcccaggt gtagtgagca gtccatatcc atggattcca cattcatgga    49320
ttccaccaag cacagaccaa aaatactcag aaaaaaaggg ggctggctgt ggtggctcat    49380
gcatgtaatc ccagcacttt gggaggctaa ggcaggcaaa ttgcttgagc ccagaagttc    49440
aagacagcct gggcaacatg gcaaaaccct gtctctacag aaaatacaaa aattagccag    49500
gcgtgcacct gtagtcccag ctactcagga ggccgaggtg cgaggatcac ctgagcctgg    49560
aaggttgaga ctgcagtgag ctatcattgt gccaactcca gcctggtaac agagtgcctt    49620
ttttcaaaaa aaaaaaaaaa aaaggatttg gaggatatg catatgttat attcaaatac     49680
atgccatttt attcatatat cagggacttg agcatccttt gatcttggtc tctgccgggt    49740
atcctgggac cagcccctg tcgatacaga gggaccgctg tctaagaacc gctggtccta     49800
tctttgactt ctggcggaat aggagctcca tgtaaaaagg aggagaagct gcagcgggtt    49860
attagccatt tgtgagtcag gtcactgtaa aactttatca aaagtttaaa agacaaaaag    49920
catcctcata aaatgcctta aaaccacctg ttgaaatatt acatatacaa ttcatgtata    49980
ctaatcatag agcatattaa agatatttta gaagactaga aacttctatt aaaccaagtt    50040
tctggatgtt tccgtattca tccttatttt ccagggacct gcataacttt tccagcgtgt    50100
aatagctacc tgattgatat tttttgaatt gaaatactga agtgactaaa atctaaactt    50160
tttccattct ggccatagga tgcttataga attttatgag tcaccagatc cagaaagaag    50220
aaaaagattt cctgggaaaa gtgttaattc caaattaagt atcaagaaga ctttaccatc    50280
aatgttgatc ttaagtggtt tgactgcagg catgcttatg accgatgctg gaaggaagct    50340
gtatgtgaac acctggatat atggaacccct acttggctgc ctgtgggtta ctattaaagc    50400
atagacaagt agctgtctcc agacagtggg atgtgctaca ttgtctattt ttggcggctg    50460
cacatgacat caaattgttt cctgaattta ttaaggagtg taaataaagc cttgttgatt    50520
gaagattgga taatagaatt tgtgacgaaa gctgatatgc aatggtcttg ggcaaacata    50580
cctggttgta caactttagc atcggggctg ctggaagggt aaaagctaaa tggagtttct    50640
cctgctctgt ccatttccta tgaactaatg acaacttgag aaggctggga ggattgtgta    50700
ttttgcaagt cagatggctg cattttttgag cattaatttg cagcgtattt cactttttct    50760 gttatttca atttattaca acttgacagc tccaagctct tattactaaa gtatttagta     50820
tcttgcagct agttaatatt tcatcttttg cttatttcta caagtcagtg aaataaattg    50880
tatttaggaa gtgtcaggat gttcaaagga aagggtaaaa agtgttcatg gggaaaaagc    50940
tctgtttagc acatgatttt attgtattgc gttattagct gattttactc attttatatt    51000
```

```
tgcaaaataa atttctaata tttattgaaa ttgcttaatt tgcacaccct gtacacacag   51060
aaaatggtat aaaatatgag aacgaagttt aaaattgtga ctctgattca ttatagcaga   51120
actttaaatt tcccagcttt ttgaagattt aagctacgct attagtactt ccctttgtct   51180
gtgccataag tgcttgaaaa cgttaaggtt ttctgttttg ttttgttttt ttaatatcaa   51240
aagagtcggt gtgaaccttg gttggacccc aagttcacaa gattttttaag gtgatgagag   51300 cctgcagaca ttctgcctag atttactagc gtgtgccttt tgcctgcttc tcttttgattt   51360 cacagaatat tcattcagaa gtcgcgtttc tgtagtgtgg tggattccca ctgggctctg   51420
gtccttccct tggatcccgt cagtggtgct gctcagcggc ttgcacgtag acttgctagg   51480
aagaaatgca gagccagcct gtgctgccca ctttcagagt tgaactcttt aagcccttgt   51540
gagtgggctt caccagctac tgcagaggca ttttgcattt gtctgtgtca agaagttcac   51600
cttctcaagc cagtgaaata cagacttaat tcgtcatgac tgaacgaatt tgtttatttc   51660
ccattaggtt tagtggagct acacattaat atgtatcgcc ttagagcaag agctgtgttc   51720
caggaaccag atcacgattt ttagccatgg aacaatatat cccatgggag aagacctttc   51780
agtgtgaact gttctatttt tgtgttataa tttaaacttc gatttcctca tagtccttta   51840
agttgacatt tctgcttact gctactggat ttttgctgca gaaatatatc agtggcccac   51900
attaaacata ccagttggat catgataagc aaaatgaaag aaataatgat taagggaaaa   51960
ttaagtgact gtgttacact gcttctccca tgccagagaa taaactcttt caagcatcat   52020
ctttgaagag tcgtgtggtg tgaattggtt tgtgtacatt agaatgtatg cacacatcca   52080
tggacactca ggatatagtt ggcctaataa tcgggcatg ggtaaaactt atgaaaattt   52140
cctcatgctg aattgtaatt ttctcttacc tgtaaagtaa aatttagatc aattccatgt   52200
ctttgttaag tacagggatt taatatattt tgaatataat gggtatgttc taaatttgaa   52260
ctttgagagg caatactgtt ggaattatgt ggattctaac tcattttaac aaggtagcct   52320
gacctgcata agatcacttg aatgttaggt ttcatagaac tatactaatc ttctcacaaa   52380
aggtctataa aatacagtcg ttgaaaaaaa ttttgtatca aaatgttgg aaattagaa    52440 gcttctcctt aacctgtatt gatactgact tgaattattt tctaaaatta agagccgtat   52500
acctacctgt aagtcttttc acatatcatt taaacttttg tttgtattat tactgattta   52560
cagcttagtt attaattttt ctttataaga atgccgtcga tgtgcatgct tttatgtttt   52620
tcagaaaagg gtgtgtttgg atgaaagtaa aaaaaaaat aaaatctttc actgtctcta   52680
atggctgtgc tgtttaacat ttttttgaccc taaaattcac caacagtctc ccagtacata   52740
aaataggctt aatgactggc cctgcattct tcacaatatt tttccctaag ctttgagcaa   52800
agttttaaaa aaatacacta aaataatcaa aactgttaag cagtatatta gtttggttat   52860
ataaattcat ctgcaatta taagatgcat ggccgatgtt aatttgcttg gcaattctgt   52920
aatcattaag tgatctcagt gaaacatgtc aaatgcctta aattaactaa gttggtgaat   52980
aaaagtgccg atctggctaa ctcttacacc atacatactg atagttttttc atatgtttca   53040 tttccatgtg attttaaaa tttagagtgg caacaatttt gcttaatatg ggttacataa    53100
gctttatttt ttcctttgtt cataattata ttctttgaat aggtctgtgt caatcaagtg   53160
atctaactag actgatcata gatagaagga aataaggcca agttcaagac cagcctgggc   53220
aacatatcga gaacctgtct acaaaaaaat taaaaaaaat tagccaggca tggtggcgta   53280
cactgagtag tttgtcccag ctactcggga gggtgaggtg ggaggatcgc ttcagcccag   53340
gaggttgaga ttgcagtgag ccatggacat accactgcac tacagcctag gtaacagcac   53400
```

-continued

```
gagaccccaa ctcttagaaa atgaaaagga aatatagaaa tataaaattt gcttattata   53460
gacacacagt aactcccaga tatgtaccac aaaaaatgtg aaaagagaga gaaatgtcta   53520
ccaaagcagt attttgtgtg tataattgca agcgcatagt aaaataattt taaccttaat   53580 ttgttttag tagtgtttag attgaagatt gagtgaaata ttttcttggc agatattccg    53640
tatctggtgg aaagctacaa tgcaatgtcg ttgtagtttt gcatggcttg ctttataaac   53700 aagattttt ctccctcctt ttgggccagt tttcattacg agtaactcac acttttgat    53760 taaagaactt gaaattacgt tatcacttag tataattgac attatataga gactatgtaa   53820
catgcaatca ttagaatcaa aattagtact ttggtcaaaa tatttacaac attcacatac   53880
ttgtcaaata ttcatgtaat taactgaatt taaaaccttc aactattatg aagtgctcgt   53940
ctgtacaatc gctaatttac tcagtttaga gtagctacaa ctcttcgata ctatcatcaa   54000
tatttgacat cttttccaat ttgtgtatga aagtaaatc tattcctgta gcaactgggg    54060
agtcatatat gaggtcaaag acatatacct tgttattata atatgtatac tataataata   54120
gctggttatc ctgagcaggg gaaaaggtta ttttaggaa aaccacttca aatagaaagc    54180
tgaagtactt ctaatatact gagggaagta taatatgtgg aacaaactct caacaaaatg   54240
tttattgatg ttgatgaaac agatcagttt ttccatccgg attattattg gttcatgatt   54300
ttatatgtga atatgtaaga tatgttctgc aatttataa atgttcatgt ctttttttaa    54360
aaaaggtgct attgaaattc tgtgtctcca gcaggcaaga atacttgact aactcttttt   54420
gtctctttat ggtattttca gaataaagtc tgacttgtgt ttttgagatt attggtgcct   54480
cattaattca gcaataaagg aaaatatgca tctcaaaaat tggtgataaa aagttatttc   54540
ttgtatatgt gataaagttt acatgttgtg tatatatgtt gtattgccaa atacggctat   54600
taaatactac gtcatatttt aaaggttcag tttgtagtga tagtaaacaa gcagtgcact   54660
aagcctcttg cgggcatcat ctcatctcac tgtcatcaca aaccccatgc cacagcgtag   54720
cttgaccact aaaagtaatg catctgcaag catactgcca ggttttggat agtttgtacc   54780
aacagttacc ttatcaaggt aaatcccaga ctctaaaaga gttggtgctg tgtcactaca   54840
tgcataactt taaataaatt tcctgccggg cgcggtggct cacgcctgta atcccagcag   54900
tttgggaggc cgaggcaagt ggatcacttg aggtcaggag tttgagacca gcctggccaa   54960
cgtggtgaaa ccctgtctct actaaaaata caaaaattag ccaggcgtgt ggtggcaggc   55020
acctgtaatc ccagctactt gggaggatga ggcaggagaa tcatttgaat cctgcaggcg   55080
gaggttgcag tgagccaaga tggcgtcatt gcactccagc ctgggcgaca agagcgagac   55140
tccgtattaa aaaaaaaaa aaaaaaaaa aaaaattcct ctcctgtttg agctttccct   55200
tacctgtaaa gagggagaa tatgtattta cttcaaagag ttcagggaaa tgactctcac   55260
tagtttgaga ttctaggtat aaaaatacat tcttatataa ttttaacacc aatgtgagag   55320
attattattc ttgctaaacc aattcagttt tatttgctgt ctaaaatgtg tgaataagta   55380
attgtccatt attttctgaa gtgttttgga actcaacaca tgattgtgag gaggatttgt   55440
tgctaaacat ctttctggtt attcaagctc gtgtatactg tgctctgttg agacatgcag   55500
agttactttc tgtctgggtc acaggtcagt tcttgatagt tttcggacaa ttaaccagtt   55560
ttcatttgcc catgaccacc tttattcttt ttcctcaact gcacccatct tttataaggt   55620 cttcagttt attgcagaga agatggtgga gaaaagccgg aattcccacc caccgctgcc   55680
atccccatgt tttatcattg gctagagtgg aaaatagcag taactactgt gagagatcat   55740
```

-continued

| | |
|---|---|
| ttgtttatat aatggaaaca aagatgagga aagaacctgg cttagatcag agaactgatg | 55800 |
| tatttagatt cttttttttt tttttttttaa gacggagtgt tgctctgttg cccagactgg | 55860 |
| agtacagtgg ctcaatctcg gctcactgca acctccattt ccctggttca agcaattatc | 55920 |
| ctgcctcagc ctcccaagta tttgggatta caggcgtgtt ccaccacacc tggctaattt | 55980 |
| tttgtattt tagtagagac ggggtttcgc catgttggcc aggctggtct cgaaatcctg | 56040 |
| acctcagatg atccacccgc cttggcctcc caaagtgctg ggattacagg cgcgagccac | 56100 |
| cgcgcctggc ccaatgtatt tggattctta agaacactt tcaaattaaa tatcagttga | 56160 |
| agagaactag aactaaagaa tttctgtgtc aaactgttta gcaaatgtaa gtagaagctg | 56220 |
| ggagatgtgt cctggaatga atgaatacat cagtaaaata ccatacgtat gttatgatgt | 56280 |
| tattgtttcc ttgccttggt tgatttggtt ttactgtgaa ataattttca atatagaatt | 56340 |
| gtgatcgttg gaatttggtc atctactaga aaatgagaaa gaagttaata gctatcttcc | 56400 |
| ttaaagattt ctgaggttgg gattaagta gtgttcccaa ggtgttctaa aacggcagcg | 56460 |
| agagctgtgc actcacttca caaatttgaa ttcctgctct gtgttaggcg ctgtgctagg | 56520 |

<210> SEQ ID NO 180
<211> LENGTH: 2000
<212> TYPE: DNA
<213> ORGANISM: Homo sapiens

<400> SEQUENCE: 180

| | |
|---|---|
| gtggatctgt gactgttcgc aggaagagag gagcgggagc aggacagaca ataactgata | 60 |
| gtcaggagct gggtttggag ataaagaggg aacaagagaa agttaagttc tgtgttttca | 120 |
| tggcaaacat tgcacaaaag tttacaactt cgtgactaac agtaatctgg ggtgattcac | 180 |
| aacaaattta cacataaaca catatttact gactttatac acagcaatcc taacgtgaac | 240 |
| acagaacctg ctttatcttt tcgcacactg ttctagtgta gagatgtctg gtctcagtta | 300 |
| aagaaagcat aaggagcatt agttgtgcac actgtccaca cccgtgactt ttttccacca | 360 |
| gtactaaacc tagtgcttct tacagtacag ggcaatgaca gccacagaaa gagagaagct | 420 |
| cctttactg tgtaatgctt cctgctggcc ttcaaatact tgttacttga gagatctcca | 480 |
| ttcacctggc tttgtcccca aggtcatca tctaccaatg atgttgttat ttgatgttaa | 540 |
| tcatgtataa agaaagtagc taccatcctg gccctgatta gaacttccca ctgaaatacc | 600 |
| gtcctgccta aggtagcac aggtttccat tatggtggtg gtggggaggg ggcgggaata | 660 |
| tatatatata tatatatata tatatatatg gtaaagcatt cggcattctt ttaaagtaca | 720 |
| actatccttg aaaagggtta catattaaac catttttacc acagccaaag gggaggagaa | 780 |
| agatccaaaa gtcctgtgga tctgctttaa catcaataaa acagttatcc acccttcgta | 840 |
| gcttttagtg aaggctacaa aagtatgctt tttatggatt acacatgtgc acgcaactac | 900 |
| tttaattact acagaaaaaa acgaggctcc ttattaaaaa aaaatcagaa acaagtccaa | 960 |
| cagactctga ggaaatgaag caagagtgaa ttctgaaaag gtctaataaa cagtatgaaa | 1020 |
| atatccttgt gggattgttc ttcagctatg cataaacatg taattatcat cattactgtg | 1080 |
| atggggaaaa acacggaccc taattctgaa acaccctggt agcgagagac gggcaggagg | 1140 |
| ggctgctgcg cactcagagc ggaggctgag gaggcggcgt ccccttgcaa aggactggca | 1200 |
| gtgagcagat ggggacactc gagctgcccc gcgacctggg ccgagctgcc tacaacctgg | 1260 |
| gcccaggtgc ctgcaagaat tagacctccg ataacgttaa cacccacttt ctcactgctc | 1320 |
| taattgtgtg catcccggcg cccagggggct tgtgagcagc aggtgcgcgt tccaggcagc | 1380 |

```
tccagcgacc cttaaacctg accgcgcgca cgtccggccc gagggagcag aacaagaggc    1440
acccggaccc tcctccggcc agcacccacc ttcacccagt tccgtcagtc gccaccacct    1500
cccttcccgc gtccgcagcc ggcccagctg gggagcatgc gcagtggccg gagccgggtt    1560
gcccgcgcca cagcaggtag ctgtactgca actgtcggcc caaaccaacc aatcaagaga    1620
cgtgttattg ccgccgaggt ggaactatgg caacgggcga ccaatcagaa ggcgcgttgt    1680
tgccgcggag cccctgccc cggcagggg atgtggcgat gggtgagggt catgggtgt     1740 gagcatccct gagccatcga tccgggaggg ccgcggggttc ccttgctttg ccgccgggag   1800
cggcgcacgc agccccgcac tcgcctaccc ggccccgggc ggcggcgcgg cccatgcggc   1860
tgggggcgga ggctgggagc gggtggcggg cgcggcggcc cgggcccggg cggtgattgg   1920
ccgcctgctg ccgcgactg aggcccggga ggcgggcggg gagcgcaggc ggagctcgct    1980
gccgccgagc tgagaagatg                                               2000

<210> SEQ ID NO 181
<211> LENGTH: 1901
<212> TYPE: DNA
<213> ORGANISM: Homo sapiens

<400> SEQUENCE: 181
taaaggttca gtttgtagtg atagtaaaca agcagtgcac taagcctctt gcgggcatca     60
tctcatctca ctgtcatcac aaacccccatg ccacagcgta gcttgaccac taaaagtaat   120
gcatctgcaa gcatactgcc aggttttgga tagtttgtac caacagttac cttatcaagg    180
taaatcccag actctaaaag agttggtgct gtgtcactac atgcataact ttaaataaat    240
ttcctgccgg gcgcggtggc tcacgcctgt aatcccagca gtttgggagg ccgaggcaag    300
tggatcactt gaggtcagga gtttgagacc agcctggcca acgtggtgaa accctgtctc    360
tactaaaaat acaaaaatta gccaggcgtg tggtggcagg cacctgtaat cccagctact    420
tgggaggatg aggcaggaga atcatttgaa tcctgcaggc ggaggttgca gtgagccaag    480
atggcgtcat tgcactccag cctgggcgac aagagcgaga ctccgtatta aaaaaaaaaa    540
aaaaaaaaaa aaaaaattcc tctcctgttt gagctttccc ttacctgtaa agaggggaga    600
atatgtattt acttcaaaga gttcagggaa atgactctca ctagtttgag attctaggta    660
taaaaataca ttcttatata attttaacac caatgtgaga gattattatt cttgctaaac    720
caattcagtt ttatttgctg tctaaaatgt gtgaataagt aattgtccat tatttttctga   780 agtgttttgg aactcaacac atgattgtga ggaggatttg ttgctaaaca tcttttctggt   840 tattcaagct cgtgtatact gtgctctgtt gagacatgca gagttacttt ctgtctgggt    900
cacaggtcag ttcttgatag ttttcggaca attaaccagt tttcatttgc ccatgaccac    960
ctttattctt tttcctcaac tgcacccatc ttttataagg tctttcagtt tattgcagag   1020
aagatggtgg agaaaagccg gaattccccac ccaccgctgc catccccatg ttttatcatt   1080
ggctagagtg gaaaatagca gtaactactg tgagagatca tttgttttata taatggaaac   1140 aaagatgagg aaagaaacctg gcttagatca gagaactgat gtatttagat tctttttttt   1200 tttttttta agacggagtg ttgctctgtt gcccagactg gagtacagtg gctcaatctc    1260
ggctcactgc aacctccatt tccctggttc aagcaattat cctgcctcag cctcccaagt   1320
atttgggatt acaggcgtgt tccaccacac ctggctaatt ttttgtattt ttagtagaga   1380 cgggtttcg ccatgttggc caggctggtc tcgaaatcct gacctcagat gatccacccg    1440
```

-continued

```
ccttggcctc ccaaagtgct gggattacag gcgcgagcca ccgcgcctgg cccaatgtat     1500
ttggattctt aaagaacact tcaaattaa atatcagttg aagagaacta gaactaaaga      1560
atttctgtgt caaactgttt agcaaatgta agtagaagct gggagatgtg tcctggaatg     1620
aatgaataca tcagtaaaat accatacgta tgttatgatg ttattgtttc cttgccttgg     1680
ttgatttggt tttactgtga ataattttc aatatagaat tgtgatcgtt ggaatttggt      1740
catctactag aaaatgagaa agaagttaat agctatcttc cttaaagatt tctgaggttg     1800
ggattaaggt agtgttccca agtgttcta aaacggcagc gagagctgtg cactcacttc      1860
acaaatttga attcctgctc tgtgttaggc gctgtgctag g                         1901

<210> SEQ ID NO 182
<211> LENGTH: 4550
<212> TYPE: DNA
<213> ORGANISM: Mus musculus
<220> FEATURE:
<221> NAME/KEY: exon
<222> LOCATION: 2259..2488
<223> OTHER INFORMATION: exon1

<400> SEQUENCE: 182
tacagctatc tgtgtgtatg ggtgcatgcc atggaccacc tgtagaggtc acaggacaat       60
ctccaattca ctttctcctt ccaccacatg ggctctgtaa tcactaaggt ttgtcaatcc      120
tgagtacaga tgttcagaac catcttactg tctcctctct tctgataaaa catgaggtgg      180
ccccagagac gttttagaca gggttataat ctgataaggg aaaagccaca tgtcctttcc      240
ttacaaatgt aatttctaca gacattccta gaaaattgaa actttatggt tgggaaagga      300 gaggggccc tcaggtacct tgttttctg ttgacaaaag ttgactctta acattgtcaa        360
gtaaatgctc ccacaaatgg atcatctgac tatttgcaga atgtcatagg ccaacagaga      420
gagaacccct gaatttccag agaccttcag gttggctcag tcccttcttt tttgatgtgt      480
acctcaattc ctgtcttcct gaactcttgt ttgccaatct gaatctacag tctatctgtc      540
aaacaattcc tttgtctgga ctggtctgct gaactgacag tgaattgtct tgacagttcc      600
tttgcctgcc cttttaccte tgcatcttca ttaaactgga cagtttgtca tatctgtgac     660
ccaccaacag ctgcttttcc cctaaagctg ggtttgtggt tcatgttatc gtgacagaca     720
ctcttatagc cctgtcagtt ctccagcact ggcttcccaa ggcttttaaa actccttct      780 tctttctaac tcttttgtagt cactgtaacc tatatatgca tatgtaaaca gagatatact    840
tacagagtga tgtatgtgtg atctgagagt taatattagt aattaagact gcaataaaag     900
aacctgtgtt tcccttagca agggctacag agtaaagtgg gcctctctgg tgccagcgaa     960
gccactgtac ttagtgaaat ttattgtcat tcaatacatt ctgatatcgt gtaaactcct     1020
aagcacgtcc atctgacata gtgtgctaat gacaggagtc acctgtatgc cttatgaagc     1080
gcatctcaga ggtgatggga agaaacatg gggcaaaaga tgaagggaaa tccaaggcaa      1140
ggaagcagag acacaggcgt cagtggtgtg gaaagggaga aaactagggg cagaataagt     1200
gaccttaggg tcacttagag aaaccaacac acacacacac acccacatat ttaaaacgta     1260
ctttatacag atctgagcgt gcgcactgac ctgtttcctt ctataccttc ttgtatagaa     1320
ttatctggtc tccactagtt agggcagtga aaggacctgg gcccctggat aagttttgc      1380 tgttacttaa ctattctagt tttctggagg gaagagaact tatggatcct acatgtatag     1440
ggaaatactt tcctacacat tgaaagaag aaatgtagga tattaggaaa acgcacagta     1500
gaaacaagtt aaagagcaag aggttattaa agggcaaaag ttaaggcttt gaaagattta     1560
```

-continued

```
atacaaggag gtgacagtcc cgtgaaaggt gaaccaaggg tacaggagac ggacccagcc    1620
tcattctgca acagccaaga ggagggaagg tgtgcttcct atgcacgtgg gggcacgggt    1680
ggccctccgg cacgcgaaga cgctgcagtt gtccataacc tgcggcatcg agctcctcct    1740
gtgctccacg acttagtcgg ctcacgcgtg tcttgcagga agcatcctcg tgtctccacg    1800
cagctctcgc acgccagcac aggccaaaac ccaccacctc acttcttccc gggctcatcc    1860
ccagccagca ttcgcagtcg agcatgcgtg gtgacgaggc caagggaccg agccaatcag    1920
aacacgtatt acgcccataa gtcggccaat caggaggcgc cttattaccc gggagccttg    1980
cttcaccccg cctccccgct gacaagcacg ggtcgcgcgg agcaaagcga gcaccccgag    2040
gcgagtgcgc ccggcaagcc gaggcgtgcc ctttccaagg cggcgagcag aggccgtcac    2100
tgtccccgcc gggtcccggg cccccgcggc ccatgctggg ggcggagcca gggcggaggg    2160
cggcggcgcg gccggccccg cgcagtgatt ggcgggcggc cggcggtggc tgaggtcctg    2220
gtggccgcgc gggcaacgca ggcggagtcg cggctggcga gccgagagga tgctgctgtc    2280
cctggtgctc cacacgtact ctatgcgcta cctgctcccc agcgtcctgt tgctgggctc    2340
ggcgcccacc tacctgctgg cctggacgct gtggcgggtg ctctccgcgc tgatgcccgc    2400
ccgcctgtac cagcgcgtgg acgaccggct ttactgcgtc taccagaaca tggtgctctt    2460
cttcttcgag aactacaccg gggtccaggt gaggcgcggc cgcgcagggc tgcgtgcgag    2520
ccctccccgc ggccggggcg cgcttcaa cccgggcgaa cactcgcagc ccggcgagca    2580
cgtgccgcag ctcacggcct cccgccgcgg ggggaagttt ctggttctca cttcggggtt    2640
ccttctggaa cgtcctgctg aggctgagtg tgttcccggg tccgcccac ccccgccccg    2700
ggccggctgt tactgcccat ctcagtgcct gccaaagtag ggcactgagt ccgaggtggt    2760
gatgctggga ctggcttcat ttgcacttcc gaggtctttt agattagcaa gacctctagg    2820
cgctgaccaa agtgacagct gtgaaggacg actcctgcct tgggttcctc ccgggtgaaa    2880
gcgagggcct agggaggaaa tgaatacatt ggttacaata ggagcctcac tgtcgataca    2940
gttctcttca gcttggactg ggcttcaatg tgggctgatc tcttgtcaga ttgctttctt    3000
cctgctactg tttctttctt tctttccanc cctccctccc ccccccccc cgccccgtgg    3060
agattgaact ctgaaaacaa taaagagtag aaagctctcc taatgtgaat tcgttatatg    3120
acatcccata aaaacctaca gttgtacttc cttttggtt ttcagtttca agaagagct    3180
ctgtttgggt tctcccagat gtatctatga ctttccccc catttctcag ttcttttcat    3240
tctgtgttag gggggtactt tggcgactgg atcccttact gagttttgcg ccagttggag    3300
attatgtctg aggtagggaa ttaagacctc tctgaatcac tatcttttta aatgttttcc    3360
tagggaatag gaaatcact gttgcacatc aaggtttctg aaaaattgac ttttagaata    3420
ggatttcatt cagaattttt aggaaccccc acactgatgt tttcaaacct ccctcttact    3480
ttactaagtt tgtcaagtga atgtatggtc taatcgtgga taagtattta atttcactag    3540
cagaagggac aagacagcgg ggagcacaac ttaaagttgc tgaccttgca catgacaagt    3600
accctcaga cgctcaggga cctctactca agtgccacct atattcttgc tgcagagacg    3660
ttaggatgag tcgaatgaa gcaaagttag tgagtttatt gattgggaga gaggacacgc    3720
acttgagggg agtcaagtgc aaaccttatt acccccacc caggctacag cagctgtttt    3780
ctaagtgatt ttagggcttt taagttaacg ccttaaaact aagattaagg agaagagaag    3840
gaaaaaatg agttcttcta ttctttccaa taatgagctc taaaaaaaa agaagcaaac    3900
```

-continued

```
caggatctca cactgtagtc ttggtgggca ggaactctat gtagacctca caggcctcaa    3960
gttcacagag atctgcctgc ctctgtctcc agagtgttag gactaaaggc atgtaccgcc    4020
atgtctggat taaactcttt tagttatatg aaatttaaaa cggattcatg gcggtactga    4080
acagtttaca tatgagggag aaatgtggtt aggcagtaat atggatcaaa ataaaatcaa    4140
agtaattagc tgatcactgg tcacaagagt ttgagatgtg agcttgtctt ctgccttagg    4200
tcaccagcta tagggataat cttttgtttg tttttttgtg ttttgtttg tttgtttttt    4260 tgttttttg agacagggtt tctctgtgta gtcctggctg tcctggaact cactctgtag    4320
gccaggctgg cctcgaactc agaactccac ctgcctctgc ctcccaagtg ctgggatgaa    4380
aggcgtgcgc caccacttgc ctataatctt acttgtaatg gttttagaat atgtgcacag    4440
tggagagcag tgttcaagca gctgtatcca accaattnca cttaaagagg gagagggtga    4500
gggtgagggc ctccttttgc tattcaaaag cagattgtgt ggacattgca                4550
```

```
<210> SEQ ID NO 183
<211> LENGTH: 37950
<212> TYPE: DNA
<213> ORGANISM: Mus musculus
<220> FEATURE:
<221> NAME/KEY: exon
<222> LOCATION: 5259..5328
<223> OTHER INFORMATION: exon2
<220> FEATURE:
<221> NAME/KEY: exon
<222> LOCATION: 12675..12791
<223> OTHER INFORMATION: exon3
<220> FEATURE:
<221> NAME/KEY: exon
<222> LOCATION: 14621..14710
<223> OTHER INFORMATION: exon4
<220> FEATURE:
<221> NAME/KEY: exon
<222> LOCATION: 19822..19912
<223> OTHER INFORMATION: exon5
<220> FEATURE:
<221> NAME/KEY: exon
<222> LOCATION: 21789..21950
<223> OTHER INFORMATION: exon6
<220> FEATURE:
<221> NAME/KEY: exon
<222> LOCATION: 23387..23510
<223> OTHER INFORMATION: exon7
<220> FEATURE:
<221> NAME/KEY: exon
<222> LOCATION: 25520..26016
<223> OTHER INFORMATION: exon8

<400> SEQUENCE: 183
tggagtgaga ggcctgggta taattccttt ttctttgtca cactgtagca gttctgcttc     60
tcagcctcag ttgagactgg aatacatttg tcatgctgtt ctgaagactt taatggttga    120
tctttactgt caccttgact ggatttagaa tcgccttgga gatgtgctta tggtatgtct    180
gggaggatgt ttccagaaag tgtttactga aggtgtcctc atctgatagg gtgggccct    240 ggactcaata aaaaccggca tttatctgtt tcctgtccag ggacacagtg tggccagcta    300
cttcacactc ttgctgcctt cctacatcga aagactgtat cttttcttaa aaggcgaggc    360
aaaataaatc cccaccccca ggattttttt tggctgtcct ggaactcagg tccacctgca    420
tctgcctcct gagtgctggg tctacaggag tacccaccag gcctggctaa agaaaccct    480 tcttaaattg ctcctgtcag acactttgac acaacaataa gaaaataat tcatacaaag    540 accaagtgag ataatatgtt atttttttag ttcatagagt agtaggtaat ccatggtgag    600
ggaaaaaaaa aaaanaaacc cttttgaaat aaggacagta ttgagaaaca tgtatgctga    660
```

```
ttgtatgagt tttgtgatat gtaagtttct actcaattca catggtaatt gtgcattctg    720
atcattaatc aaataattgt gtttactact ttaaccttct tacaaagtat agttttacta    780
attagtaatt tagtaaattt attatttatt taatgaaaca tttcaaattg gactcagaaa    840
aagaccacag tttttgtaca tattatagta gaagtccctt agtaggtgga aatcctgtgt    900
ttctttacaa ggatatgtct agaacacgtt aaacaaacag gaggaggtgt ggctgcaccc    960
gttaggctaa ccagtcaaca tgccttttaa agccatacgt gttgtgtgtg agcatttttt   1020
taaatatata gaaaatcccc aaaatagcta gtataataag cacacatgcc agtaagcctc   1080
ttattactgt aaaatactgt gtaatacttt gtgcgttctt ttatgtgact gcagtaggtc   1140
tgtttacatc agcatttacc catacaaggt ggctactgtc attcaggcct ggaaagttt    1200 tcagcttctt tgaaacttgt ggggttactt ctccagttgt atgtgctgtc catggttggc   1260
tagacatggc acatgactgg cgcatggacc taaagacaga ttaaagaatt catttcaaat   1320
gatttcaagc acagagttta aattgtacat gcactcttag tcaatgtcct tgtagctgca   1380
ttttggtgta attggaggga catggactag ttagctgttt cttttacttg atgacagttt   1440
tgaatgaaaa gcatgttaga tacaaaataa tttaactgtt gaccccccccc cacacacaca   1500 cacacactct ttttccctgt atgccttcac tcctcgaatt ggttttatc anatagctgt    1560 tccaggtgta ccaggcatat atgaagtagt ttatgtagtt tcatttatgc cagtgcaatc   1620
ctgtgaggag caattagtac attatacttt atagttaatg agatagatat agagaaagct   1680
gatacatcac atctatttct tgtgtaagat ggagggctgg gattcaaatg taagtcttag   1740
tccgtgtctt atactttgca gcctgtggtc ttagtgatga tcatgttatg aagggcaacc   1800
tctttttcag actgtgtctg caagacccgt gaattaaatg accaaaggca tactaactgt   1860
agagaaactg cccatttat  tgatgctaat attttacat ggtaggagga aacttggaag   1920
aaatgagaag ccctactcag ggggattttt caggtgagat tatgtagtga ctagtgtaaa   1980
agaagctact ataagggata ccaagtatgg gaaataagtg ctgcacacct cagggtggtc   2040
acacagactc agactgacag ctcaggtctt cctgctgaag aaggggacgt ctttgaaagt   2100
gagaaattca tgtcttcttt atagaaagtt ctactccagc tctaggccga agactggggg   2160
cagagagctt ttcttgtgcc tgcgatttct taactgtttt tattcaaaat cattcttatg   2220
ccaaaagggc atatttgggg ttgagttctt tcagcgatat catttatatt tgagaccaat   2280
gagacgtttt tctcactatg tattgtattt caactttcat gctaaaccta ctggacttta   2340
ctgagataaa tcaagaacat acctttaaac tttgtagttc ttctttgcca ctgtgaccaa   2400
aacacatgac tgggagaaat ggtttatttt gcctcccagt cttggtgatt ttagtccctc   2460
acagcagaga agcctggtag agcagctcac tgagtggcaa caggactgtg ctcatgtgat   2520
catggaccag gaagtgtaga acaaagccag aactaggggc cctagtaacc tacttctgcc   2580
agctaggccc cacttcctga aggttccacc tcctccctcc ccctcccaaa aagaaaata    2640 aaatagtac caccaactgg acagcaaaca ccccaaacat aagccagtga ggagggaagg   2700
agggaggggg gaggaaggag ggagagaggg gggaaggaga aggagagaga gaaggagaga   2760
gagagggagg gagggagaga gagagagaga gagagagaga acacaccanc tctcaagtat   2820
nnnncntnna nnncntggaa caaattaaaa actatgtaac cagaaaatta ttttaagagt   2880
atttgatttg tctgtatttta attaattaac tgaaaaaaaa aggaaaatta attcctttct   2940
ctaaagactt taaatgaacc atttttttag tgtatgtgtg tgtgtgtcta ggtcaaaaga   3000
```

```
caggtctcag gagttgatat ttgaccatgt gaaccctagg gatcgaactt ttagctcatc    3060
agctttggca gcaggaatct ttatacactg catcatctca ctggccttag ataagttttg    3120
aaaaaaagtg gaagaatcta aagttacttg gataattata taaaatataa gtctgaggtt    3180
gggctcaaga cggaaagaca tcagtaagga gccaagagaa cagcccagag agaatctga     3240 gaatcaaggg tgtgggcaaa catacagtga tctacacttt ttatctgtaa atagtttgta    3300
aattcttaac cctttaaaaa aattccctaa cccctactct gcagatcaga ctgccctgga    3360
actcattgta gaagcctaag gtggcctcgc attcacacaa tccttctgac acagctcccc    3420
aagtgctagg attacaagga taagctactg tgtctgcctt cttagctttt taaattttaa    3480
aagcactaca accttgtaac tagttttata cttgtcaata aaataacagt aactgggact    3540
ggggagatgg ctcaggctgc ttttccagag ggacccaggt tcgattccca ggagccacac    3600
aatggcttac aatcatctgt agctatagtt cccagggatc tgatgccctt ttctgattcc    3660
tgcaggcccc aggcaagcat ggggtgtaca acacacatg caggcaaaac agatgtcttt     3720
ctgcattgct cttcaccttt tatattgagg caaggtctct cacttgaacc cagatctcac    3780
tgattggcta gtgtaactaa ctggcttgct caaggaatcc ctgtctacac ttcactaaag    3840
ctcttgctgt gtagcccagg ctagcctcaa attcctaatc ctcctgcttt agccacttaa    3900
gtgtccggga tttcaggcat gcaccactac atctggttga aaggtatctt tggatggttt    3960
gggtattatt agcttggagg ctagcgatgt ctccaaagaa ccttacataa tttacatatg    4020
catacataca tacatacata aacatacata catacacaca tgcatacatt taactggatc    4080
tgtagttctt gtaaagtgta cccagtggtc cttaaatagt tctactttat ttctaagagt    4140
gatcatgatc atgagctggc atcccaatat taactctgca cagatcaact aaccattggt    4200
tacttatttg tttgatttat gtcgtttgta aacttgatta gaagtaatta gacacgtgtg    4260
aacacactgt gcagttgtct tagagcagta gcagcagcct tagtgtgagt ccttgacatc    4320
taactttata ttatgtagct acattgcttt tacacagggc ttattaatgc cctttcaggt    4380
tttgttatca ttatggtatt tgtgagtatt tcaccaccag gaaggcaaac ctttctggca    4440
tagtagactc caaagcgttc actaacttat gcataattct tagtgacaaa gtataagaac    4500
aactgctaag taaagtgat ccaaaggaag ggaacagatg agcaacagca gtcatttgct      4560
cccttcaagt cccttttctaa tcactggata cttaacactt acaaaacaga acagtacagt    4620
gaaaacctgg cctcgtccct tggtttaaaa acagagtgta gccaggaggg tacagtggca    4680
catgatgtag tgaccctgac ttgatgttcc agctcacagg gacctctggc ctccctgttg    4740
tactcccctg gctccttagc ctgcattttt gttcagcaca caagtggact aacacaagac    4800
tccagcacac agctttcatt tggtcttatg ctcagaaacc ctttcctctc atttgctaaa    4860
atatatccaa cggacacagt agctctccat tttacaaatc cttaaaatat agagtatgtt    4920
cataatattt gcgttatttc ccattatgtt attatgtata tgtccatctc ttccgctgga    4980
ctgtagagcc ttatatatta ttagtgatca ataacttctt gtggattttt cttacaggga    5040
tatcaatcat tctgtcttac tttatgatca ttaacctgtc ctacatttaa gtactttata    5100
agtatgagct atttatagtg tgtggggctc ccaagagaac tctgatgttt gttagtcatg    5160
gatagagcta gttacattgt gtccttgtct gtttcctttc acattctttt tttttttta    5220 attgtcaaag tcatgattct ttttgttttc tcttttagat attgctatat ggagatttgc    5280
caaaaaataa agaaaatgta atatatctag cgaatcatca aagcacaggt ttgtatttca    5340
tttgatgaaa tttgggtttt tctagaaatg gtaaatgagc attaatatgt acacacacat    5400
```

```
acacacaaac acacatatgt acacacacat atgttttaaa gacaggattt catgtgaccc    5460
agaatggcct catactctct gagtagctga gaatgatttt aagcttgtga cacacctgcc    5520
ttcatctcca aggtacagga attgcaggtg ctttctttgt atgcttagct tatgtggtgc    5580
tgggcatcaa acccaaggct tcatgcaaac taggcaagca ctgtcccatc tgagctacat    5640
ccccagccca tcaaaatgat attttaaggt tatttattta atgagttta tcacgtgtgt     5700 gtgtatctgt ctgtgggttt gagcttgtga gtacacatgc ctgtggaggc cagaagaaga    5760
acaccagatc ttccctggag cttgagttgc aggtagcgat tagttatcct ggatggatt     5820 ggggaactaa actggggtgc tttgaaagag aaatatgtac tcttaactgc tgggctttgt    5880
ctccagcctt taaaatatta atcttatata tttaagtaaa ctaagctagc ttttgttttt    5940
aacataaatt tgctgtggat tttgaatctg gcttgcaatt ttattttact tttttggtgg    6000
ggagggtaag gttagtaatg tgaaaggtat ggttttttgtc caggcttctc ttcttcccta   6060
tttctcaaaa taaccctta gtttatttgg ttttctgtct ctacgttata ttttctagaa     6120
tatatatata tatatacaca cacacacaca cacacatata tatacatata tatatacaca    6180
cacacatata tagtgggatt ggtggaccca agtgtataca ttttaattct taattctaca    6240
tctagcnttt tatttactct gagacatatt cttgctctgt tgcccaggct ggactcaaac    6300
tcaaaattct cctgcctccg tctctggagt gatggatcac agttgtatgc tgccactgtt    6360
tgcactctaa ctgtgtagtt gttaagctgc ttattggtat gctggtgtct gactgctcat    6420
ttcctggaca cagtgctgtt ataattagct gtagttcctg ttgctcttta atcctggtag    6480
cttaattcta acttgctatt tttccgtcag agaaggcaca agactagttt ccagtataga    6540
actgtattta cttccaatca ggtcaaatat atatatattt gtttgtttgt ttgtttgttt    6600
tgttttgttt tgtttgtttg tttttgagac agggtttctc tgtatagccc tggctgtcct    6660
ggaactcact ctgtagacca gactgacctc gaactcagaa atccacctgc ctctgcctcc    6720
tgagtgctgg gattaaaggc gtgcgccacc atgcccggcg ggtcaaatat ttaaaactac    6780
ctctttttga atgattattg atgaattgtg aattatgctg ctagtcctgc ggtcccttca    6840
tgagggtcct ccccatgagg cacctcacag gtacagggcc cagccaagag gccaaatgat    6900
tgcctaaagt gtgctttcat tctccaaata attcacctca tccaaaatcc cacttcctat    6960
attttctaaa ccacggccac gttgtgtgca tccgttctat ggttcgtttg attgcttttga   7020 caagctcagg acctagcatc ccaaagctaa cagaacccaa ccgttaggat attctgaatg    7080
gaaggtcact tgtgctgatg cttttatt tcctcccacc cccatttggt tgggattgta      7140
gctcttgata ccgcacccc aacacacaca cagacacccg gaccatagct aacacagagg     7200
taaaggagct gaaacacgtt tttctctgtg tgacacactg gaaactgat gaagctccaa     7260 agcttgatag ggattttgat atcagatgta ttatcctggg tcatgttcgt gagactggct    7320
cagactctgc atttgacttt gagtcgaacc acagagtggc ccagagtgac tctctgcttc    7380
tagccagcct gtctgacaca ctggctggcc ctcctcacca caatctgacc tcatgctggt    7440 gagggggaatt tttacctggc tggcccccag gacagggcat gggccatggc agcatcctgt   7500
cgcagttctg ttgttcagag gtggatccca ctgcaggaaa ctagagtttc ccatcaatgt    7560
ctttcttctc agttttatgg aaataaccctt tccttaatgg aactgtaatc ctacaaggac   7620
aggtgggacc atgtactctt gctctcctgt gggtctcaca gtaacagggc ggctgaaggc    7680
atggctgtgg ttgcctttgc cttcctttag agcaggcttc aggaaagca ctgtgagtaa     7740
```

```
                                                       -continued gcagcaggta acagttccta cttggtgttt gagatctgaa gataacgtgg caagcaagag    7800
gctaagccag ttcctttctt agtttagaga gacatttctt gactctgcct ccaggtgacc    7860
tcctctaggt ctgataacaa ccagcctttg gggtttgaga acattcttgt ttttgtttt     7920 tggcaacttg aaaaaagtac ccagagcctt tgcatgttaa gcaagaactc ttctgcctag    7980
acaagcaact gtgcaacaca cacagacaca agcaagcagc tcaacctaag catgctgcat    8040
tccaaatgcc tttaagaagc ccacaagttg ggaacatacc agaggaatga ctgaactgcg    8100
ttagaattgc atgttagtct acgtgatgga agaaggcatg gagtcttctc taataaaact    8160
gctcatggaa gactttgcat gaattccagg cttccagagg gttcaaacca gcaacccaag    8220
gtggatttgg ttcctgggga tgacatattt aggtaaagag agcttaagaa tcagtctctg    8280
aaagtgtaat ttacagaaag tgttctggga ctgctgttgg ttcagcctgt tcactctcac    8340
tctgttcact ctggcctgat gctcatgaag agttgacctt taccttagtc tcagttgctg    8400
cttttacttg gtatcctgct gtgtctacat ccttgctgct tctaacttgt ctgctttcaa    8460
cactgttcgc ctttaaaatt cattcctttt catttcctgt ctgatagagt atatggttca    8520
gtagatggct gtaaagctga gggctctgca ttctgggaga ccctgctcat gtgtgctgct    8580
tctgtgtgtt ctctgccagt gggcagagca cccaggctct ctgagcctgc tggttgggtc    8640
tgaatgatat ctattgatag aagcttnang nnnnnnnnna nnnnntncnn nnnaaaancc    8700
agtgcagtgc ctggcatatg ggtgacattt agcagtactg tgaatgatgg tggggatagc    8760
ccagtgctgg attcatgggc ataaacccctt atgtgtcatc ccataacact aagaattggt    8820
gagacacgac tgtacagacg aggaaagtaa ggtttatttg cctgttctcc tctcttcaag    8880
ttactgaaaa catggcttat ggctagataa gcctcatggc tagatcactg ctaaagagtc    8940
ctgacaacca aattaaatta ttcttgccaa aacacaaaat acagatatcc atgtgaatgt    9000
aatacattcc cttacatatt ttaatccagc gttatctcgg aagcagtgtg cataagtaga    9060
gnacagtatt gaatctatat tgtattcttt gactgtactt attttttttt atttgggata    9120
aggtcttacc atataacccc agctggcctt gaacttacca tatagaccag tctgccttg     9180 aactcacaga gatttgcctg cctcagcctc ctccaactct gagattaaag gccaaacttg    9240
ccaccattcc tggcttgtaa gttacttctt aagtgttgtt actaaaattt ttaaatttaa    9300
ggttatggtg taggatagtt tatcttggat gcatgacata tttaaaaata tttatatatt    9360
ctcttaatag tttttagaag gtataccgga ctccaaaata taactgctta tttaaaatata   9420 aaaacagatt tattgttcca taagcttaaa aattaaagtc tcaggaaaag ataccaaact    9480
tggcttttac ctatttatct catttatacc cagaatattc actggccagc aaactctgta    9540
gagcagtgat tctcaacctg tgggtcacaa cctatcctgc ttatcagata gttacattat    9600
gaattgtaac agcagcaaaa tcacagttac gcaatatcaa caaaataatt ttatggttga    9660
gggtcaccat aacgtgagga actgcattaa agggtcacag atttaggcag gttgagagct    9720
atagccacat agagccttta cagggttcat tctcgttgtt tctatagaaa cgtttatat     9780 tagataactt tctcacagac ttggttatat ttccaagaga tagctgtttt ataatcccta    9840
ctctaaaaca attaagattt ttctagaaag ttgattattc acgtgtaaag agataaaatt    9900
ctaggatatt tcatttgtat atgcattatg aaaaaaattt aaatggtcaa gaattatgcg    9960
atagctgtgg aaaagtgccc cattttaaca cactttgaac tccaggcttt atactgcagt    10020
ttgtttgttg ttcctccccc gccccatccc caactttctt tcatgctagg acagaaccca    10080
gggccatgca cgtgattaga atatactcct tcactgagct gcaccccccc cccccccag     10140
```

-continued

```
ttctttttatt ttattttta ttttgcgaca ttgtctcact aagttacctg ggtaggcctt    10200
gaactcatga tccttctgct tcagtctccg aagtagctgg gattagaggc ctgtgctgtc    10260
agcctggatg taagagtttg ttgttgattt aaattagata ttgtctcctc taattaactc    10320
catttgttgt cattttcatg gccctgagta cacttcaaca gcatccctgt tcatatcctt    10380
gaattcttct ctaaatccta gcagaccttt cctgatcttt cattttctgt tcacatggaa    10440
ggtacctgca gccatttatt ctcaagtctt caaatattct gcttctcagg acactttctt    10500
atttctttgt atttcaccat agaagttttg catgacctca ggcatataag aacaatataa    10560
tcaaacactg actgataata aagagtggag agattttat attttttgt ttttttgttt    10620 ttgtttgttt gtttggttgt ttggttggtt ggttggttgg tttttcgaaa cagggtttct    10680
ctgtgtagcc ctggctatcc tggaactcac tctgtagacc atgctggtct cgagtgagat    10740
ttatttttaa atacatagaa ttttagcagt tattaaagat aaaaggcagt ctacatactg    10800
tgagatggat aggtttgtat agaagaactt gactttggct gaatatttga tactatagga    10860
tgtagagcat ttccttgttt ttcagaattc atcaggattt tgattttgta gatgccagtg    10920
ctaagaatgt tgtttccaca aacacattgt acaatatggc agaattgtgt ttagtgtcat    10980
ttcagaaatt gtttgaaact ccattctaat tctaggtcaa aattcatttc atggaactca    11040
agccagtttt tataaatcaa gcattctaat gtaatacaat caaaagtgca ctagttttgt    11100
acttacatgc taaggaatgg cactgatgaa atattcacct actttctgta acagcagaaa    11160
gctctatgta tacgaaatgt acttcactta atggcacggt attacatata tgctagcatg    11220
tgcagtgaga agcacgcatg ttgcatactc aaaacagaag acgcaggggc agctgcacaa    11280
ggcagcggtg ggcagagaca cttattcatt catatgtatg tggttttgaa ttaagttttg    11340
ctcattgctt atttaaaaac ttttattcac aattttttg accactaaaa tcagtttgca    11400
acccacagtt tcaaaagctg caaaataaga cctacatatc tacctcgcac aattgtaaat    11460
cacacgagac ccttgtttgg gtattgtaag aattgaacac tgtatccagg aagtcattag    11520
taaaaaccta atgtggtgcc ttgcttttta aagatttatt tacttattta atatatatgc    11580
cctatcatat atatacctgc atgctagaag agggcatcag atgtcagtag agatggttgt    11640
gagccacgat gtggttgctg ggaattgaac gcaggacctc tggaagagca gccagtgctc    11700
ttaaccactg agccatctct ccagctctta atgtagtgcc ttttgtcaga cattgtgtat    11760
atgggatatt tagctacagt tgtttcactt gccattttt tccttataat tttccattct    11820
tcatttaaaa agaaatatct cttatttttt ttacctgtaa ttaaatatta ttcaacagtt    11880
atttagtatt tgggtgttgg gttacttagt attttgtagc ttttaaacat ttgttctttc    11940
ttttcctgag tatgtttgag tccctgcata tatgcctgtg cactgtgcat gtgcctggtg    12000
cacttggggc tcatggaggg cctcatatcc gttggaactg gagttagagg cagagctggc    12060
ttatgggtac cagacctggg ccctctgcga aagcagcaac tgaatcctta accactgaac    12120
aaaatctctt cagccccatg tattttgtac ctttgtgttt tatccttgaa ataaatggcc    12180
ttttaagaaa tgagaaaagc ctttaatccc agcagaggta agtggatcac tgagttcaag    12240
gccagcttgt ccacatagtt ccaggagagc cagggctaca cagagaaaaa aaaaatnca    12300 aaaaacagga aaaacacaca cctccttgat ttaagggttt tttgtttgtt ggttgttttt    12360 ttttttgag ttttggggag ggggtatatt ttttaatgtg tctgtagttg gctttgtttt    12420
aagcatttta atcatacttt attttaaaa aaactaaaag cttttttaag gctaggtctt    12480
```

```
gctatgtggc cctagtgttc ctgggacttg ctctgtacac cggggttgact ctgagcctgt  12540
gcgccttctg cctctgcctc catagttaga ttctcaggac atgttacaaa gactgtgctg  12600
tgaagatgag tttttgttcc tgggagggaa ggttggagct gacttgtgag gtactgactt  12660
gggtctgcct tacagttgac tggattgttg cggacatgct ggctgccaga caggatgccc  12720
taggacatgt gcgctacgta ctgaaagaca agttaaaatg gcttccgctg tatgggttct  12780
actttgctca ggtaaacttt gtctttgccc ttttatttca aacttaacac catttaatga  12840
aactatatct gatttttttg tttatgtgtt tgttttatgg tacccgtgat tgaacatggg  12900
gtcatatgtg tgctactgag tgacagcctt agttcagaca ttttttaaag cgactttttac  12960
tagtattttt atttagaatt ctatatgtgt gcacatgcat atgtgtgctt gtgtgcacac  13020
gtggatgcat gtgaggtcga aggacaattt tcagtacaag tgtgagtgtc acttttttagg  13080
caccttccac tcttattttg agacagtctc ctagacctttt gctgagttgc ccaggctagc  13140
cggccagtga gccctgggca tctaccggtc tctgcctcct tacctttact taggttacaa  13200
gtgtgtgctg ctacgcccag ctgtttacta gattctaggg atccaaatgt gggtcctcgt  13260
aacttgtgag acaagtactt tccaaactga gccacctccc tagctcttct tcacggttcc  13320
tgatggtgtg tgtctagatg gctggttgtc cgtatattta agtccagtag cagaaataca  13380
aatacctagg agtccaatag aaagctacaa gtgcagaatt gacaatcggt aatgttcgga  13440
aattgattca aaagtagtta gtgagtgaca gacaggagct aaaagcagac tctgagctca  13500
gagtgtgaag tgtggagaaa tgtgttttct cacagttctg aaggctgaaa gtctccccaa  13560
ggtcaggatg tgggtggtac tgctgtctcc caacacccac ctctttggat tatagactgc  13620
agccttctcc ctgtgttctg agccggcctt tcccacatgt ggacatcctt ggtgggtgtt  13680
ccaccagcag ggcctcagct agtgcccctta tttcacttaa ctgtaatgat tttcttaaag  13740
accctgtctc catacacagt cactgtggaa gctgaagctt caatgtaaga gttaaggggg  13800
gaggggaaa tttagtccat aatggtgtca caccaatctc tgtagctgag tccatgattc  13860
agttcttttaa aggctctgag tgtagacatt atcttaatta ttttgcccat ttatgtatta  13920
tcttttaatt attttatgta actgaatgcc tgtgtatata tgtttctggt tcctagtcca  13980
tattttaatt ccttaaagga tggaggtgta gactttttgtc ttttttaattt tctatccttc  14040
cctcctggcc tcctgtggcc tcttttacgt atttattatt tttaatttat tttatgtgtt  14100
tgagtgtttt gtatctatgc attcctgggg cccatggagg tcagaaaaac acattaggtg  14160
gcctacaact gagttatggg tggtttgtga ccatggggtg ctgggacttg atcaccagtc  14220
tctgagaaga ctcgtgtctg ctgagccttc tctccagtcc tgggagtgtg gatattttaa  14280
ggatactttt aattgacttg gtgaatgaca gtagaaaatc aatgagttag gatccatcgg  14340
aaaaagcttt tgaactaaat cttttaaaga gaaatatttt taagtgctaa caaaattaaa  14400
tgtgtatttt ccatgatgca gttttacttg ggctctgtag aaataggatt ttcaggtaca  14460
tattgtatat atagttggca atatttaaat actaactgtc gcttgagttc tgaaatgtag  14520
ttttatgttt tttactcatt aggagtacag ttgccttaat aactacggag attagttatt  14580
aaagaataat tgctcttctt ttttcttttc tgtgtaccag catggaggaa tttatgtaaa  14640
acgaagtgcc aaatttaatg ataaagaaat gagaagcaag ctgcagagct atgtgaacgc  14700
aggaacaccg gtaagtgcgc ccgcttttat tcctcaaggc aggttaagaa gttaagttct  14760
taagtcattt tgaaaatata ttaccccatg tggagcaatg gaactggttc ggggttttgt  14820
tgagataagc tgtcctctgg ccgtgaggta agattgctgc aggtgattgt aaggtttctc  14880
```

```
ctgagtaaca gtcagcatgg gctcgggacg ggcaagggca ggccttagtg tgcagaggat   14940
ggagctcact gaagccccaa agagttagtc ttcacatgag attcagttct agaagaagtt   15000
aaattgcttt cttcctgtgt aaatttggat ttttattgta gaaattaaag tttgttttct   15060
tttaaaacaa acacaaaccc agagcaaaga gtctcctagt gaagagtcat tccgtgtcag   15120
tattttacac aactgttttt ctgtaaaggg ggaaaaagaa ttcaaatctt ctctttcaag   15180
aatgctgact gctgccaact gcctctcccc gtggcccctc tctgtataga caggcatagc   15240
tatggtgagg acttgggcgg ctcttgtctt tctcctctct ctgcttctct acctttctc    15300 tcgtgccctc cacttaccag gccctgggaa gctacacacc aggcaacagt gaccagggcc   15360
tcggcctggg cttcgaccaa ttactagagc agaaacagca gcagctgcag tgttgttttg   15420
tgctgtgcac tgtattaggt tgtgttttca tcacctttgg gttttgtgat gttttgatga   15480
agtcctggta ccattctagt ttttacattc tgggtagata gagtttattc aaggtctcaa   15540
ggcatatgaa tggaagagct cctctttaca gccattcgtg tagcatgcat aactgctctt   15600
ctgtattctc tctagtgtct ttttttttgt gtgtgaatct gatgtcttgt tattcaccta   15660
caatgtggag taatggtcat aaacatataa agtacttatg cctttatctg ccaaattgta   15720 tttaacttt cagcttttaa tataacttt tatataataa ttaatttatt ttaaaaaaaa     15780
ttgaatacca gcctgttata gtggcatatg cctgtgttcc tagcactcag gagacaaagg   15840
cagaagtgtg agaacttcag actcatactc agctatatac aagacccaa atttgtgcta    15900 gattctgcag tacagccatg agtgtcccca tcttagaggg agatcgctca tccttgtgct   15960 gttcttaag tcttaccctg caacccactg taagtacact cttgctcaca gtcctttaga   16020
atctcacact ctttctcttt acagacacca tgtcattgcc cactttatta tttatctgat   16080
gtctacaaag attatgaaag agaaacttgt atgcattctg tgtaaagtac ttgacacaaa   16140
taatagtatt caagaatgac ttcttaaatg aacactgaat gaatagtttg ttctaatttt   16200
tttgatcaac aaatcaaaaa atatttagat taaatatcta agatacaaag cataatacca   16260
catgaatcat taaagtgagt aatcaatctt ataagtgact gaccctaaaa ctcatagaca   16320
ttaataattg ctttcattgc ttagatataa actttattga ttaatacgtt tcatgaaag    16380 tggttcttgg aaggttctgg aaacgaaaat attttcctta ctgctttttt cttctagtaa   16440
ctgattgaat ttttctgcag ttccataaag catctggtca attgctatta tccaatatga   16500
ggatatataa caaagtattg atttttaaat ttggcggtga taagacaaga ctgggcgtgt   16560
gaatgagggg gtctctgttt cttgtccctt ctcttgggtt cttttccttt tgttggtttg   16620
ccttctccag ctgctatgtg atgggttctg attatcttat tatatcttat tttgttattt   16680
ttcattgtta tctcttagaa gccaacatgt tatatcacct ccactcccac cattaggtgt   16740
ctcacaaata ccccaagcta acaaccaca tcatgtcatg ttctgtatac ttccataagt    16800
gttgttaact ctactgactc ttgtgagcag gcccaattgg ctttatccct agctgggtga   16860
cctgggttcc tccccaacac cataccgtcc atcaaactga gtccttttcc aagcacacac   16920
cagatactgc tcatctgagg actcttctca tccacctaag gactgcctgc tcctcggcag   16980
aaagggcctc tagtcccata cccttacgcc ctcaccaatg ccttaggaac atgtgctcaa   17040 tgccctgtg ggtcatttcc gtttacagta gggaaatttg cctgataact tgcagcacac    17100
ctataaagag gccttgcttg ctctcatatt tagctggaga agataatgta ctcaccaact   17160
ccactctatg caacccagtc tgctctgccc atgccagtca gacgtgaatc ttacacctgg   17220
```

```
attcagattg atgaatctac aacatcaccc actccatgct tccttctaaa tcagcagttc    17280
tagcctgaat gacagatgct acccaagtct catctagtta gccctgtccg gagtaaccct    17340
gaccttgagg attagaccag gatgcacatc ctgcaccagt tcccttgtc cacctgactt     17400 catcccaccc gggccatagc ccatgctcag gctccaccct ccatgcacaa agctggcttt    17460
tccagcttcc ttcacctgta tcagacacaa atagcaaaag gggtccacgt gcctaggtcc    17520
catcacaaga ccatgtgcgg tagtttggaa aacagtctcc acttgaggct cagatagntt    17580
ggaatcttgg ctctcatgta gttgtactga ttagatcagt ttaggaagta tgaccttnt     17640 ggaaagaaca tataactggg aggggctttg agatgtaaag gccccacaca attcctagtt    17700
caaactntac tgcctgctca aagcttgagg catgaactct cactgttcct gatgtcatgg    17760
ttcctgtctg cttccacaat tccctatcat taggggtccc tttccttcct ggaatttaa     17820 gataaataaa cacttcttt aaaacaacaa gaacaacaaa tctgacnctg ataatggatt     17880
ttaaggcgtc ttctctggat aagaaaaaaa aaagaatata tttgcatagg tgctgtatta    17940
cttttgtcat tggtataacc tgactggaag caacttaaag gaagaagaat gtatcttgat    18000
ttgtagatta agagcaccat gactaagaag gcatagcagc acaggtgcac cagcaagaac    18060
ataggctgct agctcagatc tctgtagata tgggaacagg gcaggaagct agtagtctat    18120
aaacctcagg acccatccca tggagttcct tgtcttccag tgatgtcctg tgtcttaaag    18180
tttcacagtt cccacagcag cacctgccgt ctgggaacca acctgtggtg gatattttac    18240
aacgtgatag gcatattttg tctctagccc tgtaggttta tagccatcct atacttcagt    18300
ttatctagtc cacctcagtc tgatggtctt atagttccaa cacttcaaaa ctacaaagtc    18360
ttaagggcca tgggctcggg tttattagag cagtaacacc tctactagct ttctgtgtta    18420
cccactcctc ttaaggtctg gttgaaatcc taataggaag cagcttgaga ggagggttta    18480
ttgtggccca tactttgttg gtacattcta tcatgcaagg gtggcactgt gatacagccg    18540
aggccatccg aggatggtac tgttggctta catctgggtg ggacaggaaa tggtaattct    18600
caaggcccac ctgcttggtg acttctttca gttaagcccc atactctaaa tcctctacaa    18660
cctcccaaca taatgccacc agctggggat cagctgttga cagtgctggc ccaggggagc    18720
agtttaaatc cagaccaggg gacctgaaaa cagagaactg cagaggggct gtgggacttt    18780
ataccagctt tgcagacaaa tcacggcatt tctttgtgag cttggttcat aaacaaatat    18840
atattctcct ataggctcct ttagtgggtg tttcatatcc acaaatttgt tcagaaaaac    18900
actgtgtttt atgctagctg tgtaggagat aataccgctg ggagtcactt gagcatggat    18960
aagtgacata gttcgtcctc atgagtccct gtcctgtttc tgtattatgt ttacttgatg    19020
agtttagttt gtcagttggc caccaattaa aaagtatcat tttatttttt ttacaatact    19080
cagttctcaa gttaggagtt ttgttattat atggcttcaa tattcacatt ttaaccttc     19140 caggagttaa gtataaaaac ttatatcaac tgttgactta gtaaatatct attacagata    19200
ctatattctt cttagtttat atcatgaata tgaggttgct taaagtaagt gatgtaaaat    19260
acactagggg atgcttataa aatggaatgt tgtgagtttt ttgaaacacg agtactaaat    19320
tcataagttt ttaaatagtt acactgttag cttcagtact gctagataca tgtctataat    19380
ggctgaagag tggagcttgg atattataag tgtactctgt atattcatgc agacatatag    19440
cagattccac tagtatgtgt ggttaatatg tgctaataaa aatttaatac aaaagtcatg    19500
ttttattact gggaaccaga ggggttggtt gtgctgattt taagtcagtg actattagca    19560
tattctaaga aacagtttta ggattttaaa gattggcttt accataaatg tagagctatg    19620
```

```
ttttactata atccatatta tggtcggcct taattcaatc tctgcagttt ggttactctg    19680
ctcaaagtga aggtcattta taaatgatac acattttctc accataggaa atactacctg    19740
gccaataaca gagttagaat tgctaaattg atggtaccaa caatggactc aacacaaact    19800
aaagtttatt tatgcccaca gatgtatctt gtgattttcc cagagggaac aaggtataat    19860
gcaacataca caaaactcct ttcagccagt caggcatttg ctgctcagcg gggtaagtaa    19920
agatttaact gtattcagaa aaacactttt ttaagaagag tgatctttgt ttccttcaga    19980
gtcatactaa agaatatgcg tttcttgtaa gagctaagtg agagaatatc cgatcttcta    20040
cagagttagg tatattctta ttagtctgtg tctgagaggt tagagacgca ggcttgctat    20100
ggcacatttc ccatgctgtg aattgagtta aaaatgtagg taaatgatat ccccaagaaa    20160
gtatactttt ggagtgactc agtataaagc ctggtgttat aacataaaca cgcacgtgcg    20220
gatgtatatg tagcacatat gtaaacacag gtatatgcat tgtaataaga aagtggaggt    20280
cggggcccac tgcaggcaag tctttagtg atgctgagct aatgctgaga ggtagaaaga    20340
ccaagaaggc tggagttgct cattcggcaa aggtcagagc tcactgtgtg ccataactcg    20400
agtgttctgt ctcccttttg atacagtttt cttgttttta attattagtt tttacaatta    20460
tcccataaaa tgtgggctca ttgtggtcat cgttttcata aagtccttca agtatacacc    20520
cagcaagtat ctaaatacac tgggaagaat cagtcagctg atggcttgaa gtttcaggac    20580
atctagtgcc acatcatgct tcagaaccga cctgcactta gtcagggtca tattcatgcc    20640
acgtgaagac gagaggaggc catgccgtct gacttaggat ggaaatttcc ttcgagcaaa    20700
cacgaacggg ctaggtctta gttataggca tagtgtctgt ggttatacta ggcagacatt    20760
agtggactgg gtgttagaag gtacagacag gcaagaattt gctgtagatt tgtttccctc    20820
atgtgttgac accacatcta acctgctttt tgagcttcta gtcctaataa tctcataaaa    20880
atactggttg aaccagaaat ggtgttgcaa agctatgatc ccagctcctg ggatctaggg    20940
tgggaggatc ataaatttga ggccagcttg ggtctgtctt agagaaaaaa gaaaataaaa    21000
aagtctggtc aaggtaacat ggagcctgga agtttcacag ggtgattctg taaaggtcct    21060
gagacaagat ggcctctagt ggcgaatgac ttagctgaca agaaaacttt cccagcttgg    21120 ttgactttc agacttcata caagtttgtg aataaattac actccttctg cccttgggac    21180
tgaactcaga tatgtggttg tgggaatggc tttctttccc acaccaccct gcattttaaa    21240
aattcttctg tagacagtcc caccatcctg tagctgttct tccttatgtc gccactttcc    21300
ctggagagag gcagtgcaga cttcaacccg cttctcccta gtcgctgttc atagcacatc    21360
gaaagaccta gtgcttcctg tgaaattgta agtacatcct ggagtccagg agaggaggaa    21420
gccgaacaga gtggagggaa tgctgagttc tgtcctaaga aagactgcgt gcttagcaag    21480
atgctgctgc tctcctgtcg tgtctttctt gtcagaactt atcaaagaga aggctcgcag    21540
tgggtcataa tcttcccaag gaccagcctt cccagcttct cgcagcatat ctcattcatg    21600
tagatgttta atggatatgt gtcaatgggg ttgacctaag tgagatggca atgtatgtga    21660
gcattctagg tgtgaggtta tggcattaaa ctttaatttc cgtctatttg tggtagttga    21720
taagtaattt agatgttgac tttcatgtat tcctaattat gaccacattg aatctaccctg   21780 cttctaggc cttgcagtat taaaacacgt actgacacca agaataaagg ccactcacgt     21840
tgcttttgat tctatgaaga gtcatttaga tgcaatttat gatgtcacag tggtttatga    21900
agggaatgag aaaggttcag gaaaatactc aaatccacca tccatgactg gtaagtccgt    21960
```

-continued

```
atttccatag aagctgaata gtacatggta caggtaagat aaactcttgt ttgttcgctt   22020
tgcttagctt ggttcagttt ggttttcagt agagggttcc actatgaagc tctggctggc   22080
cgggaactca ctatgtagac caagctggcc ttgggctcca ctacacccag caccaatcac   22140
ccactcttat cttttatgct ttttgttttt gctttgagct ttctttataa catgtttggg   22200
aaggacattg tcattattta caagaagaaa tatggtcttt tcccaacatg ctagaattta   22260
aagactcaga actcttgcct tgtcagtga caaagtgaga atggctgtga agtgacgtgg   22320
ctttgagtga gaatagttca ggtaactata gccacagact caacatttga acatgggaac   22380
aggtgagaac ggagtgatgg aagattctgg cccctttcag agaattcatt ttagagagag   22440
atgagagtag taaggaagag agaagagaga gacgtggtat tttgctgcag actaaagaga   22500
tctcttataa tcgcagtact aaggaggaag aagcagaaga tgatgactac agggccaggc   22560
tgaacaatct agtaaaatcc taagtcagga agtcagggct gaggtgcagc tcagtaggag   22620
agttgttgtc tgccctacac aaggcctgga tttagctccc agtagcaacg aagggaggcg   22680
agggtgggca aaatcgaaca cttactcttg gagactccct ttatgaatat taccacactc   22740
cagtaaatac tctccagaga tttcagatga gattctgctt cctggtaaac aggaggccaa   22800
gaatattatg tcacactgaa catgggatgg aagacatgtt ctgaggaatg tctgcactcc   22860
agtgtgatga agacttgaag tttagggaca ttttccctcc ctggcccac tcaccccatc   22920 tgtattgagt attccctag tgctcatctt tatttgtatg ttaactttca ggaaggggaa   22980
gcagattgat attcaaaccc agccagtttt cttaaatact ttgtggatgg gattggcttt   23040
gacagtaaat gaggaaatgt aaaatgtaaa agattctaat ttttaatatt ttaaaggtga   23100
ggttttctgt tagtacgcag agtgagaggt ttcttactga tgtctgcgta cctagaggaa   23160
ggatggctac ttctccaagg cttgctgtta gaagtcagtg acatgggctt aacaagagat   23220
atgtgctaat gaggttttaa tttcagctta atactgcaaa tcataagtgc atagctttat   23280
tgttttaaat tcttttagtc ttaatgtttc attttacca taagttactt tgtataatca   23340
caaattctaa actagtaaga cgtgaaattt tcttcttctt tgttagagtt tctctgcaaa   23400
cagtgcccaa aacttcatat tcactttgat cgtatagaca gaaatgaagt tccagaggaa   23460
caagaacaca tgaaaagtg gcttcatgag cgctttgaga taaagatag gtaagtggta   23520 agagctccag catttagaaa gtgcagttca accaaatttt actctcagat cctgcttgaa   23580
aggagtcttt ttatcttcat tatttagtaa atactaatca tacctgcata gacaagacca   23640
catatactta aatgtagcat gtttcatggt gcgttaccct tgtttaacaa ttaagtttaa   23700
catcctacat cagtttgcct gttgatttct gtaccatgac aactcaacac agcgatgcgt   23760
ttattccaaa gtcgatagca cagcaaaagt gaaactaaag tctgtattgt ttcaagaatg   23820 cttttttgtga actcgggtta aatcttattc tatccttcg tgttcacatt gtacattttc   23880
atgagtcact ataaaaatca tgacatggtg gcctacctgc agtgtttgct ggacagtagg   23940
ctgctgtgtg ataagagcct ttcctcttca gctacgcggg ggacacgagg ctttggggtt   24000
caagactgaa gcacgggtga gcacaacacc tttgtgttgt gggaaggaag ggaattgttc   24060
ttttcataat gaaattgtcc cctttcttga gttagtagaa agtattacaa ggatagagag   24120
ttgaaatgaa gctttatatt agatttatgc cttgtgttgt cacgtgtttc tacctgacat   24180 aactttttcaa cccagccgct caggattatt ttgatgatgg gaacaatgta agaaggccta   24240
tgtatcggta actcactgtt gtagctctgt ggaagcggct cacaggcagt agggacgctt   24300
ctgtgctttt gtgcctgtcc tgctgttaga atcttacaga ggaggatgaa tgaatgaccc   24360
```

```
tttttatttc tcttgtctgc ttttctaatt ttatgggaat aagaactttt ggtaggtctc    24420
tgtcactggc ctcttgttgt gaagagacac cttgagcaaa gcaactcttc tgagagaaag    24480
catttagttg gggaattcct tacagcttca gaggttgagt tcgttttcat catgctgagg    24540
acagggaggc actcaggcag gagaagtagt tgagagccac attctgatct acaggcagag    24600
agagacagac tgagcctggc atgggttctt ggaacctcaa agcctctcat ccctacccca    24660
tctcccgacc cctatacaca cttcctccaa caaggctaca ccttctaatc cttcttaaag    24720
agtcaccaca tccagcgact aagcattcag atatgtgaac ctgtcggagc ctttcttact    24780
cagatcacct caggaggaaa actcctatgc tataagaatt tcttttcttt cgcatctttg    24840
aaagcttgtt tttgtgtgat tagatcctgg cctcacacat gctcggcaat cattttactg    24900
ttgagctcca gcctcagccg ttttcattgg cttatgggat gcgagccatg ggagagaagc    24960
tagaaggcct ttcgttttat gagtcgggtt ggtggaacca cttacagatg gaagatttac    25020
aaacaaaaat gaagctgggg ccatcaaggc tcagcactcg ctgctcttcc agagagttca    25080
ggttcatttc tcagtaacca catggtggct ttgtaaatgt aacttcatat tcaatgaccc    25140
tgacaccctc ttctggcctc tgtgggcacc agacacaatc atggtataca gacacacaca    25200
ctagccaaca cccatctaca taaaagtata taaacatatc tttatcttaa aaatccccga    25260
agtcctcatt aaatatctta gatccccgcc gtgttttgat ttttgtttcc cacgtggtga    25320
ggatataata tcatgtccaa actgtaagga gtgaatgccc tcccgtgcct ctcggacacc    25380
tctgcactca tccaagtttt ctaaggagct gtacttgctc agcaagtact caatacctaa    25440
taaatggttt atgtttgttt caacaccaaa aatgtccaaa actgaaagat caattctgtt    25500
gttttccttc tggccatagg ttgctcatag agttctatga ttcaccagat ccagaaagaa    25560
gaaacaaatt tcctgggaaa agtgttcatt ccagactaag tgtgaagaag actttacctt    25620
cagtgttgat cttggggagt ttgactgcgg tcatgctgat gacggagtcc ggaaggaaac    25680
tgtacatggg cacctggttg tatggaaccc tccttggctg cctgtggttt gttattaaag    25740
cataagcaag tagcaggctg cagtcacagt ctcttattga tggctacaca ttgtatcaca    25800
ttgtttcctg aattaaataa ggagttttct tgttgttgtt tttttttgttt tgttttgttc    25860 tgttttaagc cttgatgatt gaacactgga taaagtagag tttgtgacca cagccaacat    25920
gcatttgatt tggggcaaac acatgtggct tttcaggtgc tggggttgct ggagacatgg    25980
aagctaagtg gagtttatgc tgttttttttt tttttttttaa tgttttcatg aattaatgtc    26040
cacttgtaaa gattattgga tactttctgt aattcagaag gttgtatttt aacactagtt    26100
tgcagtatgt ttcgctatat tggttatctt ccatttgact acttggcagc tcagactctt    26160
aatactaaag tattttacat tttgaagcta tgtgatactg gttttttgtt gttgttgttg    26220
ttgttaattt ctgaaagtca atgaaagaca ctgtaatgat gcgttaagat gttccaagaa    26280
aaaggtgaga attattcatg gcaaaaaaga tctgtctagt gtatatttt attatattgc    26340 tctatttagc taattttctt tatatttgca aaataatgaa cattttaat atttattaaa    26400 atgcttgatt tgcataccc cgattctaca gagaataatg tgtaaagtgt cagaatagac    26460
ttgaagctct gctgtgactc agtctccttt gtcagagctt ctagtagccc agctactgag    26520
ctgctttgtt agtacctcca gcacctgagc cgttaagtac ttataaatgc aagggacccg    26580
ttatcttcat atcggaatag acatgaacag agctctaagg cgatgaaagt ctgccagcat    26640
cctctctgtc ctcgcacgtg ccttctgcct ggctccattt gctttggcac tgcgttcgat    26700
```

```
ctagagtgta ggtgctcact gcttatttca gccctggctc tgtggttttg tgtcctccag  26760
tggtgctgtt cactgttggg gtgcaggtgg tgctgccctg actcagaggg gcagctccct  26820
ggctcctgag ggtgagcctt cttggctact acagaagtat tgtgcgtttg tgtatggcaa  26880
gaaccatcag gattggataa atgtgttatt tctctttgat ttccatggag ccacactgtt  26940
ggtacatgtc ccctgtgaac agagctacct ttcaggagca catcatactg tcgtgagtca  27000
cggcacggtg tgtcctgtga agagggctt tctaacgtgt gatttgccgt gtttctatgt  27060
tgtgatttaa gcgtgattgc ctactagtca ttcaaggtaa catttctgca aatttcatac  27120
agatttttgt cacaaaatta ctataccaat gatctagttg aaatagacca attgaatcac  27180
aataaataat tttttttaat tgagggaaaa tttgcttctt gttttttcaa agccagaaaa  27240
cgagccattt caaacatctt tgaagagtca tgtgctgtca cttgttttct atgtgttagt  27300
gtctatattc atgtatggat acacatgaac atgtatattc atacacacac gccaatagaa  27360
tataacagcc taaaaacaat ccagcttgtg tatcatgtta ctgtgctgaa ttgtaatggt  27420
ttttacttac aaagtgaggc taaaatcgat ttcatgtctt tgttaaatac gttttttca  27480 gcaatcctat tagagcttat tttgaccaga tcaaaataag tacaagttca gagactttaa  27540
atatggctga ggtctagagc gatagctcag tagttaggaa cacatgccac tctttcaagg  27600
gcttcagttc ccagcactca tatggaggct cacagaaggc tggaattcca gcttcatgga  27660
attggacaca tcctctagct tccatggatc tgtctgtctg tctctccctt ctctctctct  27720
ctctctctct ctctctctct ctctctcttt ctcacccttt aaatatcatg gatatgctgt  27780
gcatttaaat tttaagacac agaaccattg gaattacatg gattatagct gattctcttt  27840
gaacagggca cagtgttctg cgtaagatct cttgatcatt agcactggac tcactctcct  27900
cacaagtagc ctatcaaatg tggtattaga aaatacattg tgtcaaaatc tttgaaagat  27960
gagaagaatc tcctaaacat gtttattttg acttgacatc actatttcct gaaaattaac  28020
tgtctatgat tcttttcaca tagtgtaaga tcttacttgt atcaccatca gcttgcagct  28080
taggggctgc agttgttctc cttcataaga ctgccatccg tgtgcatgct tttatgtttt  28140
tcagaaagga tgttgggatg aaagtaagaa aacaaagtct cttcttgtct ctcatgtctg  28200
tgatcactag catttcacaa ctcagggatt catccatttt ccagcagata aaaggggttag  28260 cgattaaccc tgcattctga gtttagaaag ctacaatatt ttttaaatat tgagcaatga  28320
ttttaaaaaa atacattgga ataccccaaa ttgtgaagca atccaaaagt tggactgtat  28380
aagctaattt gcctacttta aaggatgtga ccctcaccca ggaaacctgt aggatttact  28440
taacaaggct ttacatgaaa atgccaccgt ggccatttct taaacactgg tggcttcttc  28500
cagatttcat ttctatgttt gtttgtttgt tgttttttt ttacttagat tgctgtgagg  28560
tttttttttt ataacaaata tacattttt tctttgtcac attacatgct ttgtcaatca  28620
aatgacctaa ctaggttggc tattaagaaa actacatatt gaaatctgcc aaaatgtcgg  28680
cataaacaaa ctggctccta attgtgtacc agatctacat ttgaaagaac agaaatgtct  28740
cacaagacaa taaggtcata tgtaaaacac taaataaact ttaacctcaa caattgtttc  28800
tgaagtgttg agattaaaga ctgagtgttt gcggaacgtt gacatgtcca tggccaggct  28860
agtttctcgt tttcttttg tcttaagact aaacattggc tggcttaaaa tattaccagt  28920
tctatatagt ttacattata gacagaatat ataacattta agtattagta tgaaaatcag  28980
tactttggtg agactaatat ttggaatatc cagatgattt gatatcatgt aggtaaagta  29040
agtatttgtg tgactgactg aacttaaaat ctcttattca tatatcatgg ataacagctg  29100
```

```
ggagttgtga cacatggctg ccatccaggc actcggaaaa tccaggtttt gagaaagaga    29160
gtgttttcca agtcagcctg gtctatatag caagcttcag actagccagg actgtgtacc    29220
aagatcttct tcacgccacc cacacaaaca agagaagtta tatagagaat tgcttgggat    29280
ttagttacaa cattttgtt aggatttcat ttaatgggca gggggtgggg gagttagcag     29340 tttgcattt cagagaatgg gttccattcc cagcatccac agggcagtaa ctgaagtaac     29400
tgtagttcca gggtatccaa caccttcata tggacacaca cgcaggcaaa agaccagcat    29460
gcataccatt aaaatgaatt attaaaattt ttttaaaaaa gactttgata tatttttagt    29520
ttgtgtatgc tgaggtggat ctgttgctct tggcaaactg agtagtaata cgtggagttt    29580
tataagaggc cagagatctc actttcatat aatatacctt ggataataac ctagttgcta    29640
cctaagcaaa gaagttcctt ggaagagcta catcacagaa aattggtatc agagcatata    29700
ctcagtccat ggttatgcca tgagacaggc cagtgtttta cccagactag tgttttgtca    29760
tatctgaata aataaataac aaagtcgtat tctacaactc taaatcctca tatagaaaat    29820
aaaataggaa tgcggttgac acaatttgtt gcctgaagtg atgaggaaat taagttacaa    29880
agtaatcaag aagtactcag ttactgtgtc ttcttatgta gcttcagaat aagttctgat    29940
agtgttactg ggtttcctgg tgctttataa tccagtacaa gggaaaatat gaacctcatt    30000
tttttttata aaaatttggt gacaaaaaag ttacattgtt ttataaagtg ttttgtgttt    30060
tatgtgtata tgtgtgtttg attgccagat atagctataa agctcactta tttcagatgg    30120
gtattttgtt tgagatttgc tgggtgttcg ctgtatgctg actgcttctg cacctcttgt    30180
aggcaccagc ctgtctgcag gcagaccacc caccccatgt tgggtccttc tgcctctggt    30240
tagccatcca accttggaca gctttaaata aagagtgtcc caggtttatc acctgtagaa    30300
cattgctacc acctgtagaa cattgctacg atgttagcca caagaattg ttgagagcat     30360 gtgaactact gcagatgatg cagcagatgc agagcataga aagaatgtag ctggtgctgg    30420
ctcgggttcc tgtcctctgt cttcatagat gaccttcagg tcagatgggg tttggataaa    30480
gtctagggat gggatgccat ctggtccttt cctgtttctc aaggagacag tggggtgtgg    30540
aagtggatgc tcgtagttat ggttcagatt gtaggttttg tttaagattc agatcacgtg    30600
gtgtagagag atacaacaag agaaagaaca tctccattat aagtcacatg gcctctcaac    30660
tacagctcaa tagaagctgg atcttcaggg ctaggagtgg gctcagtcct cacactttgg    30720
gcacaggtgg agggatggc atggcagctg cagtaatgtc tgagggttc cttctggcat      30780 tccgcactat ggtacgtttt agactaagtt cgagacaatg cctatcggag tgcccctta     30840 tccgtgtagt ggggagtgtg gaagtctgtg gagaggtcag tgtggtgact ccatggagtg    30900
tgggttccca tatgtaaagt tgcactcagc tgagctctat ttgtcgaaag tgtgaggta     30960 catctgttca ttattttctg acatatatta gagctcagaa ttgtcaggaa tgttcatgat    31020
taaacattgt tccttgtcat ttggaaccat gcctatattg gcttctgtcc tatgcctgca    31080
cgagttaact ttcgtctgg gccaggagtc gttttgattt ttacaggcat ctaacatatt     31140
tctgtttgtc tgataccccc ttccttctgt tttcctatct gcactgtctc ttcagtctgt    31200
cgcagaaaga gcagagaaag tccttctgtc tcccaagacc tcccatggtc tttgtgctct    31260
tgctgaagac aaccaactag tgtggcaact agtttgatat cttttctctc tataatagaa    31320
atgagatcat ccaagttacg ctggagaact ggggtgtgtg tctgtgtctc tgtattcccg    31380
ctaccccttt ctcctagaga aattcattgt agtttggtta gttggaagtc ctggtaaggt    31440
```

```
ggcaggtcct gtggtatagt gagggcctta ttgctgggct gtgggactcc aaagtgagtc    31500
tcaagtcccc cgaggactca acctagtacc caatctttcc aaccacccct tctttccaac    31560
cctatgacat taaattttca gtgcttcaat tttggagaga cattcagacc atggtaaact    31620
cacatgagca ccaagttgga ttcttagggg aattctgaag gaactgcttt taaaaataaa    31680
cagttttcct gatgaggttg cattggaacc agctgtttag aactgaaccc cctcctcccc    31740
tgtgaatggc ttgaacaggt ggtttatttt ccagaagcaa catagagctg gattaatttg    31800
ttattaggga actaaattat ctgttgacta tactgctaac ctcaacctca aaatgtagta    31860
gtggctacca gaccacccca acacctctct gattaaagcc atcaagagga cagtagagga    31920
cagaagaatg cctatttccc ttcaagacat ttccagagag tccctaatgt ttctacttag    31980
ctgtgactgc ctggaactta gtacaggctt catttagctg caagggaagc tgacaagtga    32040
aatcttcagc tttgacatcc tcaataaaat tgaaggtctg agggatgaaa ctattctgag    32100
aacagtggca gtgttcacac catcttctga atataaatgc tgaagattac taaatggata    32160
tggtgaattt taccacagtc caaaccaaca gagcaggctg gggatgtggc tgagttggta    32220
cagtacactt gcctagcata aacagctgc tgtggtaaca aacattgtta caccaaacac    32280
tcggtgtgtg gatgcaggag aattagacat ttcaaggcca tcctcagctc tgcagtgagt    32340
tcaaggccac ctgggggtaa ctgatttcca ccttactttt tgaggcagtg tcactaaacc    32400
tgtagttcac tgatgaagct acagtggccc acaaactcca gcagccctcc cagggctgtg    32460
actaccttta aacaacaaca aaacaaaaag tgctggagat ccaaactcaa gttcttatcc    32520
tcagggcaag cactttactg actgggcttc caggcctgct ctattgctgt ggcaagactc    32580
gctataacta cctacaattc ctcttcaaca tctatttgga ttctcttttt ctttgttttt    32640
gagacaaggt ttctctgtgt atctatccct ggctgtgcta gaactcacta tgtaaaccag    32700
gctgtcctcg aactcaaaga ggtctgcctg cttctgcctc atgagtgctg ggattaaagg    32760
tgtaccacca caccctacc tattgggttc ttaaagggca cttccaaaa ctgatgaagg    32820 agagttaaaa taaggagaat ttttgtaaaa ctaacatgta atgtgaactg tgaatgtatg    32880
ccccaaaatc ctacatatct acaaaataca cgagtttttc gttatttag tcaccttctc     32940 tggttggctt ggttttactc ttgagtaatt tttactaggc aactttcagg acagaatgac    33000
agttcttgaa gtttaatctt agtagaaaaa caggcaatag tgagaaagct gtgtcacagt    33060
gttgttctgc aaccactcca gatctattcc ctcccaatgt ctatggagtg cattgtctgc    33120
ttaggtgctg aataaggaca tgccaacatt tcttatctac tgtaaggcaa aattggtgag    33180
cagtgtcact aagcctgtag ttcactgatg aagctagagt gcccactagt gagccactat    33240
cactagtgag cacactagta atagtgtgaa agaaagtgac ttccactgtc ccatgaacac    33300
acccaccttc atctcctcta ccttgcacct ggttcagatt tcggcagatg cagtgagcat    33360
ggtgcttaag aagtctgaag gatagctctg ggggatggtg gcacatgaag gtcacatctt    33420
tttttaatta ggtgatttaa atgggtttgt gcacatgagt gcaacaccca tacaggccag    33480
aagggggcat aagatccccg gctctagagt gtcaggctgt tgtgaactgc ctggaatagg    33540
tgttgggaac tgatcttggg tcccctggaa gagcattgag tacatgtcat cactatctct    33600
ccagcctcac actcttatcg gtatgtctca tttgtggggg caatttgggg agtcccacct    33660
ctggatcagg tactgtgaaa tatggagttg gcggggctgg atccctgtct tgccaccagc    33720
cagctgagga aagctgtcaa ttgtcttcct gtgtctgcct cagtttccta gaaactagaa    33780
aggaaaaatg gatggtatca ctaagttcag ccttccattg taaggatcca ttgaagtagt    33840
```

-continued

```
tggtgtgatg tactcacgct ggtgccoctc cccttctgag ctgcaagcat cagctgttgg  33900
acccagcagt tctgtgctcc gacaggaagc agtgggaaac tgggctgcaa gatgatccca  33960
gttctagcat ttgctgcaac cccctttgct cacatctgtt tccacatttt atttcatcct  34020
tgagcacata acctttcat tttgatacat gcttttcttt acatagcctg ggccagcctt  34080
gaactcatgc tcctcctgcc ataattcctt aaggactgac aatgacagtg gacatgcacc  34140
gccaggtccc actgctccta gtacttttgt tatgggtctt ctatgctggt ctaatgtgga  34200
atgtgacact gcacaccagg cattgtggga tgaagtagaa catgttcatg cacacaaaga  34260
tcaatcccaa acagcatctg cccaccccte ccctctgccc cttccccegg tggatgttag  34320 cattctcttg tgtagtgctg ggtcggcccc ttctctgtct ctaaacattg aaacaagggg  34380
aacagaccca tacataactc caacacagcg atctggtcca agtctggatg tagaaccctt  34440
ggctctgctc ttttctcctc ttcccagagc tgtcccagtc gcctcccttt ctaattggct  34500
ggtgctcatc taacttgatg tatatgtttc tttcctggtc tgttttatga ctggcctgct  34560
ccagtcatta gtgcatctgg tgttagaagc taagctcaac ttggcctcac agtcttgatg  34620
ttcaggacac atggggttat ggctggatcc tgtgtcaagc acatcacttc tttctgaacc  34680
cacacatctt aagacatggg cattgtcaca tggctgacag cagtacattc ttgtatgtag  34740
ttttctctca agtgttttgg ttacatggcc ctaaagccta ggactgtctg tcttcaatca  34800
tgtctgccac ctgctgccca gcaagcccaa gttgtggttc ttcctgtcta atctgcctct  34860
tttatcttta gccctcctcc ataagcctct tttccactga gctctgggtt attcagatta  34920
cagctcccta ctgctttcct gagacccotaa gccgctccac gatgcacagc agcactttcc  34980
agcagtccta tggagatgca gtgtcgagat gatatgagct gtgctgtata tgtaaaatgc  35040
atggtagaat ctgaaaacca agcacaaaaa aataaaaaaa aagttcatta atatttatag  35100
caatcatgta atgttttgaa aatacgtgcc taataaaatt attttcacct ttttaaaaat  35160
gtgggtacta tgatgtttaa tagcgcatat tcatgtggca tatttacctc aatgggcat   35220 ggaaaacaag acgacaaagg gtgggatatt tctctcaact ttcctagctg caacttgtga  35280
taatttgtga gacacattaa gcactcaaga agggtttgat tctgtagaca aaacccgggg  35340
tcagacagtc cacagcttca gcatagtgtg ttcactatat ctaaagtagg ttttacttct  35400
ttaagattaa ttttgttctt agacagtttc ccacatgcag cacaaagcag ttatgtttta  35460
attttatagg ctacaatgac ggtatttcaa aaagtaagat gtgggagtta caccttgaat  35520
gatcacccaa ggattgttgg ccatcagcac tgaatggccc agaaccaatc tacagcaaat  35580
ctgagagagc agagacatgc tgctccactg tctgagggcc cttgcccatg gtggttgcta  35640
ttgacatctt gacaggatct aaaatcacct aggtgtgctc tgggcacctc tggacatatc  35700
tgggagtctc tagactggat tgcctgaggt tgatttaaaa accctaactg ggcagcacca  35760
ttcattggga tggggtcctg gcgtggataa agattggagg atgagggagc accaggttcc  35820
acctctctgc ctcctgactg gatgcagcat gatcagctcc ctctcctgct gtgacacaat  35880
ctctgtaccc tcaaactgaa caaaacaagc tcactcgaaa gttgctttcg ttagtcactt  35940
tgtcacagct ttgtcacagt gatgagaaaa ataacacaca ccccccaaat gaggattgga  36000
tcgaggccct gggcatgctg ggtaaactct tcaccactaa gctatattcc taacccttt   36060 tactttgaat agggtcttaa ttgcccagat tggcottaaa atgataattc tcctgtcttc  36120
agcttcccaa gcagctggaa ttacaaatgc gagcactagt atgtatatgt agtatataaa  36180
```

-continued

```
taatatattg tacatatatt cacatgtgtg tgtacatgtg tgtacacaat tacaaatggg    36240
agccccagaa tgatgtatac acatacatat aagtaggtaa ttaatatata catatttaca    36300
catattatac tagtgtgtat atatagaata tataatatgt attgcacata tattcacata    36360
tgtgtgtaca tgtccatgtc acattgtgat tgctagttaa ataccactt tccctgctct    36420 ctaatccaag tagcaattga acctgtgaat tatggtaaac ttcaggggat tgaaaagcct    36480
gacctccaca gaatcagcta acgttagctg ctactatgat tccaagcagt agttactgga    36540
agtgtttgct cctgtattct cttggaagga agaactagat tgttagtcat cagttcacag    36600
tcggttatgg tccccctgtt ggcctcatag accagaaagt agagttgcat ggttgattg     36660 taaagtgacc cacctcccac aggttcacat gcttgaacac tgggtcccca gatgatggag    36720
ctcttggggg aggttgtgga gaccatctag gaggttagct tacctggagg aaatgggctt    36780
ctaggggaca gacattgaag atgataggtt ttccctgttt ctgccctggg aatatatcca    36840
aattcctcac tcgaatgcca cagccctgag atgagccttc cccttcacag tggactctac    36900
cctcaaaccc tgagccagag tagatccttc gtcctttgct agatgtttgg tcacggcagt    36960
gaggtaaagt accgagcaca gcatcattgt tcccatttta cggatgggaa aactgagcct    37020
tgggagatgc ccaaggctgt cagccttgag tgtttaaaag ctgcaaggat tggatgcatt    37080
tgtcctatat cagggaaaca tgatggggat ggagtctggg tgctgaggca ctgagttggc    37140
aagagggaag gcctggtgtt cactcaaagt cattaaggac caattgtgtc tgcaatcctg    37200
tgccctccct tgaacaatag gtaagggtca gtgtgagccc tgattactcc cagcagaagg    37260
atacatctgc tttggagacc aaagtcccctt cactgtagaa actaggtcct tcaaggtctc    37320
agataaaaag acaatgggtt ttgtgctaat ttccacccaa tgggtgtgtg ggtcacacta    37380
ctcactgggc caacatggtg gtctggacag tcacacagga tgaagtgagg aaaggcaagt    37440
ctccccggca cctcccctat cgtcactgca aggccaccct gactaagagt cccctcttca    37500
atgctggccc tacgaatatc ttatcactct tcgtgtttac aagatttctc tccttggaag    37560
gtgtgatgtg gacagtgaag ctctcaacaa cccctactca cctaagacct agacaagaga    37620
gtctgggatg gccatgtatg tactccttca gtaattgaca gccattttct ttgtctagga    37680
agtcttccta caagcttccg caccataacg gtatcggctg tcctgattta cagacatgtc    37740
attgggactg atatctgcaa caaagagcag atctccagtc actcatctca ctccagcttg    37800
ttcacagaac aaaaaggagt tgaagggagg tcttcatcat tgggtgttcc cttccatgga    37860
gcataggaca ggcatggtgc ccagaacctg cccagcttct agctctccaa gcctcatgct    37920
ttcctgtctc naaaaaaaaa aaaaaaaaa                                      37950
```

<210> SEQ ID NO 184
<211> LENGTH: 1381
<212> TYPE: DNA
<213> ORGANISM: Mus musculus
<220> FEATURE:
<221> NAME/KEY: CDS
<222> LOCATION: 45..1109

<400> SEQUENCE: 184

```
gagccgagag gatgctgctg tccctggtgc tccacacgta ctct atg cgc tac ctg      56
                                                 Met Arg Tyr Leu
                                                   1 ctc ccc agc gtc ctg ttg ctg ggc tcg gcg ccc acc tac ctg ctg gcc     104
Leu Pro Ser Val Leu Leu Leu Gly Ser Ala Pro Thr Tyr Leu Leu Ala
  5                  10                  15                  20
```

```
tgg acg ctg tgg cgg gtg ctc tcc gcg ctg atg ccc gcc cgc ctg tac      152
Trp Thr Leu Trp Arg Val Leu Ser Ala Leu Met Pro Ala Arg Leu Tyr
            25                  30                  35 cag cgc gtg gac gac cgg ctt tac tgc gtc tac cag aac atg gtg ctc      200
Gln Arg Val Asp Asp Arg Leu Tyr Cys Val Tyr Gln Asn Met Val Leu
            40                  45                  50 ttc ttc ttc gag aac tac acc ggg gtc cag ata ttg cta tat gga gat      248
Phe Phe Phe Glu Asn Tyr Thr Gly Val Gln Ile Leu Leu Tyr Gly Asp
            55                  60                  65 ttg cca aaa aat aaa gaa aat gta ata tat cta gcg aat cat caa agc      296
Leu Pro Lys Asn Lys Glu Asn Val Ile Tyr Leu Ala Asn His Gln Ser
        70                  75                  80 aca gtt gac tgg att gtt gcg gac atg ctg gct gcc aga cag gat gcc      344
Thr Val Asp Trp Ile Val Ala Asp Met Leu Ala Ala Arg Gln Asp Ala
85                  90                  95                 100 cta gga cat gtg cgc tac gta ctg aaa gac aag tta aaa tgg ctt ccg      392
Leu Gly His Val Arg Tyr Val Leu Lys Asp Lys Leu Lys Trp Leu Pro
                105                 110                 115 ctg tat ggg ttc tac ttt gct cag cat gga gga att tat gta aaa cga      440
Leu Tyr Gly Phe Tyr Phe Ala Gln His Gly Gly Ile Tyr Val Lys Arg
            120                 125                 130 agt gcc aaa ttt aat gat aaa gaa atg aga agc aag ctg cag agc tat      488
Ser Ala Lys Phe Asn Asp Lys Glu Met Arg Ser Lys Leu Gln Ser Tyr
            135                 140                 145 gtg aac gca gga aca ccg atg tat ctt gtg att ttc cca gag gga aca      536
Val Asn Ala Gly Thr Pro Met Tyr Leu Val Ile Phe Pro Glu Gly Thr
        150                 155                 160 agg tat aat gca aca tac aca aaa ctc ctt tca gcc agt cag gca ttt      584
Arg Tyr Asn Ala Thr Tyr Thr Lys Leu Leu Ser Ala Ser Gln Ala Phe
165                 170                 175                 180 gct gct cag cgg ggc ctt gca gta tta aaa cac gta ctg aca cca aga      632
Ala Ala Gln Arg Gly Leu Ala Val Leu Lys His Val Leu Thr Pro Arg
                185                 190                 195 ata aag gcc act cac gtt gct ttt gat tct atg aag agt cat tta gat      680
Ile Lys Ala Thr His Val Ala Phe Asp Ser Met Lys Ser His Leu Asp
            200                 205                 210 gca att tat gat gtc aca gtg gtt tat gaa ggg aat gag aaa ggt tca      728
Ala Ile Tyr Asp Val Thr Val Val Tyr Glu Gly Asn Glu Lys Gly Ser
            215                 220                 225 gga aaa tac tca aat cca cca tcc atg act gag ttt ctc tgc aaa cag      776
Gly Lys Tyr Ser Asn Pro Pro Ser Met Thr Glu Phe Leu Cys Lys Gln
        230                 235                 240 tgc cca aaa ctt cat att cac ttt gat cgt ata gac aga aat gaa gtt      824
Cys Pro Lys Leu His Ile His Phe Asp Arg Ile Asp Arg Asn Glu Val
245                 250                 255                 260 cca gag gaa caa gaa cac atg aaa aag tgg ctt cat gag cgc ttt gag      872
Pro Glu Glu Gln Glu His Met Lys Lys Trp Leu His Glu Arg Phe Glu
                265                 270                 275 ata aaa gat agg ttg ctc ata gag ttc tat gat tca cca gat cca gaa      920
Ile Lys Asp Arg Leu Leu Ile Glu Phe Tyr Asp Ser Pro Asp Pro Glu
            280                 285                 290 aga aga aac aaa ttt cct ggg aaa agt gtt cat tcc aga cta agt gtg      968
Arg Arg Asn Lys Phe Pro Gly Lys Ser Val His Ser Arg Leu Ser Val
            295                 300                 305 aag aag act tta cct tca gtg ttg atc ttg ggg agt ttg act gcg gtc     1016
Lys Lys Thr Leu Pro Ser Val Leu Ile Leu Gly Ser Leu Thr Ala Val
        310                 315                 320 atg ctg atg acg gag tcc gga agg aaa ctg tac atg ggc acc tgg ttg     1064
Met Leu Met Thr Glu Ser Gly Arg Lys Leu Tyr Met Gly Thr Trp Leu
325                 330                 335                 340
```

```
tat gga acc ctc ctt ggc tgc ctg tgg ttt gtt att aaa gca taa      1109
Tyr Gly Thr Leu Leu Gly Cys Leu Trp Phe Val Ile Lys Ala
                345                 350                 355 gcaagtagca ggctgcagtc acagtctctt attgatggct acacattgta tcacattgtt 1169 tcctgaatta aataaggagt tttcttgttg ttgtttttt tgttttgttt tgttctgttt  1229
taagccttga tgattgaaca ctggataaag tcgagtcttg tgaccacagc caacatgcat  1289
ttgatttggg gcaaacacat gtggcttttc aggtgctggg gttgctggag acatggaagc  1349
taagtggagt ttatgctgtt ttttttttt tt                                1381
```

<210> SEQ ID NO 185
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-107
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-14-107.mis1
<220> FEATURE:
<221> NAME/KEY: primer_bind
<222> LOCATION: 25..47
<223> OTHER INFORMATION: complement potential microsequencing oligo
      4-14-107.mis2

<400> SEQUENCE: 185
ctaaacaacc accaaatgca tacagcaacc aggcaaatgc ctgatag              47

<210> SEQ ID NO 186
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-317
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-14-317.mis1
<220> FEATURE:
<221> NAME/KEY: primer_bind
<222> LOCATION: 25..47
<223> OTHER INFORMATION: complement potential microsequencing oligo
      4-14-317.mis2

<400> SEQUENCE: 186
cataacatgc aaggtgggca agaaaaagag gtgggcacag ctcatga              47

<210> SEQ ID NO 187
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-35
<220> FEATURE:

```
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-14-35.mis1
<220> FEATURE:
<221> NAME/KEY: primer_bind
<222> LOCATION: 25..47
<223> OTHER INFORMATION: complement potential microsequencing oligo
      4-14-35.mis2

<400> SEQUENCE: 187
atccaacaca gaaaccgcta aaaccaggca gaagctgtct gcagaga                47

<210> SEQ ID NO 188
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-20-149
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-20-149.mis1
<220> FEATURE:
<221> NAME/KEY: primer_bind
<222> LOCATION: 25..47
<223> OTHER INFORMATION: complement potential microsequencing oligo
      4-20-149.mis2

<400> SEQUENCE: 188
tttttgctgt gtcttcaaag tgactcttgg tttattgcct gctaagg                47

<210> SEQ ID NO 189
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-20-77
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-20-77.mis1
<220> FEATURE:
<221> NAME/KEY: primer_bind
<222> LOCATION: 25..47
<223> OTHER INFORMATION: complement potential microsequencing oligo
      4-20-77.mis2

<400> SEQUENCE: 189
tgcaacatga agattctgaa gggactttgt tgtctgagaa cacatct                47

<210> SEQ ID NO 190
<211> LENGTH: 47
<212> TYPE: DNA
<213> ORGANISM: Homo Sapiens
<220> FEATURE:
<221> NAME/KEY: allele
<222> LOCATION: 1..47
```

<223> OTHER INFORMATION: polymorphic fragment 4-22-174
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-22-174.mis1
<220> FEATURE:
<221> NAME/KEY: primer_bind
<222> LOCATION: 25..47
<223> OTHER INFORMATION: complement potential microsequencing oligo
      4-22-174.mis2

<400> SEQUENCE: 190
ggattgtgca gaagttgcct ttcatgttca aaaatgttaa tttgttt           47

<210> SEQ ID NO 191
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-22-176
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-22-176.mis1
<220> FEATURE:
<221> NAME/KEY: primer_bind
<222> LOCATION: 25..47
<223> OTHER INFORMATION: complement potential microsequencing oligo
      4-22-176.mis2

<400> SEQUENCE: 191
attgtgcaga agttgccttt catattcaaa aatgttaatt tgtttgt           47

<210> SEQ ID NO 192
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-26-60
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-26-60.mis1
<220> FEATURE:
<221> NAME/KEY: primer_bind
<222> LOCATION: 25..47
<223> OTHER INFORMATION: complement potential microsequencing oligo
      4-26-60.mis2

<400> SEQUENCE: 192
gatgggaaag tgcatcttaa gacagttagc aggccaagga gcgactt           47

<210> SEQ ID NO 193
<211> LENGTH: 47
<212> TYPE: DNA
<213> ORGANISM: Homo Sapiens
<220> FEATURE:

```
<221> NAME/KEY: allele
<222> LOCATION: 1..47
<223> OTHER INFORMATION: polymorphic fragment 4-26-72
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-26-72.mis1
<220> FEATURE:
<221> NAME/KEY: primer_bind
<222> LOCATION: 25..47
<223> OTHER INFORMATION: complement potential microsequencing oligo
      4-26-72.mis2

<400> SEQUENCE: 193
catcttaaga cagttagcag gccaaggagc gactttaaag ggtgagc                 47

<210> SEQ ID NO 194
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-3-130
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-3-130.mis1
<220> FEATURE:
<221> NAME/KEY: primer_bind
<222> LOCATION: 25..47
<223> OTHER INFORMATION: complement potential microsequencing oligo
      4-3-130.mis2

<400> SEQUENCE: 194
tattgggcct aaaacagtat tctataaagc ttaaattggt attaact                 47

<210> SEQ ID NO 195
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-38-63
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-38-63.mis1
<220> FEATURE:
<221> NAME/KEY: primer_bind
<222> LOCATION: 25..47
<223> OTHER INFORMATION: complement potential microsequencing oligo
      4-38-63.mis2

<400> SEQUENCE: 195
tataagttat aagaaaatca ggcagaggct aaactttttt tttgttt                 47

<210> SEQ ID NO 196
<211> LENGTH: 47
<212> TYPE: DNA
```

```
<213> ORGANISM: Homo Sapiens
<220> FEATURE:
<221> NAME/KEY: allele
<222> LOCATION: 1..47
<223> OTHER INFORMATION: polymorphic fragment 4-38-83
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-38-83.mis1
<220> FEATURE:
<221> NAME/KEY: primer_bind
<222> LOCATION: 25..47
<223> OTHER INFORMATION: complement potential microsequencing oligo
      4-38-83.mis2

<400> SEQUENCE: 196
ggcagaggct aaactttttt tttgtttggc aatgctgttg agaatat           47

<210> SEQ ID NO 197
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-4-152
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-4-152.mis1
<220> FEATURE:
<221> NAME/KEY: primer_bind
<222> LOCATION: 25..47
<223> OTHER INFORMATION: complement potential microsequencing oligo
      4-4-152.mis2

<400> SEQUENCE: 197
tactttccca ttgttcctga cttcgttatc ctatatataa acagaaa           47

<210> SEQ ID NO 198
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-4-187
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-4-187.mis1
<220> FEATURE:
<221> NAME/KEY: primer_bind
<222> LOCATION: 25..47
<223> OTHER INFORMATION: complement potential microsequencing oligo
      4-4-187.mis2

<400> SEQUENCE: 198
tataaacaga aacatggatg agtaaaaaaa aaaaaaaaa aaaaaaa           47

<210> SEQ ID NO 199
```

```
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-4-288
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-4-288.mis1
<220> FEATURE:
<221> NAME/KEY: primer_bind
<222> LOCATION: 25..47
<223> OTHER INFORMATION: complement potential microsequencing oligo
      4-4-288.mis2

<400> SEQUENCE: 199
ctgtcatcaa ctaattttca caagtaccta tgttttgatt tcatgta                 47

<210> SEQ ID NO 200
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-42-304
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-42-304.mis1
<220> FEATURE:
<221> NAME/KEY: primer_bind
<222> LOCATION: 25..47
<223> OTHER INFORMATION: complement potential microsequencing oligo
      4-42-304.mis2

<400> SEQUENCE: 200
attatttaaa actatttatg taaccttatt ttcagggtt tttaatt                  47

<210> SEQ ID NO 201
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-42-401
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-42-401.mis1
<220> FEATURE:
<221> NAME/KEY: primer_bind
<222> LOCATION: 25..47
<223> OTHER INFORMATION: complement potential microsequencing oligo
      4-42-401.mis2

<400> SEQUENCE: 201
taagaaagaa ttctgtgttc tggacaaagt ttaaacccac agagcca                 47
```

```
<210> SEQ ID NO 202
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-43-328
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-43-328.mis1
<220> FEATURE:
<221> NAME/KEY: primer_bind
<222> LOCATION: 25..47
<223> OTHER INFORMATION: complement potential microsequencing oligo
      4-43-328.mis2

<400> SEQUENCE: 202
agaattctgt gttctggcca aagcttaaac ccacagagcc agtttaa                47

<210> SEQ ID NO 203
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-43-70
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-43-70.mis1
<220> FEATURE:
<221> NAME/KEY: primer_bind
<222> LOCATION: 25..47
<223> OTHER INFORMATION: complement potential microsequencing oligo
      4-43-70.mis2

<400> SEQUENCE: 203
atcgcctcca ttattctcaa aaagaccatg ggacacaaca caagaag                47

<210> SEQ ID NO 204
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-209
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-50-209.mis1
<220> FEATURE:
<221> NAME/KEY: primer_bind
<222> LOCATION: 25..47
<223> OTHER INFORMATION: complement potential microsequencing oligo
      4-50-209.mis2

<400> SEQUENCE: 204
```
atatagagtg tgcatccctg acactgaaac tgaaggcttt atggttt        47

<210> SEQ ID NO 205
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-293
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-50-293.mis1
<220> FEATURE:
<221> NAME/KEY: primer_bind
<222> LOCATION: 25..47
<223> OTHER INFORMATION: complement potential microsequencing oligo
      4-50-293.mis2

<400> SEQUENCE: 205
cctgagtccc aggggctga caggggacag tttaaaacat tgatgaa        47

<210> SEQ ID NO 206
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-323
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-50-323.mis1
<220> FEATURE:
<221> NAME/KEY: primer_bind
<222> LOCATION: 25..47
<223> OTHER INFORMATION: complement potential microsequencing oligo
      4-50-323.mis2

<400> SEQUENCE: 206
tttaaaacat tgatgaatct ttactactac aaaagggttc gatttag        47

<210> SEQ ID NO 207
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-329
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-50-329.mis1
<220> FEATURE:
<221> NAME/KEY: primer_bind
<222> LOCATION: 25..47
<223> OTHER INFORMATION: complement potential microsequencing oligo
      4-50-329.mis2

<400> SEQUENCE: 207
acattgatga atctttatta ctacaaaagg gttcgattta ggctagc                47

<210> SEQ ID NO 208
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-330
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-50-330.mis1
<220> FEATURE:
<221> NAME/KEY: primer_bind
<222> LOCATION: 25..47
<223> OTHER INFORMATION: complement potential microsequencing oligo
      4-50-330.mis2

<400> SEQUENCE: 208
cattgatgaa tctttattac tacaaaaggg ttcgatttag gctagcc                47

<210> SEQ ID NO 209
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-52-163
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-52-163.mis1
<220> FEATURE:
<221> NAME/KEY: primer_bind
<222> LOCATION: 25..47
<223> OTHER INFORMATION: complement potential microsequencing oligo
      4-52-163.mis2

<400> SEQUENCE: 209
gaacaggata ttcttaacta ccaaagaatt ttacacatct attgttt                47

<210> SEQ ID NO 210
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-52-88
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-52-88.mis1
<220> FEATURE:
<221> NAME/KEY: primer_bind
<222> LOCATION: 25..47
<223> OTHER INFORMATION: complement potential microsequencing oligo

```
                    4-52-88.mis2

<400> SEQUENCE: 210
tccatgtcat tattattcaa aagcttaaaa aatacacaag gtgaaaa                    47

<210> SEQ ID NO 211
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-53-258
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-53-258.mis1
<220> FEATURE:
<221> NAME/KEY: primer_bind
<222> LOCATION: 25..47
<223> OTHER INFORMATION: complement potential microsequencing oligo
      4-53-258.mis2

<400> SEQUENCE: 211
gagaaatcat gcagagagaa tgcattctca ctcaaatttt aacctaa                    47

<210> SEQ ID NO 212
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-54-283
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-54-283.mis1
<220> FEATURE:
<221> NAME/KEY: primer_bind
<222> LOCATION: 25..47
<223> OTHER INFORMATION: complement potential microsequencing oligo
      4-54-283.mis2

<400> SEQUENCE: 212
aagtagtttt tcacactttc tctatgatac aatcgatggc ttaatct                    47

<210> SEQ ID NO 213
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-54-388
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-54-388.mis1
<220> FEATURE:
<221> NAME/KEY: primer_bind
```

```
<222> LOCATION: 25..47
<223> OTHER INFORMATION: complement potential microsequencing oligo
      4-54-388.mis2

<400> SEQUENCE: 213
ctctctatcg tatacatctt tacacacgct gcagcgccaa gactcca                47

<210> SEQ ID NO 214
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-55-70
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-55-70.mis1
<220> FEATURE:
<221> NAME/KEY: primer_bind
<222> LOCATION: 25..47
<223> OTHER INFORMATION: complement potential microsequencing oligo
      4-55-70.mis2

<400> SEQUENCE: 214
tattaagaac ctaggtttta aaaaactctc tatcgtatac atcttta              47

<210> SEQ ID NO 215
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-55-95
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-55-95.mis1
<220> FEATURE:
<221> NAME/KEY: primer_bind
<222> LOCATION: 25..47
<223> OTHER INFORMATION: complement potential microsequencing oligo
      4-55-95.mis2

<400> SEQUENCE: 215
ctctctatcg tatacatctt tacacacgct gcagcgccaa gactcca                47

<210> SEQ ID NO 216
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-56-159
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-56-159.mis1
```

```
<220> FEATURE:
<221> NAME/KEY: primer_bind
<222> LOCATION: 25..47
<223> OTHER INFORMATION: complement potential microsequencing oligo
      4-56-159.mis2

<400> SEQUENCE: 216 aagtttctcct tctcttctgt agacgtctcc atgttacagt caactat                        47

<210> SEQ ID NO 217
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-56-213
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-56-213.mis1
<220> FEATURE:
<221> NAME/KEY: primer_bind
<222> LOCATION: 25..47
<223> OTHER INFORMATION: complement potential microsequencing oligo
      4-56-213.mis2

<400> SEQUENCE: 217
atggctcatg ttcactctgg ttcaccttca gaggagtttg atatttt                         47

<210> SEQ ID NO 218
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-58-289
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-58-289.mis1
<220> FEATURE:
<221> NAME/KEY: primer_bind
<222> LOCATION: 25..47
<223> OTHER INFORMATION: complement potential microsequencing oligo
      4-58-289.mis2

<400> SEQUENCE: 218
catacctgca gcctgctttt ggtgaggggt gactacttta cctgcaa                         47

<210> SEQ ID NO 219
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-58-318
<220> FEATURE:
<221> NAME/KEY: allele
<222> LOCATION: 24
<223> OTHER INFORMATION: polymorphic base A
<220> FEATURE:
<221> NAME/KEY: primer_bind
```

```
<222> LOCATION: 1..23
<223> OTHER INFORMATION: potential microsequencing oligo 4-58-318.mis1
<220> FEATURE:
<221> NAME/KEY: primer_bind
<222> LOCATION: 25..47
<223> OTHER INFORMATION: complement potential microsequencing oligo
      4-58-318.mis2

<400> SEQUENCE: 219
tgactacttt acctgcaata tttatttgca agtttatttc ttccttt                47

<210> SEQ ID NO 220
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-60-266
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-60-266.mis1
<220> FEATURE:
<221> NAME/KEY: primer_bind
<222> LOCATION: 25..47
<223> OTHER INFORMATION: complement potential microsequencing oligo
      4-60-266.mis2

<400> SEQUENCE: 220
aacaggacca agacactgca ttagataaag tttcagtatt tcttagc                47

<210> SEQ ID NO 221
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-60-293
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-60-293.mis1
<220> FEATURE:
<221> NAME/KEY: primer_bind
<222> LOCATION: 25..47
<223> OTHER INFORMATION: complement potential microsequencing oligo
      4-60-293.mis2

<400> SEQUENCE: 221
aagtttcagt atttcttagc agacgaagcc agcaggaagt cctccta                47

<210> SEQ ID NO 222
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-84-241
<220> FEATURE:
<221> NAME/KEY: allele
<222> LOCATION: 24
<223> OTHER INFORMATION: polymorphic base G
```

```
<220> FEATURE:
<221> NAME/KEY: primer_bind
<222> LOCATION: 1..23
<223> OTHER INFORMATION: potential microsequencing oligo 4-84-241.mis1
<220> FEATURE:
<221> NAME/KEY: primer_bind
<222> LOCATION: 25..47
<223> OTHER INFORMATION: complement potential microsequencing oligo
      4-84-241.mis2

<400> SEQUENCE: 222
gaaaaaaaaa tagtgactgc cacggtgaat aattcagttc ttcagaa                47

<210> SEQ ID NO 223
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-84-262
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-84-262.mis1
<220> FEATURE:
<221> NAME/KEY: primer_bind
<222> LOCATION: 25..47
<223> OTHER INFORMATION: complement potential microsequencing oligo
      4-84-262.mis2

<400> SEQUENCE: 223
acggtgaata attcagttct tcaaaagcag caacatgatc tcatgga               47

<210> SEQ ID NO 224
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-86-206
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-86-206.mis1
<220> FEATURE:
<221> NAME/KEY: primer_bind
<222> LOCATION: 25..47
<223> OTHER INFORMATION: complement potential microsequencing oligo
      4-86-206.mis2

<400> SEQUENCE: 224
gtattcaaat caggacacac cacaaatggc atctacacgt taacatt               47

<210> SEQ ID NO 225
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-86-309
<220> FEATURE:
<221> NAME/KEY: allele
```

```
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 4-86-309.mis1
<220> FEATURE:
<221> NAME/KEY: primer_bind
<222> LOCATION: 25..47
<223> OTHER INFORMATION: complement potential microsequencing oligo
      4-86-309.mis2

<400> SEQUENCE: 225
tggctctagg caggccactt tagagagtga ggaaccagag agcagaa                47

<210> SEQ ID NO 226
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-88-349
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 4-88-349.mis1
<220> FEATURE:
<221> NAME/KEY: primer_bind
<222> LOCATION: 25..47
<223> OTHER INFORMATION: complement potential microsequencing oligo
      4-88-349.mis2

<400> SEQUENCE: 226
gaaactaaaa gacaatattc agtgtgagat tttccaagtt ctttatg                47

<210> SEQ ID NO 227
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-89-87
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 4-89-87.mis1
<220> FEATURE:
<221> NAME/KEY: primer_bind
<222> LOCATION: 25..47
<223> OTHER INFORMATION: complement potential microsequencing oligo
      4-89-87.mis2

<400> SEQUENCE: 227
ttcttccctg aacgctggtt tcacatagtt tttgtgttga aataga                 47

<210> SEQ ID NO 228
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-123-184
```

```
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 99-123-184.mis1
<220> FEATURE:
<221> NAME/KEY: primer_bind
<222> LOCATION: 25..47
<223> OTHER INFORMATION: complement potential microsequencing oligo
      99-123-184.mis2

<400> SEQUENCE: 228
ccagcccaga acattcacca gctgggccaa gagttctgct gggtttt                    47

<210> SEQ ID NO 229
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-202
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-128-202.mis1
<220> FEATURE:
<221> NAME/KEY: primer_bind
<222> LOCATION: 25..47
<223> OTHER INFORMATION: complement potential microsequencing oligo
      99-128-202.mis2

<400> SEQUENCE: 229
aatgtctgtt tcttagagaa ctgaaacaca cacacataca tacacac                    47

<210> SEQ ID NO 230
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-275
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-128-275.mis1
<220> FEATURE:
<221> NAME/KEY: primer_bind
<222> LOCATION: 25..47
<223> OTHER INFORMATION: complement potential microsequencing oligo
      99-128-275.mis2

<400> SEQUENCE: 230
acacccctac ctcacatgtg tagacaaatg tatgcatata tgtctct                    47

<210> SEQ ID NO 231
<211> LENGTH: 47
<212> TYPE: DNA
<213> ORGANISM: Homo Sapiens
<220> FEATURE:
<221> NAME/KEY: allele
```

```
<222> LOCATION: 1..47
<223> OTHER INFORMATION: polymorphic fragment 99-128-313
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-128-313.mis1
<220> FEATURE:
<221> NAME/KEY: primer_bind
<222> LOCATION: 25..47
<223> OTHER INFORMATION: complement potential microsequencing oligo
      99-128-313.mis2

<400> SEQUENCE: 231
tatgtctcta gacagatata cataagattc tatttggcat agaaaaa                  47

<210> SEQ ID NO 232
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-60
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-128-60.mis1
<220> FEATURE:
<221> NAME/KEY: primer_bind
<222> LOCATION: 25..47
<223> OTHER INFORMATION: complement potential microsequencing oligo
      99-128-60.mis2

<400> SEQUENCE: 232
gcactgtgac ccaggcgcta ggtccctctt acagtgacac tccgaca                  47

<210> SEQ ID NO 233
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-12907-295
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo
      99-12907-295.mis1
<220> FEATURE:
<221> NAME/KEY: primer_bind
<222> LOCATION: 25..47
<223> OTHER INFORMATION: complement potential microsequencing oligo
      99-12907-295.mis2

<400> SEQUENCE: 233
gctatatggc attatatctc cacagggcag acctgatgta caagatg                  47

<210> SEQ ID NO 234
<211> LENGTH: 47
<212> TYPE: DNA
```

```
<213> ORGANISM: Homo Sapiens
<220> FEATURE:
<221> NAME/KEY: allele
<222> LOCATION: 1..47
<223> OTHER INFORMATION: polymorphic fragment 99-130-58
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-130-58.mis1
<220> FEATURE:
<221> NAME/KEY: primer_bind
<222> LOCATION: 25..47
<223> OTHER INFORMATION: complement potential microsequencing oligo
      99-130-58.mis2

<400> SEQUENCE: 234
aaagcaaaag agcttcaaaa atacttcagg agtgtgcata tggcgag                47

<210> SEQ ID NO 235
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-134-362
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo 99-134-362.mis1
<220> FEATURE:
<221> NAME/KEY: primer_bind
<222> LOCATION: 25..47
<223> OTHER INFORMATION: complement potential microsequencing oligo
      99-134-362.mis2

<400> SEQUENCE: 235
caaaacactc atgttagtta gatgattatt cctattacaa agataag                47

<210> SEQ ID NO 236
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-140-130
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-140-130.mis1
<220> FEATURE:
<221> NAME/KEY: primer_bind
<222> LOCATION: 25..47
<223> OTHER INFORMATION: complement potential microsequencing oligo
      99-140-130.mis2

<400> SEQUENCE: 236
tgttcaaaag cagctacaga ccacatgtaa acaattgagc atggctg                47

<210> SEQ ID NO 237
```

<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1462-238
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
      99-1462-238.mis1
<220> FEATURE:
<221> NAME/KEY: primer_bind
<222> LOCATION: 25..47
<223> OTHER INFORMATION: complement potential microsequencing oligo
      99-1462-238.mis2

<400> SEQUENCE: 237
ccctttcaag gttagtaact catgtgctgt gtttctgctt cagaagg                47

<210> SEQ ID NO 238
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-147-181
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-147-181.mis1
<220> FEATURE:
<221> NAME/KEY: primer_bind
<222> LOCATION: 25..47
<223> OTHER INFORMATION: complement potential microsequencing oligo
      99-147-181.mis2

<400> SEQUENCE: 238
gtgtcatgaa aaagagcatg ataaaaagaa aaacttaaat ctttata                47

<210> SEQ ID NO 239
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1474-156
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
      99-1474-156.mis1
<220> FEATURE:
<221> NAME/KEY: primer_bind
<222> LOCATION: 25..47
<223> OTHER INFORMATION: complement potential microsequencing oligo
      99-1474-156.mis2

<400> SEQUENCE: 239
cttgtactca taagttaaat attgataaca agaagaaata tggactt         47

<210> SEQ ID NO 240
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1474-359
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo
      99-1474-359.mis1
<220> FEATURE:
<221> NAME/KEY: primer_bind
<222> LOCATION: 25..47
<223> OTHER INFORMATION: complement potential microsequencing oligo
      99-1474-359.mis2

<400> SEQUENCE: 240
aaaaaaaatc aaattattgt accaaattcc ctaatatcag atgtgta         47

<210> SEQ ID NO 241
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1479-158
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo
      99-1479-158.mis1
<220> FEATURE:
<221> NAME/KEY: primer_bind
<222> LOCATION: 25..47
<223> OTHER INFORMATION: complement potential microsequencing oligo
      99-1479-158.mis2

<400> SEQUENCE: 241
tttaaaaatc cacttgtaat cgccgctaat tggagtgtat attcagg         47

<210> SEQ ID NO 242
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1479-379
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo
      99-1479-379.mis1
<220> FEATURE:
<221> NAME/KEY: primer_bind
<222> LOCATION: 25..47

```
<223> OTHER INFORMATION: complement potential microsequencing oligo
      99-1479-379.mis2

<400> SEQUENCE: 242
gtagagctgt gtactgaggt cagagaagca gctcatggta cagcctt                    47

<210> SEQ ID NO 243
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-129
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-148-129.mis1
<220> FEATURE:
<221> NAME/KEY: primer_bind
<222> LOCATION: 25..47
<223> OTHER INFORMATION: complement potential microsequencing oligo
      99-148-129.mis2

<400> SEQUENCE: 243
ttcatatcta tacaaataat tttaaattta atacataggg ctgcaaa                    47

<210> SEQ ID NO 244
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-132
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-148-132.mis1
<220> FEATURE:
<221> NAME/KEY: primer_bind
<222> LOCATION: 25..47
<223> OTHER INFORMATION: complement potential microsequencing oligo
      99-148-132.mis2

<400> SEQUENCE: 244
atatctatac aaataatttt gaacttaata catagggctg caaaaca                    47

<210> SEQ ID NO 245
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-139
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-148-139.mis1
<220> FEATURE:
```

```
<221> NAME/KEY: primer_bind
<222> LOCATION: 25..47
<223> OTHER INFORMATION: complement potential microsequencing oligo
      99-148-139.mis2

<400> SEQUENCE: 245
tacaaataat tttgaattta atacataggg ctgcaaaaca aggttga                 47

<210> SEQ ID NO 246
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-140
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-148-140.mis1
<220> FEATURE:
<221> NAME/KEY: primer_bind
<222> LOCATION: 25..47
<223> OTHER INFORMATION: complement potential microsequencing oligo
      99-148-140.mis2

<400> SEQUENCE: 246
acaaataatt ttgaatttaa tacatagggc tgcaaaacaa ggttgat                 47

<210> SEQ ID NO 247
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-182
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-148-182.mis1
<220> FEATURE:
<221> NAME/KEY: primer_bind
<222> LOCATION: 25..47
<223> OTHER INFORMATION: complement potential microsequencing oligo
      99-148-182.mis2

<400> SEQUENCE: 247
ttgatgttga tatgggcaac tgtatgttgg atggtcccaa agcattc                 47

<210> SEQ ID NO 248
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-366
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
```

```
<223> OTHER INFORMATION: potential microsequencing oligo 99-148-366.mis1
<220> FEATURE:
<221> NAME/KEY: primer_bind
<222> LOCATION: 25..47
<223> OTHER INFORMATION: complement potential microsequencing oligo
      99-148-366.mis2

<400> SEQUENCE: 248
tccttgtcaa aggtctctcc ctggtgctca cggctgccgc ctcaaag              47

<210> SEQ ID NO 249
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-76
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-148-76.mis1
<220> FEATURE:
<221> NAME/KEY: primer_bind
<222> LOCATION: 25..47
<223> OTHER INFORMATION: complement potential microsequencing oligo
      99-148-76.mis2

<400> SEQUENCE: 249
tgatagaatg ccttcctgaa ttactactct tgatggcttc ataaaac              47

<210> SEQ ID NO 250
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1480-290
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
      99-1480-290.mis1
<220> FEATURE:
<221> NAME/KEY: primer_bind
<222> LOCATION: 25..47
<223> OTHER INFORMATION: complement potential microsequencing oligo
      99-1480-290.mis2

<400> SEQUENCE: 250
tgcaccatct tcaccacaac cccgggcaac cactgatcct tttactg              47

<210> SEQ ID NO 251
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1481-285
<220> FEATURE:
<221> NAME/KEY: allele
<222> LOCATION: 24
<223> OTHER INFORMATION: polymorphic base G
```

```
<220> FEATURE:
<221> NAME/KEY: primer_bind
<222> LOCATION: 1..23
<223> OTHER INFORMATION: potential microsequencing oligo
      99-1481-285.mis1
<220> FEATURE:
<221> NAME/KEY: primer_bind
<222> LOCATION: 25..47
<223> OTHER INFORMATION: complement potential microsequencing oligo
      99-1481-285.mis2

<400> SEQUENCE: 251
tcccataacc tgttttgctt ctcgctctaa cctcaagatg gtataaa              47

<210> SEQ ID NO 252
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1484-101
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo
      99-1484-101.mis1
<220> FEATURE:
<221> NAME/KEY: primer_bind
<222> LOCATION: 25..47
<223> OTHER INFORMATION: complement potential microsequencing oligo
      99-1484-101.mis2

<400> SEQUENCE: 252
aaaaagatca aatataagca tgtaactcct ctccttaaaa tctcagt              47

<210> SEQ ID NO 253
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1484-328
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
      99-1484-328.mis1
<220> FEATURE:
<221> NAME/KEY: primer_bind
<222> LOCATION: 25..47
<223> OTHER INFORMATION: complement potential microsequencing oligo
      99-1484-328.mis2

<400> SEQUENCE: 253
ggacacgtgg tcatgaggag tttgaaggga ttcagttttc agatccc              47

<210> SEQ ID NO 254
<211> LENGTH: 47
<212> TYPE: DNA
<213> ORGANISM: Homo Sapiens
<220> FEATURE:
<221> NAME/KEY: allele
<222> LOCATION: 1..47
```

```
<223> OTHER INFORMATION: polymorphic fragment 99-1485-251
<220> FEATURE:
<221> NAME/KEY: allele
<222> LOCATION: 24
<223> OTHER INFORMATION: polymorphic base G
<220> FEATURE:
<221> NAME/KEY: primer_bind
<222> LOCATION: 1..23
<223> OTHER INFORMATION: potential microsequencing oligo
       99-1485-251.mis1
<220> FEATURE:
<221> NAME/KEY: primer_bind
<222> LOCATION: 25..47
<223> OTHER INFORMATION: complement potential microsequencing oligo
       99-1485-251.mis2

<400> SEQUENCE: 254
gattgccttg atatatgctc ccagagaacc aagaatgtcc ccttttc                    47

<210> SEQ ID NO 255
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1490-381
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo
       99-1490-381.mis1
<220> FEATURE:
<221> NAME/KEY: primer_bind
<222> LOCATION: 25..47
<223> OTHER INFORMATION: complement potential microsequencing oligo
       99-1490-381.mis2

<400> SEQUENCE: 255
tgcacagtgg aaataccatg tcacggtacg ctactgtgca tctcttc                    47

<210> SEQ ID NO 256
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1493-280
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo
       99-1493-280.mis1
<220> FEATURE:
<221> NAME/KEY: primer_bind
<222> LOCATION: 25..47
<223> OTHER INFORMATION: complement potential microsequencing oligo
       99-1493-280.mis2

<400> SEQUENCE: 256
ggatgacaga gtattgttgg aggaatgggg tttggctgct tgttttt                    47

<210> SEQ ID NO 257
<211> LENGTH: 47
```

```
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-151-94
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-151-94.mis1
<220> FEATURE:
<221> NAME/KEY: primer_bind
<222> LOCATION: 25..47
<223> OTHER INFORMATION: complement potential microsequencing oligo
     99-151-94.mis2

<400> SEQUENCE: 257
attgagatca ttgataagga aatattctaa aatttcaaaa tctatat            47

<210> SEQ ID NO 258
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-211-291
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-211-291.mis1
<220> FEATURE:
<221> NAME/KEY: primer_bind
<222> LOCATION: 25..47
<223> OTHER INFORMATION: complement potential microsequencing oligo
     99-211-291.mis2

<400> SEQUENCE: 258
ctggttatat cagactgacc ttcatgtttt caacaggtca atgcctt            47

<210> SEQ ID NO 259
<211> LENGTH: 45
<212> TYPE: DNA
<213> ORGANISM: Homo Sapiens
<220> FEATURE:
<221> NAME/KEY: allele
<222> LOCATION: 1..45
<223> OTHER INFORMATION: polymorphic fragment 99-213-37
<220> FEATURE:
<221> NAME/KEY: allele
<222> LOCATION: 23
<223> OTHER INFORMATION: polymorphic base T
<220> FEATURE:
<221> NAME/KEY: primer_bind
<222> LOCATION: 1..22
<223> OTHER INFORMATION: potential microsequencing oligo 99-213-37.mis1
<220> FEATURE:
<221> NAME/KEY: primer_bind
<222> LOCATION: 24..45
<223> OTHER INFORMATION: complement potential microsequencing oligo
     99-213-37.mis2

<400> SEQUENCE: 259
gtgcttccgg ctgcaggact gttggaggac tccagtgtct gacag              45
```

```
<210> SEQ ID NO 260
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-221-442
<220> FEATURE:
<221> NAME/KEY: allele
<222> LOCATION: 24
<223> OTHER INFORMATION: polymorphic base A
<220> FEATURE:
<221> NAME/KEY: primer_bind
<222> LOCATION: 1..23
<223> OTHER INFORMATION: potential microsequencing oligo 99-221-442.mis1
<220> FEATURE:
<221> NAME/KEY: primer_bind
<222> LOCATION: 25..47
<223> OTHER INFORMATION: complement potential microsequencing oligo
      99-221-442.mis2

<400> SEQUENCE: 260
tgcctttgta gatatgcatg ggaattccat gacctagcca gacgaat                47

<210> SEQ ID NO 261
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-222-109
<220> FEATURE:
<221> NAME/KEY: allele
<222> LOCATION: 24
<223> OTHER INFORMATION: polymorphic base C
<220> FEATURE:
<221> NAME/KEY: primer_bind
<222> LOCATION: 1..23
<223> OTHER INFORMATION: potential microsequencing oligo 99-222-109.mis1
<220> FEATURE:
<221> NAME/KEY: primer_bind
<222> LOCATION: 25..47
<223> OTHER INFORMATION: complement potential microsequencing oligo
      99-222-109.mis2

<400> SEQUENCE: 261
caggtgagga gtgctggatt ggccacgata tgaatttctt cagcagt                47

<210> SEQ ID NO 262
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-107, variant version
      of SEQ ID185
<220> FEATURE:
<221> NAME/KEY: allele
<222> LOCATION: 24
<223> OTHER INFORMATION: base G ; A in SEQ ID185
<220> FEATURE:
<221> NAME/KEY: primer_bind
<222> LOCATION: 1..23
<223> OTHER INFORMATION: potential microsequencing oligo 4-14-107.mis1
<220> FEATURE:
<221> NAME/KEY: primer_bind
<222> LOCATION: 25..47
<223> OTHER INFORMATION: complement potential microsequencing oligo
      4-14-107.mis2

<400> SEQUENCE: 262
```
ctaaacaacc accaaatgca tacggcaacc aggcaaatgc ctgatag            47

<210> SEQ ID NO 263
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-317, variant version
      of SEQ ID186
<220> FEATURE:
<221> NAME/KEY: allele
<222> LOCATION: 24
<223> OTHER INFORMATION: base G ; A in SEQ ID186
<220> FEATURE:
<221> NAME/KEY: primer_bind
<222> LOCATION: 1..23
<223> OTHER INFORMATION: potential microsequencing oligo 4-14-317.mis1
<220> FEATURE:
<221> NAME/KEY: primer_bind
<222> LOCATION: 25..47
<223> OTHER INFORMATION: complement potential microsequencing oligo
      4-14-317.mis2

<400> SEQUENCE: 263
cataacatgc aaggtgggca agagaaagag gtgggcacag ctcatga            47

<210> SEQ ID NO 264
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-14-35, variant version
      of SEQ ID187
<220> FEATURE:
<221> NAME/KEY: allele
<222> LOCATION: 24
<223> OTHER INFORMATION: base T ; C in SEQ ID187
<220> FEATURE:
<221> NAME/KEY: primer_bind
<222> LOCATION: 1..23
<223> OTHER INFORMATION: potential microsequencing oligo 4-14-35.mis1
<220> FEATURE:
<221> NAME/KEY: primer_bind
<222> LOCATION: 25..47
<223> OTHER INFORMATION: complement potential microsequencing oligo
      4-14-35.mis2

<400> SEQUENCE: 264
atccaacaca gaaaccgcta aaatcaggca gaagctgtct gcagaga            47

<210> SEQ ID NO 265
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-20-149, variant version
      of SEQ ID188
<220> FEATURE:
<221> NAME/KEY: allele
<222> LOCATION: 24
<223> OTHER INFORMATION: base T ; C in SEQ ID188
<220> FEATURE:
<221> NAME/KEY: primer_bind
<222> LOCATION: 1..23
<223> OTHER INFORMATION: potential microsequencing oligo 4-20-149.mis1
<220> FEATURE:
<221> NAME/KEY: primer_bind
<222> LOCATION: 25..47

```
<223> OTHER INFORMATION: complement potential microsequencing oligo
      4-20-149.mis2

<400> SEQUENCE: 265
tttttgctgt gtcttcaaag tgattcttgg tttattgcct gctaagg                        47

<210> SEQ ID NO 266
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-20-77, variant version
      of SEQ ID189
<220> FEATURE:
<221> NAME/KEY: allele
<222> LOCATION: 24
<223> OTHER INFORMATION: base T ; A in SEQ ID189
<220> FEATURE:
<221> NAME/KEY: primer_bind
<222> LOCATION: 1..23
<223> OTHER INFORMATION: potential microsequencing oligo 4-20-77.mis1
<220> FEATURE:
<221> NAME/KEY: primer_bind
<222> LOCATION: 25..47
<223> OTHER INFORMATION: complement potential microsequencing oligo
      4-20-77.mis2

<400> SEQUENCE: 266
tgcaacatga agattctgaa gggtctttgt tgtctgagaa cacatct                        47

<210> SEQ ID NO 267
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-22-174, variant version
      of SEQ ID190
<220> FEATURE:
<221> NAME/KEY: allele
<222> LOCATION: 24
<223> OTHER INFORMATION: base C ; A in SEQ ID190
<220> FEATURE:
<221> NAME/KEY: primer_bind
<222> LOCATION: 1..23
<223> OTHER INFORMATION: potential microsequencing oligo 4-22-174.mis1
<220> FEATURE:
<221> NAME/KEY: primer_bind
<222> LOCATION: 25..47
<223> OTHER INFORMATION: complement potential microsequencing oligo
      4-22-174.mis2

<400> SEQUENCE: 267
ggattgtgca gaagttgcct ttcctgttca aaaatgttaa tttgttt                        47

<210> SEQ ID NO 268
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-22-176, variant version
      of SEQ ID191
<220> FEATURE:
<221> NAME/KEY: allele
<222> LOCATION: 24
<223> OTHER INFORMATION: base G ; A in SEQ ID191
<220> FEATURE:
<221> NAME/KEY: primer_bind
```

```
<222> LOCATION: 1..23
<223> OTHER INFORMATION: potential microsequencing oligo 4-22-176.mis1
<220> FEATURE:
<221> NAME/KEY: primer_bind
<222> LOCATION: 25..47
<223> OTHER INFORMATION: complement potential microsequencing oligo
      4-22-176.mis2

<400> SEQUENCE: 268
attgtgcaga agttgccttt catgttcaaa aatgttaatt tgtttgt                47

<210> SEQ ID NO 269
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-26-60, variant version
      of SEQ ID192
<220> FEATURE:
<221> NAME/KEY: allele
<222> LOCATION: 24
<223> OTHER INFORMATION: base G ; A in SEQ ID192
<220> FEATURE:
<221> NAME/KEY: primer_bind
<222> LOCATION: 1..23
<223> OTHER INFORMATION: potential microsequencing oligo 4-26-60.mis1
<220> FEATURE:
<221> NAME/KEY: primer_bind
<222> LOCATION: 25..47
<223> OTHER INFORMATION: complement potential microsequencing oligo
      4-26-60.mis2

<400> SEQUENCE: 269
gatgggaaag tgcatcttaa gacggttagc aggccaagga gcgactt                47

<210> SEQ ID NO 270
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-26-72, variant version
      of SEQ ID193
<220> FEATURE:
<221> NAME/KEY: allele
<222> LOCATION: 24
<223> OTHER INFORMATION: base G ; A in SEQ ID193
<220> FEATURE:
<221> NAME/KEY: primer_bind
<222> LOCATION: 1..23
<223> OTHER INFORMATION: potential microsequencing oligo 4-26-72.mis1
<220> FEATURE:
<221> NAME/KEY: primer_bind
<222> LOCATION: 25..47
<223> OTHER INFORMATION: complement potential microsequencing oligo
      4-26-72.mis2

<400> SEQUENCE: 270
catcttaaga cagttagcag gccgaggagc gactttaaag ggtgagc                47

<210> SEQ ID NO 271
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-3-130, variant version
      of SEQ ID194
<220> FEATURE:
```

```
<221> NAME/KEY: allele
<222> LOCATION: 24
<223> OTHER INFORMATION: base G ; A in SEQ ID194
<220> FEATURE:
<221> NAME/KEY: primer_bind
<222> LOCATION: 1..23
<223> OTHER INFORMATION: potential microsequencing oligo 4-3-130.mis1
<220> FEATURE:
<221> NAME/KEY: primer_bind
<222> LOCATION: 25..47
<223> OTHER INFORMATION: complement potential microsequencing oligo
      4-3-130.mis2

<400> SEQUENCE: 271
tattgggcct aaaacagtat tctgtaaagc ttaaattggt attaact                    47

<210> SEQ ID NO 272
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-38-63, variant version
      of SEQ ID195
<220> FEATURE:
<221> NAME/KEY: allele
<222> LOCATION: 24
<223> OTHER INFORMATION: base G ; A in SEQ ID195
<220> FEATURE:
<221> NAME/KEY: primer_bind
<222> LOCATION: 1..23
<223> OTHER INFORMATION: potential microsequencing oligo 4-38-63.mis1
<220> FEATURE:
<221> NAME/KEY: primer_bind
<222> LOCATION: 25..47
<223> OTHER INFORMATION: complement potential microsequencing oligo
      4-38-63.mis2

<400> SEQUENCE: 272
tataagttat aagaaaatca ggcggaggct aaactttttt tttgttt                    47

<210> SEQ ID NO 273
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-38-83, variant version
      of SEQ ID196
<220> FEATURE:
<221> NAME/KEY: allele
<222> LOCATION: 24
<223> OTHER INFORMATION: base T ; G in SEQ ID196
<220> FEATURE:
<221> NAME/KEY: primer_bind
<222> LOCATION: 1..23
<223> OTHER INFORMATION: potential microsequencing oligo 4-38-83.mis1
<220> FEATURE:
<221> NAME/KEY: primer_bind
<222> LOCATION: 25..47
<223> OTHER INFORMATION: complement potential microsequencing oligo
      4-38-83.mis2

<400> SEQUENCE: 273
ggcagaggct aaactttttt tttttttggc aatgctgttg agaatat                    47

<210> SEQ ID NO 274
<211> LENGTH: 47
<212> TYPE: DNA
<213> ORGANISM: Homo Sapiens
<220> FEATURE:
```

```
<221> NAME/KEY: allele
<222> LOCATION: 1..47
<223> OTHER INFORMATION: polymorphic fragment 4-4-152, variant version
      of SEQ ID197
<220> FEATURE:
<221> NAME/KEY: allele
<222> LOCATION: 24
<223> OTHER INFORMATION: base T ; C in SEQ ID197
<220> FEATURE:
<221> NAME/KEY: primer_bind
<222> LOCATION: 1..23
<223> OTHER INFORMATION: potential microsequencing oligo 4-4-152.mis1
<220> FEATURE:
<221> NAME/KEY: primer_bind
<222> LOCATION: 25..47
<223> OTHER INFORMATION: complement potential microsequencing oligo
      4-4-152.mis2

<400> SEQUENCE: 274
tactttccca ttgttcctga ctttgttatc ctatatataa acagaaa                47

<210> SEQ ID NO 275
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-4-187, variant version
      of SEQ ID198
<220> FEATURE:
<221> NAME/KEY: allele
<222> LOCATION: 24
<223> OTHER INFORMATION: base T ; A in SEQ ID198
<220> FEATURE:
<221> NAME/KEY: primer_bind
<222> LOCATION: 1..23
<223> OTHER INFORMATION: potential microsequencing oligo 4-4-187.mis1
<220> FEATURE:
<221> NAME/KEY: primer_bind
<222> LOCATION: 25..47
<223> OTHER INFORMATION: complement potential microsequencing oligo
      4-4-187.mis2

<400> SEQUENCE: 275
tataaacaga aacatggatg agttaaaaaa aaaaaaaaa aaaaaaa                 47

<210> SEQ ID NO 276
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-4-288, variant version
      of SEQ ID199
<220> FEATURE:
<221> NAME/KEY: allele
<222> LOCATION: 24
<223> OTHER INFORMATION: base C ; G in SEQ ID199
<220> FEATURE:
<221> NAME/KEY: primer_bind
<222> LOCATION: 1..23
<223> OTHER INFORMATION: potential microsequencing oligo 4-4-288.mis1
<220> FEATURE:
<221> NAME/KEY: primer_bind
<222> LOCATION: 25..47
<223> OTHER INFORMATION: complement potential microsequencing oligo
      4-4-288.mis2

<400> SEQUENCE: 276
ctgtcatcaa ctaattttca caactaccta tgttttgatt tcatgta                47
```

```
<210> SEQ ID NO 277
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-42-304, variant version
      of SEQ ID200
<220> FEATURE:
<221> NAME/KEY: allele
<222> LOCATION: 24
<223> OTHER INFORMATION: base T ; C in SEQ ID200
<220> FEATURE:
<221> NAME/KEY: primer_bind
<222> LOCATION: 1..23
<223> OTHER INFORMATION: potential microsequencing oligo 4-42-304.mis1
<220> FEATURE:
<221> NAME/KEY: primer_bind
<222> LOCATION: 25..47
<223> OTHER INFORMATION: complement potential microsequencing oligo
      4-42-304.mis2

<400> SEQUENCE: 277
attatttaaa actatttatg taatcttatt ttcagggtt tttaatt                    47

<210> SEQ ID NO 278
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-42-401, variant version
      of SEQ ID201
<220> FEATURE:
<221> NAME/KEY: allele
<222> LOCATION: 24
<223> OTHER INFORMATION: base C ; A in SEQ ID201
<220> FEATURE:
<221> NAME/KEY: primer_bind
<222> LOCATION: 1..23
<223> OTHER INFORMATION: potential microsequencing oligo 4-42-401.mis1
<220> FEATURE:
<221> NAME/KEY: primer_bind
<222> LOCATION: 25..47
<223> OTHER INFORMATION: complement potential microsequencing oligo
      4-42-401.mis2

<400> SEQUENCE: 278
taagaaagaa ttctgtgttc tggccaaagt ttaaacccac agagcca                   47

<210> SEQ ID NO 279
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-43-328, variant version
      of SEQ ID202
<220> FEATURE:
<221> NAME/KEY: allele
<222> LOCATION: 24
<223> OTHER INFORMATION: base T ; C in SEQ ID202
<220> FEATURE:
<221> NAME/KEY: primer_bind
<222> LOCATION: 1..23
<223> OTHER INFORMATION: potential microsequencing oligo 4-43-328.mis1
<220> FEATURE:
<221> NAME/KEY: primer_bind
<222> LOCATION: 25..47
<223> OTHER INFORMATION: complement potential microsequencing oligo
      4-43-328.mis2
```

```
<400> SEQUENCE: 279
agaattctgt gttctggcca aagtttaaac ccacagagcc agtttaa                47

<210> SEQ ID NO 280
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-43-70, variant version
      of SEQ ID203
<220> FEATURE:
<221> NAME/KEY: allele
<222> LOCATION: 24
<223> OTHER INFORMATION: base C ; G in SEQ ID203
<220> FEATURE:
<221> NAME/KEY: primer_bind
<222> LOCATION: 1..23
<223> OTHER INFORMATION: potential microsequencing oligo 4-43-70.mis1
<220> FEATURE:
<221> NAME/KEY: primer_bind
<222> LOCATION: 25..47
<223> OTHER INFORMATION: complement potential microsequencing oligo
      4-43-70.mis2

<400> SEQUENCE: 280
atcgcctcca ttattctcaa aaacaccatg ggacacaaca caagaag                47

<210> SEQ ID NO 281
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-209, variant version
      of SEQ ID204
<220> FEATURE:
<221> NAME/KEY: allele
<222> LOCATION: 24
<223> OTHER INFORMATION: base T ; C in SEQ ID204
<220> FEATURE:
<221> NAME/KEY: primer_bind
<222> LOCATION: 1..23
<223> OTHER INFORMATION: potential microsequencing oligo 4-50-209.mis1
<220> FEATURE:
<221> NAME/KEY: primer_bind
<222> LOCATION: 25..47
<223> OTHER INFORMATION: complement potential microsequencing oligo
      4-50-209.mis2

<400> SEQUENCE: 281
atatagagtg tgcatccctg acattgaaac tgaaggcttt atggttt                47

<210> SEQ ID NO 282
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-293, variant version
      of SEQ ID205
<220> FEATURE:
<221> NAME/KEY: allele
<222> LOCATION: 24
<223> OTHER INFORMATION: base T ; G in SEQ ID205
<220> FEATURE:
<221> NAME/KEY: primer_bind
<222> LOCATION: 1..23
<223> OTHER INFORMATION: potential microsequencing oligo 4-50-293.mis1
<220> FEATURE:
```

```
<221> NAME/KEY: primer_bind
<222> LOCATION: 25..47
<223> OTHER INFORMATION: complement potential microsequencing oligo
      4-50-293.mis2

<400> SEQUENCE: 282
cctgagtccc aggggctga cagtggacag tttaaaacat tgatgaa                    47

<210> SEQ ID NO 283
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-323, variant version
      of SEQ ID206
<220> FEATURE:
<221> NAME/KEY: allele
<222> LOCATION: 24
<223> OTHER INFORMATION: base T ; C in SEQ ID206
<220> FEATURE:
<221> NAME/KEY: primer_bind
<222> LOCATION: 1..23
<223> OTHER INFORMATION: potential microsequencing oligo 4-50-323.mis1
<220> FEATURE:
<221> NAME/KEY: primer_bind
<222> LOCATION: 25..47
<223> OTHER INFORMATION: complement potential microsequencing oligo
      4-50-323.mis2

<400> SEQUENCE: 283
tttaaaacat tgatgaatct ttattactac aaaagggttc gatttag                   47

<210> SEQ ID NO 284
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-329, variant version
      of SEQ ID207
<220> FEATURE:
<221> NAME/KEY: allele
<222> LOCATION: 24
<223> OTHER INFORMATION: base T ; C in SEQ ID207
<220> FEATURE:
<221> NAME/KEY: primer_bind
<222> LOCATION: 1..23
<223> OTHER INFORMATION: potential microsequencing oligo 4-50-329.mis1
<220> FEATURE:
<221> NAME/KEY: primer_bind
<222> LOCATION: 25..47
<223> OTHER INFORMATION: complement potential microsequencing oligo
      4-50-329.mis2

<400> SEQUENCE: 284
acattgatga atctttatta ctataaaagg gttcgattta ggctagc                   47

<210> SEQ ID NO 285
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-50-330, variant version
      of SEQ ID208
<220> FEATURE:
<221> NAME/KEY: allele
<222> LOCATION: 24
<223> OTHER INFORMATION: base T ; A in SEQ ID208
```

```
<220> FEATURE:
<221> NAME/KEY: primer_bind
<222> LOCATION: 1..23
<223> OTHER INFORMATION: potential microsequencing oligo 4-50-330.mis1
<220> FEATURE:
<221> NAME/KEY: primer_bind
<222> LOCATION: 25..47
<223> OTHER INFORMATION: complement potential microsequencing oligo
      4-50-330.mis2

<400> SEQUENCE: 285
cattgatgaa tctttattac tactaaaggg ttcgatttag gctagcc               47

<210> SEQ ID NO 286
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-52-163, variant version
      of SEQ ID209
<220> FEATURE:
<221> NAME/KEY: allele
<222> LOCATION: 24
<223> OTHER INFORMATION: base C ; A in SEQ ID209
<220> FEATURE:
<221> NAME/KEY: primer_bind
<222> LOCATION: 1..23
<223> OTHER INFORMATION: potential microsequencing oligo 4-52-163.mis1
<220> FEATURE:
<221> NAME/KEY: primer_bind
<222> LOCATION: 25..47
<223> OTHER INFORMATION: complement potential microsequencing oligo
      4-52-163.mis2

<400> SEQUENCE: 286
gaacaggata ttcttaacta ccacagaatt ttacacatct attgttt               47

<210> SEQ ID NO 287
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-52-88, variant version
      of SEQ ID210
<220> FEATURE:
<221> NAME/KEY: allele
<222> LOCATION: 24
<223> OTHER INFORMATION: base T ; C in SEQ ID210
<220> FEATURE:
<221> NAME/KEY: primer_bind
<222> LOCATION: 1..23
<223> OTHER INFORMATION: potential microsequencing oligo 4-52-88.mis1
<220> FEATURE:
<221> NAME/KEY: primer_bind
<222> LOCATION: 25..47
<223> OTHER INFORMATION: complement potential microsequencing oligo
      4-52-88.mis2

<400> SEQUENCE: 287
tccatgtcat tattattcaa aagtttaaaa aatacacaag gtgaaaa               47

<210> SEQ ID NO 288
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-53-258, variant version
``` of SEQ ID211
<220> FEATURE:
<221> NAME/KEY: allele
<222> LOCATION: 24
<223> OTHER INFORMATION: base G ; A in SEQ ID211
<220> FEATURE:
<221> NAME/KEY: primer_bind
<222> LOCATION: 1..23
<223> OTHER INFORMATION: potential microsequencing oligo 4-53-258.mis1
<220> FEATURE:
<221> NAME/KEY: primer_bind
<222> LOCATION: 25..47
<223> OTHER INFORMATION: complement potential microsequencing oligo
       4-53-258.mis2

<400> SEQUENCE: 288
gagaaatcat gcagagagaa tgcgttctca ctcaaatttt aacctaa            47

<210> SEQ ID NO 289
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-54-283, variant version
       of SEQ ID212
<220> FEATURE:
<221> NAME/KEY: allele
<222> LOCATION: 24
<223> OTHER INFORMATION: base T ; A in SEQ ID212
<220> FEATURE:
<221> NAME/KEY: primer_bind
<222> LOCATION: 1..23
<223> OTHER INFORMATION: potential microsequencing oligo 4-54-283.mis1
<220> FEATURE:
<221> NAME/KEY: primer_bind
<222> LOCATION: 25..47
<223> OTHER INFORMATION: complement potential microsequencing oligo
       4-54-283.mis2

<400> SEQUENCE: 289
aagtagtttt tcacactttc tctttgatac aatcgatggc ttaatct            47

<210> SEQ ID NO 290
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-54-388, variant version
       of SEQ ID213
<220> FEATURE:
<221> NAME/KEY: allele
<222> LOCATION: 24
<223> OTHER INFORMATION: base C ; A in SEQ ID213
<220> FEATURE:
<221> NAME/KEY: primer_bind
<222> LOCATION: 1..23
<223> OTHER INFORMATION: potential microsequencing oligo 4-54-388.mis1
<220> FEATURE:
<221> NAME/KEY: primer_bind
<222> LOCATION: 25..47
<223> OTHER INFORMATION: complement potential microsequencing oligo
       4-54-388.mis2

<400> SEQUENCE: 290
ctctctatcg tatacatctt tacccacgct gcagcgccaa gactcca            47

<210> SEQ ID NO 291
<211> LENGTH: 47
<212> TYPE: DNA

```
<213> ORGANISM: Homo Sapiens
<220> FEATURE:
<221> NAME/KEY: allele
<222> LOCATION: 1..47
<223> OTHER INFORMATION: polymorphic fragment 4-55-70, variant version
      of SEQ ID214
<220> FEATURE:
<221> NAME/KEY: allele
<222> LOCATION: 24
<223> OTHER INFORMATION: base T ; A in SEQ ID214
<220> FEATURE:
<221> NAME/KEY: primer_bind
<222> LOCATION: 1..23
<223> OTHER INFORMATION: potential microsequencing oligo 4-55-70.mis1
<220> FEATURE:
<221> NAME/KEY: primer_bind
<222> LOCATION: 25..47
<223> OTHER INFORMATION: complement potential microsequencing oligo
      4-55-70.mis2

<400> SEQUENCE: 291
tattaagaac ctaggtttta aaatactctc tatcgtatac atcttta              47

<210> SEQ ID NO 292
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-55-95, variant version
      of SEQ ID215
<220> FEATURE:
<221> NAME/KEY: allele
<222> LOCATION: 24
<223> OTHER INFORMATION: base C ; A in SEQ ID215
<220> FEATURE:
<221> NAME/KEY: primer_bind
<222> LOCATION: 1..23
<223> OTHER INFORMATION: potential microsequencing oligo 4-55-95.mis1
<220> FEATURE:
<221> NAME/KEY: primer_bind
<222> LOCATION: 25..47
<223> OTHER INFORMATION: complement potential microsequencing oligo
      4-55-95.mis2

<400> SEQUENCE: 292
ctctctatcg tatacatctt tacccacgct gcagcgccaa gactcca              47

<210> SEQ ID NO 293
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-56-159, variant version
      of SEQ ID216
<220> FEATURE:
<221> NAME/KEY: allele
<222> LOCATION: 24
<223> OTHER INFORMATION: base T ; C in SEQ ID216
<220> FEATURE:
<221> NAME/KEY: primer_bind
<222> LOCATION: 1..23
<223> OTHER INFORMATION: potential microsequencing oligo 4-56-159.mis1
<220> FEATURE:
<221> NAME/KEY: primer_bind
<222> LOCATION: 25..47
<223> OTHER INFORMATION: complement potential microsequencing oligo
      4-56-159.mis2

<400> SEQUENCE: 293 aagtttcct tctcttctgt agatgtctcc atgttacagt caactat               47
```

<210> SEQ ID NO 294
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-56-213, variant version
      of SEQ ID217
<220> FEATURE:
<221> NAME/KEY: allele
<222> LOCATION: 24
<223> OTHER INFORMATION: base G ; A in SEQ ID217
<220> FEATURE:
<221> NAME/KEY: primer_bind
<222> LOCATION: 1..23
<223> OTHER INFORMATION: potential microsequencing oligo 4-56-213.mis1
<220> FEATURE:
<221> NAME/KEY: primer_bind
<222> LOCATION: 25..47
<223> OTHER INFORMATION: complement potential microsequencing oligo
      4-56-213.mis2

<400> SEQUENCE: 294
atggctcatg ttcactctgg ttcgccttca gaggagtttg atatttt                47

<210> SEQ ID NO 295
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-58-289, variant version
      of SEQ ID218
<220> FEATURE:
<221> NAME/KEY: allele
<222> LOCATION: 24
<223> OTHER INFORMATION: base C ; G in SEQ ID218
<220> FEATURE:
<221> NAME/KEY: primer_bind
<222> LOCATION: 1..23
<223> OTHER INFORMATION: potential microsequencing oligo 4-58-289.mis1
<220> FEATURE:
<221> NAME/KEY: primer_bind
<222> LOCATION: 25..47
<223> OTHER INFORMATION: complement potential microsequencing oligo
      4-58-289.mis2

<400> SEQUENCE: 295
catacctgca gcctgctttt ggtcaggggt gactacttta cctgcaa                47

<210> SEQ ID NO 296
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-58-318, variant version
      of SEQ ID219
<220> FEATURE:
<221> NAME/KEY: allele
<222> LOCATION: 24
<223> OTHER INFORMATION: base C ; A in SEQ ID219
<220> FEATURE:
<221> NAME/KEY: primer_bind
<222> LOCATION: 1..23
<223> OTHER INFORMATION: potential microsequencing oligo 4-58-318.mis1
<220> FEATURE:
<221> NAME/KEY: primer_bind
<222> LOCATION: 25..47
<223> OTHER INFORMATION: complement potential microsequencing oligo 4-58-318.mis2

<400> SEQUENCE: 296
tgactacttt acctgcaata tttctttgca agtttatttc ttcctttt            47

<210> SEQ ID NO 297
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-60-266, variant version
      of SEQ ID220
<220> FEATURE:
<221> NAME/KEY: allele
<222> LOCATION: 24
<223> OTHER INFORMATION: base T ; G in SEQ ID220
<220> FEATURE:
<221> NAME/KEY: primer_bind
<222> LOCATION: 1..23
<223> OTHER INFORMATION: potential microsequencing oligo 4-60-266.mis1
<220> FEATURE:
<221> NAME/KEY: primer_bind
<222> LOCATION: 25..47
<223> OTHER INFORMATION: complement potential microsequencing oligo
      4-60-266.mis2

<400> SEQUENCE: 297
aacaggacca agacactgca ttatataaag tttcagtatt tcttagc            47

<210> SEQ ID NO 298
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-60-293, variant version
      of SEQ ID221
<220> FEATURE:
<221> NAME/KEY: allele
<222> LOCATION: 24
<223> OTHER INFORMATION: base T ; C in SEQ ID221
<220> FEATURE:
<221> NAME/KEY: primer_bind
<222> LOCATION: 1..23
<223> OTHER INFORMATION: potential microsequencing oligo 4-60-293.mis1
<220> FEATURE:
<221> NAME/KEY: primer_bind
<222> LOCATION: 25..47
<223> OTHER INFORMATION: complement potential microsequencing oligo
      4-60-293.mis2

<400> SEQUENCE: 298
aagtttcagt atttcttagc agatgaagcc agcaggaagt cctccta            47

<210> SEQ ID NO 299
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-84-241, variant version
      of SEQ ID222
<220> FEATURE:
<221> NAME/KEY: allele
<222> LOCATION: 24
<223> OTHER INFORMATION: base T ; G in SEQ ID222
<220> FEATURE:
<221> NAME/KEY: primer_bind
<222> LOCATION: 1..23

```
<223> OTHER INFORMATION: potential microsequencing oligo 4-84-241.mis1
<220> FEATURE:
<221> NAME/KEY: primer_bind
<222> LOCATION: 25..47
<223> OTHER INFORMATION: complement potential microsequencing oligo
      4-84-241.mis2

<400> SEQUENCE: 299
gaaaaaaaaa tagtgactgc cactgtgaat aattcagttc ttcagaa                    47

<210> SEQ ID NO 300
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-84-262, variant version
      of SEQ ID223
<220> FEATURE:
<221> NAME/KEY: allele
<222> LOCATION: 24
<223> OTHER INFORMATION: base G ; A in SEQ ID223
<220> FEATURE:
<221> NAME/KEY: primer_bind
<222> LOCATION: 1..23
<223> OTHER INFORMATION: potential microsequencing oligo 4-84-262.mis1
<220> FEATURE:
<221> NAME/KEY: primer_bind
<222> LOCATION: 25..47
<223> OTHER INFORMATION: complement potential microsequencing oligo
      4-84-262.mis2

<400> SEQUENCE: 300
acggtgaata attcagttct tcagaagcag caacatgatc tcatgga                    47

<210> SEQ ID NO 301
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-86-206, variant version
      of SEQ ID224
<220> FEATURE:
<221> NAME/KEY: allele
<222> LOCATION: 24
<223> OTHER INFORMATION: base G ; A in SEQ ID224
<220> FEATURE:
<221> NAME/KEY: primer_bind
<222> LOCATION: 1..23
<223> OTHER INFORMATION: potential microsequencing oligo 4-86-206.mis1
<220> FEATURE:
<221> NAME/KEY: primer_bind
<222> LOCATION: 25..47
<223> OTHER INFORMATION: complement potential microsequencing oligo
      4-86-206.mis2

<400> SEQUENCE: 301
gtattcaaat caggacacac cacgaatggc atctacacgt taacatt                    47

<210> SEQ ID NO 302
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-86-309, variant version
      of SEQ ID225
<220> FEATURE:
<221> NAME/KEY: allele
```

```
<222> LOCATION: 24
<223> OTHER INFORMATION: base T ; A in SEQ ID225
<220> FEATURE:
<221> NAME/KEY: primer_bind
<222> LOCATION: 1..23
<223> OTHER INFORMATION: potential microsequencing oligo 4-86-309.mis1
<220> FEATURE:
<221> NAME/KEY: primer_bind
<222> LOCATION: 25..47
<223> OTHER INFORMATION: complement potential microsequencing oligo
      4-86-309.mis2

<400> SEQUENCE: 302
tggctctagg caggccactt tagtgagtga ggaaccagag agcagaa                    47

<210> SEQ ID NO 303
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-88-349, variant version
      of SEQ ID226
<220> FEATURE:
<221> NAME/KEY: allele
<222> LOCATION: 24
<223> OTHER INFORMATION: base C ; G in SEQ ID226
<220> FEATURE:
<221> NAME/KEY: primer_bind
<222> LOCATION: 1..23
<223> OTHER INFORMATION: potential microsequencing oligo 4-88-349.mis1
<220> FEATURE:
<221> NAME/KEY: primer_bind
<222> LOCATION: 25..47
<223> OTHER INFORMATION: complement potential microsequencing oligo
      4-88-349.mis2

<400> SEQUENCE: 303
gaaactaaaa gacaatattc agtctgagat tttccaagtt ctttatg                    47

<210> SEQ ID NO 304
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 4-89-87, variant version
      of SEQ ID227
<220> FEATURE:
<221> NAME/KEY: allele
<222> LOCATION: 24
<223> OTHER INFORMATION: base T ; C in SEQ ID227
<220> FEATURE:
<221> NAME/KEY: primer_bind
<222> LOCATION: 1..23
<223> OTHER INFORMATION: potential microsequencing oligo 4-89-87.mis1
<220> FEATURE:
<221> NAME/KEY: primer_bind
<222> LOCATION: 25..47
<223> OTHER INFORMATION: complement potential microsequencing oligo
      4-89-87.mis2

<400> SEQUENCE: 304
ttcttccctg aacgctggtt tcatatagtt tttgtgttga aataga                     47

<210> SEQ ID NO 305
<211> LENGTH: 47
<212> TYPE: DNA
<213> ORGANISM: Homo Sapiens
<220> FEATURE:
<221> NAME/KEY: allele
```

```
<222> LOCATION: 1..47
<223> OTHER INFORMATION: polymorphic fragment 99-123-184, variant
      version of SEQ ID228
<220> FEATURE:
<221> NAME/KEY: allele
<222> LOCATION: 24
<223> OTHER INFORMATION: base C ; G in SEQ ID228
<220> FEATURE:
<221> NAME/KEY: primer_bind
<222> LOCATION: 1..23
<223> OTHER INFORMATION: potential microsequencing oligo 99-123-184.mis1
<220> FEATURE:
<221> NAME/KEY: primer_bind
<222> LOCATION: 25..47
<223> OTHER INFORMATION: complement potential microsequencing oligo
      99-123-184.mis2

<400> SEQUENCE: 305
ccagcccaga acattcacca gctcggccaa gagttctgct gggtttt                47

<210> SEQ ID NO 306
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-202, variant version
      of SEQ ID229
<220> FEATURE:
<221> NAME/KEY: allele
<222> LOCATION: 24
<223> OTHER INFORMATION: base C ; A in SEQ ID229
<220> FEATURE:
<221> NAME/KEY: primer_bind
<222> LOCATION: 1..23
<223> OTHER INFORMATION: potential microsequencing oligo 99-128-202.mis1
<220> FEATURE:
<221> NAME/KEY: primer_bind
<222> LOCATION: 25..47
<223> OTHER INFORMATION: complement potential microsequencing oligo
      99-128-202.mis2

<400> SEQUENCE: 306
aatgtctgtt tcttagagaa ctgcaacaca cacacataca tacacac                47

<210> SEQ ID NO 307
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-275, variant
      version of SEQ ID230
<220> FEATURE:
<221> NAME/KEY: allele
<222> LOCATION: 24
<223> OTHER INFORMATION: base G ; A in SEQ ID230
<220> FEATURE:
<221> NAME/KEY: primer_bind
<222> LOCATION: 1..23
<223> OTHER INFORMATION: potential microsequencing oligo 99-128-275.mis1
<220> FEATURE:
<221> NAME/KEY: primer_bind
<222> LOCATION: 25..47
<223> OTHER INFORMATION: complement potential microsequencing oligo
      99-128-275.mis2

<400> SEQUENCE: 307
acacccctac ctcacatgtg taggcaaatg tatgcatata tgtctct                47

<210> SEQ ID NO 308
```

```
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-313, variant
      version of SEQ ID231
<220> FEATURE:
<221> NAME/KEY: allele
<222> LOCATION: 24
<223> OTHER INFORMATION: base G ; A in SEQ ID231
<220> FEATURE:
<221> NAME/KEY: primer_bind
<222> LOCATION: 1..23
<223> OTHER INFORMATION: potential microsequencing oligo 99-128-313.mis1
<220> FEATURE:
<221> NAME/KEY: primer_bind
<222> LOCATION: 25..47
<223> OTHER INFORMATION: complement potential microsequencing oligo
      99-128-313.mis2

<400> SEQUENCE: 308
tatgtctcta gacagatata catgagattc tatttggcat agaaaaa                    47

<210> SEQ ID NO 309
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-128-60, variant version
      of SEQ ID232
<220> FEATURE:
<221> NAME/KEY: allele
<222> LOCATION: 24
<223> OTHER INFORMATION: base T ; C in SEQ ID232
<220> FEATURE:
<221> NAME/KEY: primer_bind
<222> LOCATION: 1..23
<223> OTHER INFORMATION: potential microsequencing oligo 99-128-60.mis1
<220> FEATURE:
<221> NAME/KEY: primer_bind
<222> LOCATION: 25..47
<223> OTHER INFORMATION: complement potential microsequencing oligo
      99-128-60.mis2

<400> SEQUENCE: 309
gcactgtgac ccaggcgcta ggttcctctt acagtgacac tccgaca                    47

<210> SEQ ID NO 310
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-12907-295, variant
      version of SEQ ID233
<220> FEATURE:
<221> NAME/KEY: allele
<222> LOCATION: 24
<223> OTHER INFORMATION: base G ; A in SEQ ID233
<220> FEATURE:
<221> NAME/KEY: primer_bind
<222> LOCATION: 1..23
<223> OTHER INFORMATION: potential microsequencing oligo
      99-12907-295.mis1
<220> FEATURE:
<221> NAME/KEY: primer_bind
<222> LOCATION: 25..47
<223> OTHER INFORMATION: complement potential microsequencing oligo
      99-12907-295.mis2
```

```
<400> SEQUENCE: 310
gctatatggc attatatctc cacggggcag acctgatgta caagatg                    47

<210> SEQ ID NO 311
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-130-58, variant version
      of SEQ ID234
<220> FEATURE:
<221> NAME/KEY: allele
<222> LOCATION: 24
<223> OTHER INFORMATION: base T ; C in SEQ ID234
<220> FEATURE:
<221> NAME/KEY: primer_bind
<222> LOCATION: 1..23
<223> OTHER INFORMATION: potential microsequencing oligo 99-130-58.mis1
<220> FEATURE:
<221> NAME/KEY: primer_bind
<222> LOCATION: 25..47
<223> OTHER INFORMATION: complement potential microsequencing oligo
      99-130-58.mis2

<400> SEQUENCE: 311
aaagcaaaag agcttcaaaa atatttcagg agtgtgcata tggcgag                    47

<210> SEQ ID NO 312
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-134-362, variant
      version of SEQ ID235
<220> FEATURE:
<221> NAME/KEY: allele
<222> LOCATION: 24
<223> OTHER INFORMATION: base T ; G in SEQ ID235
<220> FEATURE:
<221> NAME/KEY: primer_bind
<222> LOCATION: 1..23
<223> OTHER INFORMATION: potential microsequencing oligo 99-134-362.mis1
<220> FEATURE:
<221> NAME/KEY: primer_bind
<222> LOCATION: 25..47
<223> OTHER INFORMATION: complement potential microsequencing oligo
      99-134-362.mis2

<400> SEQUENCE: 312
caaaacactc atgttagtta gattattatt cctattacaa agataag                    47

<210> SEQ ID NO 313
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-140-130, variant
      version of SEQ ID236
<220> FEATURE:
<221> NAME/KEY: allele
<222> LOCATION: 24
<223> OTHER INFORMATION: base T ; C in SEQ ID236
<220> FEATURE:
<221> NAME/KEY: primer_bind
<222> LOCATION: 1..23
<223> OTHER INFORMATION: potential microsequencing oligo 99-140-130.mis1
<220> FEATURE:
```

```
<221> NAME/KEY: primer_bind
<222> LOCATION: 25..47
<223> OTHER INFORMATION: complement potential microsequencing oligo
      99-140-130.mis2

<400> SEQUENCE: 313
tgttcaaaag cagctacaga ccatatgtaa acaattgagc atggctg                    47

<210> SEQ ID NO 314
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1462-238, variant
      version of SEQ ID237
<220> FEATURE:
<221> NAME/KEY: allele
<222> LOCATION: 24
<223> OTHER INFORMATION: base C ; G in SEQ ID237
<220> FEATURE:
<221> NAME/KEY: primer_bind
<222> LOCATION: 1..23
<223> OTHER INFORMATION: potential microsequencing oligo
      99-1462-238.mis1
<220> FEATURE:
<221> NAME/KEY: primer_bind
<222> LOCATION: 25..47
<223> OTHER INFORMATION: complement potential microsequencing oligo
      99-1462-238.mis2

<400> SEQUENCE: 314
ccctttcaag gttagtaact catctgctgt gtttctgctt cagaagg                    47

<210> SEQ ID NO 315
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-147-181, variant
      version of SEQ ID238
<220> FEATURE:
<221> NAME/KEY: allele
<222> LOCATION: 24
<223> OTHER INFORMATION: base G ; A in SEQ ID238
<220> FEATURE:
<221> NAME/KEY: primer_bind
<222> LOCATION: 1..23
<223> OTHER INFORMATION: potential microsequencing oligo 99-147-181.mis1
<220> FEATURE:
<221> NAME/KEY: primer_bind
<222> LOCATION: 25..47
<223> OTHER INFORMATION: complement potential microsequencing oligo
      99-147-181.mis2

<400> SEQUENCE: 315
gtgtcatgaa aaagagcatg atagaaagaa aaacttaaat ctttata                    47

<210> SEQ ID NO 316
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1474-156, variant
      version of SEQ ID239
<220> FEATURE:
<221> NAME/KEY: allele
<222> LOCATION: 24
```

```
<223> OTHER INFORMATION: base T ; G in SEQ ID239
<220> FEATURE:
<221> NAME/KEY: primer_bind
<222> LOCATION: 1..23
<223> OTHER INFORMATION: potential microsequencing oligo
      99-1474-156.mis1
<220> FEATURE:
<221> NAME/KEY: primer_bind
<222> LOCATION: 25..47
<223> OTHER INFORMATION: complement potential microsequencing oligo
      99-1474-156.mis2

<400> SEQUENCE: 316
cttgtactca taagttaaat atttataaca agaagaaata tggactt                47

<210> SEQ ID NO 317
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1474-359, variant
      version of SEQ ID240
<220> FEATURE:
<221> NAME/KEY: allele
<222> LOCATION: 24
<223> OTHER INFORMATION: base G ; A in SEQ ID240
<220> FEATURE:
<221> NAME/KEY: primer_bind
<222> LOCATION: 1..23
<223> OTHER INFORMATION: potential microsequencing oligo
      99-1474-359.mis1
<220> FEATURE:
<221> NAME/KEY: primer_bind
<222> LOCATION: 25..47
<223> OTHER INFORMATION: complement potential microsequencing oligo
      99-1474-359.mis2

<400> SEQUENCE: 317
aaaaaaaatc aaattattgt accgaattcc ctaatatcag atgtgta                47

<210> SEQ ID NO 318
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1479-158, variant
      version of SEQ ID241
<220> FEATURE:
<221> NAME/KEY: allele
<222> LOCATION: 24
<223> OTHER INFORMATION: base T ; C in SEQ ID241
<220> FEATURE:
<221> NAME/KEY: primer_bind
<222> LOCATION: 1..23
<223> OTHER INFORMATION: potential microsequencing oligo
      99-1479-158.mis1
<220> FEATURE:
<221> NAME/KEY: primer_bind
<222> LOCATION: 25..47
<223> OTHER INFORMATION: complement potential microsequencing oligo
      99-1479-158.mis2

<400> SEQUENCE: 318
tttaaaaatc cacttgtaat cgctgctaat tggagtgtat attcagg                47

<210> SEQ ID NO 319
<211> LENGTH: 47
<212> TYPE: DNA
<213> ORGANISM: Homo Sapiens
```

```
<220> FEATURE:
<221> NAME/KEY: allele
<222> LOCATION: 1..47
<223> OTHER INFORMATION: polymorphic fragment 99-1479-379, variant
      version of SEQ ID242
<220> FEATURE:
<221> NAME/KEY: allele
<222> LOCATION: 24
<223> OTHER INFORMATION: base G ; A in SEQ ID242
<220> FEATURE:
<221> NAME/KEY: primer_bind
<222> LOCATION: 1..23
<223> OTHER INFORMATION: potential microsequencing oligo
      99-1479-379.mis1
<220> FEATURE:
<221> NAME/KEY: primer_bind
<222> LOCATION: 25..47
<223> OTHER INFORMATION: complement potential microsequencing oligo
      99-1479-379.mis2

<400> SEQUENCE: 319
gtagagctgt gtactgaggt cagggaagca gctcatggta cagcctt                47

<210> SEQ ID NO 320
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-129, variant
      version of SEQ ID243
<220> FEATURE:
<221> NAME/KEY: allele
<222> LOCATION: 24
<223> OTHER INFORMATION: base G ; A in SEQ ID243
<220> FEATURE:
<221> NAME/KEY: primer_bind
<222> LOCATION: 1..23
<223> OTHER INFORMATION: potential microsequencing oligo 99-148-129.mis1
<220> FEATURE:
<221> NAME/KEY: primer_bind
<222> LOCATION: 25..47
<223> OTHER INFORMATION: complement potential microsequencing oligo
      99-148-129.mis2

<400> SEQUENCE: 320
ttcatatcta tacaaataat tttgaattta atacataggg ctgcaaa                47

<210> SEQ ID NO 321
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-132, variant
      version of SEQ ID244
<220> FEATURE:
<221> NAME/KEY: allele
<222> LOCATION: 24
<223> OTHER INFORMATION: base T ; C in SEQ ID244
<220> FEATURE:
<221> NAME/KEY: primer_bind
<222> LOCATION: 1..23
<223> OTHER INFORMATION: potential microsequencing oligo 99-148-132.mis1
<220> FEATURE:
<221> NAME/KEY: primer_bind
<222> LOCATION: 25..47
<223> OTHER INFORMATION: complement potential microsequencing oligo
      99-148-132.mis2

<400> SEQUENCE: 321
atatctatac aaataatttt gaatttaata catagggctg caaaaca                47
```

```
<210> SEQ ID NO 322
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-139, variant
      version of SEQ ID245
<220> FEATURE:
<221> NAME/KEY: allele
<222> LOCATION: 24
<223> OTHER INFORMATION: base T ; C in SEQ ID245
<220> FEATURE:
<221> NAME/KEY: primer_bind
<222> LOCATION: 1..23
<223> OTHER INFORMATION: potential microsequencing oligo 99-148-139.mis1
<220> FEATURE:
<221> NAME/KEY: primer_bind
<222> LOCATION: 25..47
<223> OTHER INFORMATION: complement potential microsequencing oligo
      99-148-139.mis2

<400> SEQUENCE: 322
tacaaataat tttgaattta atatataggg ctgcaaaaca aggttga              47

<210> SEQ ID NO 323
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-140, variant
      version of SEQ ID246
<220> FEATURE:
<221> NAME/KEY: allele
<222> LOCATION: 24
<223> OTHER INFORMATION: base G ; A in SEQ ID246
<220> FEATURE:
<221> NAME/KEY: primer_bind
<222> LOCATION: 1..23
<223> OTHER INFORMATION: potential microsequencing oligo 99-148-140.mis1
<220> FEATURE:
<221> NAME/KEY: primer_bind
<222> LOCATION: 25..47
<223> OTHER INFORMATION: complement potential microsequencing oligo
      99-148-140.mis2

<400> SEQUENCE: 323
acaaataatt ttgaatttaa tacgtagggc tgcaaaacaa ggttgat              47

<210> SEQ ID NO 324
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-182, variant
      version of SEQ ID247
<220> FEATURE:
<221> NAME/KEY: allele
<222> LOCATION: 24
<223> OTHER INFORMATION: base G ; A in SEQ ID247
<220> FEATURE:
<221> NAME/KEY: primer_bind
<222> LOCATION: 1..23
<223> OTHER INFORMATION: potential microsequencing oligo 99-148-182.mis1
<220> FEATURE:
<221> NAME/KEY: primer_bind
<222> LOCATION: 25..47
<223> OTHER INFORMATION: complement potential microsequencing oligo
```

99-148-182.mis2

<400> SEQUENCE: 324
ttgatgttga tatgggcaac tgtgtgttgg atggtcccaa agcattc        47

<210> SEQ ID NO 325
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-366, variant
      version of SEQ ID248
<220> FEATURE:
<221> NAME/KEY: allele
<222> LOCATION: 24
<223> OTHER INFORMATION: base T ; G in SEQ ID248
<220> FEATURE:
<221> NAME/KEY: primer_bind
<222> LOCATION: 1..23
<223> OTHER INFORMATION: potential microsequencing oligo 99-148-366.mis1
<220> FEATURE:
<221> NAME/KEY: primer_bind
<222> LOCATION: 25..47
<223> OTHER INFORMATION: complement potential microsequencing oligo
      99-148-366.mis2

<400> SEQUENCE: 325
tccttgtcaa aggtctctcc ctgttgctca cggctgccgc ctcaaag        47

<210> SEQ ID NO 326
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-148-76, variant version
      of SEQ ID249
<220> FEATURE:
<221> NAME/KEY: allele
<222> LOCATION: 24
<223> OTHER INFORMATION: base T ; C in SEQ ID249
<220> FEATURE:
<221> NAME/KEY: primer_bind
<222> LOCATION: 1..23
<223> OTHER INFORMATION: potential microsequencing oligo 99-148-76.mis1
<220> FEATURE:
<221> NAME/KEY: primer_bind
<222> LOCATION: 25..47
<223> OTHER INFORMATION: complement potential microsequencing oligo
      99-148-76.mis2

<400> SEQUENCE: 326
tgatagaatg ccttcctgaa ttattactct tgatggcttc ataaaac        47

<210> SEQ ID NO 327
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1480-290, variant
      version of SEQ ID250
<220> FEATURE:
<221> NAME/KEY: allele
<222> LOCATION: 24
<223> OTHER INFORMATION: base T ; G in SEQ ID250
<220> FEATURE:
<221> NAME/KEY: primer_bind
<222> LOCATION: 1..23

```
<223> OTHER INFORMATION: potential microsequencing oligo
      99-1480-290.mis1
<220> FEATURE:
<221> NAME/KEY: primer_bind
<222> LOCATION: 25..47
<223> OTHER INFORMATION: complement potential microsequencing oligo
      99-1480-290.mis2

<400> SEQUENCE: 327
tgcaccatct tcaccacaac ccctggcaac cactgatcct tttactg            47

<210> SEQ ID NO 328
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1481-285, variant
      version of SEQ ID251
<220> FEATURE:
<221> NAME/KEY: allele
<222> LOCATION: 24
<223> OTHER INFORMATION: base T ; G in SEQ ID251
<220> FEATURE:
<221> NAME/KEY: primer_bind
<222> LOCATION: 1..23
<223> OTHER INFORMATION: potential microsequencing oligo
      99-1481-285.mis1
<220> FEATURE:
<221> NAME/KEY: primer_bind
<222> LOCATION: 25..47
<223> OTHER INFORMATION: complement potential microsequencing oligo
      99-1481-285.mis2

<400> SEQUENCE: 328
tcccataacc tgttttgctt ctctctctaa cctcaagatg gtataaa            47

<210> SEQ ID NO 329
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1484-101, variant
      version of SEQ ID252
<220> FEATURE:
<221> NAME/KEY: allele
<222> LOCATION: 24
<223> OTHER INFORMATION: base C ; A in SEQ ID252
<220> FEATURE:
<221> NAME/KEY: primer_bind
<222> LOCATION: 1..23
<223> OTHER INFORMATION: potential microsequencing oligo
      99-1484-101.mis1
<220> FEATURE:
<221> NAME/KEY: primer_bind
<222> LOCATION: 25..47
<223> OTHER INFORMATION: complement potential microsequencing oligo
      99-1484-101.mis2

<400> SEQUENCE: 329
aaaaagatca aatataagca tgtcactcct ctccttaaaa tctcagt            47

<210> SEQ ID NO 330
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1484-328, variant
```

```
           version of SEQ ID253
<220> FEATURE:
<221> NAME/KEY: allele
<222> LOCATION: 24
<223> OTHER INFORMATION: base C ; G in SEQ ID253
<220> FEATURE:
<221> NAME/KEY: primer_bind
<222> LOCATION: 1..23
<223> OTHER INFORMATION: potential microsequencing oligo
       99-1484-328.mis1
<220> FEATURE:
<221> NAME/KEY: primer_bind
<222> LOCATION: 25..47
<223> OTHER INFORMATION: complement potential microsequencing oligo
       99-1484-328.mis2

<400> SEQUENCE: 330
ggacacgtgg tcatgaggag tttcaaggga ttcagttttc agatccc              47

<210> SEQ ID NO 331
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1485-251, variant
       version of SEQ ID254
<220> FEATURE:
<221> NAME/KEY: allele
<222> LOCATION: 24
<223> OTHER INFORMATION: base T ; G in SEQ ID254
<220> FEATURE:
<221> NAME/KEY: primer_bind
<222> LOCATION: 1..23
<223> OTHER INFORMATION: potential microsequencing oligo
       99-1485-251.mis1
<220> FEATURE:
<221> NAME/KEY: primer_bind
<222> LOCATION: 25..47
<223> OTHER INFORMATION: complement potential microsequencing oligo
       99-1485-251.mis2

<400> SEQUENCE: 331
gattgccttg atatatgctc ccatagaacc aagaatgtcc ccttttc              47

<210> SEQ ID NO 332
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1490-381, variant
       version of SEQ ID255
<220> FEATURE:
<221> NAME/KEY: allele
<222> LOCATION: 24
<223> OTHER INFORMATION: base T ; C in SEQ ID255
<220> FEATURE:
<221> NAME/KEY: primer_bind
<222> LOCATION: 1..23
<223> OTHER INFORMATION: potential microsequencing oligo
       99-1490-381.mis1
<220> FEATURE:
<221> NAME/KEY: primer_bind
<222> LOCATION: 25..47
<223> OTHER INFORMATION: complement potential microsequencing oligo
       99-1490-381.mis2

<400> SEQUENCE: 332
tgcacagtgg aaataccatg tcatggtacg ctactgtgca tctcttc              47
```

```
<210> SEQ ID NO 333
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-1493-280, variant
      version of SEQ ID256
<220> FEATURE:
<221> NAME/KEY: allele
<222> LOCATION: 24
<223> OTHER INFORMATION: base G ; A in SEQ ID256
<220> FEATURE:
<221> NAME/KEY: primer_bind
<222> LOCATION: 1..23
<223> OTHER INFORMATION: potential microsequencing oligo
      99-1493-280.mis1
<220> FEATURE:
<221> NAME/KEY: primer_bind
<222> LOCATION: 25..47
<223> OTHER INFORMATION: complement potential microsequencing oligo
      99-1493-280.mis2

<400> SEQUENCE: 333
ggatgacaga gtattgttgg agggatgggg tttggctgct tgttttt                  47

<210> SEQ ID NO 334
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-151-94, variant version
      of SEQ ID257
<220> FEATURE:
<221> NAME/KEY: allele
<222> LOCATION: 24
<223> OTHER INFORMATION: base G ; A in SEQ ID257
<220> FEATURE:
<221> NAME/KEY: primer_bind
<222> LOCATION: 1..23
<223> OTHER INFORMATION: potential microsequencing oligo 99-151-94.mis1
<220> FEATURE:
<221> NAME/KEY: primer_bind
<222> LOCATION: 25..47
<223> OTHER INFORMATION: complement potential microsequencing oligo
      99-151-94.mis2

<400> SEQUENCE: 334
attgagatca ttgataagga aatgttctaa aatttcaaaa tctatat                  47

<210> SEQ ID NO 335
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-211-291, variant
      version of SEQ ID258
<220> FEATURE:
<221> NAME/KEY: allele
<222> LOCATION: 24
<223> OTHER INFORMATION: base G ; A in SEQ ID258
<220> FEATURE:
<221> NAME/KEY: primer_bind
<222> LOCATION: 1..23
<223> OTHER INFORMATION: potential microsequencing oligo 99-211-291.mis1
<220> FEATURE:
<221> NAME/KEY: primer_bind
<222> LOCATION: 25..47
<223> OTHER INFORMATION: complement potential microsequencing oligo
      99-211-291.mis2
```

```
<400> SEQUENCE: 335
ctggttatat cagactgacc ttcgtgtttt caacaggtca atgcctt                    47

<210> SEQ ID NO 336
<211> LENGTH: 46
<212> TYPE: DNA
<213> ORGANISM: Homo Sapiens
<220> FEATURE:
<221> NAME/KEY: allele
<222> LOCATION: 1..46
<223> OTHER INFORMATION: polymorphic fragment 99-213-37, variant version
      of SEQ ID259
<220> FEATURE:
<221> NAME/KEY: allele
<222> LOCATION: 23
<223> OTHER INFORMATION: base GC ; T in SEQ ID259
<220> FEATURE:
<221> NAME/KEY: primer_bind
<222> LOCATION: 1..22
<223> OTHER INFORMATION: potential microsequencing oligo 99-213-37.mis1
<220> FEATURE:
<221> NAME/KEY: primer_bind
<222> LOCATION: 24..46
<223> OTHER INFORMATION: complement potential microsequencing oligo
      99-213-37.mis2

<400> SEQUENCE: 336
gtgcttccgg ctgcaggact gtgcggagga ctccagtgtc tgacag                    46

<210> SEQ ID NO 337
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-221-442, variant
      version of SEQ ID260
<220> FEATURE:
<221> NAME/KEY: allele
<222> LOCATION: 24
<223> OTHER INFORMATION: base C ; A in SEQ ID260
<220> FEATURE:
<221> NAME/KEY: primer_bind
<222> LOCATION: 1..23
<223> OTHER INFORMATION: potential microsequencing oligo 99-221-442.mis1
<220> FEATURE:
<221> NAME/KEY: primer_bind
<222> LOCATION: 25..47
<223> OTHER INFORMATION: complement potential microsequencing oligo
      99-221-442.mis2

<400> SEQUENCE: 337
tgcctttgta gatatgcatg ggacttccat gacctagcca gacgaat                   47

<210> SEQ ID NO 338
<211> LENGTH: 47
<212> TYPE: DNA
<213> ORGANISM: Homo Sapiens
<220> FEATURE:
<221> NAME/KEY: allele
<222> LOCATION: 1..47
<223> OTHER INFORMATION: polymorphic fragment 99-222-109, variant
      version of SEQ ID261
<220> FEATURE:
<221> NAME/KEY: allele
<222> LOCATION: 24
<223> OTHER INFORMATION: base T ; C in SEQ ID261
<220> FEATURE:
<221> NAME/KEY: primer_bind
<222> LOCATION: 1..23
<223> OTHER INFORMATION: potential microsequencing oligo 99-222-109.mis1
```

```
<220> FEATURE:
<221> NAME/KEY: primer_bind
<222> LOCATION: 25..47
<223> OTHER INFORMATION: complement potential microsequencing oligo
      99-222-109.mis2

<400> SEQUENCE: 338
caggtgagga gtgctggatt ggctacgata tgaatttctt cagcagt                47

<210> SEQ ID NO 339
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 185, SEQ
      262, SEQ 186, SEQ 263, SEQ 187, SEQ 264

<400> SEQUENCE: 339
tctaacctct catccaac                                                18

<210> SEQ ID NO 340
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 188, SEQ
      265, SEQ 189, SEQ 266

<400> SEQUENCE: 340
gttatcgtga gactttttc                                               19

<210> SEQ ID NO 341
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 190, SEQ
      267, SEQ 191, SEQ 268

<400> SEQUENCE: 341
tgctggtgct gtgataac                                                18

<210> SEQ ID NO 342
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 192, SEQ
      269, SEQ 193, SEQ 270

<400> SEQUENCE: 342
tacagccctg taagacac                                                18

<210> SEQ ID NO 343
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 194, SEQ
```

-continued

271

<400> SEQUENCE: 343
cagtatgttc aatgcacag                                                19

<210> SEQ ID NO 344
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 195, SEQ
      272, SEQ 196, SEQ 273

<400> SEQUENCE: 344
aaaacatcga catgggac                                                 18

<210> SEQ ID NO 345
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 197, SEQ
      274, SEQ 198, SEQ 275, SEQ 199, SEQ 276

<400> SEQUENCE: 345
agcatttcga gtcatgtg                                                 18

<210> SEQ ID NO 346
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 200, SEQ
      277, SEQ 201, SEQ 278

<400> SEQUENCE: 346
ccctctttcc tcatgtag                                                 18

<210> SEQ ID NO 347
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 202, SEQ
      279, SEQ 203, SEQ 280

<400> SEQUENCE: 347
taactcgtaa acagagaac                                                19

<210> SEQ ID NO 348
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 204, SEQ
      281, SEQ 205, SEQ 282, SEQ 206, SEQ 283, SEQ 207, SEQ 284, SEQ
      208, SEQ 285

<400> SEQUENCE: 348
gcgtattgaa gctctttg                                          18

<210> SEQ ID NO 349
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 209, SEQ
      286, SEQ 210, SEQ 287

<400> SEQUENCE: 349
aacacgggga ttttaggc                                          18

<210> SEQ ID NO 350
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 211, SEQ
      288

<400> SEQUENCE: 350
cacatactaa ggctaatgg                                         19

<210> SEQ ID NO 351
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 212, SEQ
      289, SEQ 213, SEQ 290

<400> SEQUENCE: 351
gttgctggaa cctatttg                                          18

<210> SEQ ID NO 352
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 214, SEQ
      291, SEQ 215, SEQ 292

<400> SEQUENCE: 352
tcgatggctt aatctacc                                          18

<210> SEQ ID NO 353
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 216, SEQ
      293, SEQ 217, SEQ 294

<400> SEQUENCE: 353
aaagaggagt aaatgggg                                          18

<210> SEQ ID NO 354
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 218, SEQ
      295, SEQ 219, SEQ 296

<400> SEQUENCE: 354
tccccacagc taagagcc                                             18

<210> SEQ ID NO 355
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 220, SEQ
      297, SEQ 221, SEQ 298

<400> SEQUENCE: 355
atacctaatt tcaggggg                                             18

<210> SEQ ID NO 356
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 222, SEQ
      299, SEQ 223, SEQ 300

<400> SEQUENCE: 356
ttaacagagt accttggag                                            19

<210> SEQ ID NO 357
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 224, SEQ
      301, SEQ 225, SEQ 302

<400> SEQUENCE: 357
gtacagcctt ttgcttac                                             18

<210> SEQ ID NO 358
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 226, SEQ
      303

<400> SEQUENCE: 358
aacgtgtcat agaaagcc                                             18

<210> SEQ ID NO 359
<211> LENGTH: 19
<212> TYPE: DNA
<213> ORGANISM: Homo Sapiens

```
<220> FEATURE:
<221> NAME/KEY: misc_feature
<222> LOCATION: 1..19
<223> OTHER INFORMATION: upstream amplification primer for SEQ 227, SEQ
      304

<400> SEQUENCE: 359
gctgatgagt tagataacc                                                  19

<210> SEQ ID NO 360
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 228, SEQ
      305

<400> SEQUENCE: 360
aaagccagga ctagaagg                                                   18

<210> SEQ ID NO 361
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 229, SEQ
      306, SEQ 230, SEQ 307, SEQ 231, SEQ 308, SEQ 232, SEQ
      309

<400> SEQUENCE: 361
gaccagggtt taagttag                                                   18

<210> SEQ ID NO 362
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 233, SEQ
      310

<400> SEQUENCE: 362
tctgttagga cctgtgag                                                   18

<210> SEQ ID NO 363
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 234, SEQ
      311

<400> SEQUENCE: 363
ccataacagc tagtacaac                                                  19

<210> SEQ ID NO 364
<211> LENGTH: 18
<212> TYPE: DNA
<213> ORGANISM: Homo Sapiens
<220> FEATURE:
<221> NAME/KEY: misc_feature
<222> LOCATION: 1..18
```

```
<223> OTHER INFORMATION: upstream amplification primer for SEQ 235, SEQ
      312

<400> SEQUENCE: 364
tggaaaggta ctcagaag                                                    18

<210> SEQ ID NO 365
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 236, SEQ
      313

<400> SEQUENCE: 365
agagcatagt ataaagcag                                                   19

<210> SEQ ID NO 366
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 237, SEQ
      314

<400> SEQUENCE: 366
ctagaagtag ctttaacag                                                   19

<210> SEQ ID NO 367
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 238, SEQ
      315

<400> SEQUENCE: 367
gcagccaatc ttatatttc                                                   19

<210> SEQ ID NO 368
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 239, SEQ
      316, SEQ 240, SEQ 317

<400> SEQUENCE: 368
aaggttgtag agtagaaag                                                   19

<210> SEQ ID NO 369
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 241, SEQ
      318, SEQ 242, SEQ 319

<400> SEQUENCE: 369
```
caactgacac tataaccc                                                     18

<210> SEQ ID NO 370
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 243, SEQ
      320, SEQ 244, SEQ 321, SEQ 245, SEQ 322, SEQ 246, SEQ
      323, SEQ 247, SEQ 324, SEQ 248, SEQ 325, SEQ 249, SEQ 326

<400> SEQUENCE: 370
cagtggagtg tttatgtg                                                     18

<210> SEQ ID NO 371
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 250, SEQ
      327

<400> SEQUENCE: 371
ttgcacaaaa ggtatagag                                                    19

<210> SEQ ID NO 372
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 251, SEQ
      328

<400> SEQUENCE: 372
aggctcccct tttgagttg                                                    19

<210> SEQ ID NO 373
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 252, SEQ
      329, SEQ 253, SEQ 330

<400> SEQUENCE: 373
atcctttcta gctgggag                                                     18

<210> SEQ ID NO 374
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: upstream amplification primer for SEQ 254, SEQ
      331

<400> SEQUENCE: 374
gtttaagaat gtgtgatggg                                                   20

```
<210> SEQ ID NO 375
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: upstream amplification primer for SEQ 255, SEQ
      332

<400> SEQUENCE: 375
aaggcaacag cgttgtgac                                                19

<210> SEQ ID NO 376
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 256, SEQ
      333

<400> SEQUENCE: 376
tttggggggt tttcagtg                                                 18

<210> SEQ ID NO 377
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 257, SEQ
      334

<400> SEQUENCE: 377
aacacaacag caaatccc                                                 18

<210> SEQ ID NO 378
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: upstream amplification primer for SEQ 258, SEQ
      335

<400> SEQUENCE: 378
tccttacttg taacccc                                                  18

<210> SEQ ID NO 379
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: upstream amplification primer for SEQ 259, SEQ
      336

<400> SEQUENCE: 379
atactggcag cgtgtgcttc                                               20

<210> SEQ ID NO 380
<211> LENGTH: 19
<212> TYPE: DNA
```

```
<213> ORGANISM: Homo Sapiens
<220> FEATURE:
<221> NAME/KEY: misc_feature
<222> LOCATION: 1..19
<223> OTHER INFORMATION: upstream amplification primer for SEQ 260, SEQ
      337

<400> SEQUENCE: 380
ccctttttct tcactgttc                                                19

<210> SEQ ID NO 381
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: upstream amplification primer for SEQ 261, SEQ
      338

<400> SEQUENCE: 381 agggagatg agggaagttg                                                20

<210> SEQ ID NO 382
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 185,
      SEQ 262, SEQ 186, SEQ 263, SEQ 187, SEQ 264

<400> SEQUENCE: 382
gactgtatcc tttgatgcac                                               20

<210> SEQ ID NO 383
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 188,
      SEQ 265, SEQ 189, SEQ 266

<400> SEQUENCE: 383
gcataattgt gcttgactgg                                               20

<210> SEQ ID NO 384
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 190,
      SEQ 267, SEQ 191, SEQ 268

<400> SEQUENCE: 384
tgctgagagg agcttttg                                                 18

<210> SEQ ID NO 385
<211> LENGTH: 18
<212> TYPE: DNA
<213> ORGANISM: Homo Sapiens
<220> FEATURE:
<221> NAME/KEY: misc_feature
<222> LOCATION: 1..18
```

```
<223> OTHER INFORMATION: downstream amplification primer for SEQ 192,
      SEQ 269, SEQ 193, SEQ 270

<400> SEQUENCE: 385
tgaggactgc taggaaag                                                  18

<210> SEQ ID NO 386
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 194,
      SEQ 271

<400> SEQUENCE: 386
acaaaatcag gaacaatggg                                                20

<210> SEQ ID NO 387
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 195,
      SEQ 272, SEQ 196, SEQ 273

<400> SEQUENCE: 387
ttgcattttc cccccaac                                                  18

<210> SEQ ID NO 388
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 197,
      SEQ 274, SEQ 198, SEQ 275, SEQ 199, SEQ 276

<400> SEQUENCE: 388
accatttgga caatgggg                                                  18

<210> SEQ ID NO 389
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 200,
      SEQ 277, SEQ 201, SEQ 278

<400> SEQUENCE: 389
gctcttaaac tggctctgtg                                                20

<210> SEQ ID NO 390
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 202,
      SEQ 279, SEQ 203, SEQ 280

<400> SEQUENCE: 390
```

```
ggcatgactt cacgtttc                                                    18
```

```
<210> SEQ ID NO 391
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 204,
      SEQ 281, SEQ 205, SEQ 282, SEQ 206, SEQ 283, SEQ 207, SEQ
      284, SEQ 208, SEQ 285

<400> SEQUENCE: 391
```

```
aggatcttct acagtcac                                                    18
```

```
<210> SEQ ID NO 392
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 209,
      SEQ 286, SEQ 210, SEQ 287

<400> SEQUENCE: 392
```

```
tggtagcgtt tgaaatcatc                                                  20
```

```
<210> SEQ ID NO 393
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 211,
      SEQ 288

<400> SEQUENCE: 393
```

```
tataagcaca aataggttcc                                                  20
```

```
<210> SEQ ID NO 394
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 212,
      SEQ 289, SEQ 213, SEQ 290

<400> SEQUENCE: 394
```

```
gaataactga ggggagtg                                                    18
```

```
<210> SEQ ID NO 395
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 214,
      SEQ 291, SEQ 215, SEQ 292

<400> SEQUENCE: 395
```

```
gtgaatctcc ttttccaag                                                   19
```

```
<210> SEQ ID NO 396
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 216,
      SEQ 293, SEQ 217, SEQ 294

<400> SEQUENCE: 396
ctaaggtgtt gtagacag                                                   18

<210> SEQ ID NO 397
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 218,
      SEQ 295, SEQ 219, SEQ 296

<400> SEQUENCE: 397
cacctcgata aatcaagtcc                                                 20

<210> SEQ ID NO 398
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 220,
      SEQ 297, SEQ 221, SEQ 298

<400> SEQUENCE: 398
gttcacttaa ttctgttgag                                                 20

<210> SEQ ID NO 399
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 222,
      SEQ 299, SEQ 223, SEQ 300

<400> SEQUENCE: 399
cgccttttct gaaaggtg                                                   18

<210> SEQ ID NO 400
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 224,
      SEQ 301, SEQ 225, SEQ 302

<400> SEQUENCE: 400
attttctgca cagcagcg                                                   18

<210> SEQ ID NO 401
<211> LENGTH: 19
<212> TYPE: DNA
```

```
<213> ORGANISM: Homo Sapiens
<220> FEATURE:
<221> NAME/KEY: misc_feature
<222> LOCATION: 1..19
<223> OTHER INFORMATION: downstream amplification primer for SEQ 226,
      SEQ 303

<400> SEQUENCE: 401
tattttctag ctcttctgg                                                     19

<210> SEQ ID NO 402
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 227,
      SEQ 304

<400> SEQUENCE: 402
agcaagagtg attgtaaag                                                     19

<210> SEQ ID NO 403
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 228,
      SEQ 305

<400> SEQUENCE: 403
tattcagaaa ggagtggg                                                      18

<210> SEQ ID NO 404
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 229,
      SEQ 306, SEQ 230, SEQ 307, SEQ 231, SEQ 308, SEQ 232, SEQ 309

<400> SEQUENCE: 404
agagcgttct tgcctttc                                                      18

<210> SEQ ID NO 405
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 233,
      SEQ 310

<400> SEQUENCE: 405 ggtaaccta aaatgttatc                                                     20

<210> SEQ ID NO 406
<211> LENGTH: 21
<212> TYPE: DNA
<213> ORGANISM: Homo Sapiens
<220> FEATURE:
<221> NAME/KEY: misc_feature
<222> LOCATION: 1..21
```

-continued

```
<223> OTHER INFORMATION: downstream amplification primer for SEQ 234,
      SEQ 311

<400> SEQUENCE: 406
agaaaccata agggtatatt g                                              21

<210> SEQ ID NO 407
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 235,
      SEQ 312

<400> SEQUENCE: 407
acagtgcaaa ggttatatc                                                 19

<210> SEQ ID NO 408
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 236,
      SEQ 313

<400> SEQUENCE: 408
gaacaacctt gaattagctt g                                              21

<210> SEQ ID NO 409
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 237,
      SEQ 314

<400> SEQUENCE: 409
gattccagaa gtccatttca g                                              21

<210> SEQ ID NO 410
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 238,
      SEQ 315

<400> SEQUENCE: 410
aggtaagaat gagcaaaaag g                                              21

<210> SEQ ID NO 411
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 239,
      SEQ 316, SEQ 240, SEQ 317

<400> SEQUENCE: 411
```

```
gcttgtgttt gttcaattc                                                    19

<210> SEQ ID NO 412
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 241,
      SEQ 318, SEQ 242, SEQ 319

<400> SEQUENCE: 412
cttgaaatac tcccagcc                                                     18

<210> SEQ ID NO 413
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 243,
      SEQ 320, SEQ 244, SEQ 321, SEQ 245, SEQ 322, SEQ 246, SEQ 323,
      SEQ 247, SEQ 324, SEQ 248, SEQ 325, SEQ 249, SEQ 326

<400> SEQUENCE: 413
ccatgaactg agaactttg                                                    19

<210> SEQ ID NO 414
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 250,
      SEQ 327

<400> SEQUENCE: 414
ggtgacaggt aaagaaac                                                     18

<210> SEQ ID NO 415
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 251,
      SEQ 328

<400> SEQUENCE: 415
attcaggcac agaagtcata c                                                 21

<210> SEQ ID NO 416
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 252,
      SEQ 329, SEQ 253, SEQ 330

<400> SEQUENCE: 416
agggcagcac aatgtagtaa g                                                 21
```

```
<210> SEQ ID NO 417
<211> LENGTH: 18
<212> TYPE: DNA
<213> ORGANISM: Homo Sapiens
<220> FEATURE:
<221> NAME/KEY: misc_feature
<222> LOCATION: 1..18
<223> OTHER INFORMATION: downstream amplification primer for SEQ 254,
      SEQ 331

<400> SEQUENCE: 417
cctctttatc tccaaacc                                                    18

<210> SEQ ID NO 418
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 255,
      SEQ 332

<400> SEQUENCE: 418
gaaaacaatc aagctctgg                                                   19

<210> SEQ ID NO 419
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 256,
      SEQ 333

<400> SEQUENCE: 419
cctttatatc cttggagtc                                                   19

<210> SEQ ID NO 420
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 257,
      SEQ 334

<400> SEQUENCE: 420
tattacacgt tccaactctt c                                                21

<210> SEQ ID NO 421
<211> LENGTH: 20
<212> TYPE: DNA
<213> ORGANISM: Homo Sapiens
<220> FEATURE:
<221> NAME/KEY: misc_feature
<222> LOCATION: 1..20
<223> OTHER INFORMATION: downstream amplification primer for SEQ 258,
      SEQ 335

<400> SEQUENCE: 421
ctgtgtttaa gtgactgctg                                                  20

<210> SEQ ID NO 422
<211> LENGTH: 21
<212> TYPE: DNA
```

```
<213> ORGANISM: Homo Sapiens
<220> FEATURE:
<221> NAME/KEY: misc_feature
<222> LOCATION: 1..21
<223> OTHER INFORMATION: downstream amplification primer for SEQ 259,
      SEQ 336

<400> SEQUENCE: 422
ttattgcccc acatgcttga g                                              21

<210> SEQ ID NO 423
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: downstream amplification primer for SEQ 260,
      SEQ 337

<400> SEQUENCE: 423
tcattcgtct ggctaggtc                                                 19

<210> SEQ ID NO 424
<211> LENGTH: 21
<212> TYPE: DNA
<213> ORGANISM: Homo Sapiens
<220> FEATURE:
<221> NAME/KEY: misc_feature
<222> LOCATION: 1..21
<223> OTHER INFORMATION: downstream amplification primer for SEQ 261,
      SEQ 338

<400> SEQUENCE: 424
gaaacagact gaagcaagga c                                              21

<210> SEQ ID NO 425
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-14-107.mis1

<400> SEQUENCE: 425
acaaccacca aatgcatac                                                 19

<210> SEQ ID NO 426
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-14-317.mis1

<400> SEQUENCE: 426
acatgcaagg tgggcaaga                                                 19

<210> SEQ ID NO 427
<211> LENGTH: 19
<212> TYPE: DNA
<213> ORGANISM: Homo Sapiens
<220> FEATURE:
<221> NAME/KEY: misc_feature
<222> LOCATION: 1..19
```

<223> OTHER INFORMATION: potential microsequencing oligo for
     4-14-35.mis1

<400> SEQUENCE: 427
aacacagaaa ccgctaaaa                                                   19

<210> SEQ ID NO 428
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-20-149.mis1

<400> SEQUENCE: 428
tttttgctgt gtcttcaaag tga                                              23

<210> SEQ ID NO 429
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
     4-20-77.mis1

<400> SEQUENCE: 429
acatgaagat tctgaaggg                                                   19

<210> SEQ ID NO 430
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-22-174.mis1

<400> SEQUENCE: 430
ggattgtgca gaagttgcct ttc                                              23

<210> SEQ ID NO 431
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
     4-22-176.mis1

<400> SEQUENCE: 431
tgcagaagtt gcctttcat                                                   19

<210> SEQ ID NO 432
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
     4-26-60.mis1

<400> SEQUENCE: 432
ggaaagtgca tcttaagac                                                   19

<210> SEQ ID NO 433
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-26-72.mis1

<400> SEQUENCE: 433
ttaagacagt tagcaggcc                                                19

<210> SEQ ID NO 434
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-3-130.mis1

<400> SEQUENCE: 434
gggcctaaaa cagtattct                                                19

<210> SEQ ID NO 435
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-38-63.mis1

<400> SEQUENCE: 435
agttataaga aaatcaggc                                                19

<210> SEQ ID NO 436
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-38-83.mis1

<400> SEQUENCE: 436
gaggctaaac ttttttttt                                                19

<210> SEQ ID NO 437
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-4-152.mis1

<400> SEQUENCE: 437
ttcccattgt tcctgactt                                                19

<210> SEQ ID NO 438
<211> LENGTH: 23

```
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-4-187.mis1

<400> SEQUENCE: 438
tataaacaga aacatggatg agt                                               23

<210> SEQ ID NO 439
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-4-288.mis1

<400> SEQUENCE: 439
catcaactaa ttttcacaa                                                    19

<210> SEQ ID NO 440
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-42-304.mis1

<400> SEQUENCE: 440
tttaaaacta tttatgtaa                                                    19

<210> SEQ ID NO 441
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-42-401.mis1

<400> SEQUENCE: 441
taagaaagaa ttctgtgttc tgg                                               23

<210> SEQ ID NO 442
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-43-328.mis1

<400> SEQUENCE: 442
ttctgtgttc tggccaaag                                                    19

<210> SEQ ID NO 443
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-43-70.mis1
```

<400> SEQUENCE: 443
atcgcctcca ttattctcaa aaa                                            23

<210> SEQ ID NO 444
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-50-209.mis1

<400> SEQUENCE: 444
atatagagtg tgcatccctg aca                                            23

<210> SEQ ID NO 445
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-50-293.mis1

<400> SEQUENCE: 445
cctgagtccc aggggctga cag                                             23

<210> SEQ ID NO 446
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-50-323.mis1

<400> SEQUENCE: 446
tttaaaacat tgatgaatct tta                                            23

<210> SEQ ID NO 447
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-50-329.mis1

<400> SEQUENCE: 447
acattgatga atctttatta cta                                            23

<210> SEQ ID NO 448
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-50-330.mis1

<400> SEQUENCE: 448
gatgaatctt tattactac                                                 19

<210> SEQ ID NO 449
<211> LENGTH: 23

```
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-52-163.mis1

<400> SEQUENCE: 449
gaacaggata ttcttaacta cca                                              23

<210> SEQ ID NO 450
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-52-88.mis1

<400> SEQUENCE: 450
tccatgtcat tattattcaa aag                                              23

<210> SEQ ID NO 451
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-53-258.mis1

<400> SEQUENCE: 451
aatcatgcag agagaatgc                                                   19

<210> SEQ ID NO 452
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-54-283.mis1

<400> SEQUENCE: 452
aagtagtttt tcacactttc tct                                              23

<210> SEQ ID NO 453
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-54-388.mis1

<400> SEQUENCE: 453
ctatcgtata catctttac                                                   19

<210> SEQ ID NO 454
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-55-70.mis1
```

<400> SEQUENCE: 454
aagaacctag gttttaaaa                                               19

<210> SEQ ID NO 455
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-55-95.mis1

<400> SEQUENCE: 455
ctctctatcg tatacatctt tac                                          23

<210> SEQ ID NO 456
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-56-159.mis1

<400> SEQUENCE: 456
aagttttcct tctcttctgt aga                                          23

<210> SEQ ID NO 457
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
     4-56-213.mis1

<400> SEQUENCE: 457
ctcatgttca ctctggttc                                               19

<210> SEQ ID NO 458
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-58-289.mis1

<400> SEQUENCE: 458
catacctgca gcctgctttt ggt                                          23

<210> SEQ ID NO 459
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-58-318.mis1

<400> SEQUENCE: 459
tgactacttt acctgcaata ttt                                          23

<210> SEQ ID NO 460
<211> LENGTH: 23

```
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-60-266.mis1

<400> SEQUENCE: 460
aacaggacca agacactgca tta                                           23

<210> SEQ ID NO 461
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-60-293.mis1

<400> SEQUENCE: 461
aagtttcagt atttcttagc aga                                           23

<210> SEQ ID NO 462
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-84-241.mis1

<400> SEQUENCE: 462
aaaaaatagt gactgccac                                                19

<210> SEQ ID NO 463
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-84-262.mis1

<400> SEQUENCE: 463
tgaataattc agttcttca                                                19

<210> SEQ ID NO 464
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-86-206.mis1

<400> SEQUENCE: 464
tcaaatcagg acacaccac                                                19

<210> SEQ ID NO 465
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
```

```
        4-86-309.mis1

<400> SEQUENCE: 465
tctaggcagg ccactttag                                               19

<210> SEQ ID NO 466
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        4-88-349.mis1

<400> SEQUENCE: 466
ctaaaagaca atattcagt                                               19

<210> SEQ ID NO 467
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-89-87.mis1

<400> SEQUENCE: 467
ttcttccctg aacgctggtt tca                                          23

<210> SEQ ID NO 468
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        99-123-184.mis1

<400> SEQUENCE: 468
cccagaacat tcaccagct                                               19

<210> SEQ ID NO 469
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        99-128-202.mis1

<400> SEQUENCE: 469
tctgtttctt agagaactg                                               19

<210> SEQ ID NO 470
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        99-128-275.mis1

<400> SEQUENCE: 470
ccctacctca catgtgtag                                               19
```

```
<210> SEQ ID NO 471
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-128-313.mis1

<400> SEQUENCE: 471
tctctagaca gatatacat                                              19

<210> SEQ ID NO 472
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 99-128-60.mis1

<400> SEQUENCE: 472
cactgtgacc caggcgctag cgt                                         23

<210> SEQ ID NO 473
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-12907-295.mis1

<400> SEQUENCE: 473
tatggcatta tatctccac                                              19

<210> SEQ ID NO 474
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-130-58.mis1

<400> SEQUENCE: 474
caaaagagct tcaaaaata                                              19

<210> SEQ ID NO 475
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-134-362.mis1

<400> SEQUENCE: 475
acactcatgt tagttagat                                              19

<210> SEQ ID NO 476
<211> LENGTH: 19
<212> TYPE: DNA
<213> ORGANISM: Homo Sapiens
```

```
<220> FEATURE:
<221> NAME/KEY: misc_feature
<222> LOCATION: 1..19
<223> OTHER INFORMATION: microsequencing oligo for 99-140-130.mis1

<400> SEQUENCE: 476
caaaagcagc tacagacca                                                  19

<210> SEQ ID NO 477
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1462-238.mis1

<400> SEQUENCE: 477
ttcaaggtta gtaactcat                                                  19

<210> SEQ ID NO 478
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-147-181.mis1

<400> SEQUENCE: 478
catgaaaaag agcatgata                                                  19

<210> SEQ ID NO 479
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1474-156.mis1

<400> SEQUENCE: 479
tactcataag ttaaatatt                                                  19

<210> SEQ ID NO 480
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for .3
      99-1474-359.mis1

<400> SEQUENCE: 480
aaaatcaaat tattgtacc                                                  19

<210> SEQ ID NO 481
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1479-158.mis1

<400> SEQUENCE: 481
```
aaaatccact tgtaatcgc                                              19

<210> SEQ ID NO 482
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1479-379.mis1

<400> SEQUENCE: 482
agctgtgtac tgaggtcag                                              19

<210> SEQ ID NO 483
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-129.mis1

<400> SEQUENCE: 483
tatctataca aataatttt                                              19

<210> SEQ ID NO 484
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-132.mis1

<400> SEQUENCE: 484
ctatacaaat aattttgaa                                              19

<210> SEQ ID NO 485
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-139.mis1

<400> SEQUENCE: 485
aataattttg aatttaata                                              19

<210> SEQ ID NO 486
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-140.mis1

<400> SEQUENCE: 486
ataattttga atttaatac                                              19

<210> SEQ ID NO 487
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-182.mis1

<400> SEQUENCE: 487
tgttgatatg ggcaactgt                                              19

<210> SEQ ID NO 488
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-366.mis1

<400> SEQUENCE: 488
tgtcaaaggt ctctccctg                                              19

<210> SEQ ID NO 489
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-76.mis1

<400> SEQUENCE: 489
agaatgcctt cctgaatta                                              19

<210> SEQ ID NO 490
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1480-290.mis1

<400> SEQUENCE: 490
ccatcttcac cacaacccc                                              19

<210> SEQ ID NO 491
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1481-285.mis1

<400> SEQUENCE: 491
ataacctgtt ttgcttctc                                              19

<210> SEQ ID NO 492
<211> LENGTH: 19
<212> TYPE: DNA
<213> ORGANISM: Homo Sapiens

```
<220> FEATURE:
<221> NAME/KEY: misc_feature
<222> LOCATION: 1..19
<223> OTHER INFORMATION: potential microsequencing oligo for
      99-1484-101.mis1

<400> SEQUENCE: 492
agatcaaata taagcatgt                                                       19

<210> SEQ ID NO 493
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1484-328.mis1

<400> SEQUENCE: 493
acgtggtcat gaggagttt                                                       19

<210> SEQ ID NO 494
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1485-251.mis1

<400> SEQUENCE: 494
gccttgatat atgctccca                                                       19

<210> SEQ ID NO 495
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1490-381.mis1

<400> SEQUENCE: 495
cagtggaaat accatgtca                                                       19

<210> SEQ ID NO 496
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1493-280.mis1

<400> SEQUENCE: 496
gacagagtat tgttggagg                                                       19

<210> SEQ ID NO 497
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-151-94.mis1
```

```
<400> SEQUENCE: 497
agatcattga taaggaaat                                              19

<210> SEQ ID NO 498
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-211-291.mis1

<400> SEQUENCE: 498
ttatatcaga ctgaccttc                                              19

<210> SEQ ID NO 499
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-213-37.mis1

<400> SEQUENCE: 499
cttccggctg caggactgt                                              19

<210> SEQ ID NO 500
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-221-442.mis1

<400> SEQUENCE: 500
tttgtagata tgcatggga                                              19

<210> SEQ ID NO 501
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 99-222-109.mis1

<400> SEQUENCE: 501
caggtgagga gtgctggatt ggc                                         23

<210> SEQ ID NO 502
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-14-107.mis2

<400> SEQUENCE: 502
ctatcaggca tttgcctggt tgc                                         23

<210> SEQ ID NO 503
<211> LENGTH: 23
```

```
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-14-317.mis2

<400> SEQUENCE: 503
tcatgacctg tgcccacctc ttt                                              23

<210> SEQ ID NO 504
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-14-35.mis2

<400> SEQUENCE: 504
tctctgcaga cagcttctgc ctg                                              23

<210> SEQ ID NO 505
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-20-149.mis2

<400> SEQUENCE: 505
agcaggcaat aaaccaaga                                                   19

<210> SEQ ID NO 506
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-20-77.mis2

<400> SEQUENCE: 506
gtgttctcag acaacaaag                                                   19

<210> SEQ ID NO 507
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-22-174.mis2

<400> SEQUENCE: 507
aaattaacat ttttgaaca                                                   19

<210> SEQ ID NO 508
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
```

```
                4-22-176.mis2
<400> SEQUENCE: 508
acaaattaac atttttgaa                                                 19

<210> SEQ ID NO 509
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-26-60.mis2

<400> SEQUENCE: 509
aagtcgctcc tcggcctgct aac                                            23

<210> SEQ ID NO 510
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-26-72.mis2

<400> SEQUENCE: 510
accctttaaa gtcgctcct                                                 19

<210> SEQ ID NO 511
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-3-130.mis2

<400> SEQUENCE: 511
agttaatacc aatttaagct tta                                            23

<210> SEQ ID NO 512
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-38-63.mis2

<400> SEQUENCE: 512 aaaaaaaag tttagcctc                                                  19

<210> SEQ ID NO 513
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-38-83.mis2

<400> SEQUENCE: 513
atattctcaa cagcattgcc aaa                                            23
```

```
<210> SEQ ID NO 514
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-4-152.mis2

<400> SEQUENCE: 514
tgtttatata taggataac                                                    19

<210> SEQ ID NO 515
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-4-187.mis2

<400> SEQUENCE: 515
tttttttttt tttttttt                                                     19

<210> SEQ ID NO 516
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-4-288.mis2

<400> SEQUENCE: 516
tgaaatcaaa acataggta                                                    19

<210> SEQ ID NO 517
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-42-304.mis2

<400> SEQUENCE: 517
aaaaacccct gaaaataag                                                    19

<210> SEQ ID NO 518
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-42-401.mis2

<400> SEQUENCE: 518
tctgtgggtt taaactttg                                                    19

<210> SEQ ID NO 519
<211> LENGTH: 19
<212> TYPE: DNA
<213> ORGANISM: Homo Sapiens
```

```
<220> FEATURE:
<221> NAME/KEY: misc_feature
<222> LOCATION: 1..19
<223> OTHER INFORMATION: potential microsequencing oligo for
      4-43-328.mis2

<400> SEQUENCE: 519
actggctctg tgggtttaa                                              19

<210> SEQ ID NO 520
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-43-70.mis2

<400> SEQUENCE: 520
ttgtgttgtg tcccatggt                                              19

<210> SEQ ID NO 521
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-50-209.mis2

<400> SEQUENCE: 521
cataaagcct tcagtttca                                              19

<210> SEQ ID NO 522
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-50-293.mis2

<400> SEQUENCE: 522
tcaatgtttt aaactgtcc                                              19

<210> SEQ ID NO 523
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-50-323.mis2

<400> SEQUENCE: 523
atcgaaccct tttgtagta                                              19

<210> SEQ ID NO 524
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
```

```
        4-50-329.mis2

<400> SEQUENCE: 524
gcctaaatcg aacccttt                                             19

<210> SEQ ID NO 525
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        4-50-330.mis2

<400> SEQUENCE: 525
agcctaaatc gaacccttt                                            19

<210> SEQ ID NO 526
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        4-52-163.mis2

<400> SEQUENCE: 526
aatagatgtg taaaattct                                            19

<210> SEQ ID NO 527
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        4-52-88.mis2

<400> SEQUENCE: 527
caccttgtgt attttttaa                                            19

<210> SEQ ID NO 528
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-53-258.mis2

<400> SEQUENCE: 528
ttaggttaaa atttgagtga gaa                                       23

<210> SEQ ID NO 529
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
        4-54-283.mis2

<400> SEQUENCE: 529
taagccatcg attgtatca                                            19
```

```
<210> SEQ ID NO 530
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-54-388.mis2

<400> SEQUENCE: 530
gtcttggcgc tgcagcgtg                                              19

<210> SEQ ID NO 531
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-55-70.mis2

<400> SEQUENCE: 531
taaagatgta tacgatagag agt                                         23

<210> SEQ ID NO 532
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-55-95.mis2

<400> SEQUENCE: 532
gtcttggcgc tgcagcgtg                                              19

<210> SEQ ID NO 533
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-56-159.mis2

<400> SEQUENCE: 533
ttgactgtaa catggagac                                              19

<210> SEQ ID NO 534
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-56-213.mis2

<400> SEQUENCE: 534
tatcaaactc ctctgaagg                                              19

<210> SEQ ID NO 535
<211> LENGTH: 19
<212> TYPE: DNA
```

```
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-58-289.mis2

<400> SEQUENCE: 535
aggtaaagta gtcacccct                                                    19

<210> SEQ ID NO 536
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-58-318.mis2

<400> SEQUENCE: 536
gaagaaataa acttgcaaa                                                    19

<210> SEQ ID NO 537
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-60-266.mis2

<400> SEQUENCE: 537
agaaatactg aaactttat                                                    19

<210> SEQ ID NO 538
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-60-293.mis2

<400> SEQUENCE: 538
aggacttcct gctggcttc                                                    19

<210> SEQ ID NO 539
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-84-241.mis2

<400> SEQUENCE: 539
ttctgaagaa ctgaattatt cac                                               23

<210> SEQ ID NO 540
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
```

4-84-262.mis2

<400> SEQUENCE: 540
tgagatcatg ttgctgctt                                             19

<210> SEQ ID NO 541
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 4-86-206.mis2

<400> SEQUENCE: 541
aatgttaacg tgtagatgcc att                                        23

<210> SEQ ID NO 542
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-86-309.mis2

<400> SEQUENCE: 542
gctctctggt tcctcactc                                             19

<210> SEQ ID NO 543
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-88-349.mis2

<400> SEQUENCE: 543
aagaacttgg aaaatctca                                             19

<210> SEQ ID NO 544
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      4-89-87.mis2

<400> SEQUENCE: 544
ttctcaacac aaaaactat                                             19

<210> SEQ ID NO 545
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-123-184.mis2

<400> SEQUENCE: 545
cccagcagaa ctcttggcc                                             19

<210> SEQ ID NO 546
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-128-202.mis2

<400> SEQUENCE: 546
gtatgtatgt gtgtgtgtt                                               19

<210> SEQ ID NO 547
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-128-275.mis2

<400> SEQUENCE: 547
acatatatgc atacatttg                                               19

<210> SEQ ID NO 548
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-128-313.mis2

<400> SEQUENCE: 548
tctatgccaa atagaatct                                               19

<210> SEQ ID NO 549
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-128-60.mis2

<400> SEQUENCE: 549
ggagtgtcac tgtaagagg                                               19

<210> SEQ ID NO 550
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-12907-295.mis2

<400> SEQUENCE: 550
ttgtacatca ggtctgccc                                               19

<210> SEQ ID NO 551
<211> LENGTH: 23
<212> TYPE: DNA

```
<213> ORGANISM: Homo Sapiens
<220> FEATURE:
<221> NAME/KEY: misc_feature
<222> LOCATION: 1..23
<223> OTHER INFORMATION: microsequencing oligo for 99-130-58.mis2

<400> SEQUENCE: 551
ctcgccatat gcacactcct gaa                                              23

<210> SEQ ID NO 552
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-134-362.mis2

<400> SEQUENCE: 552
tctttgtaat aggaataat                                                   19

<210> SEQ ID NO 553
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-140-130.mis2

<400> SEQUENCE: 553
catgctcaat tgtttacat                                                   19

<210> SEQ ID NO 554
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1462-238.mis2

<400> SEQUENCE: 554
ctgaagcaga aacacagca                                                   19

<210> SEQ ID NO 555
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 99-147-181.mis2

<400> SEQUENCE: 555
tataaagatt taagttttc ttt                                               23

<210> SEQ ID NO 556
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1474-156.mis2

<400> SEQUENCE: 556
```
ccatatttct tcttgttat                                              19

<210> SEQ ID NO 557
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1474-359.mis2

<400> SEQUENCE: 557
catctgatat tagggaatt                                              19

<210> SEQ ID NO 558
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1479-158.mis2

<400> SEQUENCE: 558
aatatacact ccaattagc                                              19

<210> SEQ ID NO 559
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1479-379.mis2

<400> SEQUENCE: 559
ctgtaccatg agctgcttc                                              19

<210> SEQ ID NO 560
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-129.mis2

<400> SEQUENCE: 560
cagccctatg tattaaatt                                              19

<210> SEQ ID NO 561
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-132.mis2

<400> SEQUENCE: 561
ttgcagccct atgtattaa                                              19

<210> SEQ ID NO 562

```
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-139.mis2

<400> SEQUENCE: 562
ccttgttttg cagccctat                                              19

<210> SEQ ID NO 563
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-140.mis2

<400> SEQUENCE: 563
accttgtttt gcagcccta                                              19

<210> SEQ ID NO 564
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 99-148-182.mis2

<400> SEQUENCE: 564
gaatgctttg ggaccatcca aca                                         23

<210> SEQ ID NO 565
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-366.mis2

<400> SEQUENCE: 565
gaggcggcag ccgtgagca                                              19

<210> SEQ ID NO 566
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-148-76.mis2

<400> SEQUENCE: 566
tatgaagcca tcaagagta                                              19

<210> SEQ ID NO 567
<211> LENGTH: 19
<212> TYPE: DNA
<213> ORGANISM: Homo Sapiens
<220> FEATURE:
<221> NAME/KEY: misc_feature
```

<222> LOCATION: 1..19
<223> OTHER INFORMATION: microsequencing oligo for 99-1480-290.mis2

<400> SEQUENCE: 567
aaaaggatca gtggttgcc                                              19

<210> SEQ ID NO 568
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1481-285.mis2

<400> SEQUENCE: 568
taccatcttg aggttagag                                              19

<210> SEQ ID NO 569
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1484-101.mis2

<400> SEQUENCE: 569
agattttaag gagaggagt                                              19

<210> SEQ ID NO 570
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1484-328.mis2

<400> SEQUENCE: 570
tctgaaaact gaatcccctt                                             19

<210> SEQ ID NO 571
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1485-251.mis2

<400> SEQUENCE: 571 agggggacatt cttggttct                                             19

<210> SEQ ID NO 572
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-1490-381.mis2

<400> SEQUENCE: 572
agatgcacag tagcgtacc                                              19

```
<210> SEQ ID NO 573
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: microsequencing oligo for 99-1493-280.mis2

<400> SEQUENCE: 573
acaagcagcc aaacccat                                              19

<210> SEQ ID NO 574
<211> LENGTH: 23
<212> TYPE: DNA
<213> ORGANISM: Homo Sapiens
<220> FEATURE:
<221> NAME/KEY: misc_feature
<222> LOCATION: 1..23
<223> OTHER INFORMATION: microsequencing oligo for 99-151-94.mis2

<400> SEQUENCE: 574
atatagattt tgaaatttta gaa                                        23

<210> SEQ ID NO 575
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-211-291.mis2

<400> SEQUENCE: 575
cattgacctg ttgaaaaca                                             19

<210> SEQ ID NO 576
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-213-37.mis2

<400> SEQUENCE: 576
tcagacactg gagtcctcc                                             19

<210> SEQ ID NO 577
<211> LENGTH: 19
<212> TYPE: DNA
<213> ORGANISM: Homo Sapiens
<220> FEATURE:
<221> NAME/KEY: misc_feature
<222> LOCATION: 1..19
<223> OTHER INFORMATION: potential microsequencing oligo for
      99-221-442.mis2

<400> SEQUENCE: 577
gtctggctag gtcatggaa                                             19

<210> SEQ ID NO 578
<211> LENGTH: 19
<212> TYPE: DNA
<213> ORGANISM: Homo Sapiens
```

-continued

```
<220> FEATURE:
<221> NAME/KEY: misc_feature
<222> LOCATION: 1..19
<223> OTHER INFORMATION: potential microsequencing oligo for
      99-222-109.mis2

<400> SEQUENCE: 578
ctgaagaaat tcatatcgt                                                19
```